United States Patent
Biftu et al.

(10) Patent No.: US 7,196,095 B2
(45) Date of Patent: Mar. 27, 2007

(54) (PYRIMIDINYL) (PHENYL) SUBSTITUTED FUSED HETEROARYL P38 INHIBITING AND PKG KINASE INHIBITING COMPOUNDS

(75) Inventors: Tesfaye Biftu, Westfield, NJ (US); Richard Beresis, Matawan, NJ (US); Richard Berger, Cranford, NJ (US); Steven L. Colletti, Princeton Junction, NJ (US); James B. Doherty, Montvale, NJ (US); Dennis D. Feng, Branchburg Township, NJ (US); Gui-Bai Liang, Scotch Plains, NJ (US); Dennis M. Schmatz, Cranford, NJ (US); Xiaoxia Qian, New York, NY (US); David A. Claremon, Maple Glen, PA (US); Nigel J. Liverton, Harleysville, PA (US); Charles J. McIntyre, Lansdale, PA (US); Ernest W. Kovacs, Weehawken, NJ (US)

(73) Assignee: Merck & Co., Inc., Rahway, NJ (US)

( * ) Notice: Subject to any disclaimer, the term of this patent is extended or adjusted under 35 U.S.C. 154(b) by 151 days.

(21) Appl. No.: 10/477,367

(22) PCT Filed: Jun. 21, 2002

(86) PCT No.: PCT/US02/19507

§ 371 (c)(1),
(2), (4) Date: Nov. 12, 2003

(87) PCT Pub. No.: WO03/000682

PCT Pub. Date: Jan. 3, 2003

(65) Prior Publication Data

US 2004/0176396 A1 Sep. 9, 2004

Related U.S. Application Data

(60) Provisional application No. 60/300,748, filed on Jun. 25, 2001.

(51) Int. Cl.
*C07D 403/04* (2006.01)
*C07D 403/14* (2006.01)
*C07D 417/04* (2006.01)
*C07D 417/14* (2006.01)
*A61K 31/506* (2006.01)
*A61P 19/02* (2006.01)

(52) U.S. Cl. .................. 514/275; 514/243; 514/259.1; 544/331; 544/184; 544/281

(58) Field of Classification Search ............... 544/33, 544/281, 184, 331; 514/275, 258, 243, 259.1
See application file for complete search history.

(56) References Cited

FOREIGN PATENT DOCUMENTS

WO   WO 200134605 A1 * 5/2001

OTHER PUBLICATIONS

West, Anthony R., Solid State Chemistry and its Applications, Wiley, New York, 1988, pp. 358 & 365.*
Vippagunta et al., Advanced Drug Delivery Reviews 48: 3-26, 2001.*
Lubberts et al., Drug News Perspect. 14(9): 517-522, 2001.*
Foster Int. J. Exp. Pathol. 82(3): 171-192.*
Cecil Textbook of Medicine, edited by Bennet, J.C., and Plum F., 20th edition,vol. 1, 1004-1010, 1996.*

* cited by examiner

*Primary Examiner*—Venkataraman Balasubramanian
(74) *Attorney, Agent, or Firm*—Curtis C. Panzer; David L. Rose

(57) ABSTRACT

Compounds of formula (I) and pharmaceutically acceptable salts thereof are useful in the treatment of cytokine mediated diseases such as arthritis and in the treatment and/or prevention of protozoal diseases such as coccidiosis 25 Claims, No Drawings

(PYRIMIDINYL) (PHENYL) SUBSTITUTED FUSED HETEROARYL P38 INHIBITING AND PKG KINASE INHIBITING COMPOUNDS

RELATED APPLICATION DATA

This is a National filing under 35 USC 371 of PCT/US 02/19507, filed Jun. 21, 2002, which claims priority from U.S. Ser. No. 60/300,748, filed Jun. 25, 2001.

BACKGROUND OF THE INVENTION

The present invention relates to (pyrimidyl)(phenyl)substituted fused heteroaryl compounds which have cytokine inhibitory activity. The present invention also relates to (pyrimidyl)(phenyl)substituted fused heteroaryl compounds which have cGMP dependent protein kinase ("PKG") inhibitory activity.

Cytokine mediated diseases and cytokine inhibition, suppression and antagonism are used in the context of diseases or conditions in which excessive or unregulated production or activity of one or more cytokines occurs. Examples of cytokines which are effected typically include Interleukin-1 (IL-1), Interleukin-6 (IL-6), Interleukin-8 (IL-8) and Tumor Necrosis Factor (TNF).

Interleukin-1 (IL-1) and Tumor Necrosis Factor (TNF) are produced by a variety of cells that are involved in immunoregulation and other physiological conditions.

There are many disease states in which IL-1 is implicated. Examples are rheumatoid arthritis, osteoarthritis, endotoxemia, toxic shock syndrome, acute and chronic inflammatory diseases, such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis and acute synovitis. Recent evidence also links IL-1 activity to diabetes.

Interleukin-1 has been demonstrated to mediate a variety of biological activities thought to be important in immunoregulation and other physiological conditions. [See, e.g., Dinarello et al., Rev. Infect. Disease, 6, 51 (1984)]. The known biological activities of IL-1 include the activation of T helper cells, induction of fever, stimulation of prostaglandin or collagenase production, neutrophil chemotaxis, induction of acute phase proteins and the suppression of plasma iron levels.

Excessive or unregulated tumor necrosis factor (TNF) production or activity has been implicated in mediating or exacerbating rheumatoid arthritis, rheumatoid spondylitis, osteoarthritis, gouty arthritis, and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcosis, bone resorption diseases, reperfusion injury, graft v. host rejection, allograft rejections, fever and myalgia due to infection, cachexia secondary to infection or malignancy, cachexia secondary to acquired immune deficiency syndrome (AIDS), AIDS related complex (ARC), keloid formation, scar tissue formation, Crohn's disease, ulcerative colitis and pyresis.

Monokines, such as TNF, have also been shown to activate HIV replication in monocytes and/or macrophages [See Poli, et al., Proc. Natl. Acad. Sci., 87:782–784 (1990)], therefore, inhibition of monokine production or activity aids in limiting HIV progression. TNF has been implicated in various roles with other viral infections, such as the cytomegalovirus (CMV), influenza virus and the herpes virus.

Interleukin-6 (IL-6) is a cytokine effecting the immune system and hematopoiesis. It is produced by several mammalian cell types in response to agents such as IL-1, and is correlated with disease states such as angiofollicular lymphoid hyperplasia.

Interleukin-8 (IL-8) is a chemotactic factor first identified and characterized in 1987. Many different names have been applied to IL-8, such as neutrophil attractant/activation protein-1 (NAP-1), monocyte derived neutrophil chemotactic factor (MDNCF), neutrophil activating factor (NAF), and T-cell lymphocyte chemotactic factor. Like IL-1, IL-8 is produced by several cell types, including mononuclear cells, fibroblasts, endothelial cells and ketainocytes. Its production is induced by IL-1, TNF and by lipopolysaccharide (LPS). IL-8 stimulates a number of cellular functions in vitro. It is a chemoattractant for neutrophils, T-lymphocytes and basophils. It induces histamine release from basophils. It causes lysozomal enzyme release and respiratory burst from neutrophils, and it has been shown to increase the surface expression of Mac-1 (CD11b/CD 18) on neutrophils without de novo protein synthesis.

There remains a need for compounds which are useful in treating cytokine mediated diseases, and as such, inhibit, suppress or antagonize the production or activity of cytokines such as IL-1, IL-6, IL-8 and TNF.

Parasitic protozoa are responsible for a wide variety of infections in man and animals. Many of the diseases are life threatening to the host, and in animal husbandry, can cause considerable economic loss. For example, malaria remains a significant health threat to humans despite massive international attempts to eradicate the disease; trypanosomiasis such as Chagas disease caused by *Trypanosoma cruzi* and African sleeping sickness caused by *T. brucei* are not uncommon in South America and Africa, respectively; and opportunistic infections in immuno-compromised hosts caused by *Pneumocystis carinii, Toxoplasma gondii, Cryptosporidium* sp. are becoming increasingly significant in the developed countries.

Coccidiosis, a widespread disease of domesticated animals, is caused by protozoal infection. In the poultry industry, coccidiosis is responsible for high levels of morbidity and mortality in the bird population and may result in extreme economic losses. The infectious agents are protozoa of the genus *Eimeria*. Some of the most significant avian *Eimeria* species include *E. tenella, E. acervulina, E. necatrix, E. brunetti* and *E. maxima*.

In some protozoal diseases, such as Chagas disease, there is no satisfactory treatment; in others, drug-resistant strains of the protozoa may develop. A biochemical target of antiprotozoal drugs, cGMP dependent protein kinases (PKG), has been identified, the inhibition of which effectively treats protozoal infections such as coccidiosis and Chagas disease.

cGMP dependent protein kinases catalyze the phosphorylation of specific protein substrates. In the absence of cGMP the activity of these enzymes is very low. Thus, the inhibition of such PKG kinases can be lethal to the organism. There is a need for compounds that treat (or prevent by a subtherapeutic prophalactic dosing) coccidiosis, Chagas disease, and toxoplasmosis. Compounds that inhibit the PKG kinase of the infecting protozoa can be such preventive and treating compounds. Importantly, compounds that selectively inhibit the PKG kinase of the infecting protozoa without inhibiting the PKG kinase of mammalian PKG kinase would be lethal to protozoa while being safe for mammals. Accordingly, there is a need for such selective compounds for the treatment of protozoal infections such as coccidiosis, Chagas disease, and toxoplasmosis.

International Patent Publication Nos. WO 99/51233, WO 99/51232, WO 97/21704, WO 97/21703, and WO 00/04013 describe fused heteroaryl compounds that are antagonists of gonadotropin releasing hormone. International Patent Publication No. WO 96/06840 describes diaryl bicyclic heterocycles as inhibitors of cyclooxygenase-2.

International Patent Publication No. WO 98/22457 describes aryl and heteroaryl substituted fused pyrrole anti-inflammatory agents. International Patent Publication No. WO 01/22965 describes substituted imidazoles having cytokine inhibitory activity. International Patent Publication No. WO 01/34605 describes substituted 2-aryl-3-(heteroaryl)-imidazo[1,2-a]primidines. International Patent Publication No. WO 01/30778 describes tiazole and imidazo[4,5-b]pyridine compounds. International Patent Publication No. WO 00/63204 describes substituted azoles.

The compounds 3-(2-Methylsulfanylpyrimidin-4-yl)-2-(3-trifluoromethylphenyl)imidazo[1,2-a]-pyrimidine:

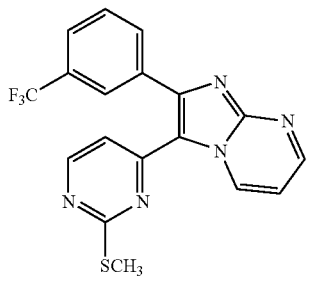

and 3-(2-Methylsulfonylpyrimidin-4-yl)-2-(3-trifluoromethylphenyl)imidazo[1,2-a]-pyrimidine:

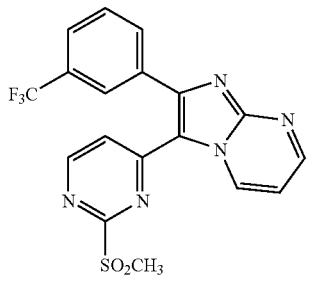

were described in International Patent Publication No. WO 01/22965 as intermediates in a process to make a substituted imidazole.

SUMMARY OF THE INVENTION

The present invention relates to compound I of the formula

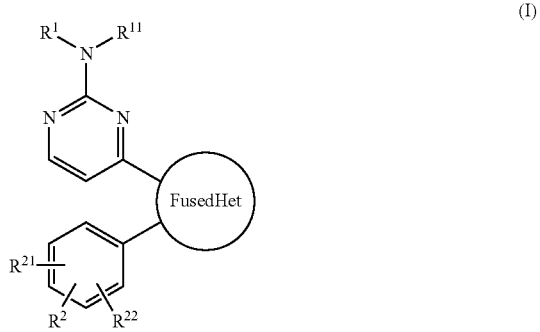

wherein FusedHet is

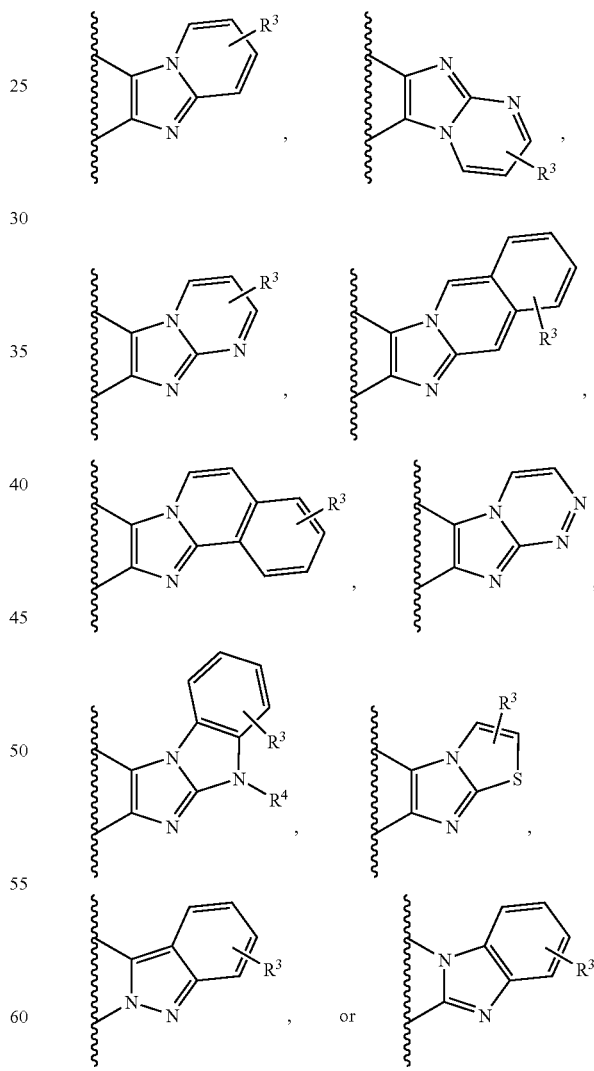

or a pharmaceutically acceptable salt and/or hydrate thereof, or where applicable, a geometric or optical isomer or racemic mixture thereof.

This invention also relates to a pharmaceutical composition that is comprised of a compound of formula I as defined above in combination with a pharmaceutically acceptable carrier.

Also included in the invention is a method of treating a cytokine mediated disease in a mammal, comprising administering to a mammalian patient in need of such treatment an amount of a compound of formula I which is effective to treat the cytokine mediated disease.

The invention includes a method of treating a protozoal disease in a mammel or bird, comprising administering to a mammalian or avian patient in need of such treatment an amount of a compound of formula I which is effective to treat the protozoal disease. Further, the invention includes a method of preventing a protozoal disease in a mammel or bird, comprising administering to a mammalian or avian patient in need of such treatment a prophalactic amount of a compound of formula I which is effective to prevent the protozoal disease.

DETAILED DESCRIPTION OF THE INVENTION

The present invention relates to compounds represented by formula (I):

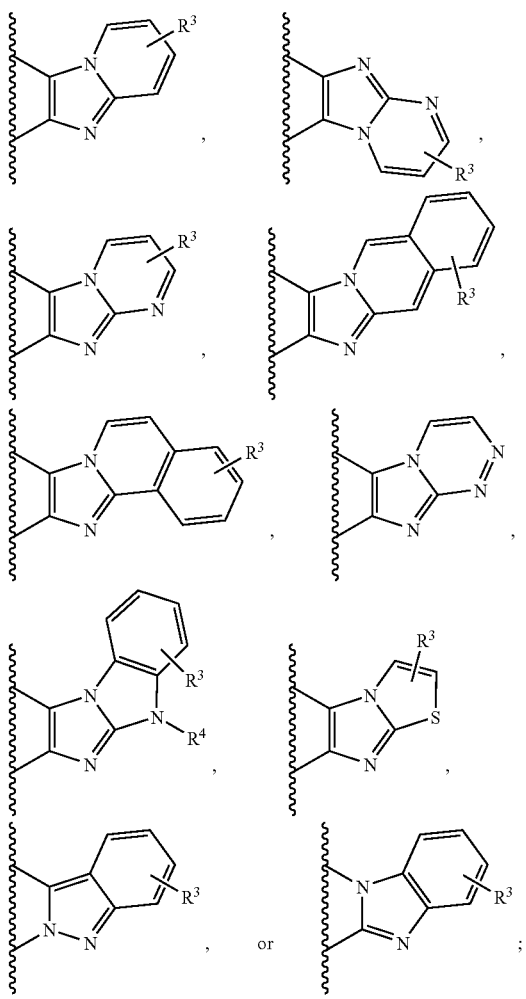

or a pharmaceutically acceptable salt or hydrate thereof, wherein FusedHet is

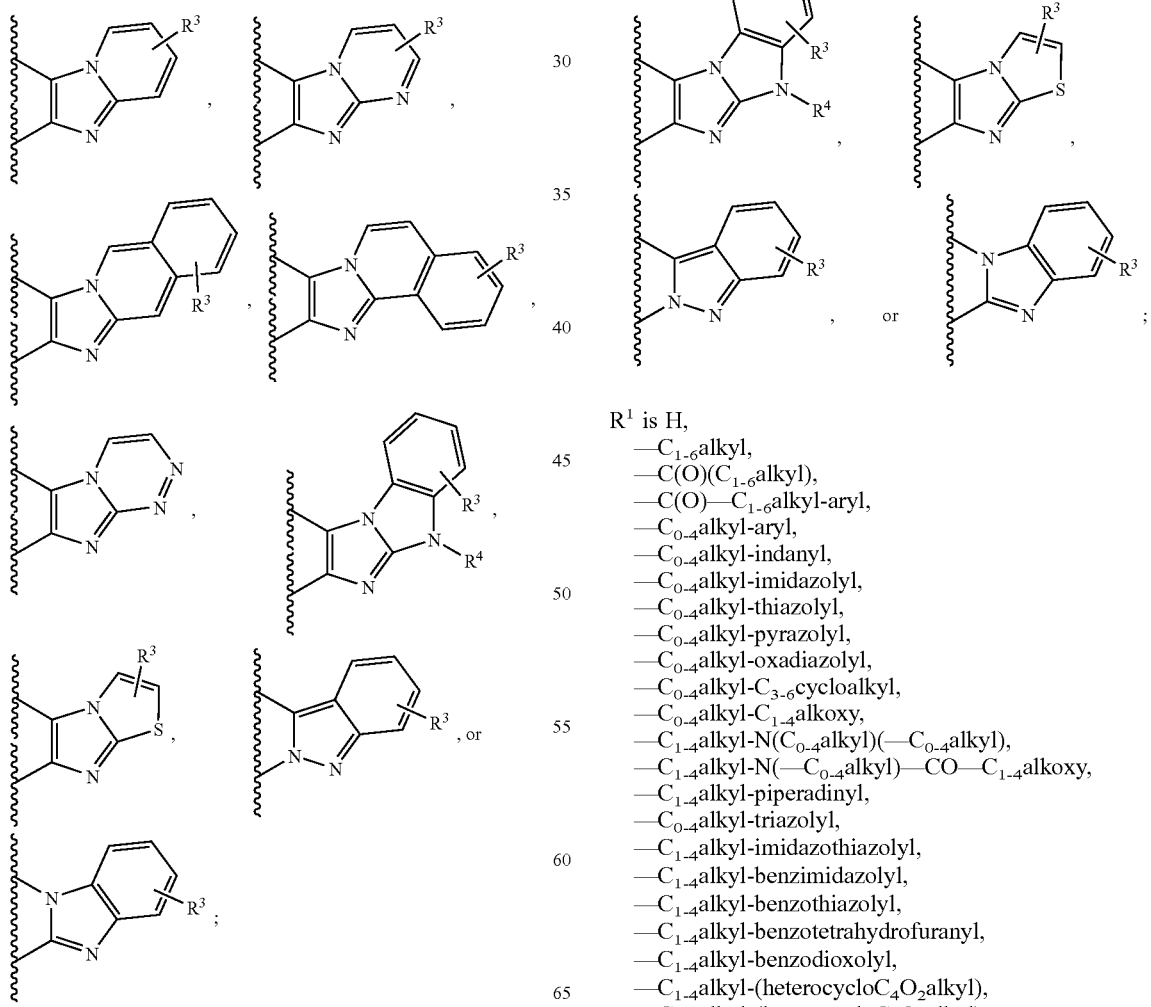

$R^1$ is H,
—$C_{1-6}$alkyl,
—$C(O)(C_{1-6}$alkyl),
—$C(O)$—$C_{1-6}$alkyl-aryl,
—$C_{0-4}$alkyl-aryl,
—$C_{0-4}$alkyl-indanyl,
—$C_{0-4}$alkyl-imidazolyl,
—$C_{0-4}$alkyl-thiazolyl,
—$C_{0-4}$alkyl-pyrazolyl,
—$C_{0-4}$alkyl-oxadiazolyl,
—$C_{0-4}$alkyl-$C_{3-6}$cycloalkyl,
—$C_{0-4}$alkyl-$C_{1-4}$alkoxy,
—$C_{1-4}$alkyl-N($C_{0-4}$alkyl)(—$C_{0-4}$alkyl),
—$C_{1-4}$alkyl-N(—$C_{0-4}$alkyl)—CO—$C_{1-4}$alkoxy,
—$C_{1-4}$alkyl-piperadinyl,
—$C_{0-4}$alkyl-triazolyl,
—$C_{1-4}$alkyl-imidazothiazolyl,
—$C_{1-4}$alkyl-benzimidazolyl,
—$C_{1-4}$alkyl-benzothiazolyl,
—$C_{1-4}$alkyl-benzotetrahydrofuranyl,
—$C_{1-4}$alkyl-benzodioxolyl,
—$C_{1-4}$alkyl-(heterocyclo$C_4O_2$alkyl),
—$C_{1-4}$alkyl-(heterocyclo$C_5O_1$alkyl),
—$C_{1-4}$alkyl-tetrahydrofuran, or —$C_{1-4}$alkyl-oxetanyl;
$R^{11}$ is H or —$C_{1-6}$alkyl;
or $R^1$ and $R^{11}$, together with the N to which they are attached, form a morpholinyl;
$R^2$, $R^{21}$, $R^{22}$ each independently is H, halogen, or —$C_{1-4}$ alkyl;
$R^3$ is H,
—$C_{1-4}$alkyl,
—$C_{3-6}$cycloalkyl,
—$C_{1-4}$alkyl-aryl,
—$C_{1-4}$alkyl-azetidinyl,
—$C_{1-4}$alkyl-azetidinyl-CO—$C_{0-4}$alkyl-N($C_{0-4}$alkyl)($C_{0-4}$alkyl),
—$C_{1-4}$alkyl-pyrrolidinyl,
—$C_{1-4}$alkyl-piperidinyl,
—$C_{1-4}$alkyl-morpholinyl,
—$C_{0-4}$alkyl-N($C_{0-4}$alkyl)($C_{0-4}$alkyl),
—$C_{0-4}$alkyl-N($C_{0-4}$alkyl)($C_{0-4}$alkyl-$C_{1-4}$alkoxy),
—$C_{0-4}$alkyl-N($C_{0-4}$alkyl-$C_{1-4}$alkoxy)($C_{0-4}$alkyl-$C_{1-4}$alkoxy),
—$C_{1-4}$alkyl-N($C_{0-4}$alkyl)($C_{1-4}$alkyl)-aryl,
—$C_{1-4}$alkyl-N($C_{0-4}$alkyl)—$C_{1-4}$alkyl-tetrahydrofuranyl,
—$C_{1-4}$alkyl-N($C_{0-4}$alkyl)—$C_{1-4}$alkyl-azetidinyl,
—$C_{1-4}$alkyl-N($C_{0-4}$alkyl)—$C_{1-4}$alkyl-N($C_{0-4}$alkyl)($C_{0-4}$ alkyl),
—$C_{1-4}$alkyl-N($C_{0-4}$alkyl)—$C_{1-4}$alkyl-N($C_{0-4}$alkyl)—$C_{0-4}$alkyl-$SO_2C_{1-4}$alkyl),
—CO—N($C_{0-4}$alkyl)—$C_{1-4}$alkyl-aryl,
—CO—N($C_{0-4}$alkyl)—$C_{1-4}$alkyl-N($C_{0-4}$alkyl)($C_{0-4}$ alkyl),
—$C_{0-4}$alkyl-CO—$C_{0-4}$alkyl,
—$C_{0-4}$alkyl-CO—$C_{0-4}$alkoxy,
—$C_{0-4}$alkyl-CO—N($C_{0-4}$alkyl)—$C_{1-4}$alkyl-$C_{1-4}$alkoxy,
—$C_{0-4}$alkyl-CO—N($C_{0-4}$alkyl)—$C_{1-4}$alkyl-aryl,
—$C_{0-4}$alkyl-CO-piperidinyl,
—$C_{1-4}$alkyl-N($C_{0-4}$alkyl)—$C_{0-4}$alkyl-CO—$C_{0-4}$alkyl-N($C_{0-4}$alkyl)($C_{0-4}$alkyl),
—$C_{0-4}$alkyl-CO—$C_{0-4}$alkyl-N($C_{0-4}$alkyl)($C_{0-4}$alkyl),
—O—$C_{1-4}$alkyl-aryl,
—$C_{1-4}$alkyl-O—$C_{1-4}$alkyl,
—$C_{0-4}$alkyl-N($C_{0-4}$alkyl)—$C_{0-4}$alkyl-CO—$C_{0-4}$alkyl,
—$C_{0-4}$alkyl-N($C_{0-4}$alkyl)—$C_{0-4}$alkyl-CO—$C_{0-4}$alkoxy,
—$C_{0-4}$alkyl-N($C_{0-4}$alkyl)—$C_{0-4}$alkyl-CO—$C_{0-4}$alkyl-aryl,
—CO-alkyl-N($C_{0-4}$alkyl)—$C_{0-4}$alkyl-CO—$C_{0-4}$alkyl(aryl)$_2$,
—$C_{0-4}$alkyl-N($C_{0-4}$alkyl)—$C_{0-4}$alkyl-CO—$C_{0-4}$alkyl-pyrrolyl,
—$C_{0-4}$alkyl-N($C_{0-4}$alkyl)—$C_{0-4}$alkyl-CO—$C_{0-4}$alkyl-pyrrolidinyl,
—$C_{0-4}$alkyl-N($C_{0-4}$alkyl)—$C_{0-4}$alkyl-CO—$C_{0-4}$alkyl-azetidinyl,
—$C_{0-4}$alkyl-N($C_{0-4}$alkyl)—$C_{0-4}$alkyl-CO—$C_{2-4}$alkenyl-pyrrolidinyl,
—$C_{0-4}$alkyl-N($C_{0-4}$alkyl)—$C_{0-4}$alkyl-CO—$C_{0-4}$alkyl-thiophenyl,
—$C_{0-4}$alkyl-N($C_{0-4}$alkyl)—$C_{0-4}$alkyl-CO—$C_{2-4}$alkenyl-thiophenyl,
—$C_{0-4}$alkyl-N($C_{0-4}$alkyl)—$C_{0-4}$alkyl-CO—S—$C_{1-4}$alkyl-aryl,
—$C_{0-4}$alkyl-N($C_{0-4}$alkyl)—$C_{0-4}$alkyl-CO—$C_{3-6}$cyclolkyl,
—$C_{0-4}$alkyl-N($C_{0-4}$alkyl)—$C_{0-4}$alkyl-CO—O—$C_{1-4}$alkyl-aryl,
—$C_{0-4}$alkyl-CO—N($C_{0-4}$alkyl)—$C_{0-4}$alkyl-$C_{1-4}$alkoxy,
—$C_{1-4}$alkyl-N($C_{0-4}$alkyl)(—$SO_2C_{1-4}$alkyl),
—$C_{0-4}$alkyl-N($C_{0-4}$alkyl)—$C_{1-4}$alkyl-$SO_2C_{1-4}$alkyl,
—$C_{0-4}$alkyl-S—$C_{1-4}$alkyl-aryl,
—$C_{1-4}$alkyl-PO($C_{1-4}$alkoxy)($C_{1-4}$alkoxy),
—$C_{1-4}$alkyl-azetidinyl-CO—N($C_{0-4}$alkyl)($C_{0-4}$alkyl),
—$C_{1-4}$alkyl-(heterocyclo$C_4N_1O_1$alkyl),
—$C_{0-4}$alkyl-CO—(heterocyclo$C_5N_1$alkyl),
—$C_{0-4}$alkyl-CO—N($C_{0-4}$alkyl)-(heterocyclo$C_5N_1$alkyl),
—$C_{1-4}$alkyl-(heterocyclo$C_4N_2$alkyl)—$C_{1-4}$alkyl,
—$C_{1-4}$alkyl-(heterocyclo$C_4N_2$alkyl)—CO—$C_{0-4}$ alkoxy,
—$C_{1-4}$alkyl-(heterocyclo$C_4N_2$alkyl)—$C_{1-4}$alkyl-N($C_{0-4}$alkyl)($C_{0-4}$alkyl),
—$C_{1-4}$alkyl-(heterobicyclo$C_5N_2$alkyl)—$C_{1-4}$alkyl, or
—$C_{1-4}$alkyl-NH—(heterobicyclo$C_7N_1$alkyl); and
$R^4$ is —$C_{1-6}$alkyl;
wherein any of the above aryl, hetaryl, cycloalkyl, or heterocycloalkyl optionally may be substituted with 1–4 substituents, each substituent independently is halogen, $NO_2$, —CN, —$C_{1-4}$alkyl, —$C_{0-4}$alkoxy, —S—$C_{1-4}$alkyl, or —$C_{0-4}$alkyl-(CO)—$C_{0-4}$alkoxy; and any of the above alkyl optionally may be substituted with 1–4 substituents, each substituent independently is halogen, —$N_3$, —CN, —COOH, or —$C_{0-4}$ alkoxy.

This invention also includes a binary compound formed from two compounds of formula (I), as described above, connected together by linking the respective R3 groups of each compound. In one aspect the binary compound is a dimer of two identical compounds of formula (I), as described above.

In one aspect, the compound of this invention is represented by formula (I), or a pharmaceutically acceptable salt or hydrate thereof, wherein FusedHet is

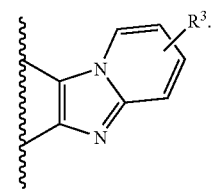

In a second aspect, the compound of this invention is represented by formula (I), or a pharmaceutically acceptable salt or hydrate thereof, wherein FusedHet is

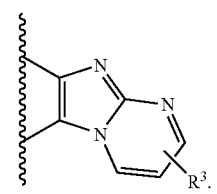

In a third aspect, the compound of this invention is represented by formula (I), or a pharmaceutically acceptable salt or hydrate thereof, wherein FusedHet is

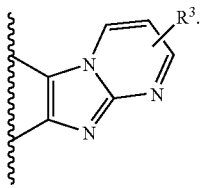

In a fourth aspect, the compound of this invention is represented by formula (I), or a pharmaceutically acceptable salt or hydrate thereof, wherein FusedHet is

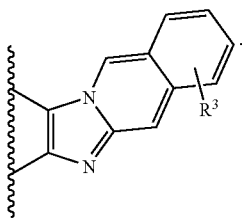

In a fifth aspect, the compound of this invention is represented by formula (I), or a pharmaceutically acceptable salt or hydrate thereof, wherein FusedHet is

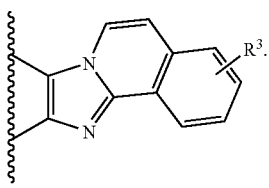

In a sixth aspect, the compound of this invention is represented by formula (I), or a pharmaceutically acceptable salt or hydrate thereof, wherein FusedHet is

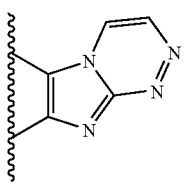

In a seventh aspect, the compound of this invention is represented by formula (I), or a pharmaceutically acceptable salt or hydrate thereof, wherein FusedHet is

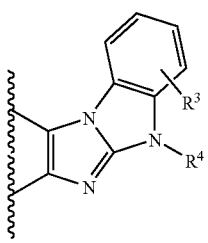

In an eighth aspect, the compound of this invention is represented by formula (I), or a pharmaceutically acceptable salt or hydrate thereof, wherein FusedHet is

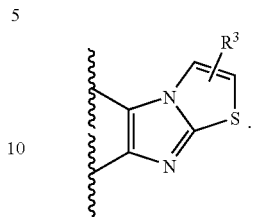

In a ninth aspect, the compound of this invention is represented by formula (I), or a pharmaceutically acceptable salt or hydrate thereof, wherein FusedHet is

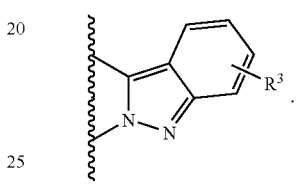

In a tenth aspect, the compound of this invention is represented by formula (I), or a pharmaceutically acceptable salt or hydrate thereof, wherein FusedHet is

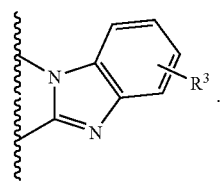

This invention also relates to a pharmaceutical composition that is comprised of a compound of formula (I) as defined above in combination with a pharmaceutically acceptable carrier.

Also included in the invention is a method of treating a cytokine mediated disease in a mammal, comprising administering to a mammalian patient in need of such treatment an amount of a compound of formula (I), which is effective to treat the cytokine mediated disease.

The invention includes a method of treating a protozoal disease in a mammel, comprising administering to a mammalian patient in need of such treatment an amount of a compound of formula (I), which is effective to treat the protozoal disease. Further, the invention includes a method of preventing a protozoal disease in a mammel, comprising administering to a mammalian patient in need of such treatment a prophalactic amount of a compound of formula (I), which is effective to prevent the protozoal disease.

Unless otherwise stated or indicated, the following definitions shall apply throughout the specification and claims.

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "aryl" means an aromatic subsituent which is a single ring or multiple rings fused together. When formed of multiple rings, at least one of the constituent rings is aromatic. The preferred aryl substituents are phenyl and napthyl groups.

The term "cycloalkyloxy" unless specifically stated otherwise includes a cycloalkyl group connected by a short $C_1$–$C_2$alkyl length to the oxy connecting atom.

The term "$C_0$–$C_6$alkyl" includes alkyls containing 6, 5, 4, 3, 2, 1, or no carbon atoms. A terminal alkyl with no carbon atoms is a hydrogen atom. A bridging alkyl with no carbon atoms is a direct bond. It is understood that, for the purposes of substitution, an alkyl with no carbon atoms has no substituents and takes no substitution. The term "—$C_{0-4}$alkoxy" is —OH for —$C_0$alkoxy.

The term "hetero" unless specifically stated otherwise includes one or more O, S, or N atoms. For example, heterocycloalkyl ("heterocycle") and heteroaryl include ring systems that contain one or more O, S, or N atoms in the ring, including mixtures of such atoms. The hetero atoms replace ring carbon atoms. Thus, for example, a heterocyclo$C_5$alkyl is a five member ring containing from 5 to no carbon atoms. However, the heteroatoms can be specified. Thus, a heterocyclo$C_4N_1O_1$alkyl is a six member saturated ring containing 4 carbon atoms, 1 nitrogen atom, and 1 oxygen atom. Similar notation is used for heterobicycloclkyls.

Generally, unless otherwise stated, "heterocycle" is a 3- to 7-membered non-aromatic ring containing 1–4 heteroatoms selected from N, O and S(O)m, which may be optionally fused to a benzene ring, and in which up to three additional carbon atoms may be replaced by said heteroatoms. When three heteroatoms are present in the heterocycle, they are not all linked together. Examples of heterocycle include oxiranyl, aziridinyl, azetidinyl, oxetanyl, tetrahydrofuranyl, tetrahydropyranyl, tetrahydrothienyl including sulfoxide and sulfones thereof, 2,3- and 2,5-dihydrofuranyl, 1,3-dioxanyl, 1,3-dioxolanyl, pyrrolidinyl, imidazolinyl, imidazolidinyl, piperidinyl, morpholinyl, thiomorpholinyl, piperazinyl, benzoxazinyl, 2,3-dihydrobenzofuranyl 1,2,3,4-tetrahydroisoquinolinyl, 1,2,3,4-tetrahydroquinolinyl., "Heteroaryl" is a mono-or bicyclic aromatic ring containing from 1 to 6 heteroatoms independently selected from N, O and S wherein each ring has five or six ring atoms. Examples of heteroaryl include pyridyl, pyrimidinyl, pyrrolyl, furyl, thienyl, imidazolyl, thiazolyl, thiadiazolyl, triazolyl, tetrazolyl, oxadiazolyl, oxazolyl, imidazolidinyl, pyrazolyl, isoxazolyl, benzothiadiazolyl, indolyl, indolinyl, benzodioxolyl, benzodioxanyl, benzothiophenyl, benzofuranyl, benzimidazolyl, benzisoxazolyl, benzothiazolyl, quinolinyl, benzotriazolyl, benzoxazolyl, purinyl, furopyridine and thienopyridine.

The term "amine" unless specifically stated otherwise includes primary, secondary and tertiary amines.

The term "halogen" or "halo" is intended to include fluorine, chlorine, bromine and iodine.

The term "optionally substituted" is intended to include both substituted and unsubstituted. Thus, for example, optionally substituted aryl could represent a pentafluorophenyl or a phenyl ring. Further, optionally substituted multiple moieties such as, for example, alkylaryl are intended to mean that the aryl and the aryl groups are optionally substituted. If only one of the multiple moieties is optionally substituted then it will be specifically recited such as "an alkylaryl, the aryl optionally substituted with halogen or hydroxyl."

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Compounds described herein contain one or more double bonds and may thus give rise to cis/trans isomers as well as other conformational isomers. The present invention includes all such possible isomers as well as mixtures of such isomers.

Compounds described herein can contain one or more asymmetric centers and may thus give rise to diastereomers and optical isomers. The present invention includes all such possible diastereomers as well as their racemic mixtures, their substantially purse resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

The compounds of the present invention may have chiral centers other than those centers whose stereochemistry is depicted in formula I, and therefore may occur as racemates, racemic mixtures and as individual enantiomers or diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The term "TNF mediated disease or disease state" refers to disease states in which TNF plays a role, either by production or increased activity levels of TNF itself, or by causing another cytokine to be released, such as but not limited to IL-1 or IL-6. A disease state in which IL-1, for instance is a major component, and whose production or action, is exacerbated or secreted in response to TNF, would therefore be considered a disease state mediated by TNF.

The term "cytokine" as used herein means any secreted polypeptide that affects the functions of cells and is a molecule which modulates interactions between cells in the immune, inflammatory or hematopoietic response. A cytokine includes, but is not limited to, monokines and lymphokines regardless of which cells produce them. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor-beta (TNF-β).

By the term "cytokine interfering or cytokine suppresive amount" is meant an effective amount of a compound of formula I which will cause a decrease in the in vivo activity or level of the cytokine to normal or sub-normal levels, when given to the patient for the prophylaxis or therapeutic treatment of a disease state which is exacerbated by, or caused by, excessive or unregulated cytokine production or activity.

The compounds of formula I can be used in the prophylactic or therapeutic treatment of disease states in mammals which are exacerbated or caused by excessive or unregulated cytokines, e.g., IL-1, IL-6, IL-8 or TNF.

Because the compounds of formula I inhibit cytokines, the compounds are useful for treating diseases in which cytokine presence or activity is implicated, such as rheumatoid arthritis, rheumatoid spondylitis, osteoarthritis, gouty arthritis and other arthritic conditions.

The compounds of formula I are useful to treat disease states mediated by excessive or unregulated TNF production or activity. Such diseases include, but are not limited to sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, such as osteoporosis, reperfusion injury, graft v. host rejection, allograft rejection, fever, myalgia due to infection, cachexia secondary to infection or malignancy, cachexia secondary to acquired immune deficiency syndrome (AIDS), AIDS, ARC (AIDs related complex), keloid formation, scar tissue formation, Crohn's disease, ulcerative colitis, pyresis, AIDS and other viral infections, such as cytomegalovirus (CMV), influenza virus, and the herpes family of viruses such as Herpes Zoster or Simplex I and II.

The compounds of formula I are also useful topically in the treatment of inflammation such as in the treatment of rheumatoid arthritis, rheumatoid spondylitis, osteoarthritis, gouty arthritis and other arthritic conditions; inflamed joints, eczema, psoriasis or other inflammatory skin conditions such as sunburn; inflammatory eye conditions including conjunctivitis; pyresis, pain and other conditions associated with inflammation.

The compounds of formula I are also useful in treating diseases characterized by excessive IL-8 activity. These disease states include psoriasis, inflammatory bowel disease, asthma, cardiac and renal reperfusion injury, adult respiratory distress syndrome, thrombosis and glomerulonephritis.

The invention thus includes a method of treating psoriasis, inflammatory bowel disease, asthma, cardiac and renal reperfusion injury, adult respiratory distress syndrome, thrombosis and glomerulonephritis, in a mammal in need of such treatment, which comprises administering to said mammal a compound of formula I in an amount which is effective for treating said disease or condition.

When administered to a patient for the treatment of a disease in which a cytokine or cytokines are implicated, the dosage used can be varied within wide limits, depending upon the type of disease, the age and general condition of the patient, the particular compound administered, the presence or level of toxicity or adverse effects experienced with the drug and other factors. A representative example of a suitable dosage range is from as low as about 0.01 mg/kg to as high as about 100 mg/kg. However, the dosage administered is generally left to the discretion of the physician.

The methods of treatment can be carried out by delivering the compound of formula I parenterally. The term 'parenteral' as used herein includes intravenous, intramuscular, or intraperitoneal administration. The subcutaneous and intramuscular forms of parenteral administration are generally preferred. The instant invention can also be carried out by delivering the compound of formula I through subcutaneous, intranasal, intrarectal, transdermal or intravaginal routes.

The compounds of formula I may also be administered by inhalation. By 'inhalation' is meant intranasal and oral inhalation administration. Appropriate dosage forms for such administration, such as an aerosol formulation or a metered dose inhaler, may be prepared by convention techniques.

The invention also relates to a pharmaceutical composition comprising a compound of formula I and a pharmaceutically acceptable carrier. The compounds of formula I may also be included in pharmaceutical compositions in combination with a second therapeutically active compound.

The pharmaceutical carrier employed may be, for example, either a solid, liquid or gas. Examples of solid carriers include lactose, terra alba, sucrose, talc, gelatin, agar, pectin, acacia, magnesium stearate, stearic acid and the like. Examples of liquid carriers are syrup, peanut oil, olive oil, water and the like. Examples of gaseous carriers include carbon dioxide and nitrogen.

Similarly, the carrier or diluent may include time delay material well known in the art, such as glyceryl monostearate or glyceryl distearate, alone or with a wax.

A wide variety of pharmaceutical dosage forms can be employed. If a solid dosage is used for oral administration, the preparation can be in the form of a tablet, hard gelatin capsule, troche or lozenge. The amount of solid carrier will vary widely, but generally the amount of the present compound will be from about 0.025 mg to about 1 g with the amount of solid carrier making up the difference to the desired tablet, hard gelatin capsule, troche or lozenge size. Thus, the tablet, hard gelatin capsule, troche or lozenge conveniently would have, for example, 0.025 mg, 0.05 mg, 0.1 mg, 0.5 mg, 1 mg, 5 mg, 10 mg, 25 mg, 100 mg, 250 mg, 500 mg, or 1000 mg of the present compound. The tablet, hard gelatin capsule, troche or lozenge is given conveniently once, twice or three times daily.

When a liquid dosage form is desired for oral administration, the preparation is typically in the form of a syrup, emulsion, soft gelatin capsule, suspension or solution. When a parenteral dosage form is to be employed, the drug may be in solid or liquid form, and may be formulated for administration directly or may be suitable for reconstitution.

Topical dosage forms are also included. Examples of topical dosage forms are solids, liquids and semi-solids. Solids would include dusting powders, poultices and the like. Liquids include solutions, suspensions and emulsions. Semi-solids include creams, ointments, gels and the like.

The amount of a compound of formula I used topically will, of course, vary with the compound chosen, the nature and severity of the condition, and can be varied in accordance with the discretion of the physician. A representative, topical, dose of a compound of formula I is from as low as about 0.01 mg to as high as about 2.0 g, administered one to four, preferably one to two times daily.

The active ingredient may comprise, for topical administration, conveniently from about 0.001% to about 10% w/w.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container aseptically. Examples of bactericidal and fungicidal agents suitable for inclusion in the drops are phenyl-mercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous liquid, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surfactant such as sorbitan esters or polyoxyethylene derivatives thereof. Suspending agents such as natural gums, cellulose derivatives or inorganic materials such as silicas, and other ingredients such as lanolin may also be included.

The ability of compounds of the present invention to inhibit the synthesis or the activity of cytokines can be demonstrated using the following in vitro assays.

Biological Assays

Lipopolysaccharide Mediated Production of Cytokines

Human peripheral blood mononuclear cells (PBMC) are isolated from fresh human blood according to the procedure of Chin and Kostura, *J. Immunol.*, 151:5574–5585(1993). Whole blood is collected by sterile venipuncture into 60 mL syringes coated with 1.0 mL of sodium-heparin (Upjohn, 1000 µ/mL) and diluted 1:1 in Hanks Balanced Salt Solution (Gibco). The erythrocytes are separated from the PBMC's by centrifugation on a Ficoll-Hypaque lymphocyte separation media. The PBMC's are washed three times in Hanks Balanced Salt Solution and then resuspended to a final concentration of $2 \times 10^6$ cell/mL in RPMI containing 10% fresh autologous human serum, penicillin streptomycin (10/mL) and 0.05% DMSO. Lipopolysaccharide (Salmonella type Re545; Sigma Chemicals) is added to the cells to a final concentration of 100 ng/mL. An aliquot (0.1 mL) of the cells is quickly dispensed into each well of a 96 well plate containing 0.1 mL of the test compound, at the appropriate dilution, and are incubated for 24 hours at 37° C. in 5% $CO_2$. At the end of the culture period, cell culture supernatants are assayed for IL-1β, TNF-α, IL-6 and PGE2 production using specific ELISA.

IL-1 Mediated Cytokine Production

Human peripheral blood mononuclear cells are isolated from fresh human blood according to the procedure of Chin and Kostura, *J. Immunol.*, 151:5574–5585(1993). Whole blood is collected by sterile venipuncture into 60 mL syringes coated with 1.0 mL of sodium-heparin (Upjohn, 1000 µ/mL) and diluted 1:1 in Hanks Balanced Salt Solution (Gibco). The erythrocytes are separated from the PBMC's by centrifugation on a Ficoll-Hypaque lymphocyte separation media. The PBMC's are washed three times in Hanks Balanced Salt Solution and then resuspended to a final concentration of $2 \times 10^6$ cell/mL in RPMI containing 10% fresh autologous human serum, penicillin streptomycin (10 µ/mL) and 0.05% DMSO. Endotoxin free recombinant human IL-1b is then added to a final concentration of 50 pMolar. An aliquot (0.1 mL) of the cells is quickly dispensed into each well of a 96 well plate containing 0.1 mL of the compound at the appropriate dilution and incubated for 24 hours at 37° C. in 5% $CO_2$. At the end of the culture period, cell culture supernatants are assayed for TNF-a, IL-6 and PGE2 synthesis using specific ELISA.

Determination of IL-1β, TNF-α, IL-6 and Prostanoid Production from LPS or IL-1 Stimulated PBMC's

IL-1β ELISA

Human IL-1β can be detected in cell-culture supernatants or whole blood with the following specific trapping ELISA. 96 well plastic plates (Immulon 4; Dynatech) are coated for 12 hours at 4° C. with 1 mg/mL protein-A affinity chromatography purified mouse anti-human IL-1β monoclonal antibody (purchased as an ascites preparation from LAO Enterprise, Gaithersburg Md.) diluted in Dulbecco's phosphate-buffered saline (—$MgCl_2$, —$CaCl_2$). The plates are washed with PBS-Tween (Kirkegaard and Perry) then blocked with 1% BSA diluent and blocking solution (Kirkegaard and Perry) for 60 minutes at room temperature followed by washing with PBS Tween. IL-1β standards are prepared from purified recombinant IL-1β produced from *E. coli*. The highest concentration begins at 10 ng/mL followed by 11 two-fold serial dilutions. For detection of IL-1β from cell culture supernatants or blood plasma, 10–25 mL of supernatant is added to each test well with 75–90 mL of PBS Tween. Samples are incubated at room temperature for 2 hours then washed 6 times with PBS Tween on an automated plate washer (Dennly). Rabbit anti-human IL-1β polyclonal antisera diluted 1:500 in PBS-Tween is added to the plate and incubated for 1 hour at room temperature followed by six washes with PBS-Tween. Detection of bound rabbit anti-IL-1β IgG is accomplished with Fab' fragments of Goat anti-rabbit IgG-horseradish peroxidase conjugate (Accurate Scientific) diluted 1:10,000 in PBS-Tween. Peroxidase activity was determined using TMB peroxidase substrate kit (Kirkegaard and Perry) with quantitation of color intensity on a 96-well plate Molecular Devices spectrophotometer set to determine absorbance at 450 nM. Samples are evaluated using a standard curve of absorbance versus concentration. Four-parameter logistics analysis generally is used to fit data and obtain concentrations of unknown compounds.

TNF-α ELISA

Immulon 4 (Dynatech) 96-well plastic plates are coated with a 0.5 mg/mL solution of mouse anti-human TNF-a monoclonal antibody. The secondary antibody is a 1:2500 dilution of a rabbit anti-human TNF-α polyclonal serum purchased from Genzyme. All other operations are identical to those described above for IL-1β. The standards are prepared in PBS-Tween+10% FBS or HS. Eleven two-fold dilutions are made beginning at 20 ng/mL TNF-α.

IL-6 ELISA

Levels of secreted human IL-6 are also determined by specific trapping ELISA as described previously in Chin and Kostura, *J. Immunol.*, 151:5574–5585(1993). (Dynatech) ELISA plates are coated with mouse anti-human IL-6 monoclonal antibody diluted to 0.5 mg/mL in PBS. The secondary antibody, a rabbit anti-human IL-6 polyclonal antiserum, is diluted 1:5000 with PBS-Tween. All other operations are identical to those described above for IL-1β. The standards are prepared in PBS-Tween+10% FBS or HS. Eleven two-fold dilutions are made beginning at 50 ng/mL IL-6.

$PGE_2$ Production

Prostaglandin E2 is detected in cell culture supernatants from LPS or IL-1 stimulated PBMC's using a commercially available enzyme immunoassay. The assay purchased from the Cayman Chemical (Catalogue No. 514010) and is run exactly according to the manufacturers instructions.

Interleukin-8 (IL-8)

The present compounds can also be assayed for IL-8 inhibitory activity as discussed below. Primary human umbilical cord endothelial cells (HUVEC) (Cell Systems, Kirkland, Wash.) are maintained in culture medium supplemented with 15% fetal bovine serum and 1% CS-HBGF consisting of aFGF and heparin. The cells are then diluted 20-fold before being plated (250 µL) into gelatin coated 96-well plates. Prior to use, culture medium is replaced with fresh medium (200 µL). Buffer or test compound (25 µL, at appropriate concentrations) is then added to each well in quadruplicate wells and the plates incubated for 6 h in a humidified incubator at 37° C. in an atmosphere of 5% $CO_2$. At the end of the incubation period, supernatant is removed and assayed for IL-8 concentration using an IL-8 ELISA kit obtained from R&D Systems (Minneapolis, Minn.). All data is presented as mean value (ng/mL) of multiple samples based on the standard curve. $IC_{50}$ values where appropriate are generated by non-linear regression analysis.

The compounds of this invention, in the above functional activity assay, suppress TNF-α in monocytes with $IC_{50}$ of less than 5 µM. Advantageously, the $IC_{50}$ should be less than 3 µM. Even more advantaeously, the $IC_{50}$ should be less than 1 µM. Still more advantageously, the $IC_{50}$ should be less than 0.1 µM.

Further, in the other assays, the results from the present compounds are better than 5 µM. Advantageously, the $IC_{50}$ results should be less than 3 µM. Even more advantaeously, the $IC_{50}$ should be less than 1 µM. Still more advantageously, the $IC_{50}$ should be less than 0.1 µM.

The ability of compounds of the present invention to inhibit the activity of protozoa can be demonstrated using the following assays.

Anticoccidiosis Assay.

One-day-old White Leghorn chickens are obtained from a commercial hatchery and acclimated in a holding room. At three days of age the test animals are selected by weight, wingbanded, and randomly placed on medicated or control diets for the duration of the experiment. One or two replicates of two birds are utilized per treatment. Following 24 h premedication, in each replicate one bird is infected with *Eimeria acervulina*, the other bird is infected with *E. tenella*. Both strains of *Eimeria* are sensitive to all anticoccidial products, and have been maintained in laboratory conditions for over 25 years. The inocula consist of sporulated oocysts in tap water suspensions, administered at a dose rate of 0.25 mL per bird. The inocula levels are selected by previous dose titrations to provide a low to moderate level of infection. The *E. acervulina* portion of the experiment is terminated on Day 5, the *E. tenella* on Day 6 post infection. The measured parameters are weight gain, feed consumption and oocyst production. *E. tenella* lesion scores are also recorded for background information. Treatments which provide at least 80% reduction in oocyst production are considered active, those with 50–79% are considered partially active, and those with <50% are considered inactive. The same numerical categories in weight gain and feed consumption differentiate among treatments with good, fair or poor productivity.

PKG Catalytic Assay

Kinase activity was detected using a peptide substrate and [$^{33}$P]-ATP. An aliquot containing enzyme (1 µl) was mixed with a reaction mix (10 µl) whose composition is as follows:

25 mM HEPES pH 7.4, 10 mM MgCl$_2$, 20 mM β-glycerophosphate, 5 mM β mercaptoethanol, 10 μM cGMP, 1 mg/mL BSA, 400 μM kemptide, 2 μM [$^{33}$P]ATP (0.1 mCi/ml). The reaction was allowed to proceed for 1 hour at room temperature prior to addition of phosphoric acid to a final concentration of 2.5 mM. Labeled peptide was captured on filters using either P81 filters or on Millipore 96-well plates, MAPH-NOB (Millipore). In both cases filters were washed with 75 mM phosphoric acid, dried and [$^{33}$P]-ATP detected using scintillation counting.

Enzyme Assay and Data Analysis

The peptide substrate biotinyl-ϵ-aminocaproyl-GRTGR-RNSI-OH was synthesized in house by standard methods. PET-cGMP, 1-NH$_2$-cGMP, 8-APT-cGMP, and 8-NBD-cGMP were obtained from Biolog Life Science Institute (Bremen, FRG), while 8-Br-cGMP came from Biomol Research Laboratories and 8-pCPT-cGMP came from Calbiochem. Bovine PKG was obtained commercially; recombinant isoform Iα (Genbank Accession No. X16086) was purchased from Calbiochem, while native Iα enzyme was purchased from Promega.

The kinase assay was performed in a 50 μL reaction volume containing 25 mM HEPES (pH 7.0), 10 mM MgCl$_2$, 20 mM beta-glycerophosphate, 1 mM DTT, 0.1 mg/mL bovine serum albumin, 20 μM ATP, 20 μM peptide substrate and 2.5 μCi [gamma-$^{33}$P]ATP (Amersham). Cyclic nucleotide was serially diluted in buffer before adding 5 μL of each concentration into 40 μL of the assay mix. The reaction was initiated with 5 μL of enzyme (or buffer for the background) and incubated for 30 minutes in a heating block at 30° C. The assays were terminated by the addition of 25 μL 8M guanidine-HCl solution (Pierce) before spotting 15 μL onto a SAM$^2$ streptavidin membrane (Promega). The membrane was washed twice with 1M NaCl and twice with 1M NaCl+1% H$_3$PO$_4$ on a rotating mixer for 20 minutes. The membrane was then rinsed successively with water and ethanol and dried under a heat lamp.

The individual assays were then separated, placed in scintillation vials containing 2 mL of Ultima Gold cocktail (Packard), and counted in a Packard TriCarb 2500 liquid scintillation counter. The amount of enzyme was adjusted to give between 10,000 and 140,000 cpm when maximally activated; substrate turnover was less than 10% in all cases. The concentration of Et-PKG varied between 0.26 and 3.4 μg/mL for cGMP titrations and between 7 and 25 μg/mL for 8-NBD-cGMP titrations, depending on the activity of the enzyme form used. Assays with bovine PKG used 0.059 μg/mL recombinant or 0.034 μg/mL native enzyme with both activators. After subtracting the appropriate background for each assay point, titrations were fit to the following modified Hill equation using Kaleidagraph (Synergy Software):

$$V_A = V_0 + (V_{max} - V_0)/(1 + (K_A/[A])^h)$$

$V_A$ is the observed velocity at concentration [A] of cyclic nucleotide,
$V_0$ is the velocity in the absence of activator,
$V_{max}$ is the velocity of the maximally activated enzyme,
$K_A$ is the concentration for half maximal activation, and
h is the Hill coefficient. The activation parameters are determined from a curve fit.

cGMP-Agarose Affinity Chromatography

Purification of PKG enzyme was perfoemed as follows. Chromatography on cGMP-agarose was performed according to the manufacturers instructions (Biolog, A019). Briefly, a 0.6 mL column was equilibrated with Buffer G (50 mM HEPES pH 7.4, 10% glycerol, 10 mM sodium fluoride, 0.1 mM sodium orthovanadate, 1 mM EDTA). The sample (crude S100 extract or purified protein) was mixed with an equal volume of Buffer G and applied to the column; the column was then washed with 10 mL of the same buffer. The column was then washed with 10 mL of Buffer G containing 1 mM GMP. PKG was then eluted with 10 mL of Buffer G containing 15 mM cGMP.

In the above assays, the compounds show selectivity, with inhibition of the parasitic enzyme with negligible inhibition of the host enzyme. Thus, it is advantageous that the parasite PKG enzyme IC50 be less than 0.5 μM while the host PKG enzyme IC50 be greater than 1 μM. It is more advantageous that the host PKG IC50 be greater than 5 μM. It is also more advantageous that the parasite PKG enzyme IC50 be less than 0.1 μM. It is even more advantageous that the parasite PKG enzyme IC50 be less than 50 nM, and particularly advantageous that the parasite PKG enzyme IC50 be less than 10 nM.

Utility

The (pyrimidyl)(phenyl)substituted fused heteroaryl compounds of the present invention are useful as antiprotozoal agents. As such, they may be used in the treatment and prevention of protozoal diseases in human and animals, including poultry. Examples of protozoal diseases against which compounds of formula I may be used, and their respective causative pathogens, include: 1) amoebiasis (*Dientamoeba* sp., *Entamoeba histolytica*); 2) giardiasis (*Giardia lamblia*); 3) malaria (*Plasmodium* species including *P. vivax, P. falciparum, P. malariae* and *P. ovale*); 4) leishmaniasis (*Leishmania* species including *L. donovani, L. tropica, L. mexicana,* and *L. braziliensis*); 5) trypanosomiasis and Chagas disease (*Trypanosoma* species including *T. brucei, T. theileri, T. rhodesiense, T. gambiense, T. evansi, T. equiperdum, T. equinum, T. congolense, T. vivax* and *T. cruzi*); 6) toxoplasmosis (*Toxoplasma gondii*); 7) babesiosis (*Babesia* sp.); 8) cryptosporidiosis (*Cryptosporidium* sp.); 9) dysentery (*Balantidium coli*); 10) vaginitis (*Trichomonas* species including *T. vaginitis,* and *Tritrichomonas foetus*); 11) coccidiosis (*Eimeria* species including *E. tenella, E. necatrix, E. acervulina, E. maxima* and *E. brunetti, E. mitis, E. bovis, E. melagramatis,* and *Isospora* sp.); 12) enterohepatitis (*Histomonas gallinarum*), and 13) infections caused by *Anaplasma* sp., *Besnoitia* sp., *Leucocytozoan* sp., *Microsporidia* sp., Sarcocystis sp., *Theileria* sp., and *Pneumocystis carinii*.

Dose Range:

Compounds of formula I may be administered to a host in need of treatment in a manner similar to that used for other antiprotozoal agents; for example, they may be administered parenterally, orally, topically, or rectally. The dosage to be administered will vary according to the particular compound used, the infectious organism involved, the particular host, the severity of the disease, physical condition of the host, and the selected route of administration; the appropriate dosage can be readily determined by a person skilled in the art.

For the treatment of protozoal diseases in humans, the oral dosage may range from 1 mg/kg to 1000 mg/kg; and the parenteral dosage may range from 0.5 mg/kg to 500 mg/kg. For veterinary therapeutic use, the oral dosage may range from 1 mg/kg to 1000 mg/kg; and the parenteral dosage may range from 0.5 mg/kg to 500 mg/kg. For prophylactic use in humans, the oral dosage may range from 1 mg/kg to 1000 mg/kg; and the parenteral dosage may range from 0.5 mg/kg to 500 mg/kg.

Thus, the tablet, hard gelatin capsule, troche or lozenge conveniently would have, for example, 0.1 mg, 0.5 mg, 1 mg, 5 mg, 10 mg, 25 mg, 100 mg, 250 mg, 500 mg, or 1000 mg of the present compound. The tablet, hard gelatin capsule, troche or lozenge is given conveniently once, twice or three times daily.

For prophylactic use in animal, the oral dosage may range from 1 mg/kg to 1000 mg/kg; and the parenteral dosage may range from 0.5 mg/kg to 500 mg/kg. For use as an anticoccidial agent, particularly in poultry, the compound may be administered in the animals' feed or drinking water in accordance with common practice in the poultry industry and as described below.

The compositions of the present invention comprises a compound of formula I and an inert carrier. The compositions may be in the form of pharmaceutical compositions for human and veterinary usage, or in the form of feed composition for the control of coccidiosis in poultry.

The pharmaceutical compositions of the present invention comprise a compound of formula I as an active ingredient, and may also contain a physiologically acceptable carrier and optionally other therapeutic ingredients. The compositions include compositions suitable for oral, rectal, topical, and parenteral (including subcutaneous, intramuscular, and intravenous) administrations, although the most suitable route in any given case will depend on the particular host, and nature and severity of the conditions for which the active ingredient is being administered. The pharmaceutical compositions may be conveniently presented in unit dosage form and prepared by any of the methods well-known in the art of pharmacy.

In practical use, compounds of formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous).

In preparing the compositions for oral dosage form, any of the usual pharmaceutical media may be employed. For example, in the case of oral liquid preparations such as suspensions, elixirs and solutions, water, glycols, oils, alcohols, flavoring agents, preservatives, coloring agents and the like may be used; or in the case of oral solid preparations such as powders, capsules and tablets, carriers such as starches, sugars, microcrystalline cellulose, diluents, granulating agents, lubricants, binders, disintegrating agents, and the like may be included. Because of their ease of administration, tablets and capsules represent the most advantageous oral dosage unit form in which case solid pharmaceutical carriers are obviously employed. If desired, tablets may be coated by standard aqueous or nonaqueous techniques. In addition to the common dosage forms set out above, compounds of formula I may also be administered by controlled release means and/or delivery devices.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

Pharmaceutical compositions of the present invention suitable for parenteral administration may be prepared as solutions or suspensions of these active compounds in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Suitable topical formulations include transdermal devices, aerosols, creams, ointments, lotions, dusting powders, and the like. These formulations may be prepared via conventional methods containing the active ingredient. To illustrate, a cream or ointment is prepared by mixing sufficient quantities of hydrophilic material and water, containing from about 5–10% by weight of the compound, in sufficient quantities to produce a cream or ointment having the desired consistency.

Pharmaceutical compositions suitable for rectal administration wherein the carrier is a solid may be presented as unit dose suppositories. Suitable carriers include cocoa butter and other materials commonly used in the art, and the suppositories may be conveniently formed by admixture of the combination with the softened or melted carrier(s) followed by chilling and shaping molds.

It should be understood that in addition to the aforementioned carrier ingredients the pharmaceutical formulations described above may include, as appropriate, one or more additional carrier ingredients such as diluents, buffers, flavoring agents, binders, surface-active agents, thickeners, lubricants, preservatives (including anti-oxidants) and the like, and substances included for the purpose of rendering the formulation isotonic with the blood of the intended recipient.

For use in the management of coccidiosis in poultry, a compound of formula I may be conveniently administered as a component of a feed composition. Suitable poultry feed composition will typically contain from about 1 ppm to about 1000 ppm, or from about 0.0005% to about 0.05% percent, by weight of a compound of formula I. The optimum levels will naturally vary with the species of *Eimeria* involved, and can be readily determined by one skilled in the art.

In the preparation of poultry feed, a compound of formula I may be readily dispersed by mechanically mixing the same in finely ground form with the poultry feedstuff, or with an intermediate formulation (premix) that is subsequently blended with other components to prepare the final poultry feedstuff that is fed to the poultry. Typical components of poultry feedstuff include molasses, fermentation residues, corn meal, ground and rolled oats, wheat shorts and middlings, alfalfa, clover and meat scraps, together with mineral supplements such as bone meal, calcium carbonate and vitamins.

When the compound according to the present invention is used as an additive to the feed, it is typically incorporated into a "premix." The premix contains the active agent or agents as well as physiologically acceptable carriers and feedstuffs. The premix is relatively concentrated and is adapted to be diluted with other carriers, vitamin and mineral supplements, and feedstuffs to form the final animal feed. Premixes which are intermediate in concentration of active agent between a first premix and the final animal feed are sometimes employed in the industry and can be used in implementing the present invention. When employing the present compound as sole active agent, a premix desirably contains the agent at a concentration of from 0.1 to 50.0% by weight. Preferred premixes will generally contain the present compound at a concentration of from 0.5 to 25.0%, by weight. The identity of the other components of the premix and ultimate animal feed is not critical. In final feeds, the concentration of the active agent is not critical and will depend on various factors known to those skilled in the art. Such factors include the relative potency of the particular active agent and the severity of the coccidial challenge. In general, a final feed employing compound of the present invention as the sole anticoccidial will contain from about 0.0005 to about 0.05% by weight of said compound, preferably from about 0.0005 to about 0.005%.

Compositions containing a compound of formula I may also be prepared in powder or liquid concentrate form. In accordance with standard veterinary formulation practice, conventional water soluble excipients, such as lactose or sucrose, may be incorporated in the powders to improve their physical properties. Thus one embodiment of suitable powders of this invention comprises 50 to 100% w/w, and for example 60 to 80% w/w of the compound and 0 to 50% w/w and for example 20 to 40% w/w of conventional veterinary excipients. These powders may either be added to animal feedstuff, for example by way of an intermediate premix, or diluted in animal drinking water.

Liquid concentrates of this invention suitably contain a water-soluble compound combination and may optionally include a veterinarily acceptable water miscible solvent, for example polyethylene glycol, propylene glycol, glycerol, glycerol formal or such a solvent mixed with up to 30% v/v of ethanol. The liquid concentrates may be administered to the drinking water of animals, particularly poultry.

The present invention contemplates using a compound of formula (I) as sole anticoccidial agent as well as in combination with one or more other anticoccidial agents. Suitable anticoccidials for combination use include, but are not limited to, amprolium, ethopabate, clopidol, meticlorpindol, decoquinate, dinitolmide, halofuginone, lasalocid, maduramicin, monensin, narasin, nicarbazin, chlortetracycline, oxytetracycline, robenidine, salinomycin, semduramicin, and diclazuril. When used in combination with one or more other anticoccidial agent, the compound of formula (I) may be administered at or lower than the effective doses when used alone; for example, the final feed may contain about 0.0001 to about 0.02% by weight, or preferably from about 0.0005 to about 0.005% of a compound of formula (I). Similarly, the second anticoccidial agent in the combination may be used in an amount at or lower than those commonly used as a sole anticoccidial. The combination may be formulated into medicament for poultry use as described previously.

The formulated medicament may contain, in addition to anticoccidial agent(s) other therapeutic or nutritional agents commonly administered to poultry in the feed or drinking water; such other agents may be, for example, parasiticides, antibacterials, and growth promoters.

The compounds of the invention are prepared by the following reaction scheme(s). All substituents are as defined above unless indicated otherwise.

SCHEME 1:

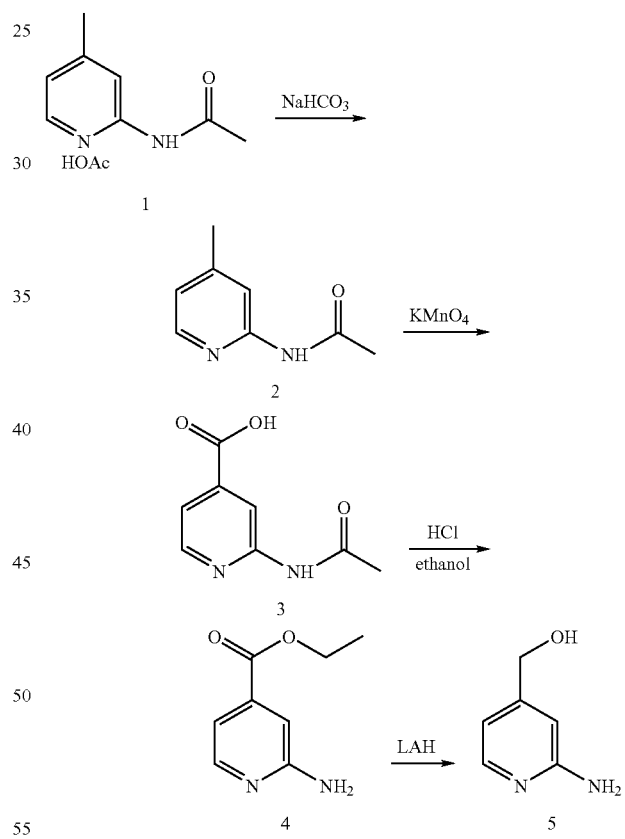

SCHEME 2:

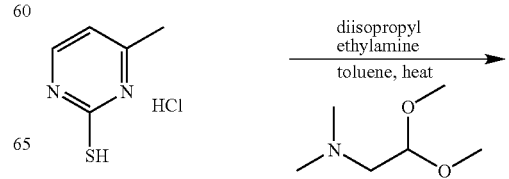

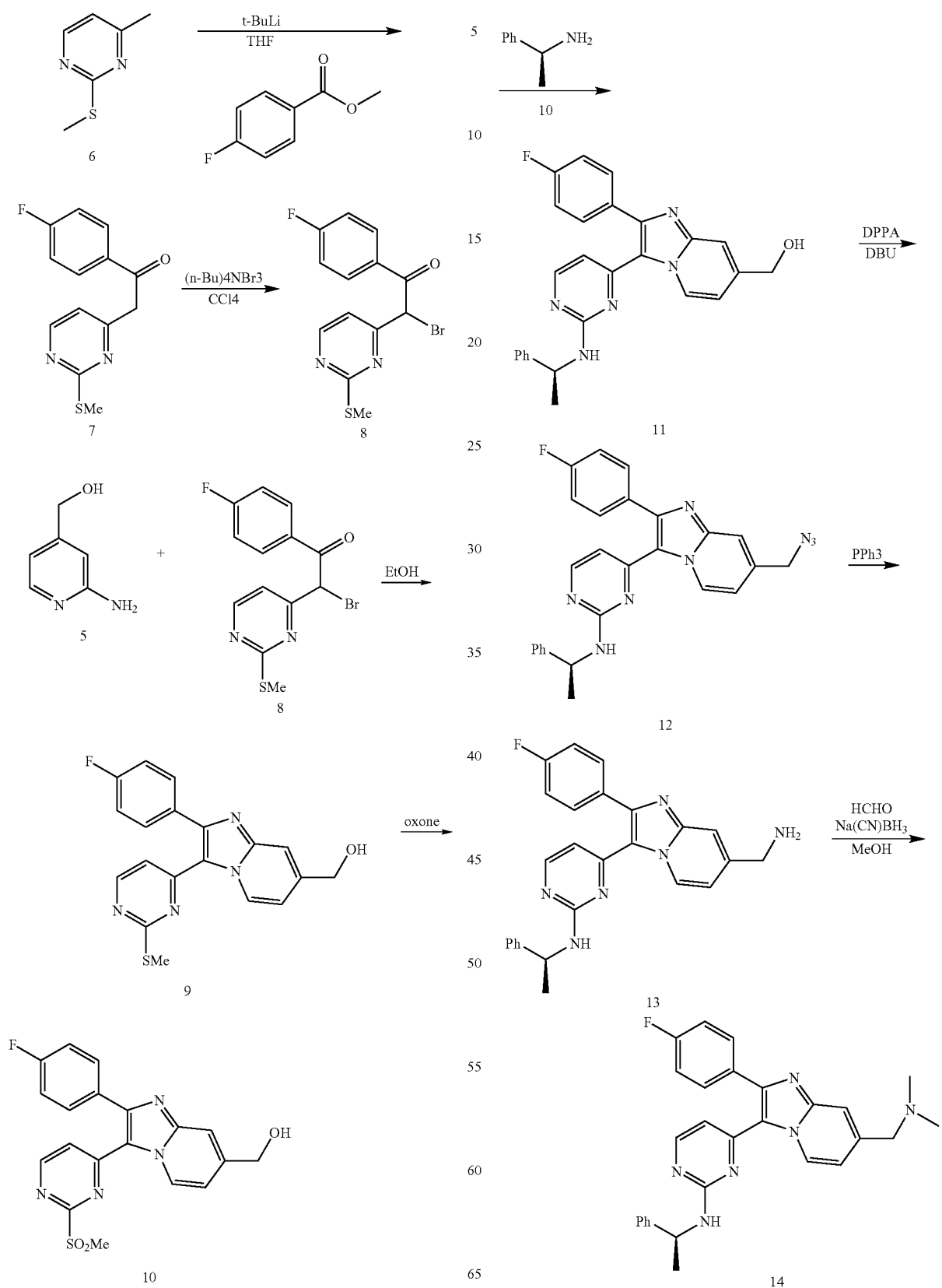

SCHEME 4:
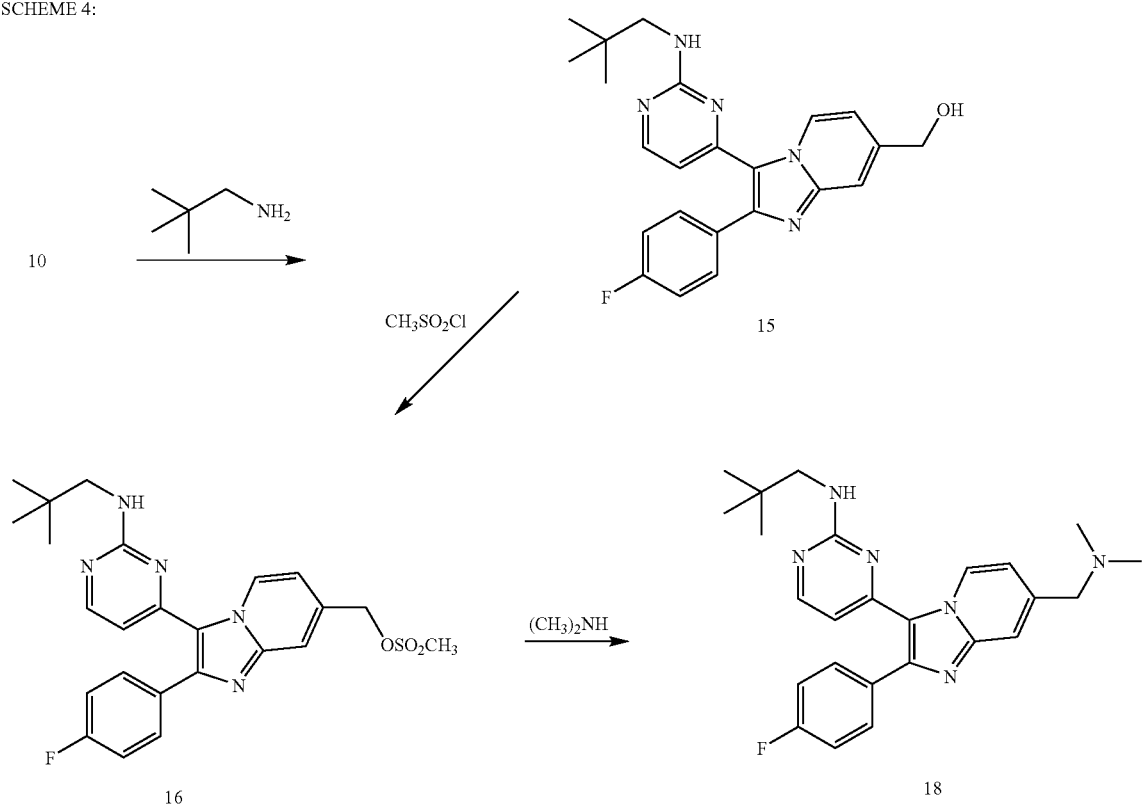
SCHEME 5:
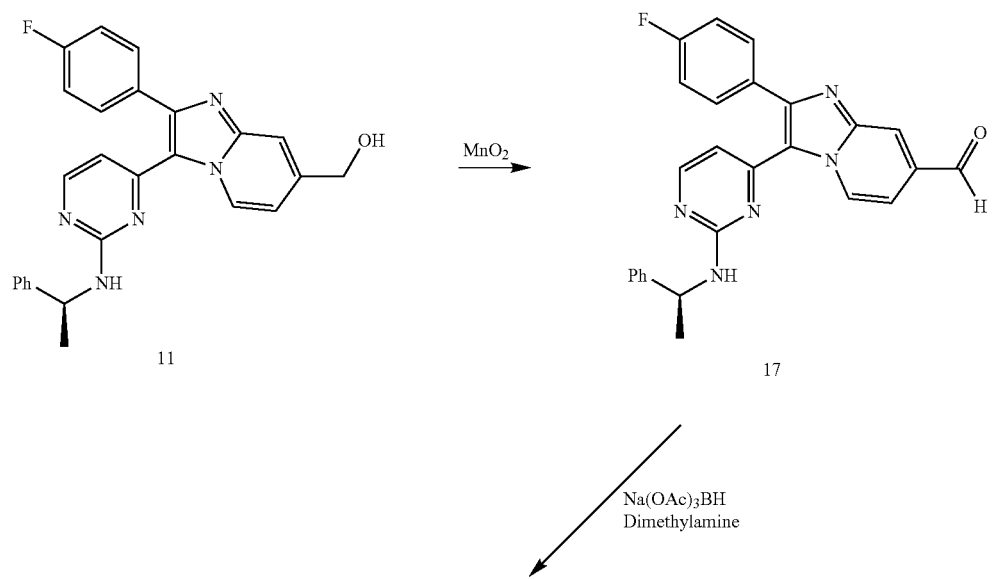

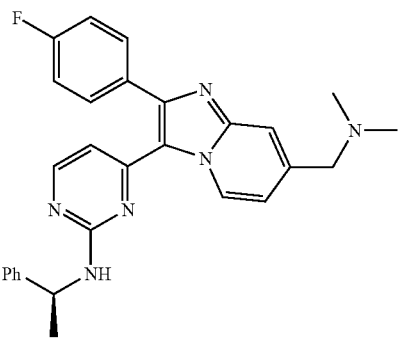
14
Pyrimidyl imidazopyrimidines of formula (IA1) and (IA2) may be prepared according to the procedure shown in Scheme 6 below.
SCHEME 6:
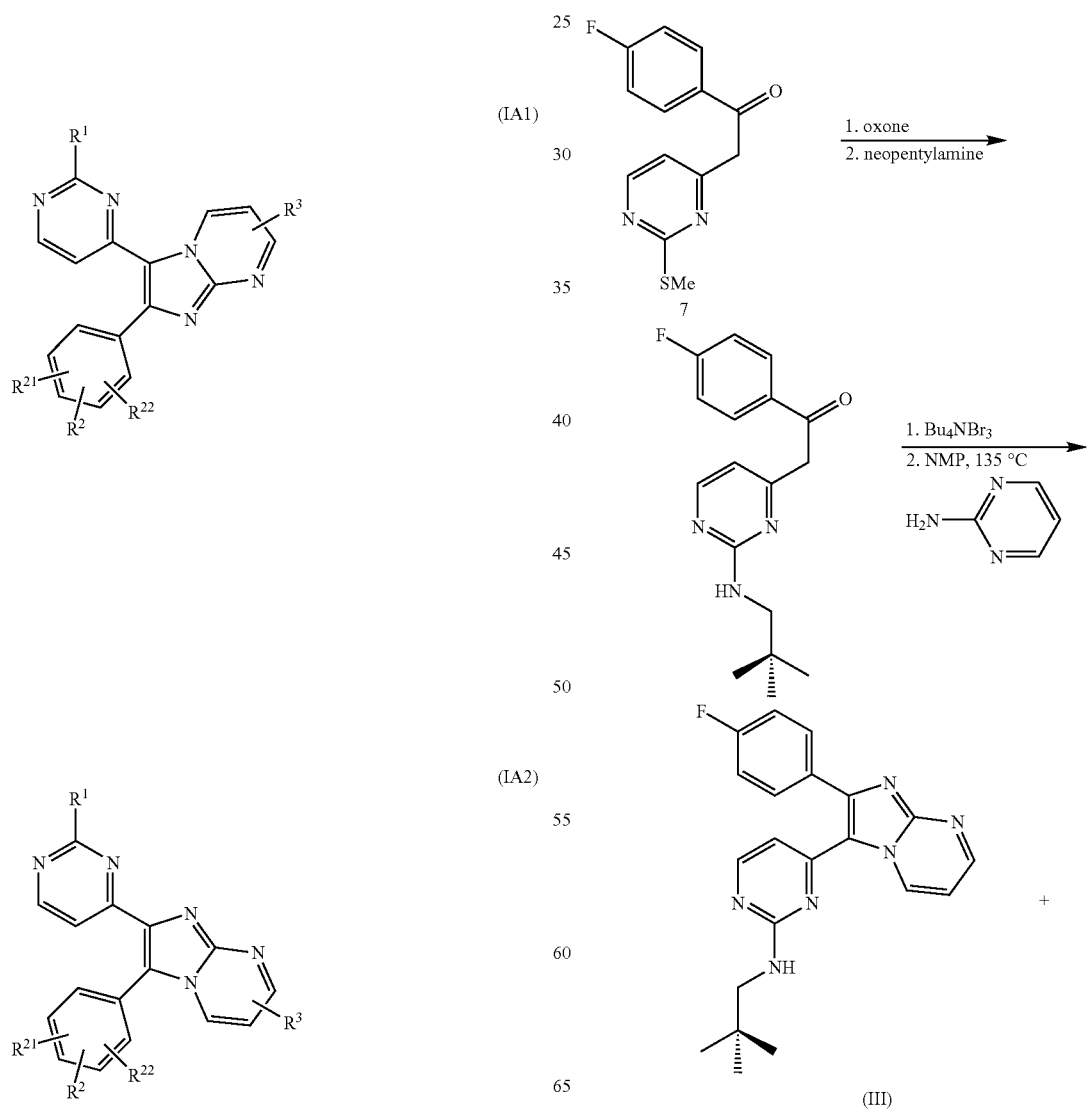

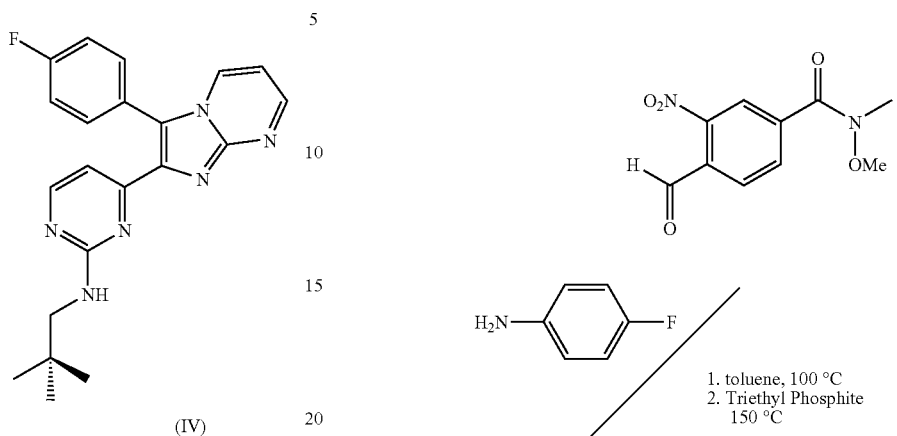
(IV)
Pyrimidyl indazoles of formula (IB) may be prepared according to the procedure shown in Scheme 7 below.
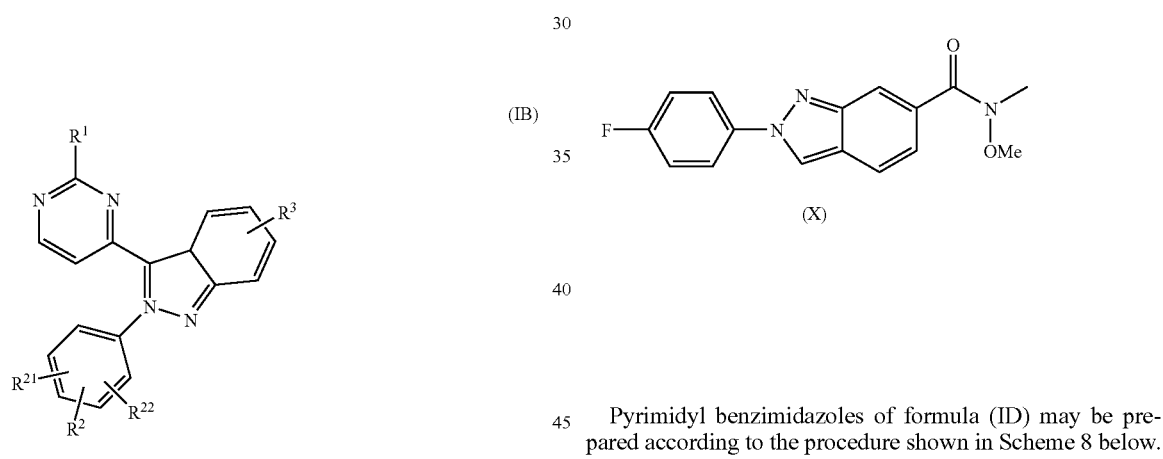
(IB)
(X)
Pyrimidyl benzimidazoles of formula (ID) may be prepared according to the procedure shown in Scheme 8 below.
SCHEME 7:
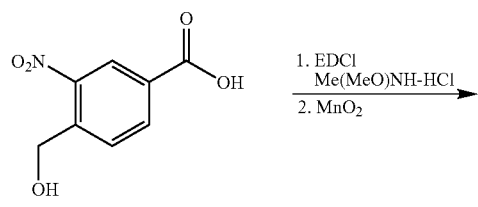
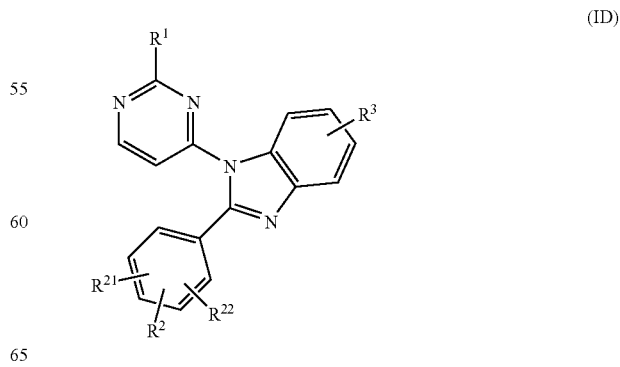
(ID)

SCHEME 8:

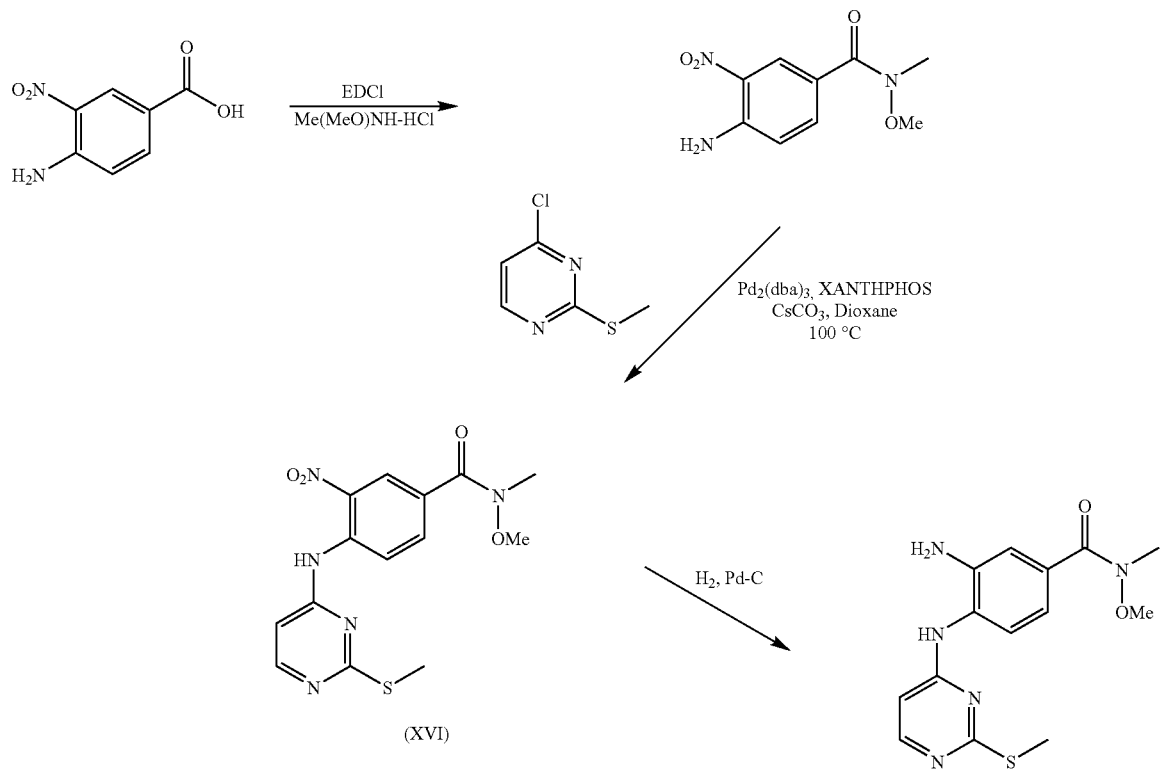

(XVI)

INTERMEDIATE COMPOUND 3

The following examples illustrate the preparation of some of the compounds of the invention and are not to be construed as limiting the invention disclosed herein.

INTERMEDIATE COMPOUND 2

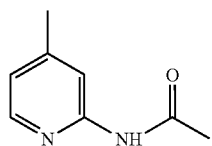

2

2-Aminopicoline (100 g, 924.7 mmol) was suspended in methylene chloride (1000 mL), cooled to 0° C. and treated dropwise with acetic anhydride (94 mL, 1000 mmol) over a period of 20 min., followed by addition of triethyl amine (101 g, 1000 mmol). The resulting homogeneous solution was warmed up to room temperature and then concentrated to dryness under reduced pressure. The resulting residue was taken up in ethyl acetate (500 mL) and water (100 mL), and the pH was then adjusted to 6.0 with 2N HCl or NaOH. The organic layer was separated, dried over anhydrous sodium sulfate, filtered, and evaporated. Recrystallization of the residue from ethyl acetate/hexane gave INTERMEDIATE COMPOUND 2 (101 g).

INTERMEDIATE COMPOUND 3

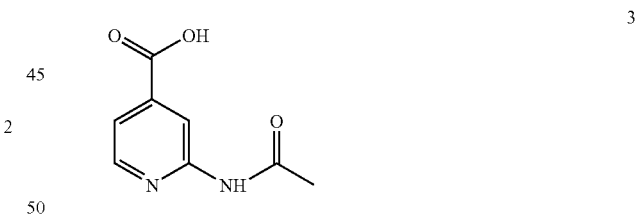

3

The amide INTERMEDIATE COMPOUND 2 (62.9 g, 419 mmol) was dissolved in water (650 mL) by warming to 60°. Potassium permanganate (30.6 g) was added and the stirred mixture was heated to 75° C. Additional $KMnO_4$ (30.6 g) was added, and the mixture was heated to reflux. After 3 h. of reflux, the mixture was cooled to 75° C. and additional $KMnO_4$ (70.2 g) was added cautiously in small portions and refluxed for 15 h. The mixture was cooled to room temperature, filtered over celite and extracted with diethyl ether. The aqueous layer was neutralized with 2N HCl to pH 7.0 and evaporated to yield 86 g of INTERMEDIATE COMPOUND 3 which was used in the preparation of INTERMEDIATE COMPOUND 4 below without further purification.

INTERMEDIATE COMPOUND 4

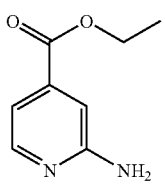

4

The acid INTERMEDIATE COMPOUND 3 (10.0 g, 55.6 mmol) was suspended in absolute ethanol (300 mL) at room temperature, HCl gas was bubbled for 10 minutes and then refluxed for 6 h. The ethanol was removed under reduced pressure, the resulting viscous liquid was neutralized with std. sodium bicarbonate and the mixture was extracted with ethyl acetate. The organic phase was dried over anhydrous sodium sulfate, filtered and evaporated to yield the ester INTERMEDIATE COMPOUND 4 (2.42 g).

INTERMEDIATE COMPOUND 5

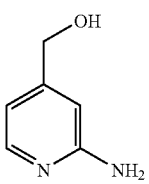

5

To a solution of the ester INTERMEDIATE COMPOUND 4 (48.2 g, 290 mmol) in anhydrous tetrahydrofuran (480 mL) at −30° C., lithium aluminum hydride (1.0M in THF, 580 mL, 580 mmol) was added dropwise. The resulting solution was warmed to 0° C. and then refluxed for 1 h. The resulting solution was cooled to room temperature, quenched with water (15.4 mL) followed by addition of NaOH (5N, 15.4 mL) and filtration. The filtrate was evaporated and triturated with diethyl ether to yield the alcohol INTERMEDIATE COMPOUND 5 (25.4 g).

Alternatively, the alcohol INTERMEDIATE COMPOUND 5 could be made from 2-chloro isonicotinic acid by the following sequence of reactions: i) reduction with diborane to alcohol, ii) conversion to tetrazolopyridine with ammonium azide and iii) reduction of the tetrazolopyridine to 2-amino pyridine with zinc in acetic acid or tin dichloride.

INTERMEDIATE COMPOUND 6

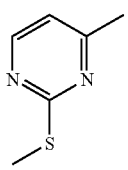

6

To 2-mercapto-4-methylpyrimidine.HCl (20 g, 123 mmol) in toluene (300 mL) at room temperature under argon, diisopropylethylamine (34.6 mL, 184.5 mmol) and N,N-dimethylformamide dimethyl acetal (40 mL, 301 mmol) were added, refluxed for 4 h., cooled to room temperature and then concentrated under reduced pressure. The resulting viscous liquid was dissolved in diethyl ether (200 mL), diluted with water (50 mL) and the pH adjusted to 5.0 with sodium bisulfate (aq. sat.). The organic phase was dried over anhydrous sodium sulfate and concentrated to yield INTERMEDIATE COMPOUND 6 (15.3 g) as a light brown oil.

INTERMEDIATE COMPOUND 7

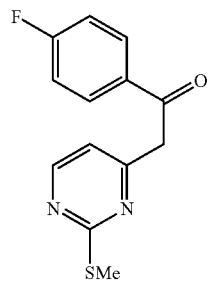

7

To a solution of INTERMEDIATE COMPOUND 6 (6.3 g, 45.0 mmol) in THF (100 mL, anhydrous) at −78° C. under argon, lithium diisopropyl amide (2.0M in THF, 27.0 mL, 54.0 mmol) was added dropwise. The resulting solution was stirred for 1 hr at −78° C. and then treated dropwise with a solution of methyl 4-fluorobenzoate (6.4 g, 49.5 mmol) in THF (20 mL, anhydrous). The mixture was stirred for 2 h. at −78°, and then warmed up to room temperature. The resulting solution was quenched with ammonium chloride (aq. sat.) and extracted with ethyl acetate. The organic phase was concentrated and purified by flash column chromatography (silica, 15:85=EtOAc:Hexane) to yield the ketone INTERMEDIATE COMPOUND 7 (7.58 g).

INTERMEDIATE COMPOUND 8

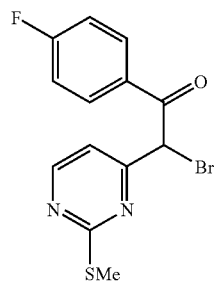

8

Tetrabutylammonium tribromide (52.3 g, 108 mmol) was added to the ketone INTERMEDIATE COMPOUND 7 (28.5 g, 108 mmol) suspended in carbon tetrachloride (325 mL) at room temperature. After 15 minutes, methylene chloride (650 mL) was added. The resulting solution was stirred for 4 hours at room temperature. The reaction mixture was quenched with sodium bicarbonate (250 mL, sat., aq.) and extracted with ethyl acetate. The organic layer was dried over anhydrous sodium sulfate, filtered and concentrated to a brown oil INTERMEDIATE COMPOUND 8 (78 g) which was used in the next step to prepare COMPOUND 9 without further purification.

INTERMEDIATE COMPOUND 9

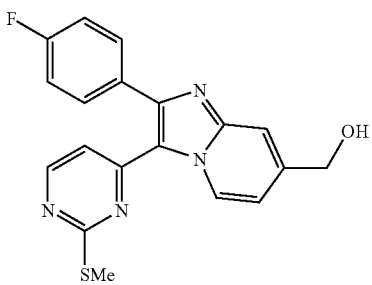

To a solution of the crude bromide INTERMEDIATE COMPOUND 8 (5.45 g, 16.0 mmol) in absolute ethanol (30 mL) at room temperature, the alcohol INTERMEDIATE COMPOUND 5 (894 mg, 7.2 mmol) dissolved in absolute ethanol (20 mL, anhydrous) was added dropwise. The combined solution was heated to 60° C. overnight under argon. The resulting solution was diluted with sodium bicarbonate (sat., aq.) and extracted with ethyl acetate. The organic phase was dried over anhydrous sodium sulfate, filtered, concentrated, and purified by flash silica column chromatography (60:40 EtOAc:Hexane first, then 100% EtOAc) to yield the imidazopyridine INTERMEDIATE COMPOUND 9 (806 mg).

INTERMEDIATE COMPOUND 10

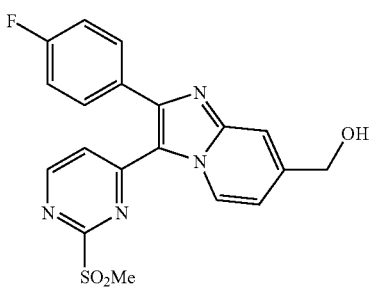

The imidazopyridine INTERMEDIATE COMPOUND 9 (322 mg, 0.88 mmol) in methanol (25 mL) at room temperature was treated dropwise with a solution of oxone (1082 mg, 1.76 mmol) in water (10 mL). The resulting mixture was stirred at room temperature overnight and extracted with ethyl acetate. The organic phase was dried over anhydrous sodium sulfate, filtered, concentrated, and purified by flash column chromatography (silica, 55:45 EtOAc:Hexane) to yield the sulfone INTERMEDIATE COMPOUND 10 (301 mg).

COMPOUND 14 (EXAMPLE A04)

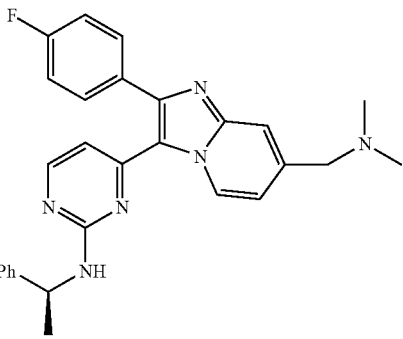

Method I:

Step A:

COMPOUND 11 (EXAMPLE A01)

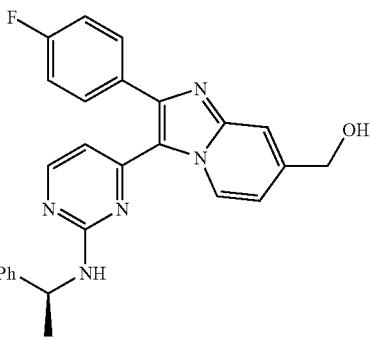

A suspension of the sulfone INTERMEDIATE COMPOUND 10 (300 mg, 0.75 mmol) in (S)-(−)-alpha-methyl-benzylamine (6.0 mL) was heated to 60° C. for 4 h while stirring under an atmosphere of argon. The resulting solution was cooled to room temperature, acidified with citric acid (5%, aq.) to pH=4.5 and extracted with ethyl acetate. The organic phase was dried over anhydrous sodium sulfate, filtered, concentrated, and purified by flash column chromatography (5:95 10% $NH_4OH$ in MeOH: $CH_2Cl_2$) to yield the amine EXAMPLE A01 (307 mg).

Step B:

COMPOUND 12 (EXAMPLE A02)

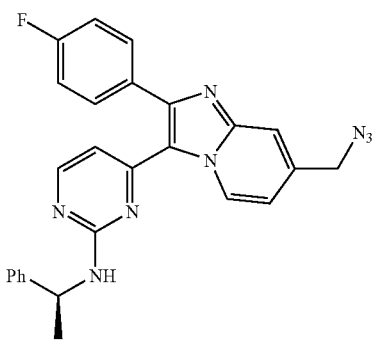

To a solution of EXAMPLE A01 (75 mg, 0.17 mmol) in toluene (3.0 mL) at 0° C. under argon, 1,8-diazabicyclo[5.4.0]undec-7-ene (0.062 mL, 0.40 mmol) and diphenylphosphoryl azide (0.088 mL, 0.40 mmol) were added. The resulting solution was stirred at room temperature overnight, concentrated, and purified by prep silica gel TLC (50:50 EtOAc:Hexane) to give the azide EXAMPLE A02 (47 mg).

Step C:

COMPOUND 13 (EXAMPLE A03)

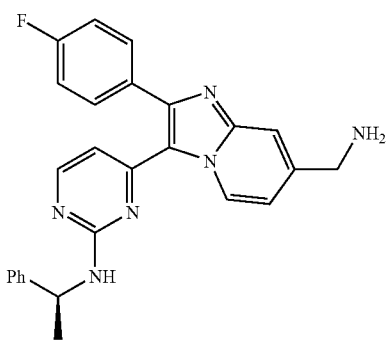

13

To a solution of the azide EXAMPLE A02 (45 mg, 0.10 mmol) in THF (1.5 mL) at room temperature, triphenylphosphine (65 mg, 0.25 mmol) and water (1.5 mL) were added and stirred at room temperature overnight. The resulting solution was diluted with water, extracted with ethyl acetate, and the organic phase was concentrated and purified by prep silica gel TLC (5:95=10% NH$_4$OH in MeOH:CH$_2$Cl$_2$) to yield the amine EXAMPLE A03 (29 mg).

Step D:

EXAMPLE A04

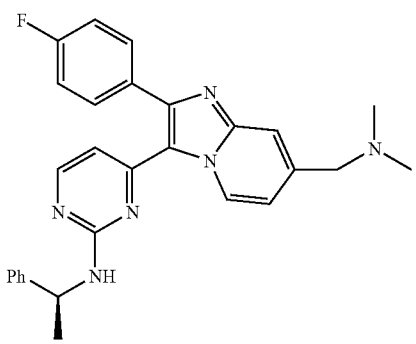

14

To the solution of the amine EXAMPLE A03 (29 mg, 0.10 mmol) in methanol (1.0 mL) at room temperature under argon, acetic acid (glacial, 0.033 mL), formaldehyde (36~38% in water, 0.033 mL) and sodium cyanoborohydride (1.0M in THF, 0.52 mL, 0.52 mmol) were added and stirred at room temperature overnight. The resulting solution was concentrated and purified by prep silica gel TLC (10:90 10% NH$_4$OH in MeOH:CH$_2$Cl$_2$) to yield the dimethyl amine EXAMPLE A04 (26 mg).

INTERMEDIATE COMPOUND 18

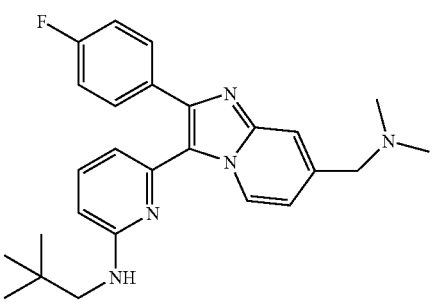

18

Method II:

INTERMEDIATE COMPOUND 15

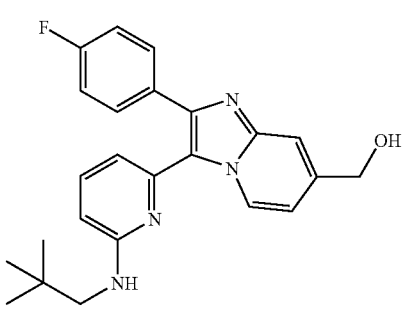

15

Step A:

Treatment of INTERMEDIATE COMPOUND 10 with neopentyl amine following the procedure described in Method I, Step A gave INTERMEDIATE COMPOUND 15.

Step B:

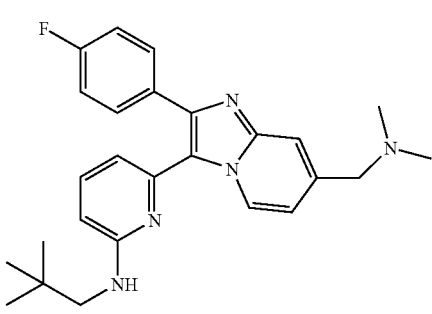

18

To a stirred solution of INTERMEDIATE COMPOUND 15 (937 mg, 2.31 mmol) in chloroform (15 mL) at −10° C., was added triethyl amine (0.64 mL, 4.62 mmol) followed by methane sulfonyl chloride (0.197 mL). After 4 h., the resulting mesylate COMPOUND 16 (EXAMPLE A06) was treated with dimethylamine (2M in THF, 5 mL) and stirring continued overnight at room temperature. The following day, the solution was evaporated and purified by flash column chromatography (silica, 0.6% NH4OH, 5.4% methanol, 94% methylene chloride) to yield INTERMEDIATE COMPOUND 18 (720 mg).

COMPOUND 20 (EXAMPLE A20)

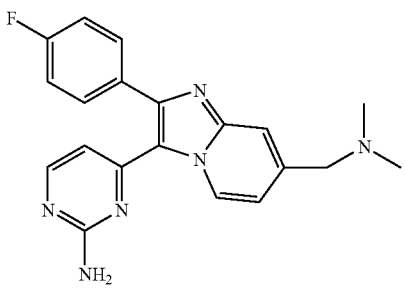

In a pressure vessel, the sulfone INTERMEDIATE COMPOUND 10 (1.1 g) was suspended in tetrahydrofuran (65 mL) saturated with ammonia at −20° C. The tube was closed, warmed up to room temperature and stirred for two days. The vessel was cooled to −35° C., opened, warmed up to room temperature, and then evaporated under reduced pressure. The resulting residue was purified by flash column chromatography (silica, 9% methanol with 1% ammonium hydroxide, 90% methylene chloride) to yield the amine COMPOUND 19 (EXAMPLE A09) (895 mg). Treatment of EXAMPLE A09 (729 mg, 2.17 mmol) in methylene chloride (10 mL) sequentially with triethylamine (0.453, 3.26 mmol), methane sulfonyl chloride (0.185 mL, 2.39 mmol) followed by the treatment of the mesylate with a solution of 2M dimethylamine in tetrahydrofuran as shown in Method II, Step B gave EXAMPLE A20 (215 mg).

Method III

COMPOUND 17 (EXAMPLE A07)

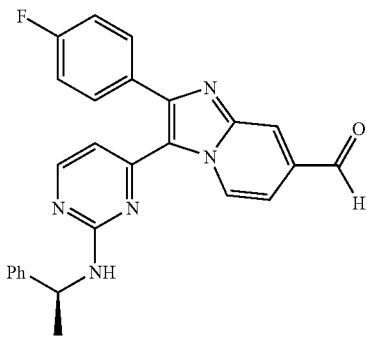

Step A:

To a solution of EXAMPLE A01 (150 mg, 0.34 mmol) in methylene chloride (15 mL), manganese dioxide (300 mg) was added and stirred for 6 h. Filtration over celite and purification by prep TLC (silica, 0.5% NH4OH, 4.5% methanol, 95% methylene chloride) gave the aldehyde COMPOUND 17 (EXAMPLE A07) (122 mg).

Step B:

COMPOUND 14 (EXAMPLE A04)

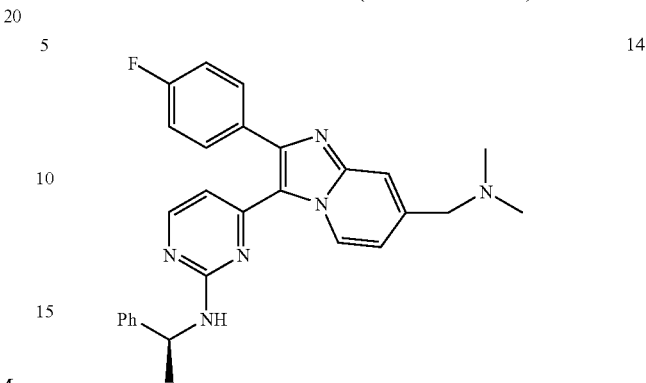

To the aldehyde EXAMPLE A07 (30 mg, 0.074 mmol) in methylene chloride (1 mL) was added dimethyl amine (2M in THF, 0.056 mL, 0.117 mmol), diisopropylethylamine (0.042 mL, 0.222 mmol), sodium tiracetoxyborohydride (31.1 mg, 0.148 mmol) and stirred for 4 h. The resulting solution was concentrated and purified by prep silica gel TLC (10:90 10% NH$_4$OH in MeOH:CH$_2$Cl$_2$) to yield the dimethyl amine EXAMPLE A04 (21 mg).

COMPOUND II (EXAMPLE 1)

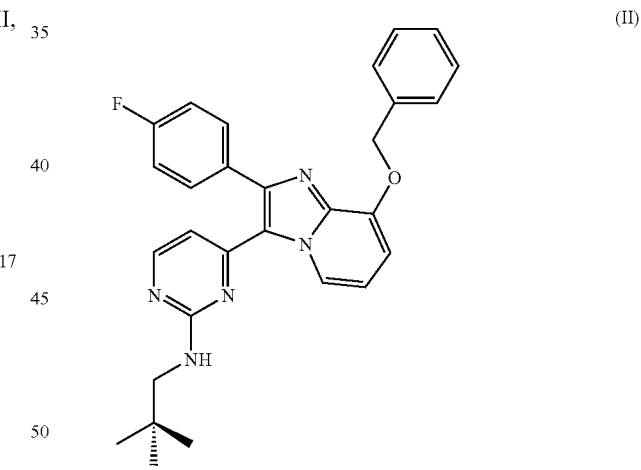

EXAMPLE 1 was prepared under conditions similar to those used for the synthesis of INTERMEDIATE COMPOUND 15. The key cyclization reaction to form the imidazopyridine ring required the use of 2-amino-3-benzyloxypyridine (2.5 equivalents) in isopropanol solvent at a concentration of 0.2 M, heated at 90° C. for 14 h. The resulting mixture was then concentrated in vacuo and purified by flash chromatography (Biotage 40S, SiO$_2$, 20% EtOAc-hexane) to provide the imidazopyridine cyclization product. This intermediate was elaborated into EXAMPLE 1 using methodology displayed in Schemes 2–4 and was characterized by $^1$H NMR, HPLC and mass spectrometry (m/z: 482 (M$^+$+1)).

EXAMPLES 2–32

The following imidazopyridines were prepared under conditions similar to those displayed in Schemes 1–5. The 2,4-difluorophenyl moiety of EXAMPLES 2–6 was introduced by the substitution of methyl 2,4-difluorobenzoate in place of methyl 4-fluorobenzoate shown in Scheme 2. The 3-trifluoromethylphenyl moiety of EXAMPLES 7–11 was introduced by the substitution of methyl 3-trifluoromethylbenzoate in place of methyl 4-fluorobenzoate also shown in Scheme 2. The 2-chloro-4-fluorophenyl moiety of EXAMPLES 12–14 was introduced by the substitution of methyl 2-chloro-4-fluorobenzoate in place of methyl 4-fluorobenzoate also shown in Scheme 2. The 2-chlorophenyl moiety of EXAMPLES 15 and 16 was introduced by the substitution of methyl 2-chlorobenzoate in place of methyl 4-fluorobenzoate also shown in Scheme 2. The 4-chlorophenyl moiety of EXAMPLES 17 and 18 was introduced by the substitution of methyl 4-chlorobenzoate in place of methyl 4-fluorobenzoate also shown in Scheme 2. The 3,4-dichlorophenyl moiety of EXAMPLES 19 and 20 was introduced by the substitution of methyl 3,4-dichlorobenzoate in place of methyl 4-fluorobenzoate also shown in Scheme 2. The 2,3-dichlorophenyl moiety of EXAMPLES 21 and 22 was introduced by the substitution of methyl 2,3-dichlorobenzoate in place of methyl 4-fluorobenzoate also shown in Scheme 2. The cyclohexylamine moiety in EXAMPLES 4 and 5 was introduced by the substitution of cyclohexylamine in place of neopentylamine shown in Scheme 4. The alcohol moiety in EXAMPLE 27 was introduced by the substitution of (R)-phenyl glycinol in place of neopentylamine shown in Scheme 4. The hydroxyneopentylamine moiety in EXAMPLES 24–26 was introduced by the substitution of 2,2-dimethyl-3-amino-1-propanol in place of neopentylamine displayed in Scheme 4. The sulfonamide moiety in EXAMPLE 26 was introduced by treatment with methanesulfonyl chloride prior to the introduction of the 2,2-dimethyl-3-amino-1-propanol subunit. The methyl ether moiety in EXAMPLE 6 was introduced by the substitution of sodium methoxide in place of dimethylamine displayed in Scheme 4. The methyl sulfone moiety in EXAMPLE 31 was introduced by the substitution of sodium thiolate in place of dimethylamine shown in Scheme 4 to provide the methyl sulfide intermediate. This methyl sulfide was then oxidized with 2 equivalents of oxone in 2:1 methanol-water to provide the methyl sulfone in EXAMPLE 31. The dimethyl phosphonate moiety in EXAMPLE 30 was introduced by the substitution of sodium dimethylphosphite in place of dimethylamine described in Scheme 4. The morpholine moiety in EXAMPLE 7 was introduced by the substitution of morpholine in place of dimethylamine described in Scheme 4. The dimethylaminoethylpiperazine moiety in EXAMPLE 8 was introduced by the substitution of N-(2-(N,N-dimethylamino)ethyl)piperazine in place of dimethylamine described in Scheme 4. The isopropylpiperazine moiety in EXAMPLE 9 was introduced by the substitution of N-isopropylpiperazine in place of dimethylamine shown in Scheme 4. The methylamine moiety in EXAMPLE 25 was introduced by the substitution of methylamine (2M in THF) in place of dimethylamine shown in Scheme 4. The sulfonamide moiety in Example 28 was introduced by treating the analogous neopentyl derivative of EXAMPLE A03 (COMPOUND 13) shown in Scheme 3 with methanesulfonyl chloride. This sulfonamide was subsequently alkylated with KHMDS/MeI to provide EXAMPLE 29. EXAMPLES 23–24 (Z=H) and 27 (Z=CH$_3$) were prepared under conditions where 2-amino-4-hydroxymethylpyridine (INTERMEDIATE COMPOUND 5) was substituted by 2-aminopyridine and 2-amino-4-picoline respectively as shown in Scheme 2. The aldehydes in EXAMPLES 13 and 32 were prepared by oxidation of EXAMPLE 12 and INTERMEDIATE COMPOUND 15 (Scheme 4) using Dess-Martin periodinane in methylene chloride in a similar manner shown in Scheme 5. With the exception of EXAMPLE 16 ($^1$H NMR only), the following imidazopyridines were characterized by $^1$H NMR, HPLC and mass spectrometry.

The following TABLE 1 of EXAMPLES 2–32 refer to the following general chemical structure:

TABLE 1

| EX. | Ar Group | R Group | Z Group | MS (m/z) |
|---|---|---|---|---|
| 2 | 2,4-Difluorophenyl | NHCH$_2$C(CH$_3$)$_3$ | CH$_2$OH | 424 (M$^+$+1) |
| 3 | 2,4-Difluorophenyl | NHCH$_2$C(CH$_3$)$_3$ | CH$_2$N(CH$_3$)$_2$ | 451 (M$^+$+1) |
| 4 | 2,4-Difluorophenyl | 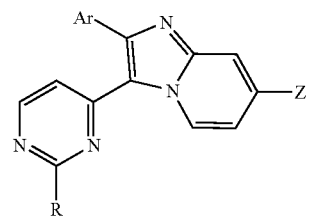 | CH$_2$OH | 436 (M$^+$+1) |

TABLE 1-continued

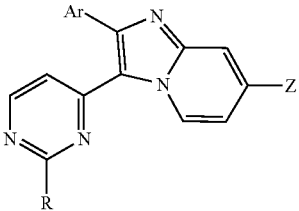

| EX. | Ar Group | R Group | Z Group | MS (m/z) |
|---|---|---|---|---|
| 5 | 2,4-Difluorophenyl | 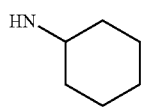 | CH$_2$N(CH$_3$)$_2$ | 463 (M$^+$+1) |
| 6 | 2,4-Difluorophenyl | NHCH$_2$C(CH$_3$)$_3$ | CH$_2$OCH$_3$ | 438 (M$^+$+1) |
| 7 | 3-Trifluoromethylphenyl | NHCH$_2$C(CH$_3$)$_3$ | 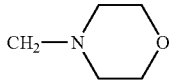 | 525 (M$^+$+1) |
| 8 | 3-Trifluoromethylphenyl | NHCH$_2$C(CH$_3$)$_3$ | 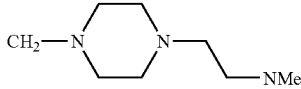 | 595 (M$^+$+1) |
| 9 | 3-Trifluoromethylphenyl | NHCH$_2$C(CH$_3$)$_3$ | 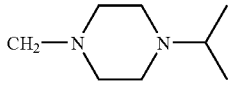 | 566 (M$^+$+1) |
| 10 | 3-Trifluoromethylphenyl | NHCH$_2$C(CH$_3$)$_3$ | CH$_2$OH | 458 (M$^+$+1) |
| 11 | 3-Trifluoromethylphenyl | NHCH$_2$C(CH$_3$)$_3$ | CH$_2$N(CH$_3$)$_2$ | 483 (M$^+$+1) |
| 12 | 2-Chloro-4-fluorophenyl | NHCH$_2$C(CH$_3$)$_3$ | CH$_2$OH | 442 (M$^+$+1) |
| 13 | 2-Chloro-4-fluorophenyl | NHCH$_2$C(CH$_3$)$_3$ | CHO | 438 (M$^+$+1) |
| 14 | 2-Chloro-4-fluorophenyl | NHCH$_2$C(CH$_3$)$_3$ | CH$_2$N(CH$_3$)$_2$ | 467 (M$^+$+1) |
| 15 | 2-Chlorophenyl | NHCH$_2$C(CH$_3$)$_3$ | CH$_2$OH | 422 (M$^+$+1) |
| 16 | 2-Chlorophenyl | NHCH$_2$C(CH$_3$)$_3$ | CH$_2$N(CH$_3$)$_2$ | — |
| 17 | 4-Chlorophenyl | NHCH$_2$C(CH$_3$)$_3$ | CH$_2$OH | 422 (M$^+$+1) |
| 18 | 4-Chlorophenyl | NHCH$_2$C(CH$_3$)$_3$ | CH$_2$N(CH$_3$)$_2$ | 450 (M$^+$+1) |
| 19 | 3,4-Dichlorophenyl | NHCH$_2$C(CH$_3$)$_3$ | CH$_2$OH | 457 (M$^+$+1) |
| 20 | 3,4-Dichlorophenyl | NHCH$_2$C(CH$_3$)$_3$ | CH$_2$N(CH$_3$)$_2$ | 484 (M$^+$+1) |
| 21 | 2,3-Dichlorophenyl | NHCH$_2$C(CH$_3$)$_3$ | CH$_2$OH | 457 (M$^+$+1) |
| 22 | 2,3-Dichlorophenyl | NHCH$_2$C(CH$_3$)$_3$ | CH$_2$N(CH$_3$)$_2$ | 484 (M$^+$+1) |
| 23 | 4-Fluorophenyl | NHCH$_2$C(CH$_3$)$_3$ | H | 376 (M$^+$+1) |
| 24 | 4-Fluorophenyl | NHCH$_2$C(CH$_3$)$_2$CH$_2$OH | H | 392 (M$^+$+1) |
| 25 | 4-Fluorophenyl | NHCH$_2$C(CH$_3$)$_2$CH$_2$OH | CH$_2$NHCH$_3$ | 435 (M$^+$+1) |
| 26 | 4-Fluorophenyl | NHCH$_2$C(CH$_3$)$_2$CH$_2$OH | CH$_2$N(CH$_3$)SO$_2$CH$_3$ | 513 (M$^+$+1) |
| 27 | 4-Fluorophenyl | 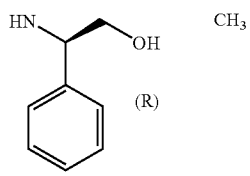 | CH$_3$ | 440 (M$^+$+1) |
| 28 | 4-Fluorophenyl | NHCH$_2$C(CH$_3$)$_3$ | CH$_2$NHSO$_2$CH$_3$ | 483 (M$^+$+1) |
| 29 | 4-Fluorophenyl | NHCH$_2$C(CH$_3$)$_3$ | CH$_2$N(CH$_3$)SO$_2$CH$_3$ | 497 (M$^+$+1) |
| 30 | 4-Fluorophenyl | NHCH$_2$C(CH$_3$)$_3$ | CH$_2$PO(OMe)$_2$ | 498 (M$^+$+1) |
| 31 | 4-Fluorophenyl | NHCH$_2$C(CH$_3$)$_3$ | CH$_2$SO$_2$CH$_3$ | 468 (M$^+$+1) |
| 32 | 4-Fluorophenyl | NHCH$_2$C(CH$_3$)$_3$ | CHO | 404 (M$^+$+1) |

EXAMPLE 33A (COMPOUND III) AND EXAMPLE 33B (COMPOUND IV)

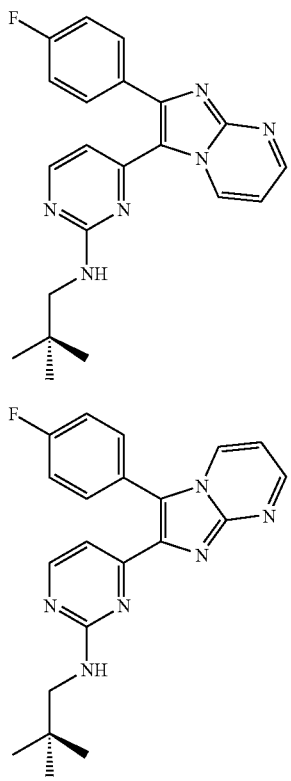

(III)

(IV)

Compounds (III) and (IV) were prepared from INTERMEDIATE COMPOUND 7 as shown in Schemes 2 and 6. Thus, the methylsulfide INTERMEDIATE COMPOUND 7 (8 g, 30.7 mmol) was diluted into 2:1 MeOH—H$_2$O (700 mL), oxone (38 g, 61.4 mmol) added, and the suspension stirred at 23° C. for 15 h. The resulting reaction mixture was concentrated in vacuo, and the residue purified by flash column chromatography (Biotage 40M, SiO$_2$, 50% EtOAc-hexane) to provide the sulfone intermediate (6.8 g). This material (6.8 g, 23.2 mmol) was diluted into dichloroethane (100 mL) and neopentylamine (6.1 g, 69.5 mmol) added.

The resulting reaction mixture was heated at 50° C. for 15 h., cooled, partitioned between aqueous sodium bicarbonate and methylene chloride, the organic phase dried with anhydrous sodium sulfate, and concentrated in vacuo. The residue was purified by flash column chromatography (Biotage 40M, SiO$_2$, 15% EtOAc-hexane) to provide the aminopyrimidine intermediate (2 g). This material (1.9 g, 6.45 mmol) was diluted into 2:1 methylene chloride-CCl$_4$ (60 mL) and treated with tetrabutylammonium tribromide (3.4 g, 7.1 mmol) added. The reaction mixture was maintained at 23° C. for 30 min., partitioned between aqueous sodium bicarbonate and methylene chloride, the organic phase dried with anhydrous sodium sulfate, and concentrated in vacuo.

The resulting residue was purified by flash column chromatography (Biotage 40M, SiO$_2$, 5–20% EtOAc-hexane) to provide the bromide intermediate (2.2 g). This material (200 mg, 0.53 mmol) was diluted into NMP (0.53 mL) and treated with 2-aminopyrimidine (505 mg, 5.3 mmol). The resulting reaction mixture was maintained at 135° C. for 4 h., cooled, and purified by flash column chromatography (Biotage 40M, SiO$_2$, 20% EtOAc-hexane) to provide a mixture of two regioisomeric products. This mixture was separated by preparative thin layer chromatography (3×1500 u, SiO$_2$, 2% methanol-chloroform) to provide (III) and (IV) which were each characterized by $^1$H NMR, HPLC and mass spectrometry (m/z: 377 (M$^+$+1)) for (III) and (m/z: 377 (M$^+$+1)) for (IV).

EXAMPLE 34 (COMPOUND V)

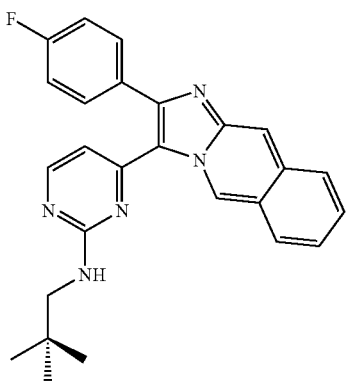

(V)

Compound (V) was prepared under conditions similar to those used for the synthesis of INTERMEDIATE COMPOUND 15. The key cyclization reaction to form the imidazoisoquinoline ring required the use of isoquinolin-3-amine (2.5 equivalents) in isopropanol solvent at a concentration of 0.2M, heated at 90° C. for 14 h. The mixture was then concentrated in vacuo and purified by flash chromatography (Biotage 40S, SiO$_2$, 20% EtOAc-hexane) to provide the imidazoisoquinoline cyclization product. This intermediate was elaborated into (V) using methodology displayed in Schemes 2–4 and was characterized by $^1$H NMR, HPLC and mass spectrometry (m/z: 426 (M$^+$+1)).

EXAMPLE 35 (COMPOUND VI)

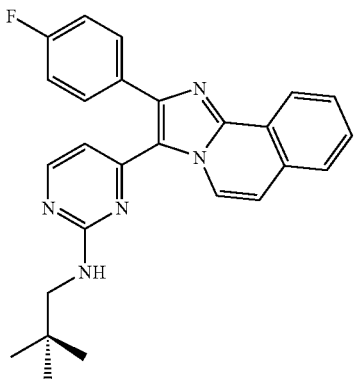

(VI)

EXAMPLE 35 was prepared under conditions similar to those used for the synthesis of INTERMEDIATE COMPOUND 15. The key cyclization reaction to form the imidazoisoquinoline ring required the use of 1-aminoisoquinoline (2.5 equivalents) in isopropanol solvent at a concentration of 0.2M, heated at 90° C. for 14 h. The resulting mixture was then concentrated in vacuo and purified by flash chromatography (Biotage 40S, SiO$_2$, 20% EtOAc-hexane) to provide the imidazoisoquinoline cyclization product. This intermediate was elaborated into (VI) using methodology displayed in Schemes 2–4 and was characterized by $^1$H NMR, HPLC and mass spectrometry (m/z: 426 (M$^+$+1)).

EXAMPLE 36 (COMPOUND VII)

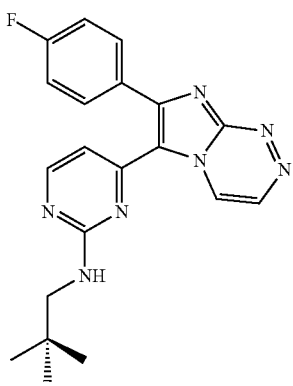

(VII)

Compound (VII) was prepared under conditions similar to those used for the synthesis of INTERMEDIATE COMPOUND 15. The key cyclization reaction to form the imidazotriazine ring required the use of 3-amino-1,2,4-triazine (2.5 equivalents) in isopropanol solvent at a concentration of 0.2M, heated at 90° C. for 14 h. The resulting mixture was then concentrated in vacuo and purified by flash chromatography (Biotage 40M, SiO$_2$, 70% EtOAc-hexane) to provide the imidazotriazine cyclization product in 38% yield. This intermediate was elaborated into (VII) using methodology displayed in Schemes 2–4 and was characterized by $^1$H NMR, HPLC and mass spectrometry (m/z: 378 (M$^+$+1)).

EXAMPLE 37 (COMPOUND VIII)

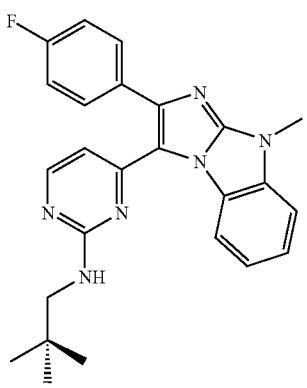

(VIII)

Compound (VIII) was prepared under conditions similar to those used for the synthesis of INTERMEDIATE COMPOUND 15. The key cyclization reaction to form the imidazobenzimidazole ring required the use of 2-amino-1-methylbenzimidazole (2.5 equivalents) in isopropanol solvent at a concentration of 0.2M, heated at 90° C. for 14 h. The resulting mixture was then concentrated in vacuo and purified by flash chromatography (Biotage 40M, SiO$_2$, 70% EtOAc-hexane) to provide the intermediate hydrated pre-cyclization product. This intermediate was dehydrated with Burgess Reagent (5 equivalents) in dioxane at 90° C. for 12 h to form the imidazobenzimidazole cyclization product (30% yield) which was elaborated into (VIII) using methodology displayed in Schemes 2–4 and was characterized by $^1$H NMR, HPLC and mass spectrometry (m/z: 429 (M$^+$+1)).

EXAMPLE 38 (COMPOUND IX)

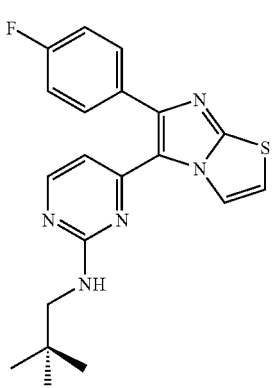

(IX)

Compound (IX) was prepared under conditions similar to those used for the synthesis of INTERMEDIATE COMPOUND 15. The key cyclization reaction to form the imidazothiazole ring required the use of 2-aminothiazole (3 equivalents) in isopropanol solvent at a concentration of 0.2M, heated at 90° C. for 14 h. The mixture was then concentrated in vacuo and purified by flash chromatography (Biotage 40M, SiO$_2$, 25% EtOAc-hexane) to provide the imidazotriazine cyclization product in 41% yield. This intermediate was elaborated into (IX) using methodology displayed in Schemes 2–4 and was characterized by $^1$H NMR, HPLC and mass spectrometry (m/z: 382 (M$^+$+1)).

EXAMPLES 39–64

The following imidazothiazoles were prepared under conditions similar to those described in EXAMPLE 38 for the synthesis of (IX). The 2,4-difluorophenyl moiety of EXAMPLE 39 was introduced by the substitution of methyl 2,4-difluorobenzoate in place of methyl 4-fluorobenzoate shown in Scheme 2. The 3-trifluoromethylphenyl moiety of EXAMPLES 40–42 was introduced by the substitution of methyl 3-trifluoromethylbenzoate in place of methyl 4-fluorobenzoate shown in Scheme 2. The R-Groups in EXAMPLES 41–64 were introduced by the substitution of the respective amines in place of neopentylamine shown in Scheme 4. The following imidazothiazoles were characterized by $^1$H NMR, HPLC and mass spectrometry.

The following TABLE 2 of EXAMPLES 39–64 refer to the following general chemical structure:

TABLE 2

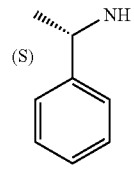

| EX. | Ar Group | R Group | MS (m/z) |
| --- | --- | --- | --- |
| 39 | 2,4-Difluorophenyl | NHCH$_2$C(CH$_3$)$_3$ | 400 (M$^+$+1) |
| 40 | 3-Trifluoromethylphenyl | NHCH$_2$C(CH$_3$)$_3$ | 432 (M$^+$+1) |
| 41 | 3-Trifluoromethylphenyl | 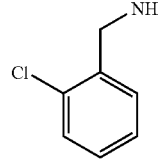 | 466 (M$^+$+1) |
| 42 | 3-Trifluoromethylphenyl | NH(CH$_2$)$_3$OCH$_3$ | 434 (M$^+$+1) |
| 43 | 4-Fluorophenyl | 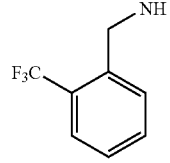 | 436 (M$^+$+1) |
| 44 | 4-Fluorophenyl | 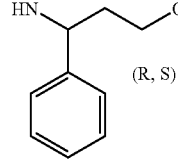 | 470 (M$^+$+1) |
| 45 | 4-Fluorophenyl | 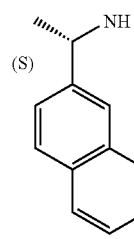 | 446 (M$^+$+1) |
| 46 | 4-Fluorophenyl | NHCH$_2$C(CH$_3$)$_2$CH$_2$OH | 398 (M$^+$+1) |
| 47 | 4-Fluorophenyl | 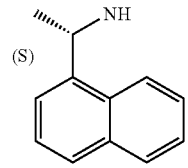 | 466 (M$^+$+1) |

TABLE 2-continued

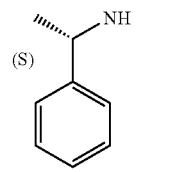

| EX. | Ar Group | R Group | MS (m/z) |
| --- | --- | --- | --- |
| 48 | 4-Fluorophenyl | 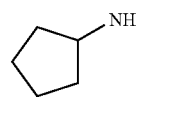 | 466 (M$^+$+1) |
| 49 | 4-Fluorophenyl | 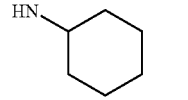 | 416 (M$^+$+1) |
| 50 | 4-Fluorophenyl | NH(CH$_2$)$_3$OCH$_3$ | 384 (M$^+$+1) |
| 51 | 4-Fluorophenyl |  | 380 (M$^+$+1) |
| 52 | 4-Fluorophenyl | 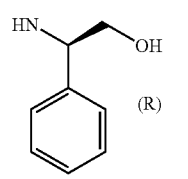 | 394 (M$^+$+1) |
| 53 | 4-Fluorophenyl | 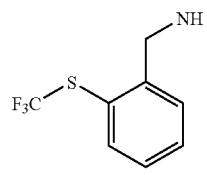 | 416 (M$^+$+1) |
| 54 | 4-Fluorophenyl |  | 432 (M$^+$+1) |
| 55 | 4-Fluorophenyl |  | 502 (M$^+$+1) |

TABLE 2-continued

| EX. | Ar Group | R Group | MS (m/z) |
|---|---|---|---|
| 56 | 4-Fluorophenyl | 4-(aminomethyl)benzoic acid | 446 (M⁺+1) |
| 57 | 4-Fluorophenyl | (S)-3-amino-3-phenylpropanoic acid | 460 (M⁺+1) |
| 58 | 4-Fluorophenyl | (R)-3-amino-3-phenylpropanoic acid | 460 (M⁺+1) |
| 59 | 4-Fluorophenyl | (S,S)-3-amino-2-hydroxy-3-phenylpropanoic acid | 476 (M⁺+1) |
| 60 | 4-Fluorophenyl | 2-(methylthio)benzylamine | 448 (M⁺+1) |
| 61 | 4-Fluorophenyl | (R)-2-methoxy-1-phenylethylamine | 446 (M⁺+1) |
| 62 | 4-Fluorophenyl | (R,S)-1,4-dioxan-2-ylmethylamine | 412 (M⁺+1) |
| 63 | 4-Fluorophenyl | (R,S)-tetrahydropyran-2-ylmethylamine | 410 (M⁺+1) |
| 64 | 4-Fluorophenyl | (3-methyloxetan-3-yl)methylamine | 396 (M⁺+1) |

INTERMEDIATE COMPOUND X

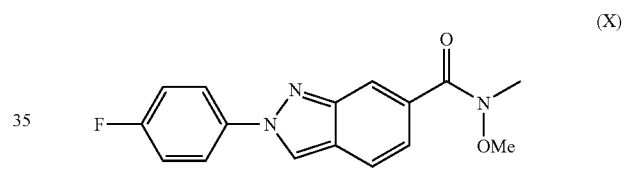

To a solution of Me(MeO)NH—HCl (4.9 g, 50.7 mmol), EDCI (2.1 g, 11.2 mmol) and DIEA (10.6 mL, 60.9 mmol) in 1:1 DMF-CH$_2$Cl$_2$ (75 mL) at 0° C. was added 3-nitro-4-(hydroxymethyl)benzoic acid (2 g, 10.1 mmol) in 1:1 DMF-CH$_2$Cl$_2$ (50 mL). The resulting reaction mixture was warmed to 23° C., maintained 15 h., partitioned between NH$_4$Cl$_{(aq)}$ and CH$_2$Cl$_2$, the organic phase washed with NaHCO$_{3(aq)}$, then dried over anhydrous sodium sulfate and concentrated in vacuo. The crude product (1.4 g, 5.8 mmol) was then diluted into acetonitrile (40 mL) and treated with MnO$_2$ (2.5 g, 29.2 mmol). The resulting reaction mixture was maintained at 23° C. for 15 h., filtered through celite and concentrated in vacuo. The crude material was purified by flash column chromatography (SiO$_2$, acetone-hexane) to provide 880 mg of product which was characterized by $^1$H NMR, HPLC and mass spectrometry (m/z: 239 (M⁺+1)).

This material (800 mg, 3.3 mmol) was then diluted into toluene (3.3 mL), 4-fluoroaniline (0.35 mL, 3.6 mmol) was added, and the resulting reaction mixture was heated at 100° C. Concentration in vacuo of the reaction mixture provided 900 mg (2.7 mmol) of crude product which was diluted into triethyl phosphite (3 mL) and heated at 150° C. for 15 h., the excess triethyl phosphite removed by distillation, and the residue purified by flash column chromatography (SiO$_2$, acetone-hexane) to provide 680 mg of (X) which was characterized by $^1$H NMR, HPLC and mass spectrometry (m/z: 300 (M⁺+1)).

INTERMEDIATE COMPOUND XI

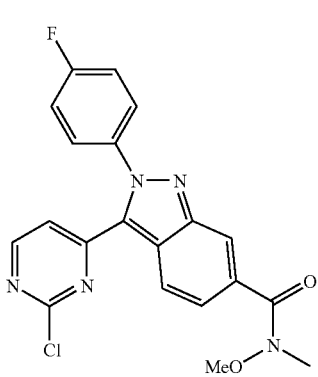

(XI)

INTERMEDIATE COMPOUND X (660 mg, 2.2 mmol) was diluted into glacial acetic acid (15 mL) and slowly treated with a solution of bromine (0.11 mL, 350 mg, 2.2 mmol) in glacial acetic acid (10 mL) over 3 h. The resulting reaction mixture was maintained at 23° C. for 15 h., poured into ice water, filtered, and the residue purified by flash column chromatography (SiO$_2$, acetone-hexane) to provide 550 mg of product which was characterized by $^1$H NMR, HPLC and mass spectrometry (m/z: 378 (M$^+$+1)).

This material (25 mg, 0.068 mmol) was then diluted into DMF (0.5 mL), 2-chloro-4-(trimethylstannyl)pyrimidine (38 mg, 0.14 mmol) was added, followed by Pd$_2$(dba)$_3$ (4 mg) and P(o-tol)$_3$ (2.5 mg), and the reaction mixture was heated at 100° C. The reaction mixture was concentrated in vacuo and the residue purified by preparative thin layer chromatography (SiO$_2$, 5% MeOH—CH$_2$Cl$_2$) to provide 20 mg of (XI) which was characterized by $^1$H NMR, HPLC and mass spectrometry (m/z: 412 (M$^+$+1)).

EXAMPLE 67 (COMPOUND XII)

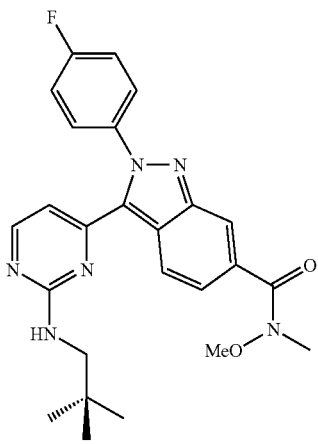

(XII)

COMPOUND XI (20 mg, 0.049 mmol) was diluted into DMSO (0.5 mL) and treated with neopentylamine (0.011 mL, 0.097 mmol). The resulting reaction mixture was maintained at 100° C. for 15 h., and the reaction mixture partitioned between water and chloroform, the organic phase dried over anhydrous sodium sulfate and concentrated in vacuo. The residue was purified by preparative thin layer chromatography (SiO$_2$, 5% MeOH—CH$_2$Cl$_2$) to provide 10 mg of COMPOUND XII which was characterized by $^1$H NMR, HPLC and mass spectrometry (m/z: 463 (M$^+$+1)).

EXAMPLE 68 (COMPOUND XIII)

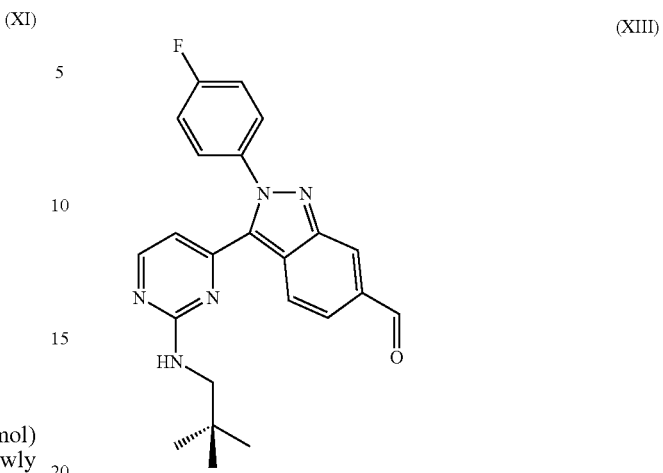

(XIII)

COMPOUND XII (45 mg, 0.097 mmol) was diluted into toluene (1.5 mL), cooled to −78° C. and treated with DIBAL-H (1 M in toluene, 0.107 mL, 0.107 mmol). The resulting reaction mixture was maintained at −78° C. for 1 h., and then quenched with aqueous potassium sodium tartrate (0.060 mL), warmed to 23° C., filtered through celite, washed with Et$_2$O, the solution then dried over anhydrous sodium sulfate and concentrated in vacuo. The residue was purified by preparative thin layer chromatography (SiO$_2$, acetone-hexane) to provide 20 mg of COMPOUND XIII which was used directly in EXAMPLE 69 below.

EXAMPLE 69 (COMPOUND XIV)

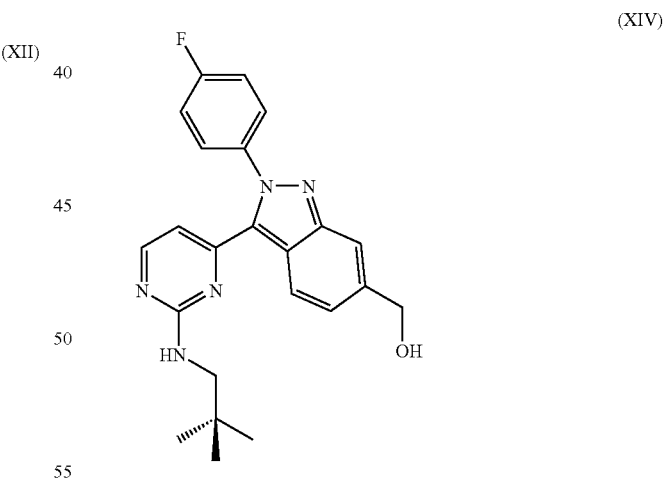

(XIV)

COMPOUND XIII (25 mg, 0.062 mmol) was diluted into THF (1 mL) and treated with NaBH$_4$ (24 mg, 0.62 mmol). The resulting reaction mixture was maintained at 23° C. for 1 h., partitioned between aqueous sodium bicarbonate and methylene chloride, dried over anhydrous sodium sulfate and concentrated in vacuo. The residue was purified by preparative thin layer chromatography (SiO$_2$, 5% MeOH-chloroform) to provide 15 mg of COMPOUND XIV which was characterized as two isomers by $^1$H NMR, HPLC and mass spectrometry (m/z: 406 (M$^+$+1)).

EXAMPLE 70 (COMPOUND XV)

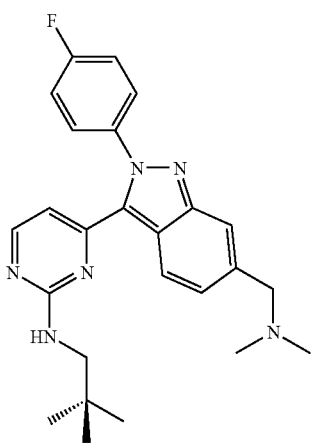

(XV)

COMPOUND XIII (20 mg, 0.050 mmol) was diluted into CH$_2$Cl$_2$ (1 mL) and treated with dimethylamine (0.037 mL, 0.074 mmol), DIEA (0.030 mL, 0.150 mmol) and Na(OAc)$_3$BH (21 mg, 0.10 mmol). The resulting reaction mixture was maintained at 23° C. for 4 h., partitioned between aqueous sodium bicarbonate and methylene chloride, dried over anhydrous sodium sulfate and concentrated in vacuo. The residue was purified by preparative thin layer chromatography (SiO$_2$, 5% MeOH-chloroform) to provide 21 mg of COMPOUND XV which was characterized by $^1$H NMR, HPLC and mass spectrometry (m/z: 433 (M$^+$+1)).

EXAMPLES 71–78

The following indazoles were prepared under conditions similar to those described in EXAMPLES 65–70 as shown in Scheme 7 and were characterized by $^1$H NMR, HPLC and mass spectrometry. The TABLE 3 below for EXAMPLES 65–70 refer to the following general chemical formula:

TABLE 3

| EX. | R Group | Z Group | MS (m/z) |
|---|---|---|---|
| 71 | NHCH$_2$C(CH$_3$)$_3$ | CON(OMe)Me | 481 (M$^+$+1) |
| 72 | NHCH$_2$C(CH$_3$)$_3$ | CHO | 422 (M$^+$+1) |
| 73 | NHCH$_2$C(CH$_3$)$_3$ | CH$_2$OH | 424 (M$^+$+1) |
| 74 | NHCH$_2$C(CH$_3$)$_3$ | CH$_2$N(CH$_3$)$_2$ | 451 (M$^+$+1) |

TABLE 3-continued

| EX. | R Group | Z Group | MS (m/z) |
|---|---|---|---|
| 75 | HN-CH(CH$_3$)-Ph (S) | CON(OMe)Me | 515 (M$^+$+1) |
| 76 | HN-CH(CH$_3$)-Ph (S) | CHO | 456 (M$^+$+1) |
| 77 | HN-CH(CH$_3$)-Ph (S) | CH$_2$OH | 458 (M$^+$+1) |
| 78 | HN-CH(CH$_3$)-Ph (S) | CH$_2$N(CH$_3$)$_2$ | 485 (M$^+$+1) |

INTERMEDIATE COMPOUND XVI

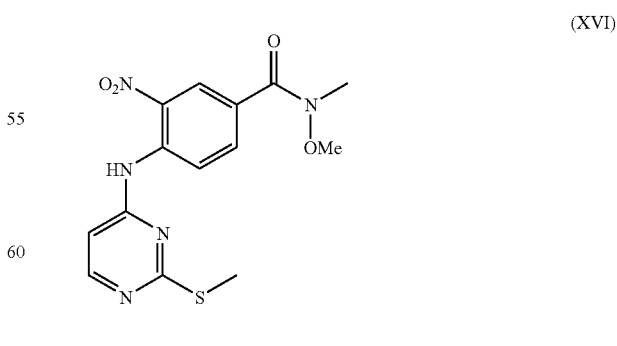

(XVI)

To a solution of Me(MeO)NH—HCl (26.8 g, 275 mmol), EDCI (10.6 g, 54.9 mmol) and DIEA (67 mL, 384.6 mmol) in 1:4 DMF-CH$_2$Cl$_2$ (75 mL) at 0° C. was added 3-nitro-4- aminobenzoic acid (10 g, 54.9 mmol) in 1:1 DMF-CH₂Cl₂ (50 mL). The resulting reaction mixture was warmed to 23° C., maintained 15 h., partitioned between NH₄Cl$_{(aq)}$ and CH₂Cl₂, the organic phase washed with NaHCO$_{3(aq)}$, then dried over anhydrous sodium sulfate and concentrated in vacuo. The crude material was purified by flash column chromatography (SiO₂, acetone-hexane) to provide 8.9 g of product which was characterized by ¹H NMR, HPLC and mass spectrometry (m/z: 226 (M⁺+1)).

This material (10 g, 44.4 mmol) was then diluted into dioxane (100 mL), 2-(methylthio)-4-chloropyrimidine (8.6 g, 53 mmol) was added, followed by cesium carbonate (25.7 g, 133 mmol), Pd₂(dba)₃ (900 mg) and XANTHPHOS (1 g), and the resulting reaction mixture was heated at 90° C. for 15 h. The reaction mixture was partitioned between water and methylene chloride, the organic phase dried over anhydrous sodium sulfate, concentrated in vacuo and the solid purified by recrystallization from acetone-hexane (primary) and then ethyl acetate-hexane (secondary) to provide 10.3 g of INTERMEDIATE COMPOUND XVI which was characterized by ¹H NMR, HPLC and mass spectrometry (m/z: 350 (M⁺+1)).

INTERMEDIATE COMPOUND XVII

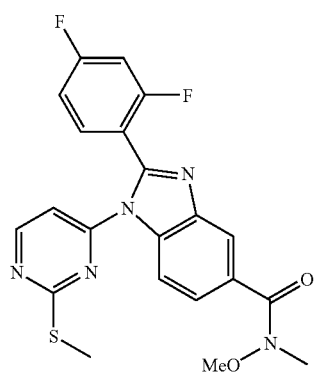

(XVII)

INTERMEDIATE COMPOUND XVI (1 g, 3.13 mmol) was diluted into CH₂Cl₂ (75 mL) and treated with Pd—C (300 mg), vacuum-purged with hydrogen gas via a balloon, and the resulting reaction mixture maintained at 23° C. for 15 h under 1 atm of hydrogen. The reaction mixture was filtered through celite, and the residue purified by flash column chromatography (SiO₂, acetone-hexane) to provide 980 mg of product. This material (2.7 g, 9.2 mmol) was diluted into nitrobenzene (15 mL), 2,4-difluorobenzaldehyde (1.4 g, 10.1 mmol) was added, and the resulting reaction mixture was heated at 175° C. for 15 h. The reaction mixture was loaded directly on silica gel and purified by flash column chromatography (SiO₂, acetone-hexane) to provide 1 g of product and 1.6 g of intermediate imine. This imine was recycled through the reaction conditions and purified to provide an additional 1.1 g of product (total 2.1 g of INTERMEDIATE COMPOUND XVII) which was characterized by ¹H NMR, HPLC and mass spectrometry (m/z: 442 (M⁺+1)).

EXAMPLE 81 (COMPOUND XVIII)

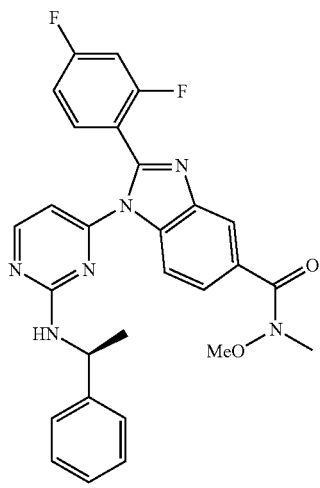

(XVIII)

INTERMEDIATE COMPOUND XVII (2 g, 4.54 mmol) was diluted into CH₂Cl₂ (15 mL) and methanol (150 mL), and treated with a solution of oxone (5.6 g, 9.1 mmol) in water (75 mL). The resulting reaction mixture was maintained at 23° C. for 15 h., and the reaction mixture was filtered to remove the precipitate, the filtrate evaporated and then partitioned between aqueous sodium bicarbonate and methylene chloride, the organic phase dried over anhydrous sodium sulfate and concentrated in vacuo. The residue was purified by flash column chromatography (SiO₂, acetone-hexane) to provide 600 mg of sulfone. This material (50 mg, 0.106 mmol) was diluted into DMSO (1 mL) and treated with (S)-(−)-alpha-methylbenzylamine (64 mg, 0.528 mmol). The resulting reaction mixture was maintained at 80° C. for 15 h., and the reaction mixture partitioned between water and methylene chloride, the organic phase dried over anhydrous sodium sulfate and concentrated in vacuo. The residue was purified by preparative thin layer chromatography (SiO₂, acetone-hexane) to provide 48 mg of COMPOUND XVIII which was characterized by ¹H NMR, HPLC and mass spectrometry (m/z: 515 M⁺+1)).

EXAMPLE 82 (COMPOUND XIX)

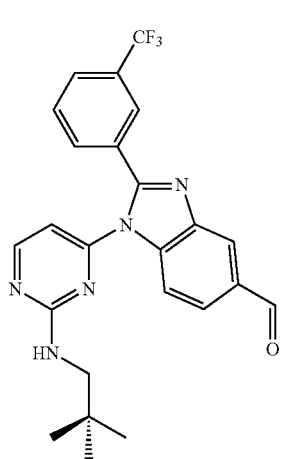

(XIX)

Representative Procedure from Scheme 8. The starting methoxy methyl amide (60 mg, 0.12 mmol) was diluted into toluene (1.5 mL), cooled to −78° C. and treated with DIBAL-H (1 M in toluene, 0.142 mL, 0.142 mmol). The resulting reaction mixture was maintained at −78° C. for 1 h., and then quenched with aqueous potassium sodium tartrate (0.022 mL), warmed to 23° C., filtered through celite, washed with Et₂O, the solution then dried over anhydrous sodium sulfate and concentrated in vacuo. The product (COMPOUND XIX) (56 mg) was used directly in EXAMPLE 83 to generate COMPOUND XX below.

EXAMPLE 83 (COMPOUND XX)

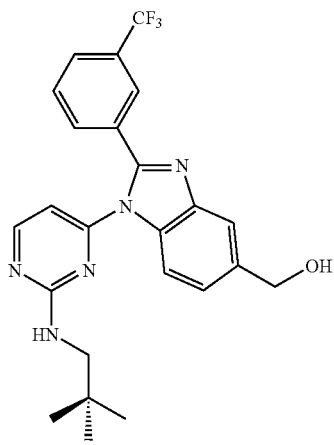

(XX)

Representative Procedure from Scheme 8. COMPOUND XIX (25 mg, 0.055 mmol) was diluted into THF (1 mL) and treated with NaBH₄ (21 mg, 0.55 mmol). The resulting reaction mixture was maintained at 23° C. for 1 h., partitioned between aqueous sodium bicarbonate and methylene chloride, dried over anhydrous sodium sulfate and concentrated in vacuo. The residue was purified by preparative thin layer chromatography (SiO₂, 5% MeOH-chloroform) to provide 15 mg of COMPOUND XX which was characterized by ¹H NMR, HPLC and mass spectrometry (m/z: 456 (M⁺+1)).

EXAMPLE 84 (COMPOUND XXI)

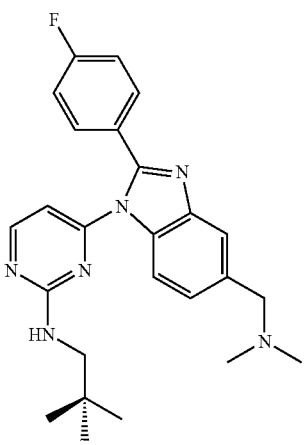

(XXI)

Representative Procedure from Scheme 8. The requisite aldehyde (30 mg, 0.074 mmol) was diluted into CH₂Cl₂ (1 mL) and treated with dimethylamine (0.056 mL, 0.117 mmol), DIEA (0.042 mL, 0.222 mmol) and Na(OAc)₃BH (31 mg, 0.15 mmol). The resulting reaction mixture was maintained at 23° C. for 4 h., partitioned between aqueous sodium bicarbonate and ethyl acetate, dried over anhydrous sodium sulfate and concentrated in vacuo. The residue was purified by preparative thin layer chromatography (SiO₂, 10% MeOH-chloroform) to provide 21 mg of COMPOUND XXI which was characterized by ¹H NMR, HPLC and mass spectrometry (m/z: 433 (M⁺+1)).

EXAMPLES 85–125

The following benzimidazoles were prepared under conditions similar to those described in EXAMPLES 79–84 as shown in Scheme 8 and were characterized by ¹H NMR, HPLC and mass spectrometry. The following TABLE 4 refers to the following chemical structure:

TABLE 4

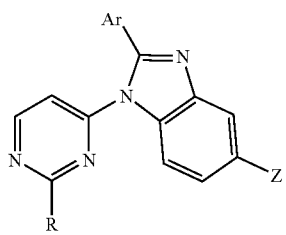

| EX | Ar Group | R Group | Z Group | Ms (m/z) |
|---|---|---|---|---|
| 85 | 4-Fluorophenyl | NHCH₂C(CH₃)₃ | CH₂OH | 406 (M⁺+1) |
| 86 | 4-Fluorophenyl | NHCH₂C(CH₃)₃ | CON(OMe)Me | 463 (M⁺+1) |
| 87 | 3-Trifluoromethylphenyl | NHCH₂C(CH₃)₃ | CON(OMe)Me | 513 (M⁺+1) |
| 88 | 3-Trifluoromethylphenyl | NHCH₂C(CH₃)₃ | CH₂N(CH₃)₂ | 483 (M⁺+1) |
| 89 | 2-Chlorophenyl | NHCH₂C(CH₃)₃ | CH₂N(CH₃)₂ | 450 (M⁺+1) |
| 90 | 2-Chloro-4-fluorophenyl | NHCH₂C(CH₃)₃ | CH₂N(CH₃)₂ | 467 (M⁺+1) |

TABLE 4-continued

| EX | Ar Group | R Group | Z Group | Ms (m/z) |
|---|---|---|---|---|
| 91 | 2,4-Difluorophenyl | $NHCH_2C(CH_3)_3$ | $CH_2N(CH_3)_2$ | 451 ($M^+$+1) |
| 92 | 2,4-Difluorophenyl | $NHCH_2C(CH_3)_3$ | $CH_2OH$ | 424 ($M^+$+1) |
| 93 | 2,4-Difluorophenyl | $NHCH_2C(CH_3)_3$ | CON(OMe)Me | 481 ($M^+$+1) |
| 94 | 2,4-Difluorophenyl | $NHCH_2C(CH_3)_3$ | 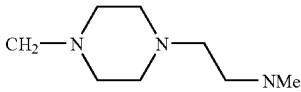 | 534 ($M^+$+1) |
| 95 | 2,4-Difluorophenyl | $NHCH_2C(CH_3)_3$ | 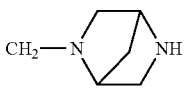 | 563 ($M^+$+1) |
| 96 | 2,4-Difluorophenyl | $NHCH_2C(CH_3)_3$ | 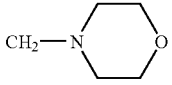 | 504 ($M^+$+1) |
| 97 | 2,4-Difluorophenyl | $NHCH_2C(CH_3)_3$ | 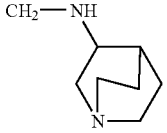 | 493 ($M^+$+1) |
| 98 | 2,4-Difluorophenyl | $NHCH_2C(CH_3)_3$ | 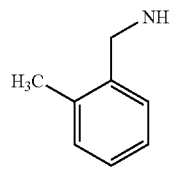 | 532 ($M^+$+1) |
| 99 | 2,4-Difluorophenyl | $NHCH_2C(CH_3)_3$ | $CH_2NH(CH_2)_2OCH_3$ | 481 ($M^+$+1) |
| 100 | 2,4-Difluorophenyl | $NHCH_2C(CH_3)_3$ | $CH_2NH(CH_2)_2N(CH_3)_2$ | 494 ($M^+$+1) |
| 101 | 2,4-Difluorophenyl | $NH(CH_2)_3OCH_3$ | CON(OMe)Me | 483 ($M^+$+1) |
| 102 | 2,4-Difluorophenyl | 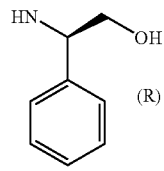 | CON(OMe)Me | 515 ($M^+$+1) |
| 103 | 2,4-Difluorophenyl | 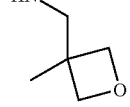 | CON(OMe)Me | 531 ($M^+$+1) |
| 104 | 2,4-Difluorophenyl | $NHCH_2C(CH_3)_2CH_2OH$ | $CH_2OH$ | 440 ($M^+$+1) |
| 105 | 2,4-Difluorophenyl |  | CON(OMe)Me | 495 ($M^+$+1) |

TABLE 4-continued

Structure: benzimidazole with Ar at 2-position, pyrimidine (with R at 2-position) attached to N1, Z substituent on benzimidazole.

| EX | Ar Group | R Group | Z Group | Ms (m/z) |
|---|---|---|---|---|
| 106 | 2,4-Difluorophenyl | HN-CH(CH₃)-phenyl (S) | CH₂N(CH₃)₂ | 485 (M⁺+1) |
| 107 | 2,4-Difluorophenyl | HN-CH(CH₃)-phenyl (S) | CH₂-morpholine | 527 (M⁺+1) |
| 108 | 2,4-Difluorophenyl | HN-CH(CH₃)-phenyl (S) | CH₂-(2,5-diazabicyclic NH) | 538 (M⁺+1) |
| 109 | 2,4-Difluorophenyl | NHCH₂C(CH₃)₂CH₂OH | CH₂N(CH₃)₂ | 467 (M⁺+1) |
| 110 | 2,4-Difluorophenyl | NH(CH₂)₃OCH₃ | CH₂-morpholine | 495 (M⁺+1) |
| 111 | 2,4-Difluorophenyl | NH(CH₂)₃OCH₃ | CH₂N(CH₃)₂ | 453 (M⁺+1) |
| 112 | 2,4-Difluorophenyl | NHCH₂C(CH₃)₂CH₂OH | CON(OMe)Me | 497 (M⁺+1) |
| 113 | 2,4-Difluorophenyl | NH(CH₂)₄OH | CH₂N(CH₃)₂ | 453 (M⁺+1) |
| 114 | 2,4-Difluorophenyl | (3-methylpyridin-4-yl)CH₂NH | CH₂N(CH₃)₂ | 485 (M⁺+1) |
| 115 | 2,4-Difluorophenyl | HN-CH(CH₂OH)-phenyl (R) | CH₂N(CH₃)₂ | 501 (M⁺+1) |
| 116 | 2,4-Difluorophenyl | HN-cyclohexyl | CH₂N(CH₃)₂ | 463 (M⁺+1) |

TABLE 4-continued

| EX | Ar Group | R Group | Z Group | Ms (m/z) |
|---|---|---|---|---|
| 117 | 2,4-Difluorophenyl | HN-CH2-(3-methyloxetan-3-yl) | CH2N(CH3)2 | 465 (M++1) |
| 118 | 2,4-Difluorophenyl | HN-CH(CH3)-(4-methoxyphenyl) (S) | CH2N(CH3)2 | 515 (M++1) |
| 119 | 2,4-Difluorophenyl | HN-CH(CH3)-(4-nitrophenyl) (S) | CH2N(CH3)2 | 530 (M++1) |
| 120 | 2,4-Difluorophenyl | HN-CH(CH3)-(3-methoxyphenyl) (S) | CH2N(CH3)2 | 499 (M+−15) |
| 121 | 2,4-Difluorophenyl | HN-CH(CH3)-(4-bromophenyl) (S) | CH2N(CH3)2 | 564 (M++1) |
| 122 | 2,4-Difluorophenyl | HN-CH(CH3)-(4-cyanophenyl) (S) | CH2N(CH3)2 | 510 (M++1) |

TABLE 4-continued

| EX | Ar Group | R Group | Z Group | Ms (m/z) |
|---|---|---|---|---|
| 123 | 2,4-Difluorophenyl | (S)-HN-CH(CH3)-[3-(methoxycarbonyl)phenyl] | CH₂N(CH₃)₂ | 543 (M⁺+1) |
| 124 | 2,4-Difluorophenyl | (S)-HN-CH(CH3)-[4-(methoxycarbonyl)phenyl] | CH₂N(CH₃)₂ | 543 (M⁺+1) |
| 125 | 2,4-Difluorophenyl | NH(CH₂)₃CO₂H | CH₂N(CH₃)₂ | 467 (M⁺+1) |

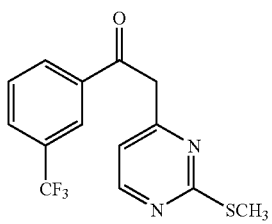

INTERMEDIATE COMPOUND 106 was prepared by the literature procedure: *J. Med. Chem.* 1999, 42 2180–2190.

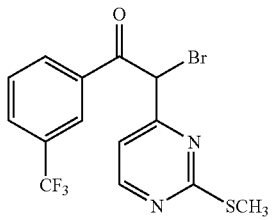

INTERMEDIATE COMPOUND 107 was prepared from INTERMEDIATE COMPOUND 106 (10 g, 32 mmol) using a procedure like that described for the preparation of INTERMEDIATE COMPOUND 8 above in Scheme 2. Yellow oil, (9.91 g).

¹H NMR (CDCl₃, 300 MHz) δ 8.61 (d, J=5.2 Hz, 1H), 8.32 (s, 1H), 8.22 (d, J=8.2 Hz, 1H), 7.88 (d, J=7.6 Hz, 1H), 7.66 (t, J=7.9 Hz, 1), 7.41 (d, J=5.2 Hz, 1H), 6.19 (s, 1H), 2.52 (s, 3H).

INTERMEDIATE COMPOUNDS 108 and 109

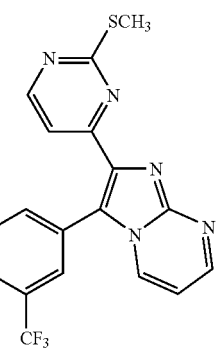

INTERMEDIATE COMPOUND 108

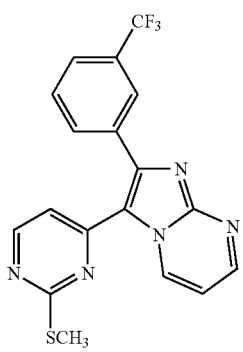

INTERMEDIATE COMPOUND 109

An ethanol (150 mL) solution of INTERMEDIATE COMPOUND 107 (5.0 g, 13 mmol) and 2-aminopyrimidine (5.1 g, 53 mmol) was heated at reflux for 18 h under argon. The contents of the reaction flask were cooled and concentrated in vacuo. Water and sat. NaHCO$_3$ (aq.) were added and the resulting mixture was extracted with methylene chloride (3×). The combined organic extracts were dried with Na$_2$SO$_4$ (anh.), filtered, and concentrated in vacuo. The crude product was subjected to flash column chromatography (methylene chloride methanol 99:1). Two products co-eluted. Product containing fractions were combined and the solvent removed in vacuo to give a tan solid which was triturated with ether and filtered to give a white solid, INTERMEDIATE COMPOUND 108 (1.24 g). The filtrate was concentrated in vacuo and rechromatographed using hexane ethyl acetate 30:70 to give after evaporation a tan foam, INTERMEDIATE COMPOUND 109 (2.32 g).

INTERMEDIATE COMPOUND 108: $^1$H NMR (CDCl$_3$, 300 MHz) δ 8.68 (m, 1H), 8.58 (d, 1H), 8.15 (m, 1H), 8.02 (d, 1H), 7.80 (s, br, 2H), 7.70 (m, 2H), 6.92 (m, 1H), 1.84 (s, 3H).

INTERMEDIATE COMPOUND 109: $^1$H NMR (CDCl$_3$, 300 MHz) δ 9.88 (dd, J=6.9, 2.1 Hz, 1H), 8.74 (dd, J=4.1, 2.1 Hz, 1H), 8.36 (d, J=5.4 Hz, 1H), 8.06 (s, 1H), 7.91 (d, J=7.8 Hz, 1H), 7.72 (d, J=7.8 Hz, 1H), 7.59 (t, J=7.7 Hz, 1H), 7.09 (dd, J=6.9, 3.9 Hz, 1H), 6.88 (d, J=5.4 Hz, 1H), 2.65 (s, 3H).

INTERMEDIATE COMPOUND 110 was prepared using INTERMEDIATE COMPOUND 108 by a procedure like that described for the preparation of INTERMEDIATE COMPOUND 10 above in Scheme 2.

$^1$H NMR (CDCl$_3$, 300 MHz) δ 9.00 (d, 1H), 8.75 (m, 1H), 8.56 (d, 1H), 8.18 (m, 1H), 2.73 (s, 3H).

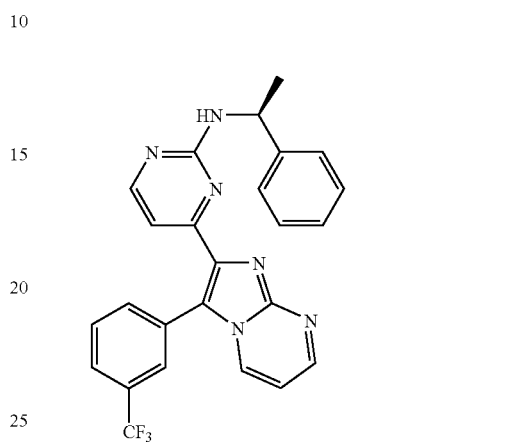

EXAMPLE 126 was prepared using INTERMEDIATE COMPOUND 110 by a procedure like that described above for the preparation of COMPOUND 11 (EXAMPLE A01).

MS (M+H) m/z 461

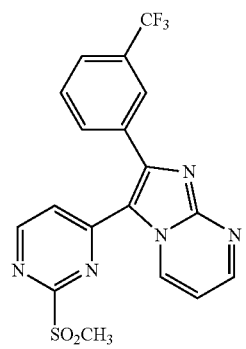

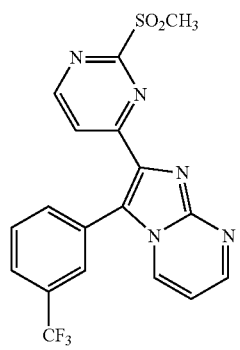

INTERMEDIATE COMPOUND 112 was prepared using INTERMEDIATE COMPOUND 109 by a procedure like that described for the preparation of INTERMEDIATE COMPOUND 10 above in Scheme 2.

MS (M+H) m/z 420

EXAMPLES 127–130 in TABLE 5 below were prepared by reacting INTERMEDIATE COMPOUND 112 with an amine using a procedure like that described above for the preparation of EXAMPLE A01 (COMPOUND 11).

TABLE 5

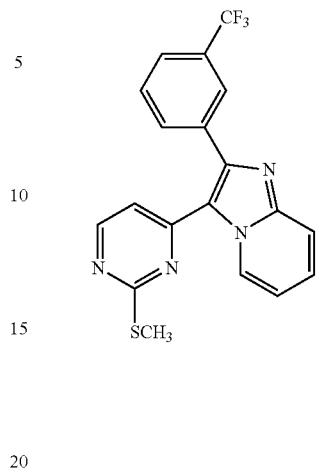

| EXAMPLE | R | MS (M+H) m/z |
|---|---|---|
| 127 | ⸺CH(CH₃)Ph | 461 |
| 128 | ⸺CH₂-cyclopentyl | 425 |
| 129 | ⸺CH₂-cyclopropyl | 361 |
| 130 | ⸺CH₂CH₂-(3-Cl-C₆H₄) | 495 |

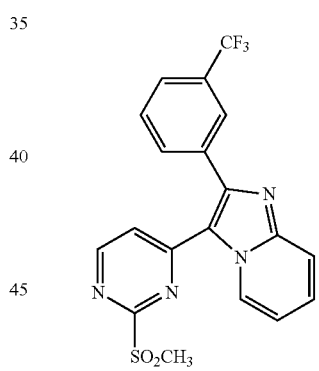

INTERMEDIATE COMPOUND 117 was prepared from INTERMEDIATE COMPOUND 107 and 2-aminopyridine using a procedure like that described for the preparation of INTERMEDIATE COMPOUND 9.

$^1$H NMR (CDCl$_3$, 300 MHz) δ 9.55 (m, 1H), 8.32 (d, 1H), 8.00 (s, 1H), 7.00 (m, 1H), 6.80 (d, 1H), 2.62 (s, 3H).

INTERMEDIATE COMPOUND 118 was prepared using INTERMEDIATE COMPOUND 117 by a procedure like that described for the preparation of INTERMEDIATE COMPOUND 10.

$^1$H NMR (CDCl$_3$, 300 MHz) δ 9.90 (d, 1H), 8.55 (d, 1H), 7.99 (s, 1H), 7.28 (m, 1H), 7.15 (m, 1H), 3.42 (s, 3H).

EXAMPLES 131–134 in TABLE 6 were prepared by reacting INTERMEDIATE COMPOUND 118 with an amine using a procedure like that described for the preparation of EXAMPLE A01 (COMPOUND 11).

TABLE 6

| EXAMPLE | R | $^1$H NMR (CDCl$_3$, 300MHz) δ | MS (M+H) m/z |
|---|---|---|---|
| 131 | (R)-CH(CH$_3$)Ph | | 460 |
| 132 | -(CH$_2$)$_3$-O-CH$_3$ | 8.14(m, 1H), 8.03(s, br, 1H), 7.75–7.65(m, 2H), 7.55(m, 1H), 7.36(m, 1H), | |
| 133 | -(CH$_2$)$_3$-O-CH$_2$CH$_3$ | 9.50(d, 1H), 8.15(d, 1H), 8.04(s, 1H), 7.85(d, 1H), 6.94(m, 1H), 6.40(d, 1H), | |
| 134 | -(CH$_2$)$_2$-NH-C(O)-O-C(CH$_3$)$_3$ | 9.45(d, 1H), 8.15(d, 1H), 8.03(s, 1H), 7.85(d, 1H), 7.75–7.65(m, 2H), 7.53(m, 1H), 7.39(m, 1H), 6.95(m, | |

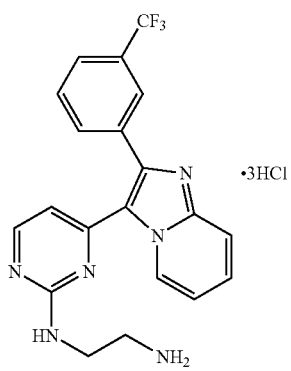

An ethyl acetate (100 mL) solution of EXAMPLE 134 (0.50 g, 1.02 mmol) was cooled in an ice bath with stirring. Hydrogen chloride gas was bubbled through the solution for 5 min. After 15 min. the solvent was removed in vacuo and the remaining solid was recrystallized from acetonitrile to give EXAMPLE 135 as a solid (84 mg).

$^1$H NMR (DMSO-d$_6$, 300 MHz) δ 8.33 (d, 1H), 8.09–7.95 (m, 5H), 7.83 (m, 1H), 7.54 (m, 1H), 3.70 (m, 2H), 3.11 (m, 2H).

Scheme 12:

EXAMPLES 136–138 in TABLE 7 were prepared using a synthetic sequence like that described for the preparation of compounds in TABLE 6 except 2-amino-4-picoline was used in the place of 2-aminopyridine in the initial condensation reaction with compound INTERMEDIATE COMPOUND 107.

TABLE 7

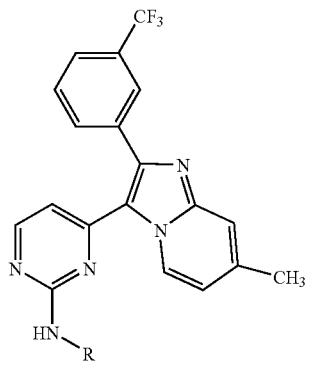

| EXAMPLE | R | ¹H NMR (CDCl₃, 300MHz) δ | MS (M+H) m/z |
|---|---|---|---|
| 136 | (chiral CH with Ph) | 8.10(d, 1H), 7.95(s, 1H), 7.80(d, 1H), 7.64(m, 1H), 7.53–7.30(m, 8H), 6.38(m, | |
| 137 | -(CH₂)₃-O-CH₃ | 9.40(m, 1H), 8.13(d, 1H), 8.03(s, 1H), 7.85(d, 1H), 7.65(d, 1H), 7.52(m, 2H), 6.79(m, 1H), 6.40(d, 1H), | |
| 138 | -(CH₂)₃-NH-C(O)-O-tBu | 9.37(d, 1H), 8.10(d, 1H), 8.00(s, 1H), 7.83(m, 1H), 7.65(m, 1H), 7.50(m, 2H), 6.79(m, 1H), 6.40(d, 1H), | |

EXAMPLE 139 was prepared using a synthetic sequence like that described for the preparation of the compounds in TABLE 6 except 2-amino-5-picoline was used in the place of 2-aminopyridine in the initial condensation reaction with INTERMEDIATE COMPOUND 107.

¹H NMR (CDCl₃, 300 MHz) δ 8.95 (s, br, 1H), 8.11 (d, 1H), 8.00 (s, 1H), 7.81 (d, 1H), 7.65–7.55 (m, 2H), 7.52–7.42 (m, 3H), 7.38 (m, 1H), 7.29 (m, 1H), 7.15 (m, 1H), 6.41 (d, 1H), 5.81 (m, 1H), 5.30 (m, 1H), 2.20 (s, br, 3H), 1.61 (d, 3H).

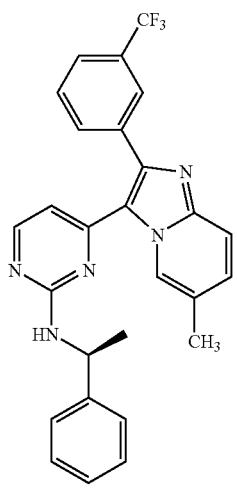

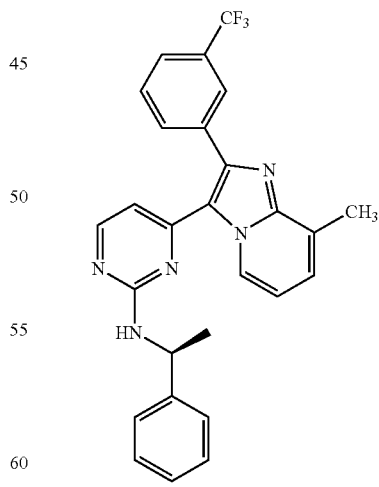

EXAMPLE 140 was prepared using a synthetic sequence like that described for the preparation of compounds in TABLE 6 except 2-amino-3-picoline was used in the place of 2-aminopyridine in the initial condensation reaction with compound INTERMEDIATE COMPOUND 107.

MS (M+) m/z 474

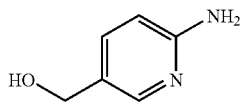

INTERMEDIATE COMPOUND 129 was prepared using a synthetic sequence similar to that described for the preparation of INTERMEDIATE COMPOUND 5 except 6-aminonicotinic acid was used in the place of INTERMEDIATE COMPOUND 3.

$^1$H NMR (CD$_3$OD, 300 MHz) δ 7.85 (m, 1H), 7.48 (m, 1H), 6.59 (m, 1H), 4.42 (s, 2H).

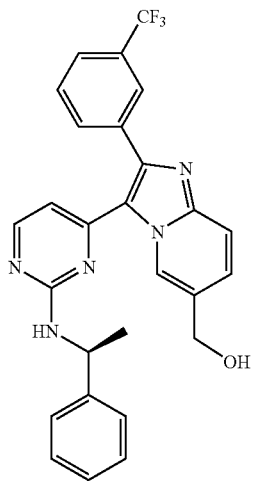

EXAMPLE 141 was prepared using a synthetic sequence like that described in Scheme 10 for the preparation of EXAMPLE 127 except INTERMEDIATE COMPOUND 129 was used in the place of 2-aminopyrimidine in the condensation reaction with compound INTERMEDIATE COMPOUND 107.

$^1$H NMR (CDCl$_3$, 300 MHz) δ 9.10 (m, 1H), 8.15 (d, 1H), 8.00 (s, 1H), 7.82 (d, 1H), 7.65 (m, 1H), 7.54–7.30 (m, 7H), 6.42 (d, 1H), 5.60 (m, 1H), 5.25 (m, 1H), 4.45 (s, br, 1H), 1.62 (d, 3H).

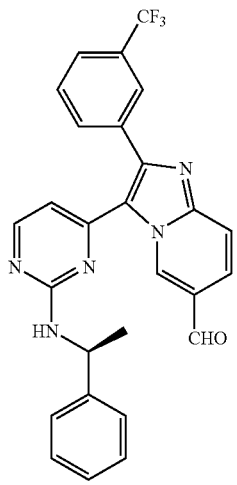

Molecular sieves (4 Å) were added to a methylene chloride (3 mL) solution of EXAMPLE 141 (50 mg, 0.10 mmol) under argon. After 5 min 4-methylmorpholine N-oxide (18 mg, 0.15 mmol) and tetrapropylammonium perruthenate (4 mg, 0.10 mmol) were added. After 1 h the contents of the reaction flask were subjected to flash column chromatography purification (hexane ethyl acetate 1:1) to give EXAMPLE 142 as a white solid (28 mg).

MS (M+H) m/z 488

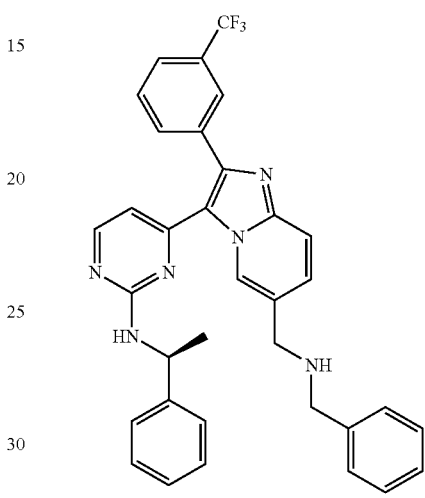

EXAMPLE 143 was prepared by reductive amination of EXAMPLE 142 with benzylamine using a procedure like that described for the preparation of compound 14 (EXAMPLE A04).

MS (M+H) m/z 579

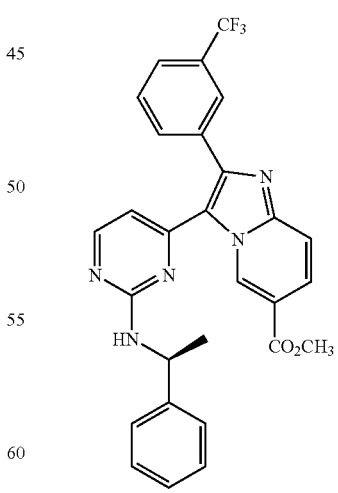

EXAMPLE 144 was prepared using a synthetic sequence like that described in Scheme 10 for the preparation of EXAMPLE 127 except methyl 6-aminonicotinate was used in the place of 2-aminopyrimidine in the condensation reaction with compound INTERMEDIATE COMPOUND 107.

MS (M+H) m/z 518

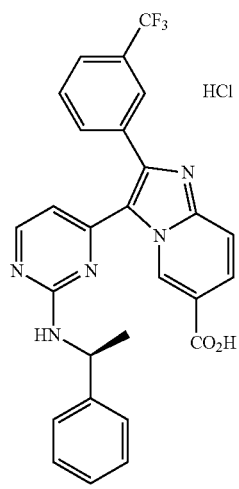

A solution of lithium hydroxide (7 mg, 0.29 mmol) in a minimum amount of water was added to a THF (1.5 mL) solution of EXAMPLE 144 (140 mg, 0.27 mmol) under argon. After 1.5 h THF was removed in vacuo and the contents of the reaction flask were acidified with 1N hydrochloric acid. A solid appeared which was isolated by vacuum filtration. Toluene was added to the solid, stirred, then removed in vacuo. The remaining solid was triturated with ether and isolated to give EXAMPLE 145 (60 mg).

MS (M+H) m/z 504

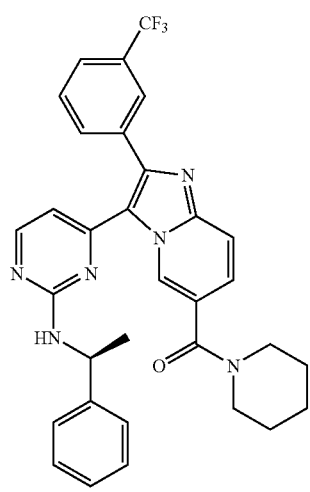

Triethylamine (0.122 mL, 0.88 mmol) was added with stirring to a N,N-dimethylformamide (5 mL) solution of EXAMPLE 145 (400 mg, 0.794 mmol), 1-[3-(dimethylamino)propyl]-3-ethylcarbodiimide hydrochloride (167 mg, 0.874 mmol), 1-hydroxy-7-azabenzotriazole (118 mg, 0.874 mmol), and piperidine (0.087 mL, 0.874 mmol) under argon. After 48 h the contents of the reaction flask were poured into water and the resulting mixture was extracted with ethyl acetate (3×). The combined organic extracts were dried with $Na_2SO_4$ (anh.), filtered, and concentrated in vacuo. The crude product was subjected to flash column chromatography (ethyl acetate) to give after evaporation a yellow oil, (360 mg).

MS (M+H) m/z 571

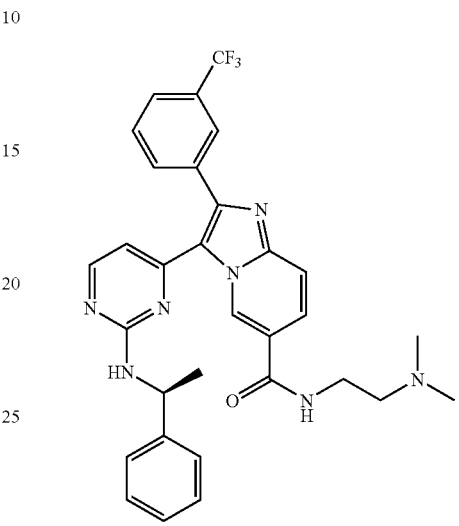

EXAMPLE 147 was prepared from EXAMPLE 145 using a procedure like that described for compound EXAMPLE 146 except replacing piperidine with N,N-dimethylethylenediamine.

MS (M+H) m/z 574

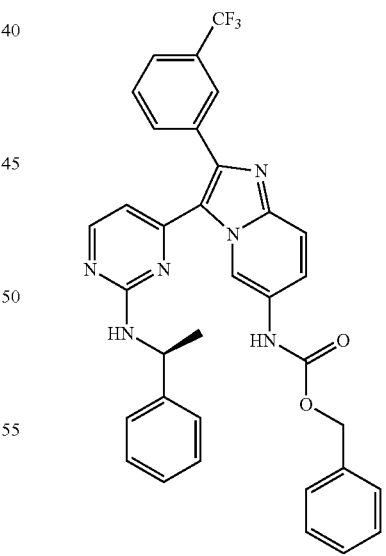

Diphenylphophoryl azide (0.130 mL, 0.596 mmol) and benzyl alcohol (0.093 mL, 0.891 mmol) were added to a toluene (5 mL) solution of 134 (150 mg, 0.297 mmol) and the resulting solution was heated at reflux 24 h. The contents of the reaction flask were cooled and the solvent removed in vacuo. The remaining residue was subjected to flash column chromatography (ethyl acetate hexane 30:70 then 50:50) to give after evaporation EXAMPLE 148 (96 mg).

MS (M+H) m/z 609

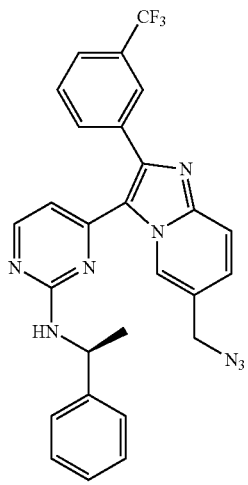

EXAMPLE 149 was prepared from EXAMPLE 141 using a procedure like that described for the preparation of EXAMPLE A02 (COMPOUND 12).

MS (M+m) m/z 515

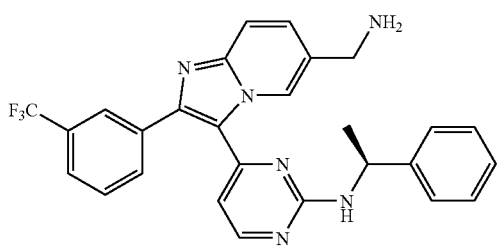

EXAMPLE 150 was prepared from EXAMPLE 149 using a procedure like that described for the preparation of EXAMPLE A03 (COMPOUND 13).

MS (M+H) m/z 489

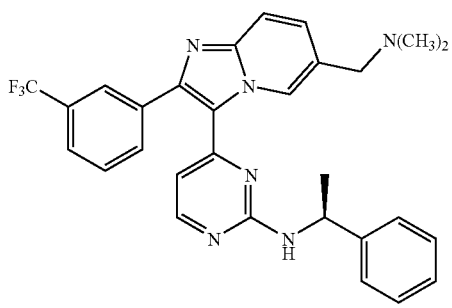

EXAMPLE 151 was prepared from EXAMPLE 150 by reductive amination with formaldehyde using a procedure like that described for the preparation of EXAMPLE A04 (COMPOUND 14).

MS (M+H) m/z 517

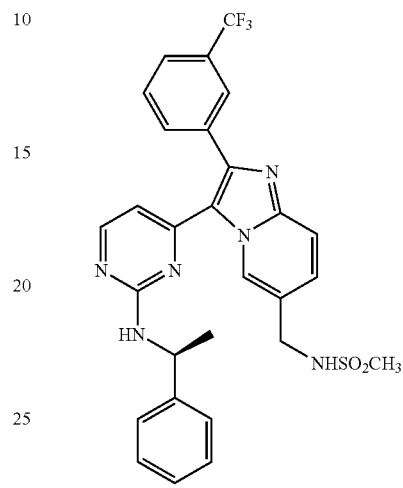

A methylene chloride (3 mL) solution of EXAMPLE 150 (25 mg, 0.05 mmol) was cooled in an ice bath under argon. Methanesulfonyl chloride (0.020 mL, 0.263 mmol) and triethylamine (0.041 mL, 0.297 mmol) were added and the reaction was allowed to warm to room temperature. The solvent was removed in vacuo and the remaining residue was subjected to flash column chromatography (ethyl acetate) to afford after evaporation a white solid 141 (15 mg).

MS (M+H) m/z 567

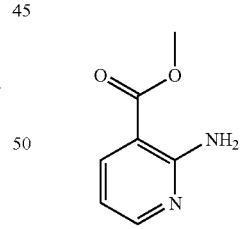

A methanol (250 mL) solution of 2-aminonicotinic acid (10.5 g, 76 mmol), and sulfuric acid (20 mL) was refluxed 18 h. The reaction was cooled to room temperature and the solvent was removed in vacuo. Sat. sodium bicarbonate (aq.) was added and the mixture was extracted with ethyl acetate. The organic layer was dried with anhydrous sodium sulfate, filtered, and evaporated in vacuo to give a white solid INTERMEDIATE COMPOUND 142 (5.5 g).

$^1$H NMR (CD$_3$OD, 300 MHz) δ 8.19 (m, 2H), 7.64 (m, 1H), 3.89 (s, 3H).

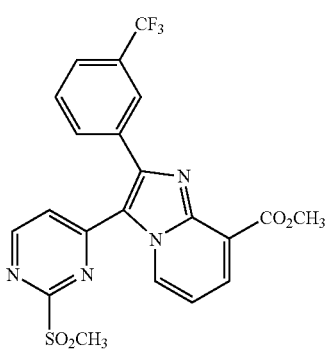

INTERMEDIATE COMPOUND 143 was prepared using a synthetic sequence like that described in Scheme 10 for the preparation of INTERMEDIATE COMPOUND 112 except INTERMEDIATE COMPOUND 142 was used in the place of 2-aminopyrimidine in the condensation reaction with compound INTERMEDIATE COMPOUND 107.

$^1$H NMR (CDCl$_3$, 300 MHz) δ 10.10 (m, 1H), 8.58 (d, 1H), 8.25 (m, 1H), 8.00 (s, 1H), 7.85 (m, 1H), 7.76 (m, 1H), 7.63 (m, 1H), 7.26 (m, 2H), 4.09 (s, 3H), 3.43 (s, 3H).

EXAMPLES 153 (COMPOUND 144) AND 154 (COMPOUND 145)

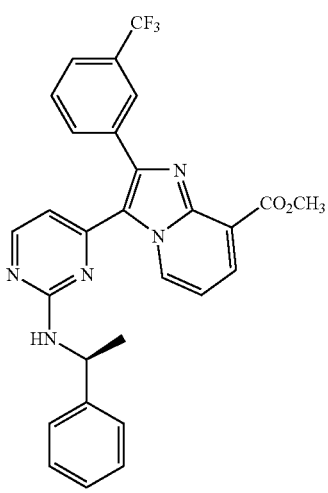

EXAMPLE 153 (COMPOUND 144)

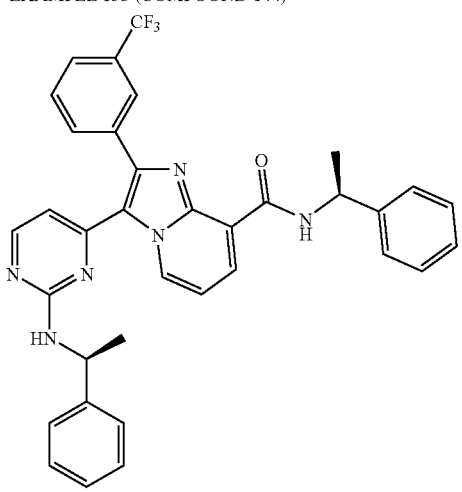

EXAMPLE 154 (COMPOUND 145)

S-(−)-α-Methylbenzylamine (15 mL) and INTERMEDIATE COMPOUND 143 (2.61 g, 5.48 mmol) were combined under argon and heated at 60° C. for 1 h. Cooled, added citric acid (aq.) and extracted with ethyl acetate. Dried the organic layer with anhydrous sodium sulfate and removed solvent in vacuo to give a yellow solid. Flash column chromatography (ethyl acetate hexane 25:75) followed by reverse phase preparative HPLC afforded, after evaporation, EXAMPLES 153 and EXAMPLES 154.

EXAMPLE 153

MS (M+H) m/z 518

EXAMPLE 154

MS (M+H) m/Z 607

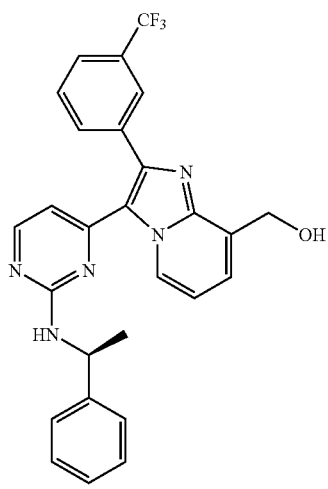

Lithium aluminum hydride solution (1 mL, 1M) was slowly added to a THF solution of EXAMPLE 154 (300 mg, 0.580 mmol) under argon at room temperature. After 18 h the reaction was quenched with water and sodium hydroxide (aq.). Magnesium sulfate was added and the mixture was filtered. The filtrate was evaporated in vacuo to give a red oil. Flash column chromatography gave EXAMPLE 155 after evaporation as a white solid (60 mg).

MS (M+H) m/z 490

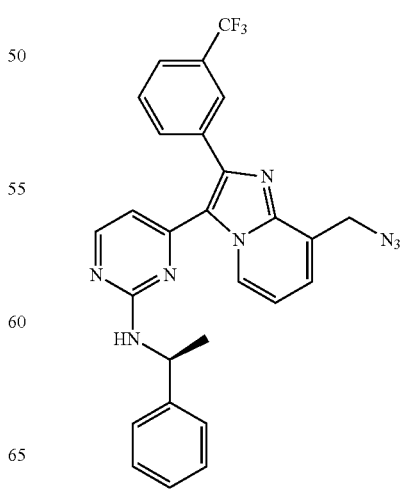

EXAMPLE 156 was prepared from EXAMPLE 155 using a procedure like that described for the preparation of EXAMPLE A02 (COMPOUND 12).

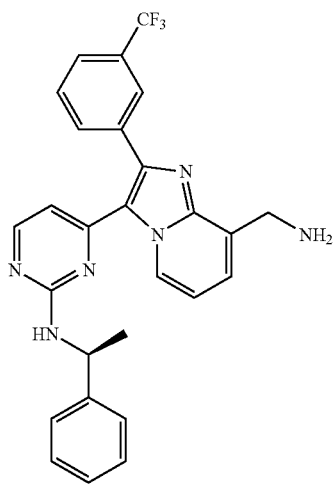

EXAMPLE 157 was prepared from EXAMPLE 156 using a procedure like that described for the preparation of EXAMPLE A03 (COMPOUND 13).

Combustion analysis for EXAMPLE 157: Calculated for $C_{27}H_{23}N_6F_3 \cdot 0.05H_2O \cdot 0.45MeOH$ C 65.43%; H 4.98%; N 16.68%. Found: C 65.43%; H 4.62%; N 16.61%.

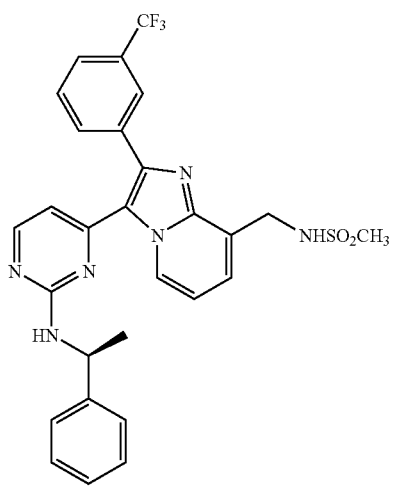

EXAMPLE 158 was prepared from EXAMPLE 157 using a procedure like that described for the preparation of EXAMPLE 152.

MS (M+H) m/z 567

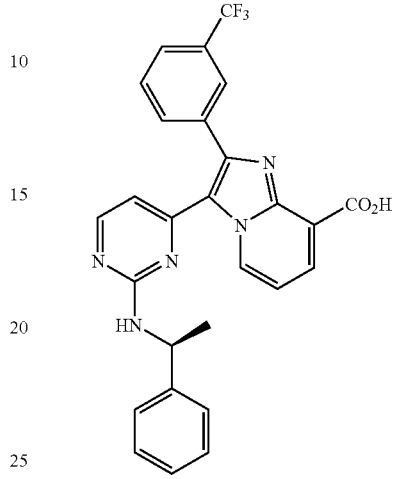

EXAMPLE 159 was prepared from EXAMPLE 153 using a procedure like that described for the preparation of compound EXAMPLE 145.

Combustion analysis for EXAMPLE 159: Calculated for $C_{27}H_{20}N_5O_2F_3 \cdot 0.10H_2O \cdot 1.95TFA$ C 51.00%; H 3.07%; N 9.63%. Found: C 51.00%; H 3.04%; N 9.62%.

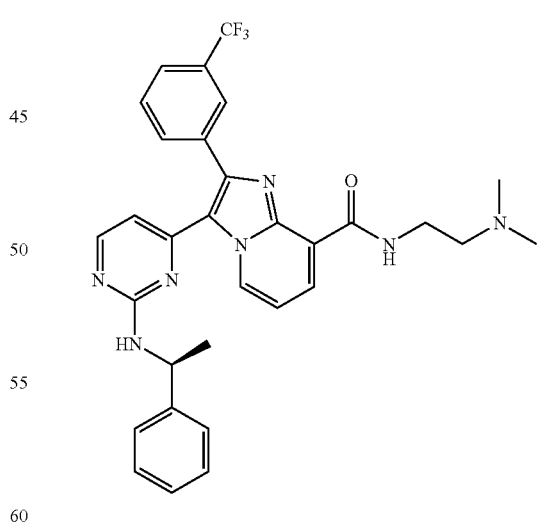

A neat solution of COMPOUND 144 in N,N-dimethylethylenediamine was heated at 80° C. under argon for 2 h. The contents of the reaction flask were cooled to room temperature and acetonitrile/water/methanol was added. The resulting solution was subjected to reverse phase preparative HPLC to give after evaporation COMPOUND 151.

MS (M+H) m/z 574

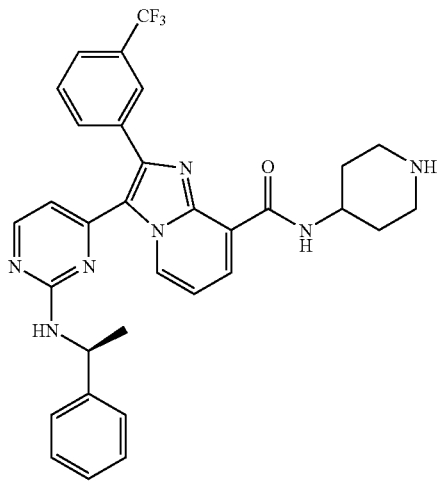

A neat solution of 4-amino-1-BOC-piperidine (300 mg, 1.5 mmol) and 144 (50 mg, 0.1 mmol) was heated at 80° C. under argon for 18 h. cooled to room temperature and added ethyl acetate and water. The organic layer was dried with anhydrous sodium sulfate, filtered and concentrated in vacuo. Methylene chloride (4 mL) and trifluoroacetic acid (4 mL) were added. After 3 h the solvents were evaporated in vacuo and the remaining residue was subjected to reverse phase preparative HPLC to give after evaporation a yellow solid, 152 (10 mg, 17%).

MS (M+H) m/z 586

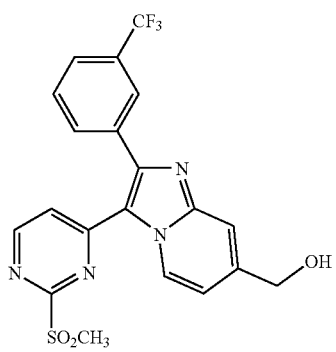

INTERMEDIATE COMPOUND 153 was prepared using a synthetic sequence like that described in Scheme 10 for the preparation of INTERMEDIATE COMPOUND 112 except INTERMEDIATE COMPOUND 5 was used in the place of 2-aminopyrimidine in the condensation reaction with compound INTERMEDIATE COMPOUND 107.

INTERMEDIATE COMPOUND 153: $^1$H NMR (CDCl$_3$, 300 MHz) δ 9.81 (d, 1H), 8.55 (d, 1H), 7.95 (s, 1H), 7.80 (m, 3H), 7.65 (m, 1H), 7.25 (m, 1H), 7.11 (m, 1H), 4.86 (s, 2H), 3.41 (m, 2H).

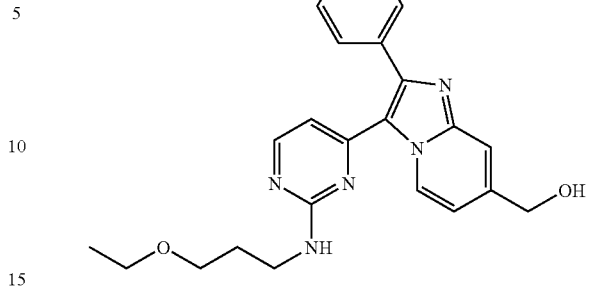

EXAMPLE 162 was prepared from INTERMEDIATE COMPOUND 153 using a procedure like that described for the preparation of EXAMPLE A01 (COMPOUND 11) except 3-ethoxypropylamine was used in the place of s-(−)-α-methylbenzylamine.

MS (M+H) m/z 472

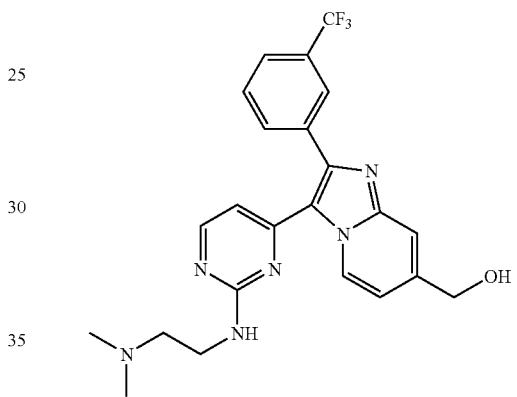

EXAMPLE 163 was prepared from INTERMEDIATE COMPOUND 153 using a procedure like that described for the preparation of EXAMPLE A01 (COMPOUND 11) except N,N-ethylenediamine was used in the place of s-(−)-α-methylbenzylamine.

MS (M+H) m/z 457

EXAMPLE 164 (COMPOUND 156) AND INTERMEDIATE COMPOUND 157

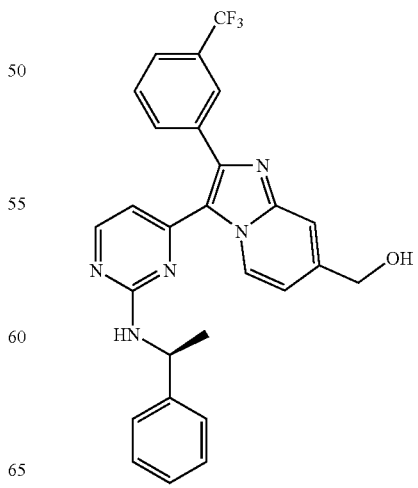

EXAMPLE 164 (COMPOUND 156)

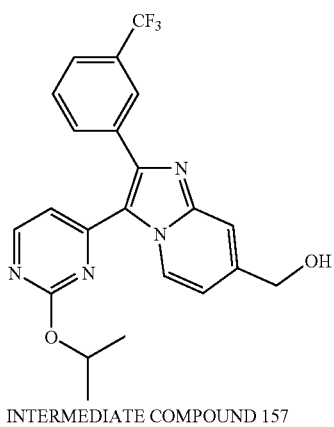

INTERMEDIATE COMPOUND 157

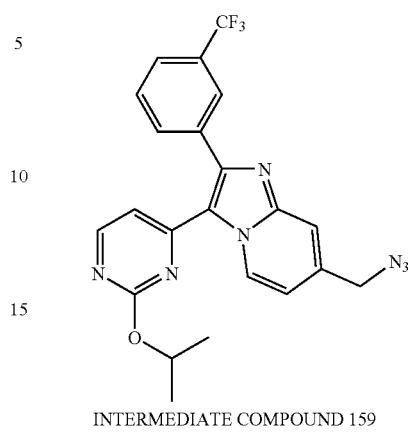

INTERMEDIATE COMPOUND 159

S-(−)-α-Methylbenzylamine (5 mL) was added to an isopropanol (15 mL) solution of INTERMEDIATE COMPOUND 153 (1.90 g, 4.24 mol) under argon and the resulting mixture was heated at 60° C. 18 h. The contents of the reaction flask were cooled to room temperature and treated with citric acid (aq.). The pH was adjusted to 4.5 with NaOH (aq.) and extracted with ethyl acetate (2×). The combined organic extracts were dried with anhydrous sodium sulfate, filtered, and the filtrate concentrated in vacuo to give a red oil. Flash column chromatography (ethyl acetate hexane 40:60 then 70:30) to give two portions after evaporation: 1. 156 (349 mg) and 2. A mixture (610 mg) of 156 and 157.

156: $^1$H NMR (CDCl$_3$, 300 MHz) δ 8.11 (d, 1H), 7.95 (s, 1H), 7.80 (d, 1H), 7.70–7.30 (m, 10H), 6.36 (d, 1H), 5.68 (m, 1H), 5.16 (m, 1H), 4.72 (m, 2H), 1.63 (d, 3H).

EXAMPLE 166 (COMPOUND 158) AND INTERMEDIATE COMPOUND 159

Diphenylphophoryl azide (0.0.323 mL, 1.50 mmol) and 1,8-diazabicyclo[4.5.0]undec-7-ene (0.224 mL, 1.50 mmol) were added to a toluene (5 mL) solution of EXAMPLE 141 (115 mg, 0.235 mmol) under argon. After 18 h the reaction was poured into water and extracted (3×) with ethyl acetate. The combined organic portions were dried with Na$_2$SO$_4$ (anh.), filtered, and concentrated in vacuo. The crude product was subjected to flash column chromatography (ethyl acetate hexane 10:90 then 20:80) to give after evaporation two products: 1. White solid, 158 (100 mg) and 2. Solid, 159 (38 mg).

158: $^1$HNMR (CDCl$_3$, 300 MHz) δ 8.15 (d, 1H), 7.97 (s, 1H), 7.83 (d, 1H), 7.66 (d, 1H), 7.59–7.33 (m, 9H), 5.70 (m, 1H), 5.16 (m, 1H), 4.40 (s, 2H), 1.65 (d, 3H).

159: $^1$H NMR (CDCl$_3$, 300 MHz) δ 9.60 (d, 1H), 8.32 (d, 1H), 8.00 (s, 1H), 7.82 (d, 1H), 7.70 (m, 2H), 7.57 (m, 1H), 6.95 (m, 1H), 6.75 (m, 1H), 5.39 (m, 1H), 4.50 (s, 2H), 1.50 (d, 6H).

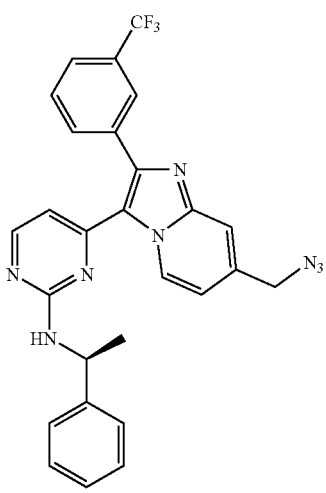

EXAMPLE 166 (COMPOUND 158)

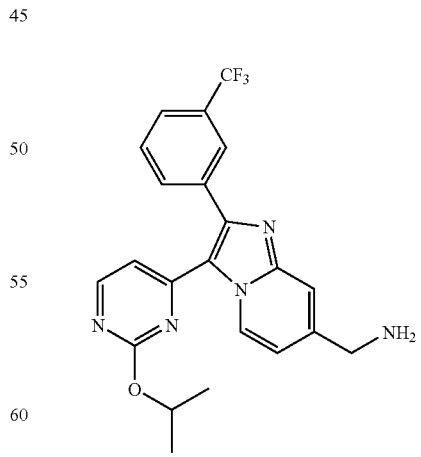

INTERMEDIATE COMPOUND 160 was prepared from INTERMEDIATE COMPOUND 159 using a procedure like that described for the preparation of EXAMPLE A03 (COMPOUND 13).

MS (M+H) m/z 428

EXAMPLE 169 (COMPOUND 161)

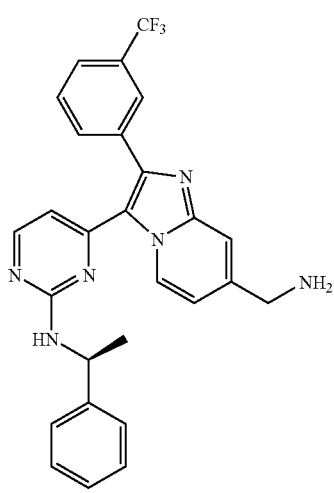

EXAMPLE 169 was prepared from EXAMPLE 166 using a procedure like that described for the preparation of EXAMPLE A03 (COMPOUND 13).

MS (M+H) m/z 489

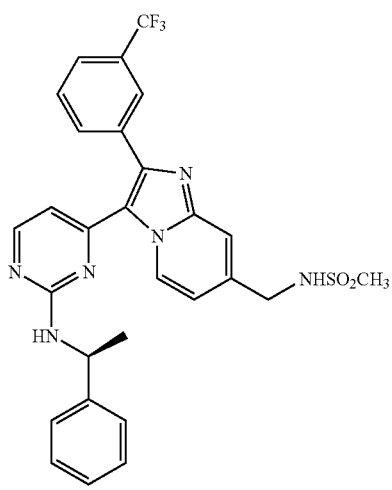

EXAMPLE 170 was prepared from EXAMPLE 169 using a procedure like that described for the preparation of EXAMPLE 152 (COMPOUND 141).

MS (M+H) m/z 567

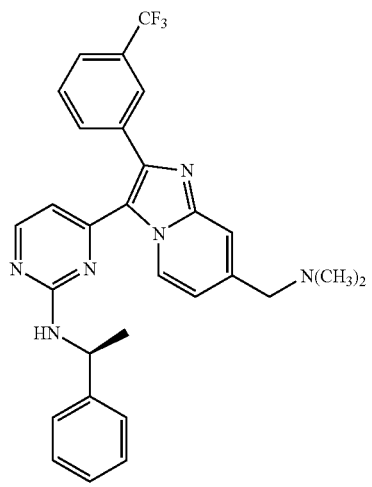

EXAMPLE 171 was prepared from EXAMPLE 169 by reductive amination using a procedure like that described for the preparation of EXAMPLE A04 (COMPOUND 14).

MS (M+H) m/z 517

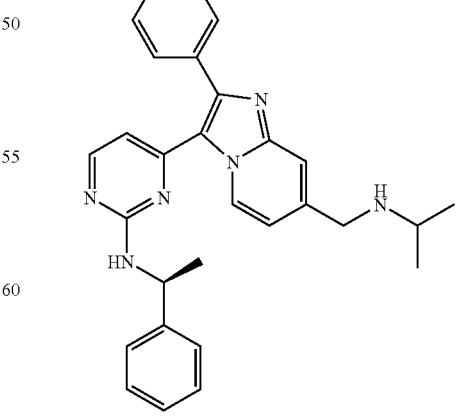

EXAMPLE 172 was prepared from EXAMPLE 169 by reductive amination using a procedure like that described for the preparation of EXAMPLE A04 (COMPOUND 14) except formaldehyde (aq.) was replaced with acetone.

MS (M+H) m/z 531

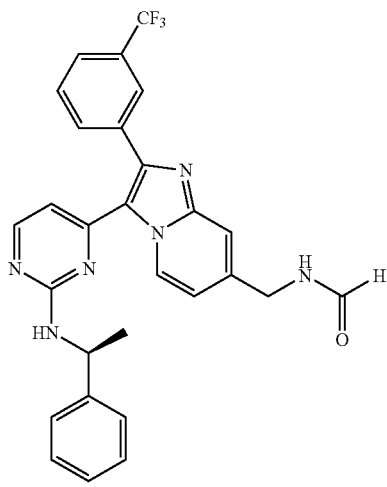

EXAMPLE 173 was prepared from EXAMPLE 169 by reductive amination using a procedure like that described for the preparation of EXAMPLE A04 except formaldehyde (aq.) was replaced with ethyl formate.

MS (M+H) m/z 517

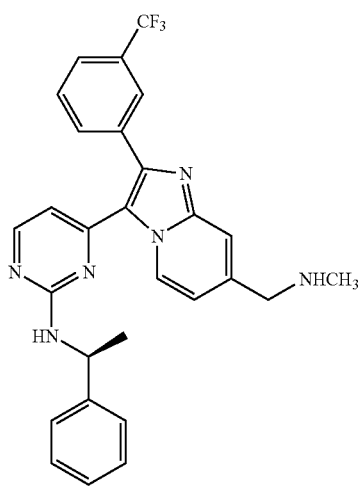

A THF solution of EXAMPLE 173 (61 mg, 0.12 mmol) under argon was treated with 1M borane-THF solution (0.59 mL, 0.59 mmol) and stirred at room temperature. After 18 h, 2M hydrochloric acid was added and after 2 h the reaction was made basic with sat. sodium bicarbonate (aq.). The resulting mixture was extracted with ethyl acetate (2×). The combined organic extracts were dried with anhydrous sodium sulfate, filtered, and evaporated in vacuo to give a yellow oil. Flash column chromatography (methylene chloride methanol ammonium hydroxide 95:5:0.5 gave after evaporation a yellow solid of EXAMPLE 173 (31 mg).

MS (M+H) m/z 503

Compounds in TABLE 8 below were prepared by reacting EXAMPLE 169 with a carboxylic acid using a coupling procedure like that described for the preparation of EXAMPLE 146.

TABLE 8

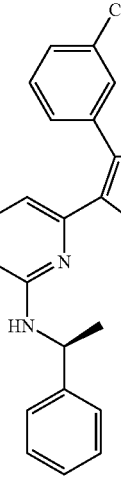

| EXAMPLE | R | MS (M+H) m/z |
|---|---|---|
| 175 | 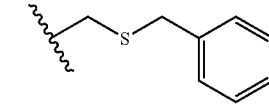 | 653 |
| 176 |  | 557 |
| 177 | 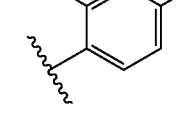 | 629 |
| 178 | 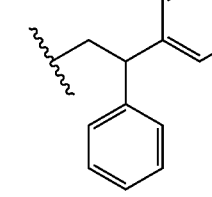 | 697 |
| 179 | 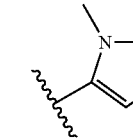 | 596 |
| 180 | 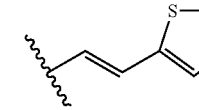 | 625 |

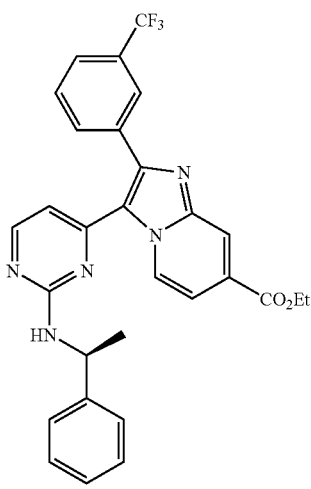

EXAMPLE 181 was prepared using a synthetic sequence like that described in Scheme 10 for the preparation of EXAMPLE 127 except INTERMEDIATE COMPOUND 4 was used in the place of 2-aminopyrimidine in the condensation reaction with compound INTERMEDIATE COMPOUND 107.

MS (M+M) m/z 532

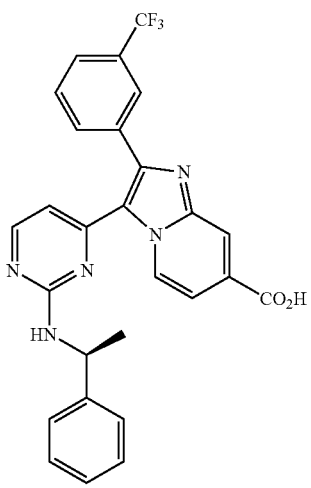

EXAMPLE 182 was prepared from EXAMPLE 181 using a procedure like that described for the preparation of EXAMPLE 145.

$^1$H NMR (CD$_3$OD, 300 MHz) δ 8.18 (s, 1H), 8.10 (d, 1H), 7.90 (s, 1H), 7.85 (m, 1H), 7.75 (m, 10), 7.65 (m, 1H), 7.48–7.25 (m, 7H), 6.30 (d, 2H), 1.60 (d, 3H).

Compounds in TABLE 9 below were prepared by reacting EXAMPLE 182 with an amine using a coupling procedure like that described for the preparation of EXAMPLE 146.

TABLE 9

| EXAMPLE | R | MS (M+H) m/z |
|---|---|---|
| 183 | piperidinyl | 571 |
| 184 | NH-CH$_2$CH$_2$CH$_2$-O-Et | 589 |
| 185 | N(CH$_3$)$_2$ | 531 |
| 186 | NH-CH(CH$_3$)-phenyl | 472 |
| 187 | NH-CH(CH$_3$)-(4-F-phenyl) | 625 |

Other EXAMPLES of the invention are shown in the following TABLE 10. These EXAMPLES are made similarly to the compounds and Schemes shown above.

TABLE 10

| Example | M+1 | H-NMR: (400MHz) δ |
|---|---|---|
| B001 | 467.4 | CDCl₃: 8.60(br, 1H), 8.38(s, 1H), 8.10(d, J=5.5Hz, 1H), 7.63(m, 2H), 7.45(m, 6H), 7.12(m, 2H), 6.53(br, 1H), 6.42(d, J=5.3Hz, 1H), 6.12(br, 1H), 5.84(br, 1H), 5.16(m, 1H), 4.56(d, J=6.3Hz, 2H), 1.63(d, J=7.0Hz, 3H) |
| B002 | 422.3 | CD₃OD: 8.58(br, 1H), 8.04(d, J=5.3Hz, 1H), 7.56(m, 3H), 7.42(m, 4H), 7.28(m, 1H), 7.18(m, 2H), 6.82(br, 1H), 6.27(d, J=5.3Hz, 1H), 5.11(m, 1H), 4.01(s, 2H), 3.68(m, 4H), 2.82(m, 1H), 1.56(d, J=7.1Hz, 3H) |
| B003 | 453.3 | CDCl3: 8.56(br, 1H), 8.11(d, J=5.3Hz, 1H), 7.42(m, 7H), 7.24(m, 1H), 7.18(m, 2H), 6.66(br, 1H), 6.22(d, J=5.3Hz, 1H), 5.10(m, 1H), 3.78(s, 2H), 2.41(s, 3H), 1.58(d, J=7.0Hz, 3H) |

TABLE 10-continued

| Example | M+1 | H-NMR: (400MHz) δ |
|---|---|---|
| B004 (Chiral structure) | 481.3 | CD3OD: 8.56(br, 1H), 8.02(d, J=5.3Hz, 1H), 7.56(m, 3H), 7.42(m, 5H), 7.28(m, 1H), 7.14(m, 2H), 6.76(br, 1H), 6.28(d, J=5.3Hz, 1H), 5.12(m, 1H), 3.85(s, 2H), 2.88(m, 1H), 1.57(d, J=7.0Hz, 3H), 1.25(m, 6H) |
| B005 (Chiral structure) | 497.4 | CDCl3: 8.62(br, 1H), 8.12(d, J=5.3Hz, 1H), 7.64(m, 2H), 7.45(m, 6H), 7.13(m, 2H), 6.62(br, 1H), 6.42(d, J=5.3Hz, 1H), 5.62(m, 1H), 5.18(m, 1H), 3.71(t, J=5.2Hz, 2H), 3.67(s, 2H), 2.70(t, J=5.3Hz, 2H), 2.34(s, 3H), 1.63(d, J=7.1Hz, 3H) |
| B006 (Chiral structure) | 537.4 | CD3OD: 8.56(br, 1H), 8.04(d, J=5.3Hz, 1H), 7.57(m, 3H), 7.42(m, 4H), 7.26(m, 1H), 7.18(m, 2H), 6.82(br, 1H), 6.28(d, J=5.3Hz, 1H), 5.12(m, 1H), 4.16(m, 1H), 3.80(m, 4H), 2.62(m, 2H), 2.40(s, 3H), 2.02(m, 4H), 1.56(d, J=7.1Hz, 3H) |

TABLE 10-continued
| Example | M+1 | H-NMR: (400MHz) δ |
|---|---|---|
| B007 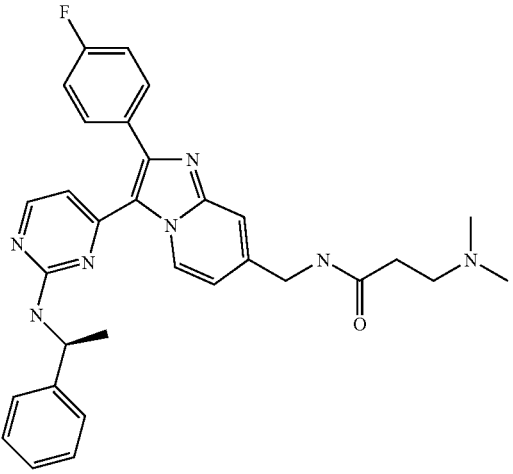 | 538.5 | CD3OD: 8.42(br, 1H), 8.05(d, J=5.2Hz, 1H), 7.52(m, 2H), 7.40(m, 5H), 7.24(m, 1H), 6.62(br, 1H), 6.29(d, J=5.3Hz, 1H), 5.10(m, 1H), 4.62(s, 2H), 2.97(t, J=6.6H 2H), 2.62(t, J=6.5z, 2H), 2.15(s, 6H), 1.56(d, J=7.1Hz, 3H) |
| B008 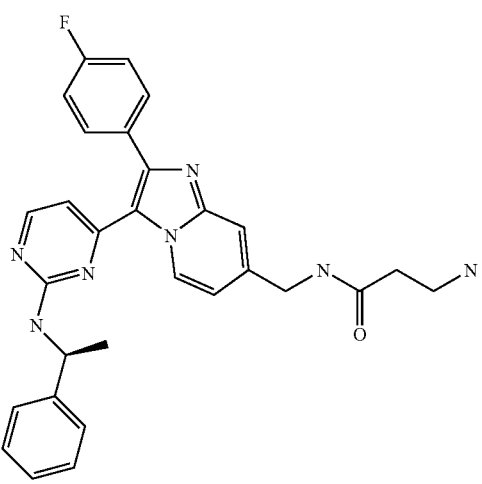 | 510.4 | CD3OD: 8.42(br, 1H), 8.01(d, J=5.2Hz, 1H), 7.52(m, 2H), 7.40(m, 5H), 7.24(m, 1H), 6.62(br, 1H), 6.21(d, J=5.3Hz, 1H), 5.07(m, 1H), 4.45(s, 2H), 3.10(t, J=6.7Hz, 2H), 2.61(t, J=6.6Hz, 2H), 1.54(d, J=6.8Hz, 3H) |
| B009 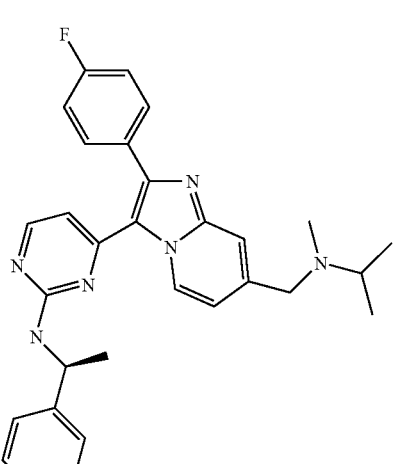 | 495.4 | CDCl3: 8.72(br, 1H), 8.10(d, J=5.3Hz, 1H), 7.61(m, 3H), 7.46(m, 4H), 7.36(m, 1H), 7.11(m, 2H), 6.72(br, 1H), 6.42(d, J=5.3Hz, 1H), 5.61(br, 1H), 5.20(m, 1H), 3.60(br, 2H), 2.98(br, 1H), 2.23(br, 3H), 1.64(d, J=7.0Hz, 3H), 1.27(br, 6H) |

TABLE 10-continued

| Example | M+1 | H-NMR: (400MHz) δ |
|---|---|---|
| B010 | 538.5 | CD3OD: 8.54(br, 1H), 8.03(d, J=5.1Hz, 1H), 7.55(m, 2H), 7.48(s, 1H), 7.42(m, 4H), 7.24(m, 1H), 7.18(m, 2H), 6.78(br, 1H), 6.25(d, J=5.2Hz, 1H), 5.12(m, 1H), 3.57(s, 2H), 2.42(m, 4H), 2.27(s, 6H), 1.77(m, 2H), 1.56(d, J=7.1Hz, 3H) |
| B011 | 574.4 | CD3OD: 8.56(br, 1H), 8.04(d, J=5.3Hz, 1H), 7.56(m, 2H), 7.52(s, 1H), 7.43(m, 4H), 7.28(m, 1H), 7.18(m, 2H), 6.81(br, 1H), 6.30(d, J=5.2Hz, 1H), 5.12(m, 1H), 3.65(s, 2H), 3.27(t, J=6.4Hz, 2H), 2.97(s, 3H), 2.64(t, J=6.4Hz, 2H), 2.31(s, 3H), 1.56(d, J=7.0Hz, 3H) |
| B012 | 536.4 | CD3OD: 8.58(br, 1H), 8.04(d, J=5.3Hz, 1H), 7.56(m, 2H), 7.52(s, 1H), 7.43(m, 4H), 7.28(m, 1H), 7.18(m, 2H), 6.78(br, 1H), 6.28(d, J=5.3Hz, 1H), 5.12(m, 1H), 3.60(s, 2H), 3.40(m, 4H), 2.76(t, J=6.7Hz, 2H), 2.47(t, J=6.7Hz, 2H), 2.27(s, 3H), 2.17(m, 2H), 1.57(d, J=7.1Hz, 3H) |

TABLE 10-continued

| Example | M+1 | H-NMR: (400MHz) δ |
|---------|-----|-------------------|
| B013 | 527.4 | CDCl3: 8.58(br, 1H), 8.10(d, J=5.3Hz, 1H), 7.64(m, 2H), 7.45(m, 6H), 7.13(m, 2H), 6.60(br, 1H), 6.41(d, J=5.3Hz, 1H), 5.80(br, 1H), 5.12(m, 1H), 3.90(s, 2H), 3.74(m, 4H), 3.14(m, 1H), 2.38(s, 3H), 2.20(br, 2H), 1.62(d, J=7.0Hz, 3H) |
| B014 | 433.4 | CD3OD: 9.62(br, 1H), 8.05(d, J=5.4Hz, 1H), 7.61(m, 3H), 7.21(m, 3H), 6.31(d, J=5.3Hz, 1H), 3.74(s, 2H), 3.38(s, 2H), 2.41(s, 6H), 1.01(s, 9H) |
| B015 | 447.3 | CD3OD: 9.61(br, 1H), 8.05(d, J=5.4Hz, 1H), 7.61(m, 3H), 7.21(m, 3H), 6.31(d, J=5.3Hz, 1H), 3.73(s, 2H), 3.36(s, 2H), 2.61(m, 2H), 2.34(s, 3H), 1.18(t, J=7.3Hz, 3H), 1.01(s, 9H) |

TABLE 10-continued
| Example | M+1 | H-NMR: (400MHz) δ |
|---|---|---|
| B016 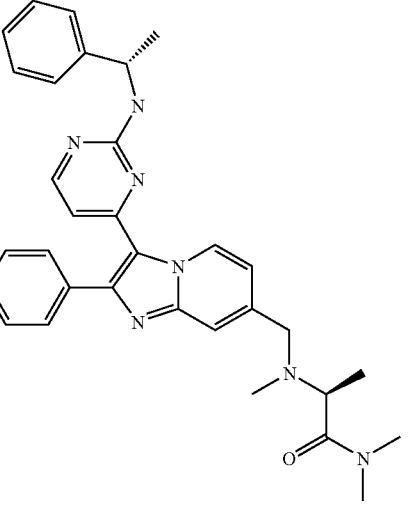 | 552.3 | CD3OD: 8.57(br, 1H), 8.06(d, J=5.3Hz, 1H), 7.57(m, 2H), 7.50(s, 1H), 7.42(m, 4H), 7.28(m, 1H), 7.18(m, 2H), 6.71(br, 1H), 6.29(d, J=5.5Hz, 1H), 3.91(m, 1H), 3.69(m, 2H), 3.25(s, 3H), 2.99(s, 3H), 2.26(s, 3H), 1.58(d, J=7.0Hz, 3H), 1.25(d, J=6.6Hz, 3H) |
| B017 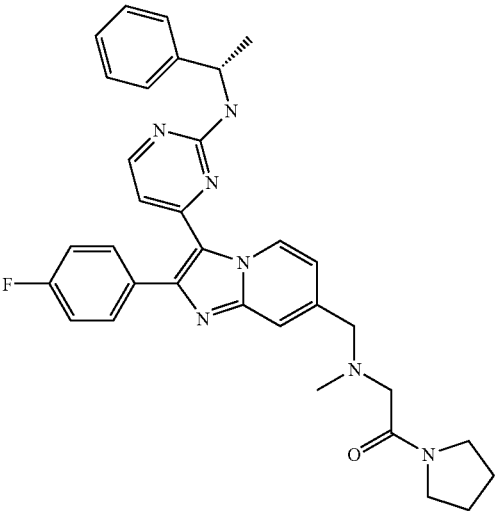 | 564.1 | CD3OD: 8.58(br, 1H), 8.05(d, J=5.3Hz, 1H), 7.58(m, 2H), 7.51(s, 1H), 7.42(m, 4H), 7.27(m, 1H), 7.18(m, 2H), 6.81(br, 1H), 6.29(d, J=5.3Hz, 1H), 5.13(m, 1H), 3.71(s, 2H), 3.55(t, J=6.7Hz, 2H), 3.42(t, J=6.9Hz, 2H), 3.34(s, 2H), 2.36(s, 3H), 1.99(m, 2H), 1.87(m, 2H), 1.57(d, J=7.0Hz, 3H) |
| B018 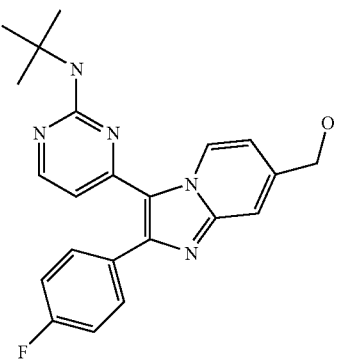 | 392.2 | CDCl3: 9.31(d, 1H), 8.11(d, 1H), 7.64(m, 3H), 7.11(m, 2H), 6.92(m, 1H), 6.41(d, 1H), 5.26(br, 1H), 4.80(s, 2H), 1.54(s, 9H) |

TABLE 10-continued
| Example | M+1 | H-NMR: (400MHz) δ |
|---|---|---|
| B019 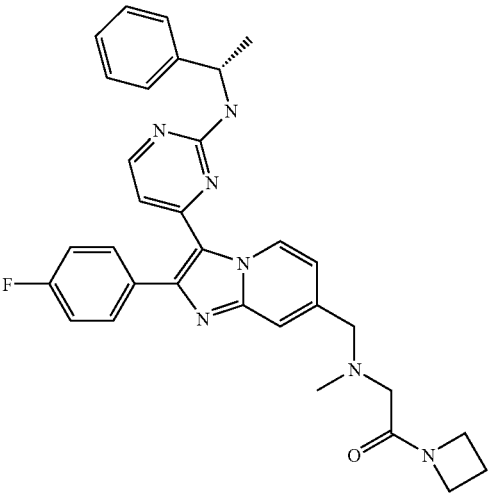 | 550.1 | CD3OD: 8.58(br, 1H), 8.04(d, J=5.3Hz, 1H), 7.58(m, 2H), 7.51(s, 1H), 7.43(m, 4H), 7.25(m, 1H), 7.18(m, 2H), 6.81(br, 1H), 6.28(d, J=5.2Hz, 1H), 5.13(m, 1H), 4.30(m, 2H), 4.04(m, 2H), 3.66(s, 2H), 3.13(s, 2H), 2.32(m, 5H), 1.57(d, J=7.1Hz, 3H) |
| B020 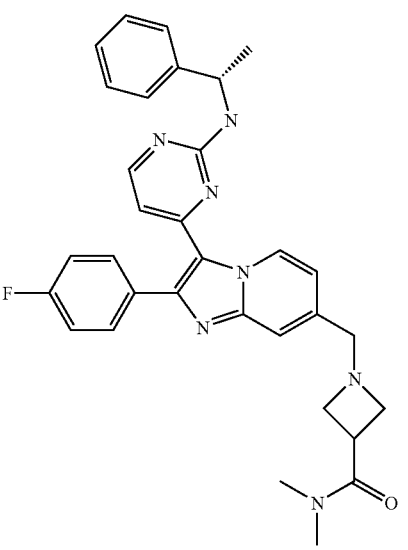 | 550.1 | CD3OD: 8.57(br, 1H), 8.04(d, J=5.3Hz, 1H), 7.57(m, 2H), 7.48(s, 1H), 7.43(m, 4H), 7.30(m, 1H), 7.18(m, 2H), 6.70(br, 1H), 6.28(d, J=5.3Hz, 1H), 5.12(m, 1H), 3.71(s, 2H), 3.65(m, 3H), 2.94(s, 6H), 1.57(d, J=7.0Hz, 3H) |

TABLE 10-continued
| Example | | M+1 | H-NMR: (400MHz) δ |
|---|---|---|---|
| B021 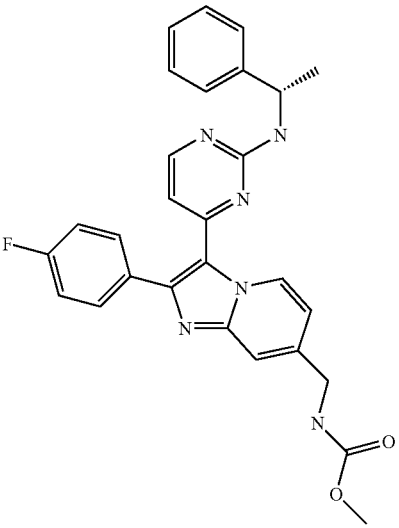 | | 497.1 | CD3OD: 8.48(br, 1H), 8.02(d, J=5.3Hz, 1H), 7.54(m, 2H), 7.41(m, 5H), 7.23(m, 1H), 7.17(m, 2H), 6.61(br, 1H), 6.23(d, J=5.5Hz, 1H), 5.07(m, 1H), 4.34(s, 2H), 3.72(s, 3H), 1.55(d, J=7.1Hz, 3H) |
| B022 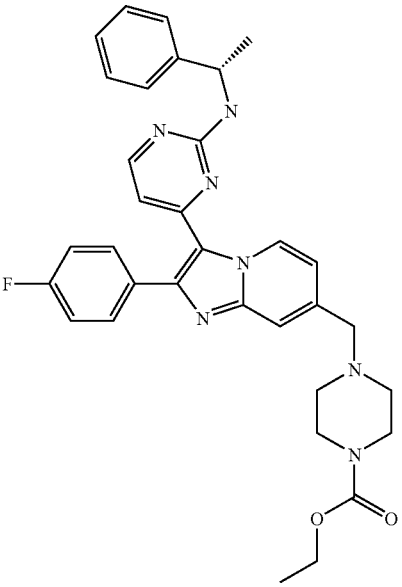 | | 580.2 | CD3OD: 8.60(br, 1H), 8.05(d, J=5.6Hz, 1H), 7.57(m, 2H), 7.53(s, 1H), 7.43(m, 4H), 7.28(m, 1H), 7.18(m, 2H), 6.80(br, 1H), 6.29(d, J=5.3Hz, 1H), 5.12(m, 1H), 4.14(m, 2H), 3.63(s, 2H), 3.53(m, 4H), 2.49(m, 4H), 1.57(d, J=7.0Hz, 3H), 1.25(m, 3H) |
| B023 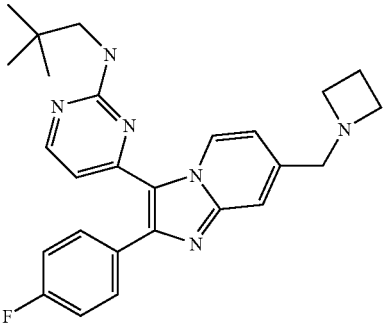 | | 445.2 | CD3OD: 9.62(br, 1H), 8.05(d, J=5.3Hz, 1H), 7.61(m, 2H), 7.59(s, 1H), 7.21(m, 2H), 7.05(m, 1H), 6.31(d, J=5.3Hz, 1H), 3.78(s, 2H), 3.42(m, 4H), 3.36(s, 2H), 2.21(m, 2H), 1.01(s, 9H) |

TABLE 10-continued

| Example | M+1 | H-NMR: (400MHz) δ |
|---|---|---|
| B024 | 447.2 | CD3OD: 9.62(br, 1H), 8.05(d, J=5.2Hz, 1H), 7.61(m, 3H), 7.21(m, 2H), 7.15(m, 1H), 6.31(d, J=5.3Hz, 1H), 3.97(s, 2H), 3.00(m, 1H), 1.27(d, J=6.3Hz, 6H), 1.01(s, 9H) |
| B025 | 419.1 | CD3OD: 9.42(m, 1H), 8.09(d, J=5.1Hz, 1H), 7.61(m, 3H), 7.21(m, 2H), 7.10(m, 1H), 6.35(d, J=5.2Hz, 1H), 3.60(s, 2H), 2.30(s, 6H), 1.48(s, 9H) |
| B026 | 412.0 | CD3OD: 9.64(d, J=7.3Hz, 1H), 8.21(d, J=5.2Hz, 1H), 7.65(m, 5H), 7.32(m, 4H), 7.05(m, 2H), 6.53(d, J=5.3Hz, 1H), 4.74(s, 2H) |

TABLE 10-continued
| Example | M+1 | H-NMR: (400MHz) δ |
|---|---|---|
| B027 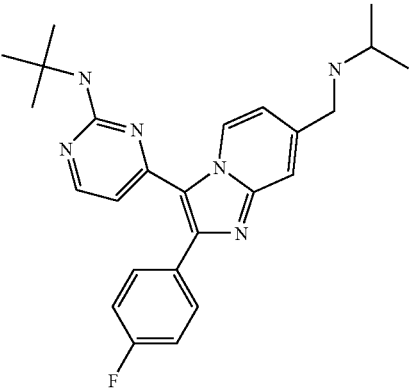 | 433.1 | CD3OD: 9.42(m, 1H), 8.09(d, 1H), 7.62(m, 3H), 7.21(m, 2H), 7.13(m, 1H), 6.36(d, 1H), 4.13(s, 2H), 3.12(m, 1H), 1.48(s, 9H), 1.23(d, 6H) |
| B028 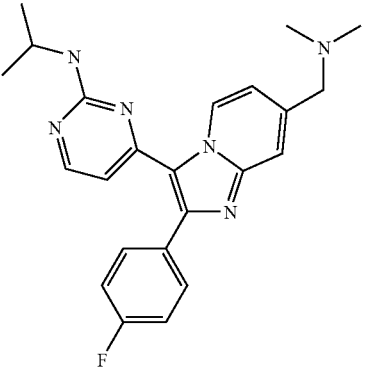 | 405.1 | CD3OD: 9.63(d, J=7.0Hz, 1H), 8.04(d, J=5.2Hz, 1H), 7.62(m, 3H), 7.20(m, 2H), 7.10(m, 1H), 6.30(d, J=5.3Hz, 1H), 4.18(m, 1H), 3.62(s, 2H), 2.34(s, 6H), 1.29(d, J=6.4Hz, 6H) |
| B029 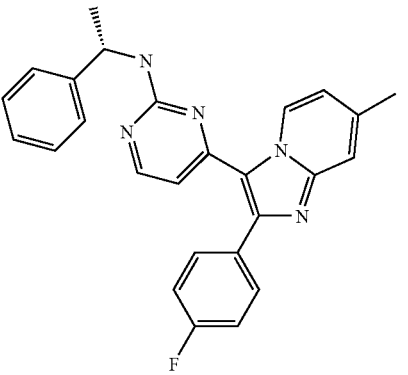 | 424.1 | CDCl3: 9.60(br, 1H), 8.08(d, J=5.2Hz, 1H), 7.63(m, 2H), 7.45(m, 6H), 7.11(m, 2H), 6.41(d, J=5.4Hz, 1H), 5.63(m, 1H), 5.21(m, 1H), 2.42(s, 3H), 1.63(d, J=7.1Hz, 3H) |

TABLE 10-continued

| Example | M+1 | H-NMR: (400MHz) δ |
|---|---|---|
| B030 | 390.1 | CDCl3: 9.42(br, 1H), 8.08(d, J=5.1Hz, 1H), 7.66(m, 2H), 7.46(s, 1H), 7.14(m, 2H), 6.78(m, 1H), 6.42(d, J=5.3Hz, 1H), 5.28(br, 1H), 3.38(d, J=6.3Hz, 2H), 2.48(s, 3H), 1.06(s, 9H) |
| B031 | 417.1 | CD3OD: 9.60(d, J=7.0Hz, 1H), 8.02(d, J=5.3Hz, 1H), 7.61(m, 2H), 7.53(s, 1H), 7.20(m, 2H), 7.02(m, 1H), 6.30(d, J=5.4Hz, 1H), 4.17(m, 1H), 3.74(s, 2H), 3.38(m, 4H), 2.17(m, 2H), 1.28(d, J=6.4Hz, 6H) |
| B032 | 419.1 | CD3OD: 9.61(d, J=7.0Hz, 1H), 8.01(d, J=5.3Hz, 1H), 7.60(m, 3H), 7.20(m, 2H), 7.11(m, 1H), 6.28(d, J=5.3Hz, 1H), 4.16(m, 1H), 3.90(s, 2H), 2.90(m, 1H), 1.28(d, J=6.4Hz, 6H), 1.16(d, J=6.2Hz, 6H) |

TABLE 10-continued

| Example | M+1 | H-NMR: (400MHz) δ |
|---|---|---|
| B033 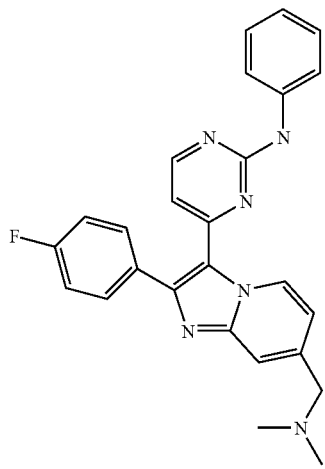 | 439.1 | CD3OD: 9.64(d, J=7.3Hz, 1H), 8.21(d, J=5.2Hz, 1H), 7.65(m, 5H), 7.32(m, 4H), 7.05(m, 2H), 6.53(d, J=5.3Hz, 1H), 4.74(s, 2H) |

Other EXAMPLES of the invention are shown in the following TABLE 11. These EXAMPLES are made similarly to the compounds and Schemes shown above.

TABLE 11

| EXAMPLE | M+1 | NMR(CDCl3) |
|---|---|---|
| C001 | 479.4 | (d, J=6.9Hz, 3H), 2.2(qn, J=7.0Hz, 2H), 3.3(t, J=7.0Hz, 4H), 3.6(s, 2H), 5.2(qn J=6.9Hz, 1H), 5.8(broad, 1H), 6.4(d, J=5.3Hz, 1H), 6.6(broad, 1H), 7.1(m, 2H), 7.3(m, 1H), 7.4(m, 5H), 7.6(m, 2H), 8.1(d, J=5.2Hz, 1H), 8.7(broad, 1H). |
| C002 | 422.3 | 1.6(d, J=7.0Hz, 3H), 1.8(broad, 4H), 2.6(broad, 4H), 3.7(broad, 2H), 5.2(qn J=7.0Hz, 1H), 5.6(broad, 1H), 6.4(d, J=5.2Hz, 1H), 6.7(broad, 1H), 7.1(m, 2H), 7.3(m, 1H), 7.4(m, 5H), 7.6(m, 2H), 8.1(d, J=5.2Hz, 1H), 8.7(broad, 1H). |

TABLE 11-continued
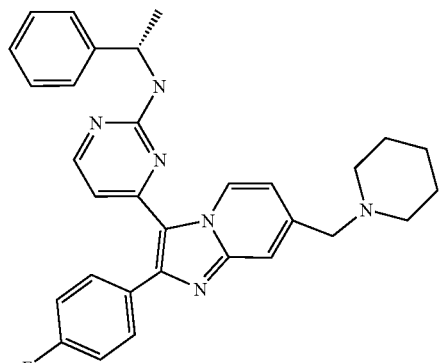
C003
507.4  1.5(m, 2H), 1.6(d, J=6.9Hz, 3H), 1.6–1.8(broad, 4H), 2.4 (broad, 4H), 3.5(s, 2H), 5.2(qn J=6.9Hz, 1H), 5.6(broad, 1H), 6.4(d, J=5.3Hz, 1H), 6.7(broad, 1H), 7.1(m, 2H), 7.3(m, 1H), 7.4 (m, 4H), 7.6(m, 3H), 8.1(d, J=5.3Hz, 1H), 8.7(broad, 1H).
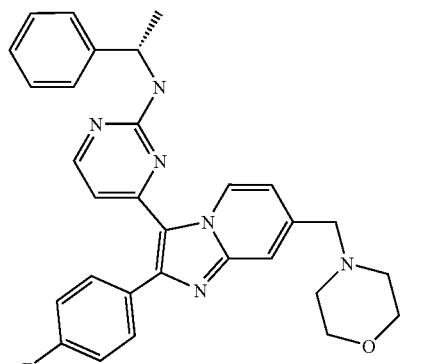
C004
509.4  1.6(d, J=6.9Hz, 3H), 2.5(m, 4H), 3.6(s, 2H), 3.8(m, 4H), 5.2 (qn J=6.9Hz, 1H), 5.8(broad, 1H), 6.4(d, J=5.2Hz, 1H), 6.7 (broad, 1H), 7.1(m, 2H), 7.3(m, 1H), 7.4(m, 4H), 7.6(m, 3H), 8.1 (d, J=5.2Hz, 1H), 8.7(broad, 1H).
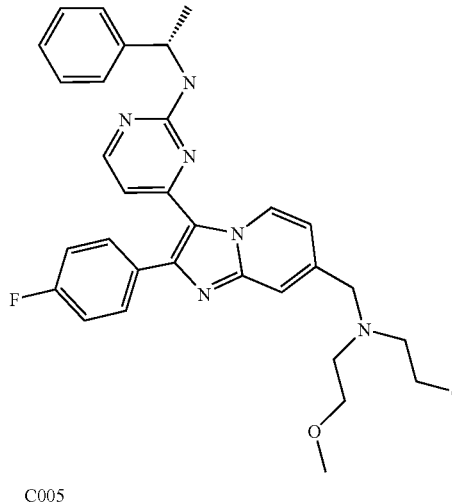
C005
555.4  1.6(d, J=7.1Hz, 3H), 2.8(d, J=5.7Hz, 4H), 3.4(s, 6H), 3.5(t, J=5.8Hz, 4H), 3.8(s, 2H), 5.2 (qn J=7.0Hz, 1H), 5.7(broad, 1H), 6.4(d, J=5.3Hz, 1H), 6.7 (broad, 1H), 7.1(m, 2H), 7.3(m, 1H), 7.4(m, 4H), 7.6(m, 3H), 8.1 (d, J=5.3Hz, 1H), 8.7(broad, 1H).

TABLE 11-continued
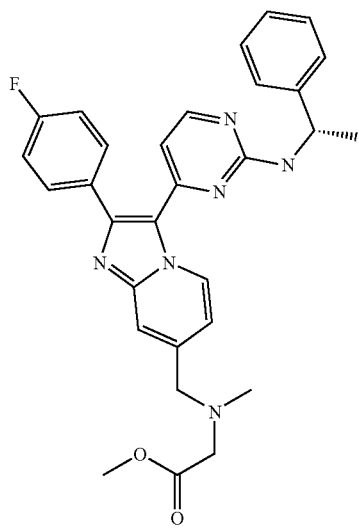
C006
525.4   1.6(d, J=6.9Hz, 3H), 2.4(s, 3H), 3.4(s, 2H), 3.8(m, 5H), 5.2(qn J=6.8Hz, 1H), 5.8(broad, 1H), 6.4(d, J=5.2Hz, 1H), 6.7(broad, 1H), 7.1(m, 2H), 7.3(m, 1H), 7.4(m, 4H), 7.6(m, 3H), 8.1(d, J=5.2Hz, 1H), 8.7(broad, 1H).
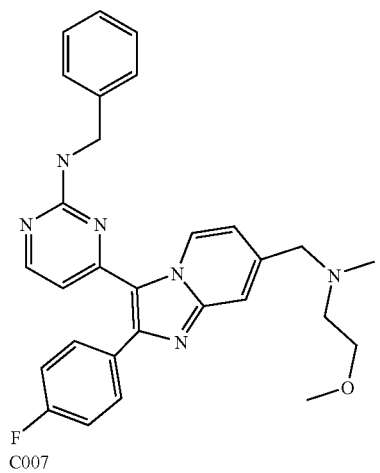
C007
497.4   2.2(s, 3H), 2.7(2.7, 2H), 3.4(s, 3H), 3.6(t, J=5.7Hz, 2H), 3.7(s, 2H), 4.8(d, J=5.9Hz, 2H), 5.8 (broad, 1H), 6.5(d, J=5.3Hz, 1H), 6.8(broad, 1H), 7.1(m, 2H), 7.4(m, 5H), 7.6(m, 3H), 8.1(d, J=5.2Hz, 1H), 9.1(broad, 1H).
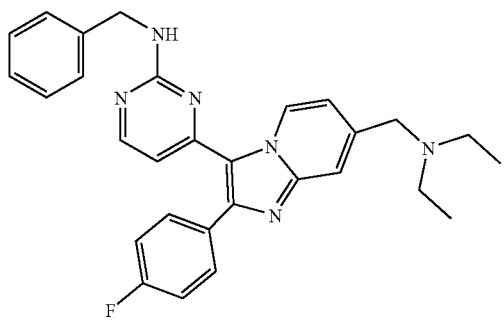
C008
481.5   1.1(broad, 6H), 2.6(broad, 4H), 3.6(s, 2H), 4.8(d, J=5.9Hz, 2H), 5.8(broad, 1H), 6.5(d, J=5.3Hz, 1H), 6.8(broad, 1H), 7.1(m, 2H), 7.3(m, 1H), 7.4(m, 4H), 7.6(m, 3H), 8.1(d, J=5.2Hz, 1H), 9.1 (broad, 1H).

TABLE 11-continued
| | | |
|---|---|---|
| 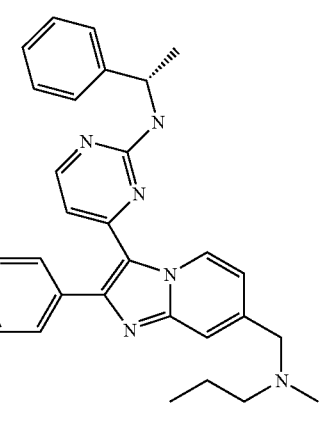 C009 | 495.4 | 1.0(t, J=7.2Hz, 3H), 1.6(m, 2H), 1.6(d, J=6.8Hz, 3H), 2.2(s, 3H), 4.4(t, J=7.2Hz, 2H), 3.6(s, 2H), 5.2(qn J=6.8Hz, 1H), 5.8(broad, 1H), 6.4(d, J=5.3Hz, 1H), 6.7(broad, 1H), 7.1(m, 2H), 7.3(m, 1H), 7.4(m, 5H), 7.6(m, 2H), 8.1(d, J=5.3Hz, 1H), 8.7(broad, 1H). |
| 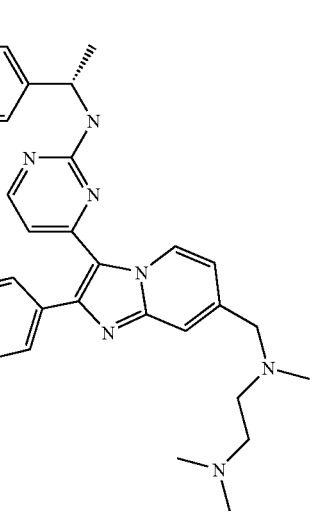 C010 | 524.4 | 1.6(d, J=7.0Hz, 3H), 2.29(s, 2H), 2.33(s, 3H), 2.6(m, 4H), 3.6(s, 2H), 5.2(qn J=7.0Hz, 1H), 5.6(d, J=6.4Hz, 1H), 6.4(d, J=5.3Hz, 1H), 6.7(broad, 1H), 7.1(m, 2H), 7.3(m, 1H), 7.4(m, 5H), 7.6(m, 2H), 8.1(d, J=5.3Hz, 1H), 8.7(broad, 1H). |
| 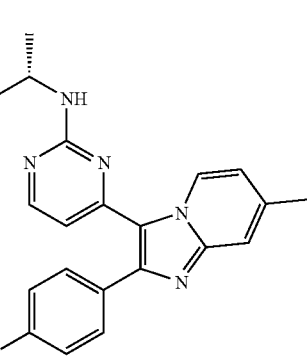 C011 | 945.8 | |

TABLE 11-continued
| | | | |
|---|---|---|---|
| C012 | 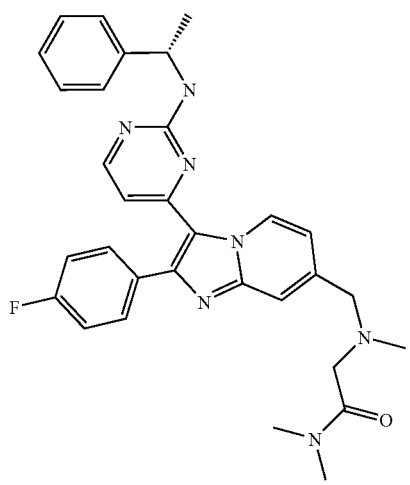 | 538.4 | 1.6(d, J=6.8Hz, 3H), 2.4(s, 3H), 3.0(s, 3H), 3.1(s, 3H), 3.3(s, 2H), 3.7(s, 2H), 5.2(qn J=6.8Hz, 1H), 5.8(broad, 1H), 6.4(d, J=5.4Hz, 1H), 6.7(broad, 1H), 7.1(m, 2H), 7.3(m, 1H), 7.4(m, 4H), 7.6(m, 3H), 8.1(d, J=5.3Hz, 1H), 8.7(broad, 1H). |
| C013 | 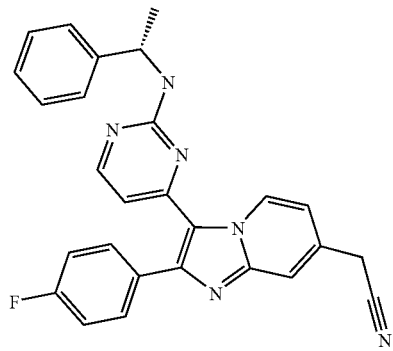 | | 1.6(d, J=6.9Hz, 3H), 3.4(s, 2H), 5.2(qn J=6.9Hz, 1H), 5.6(broad, 1H), 6.4(d, J=5.3Hz, 1H), 6.6 (broad, 1H), 7.1(m, 2H), 7.3(m, 1H), 7.4(m, 4H), 7.6(m, 3H), 8.1 (d, J=5.3Hz, 1H), 8.7(broad, 1H). |
| C014 | 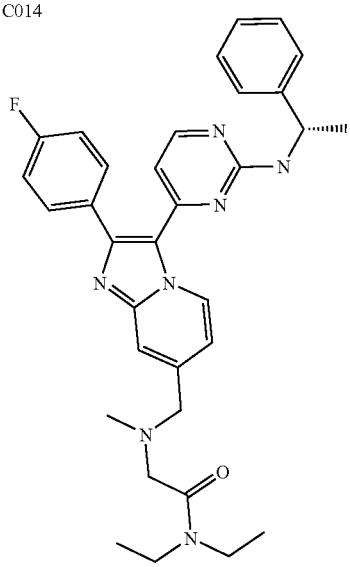 | 566.2 | 1.0(m, 6H), 1.6(d, J=6.9Hz, 3H), 2.4(s, 3H), 3.3(s 2H), 3.4 (m, 4H), 3.7(s, 2H), 5.2(qn J= 6.9Hz, 1H), 5.7(broad, 1H), 6.4(d, J=5.2Hz, 1H), 6.7(broad, 1H), 7.1(m, 2H), 7.3(m, 1H), 7.4(m, 4H), 7.6(m, 3H), 8.1(d, J= 5.2Hz, 1H), 8.7(broad, 1H). |

TABLE 11-continued
| | | | |
|---|---|---|---|
| C015 | 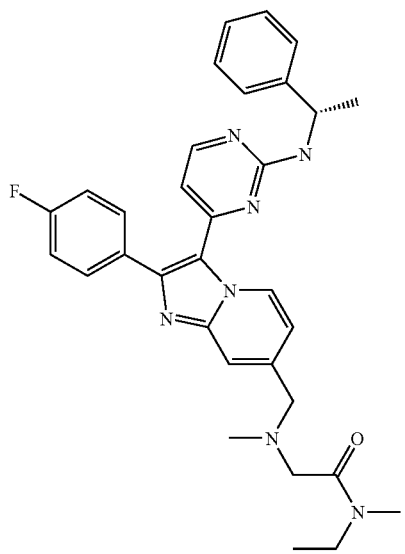 | 552.2 | 1.1(m, 3H), 1.6(d, J=6.9Hz, 3H), 2.4(2s, 3H), 2.9 & 3.1(2s 2H), 3.3(2s, 2H), 3.5(m, 2H), 3.7 (m, 2H), 5.2(qn J=6.7Hz, 1H), 5.7(broad, 1H), 6.4(d, J=5.2Hz, 1H), 6.7(broad, 1H), 7.1(m, 2H), 7.3(m, 1H), 7.4(m, 4H), 7.6(m, 3H), 8.1(d, J=5.2Hz, 1H), 8.7(broad, 1H). |
| C016 | 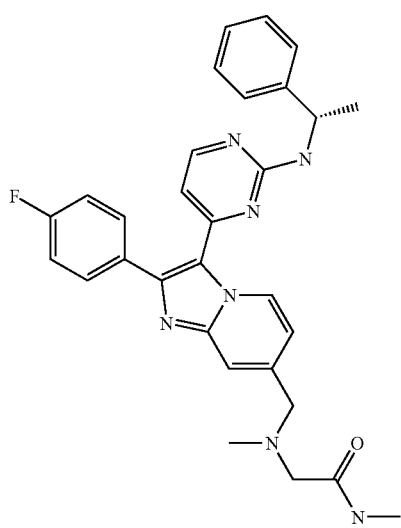 | 524.1 | 1.6(d, J=6.8Hz, 3H), 2.4(s, 3H), 2.9(d, J=5.1Hz, 2H), 3.1(s, 3H), 3.7(s, 2H), 5.2(qn J=6.9Hz, 1H), 5.7(broad, 1H), 6.4(d, J=5.3Hz, 1H), 6.5(broad, 1H), 7.1(m, 3H), 7.3(m, 1H), 7.4(m, 4H), 7.6(m, 3H), 8.1(d, J=5.3Hz, 1H), 8.7(broad, 1H). |

| | | | |
|---|---|---|---|
| C017 | 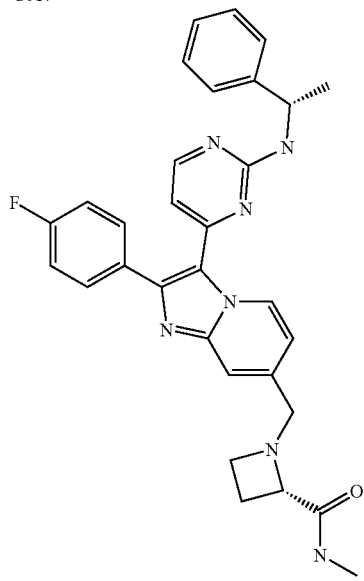 | 536.2 | 1.6(d, J=6.8Hz, 3H), 2.2(m, 2H), 2.5(m, 1H), 2.8(d, J=5.1Hz, 3H), 3.5(m, 1H), 3.6(m, 1H), 3.8(m, 2H), 5.2(qn J=6.9Hz, 1H), 5.7(broad, 1H), 6.4(d, J=5.2Hz, 1H), 6.5(broad, 1H), 7.1(m, 3H), 7.3(m, 1H), 7.4(m, 4H), 7.6(m, 3H), 8.1(d, J=5.2Hz, 1H), 8.7(broad, 1H). |
| C018 | 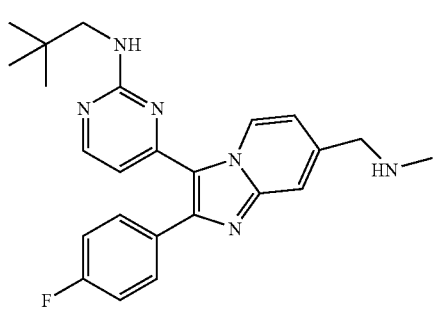 | 419.2 | 1.01(s, 9h), 2.46(s, 3H), 3.34(s, 2H), 3.87(s, 2H), 6.32(d, J=5.3Hz, iH), 7.11(m, 1H), 7.21(m, 2H), 7.60(m, 3H), 8.05(d, J=5.3Hz, 2H), 9.62(br, 1H), |
| C019 | 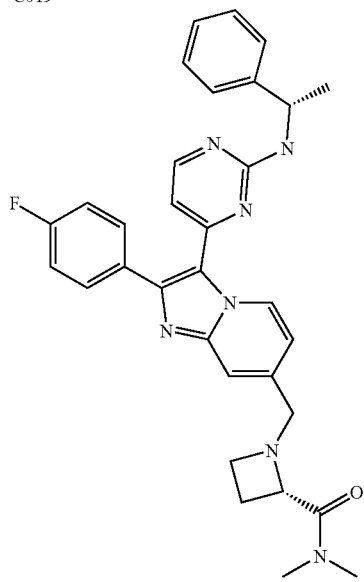 | 550.2 | 1.6(d, J=6.8Hz, 3H), 2.3(m, 2H), 2.8(m, 7H), 3.4(m, 1H), 3.5(m, 1H), 4.0(m, 2H), 5.2(qn J=7.0Hz, 1H), 5.7(broad, 1H), 6.4(d, J=5.3Hz, 1H), 6.5(broad, 1H), 7.1(m, 3H), 7.3(m, 1H), 7.4(m, 5H), 7.6(m, 2H), 8.1(d, J=5.3Hz, 1H), 8.8(broad, 1H). |

TABLE 11-continued
| Ex. | STRUCTURE | ES+ (M+1) |
|---|---|---|
| D01 | 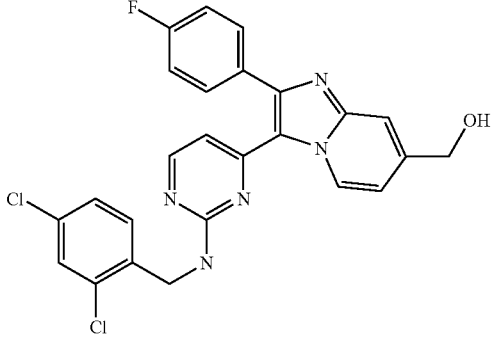 | 494.1 |
| D02 | 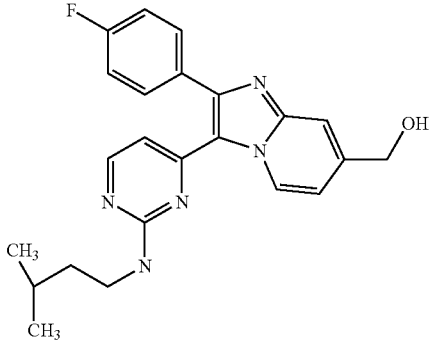 | 406.2 |
| D03 | 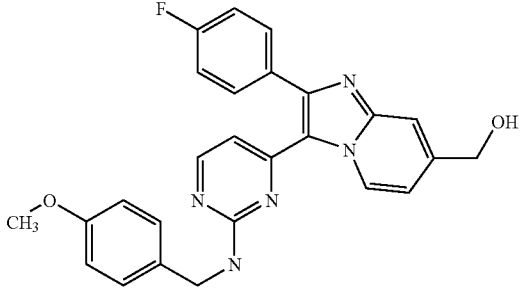 | 456.2 |
| D04 | 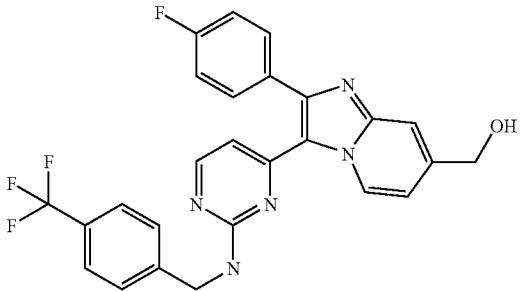 | 494.2 |

TABLE 11-continued

| | | |
|---|---|---|
| D05 | (structure) | 483.3 |
| D06 | (structure) | 416.1 (ES−) |
| D07 | (structure) | 454.3 |
| D08 | (structure) | 592.3 |
| D09 | (structure) | 440.3 |

TABLE 11-continued
| | | |
|---|---|---|
| D10 | 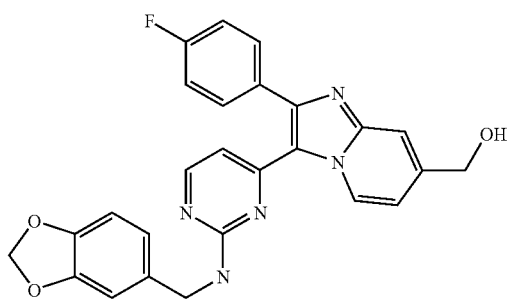 | 470.2 |
| D11 | 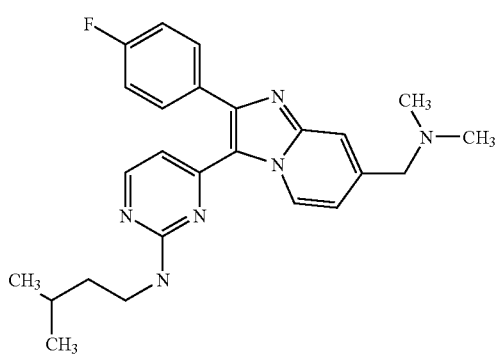 | 433.3 |
| D12 | 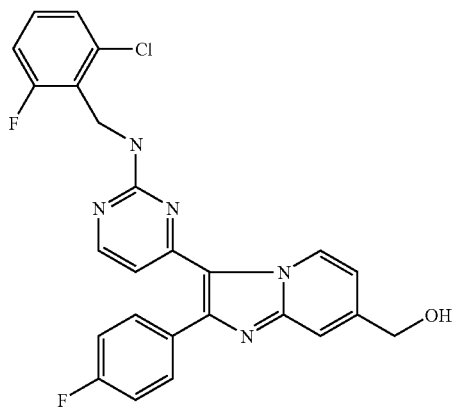 | 478.2 |
| D13 | 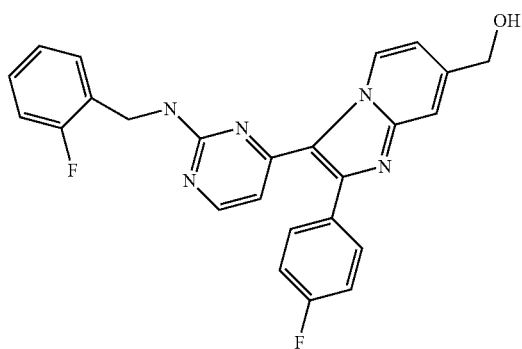 | 444.2 |

TABLE 11-continued
| | | |
|---|---|---|
| D14 | 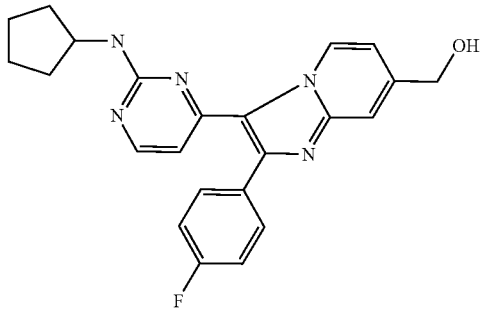 | 404.2 |
| D15 | 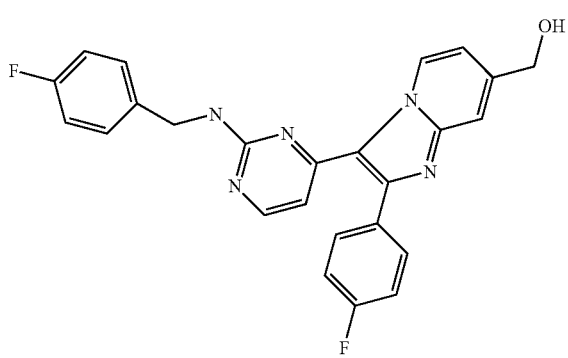 | 444.2 |
| D16 | 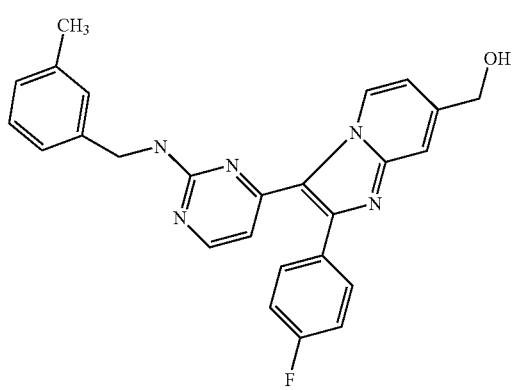 | 440.2 |
| D17 | 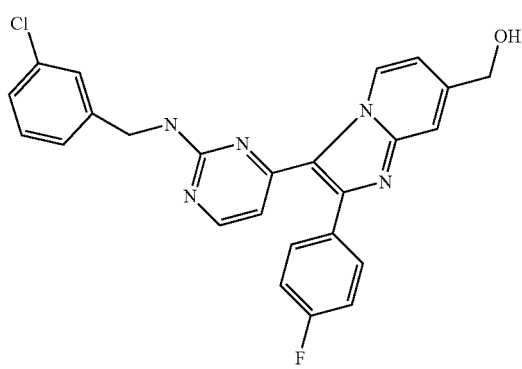 | 460.3 |

TABLE 11-continued

| | | |
|---|---|---|
| D18 | (structure) | 420.3 |
| D19 | (structure) | 486.2 |
| D20 | (structure) | 456.2 |
| D21 | (structure) | 510.2 |

TABLE 11-continued
| | | |
|---|---|---|
| D22 | 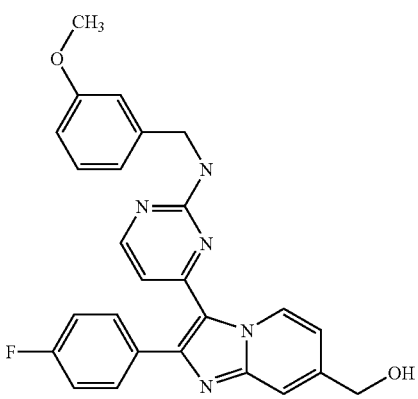 | 456.2 |
| D23 | 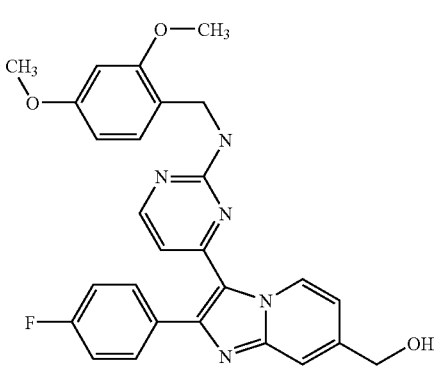 | 486.2 |
| D24 | 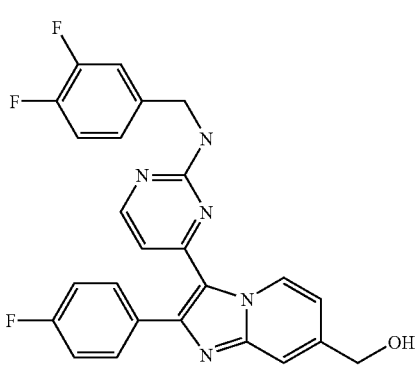 | 462.3 |
| D25 | 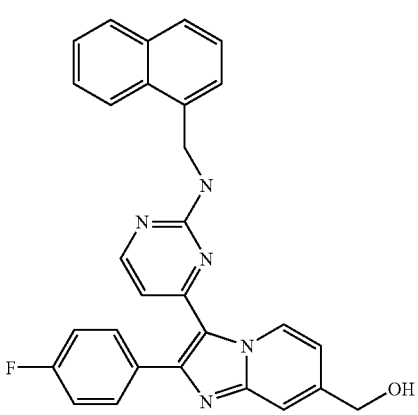 | 476.3 |

TABLE 11-continued
| | | |
|---|---|---|
| D26 | 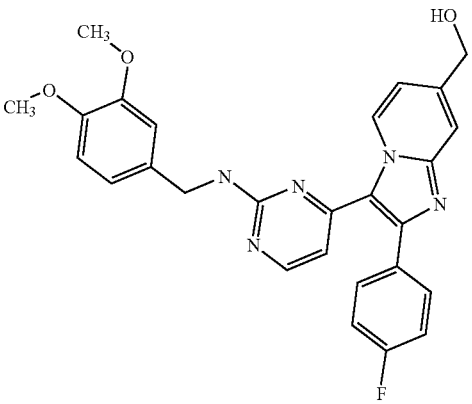 | 486.2 |
| D27 | 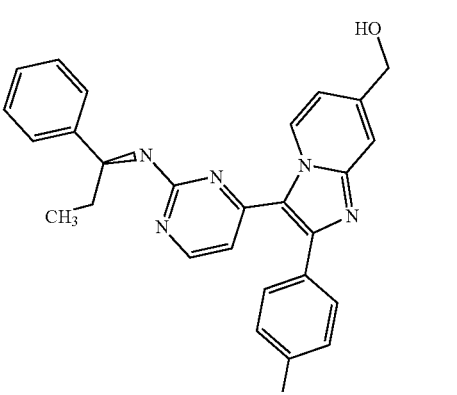 | 454.3 |
| D28 | 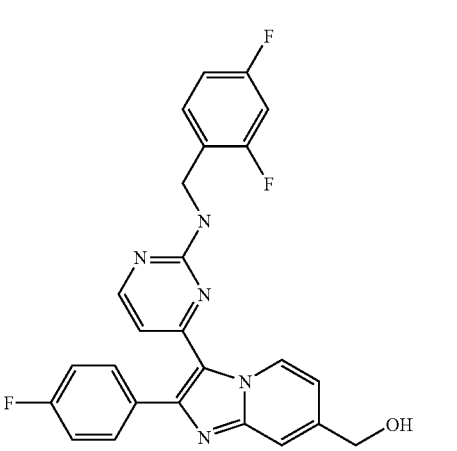 | 462.3 |
| D29 | 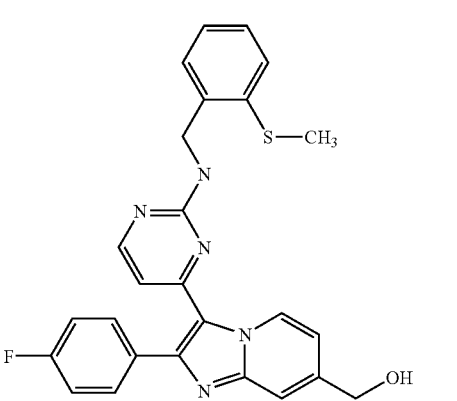 | 472.2 |

TABLE 11-continued
| D30 | 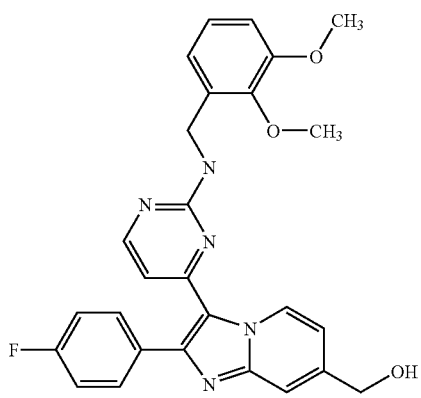 | 486.2 |
| D31 | 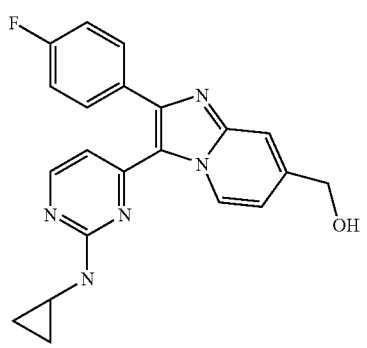 | 376.3 |
| D32 | 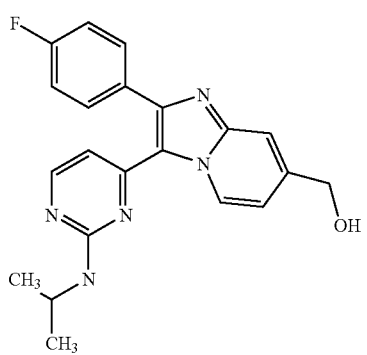 | 378.2 |
| D33 | 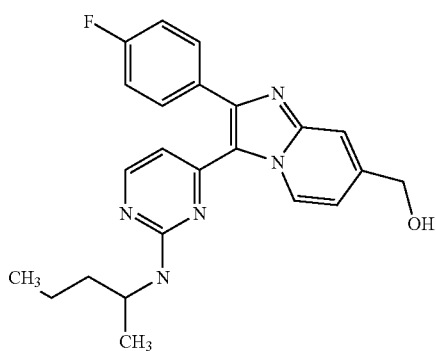 | 406.3 |

TABLE 11-continued

| | | |
|---|---|---|
| D34 | (structure) | 438.6 (ES−) |
| D35 | (structure) | 444.3 |
| D36 | (structure) | 392.3 |
| D37 | (structure) | 406.3 |
| D38 | (structure) | 364.3 |

TABLE 11-continued
| | | |
|---|---|---|
| D39 | 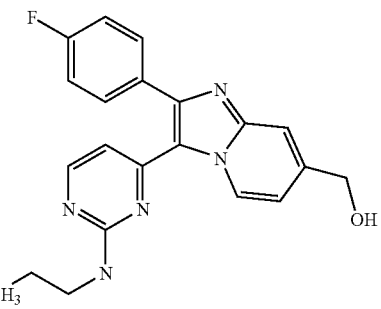 | 378.3 |
| D40 | 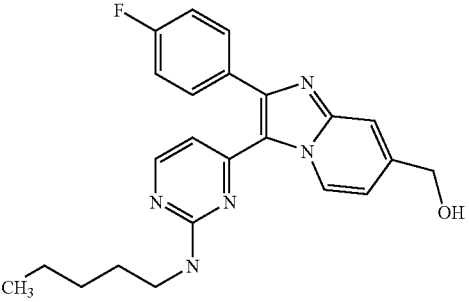 | 406.3 |
| D41 | 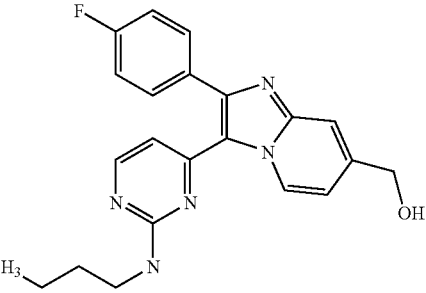 | 392.3 |
| D42 | 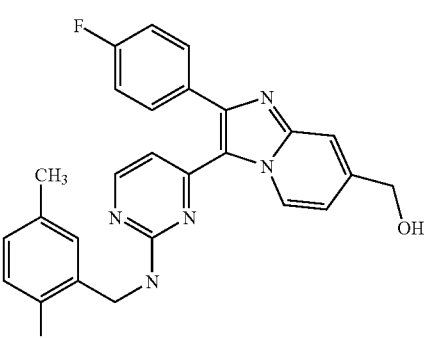 | 454.3 |
| D43 | 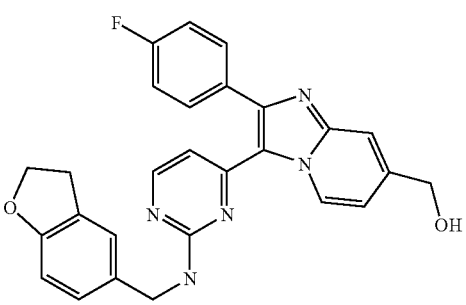 | 468.3 |

TABLE 11-continued
| D44 | 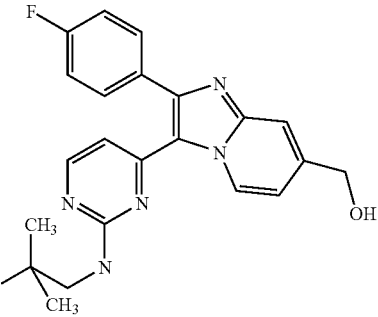 | 408.3 |
| D45 | 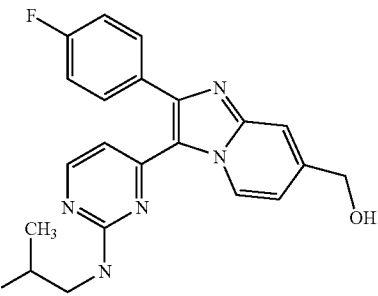 | 394.3 |
| D46 | 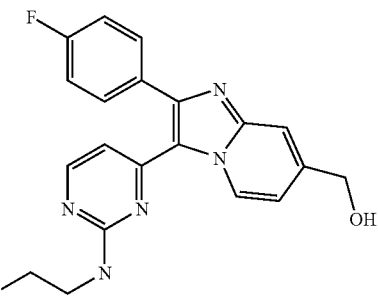 | 380.3 |
| D47 | 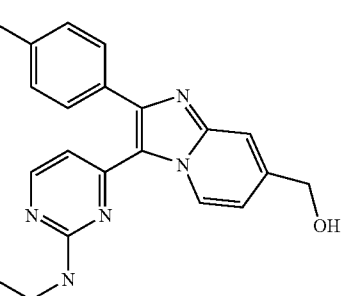 | 390.3 |
| D48 | 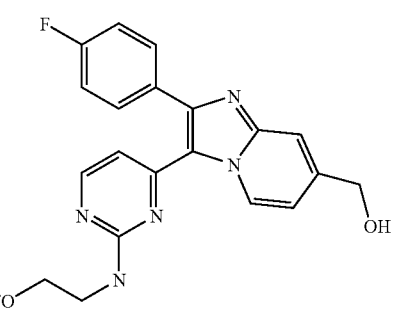 | 394.3 |

TABLE 11-continued
| | | |
|---|---|---|
| D49 | 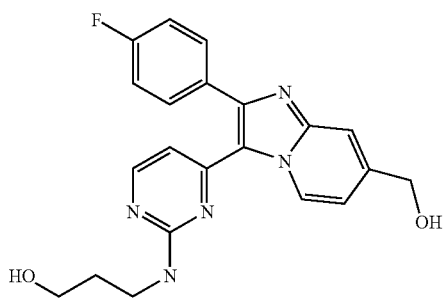 | 349.2 |
| D50 | 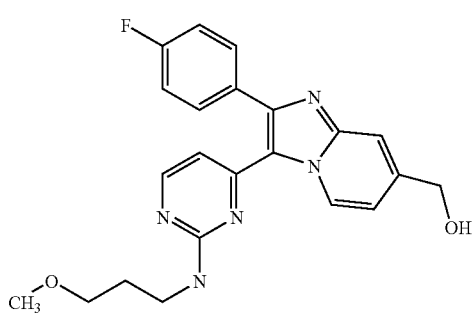 | 408.3 |
| D51 | 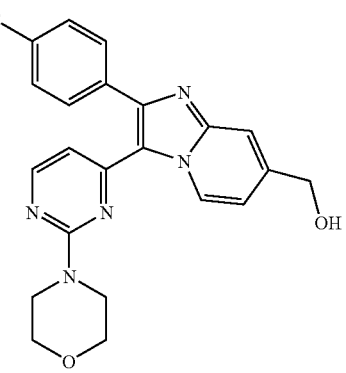 | 406.3 |
| D52 | 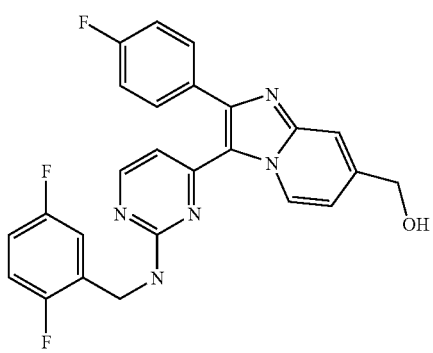 | 462.3 |

TABLE 11-continued
| D53 | 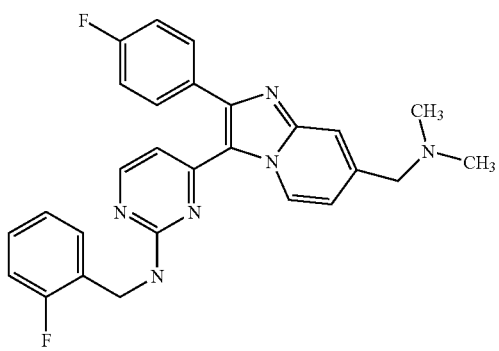 | 471.3 |
| D54 | 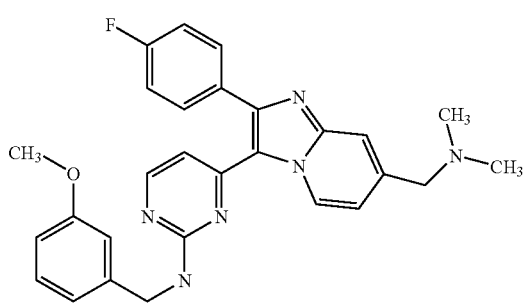 | 483.3 |
| D55 | 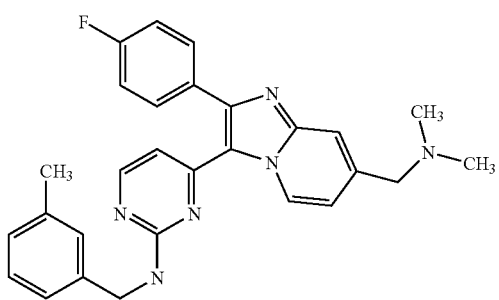 | 467.3 |
| D56 | 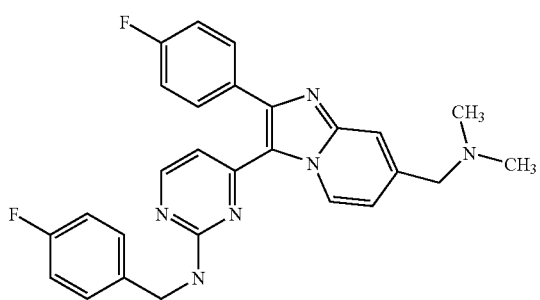 | 471.3 |

TABLE 11-continued

| | | |
|---|---|---|
| D57 | (structure) | 505.3 |
| D58 | (structure) | 513.3 |
| D59 | (structure) | 513.4 |
| D60 | (structure) | 499.3 |

TABLE 11-continued
| | | |
|---|---|---|
| D61 | 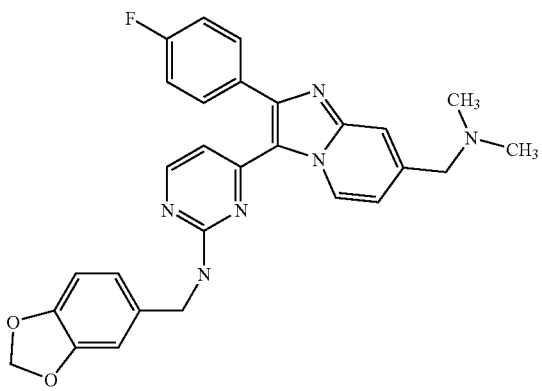 | 497.4 |
| D62 | 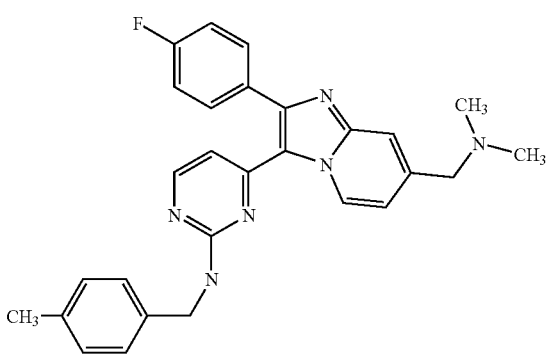 | 467.4 |
| D63 | 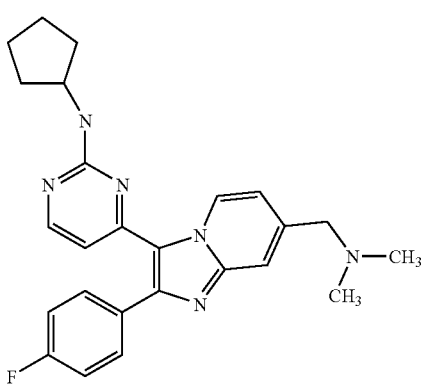 | 431.4 |
| D64 | 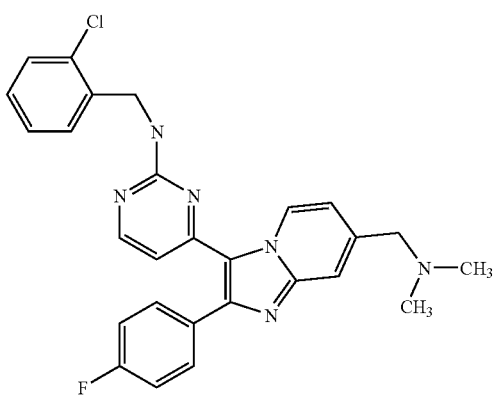 | 487.3 |

TABLE 11-continued

| | | |
|---|---|---|
| D65 | (structure) | 509.4 |
| D66 | (structure) | 363.5 |
| D67 | (structure) | 417.9 (ES−) |
| D68 | (structure) | 405.9 |

TABLE 11-continued
| | | |
|---|---|---|
| D69 | 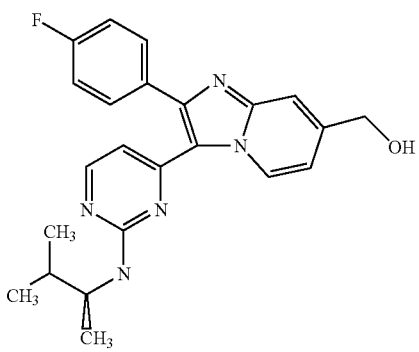 | 405.7 |
| D70 | 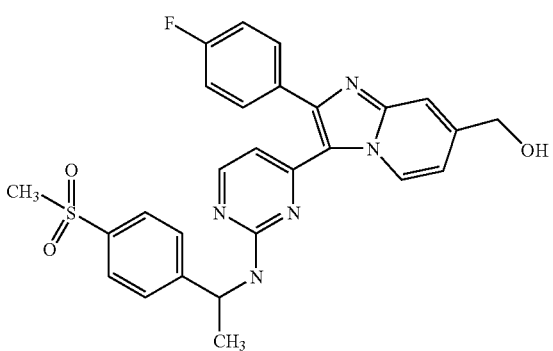 | 517.6 |
| D71 | 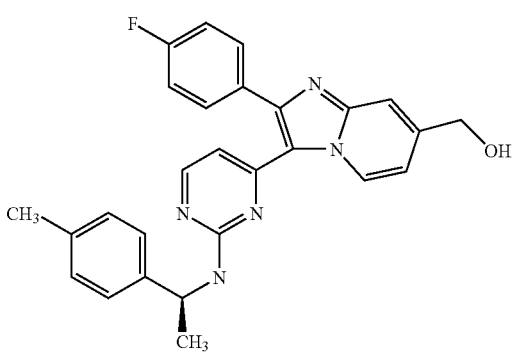 | 453.8 |
| D72 | 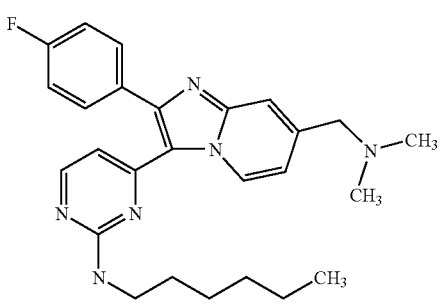 | 446.7 |

TABLE 11-continued

| | | |
|---|---|---|
| D73 | (structure) | 567.7 |
| D74 | (structure) | 553.7 |
| D75 | (structure) | 537.8 |
| D76 | (structure) | 538.4 |
| D77 | (structure) | 551.7 |

TABLE 11-continued
| | | |
|---|---|---|
| D78 | 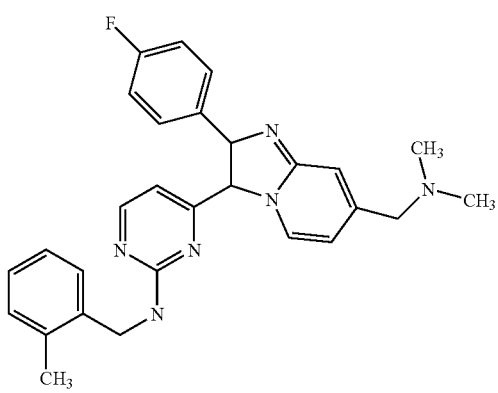 | 466.7 |
| D79 | 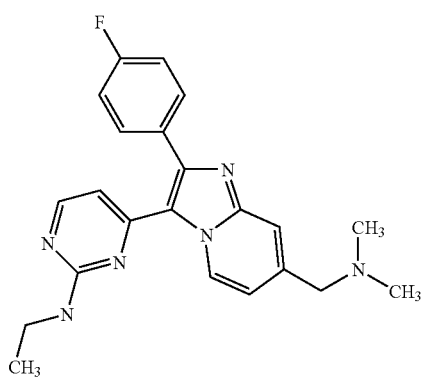 | 390.7 |
| D80 | 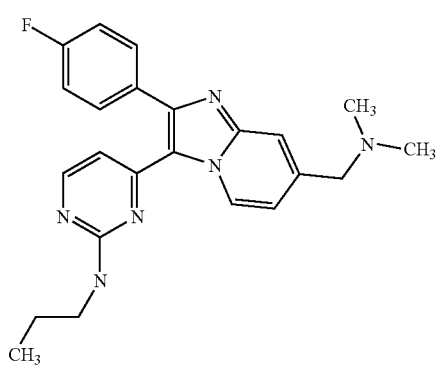 | 404.7 |
| D81 | 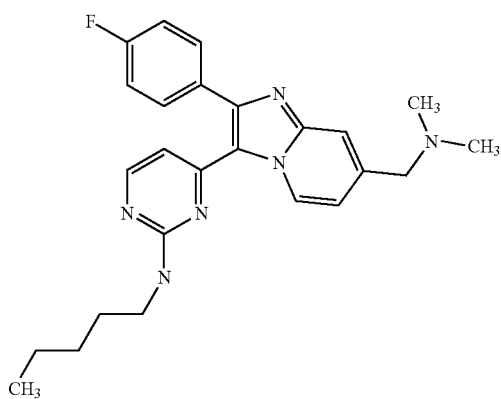 | 432.8 |

TABLE 11-continued

| | | |
|---|---|---|
| D82 | (structure) | 432.6 |
| D83 | (structure) | 402.7 |
| D84 | (structure) | 418.7 |
| D85 | (structure) | 512.7 |

TABLE 11-continued
| | | |
|---|---|---|
| D86 | 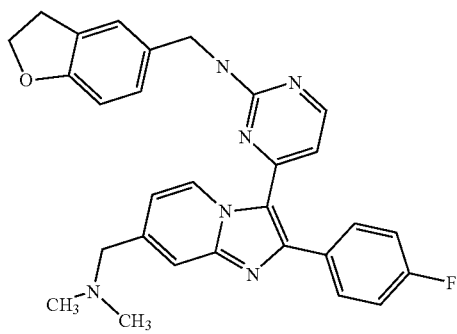 | 494.7 |
| D87 | 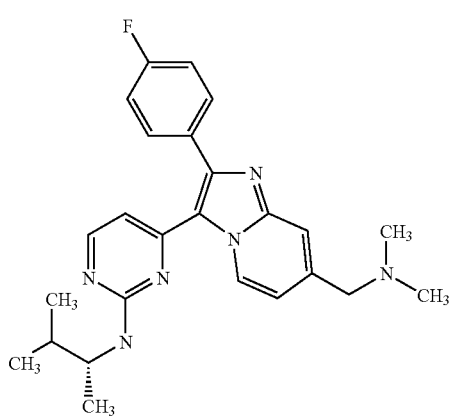 | 432.7 |
| D88 | 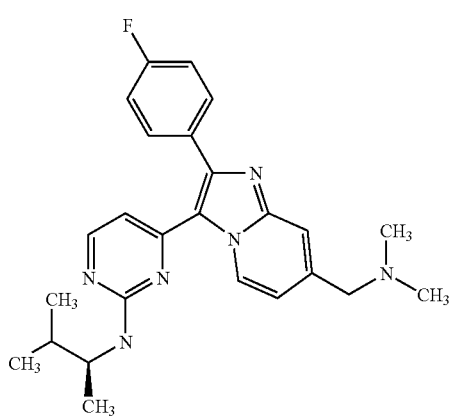 | 432.7 |
| D89 | 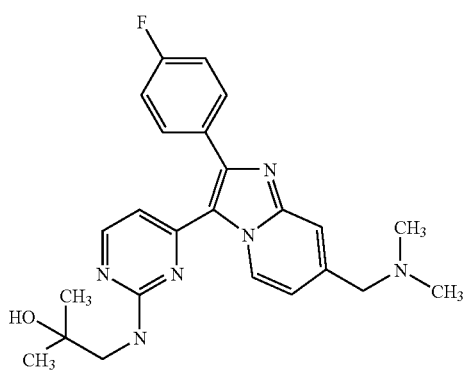 | 434.6 |

TABLE 11-continued

| | | |
|---|---|---|
| D90 | (structure) | 416.7 |
| D91 | (structure) | 420.7 |
| D92 | (structure) | 435.7 |
| D93 | (structure) | 488.6 |

TABLE 11-continued
| | | |
|---|---|---|
| D94 | 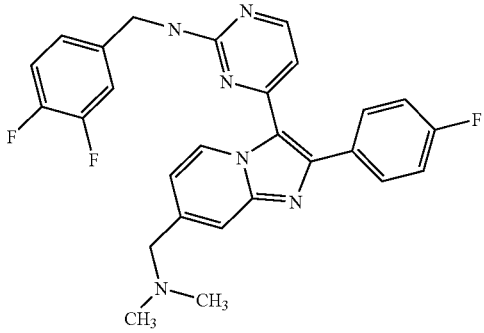 | 488.6 |
| D95 | 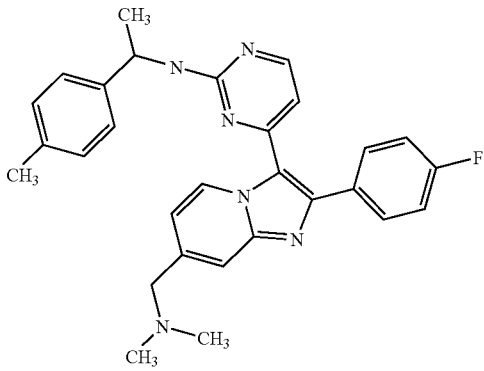 | 480.7 |
| D96 | 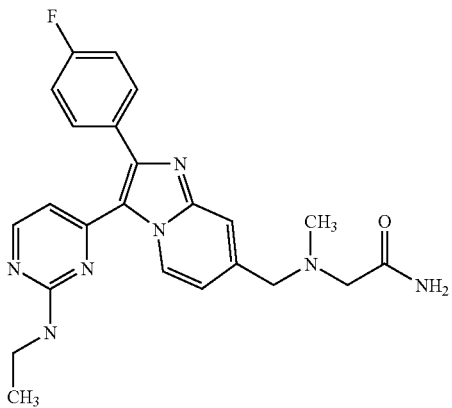 | 433.7 |
| D97 | 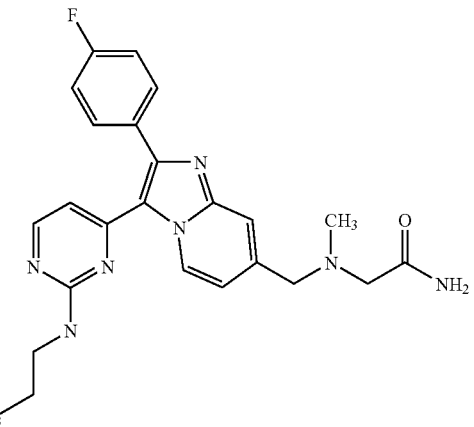 | 447.7 |

TABLE 11-continued
| | | |
|---|---|---|
| D98 | 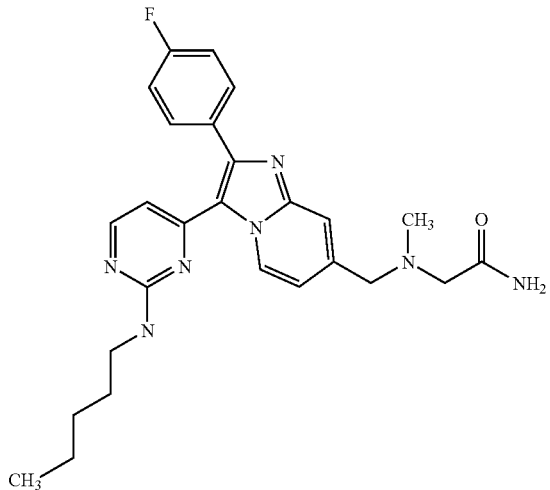 | 475.7 |
| D99 | 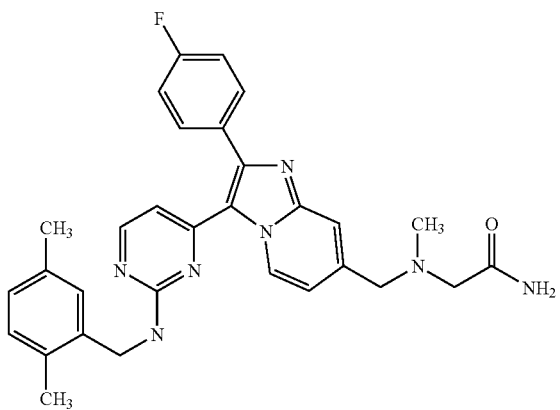 | 523.7 |
| D100 | 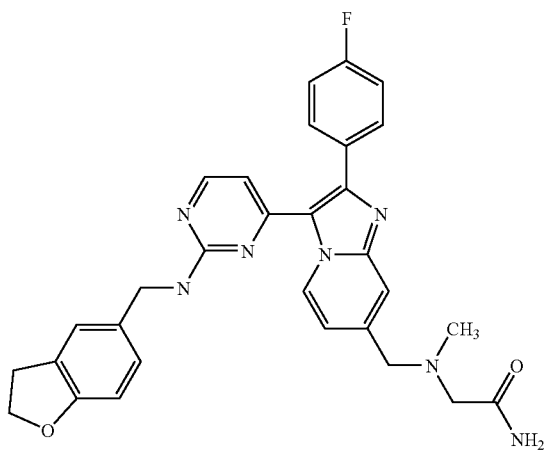 | 537.7 |

TABLE 11-continued
| D101 | 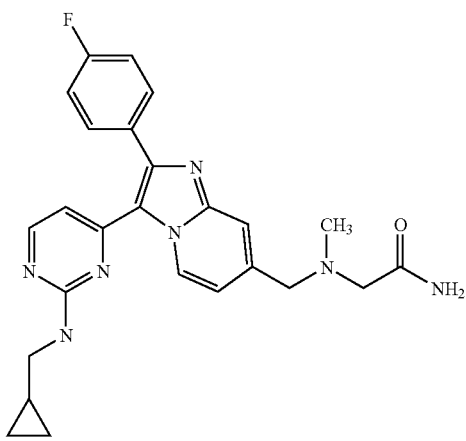 | 459.9 |
| D102 | 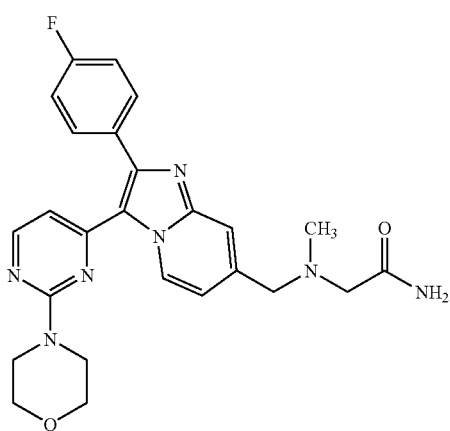 | 475.7 |
| D103 | 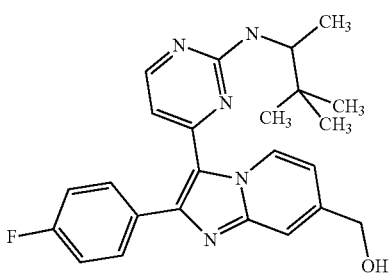 | 418.0 (ES−) |
| D104 | 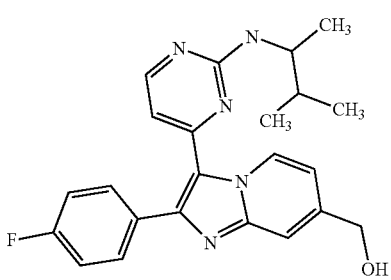 | 406.5 |

TABLE 11-continued
| | | |
|---|---|---|
| D105 | 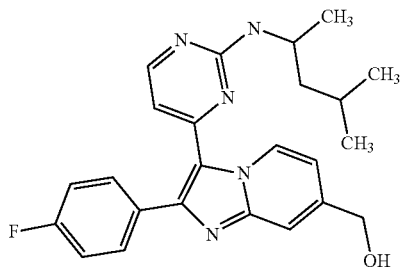 | 420.5 |
| D106 | 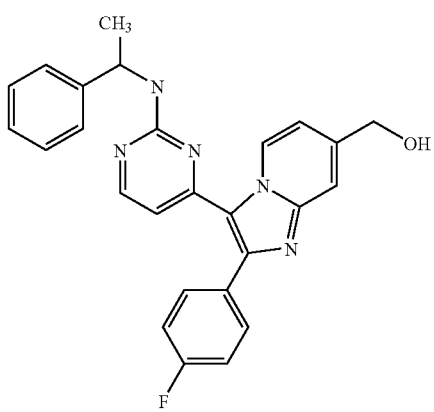 | 452.2 (ES−) |
| D107 | 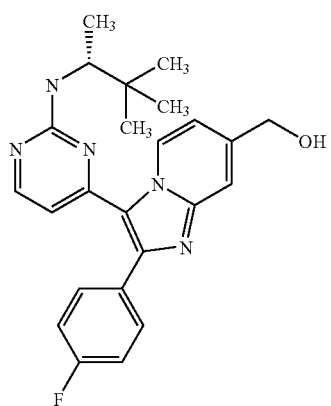 | 420.5 |
| D108 | 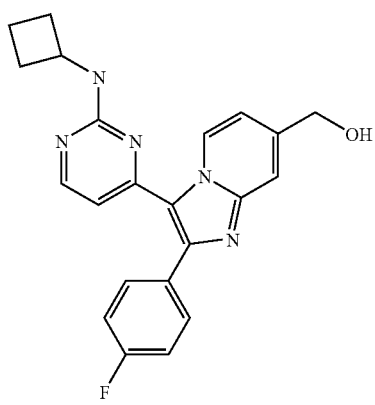 | 390.4 |

TABLE 11-continued
| | | |
|---|---|---|
| D109 | 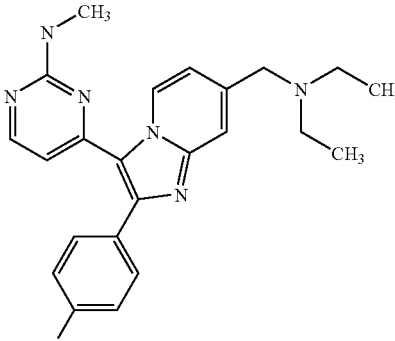 | 405.4 |
| D110 | 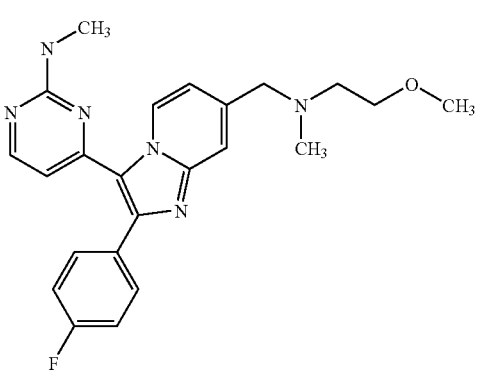 | 419.0 (ES−) |
| D111 | 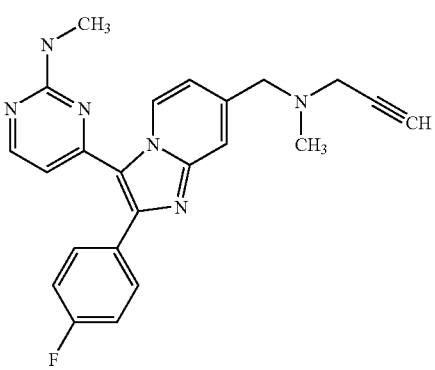 | 401.4 |
| D112 | 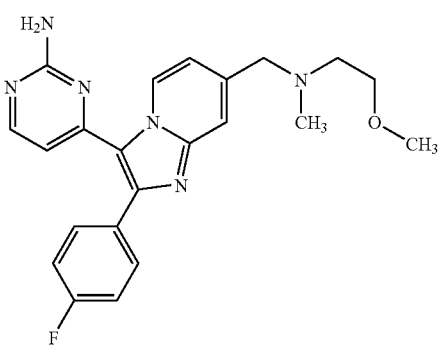 | 407.4 |

TABLE 11-continued

| | | |
|---|---|---|
| D113 | (structure) | 387.4 |
| D114 | (structure) | 407.4 |
| D115 | (structure) | 402.4 |
| D116 | (structure) | 432.5 |

TABLE 11-continued

| D117 | [structure] | 420.4 |
| D118 | [structure] | 459.3 ES −0 |
| D119 | [structure] | 463.5 |
| D120 | [structure] | 475.3 (ES−) |

TABLE 11-continued
| | | |
|---|---|---|
| D121 | 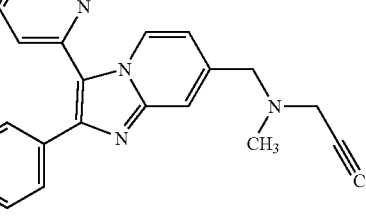 | 457.5 |
| D122 | 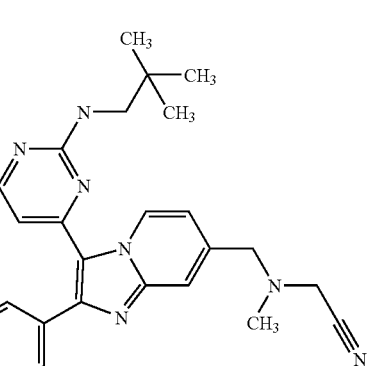 | 458.5 |
| D123 | 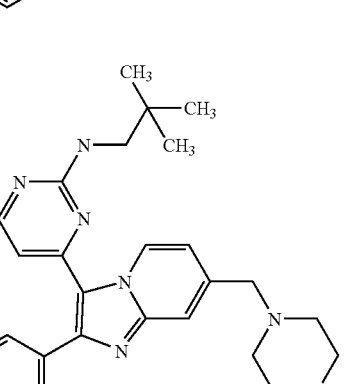 | 488.5 |
| D124 | 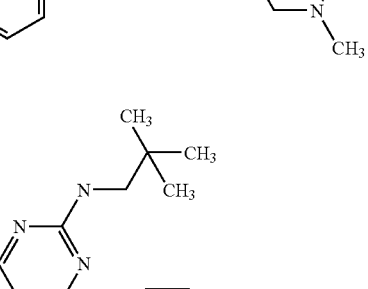 | 476.5 |

TABLE 11-continued
| | | |
|---|---|---|
| D125 | 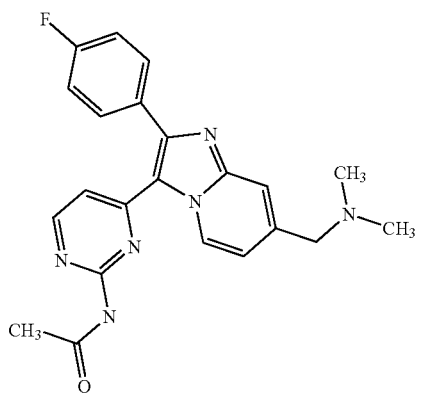 | 405.1 |
| D126 | 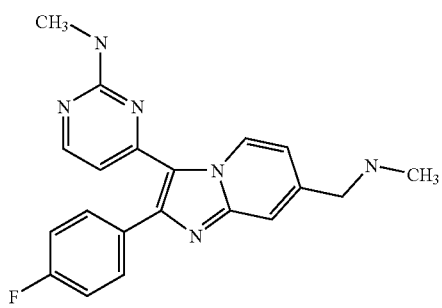 | 363 |
| D127 | 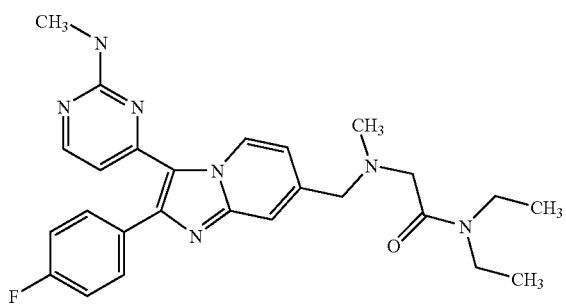 | 475.8 |
| D128 | 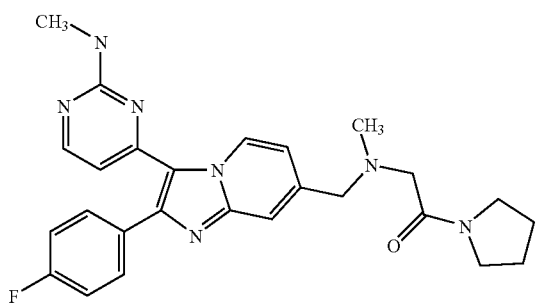 | 473.7 |

TABLE 11-continued
| | | |
|---|---|---|
| D129 | 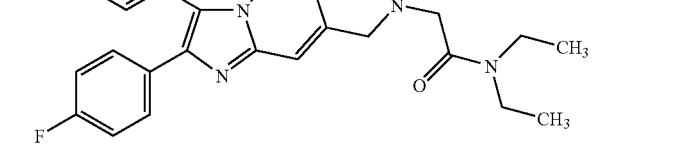 | 531.8 |
| D130 |  | 529.9 |
| D131 | 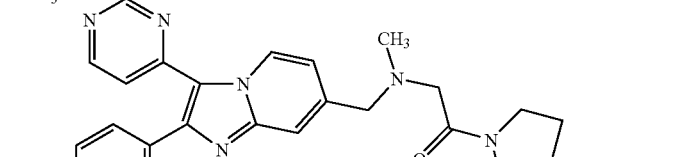 | 478.8 |
| D132 |  | 432.8 |

TABLE 11-continued
| D133 | 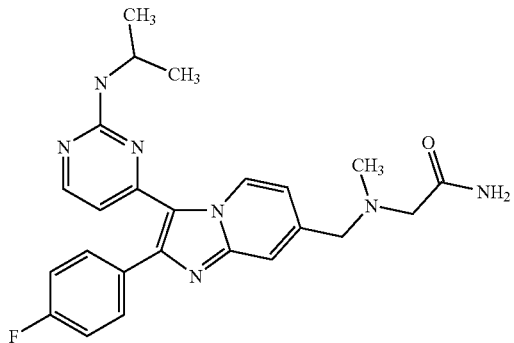 | 447.8 |
| D134 | 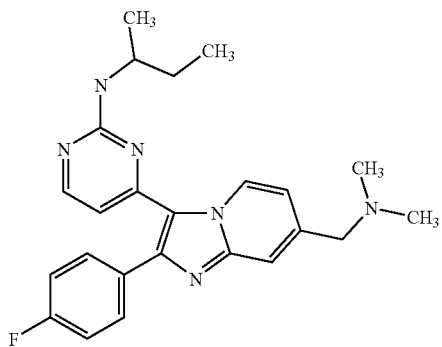 | 418.8 |
| D135 | 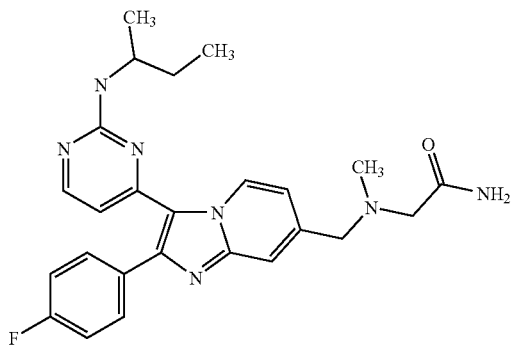 | 461.8 |
| D136 | 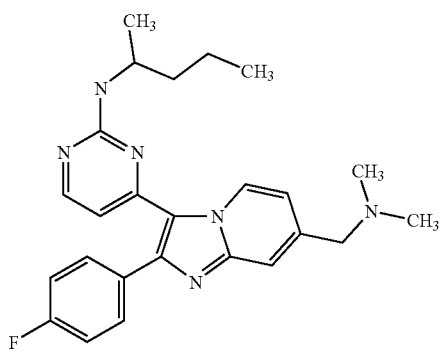 | 432.8 |

TABLE 11-continued
| D137 | 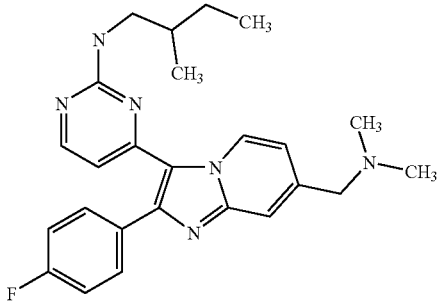 | 432.8 |
| D138 | 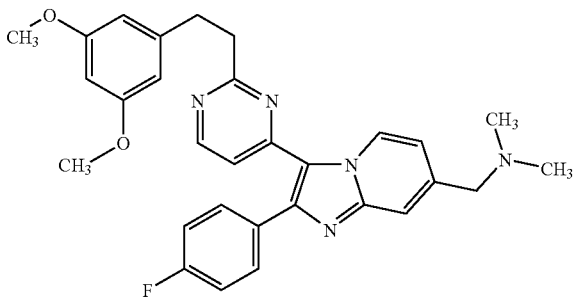 | 512.9 |
| D139 | 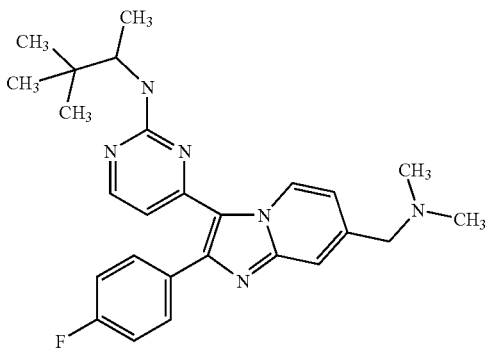 | 446.8 |
| D140 | 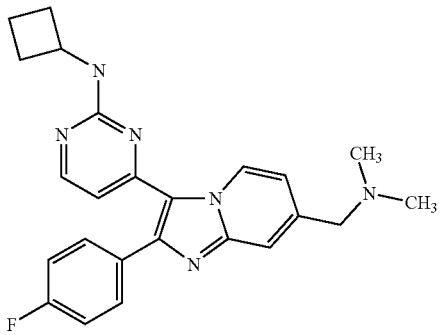 | 416.8 |

TABLE 11-continued
| D141 | 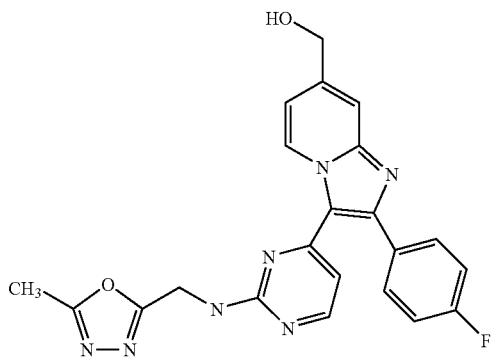 | 431.7 |
| D142 | 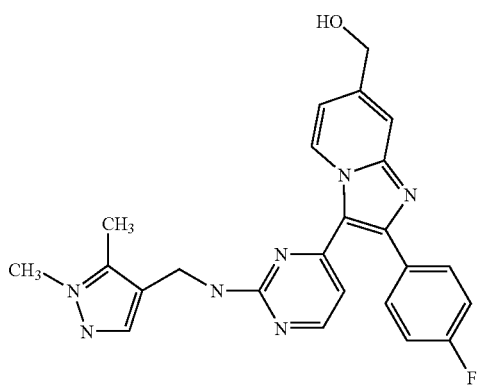 | 443.7 |
| D143 | 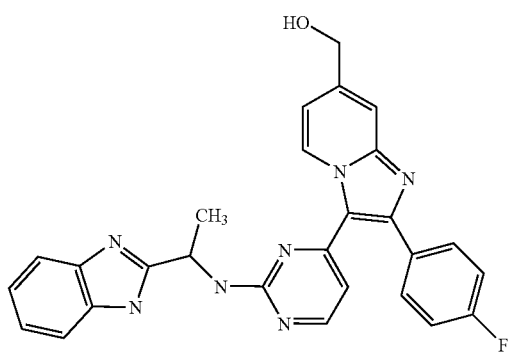 | 479.7 |
| D144 | 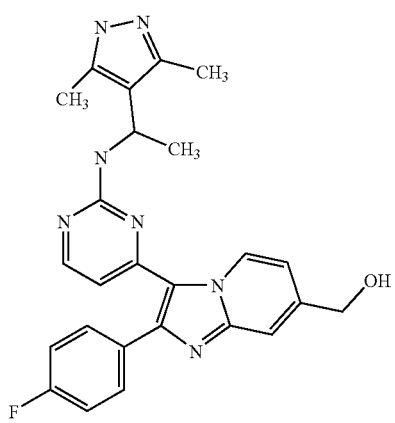 | 457.8 |

TABLE 11-continued
| | | |
|---|---|---|
| D145 | 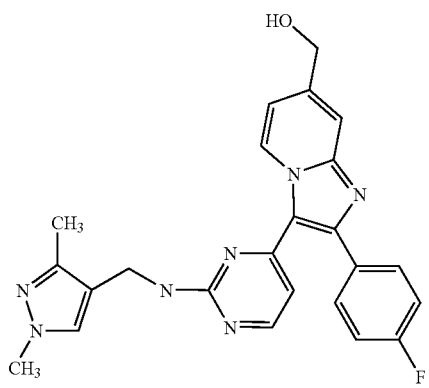 | 443.7 |
| D146 | 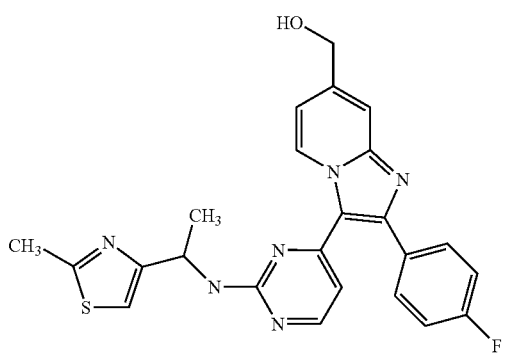 | 460.7 |
| D147 | 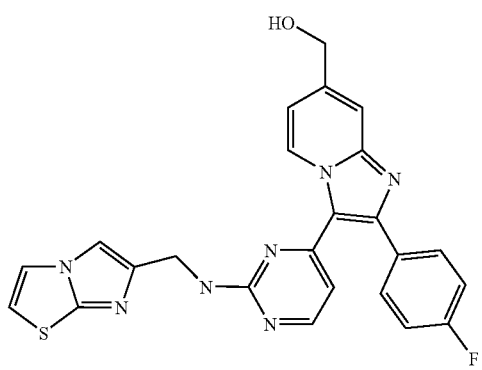 | 471.7 |
| D148 | 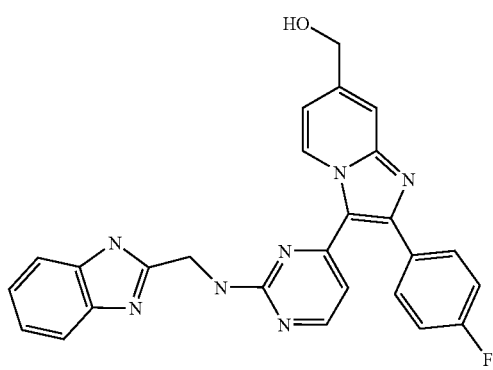 | 465.7 |

TABLE 11-continued
| | | |
|---|---|---|
| D149 | 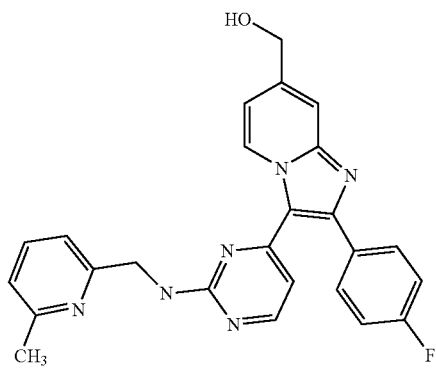 | 440.6 |
| D150 | 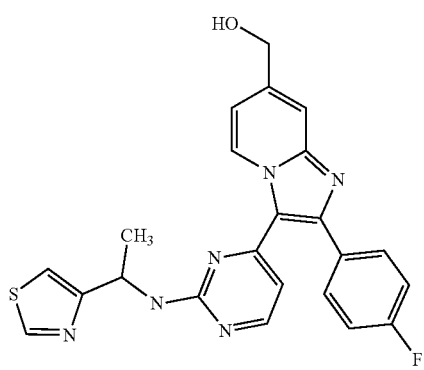 | 446.7 |
| D151 | 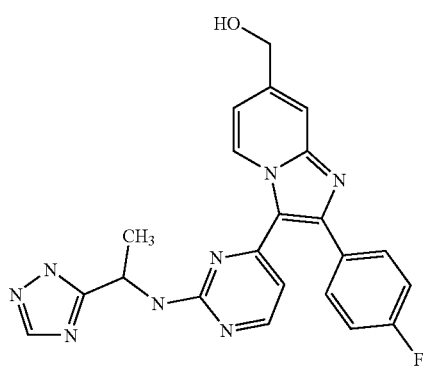 | 430.7 |
| D152 | 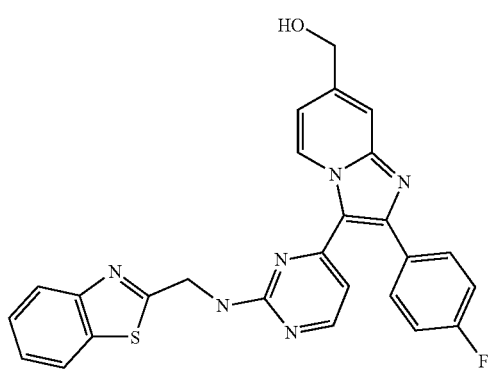 | 482.7 |

TABLE 11-continued
| D153 | 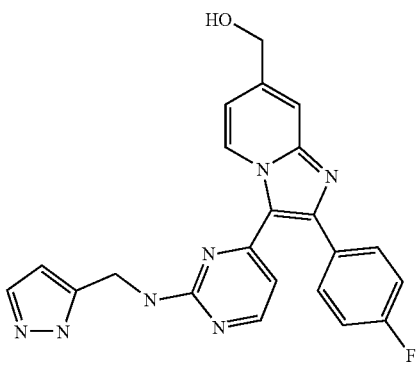 | 415.8 |
EXAMPLE E1 to EXAMPLE E192 below were made by procedures similar to those described above.
EX. E1
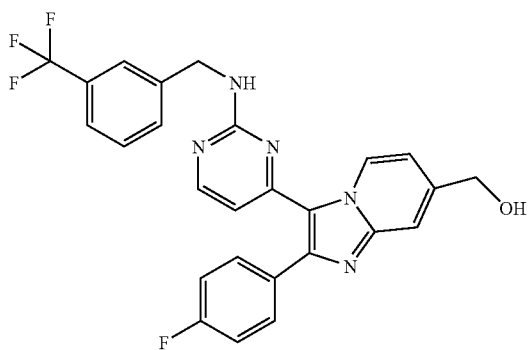
EX. E2
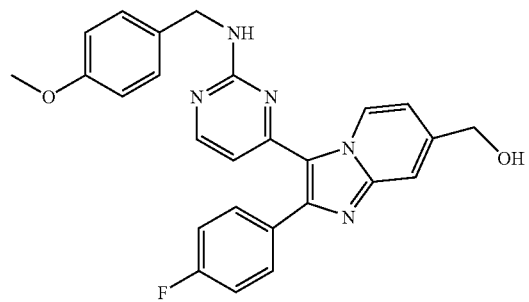
EX. E3
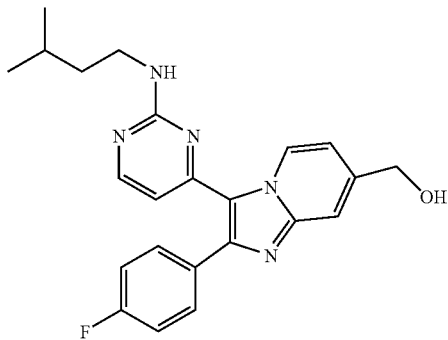

-continued
EX. E4
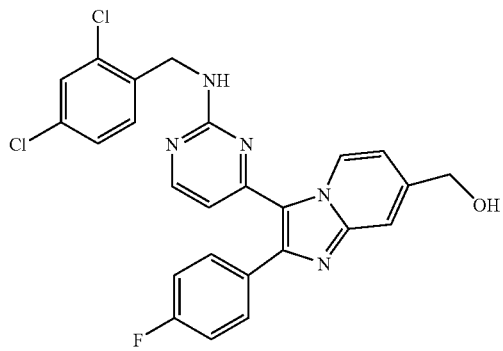
EX. E5
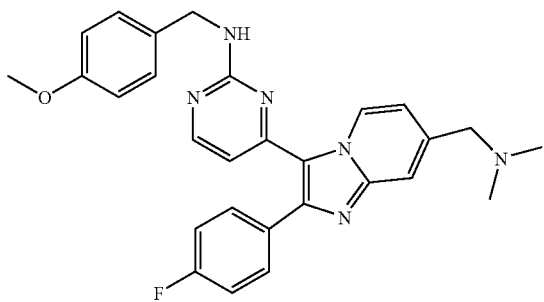
EX. E6
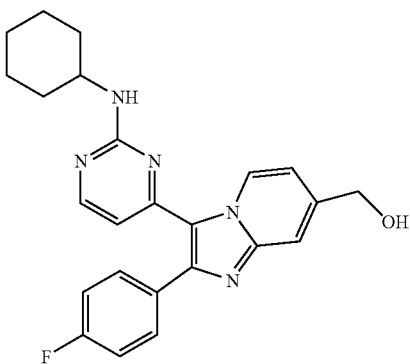
EX. E7
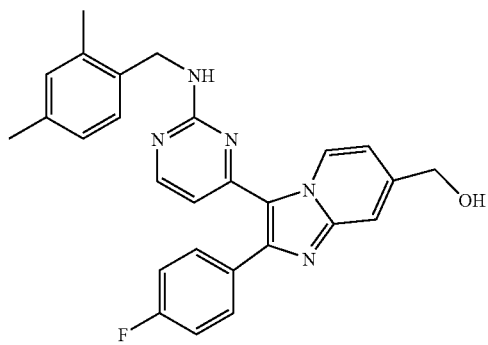

-continued
EX. E8
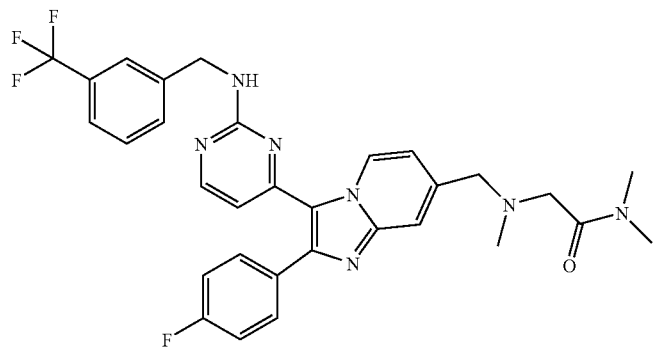
EX. E9
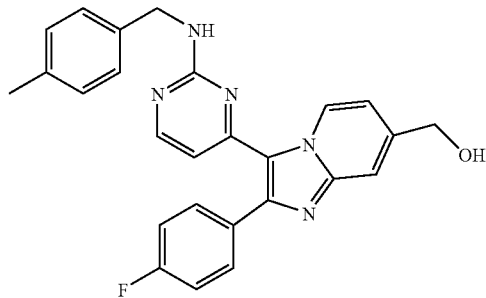
EX. E10
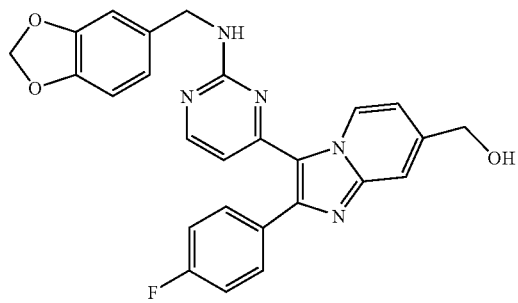
EX. E11
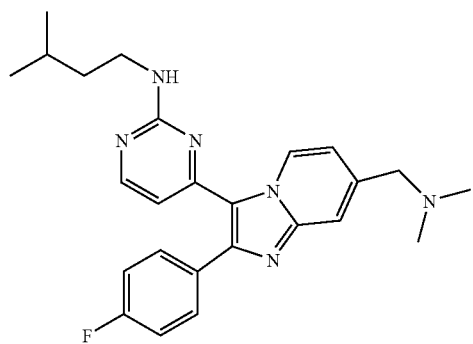

-continued
EX. E12
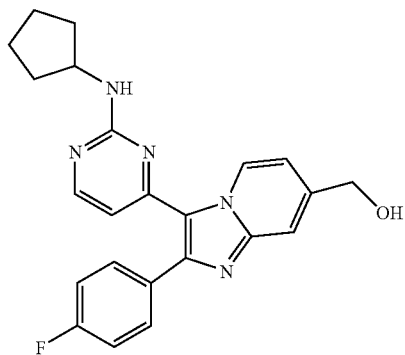
EX. E13
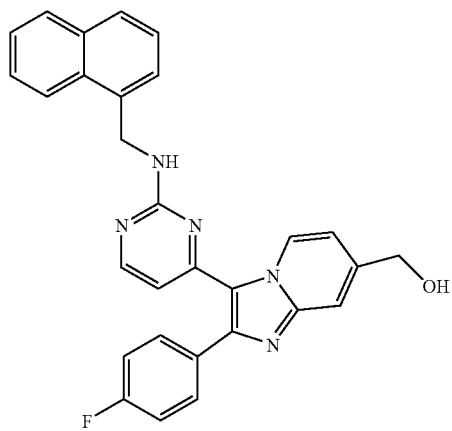
EX. E14
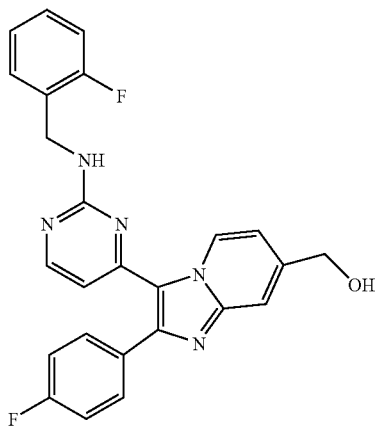

-continued
EX. E15
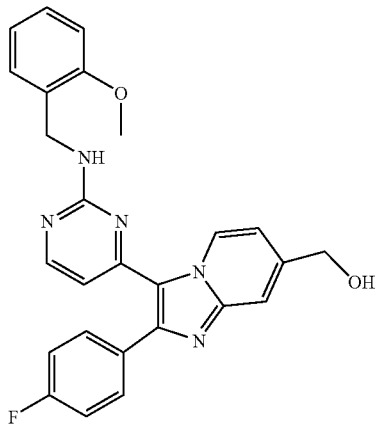
EX. E16
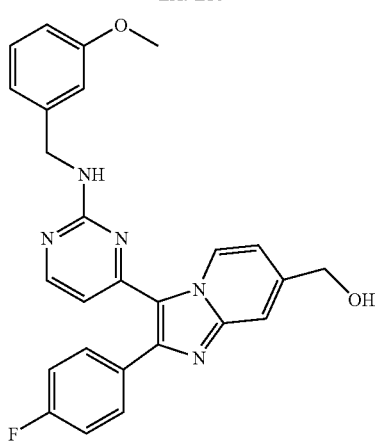
EX. E17
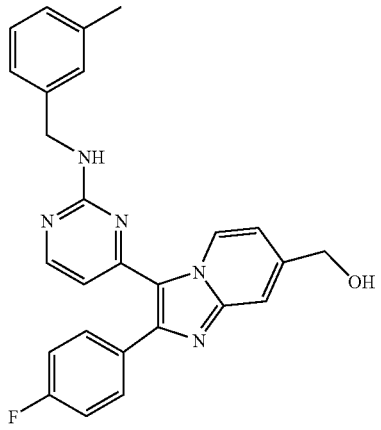

-continued
EX. E18
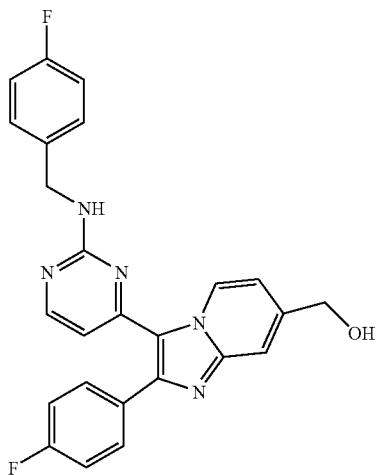
EX. E19
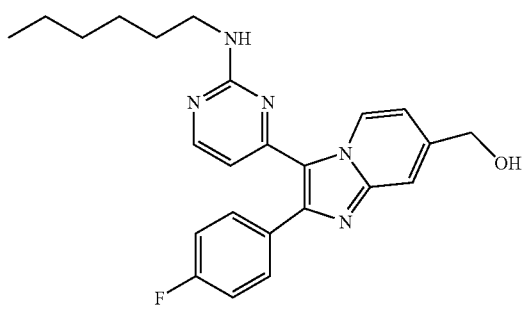
EX. E20
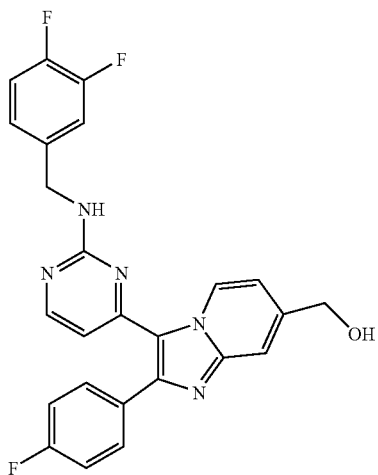

-continued
EX. E21
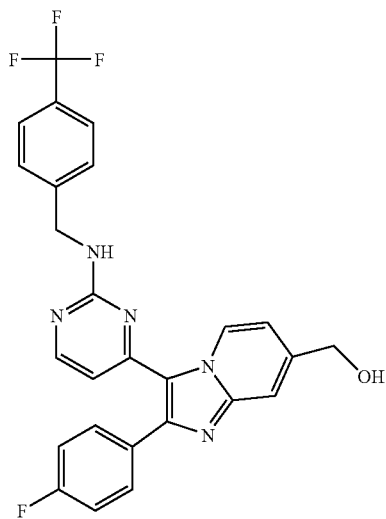
EX. E22
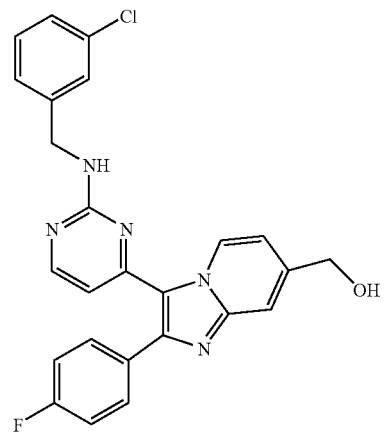
EX. E23
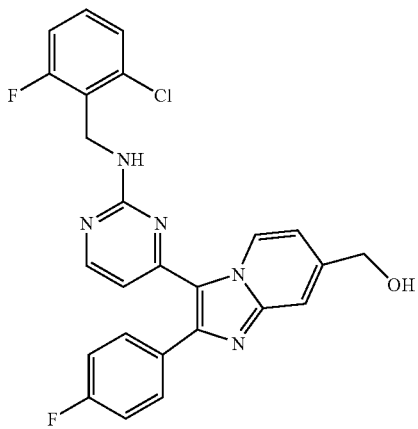

EX. E24
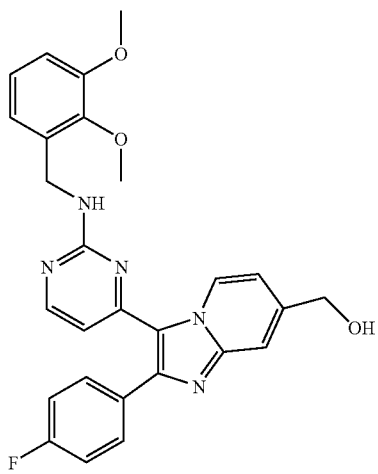
EX. E25
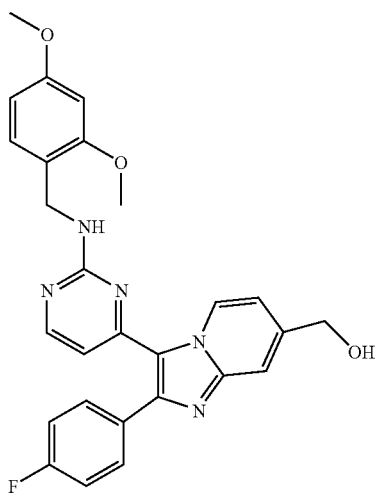
EX. E26
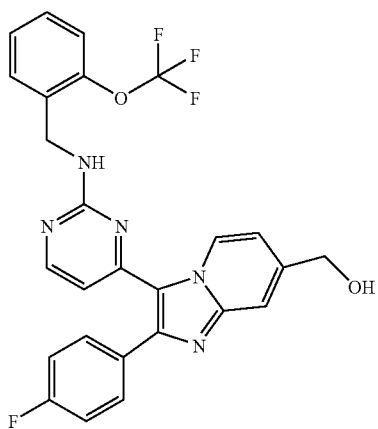

-continued
EX. E27
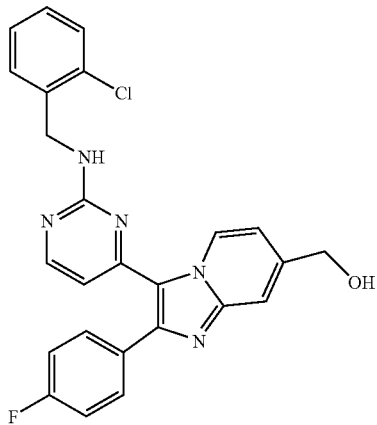
EX. E28
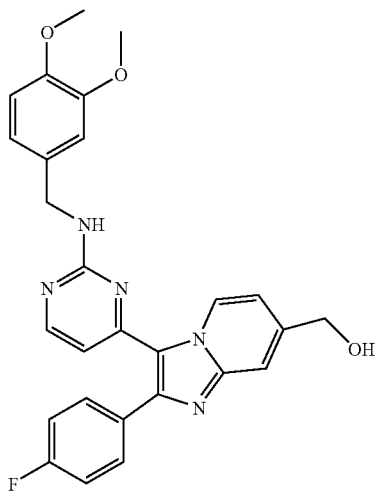
EX. E29
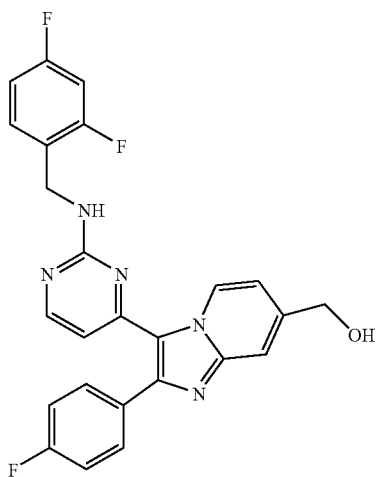

EX. E30
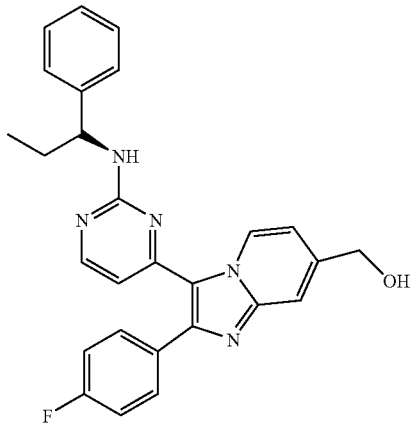
EX. E31
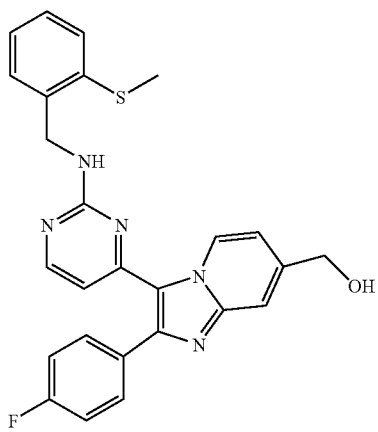
EX. E32
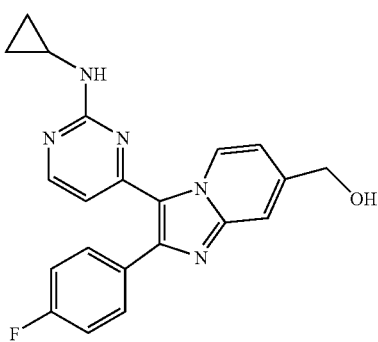

-continued
EX. E33
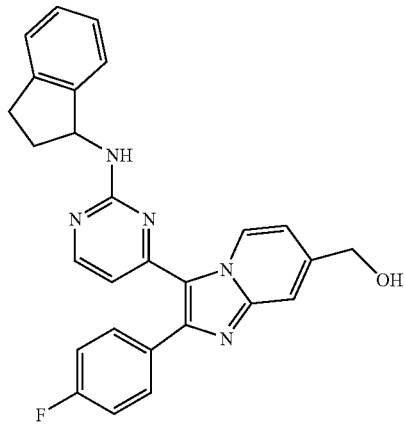
EX. E34
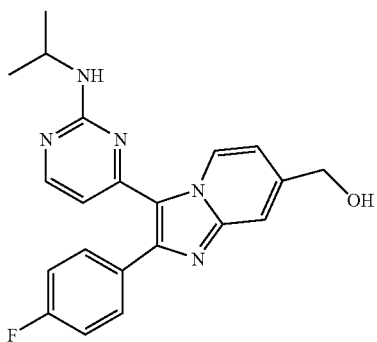
EX. E35
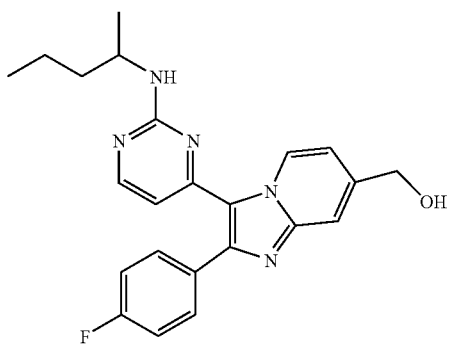

EX. E36
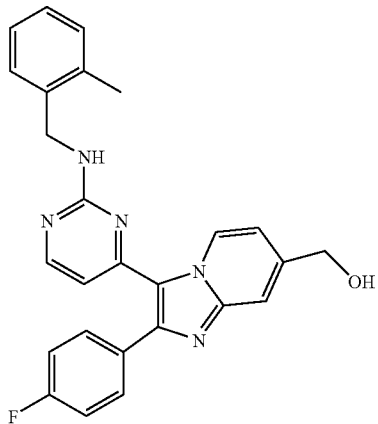
EX. E37
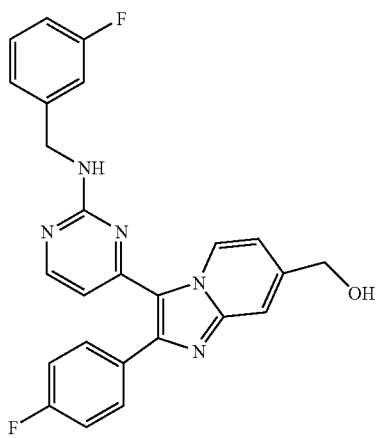
EX. E38
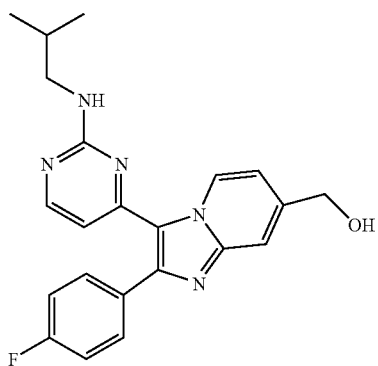

-continued
EX. E39
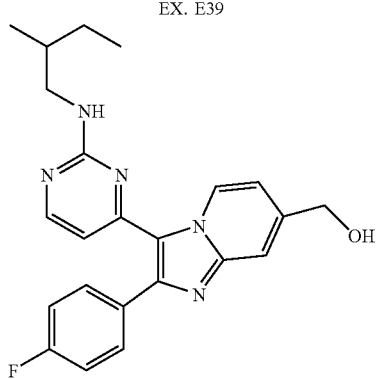
EX. E40
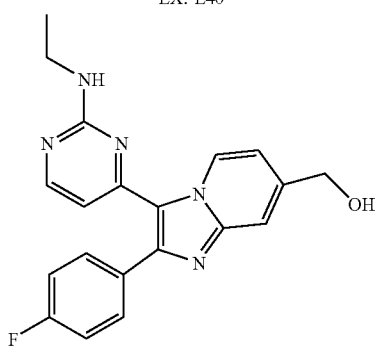
EX. E41
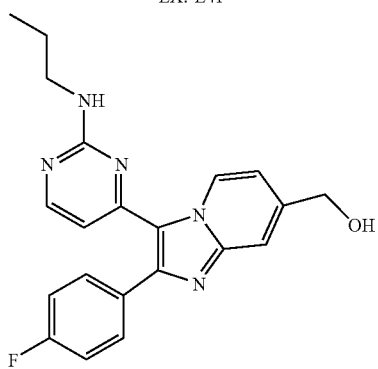
EX. E42
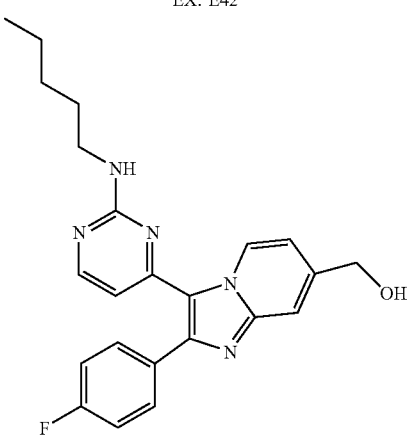

-continued
EX. E43
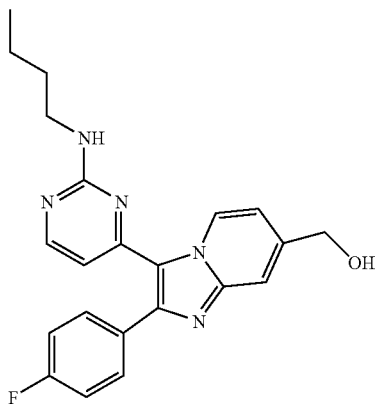
EX. E44
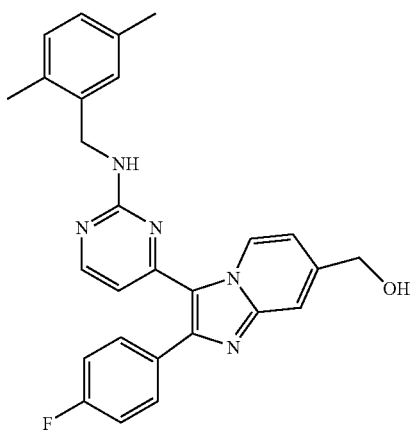
EX. E45
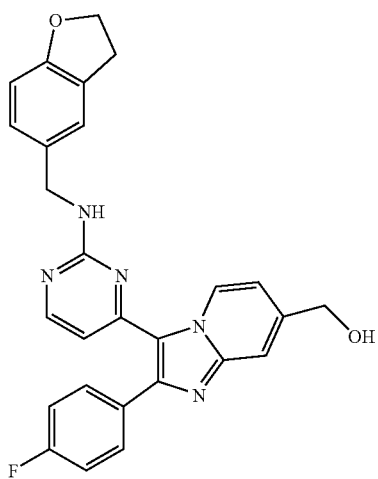

-continued
EX. E46
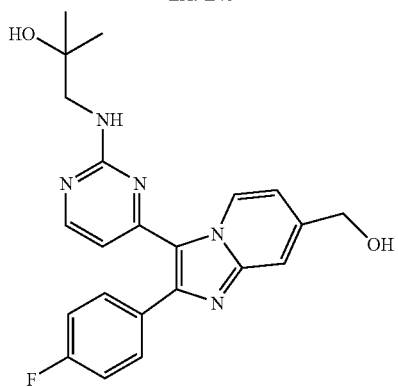
EX. E47
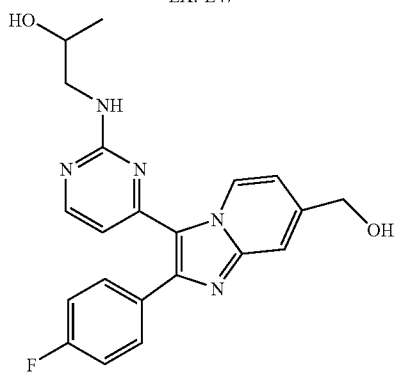
EX. E48
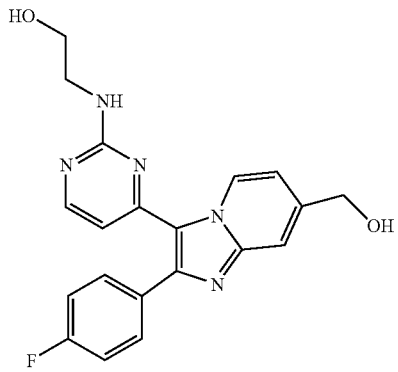
EX. E49
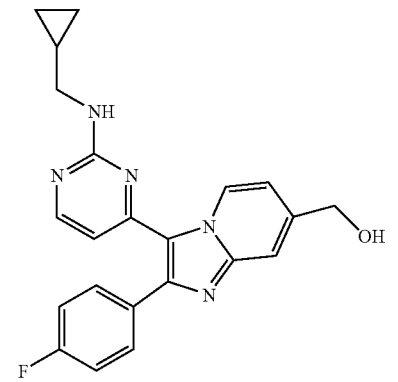

-continued
EX. E50
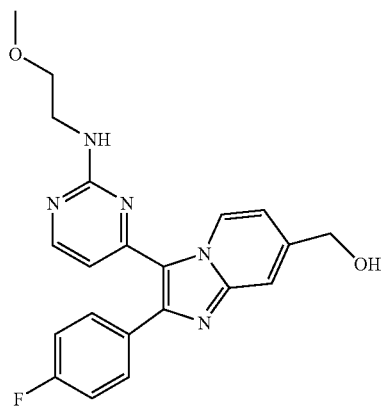
EX. E51
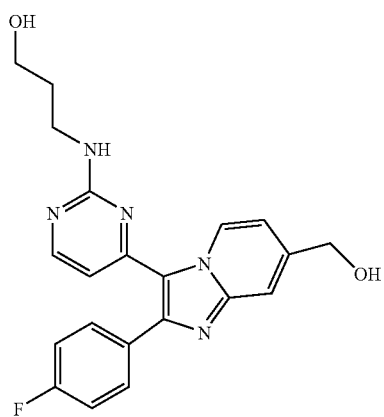
EX. E52
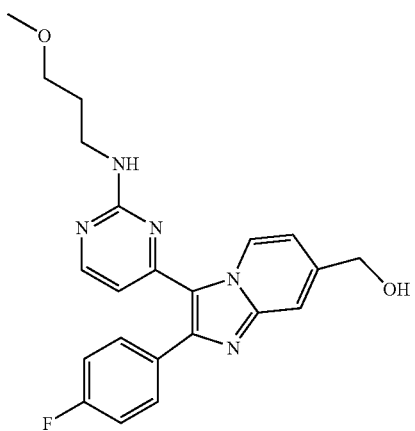

-continued
EX. E53
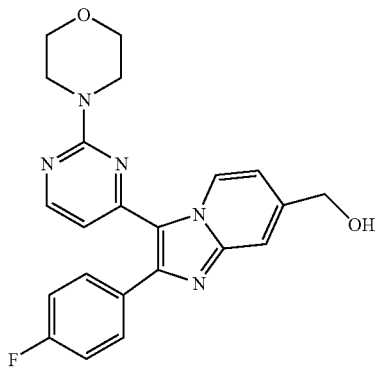
EX. E54
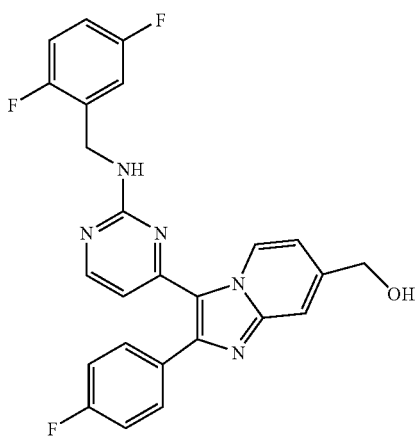
EX. E55
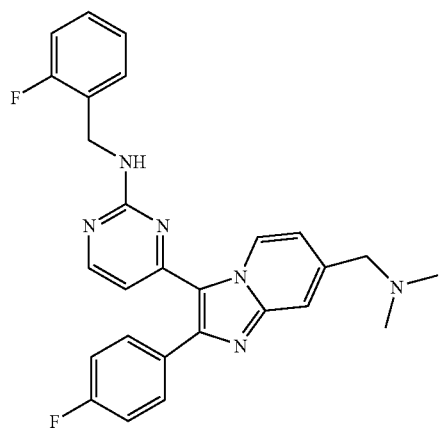

-continued
EX. E56
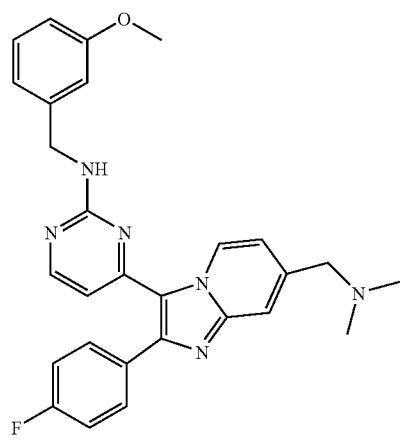
EX. E57
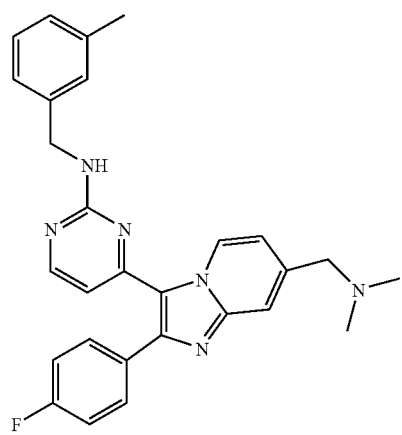
EX. E58
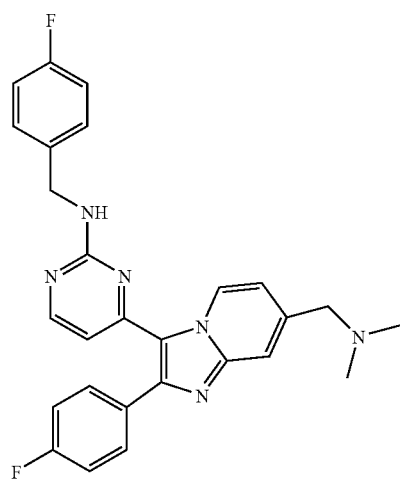

-continued
EX. E59
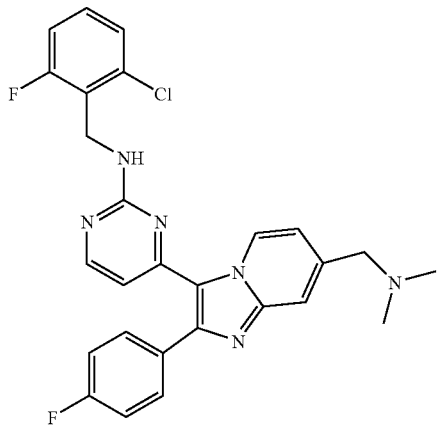
EX. E60
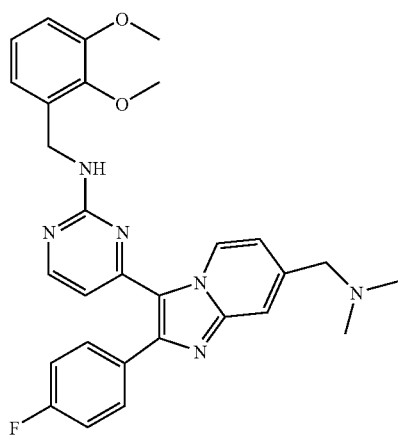
EX. E61
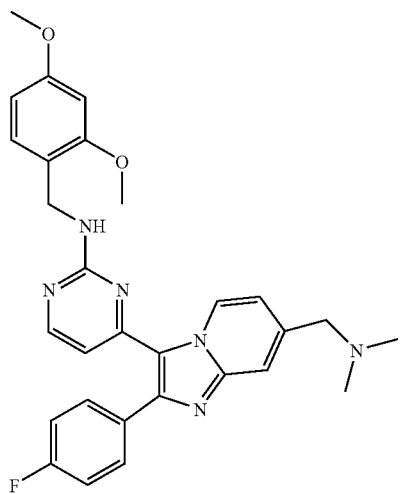

-continued
EX. E62
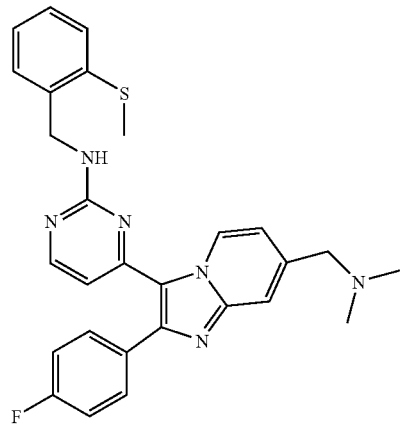
EX. E63
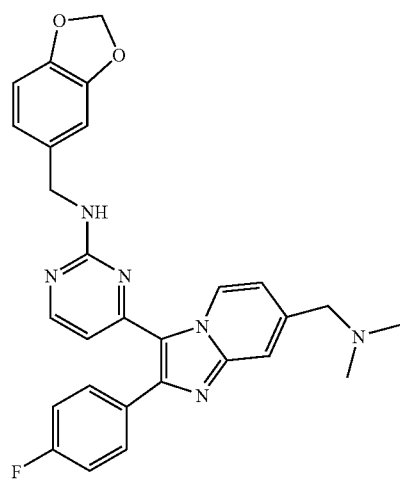
EX. E64
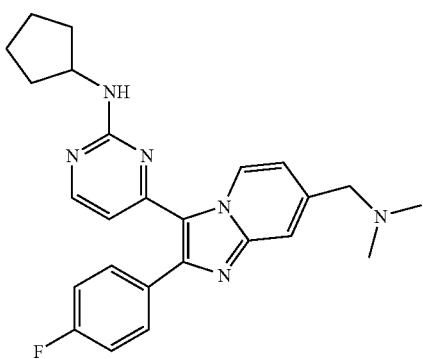

-continued
EX. E65
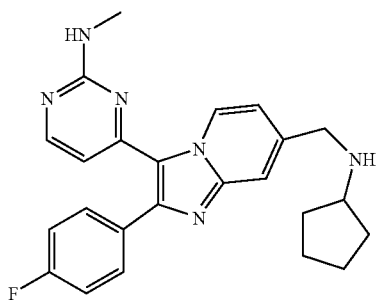
EX. E66
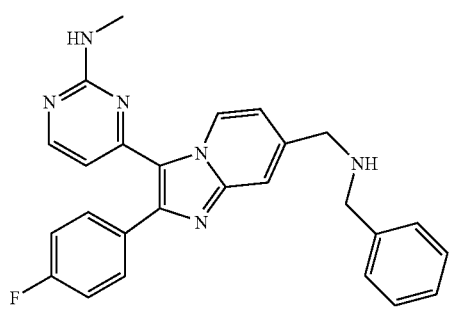
EX. E67
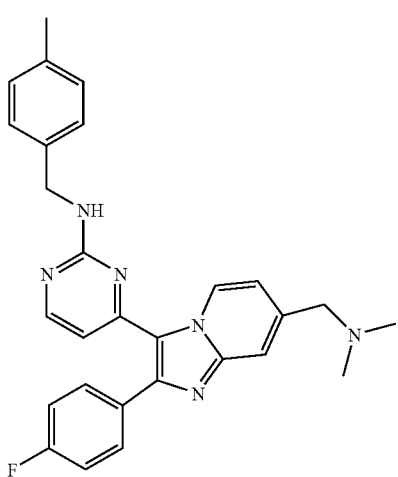
EX. E68
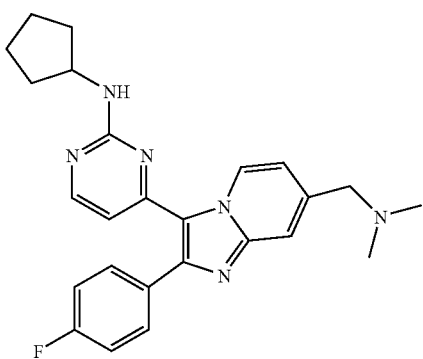

-continued
EX. E69
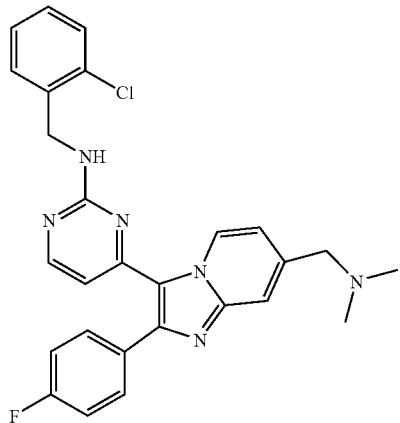
EX. E70
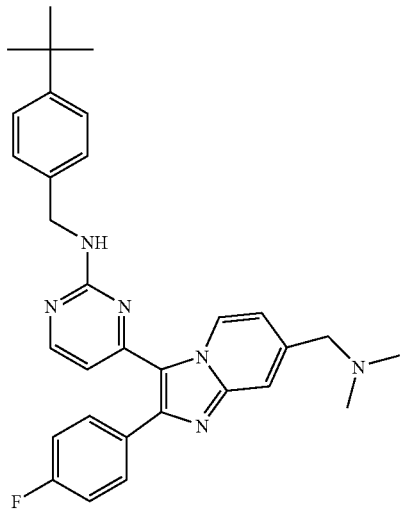
EX. E71
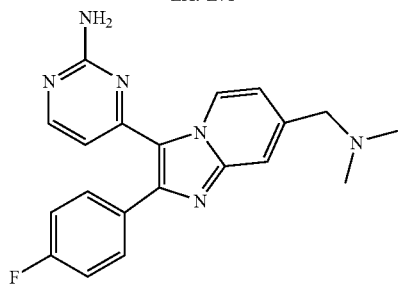
EX. E72
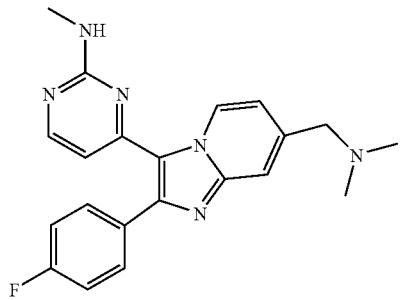

EX. E73
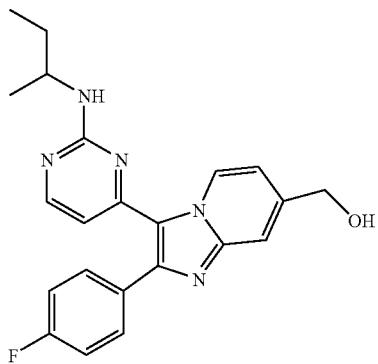
EX. E74
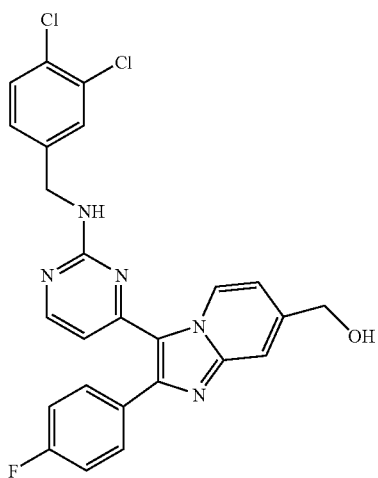
EX. E75
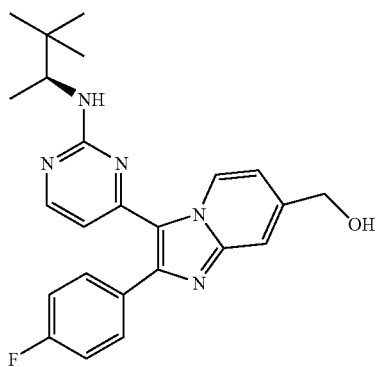

-continued
EX. E76
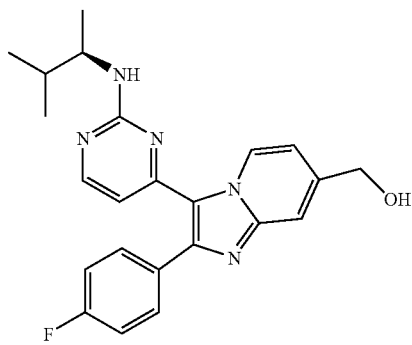
EX. E77
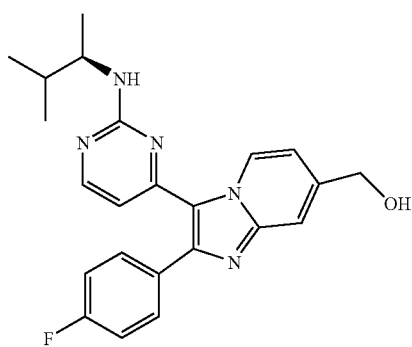
EX. E78
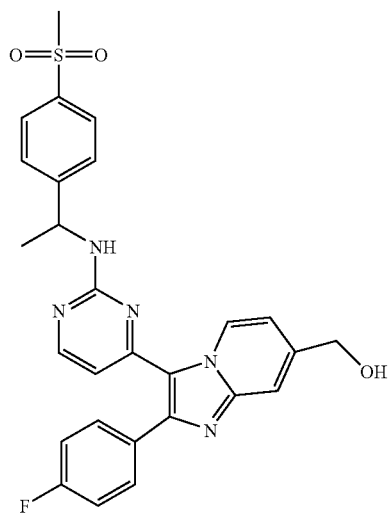

EX. E79
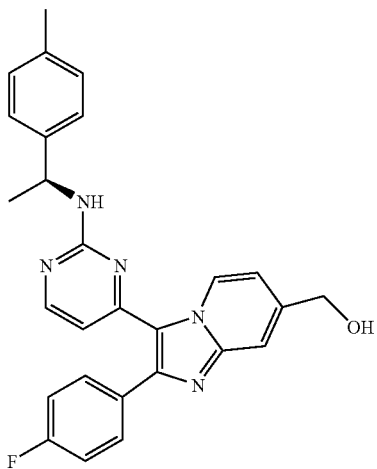
EX. E80
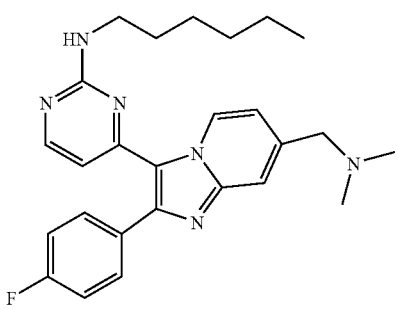
EX. E81
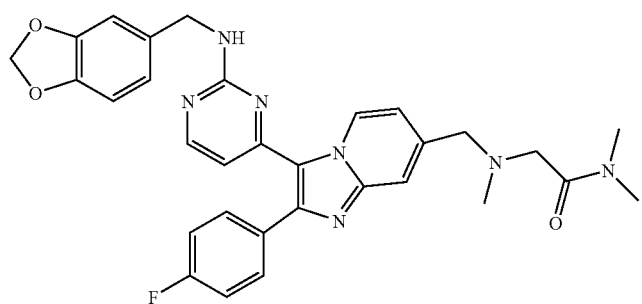
EX. E82
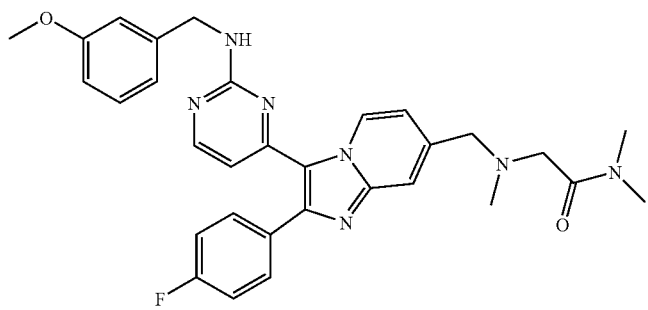

-continued
EX. E83
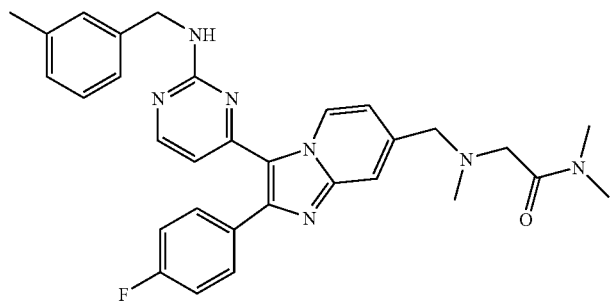
EX. E84
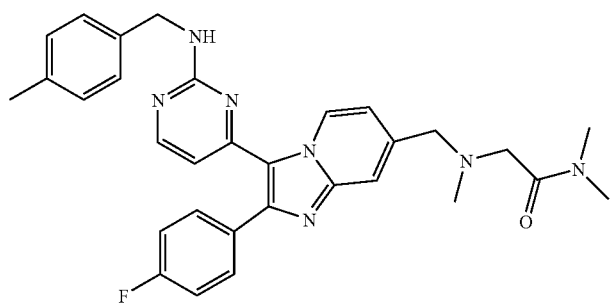
EX. E85
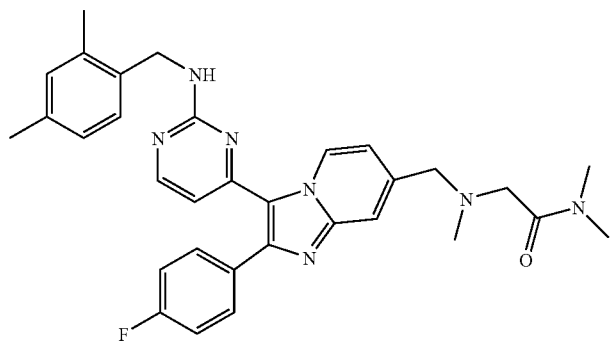
EX. E86
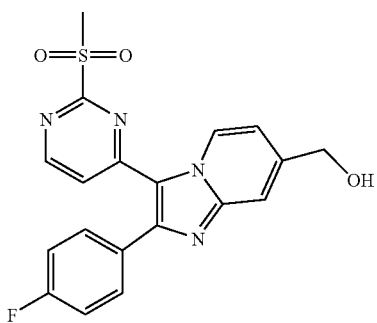

EX. E87
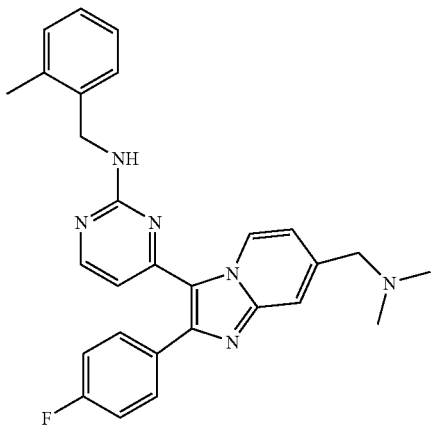
EX. E88
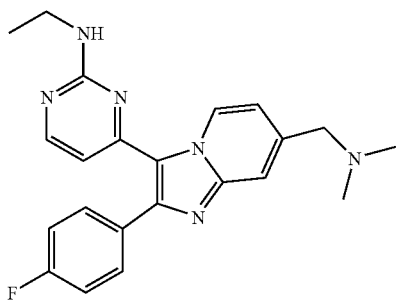
EX. E89
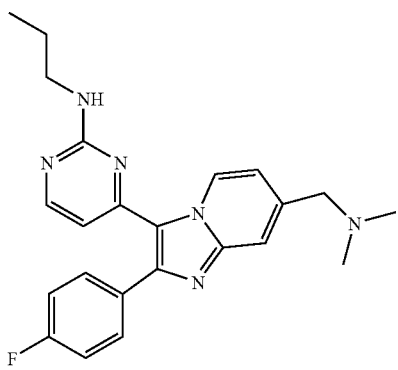
EX. E90
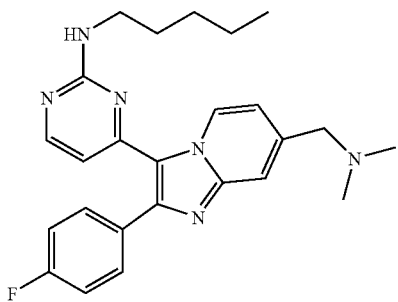

-continued
EX. E91
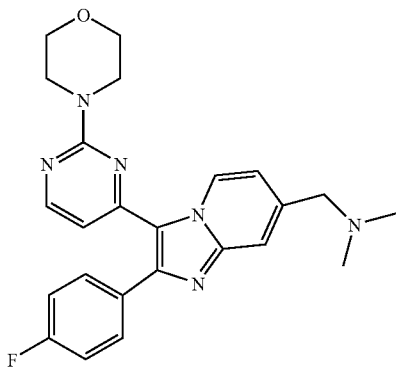
EX. E92
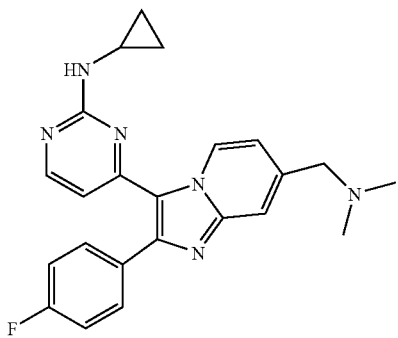
EX. E93
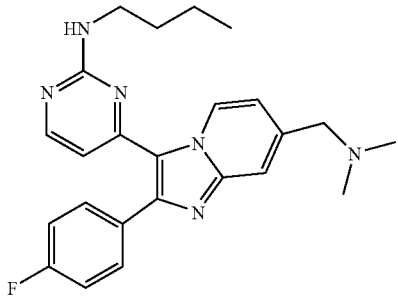
EX. E94
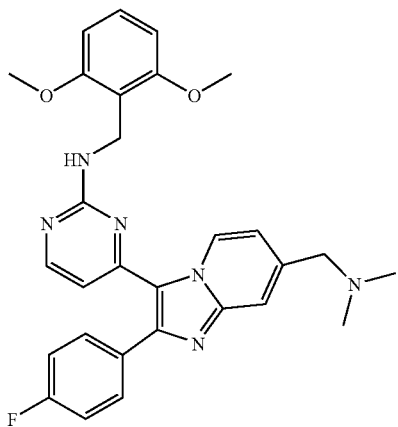

EX. E95
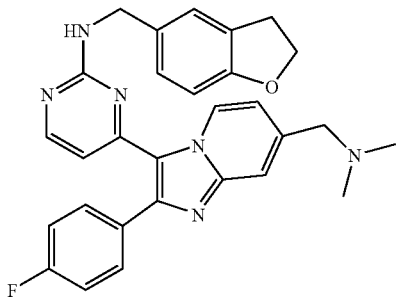
EX. E96
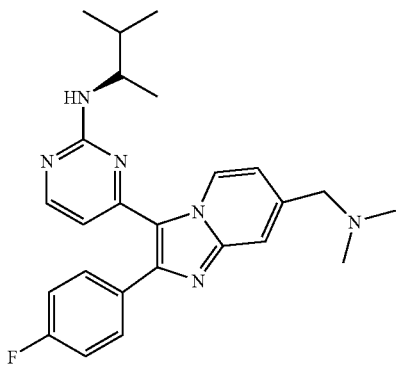
EX. E97
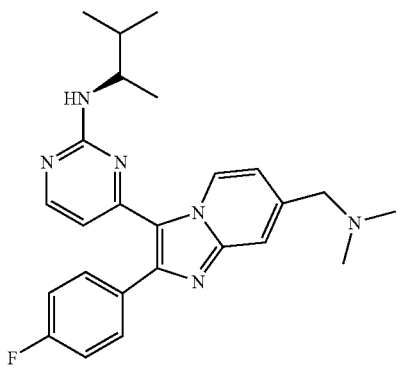
EX. E98
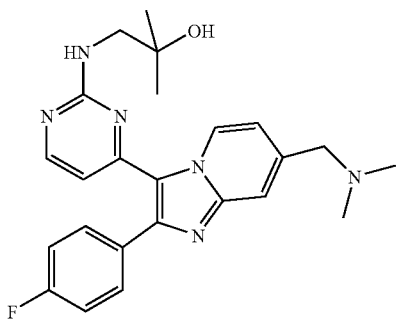

EX. E99
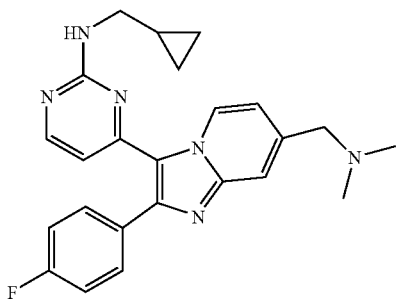
EX. E100
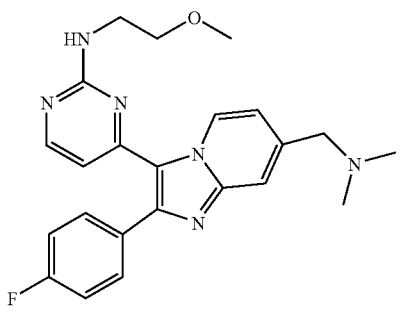
EX. E101
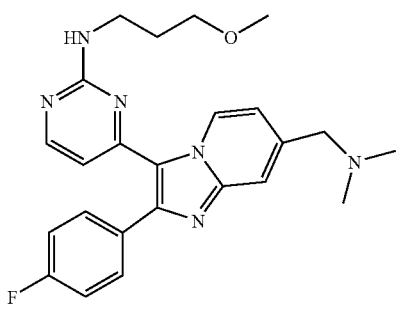
EX. E102
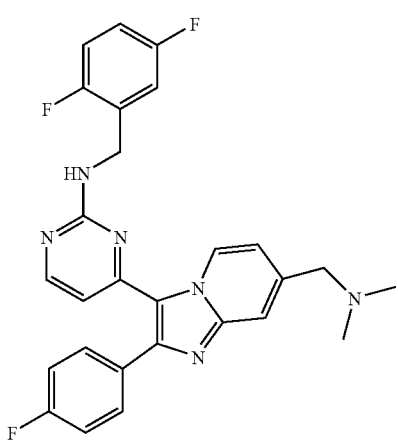

-continued
EX. E103
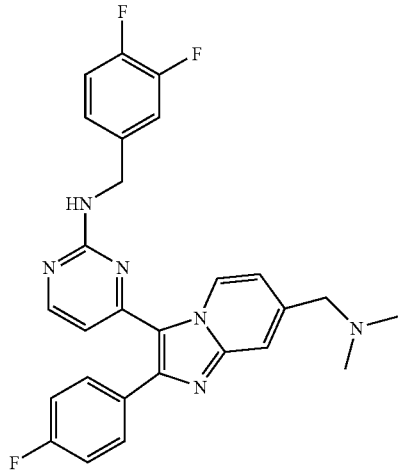
EX. E104
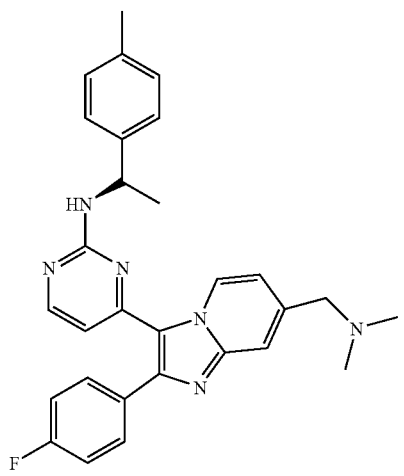
EX. E105
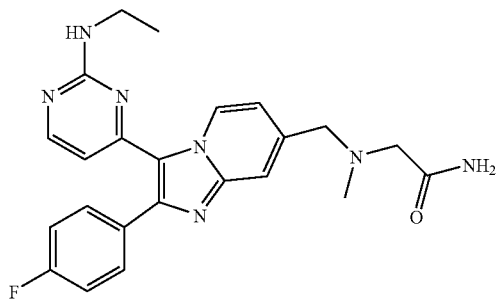

EX. E106
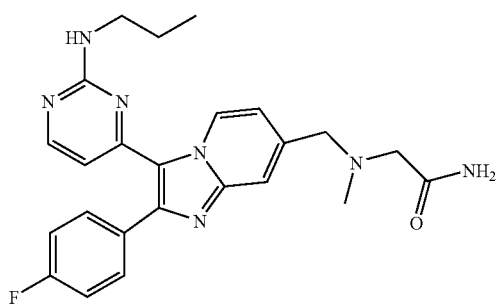
EX. E107
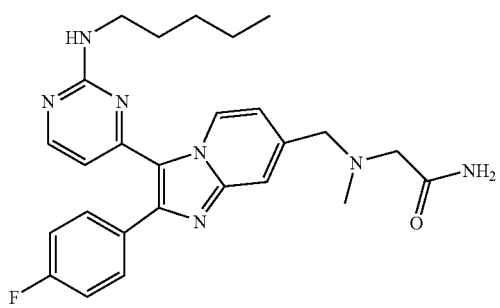
EX. E108
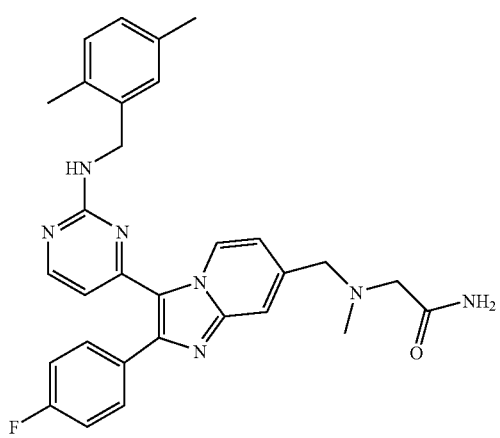
EX. E109
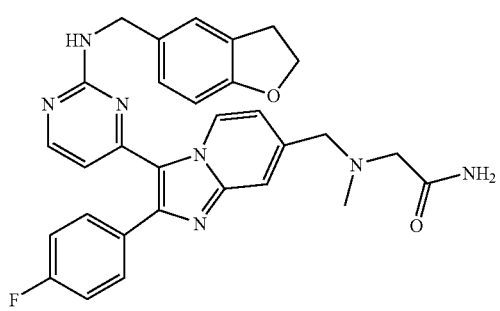

-continued
EX. E110
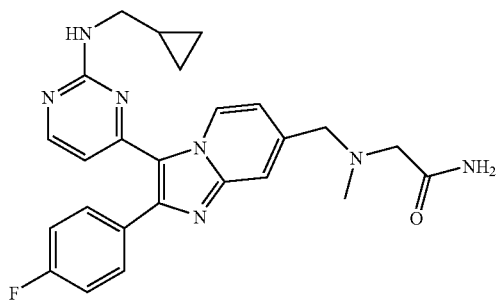
EX. E111
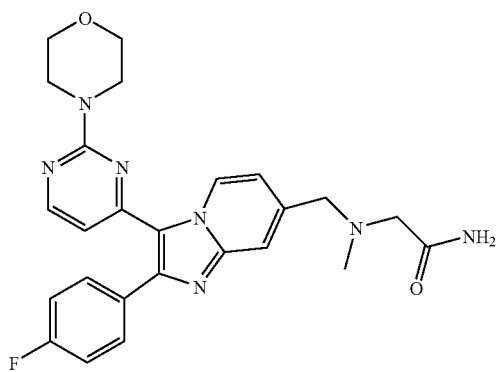
EX. E112
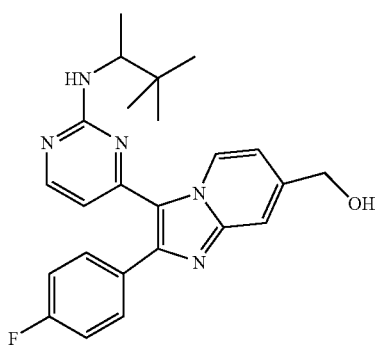
EX. E113
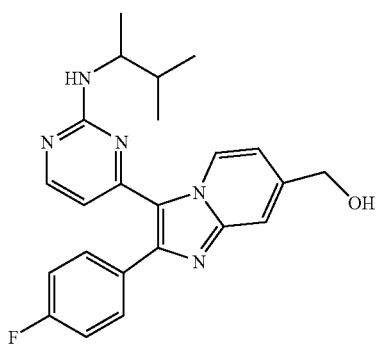

-continued
EX. E114
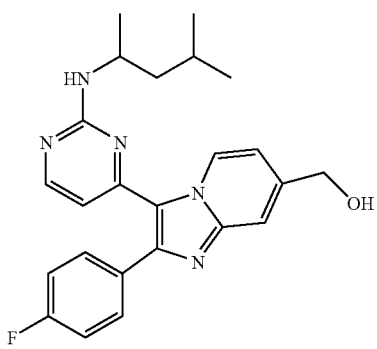
EX. E115
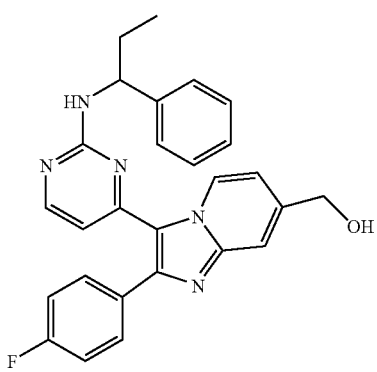
EX. E116
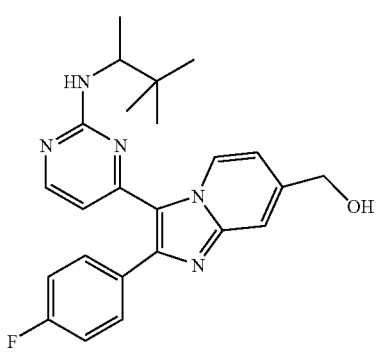
EX. E117
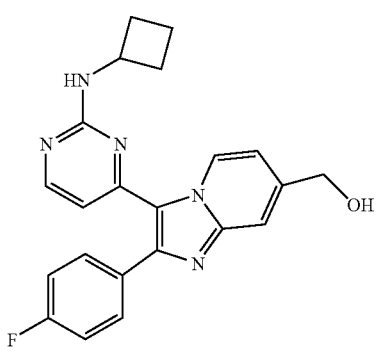

-continued
EX. E118
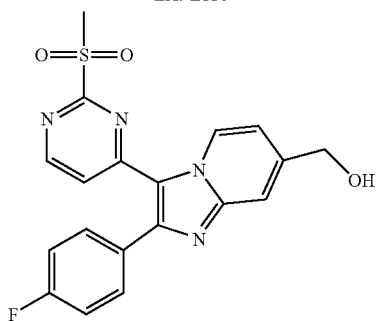
EX. E119
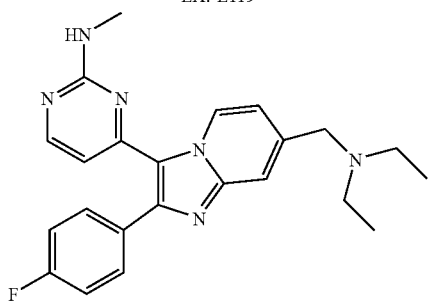
EX. E120
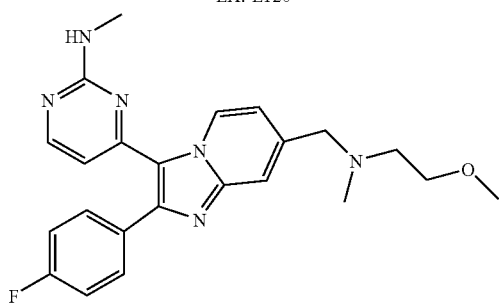
EX. E121
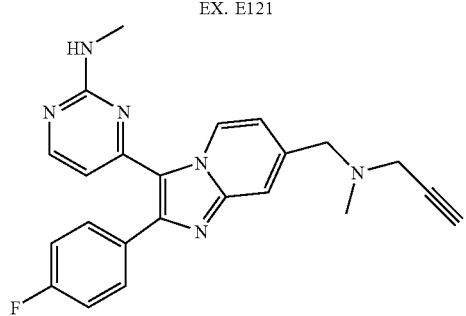

-continued
EX. E122
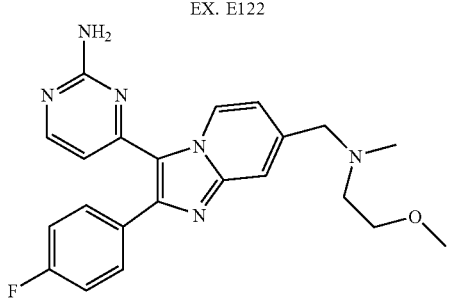
EX. E123
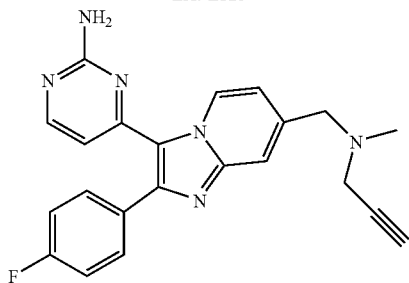
EX. E124
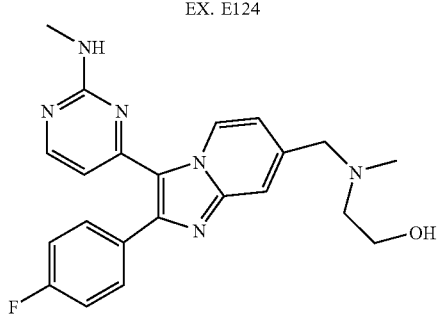
EX. E125
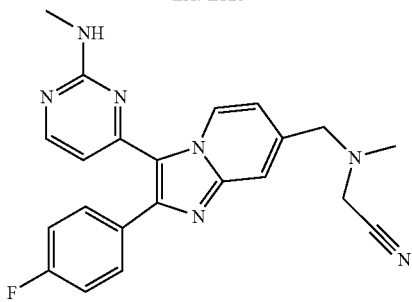
EX. E126
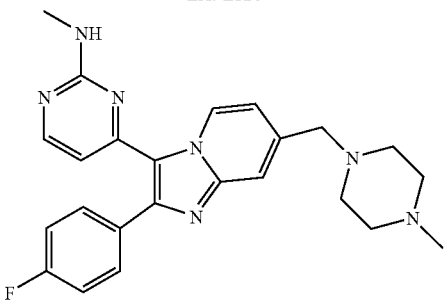

-continued
EX. E127
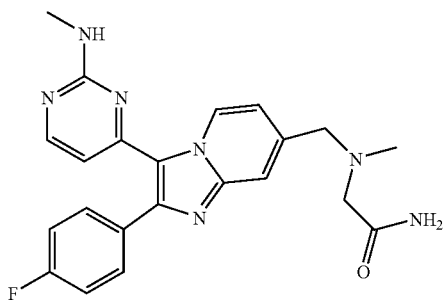
EX. E128
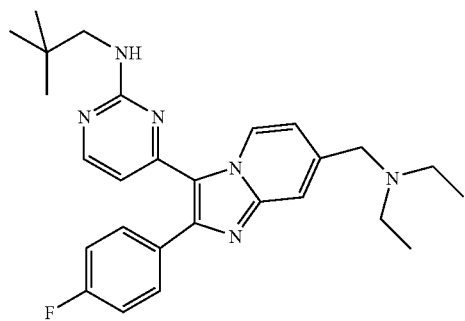
EX. E129
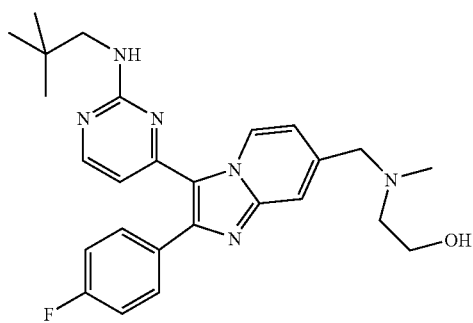
EX. E130
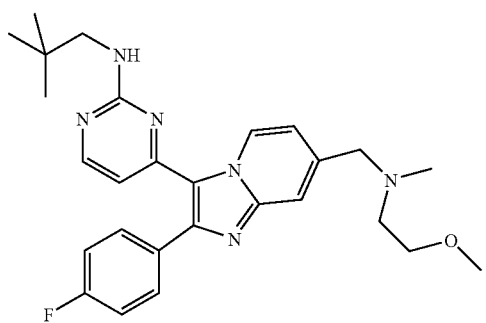

-continued
EX. E131
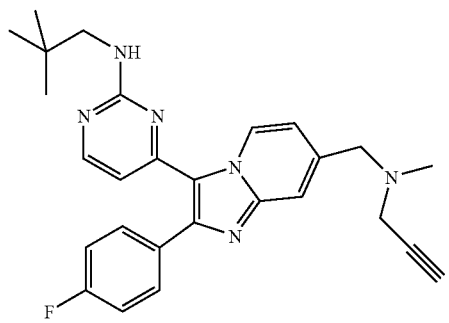
EX. E132
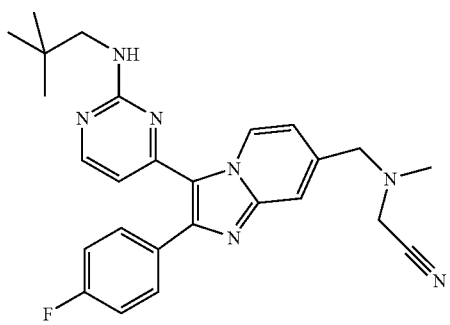
EX. E133
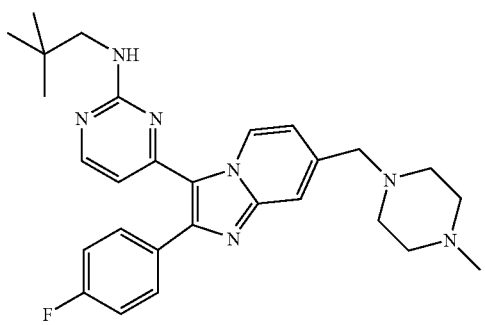
EX. E134
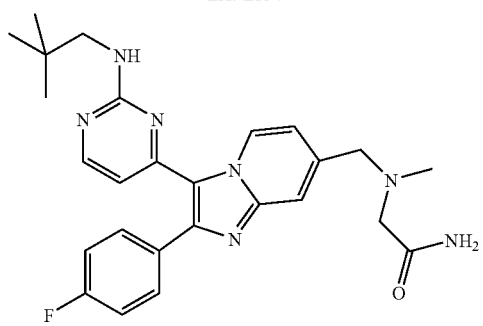

-continued
EX. E135
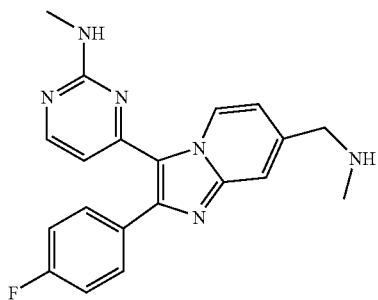
EX. E136
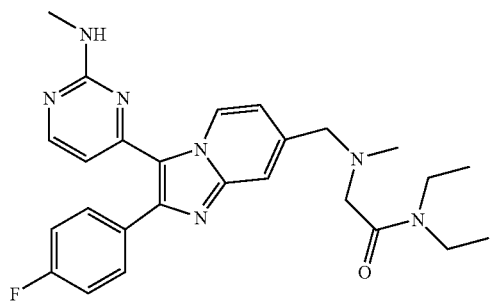
EX. E137
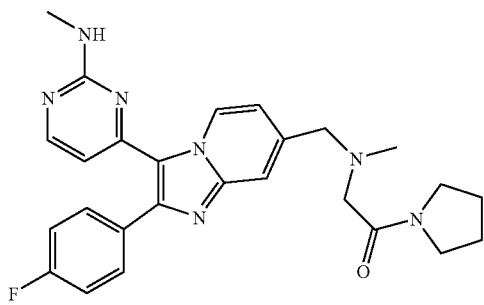
EX. E138
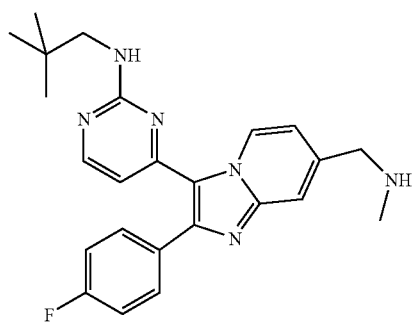

-continued
EX. E139
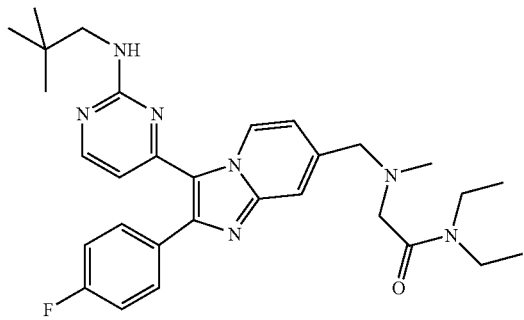
EX. E140
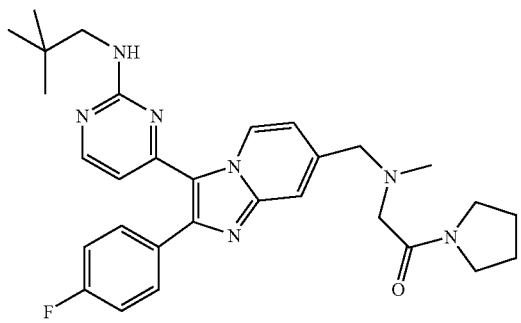
EX. E141
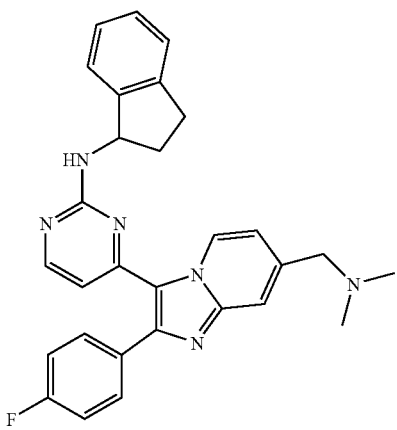
EX. E142
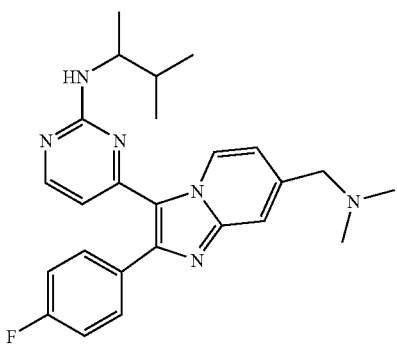

-continued
EX. E143
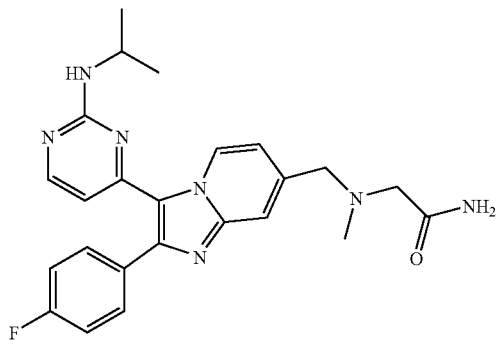
EX. E144
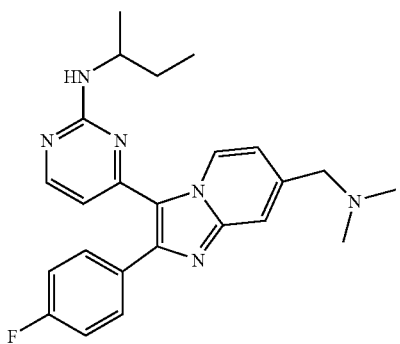
EX. E145
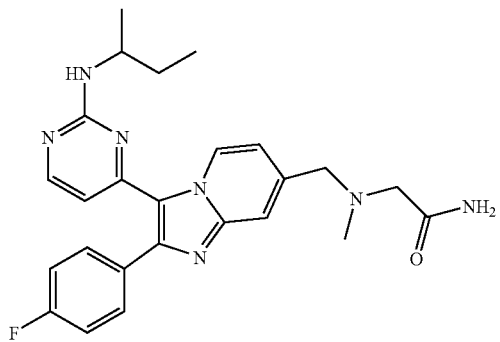
EX. E146
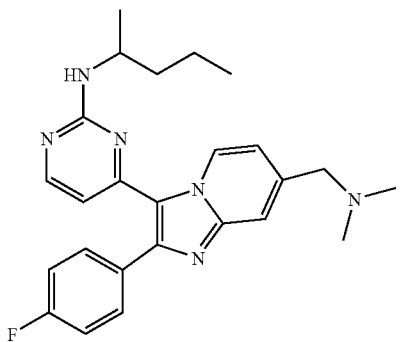

-continued
EX. E147
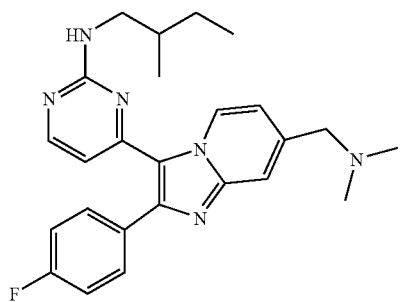
EX. E148
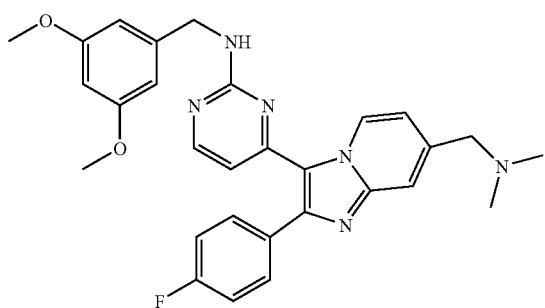
EX. E149
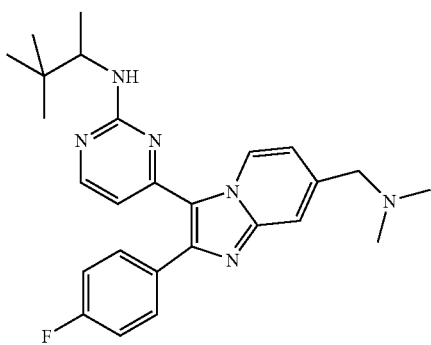
EX. E150
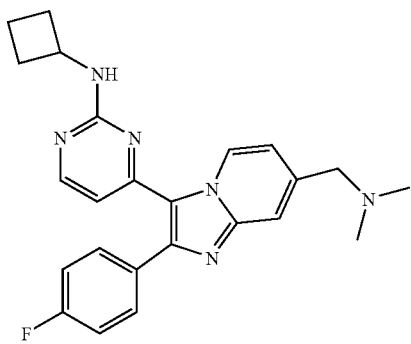

-continued
EX. E151
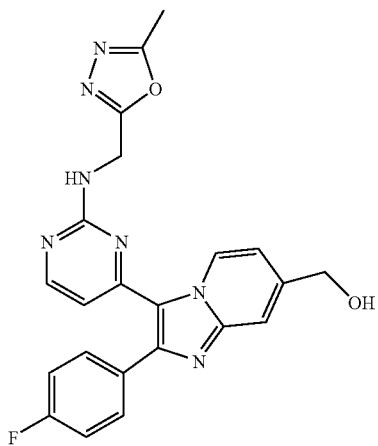
EX. E152
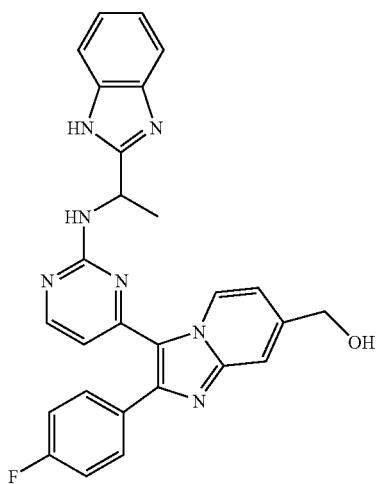
EX. E153
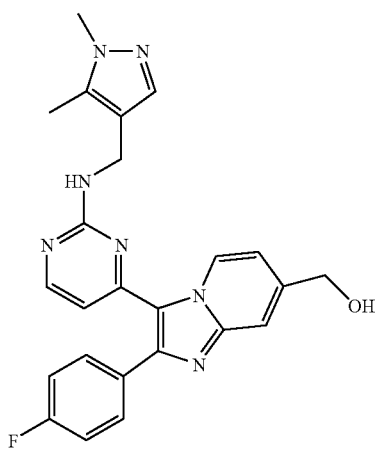

-continued
EX. E154
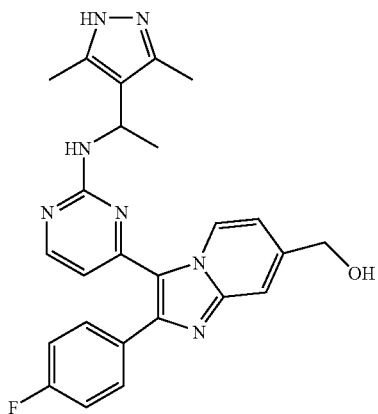
EX. E155
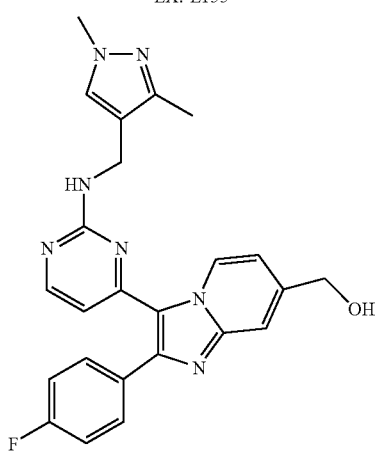
EX. E156
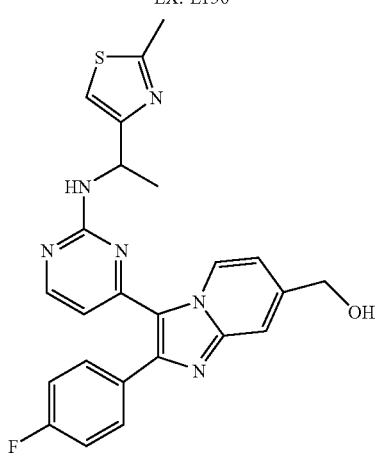

-continued
EX. E157
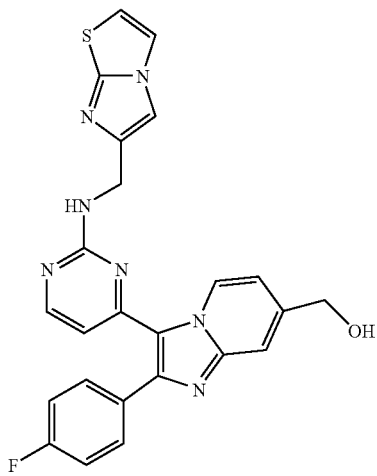
EX. E158
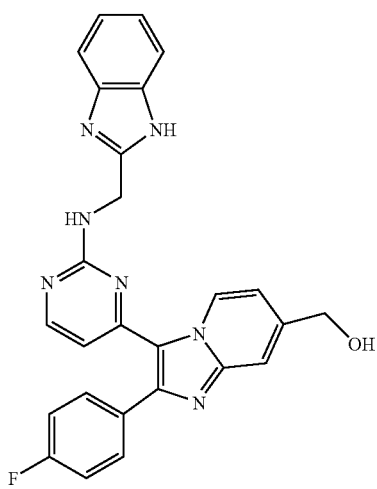
EX. E159
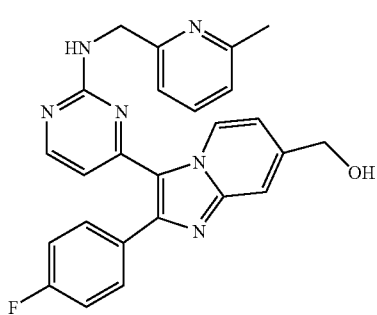

-continued
EX. E160
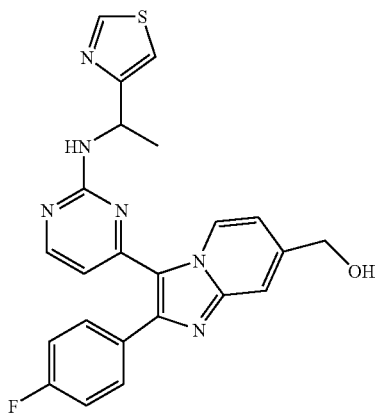
EX. E161
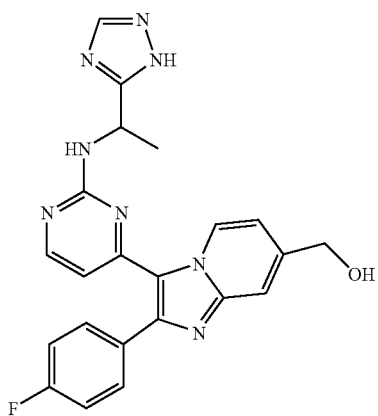
EX. E162
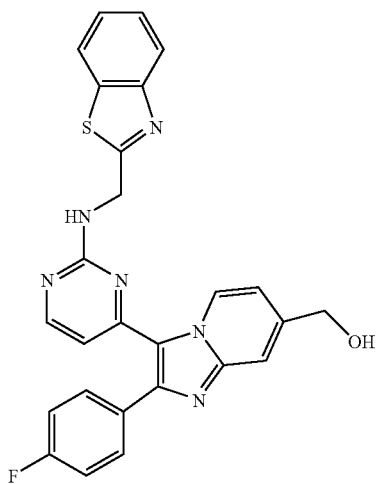

-continued
EX. E163
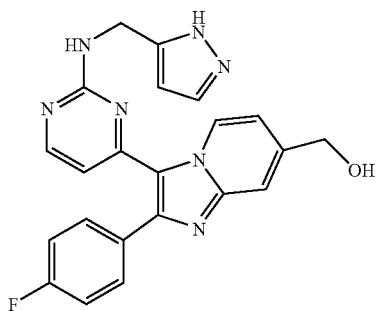
EX. E164
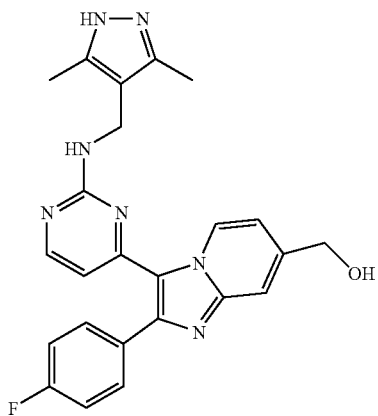
EX. E165
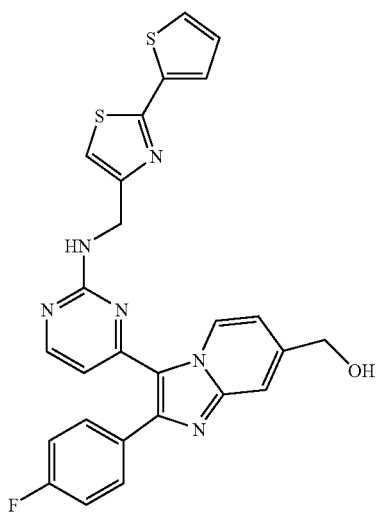

-continued
EX. E166
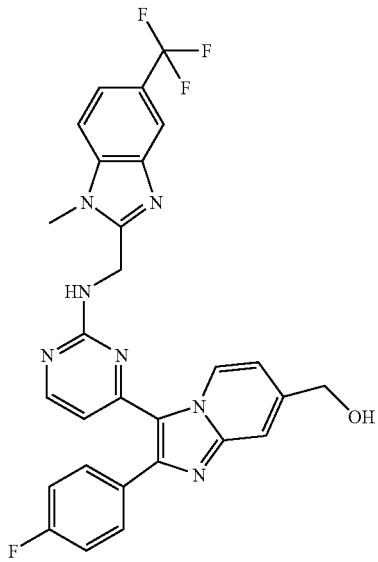
EX. E167
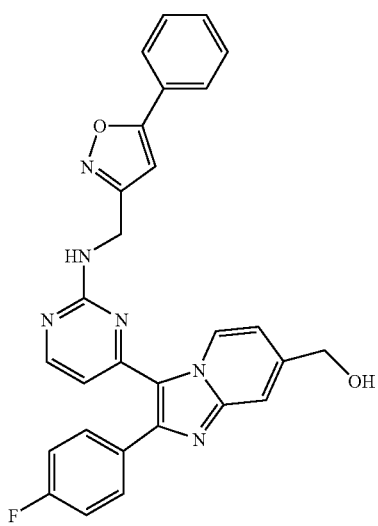

EX. E168
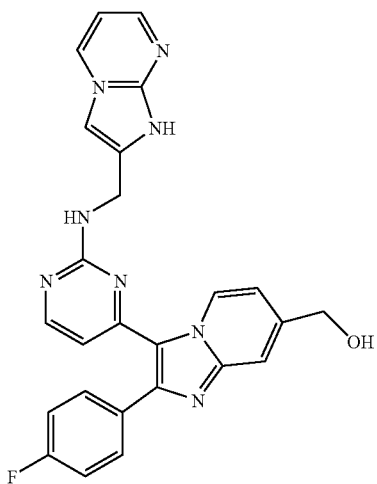
EX. E169
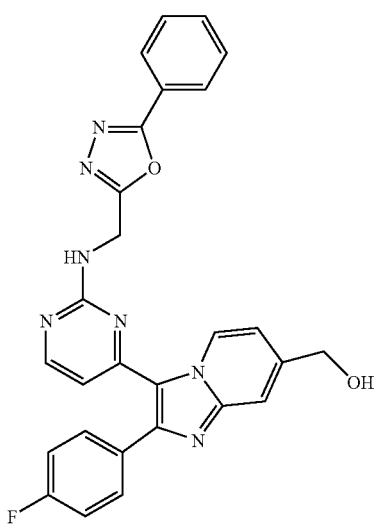
EX. E170
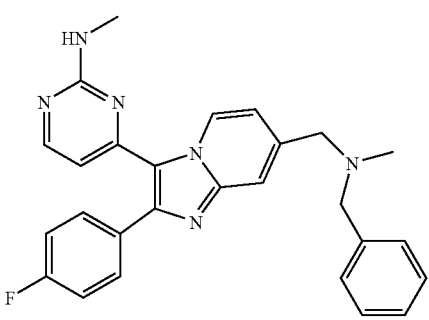

-continued
EX. E171
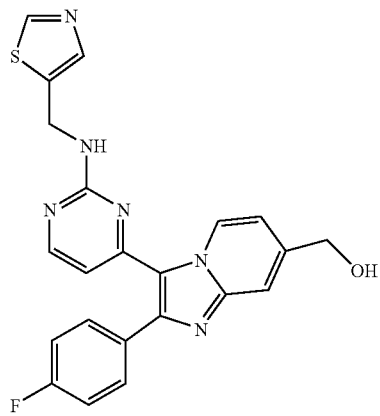
EX. E172
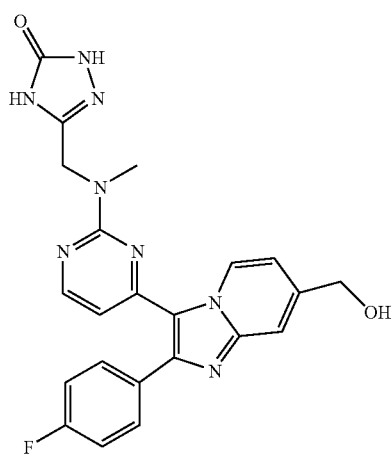
EX. E173
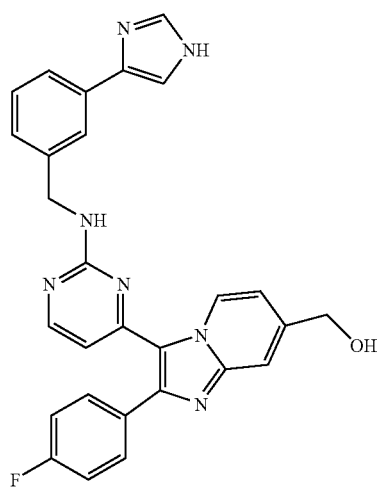

EX. E174
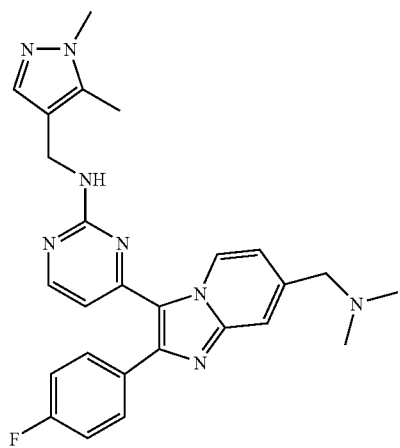
EX. E175
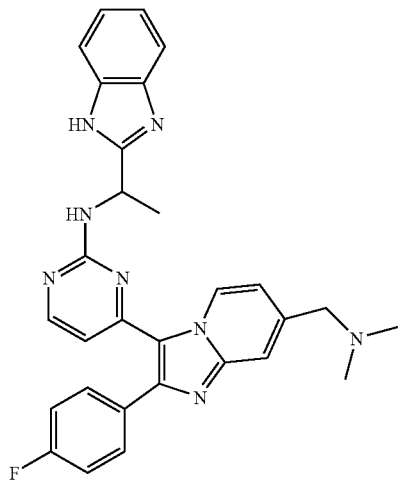
EX. E176
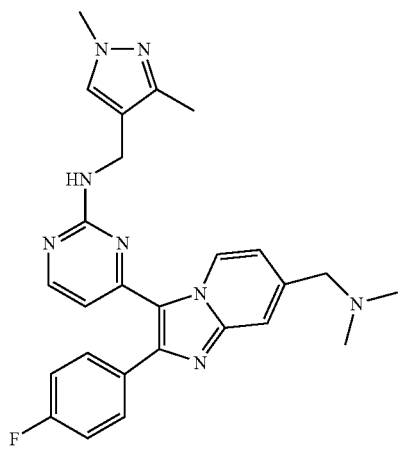

-continued
EX. E177
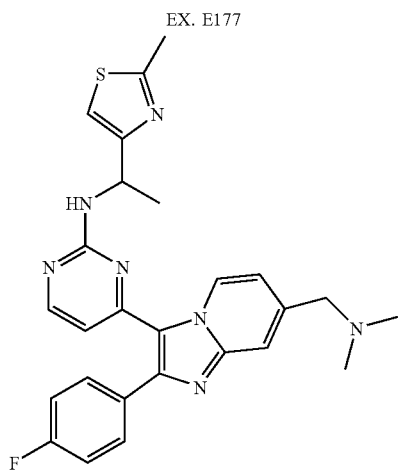
EX. E178
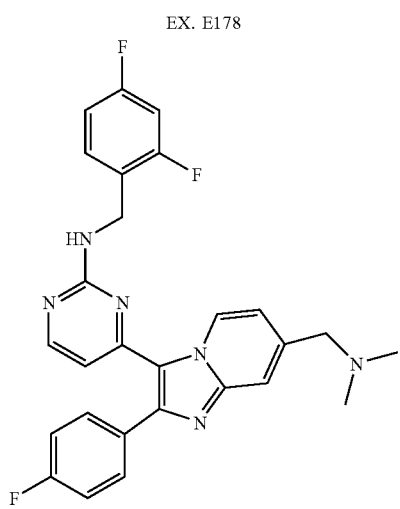
EX. E179
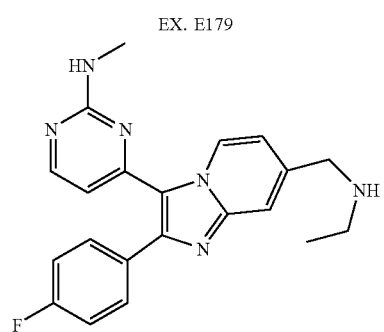

-continued
EX. E180
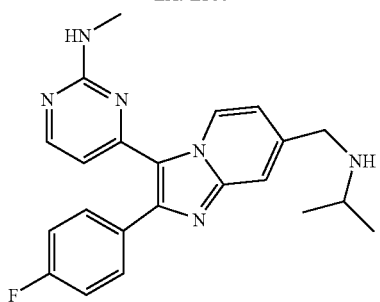
EX. E181
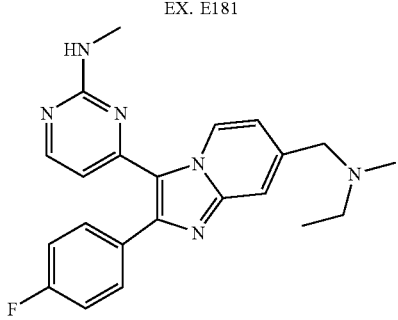
EX. E182
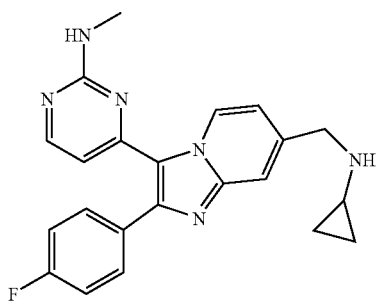
EX. E183
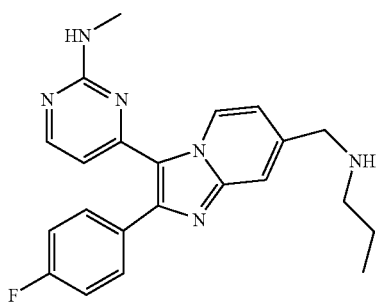

-continued
EX. E184
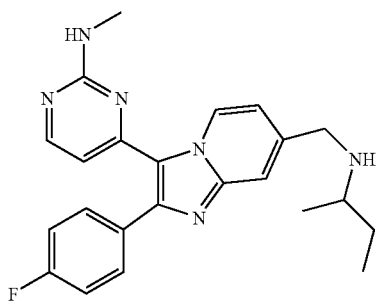
EX. E185
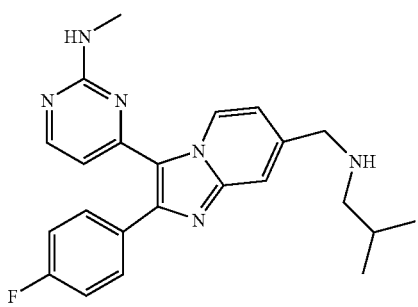
EX. E186
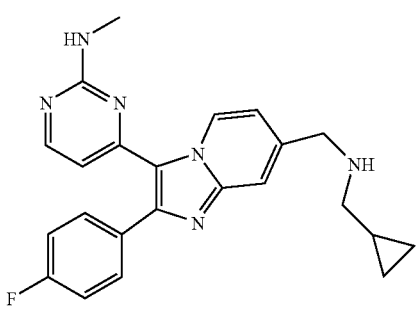
EX. E187
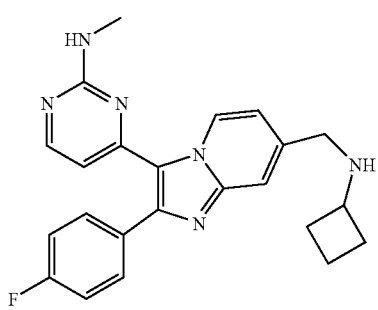

-continued
EX. E188
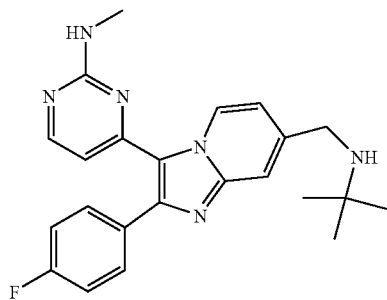
EX. E189
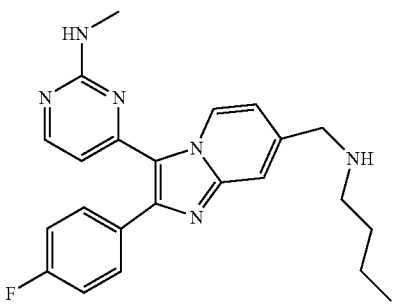
EX. E190
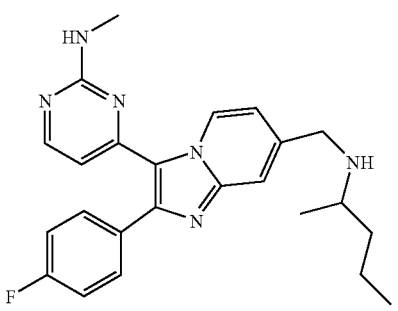
EX. E191
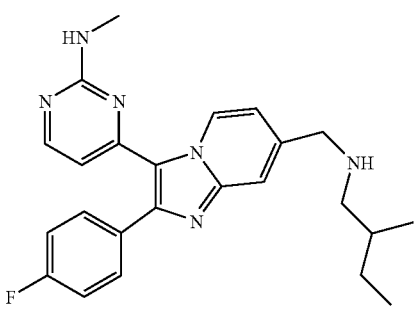

-continued
EX. E192
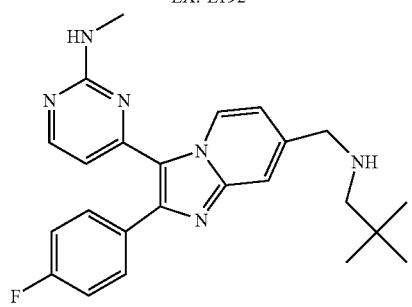
EXAMPLE F1 to EXAMPLE F182 below were made by procedures similar to those described above.
EX. F1
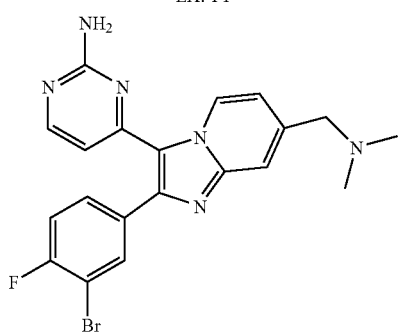
EX. F2
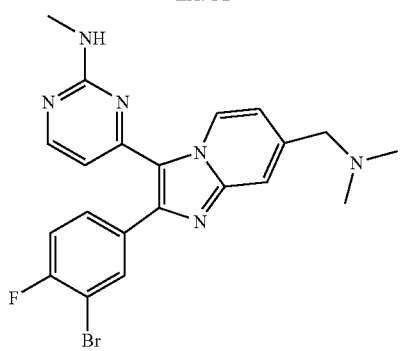
EX. F3
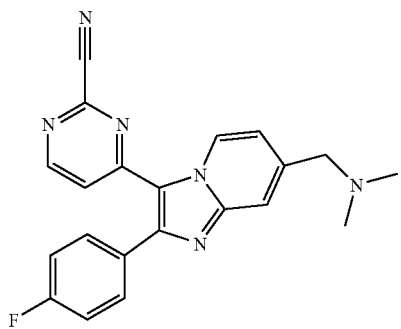
-continued
EX. F4
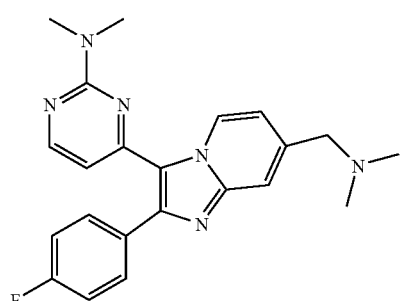
EX. F5
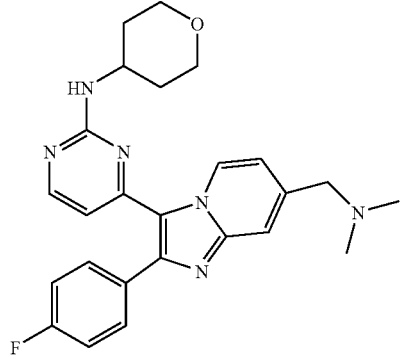
EX. F6
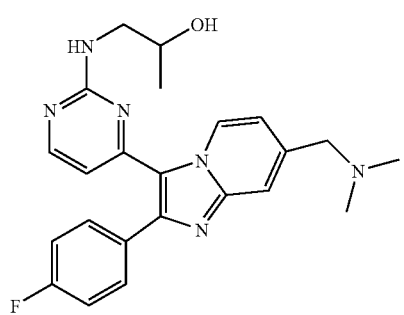

| | |
|---|---|
| EX. F7 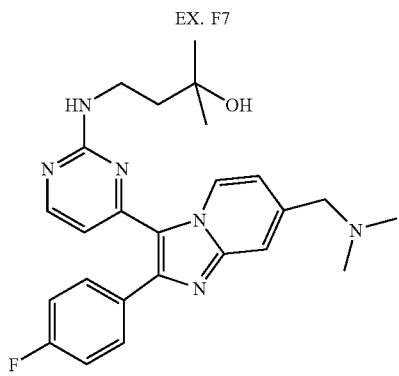 | EX. F11 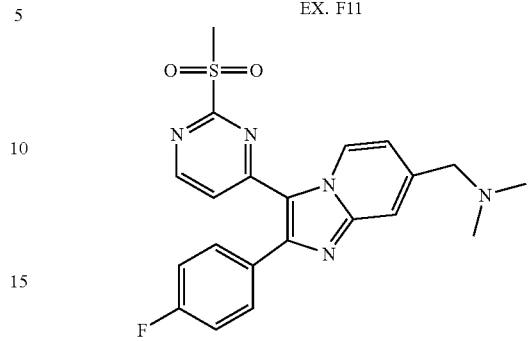 |
| EX. F8 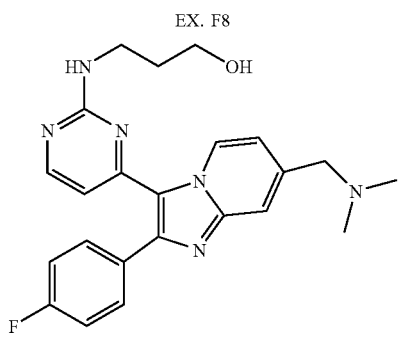 | EX. F12 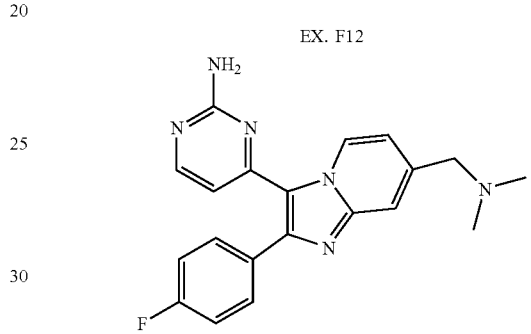 |
| EX. F9 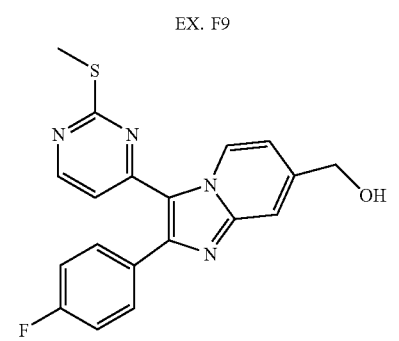 | EX. F13 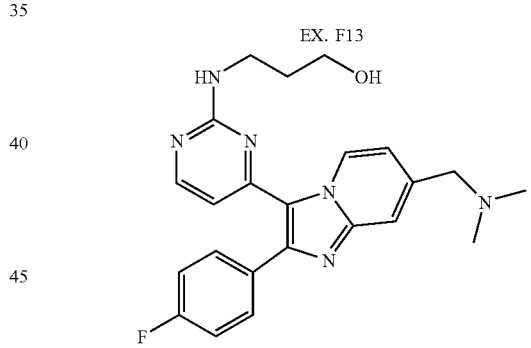 |
| EX. F10 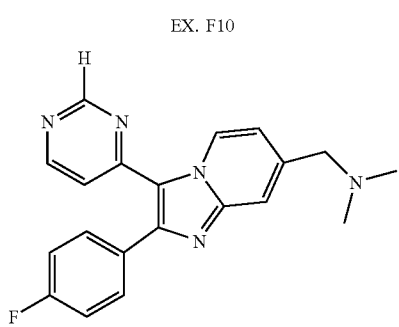 | EX. F14 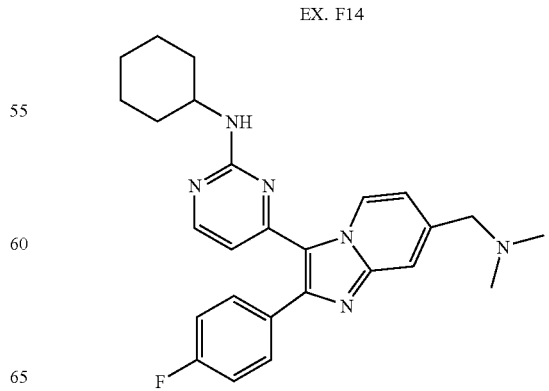 |

-continued
EX. F15
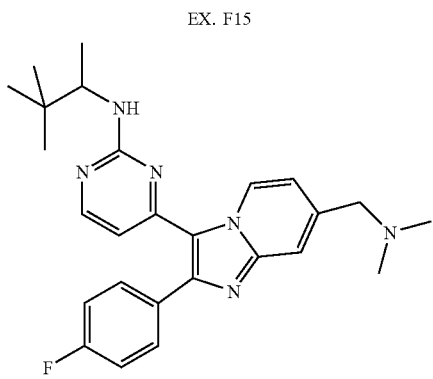
EX. F16
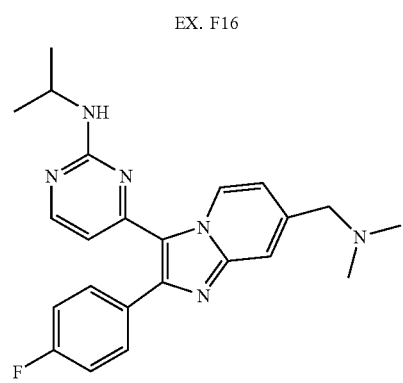
EX. F17
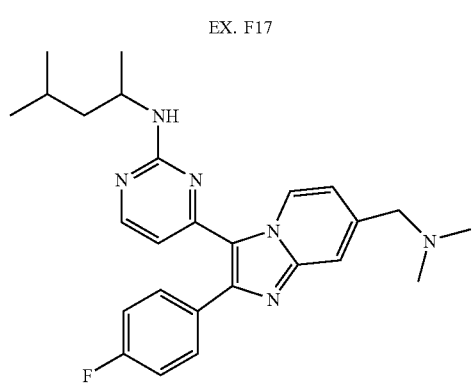
EX. F18
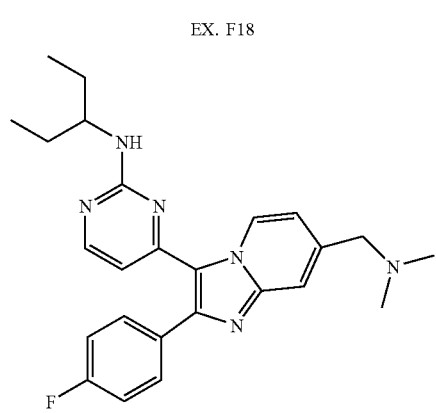
-continued
EX. F19
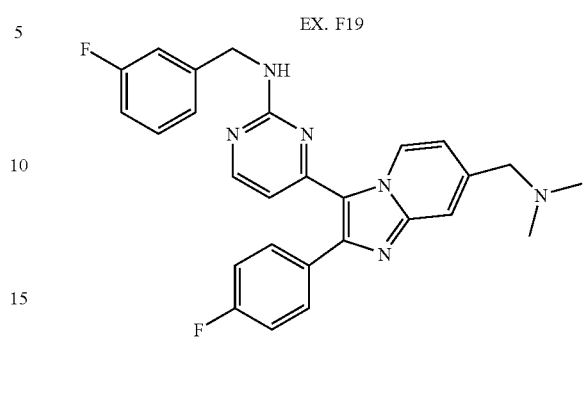
EX. F20
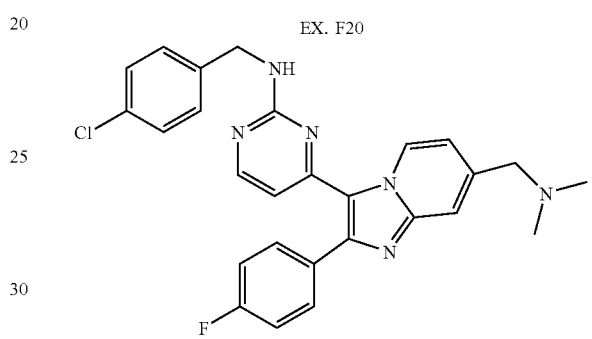
EX. F21
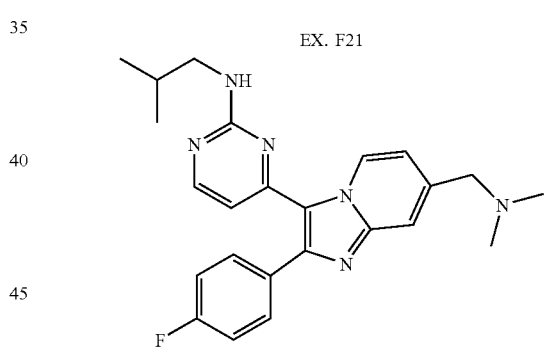
EX. F22
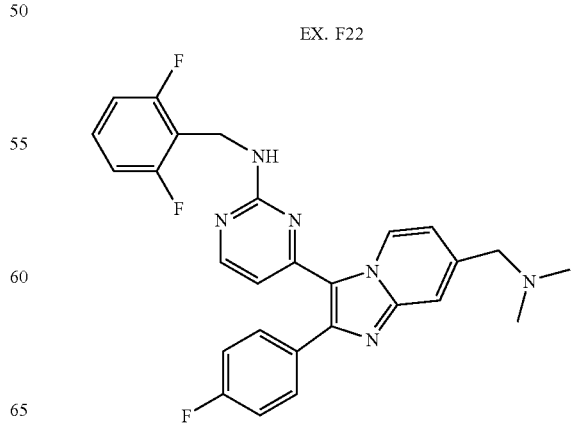

| -continued | -continued |
|---|---|
| EX. F23 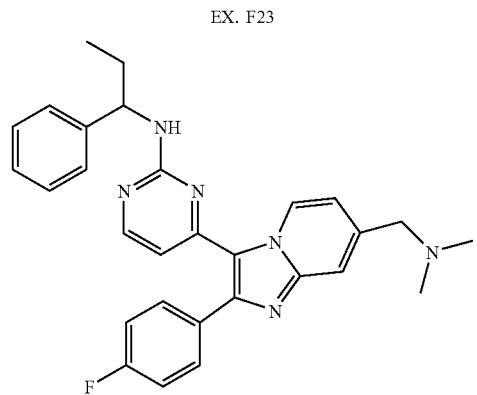 | EX. F27 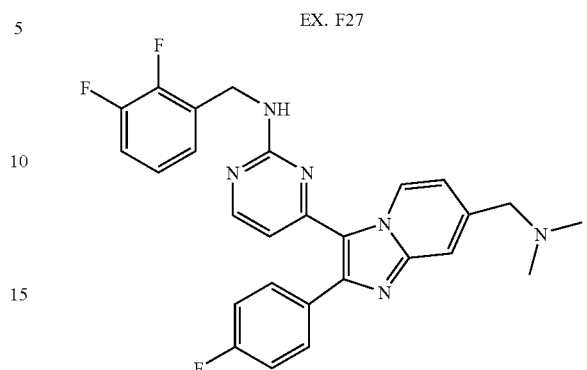 |
| EX. F24 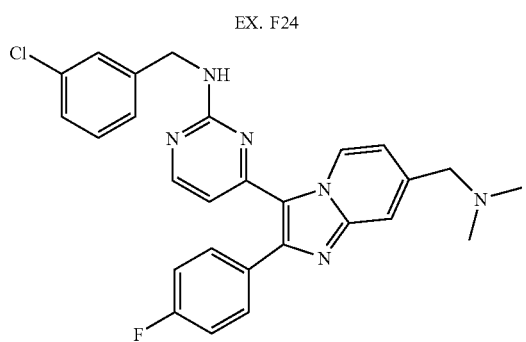 | EX. F28 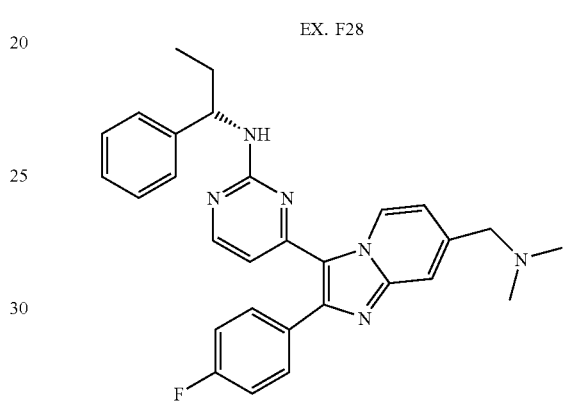 |
| EX. F25 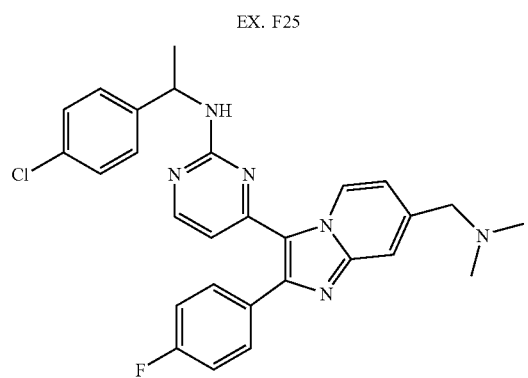 | EX. F29 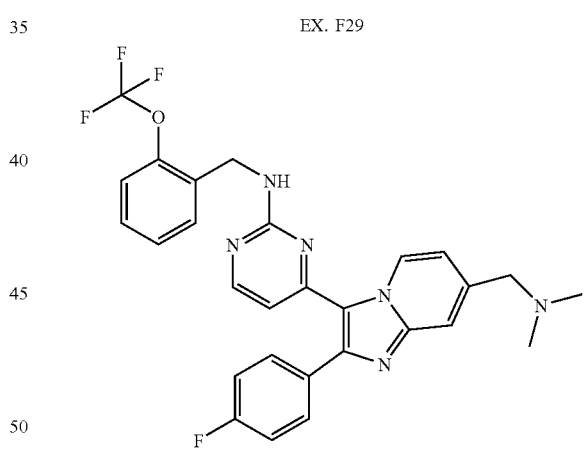 |
| EX. F26 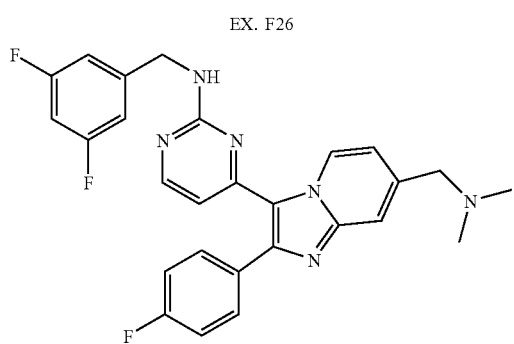 | EX. F29 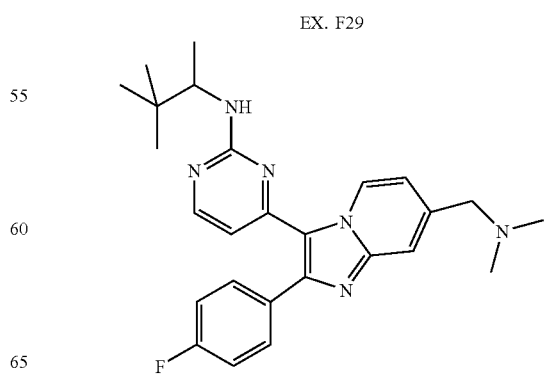 |

-continued
EX. F30
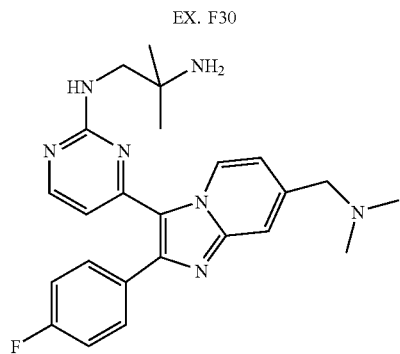
EX. F31
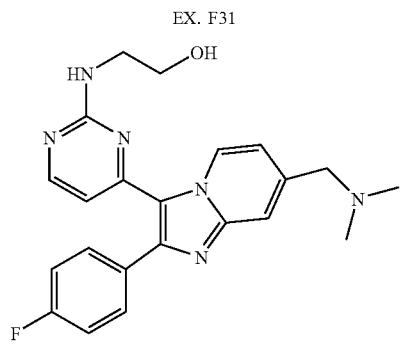
EX. F32
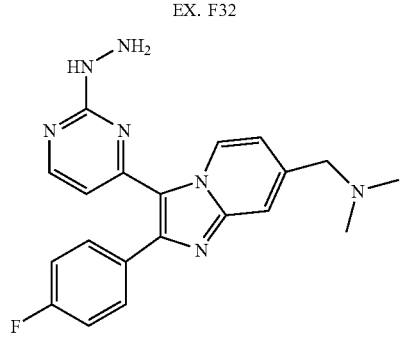
EX. F33
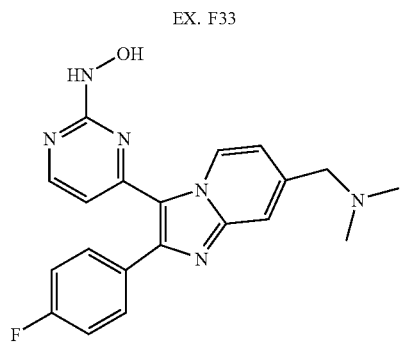
-continued
EX. F34
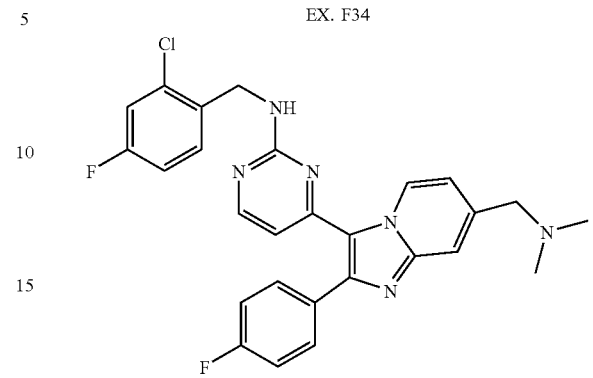
EX. F35
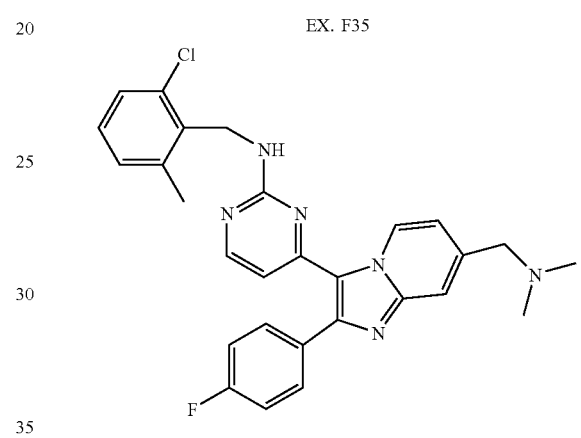
EX. F36
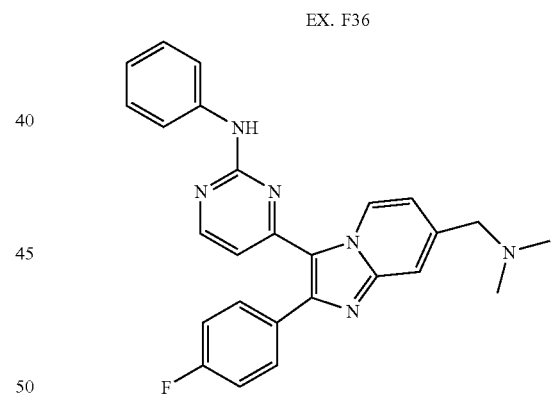
EX. F37
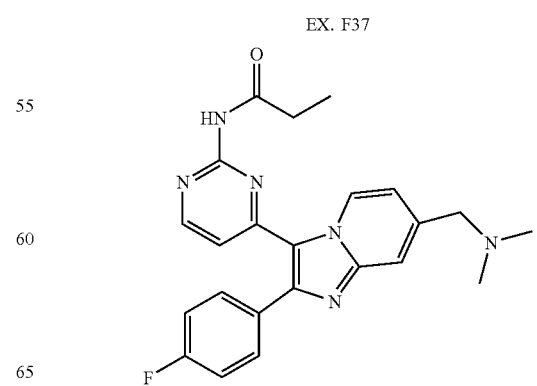

-continued
EX. F38
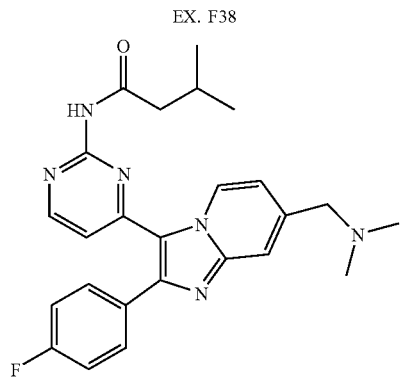
EX. F39
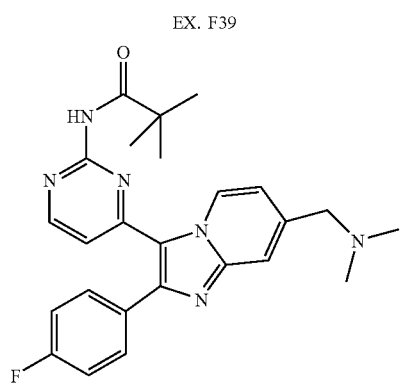
EX. F40
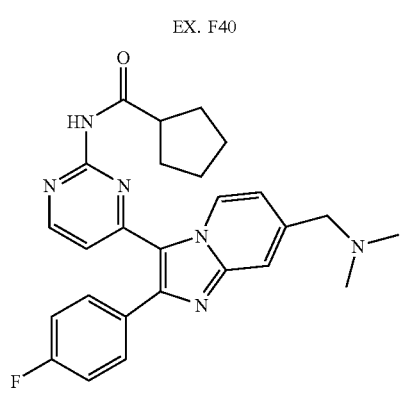
EX. F41
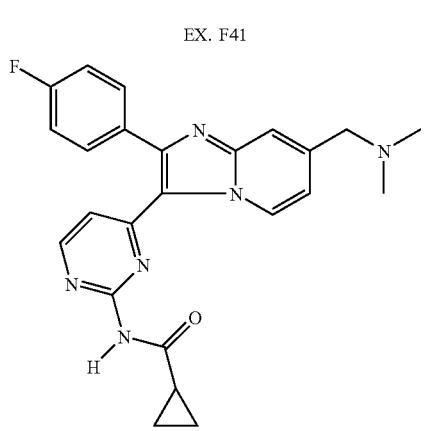
-continued
EX. F42
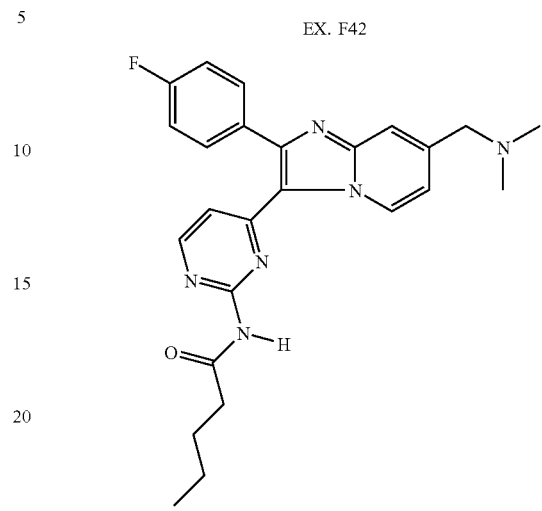
EX. F43
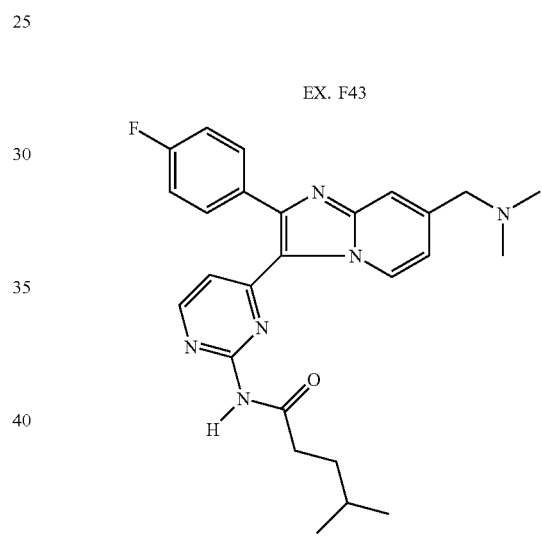
EX. F44
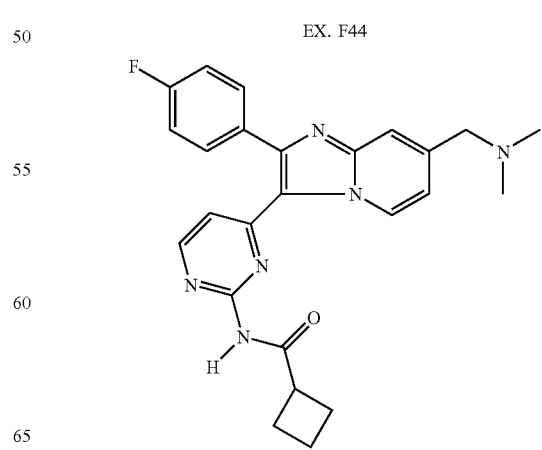

-continued
EX. F45
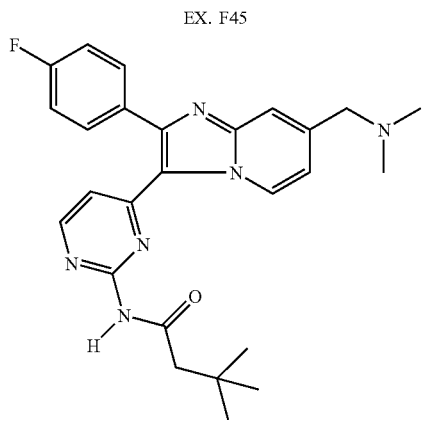
EX. F46
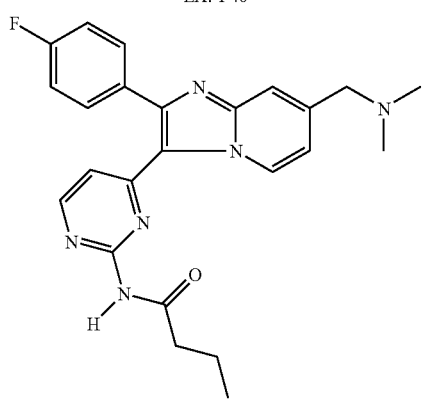
EX. F47
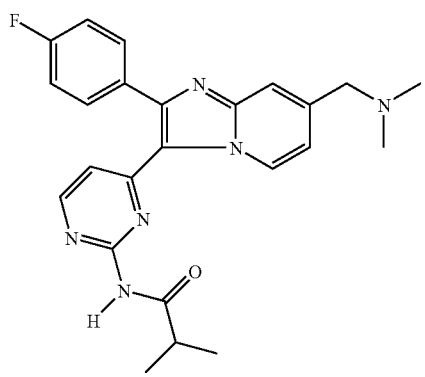
EX. F48
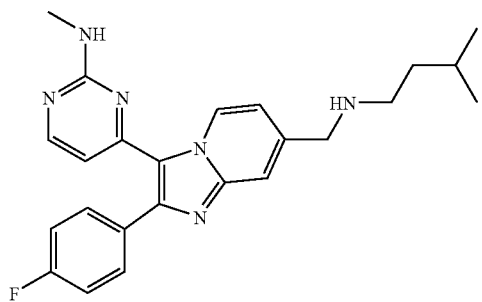
-continued
EX. F49
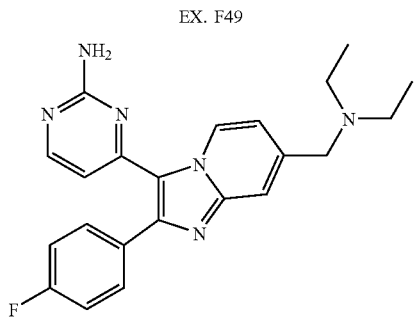
EX. F50
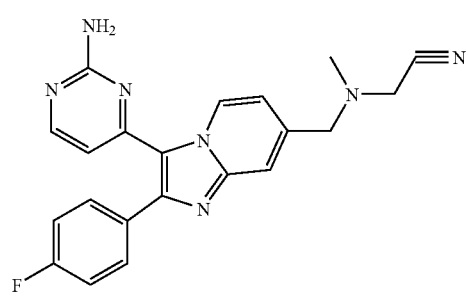
EX. F51
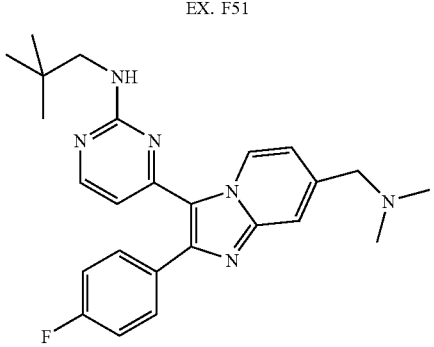
EX. F52
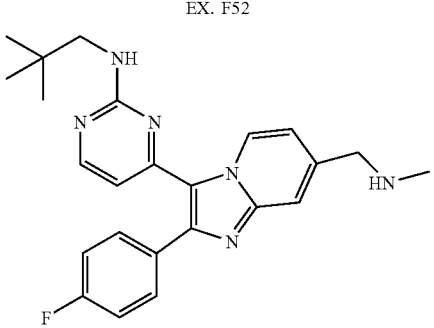

-continued
EX. F53
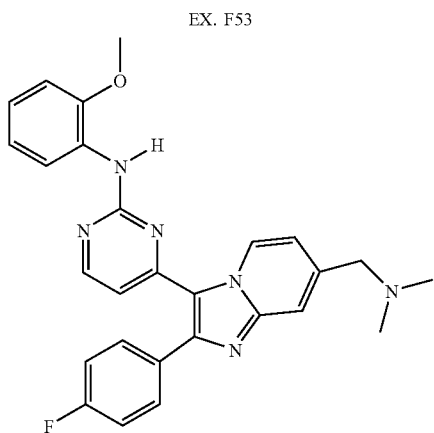
EX. F54
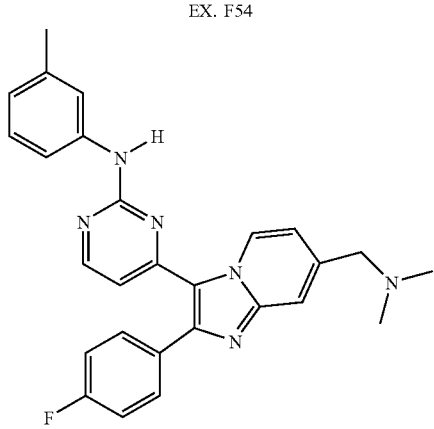
EX. F55
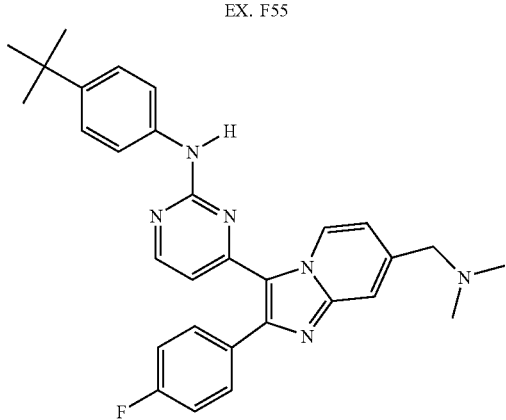
-continued
EX. F56
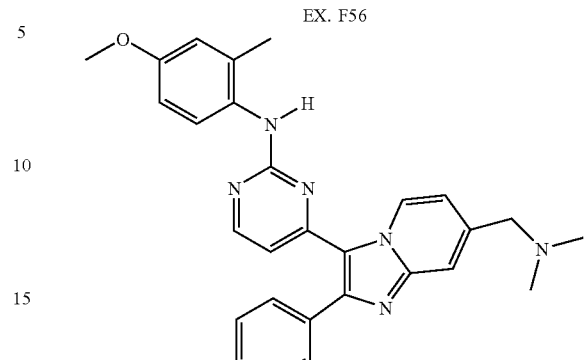
EX. F57
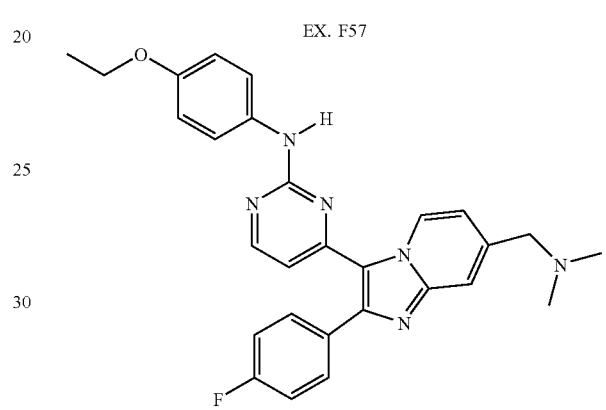
EX. F58
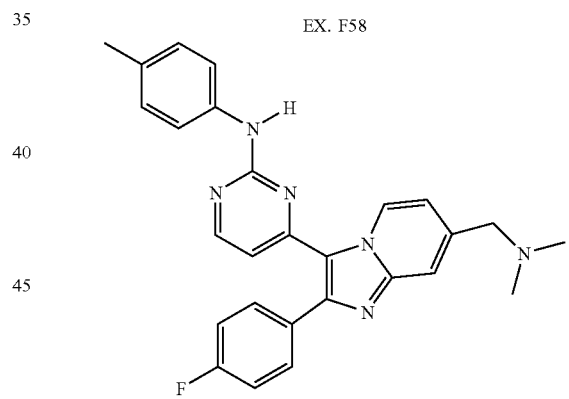
EX. F59
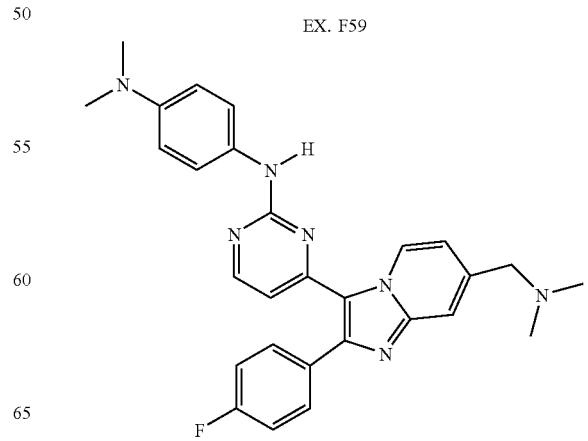

-continued
EX. F60
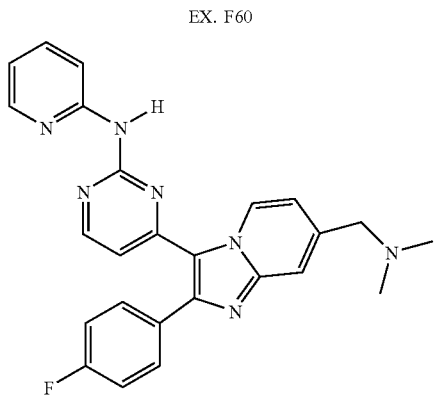
EX. F61
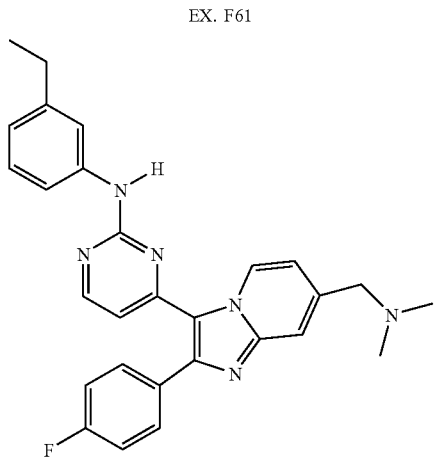
EX. F62
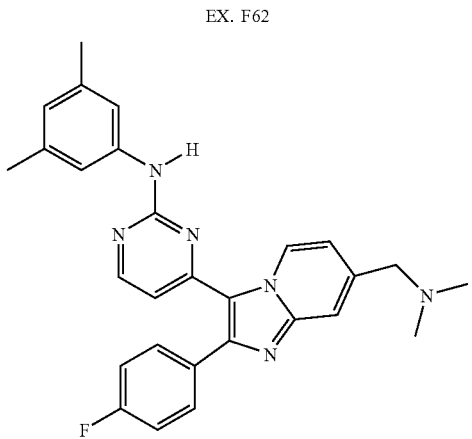
-continued
EX. F63
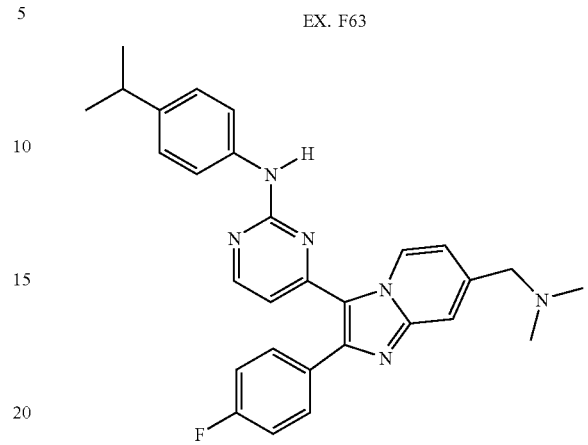
EX. F64
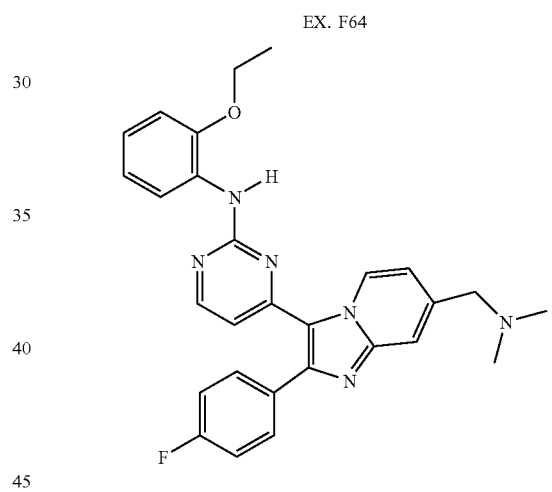
EX. F65
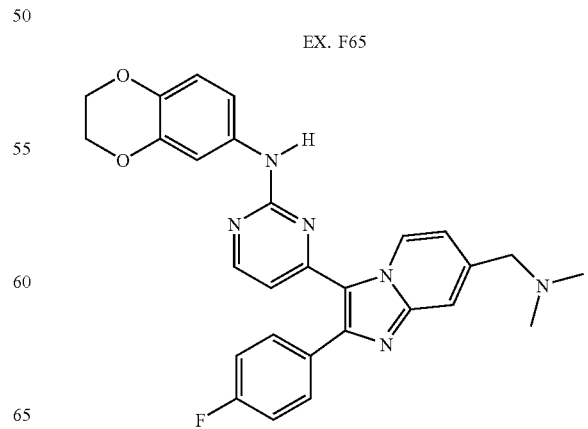

-continued
EX. F66
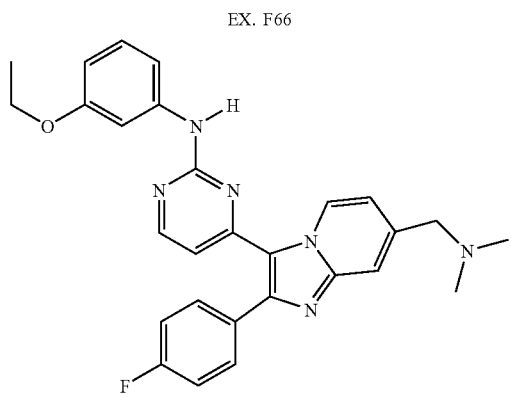
EX. F67
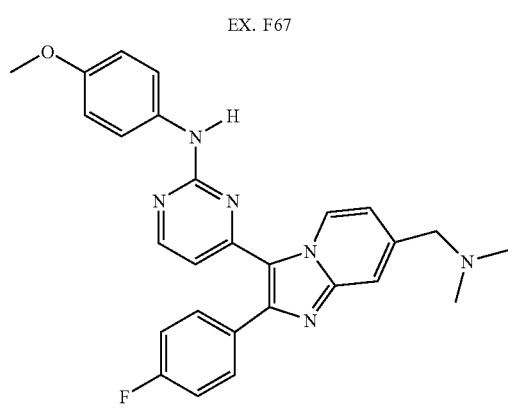
EX. F68
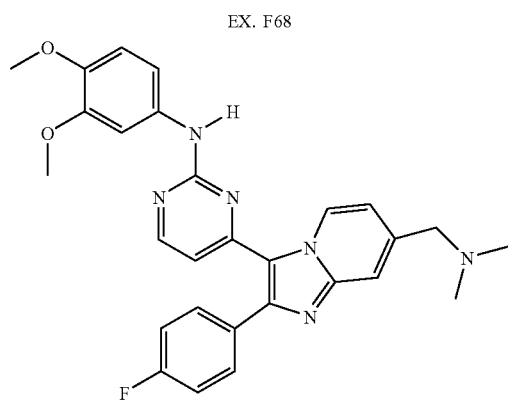
EX. F69
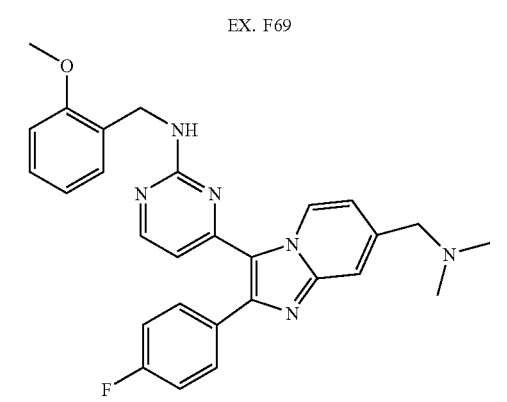
-continued
EX. F70
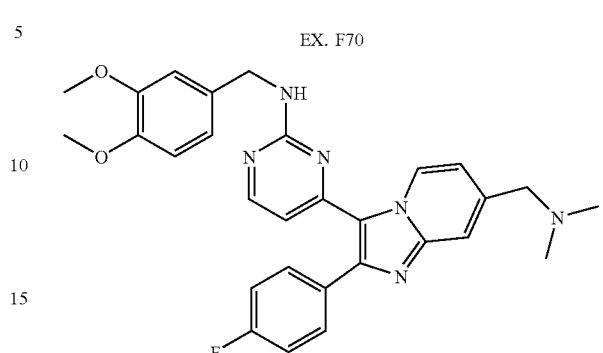
EX. F71
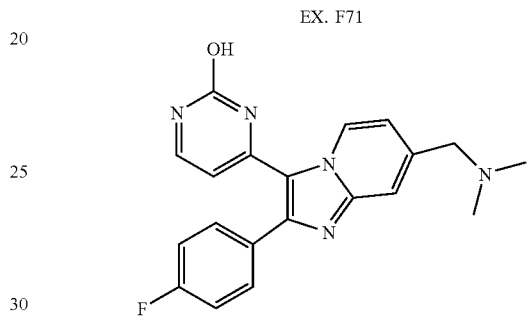
EX. F72
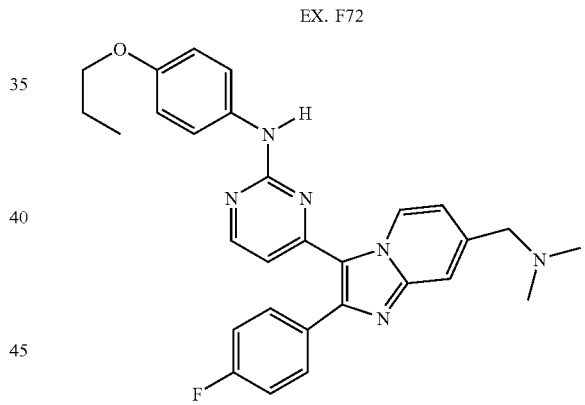
EX. F73
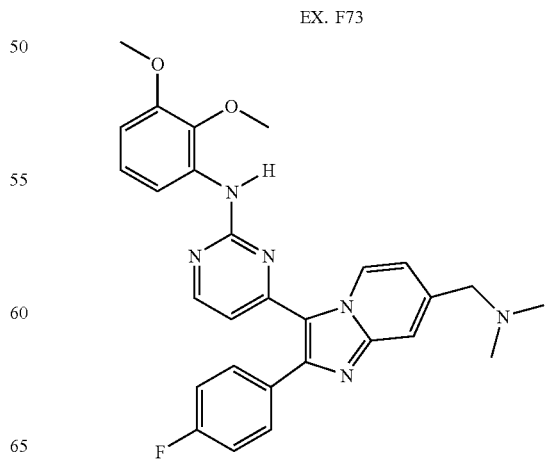

EX. F74
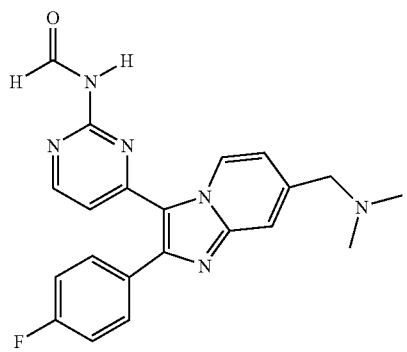
EX. F75
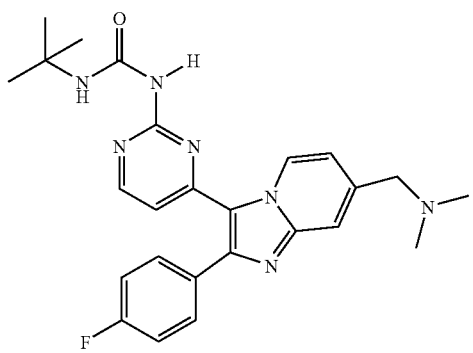
EX. F78
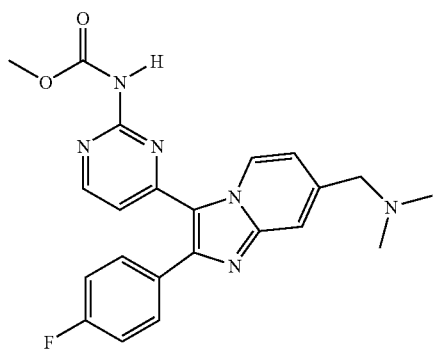
EX. F79
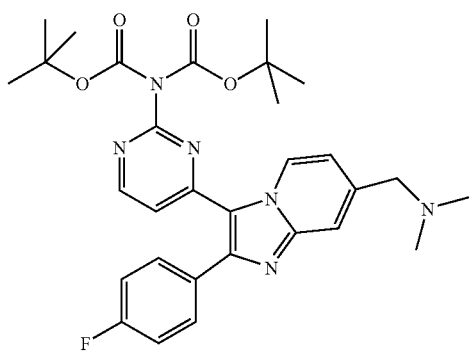
EX. F80
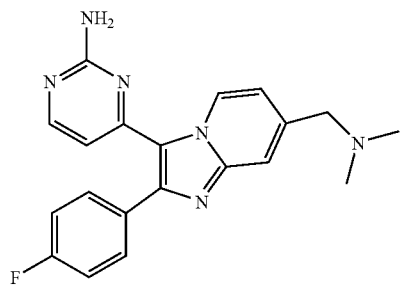
EX. F81
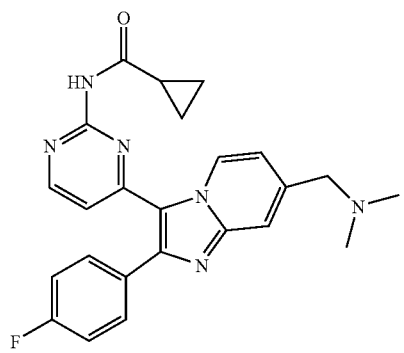
EX. F82
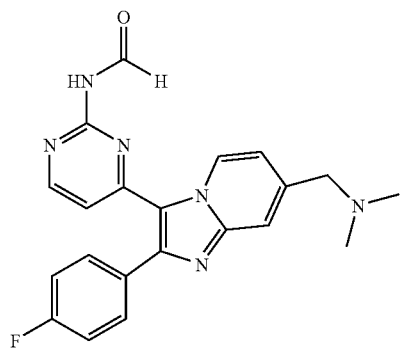
EX. F83
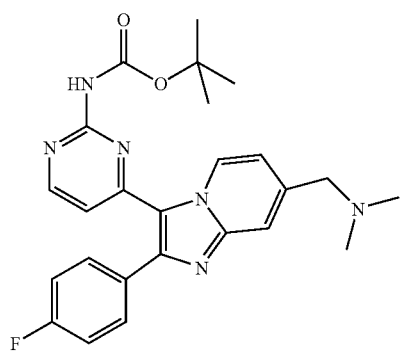

-continued
EX. F84
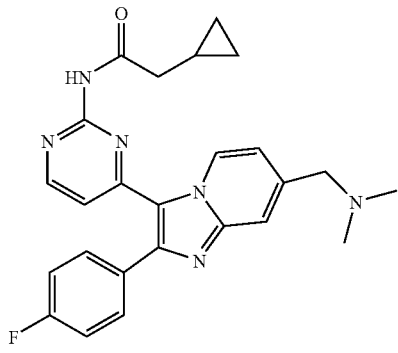
EX. F85
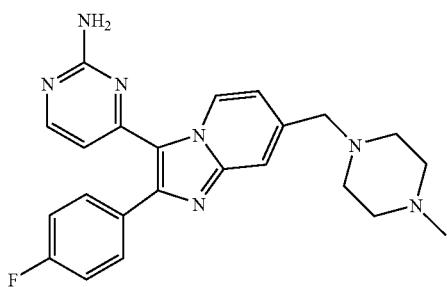
EX. F86
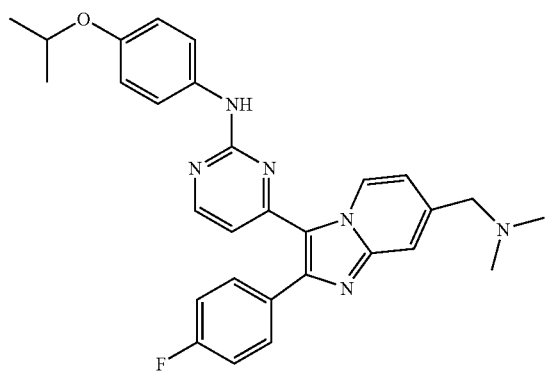
EX. F87
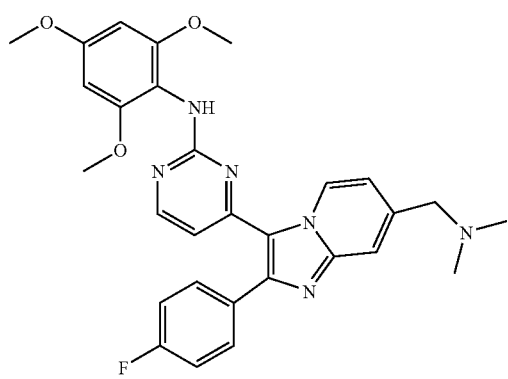
-continued
EX. F88
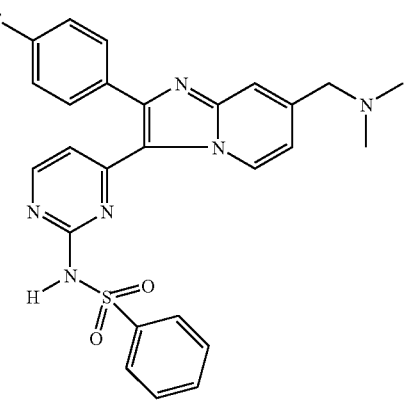
EX. F89
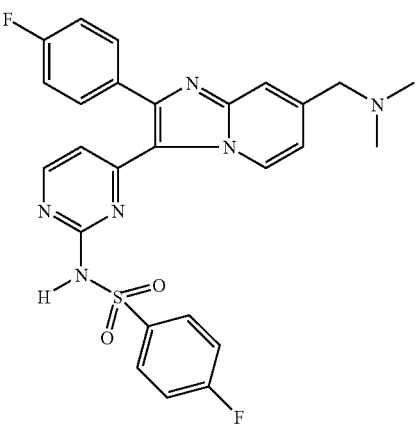
EX. F90
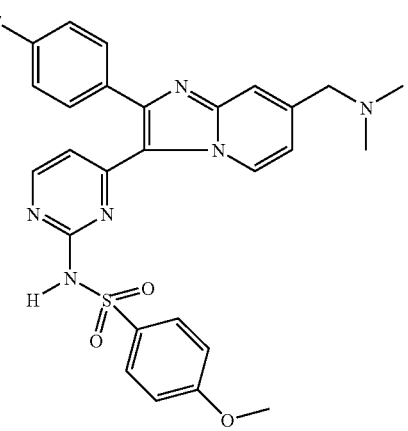

-continued
EX. F91
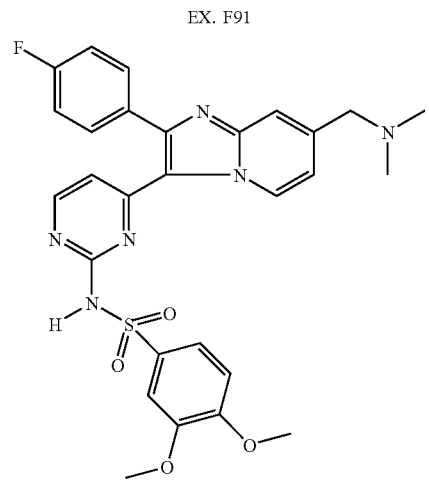
EX. F92
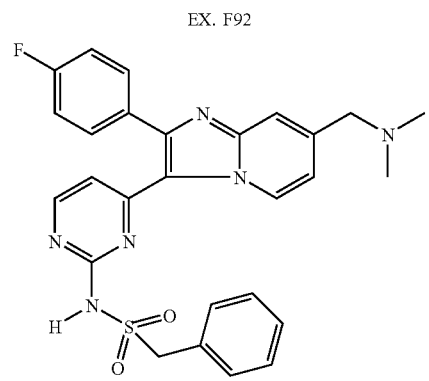
EX. F93
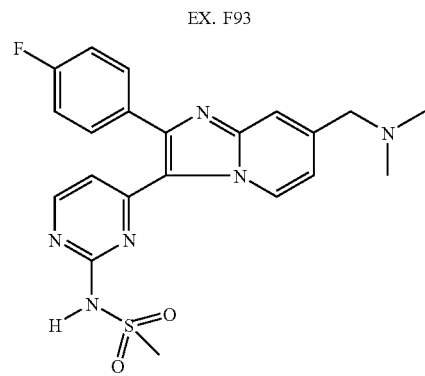
EX. F94
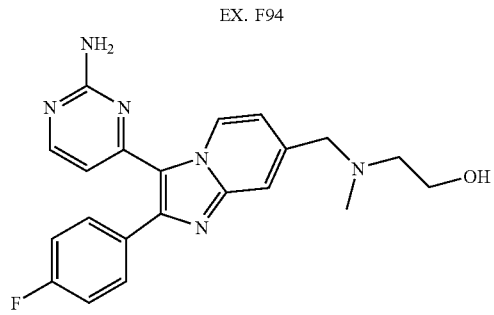
-continued
EX. F95
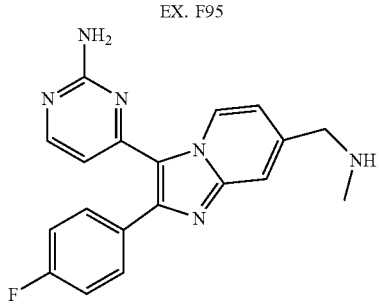
EX. F96
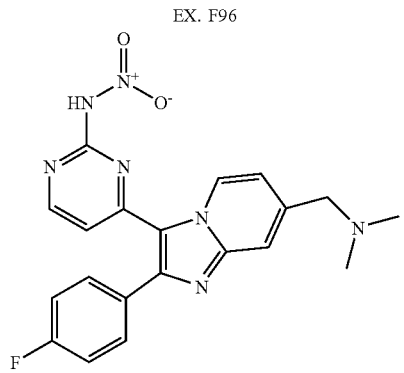
EX. F97
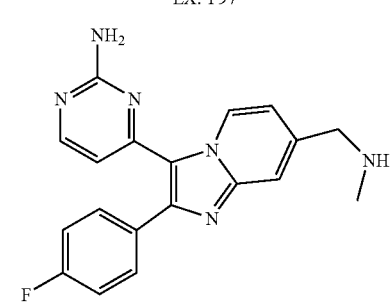
EX. F98
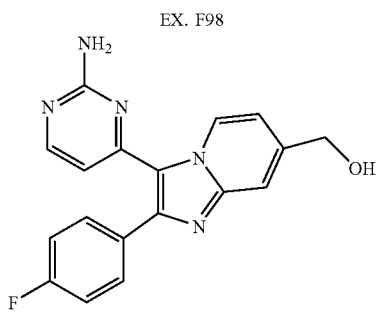
EX. F99
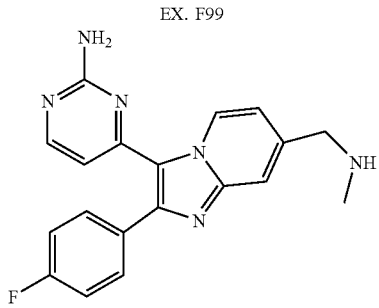

-continued
EX. F100
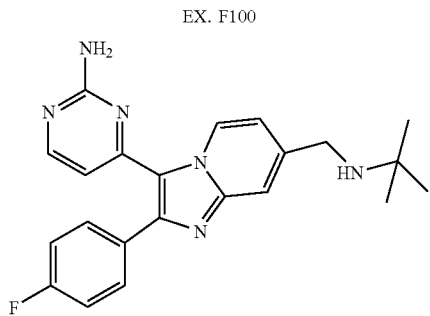
EX. F101
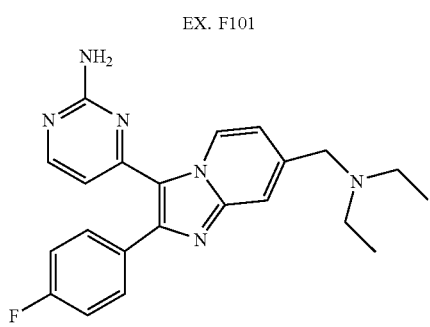
EX. F102
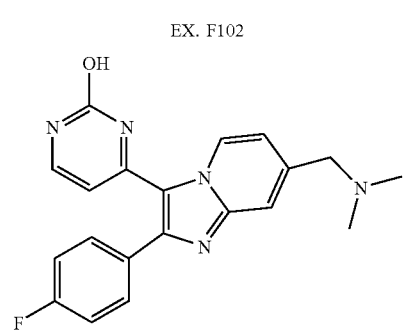
EX. F103
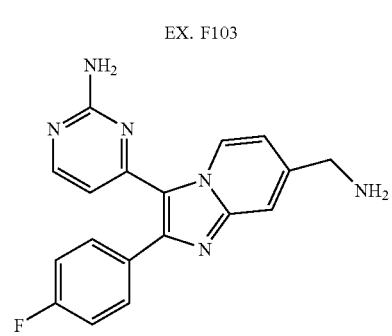
EX. F104
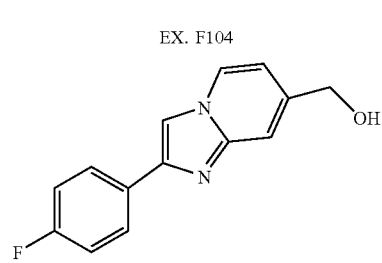
-continued
EX. F105
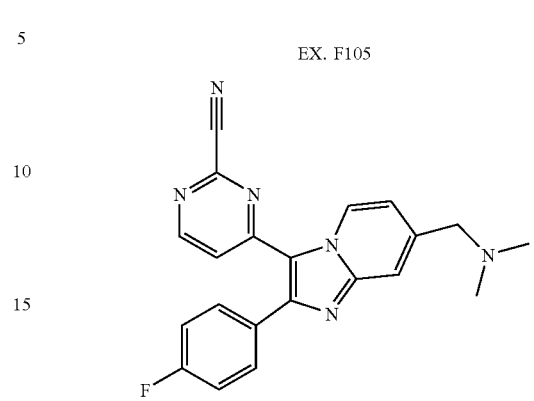
EX. F106
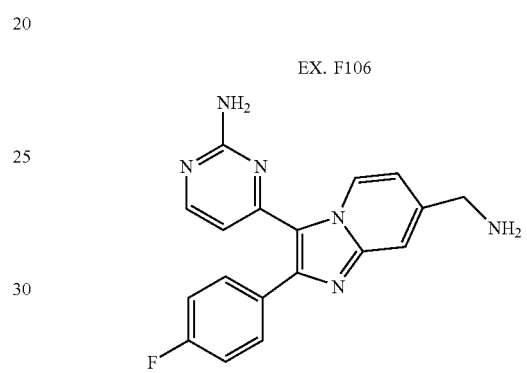
EX. F107
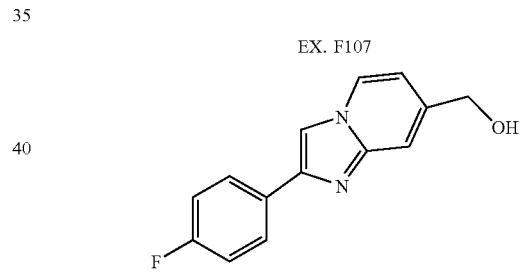
EX. F108
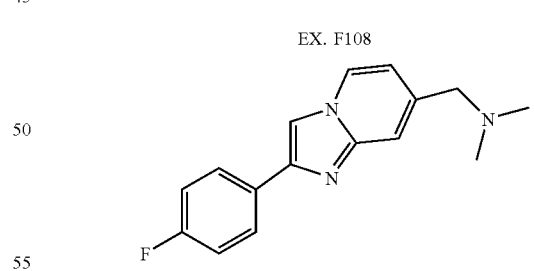
EX. F109
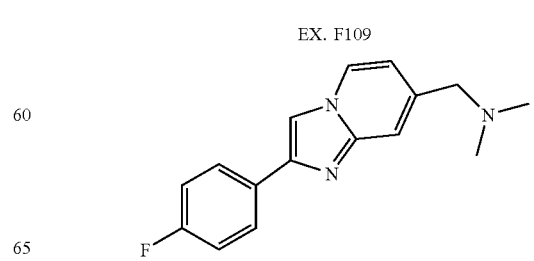

EX. F110
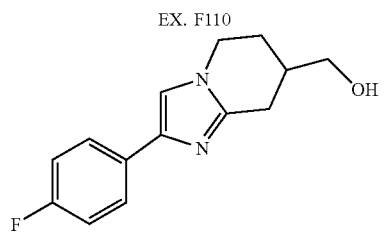
EX. F111
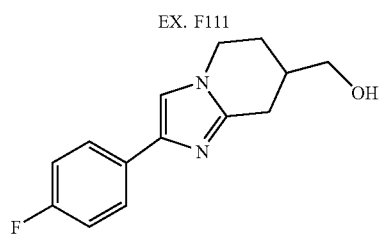
EX. F112
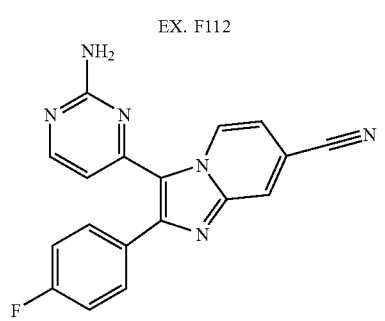
EX. F113
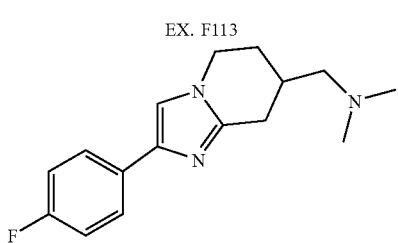
EX. F114
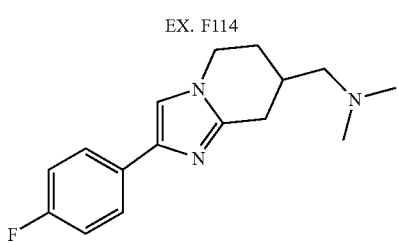
EX. F115
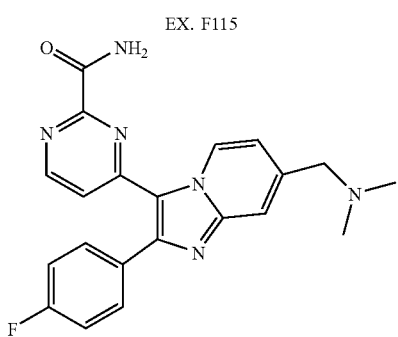
EX. F116
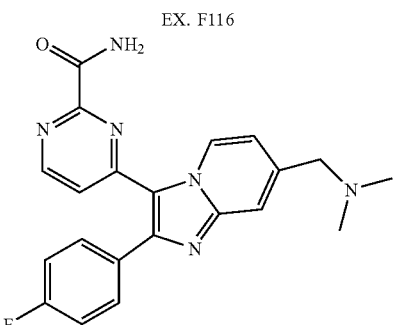
EX. F117
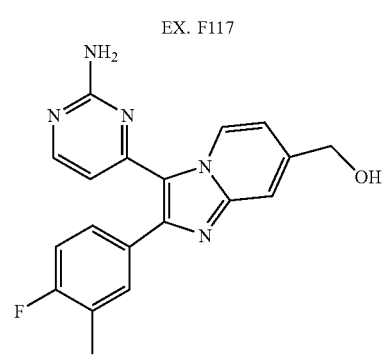
EX. F118
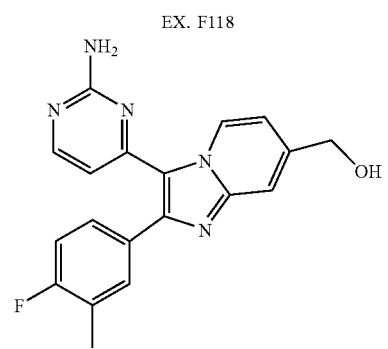
EX. F119
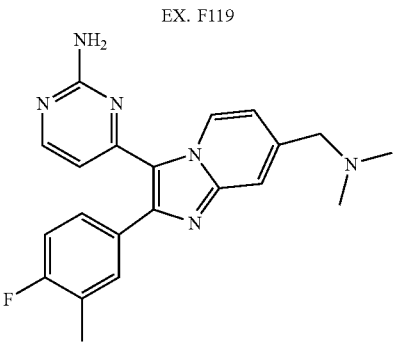

-continued
EX. F120
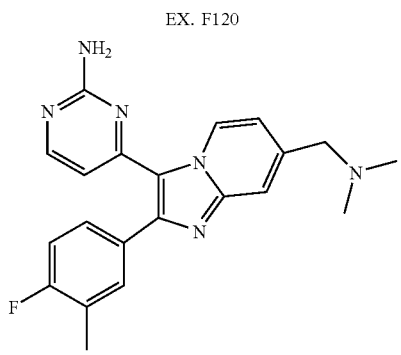
EX. F121
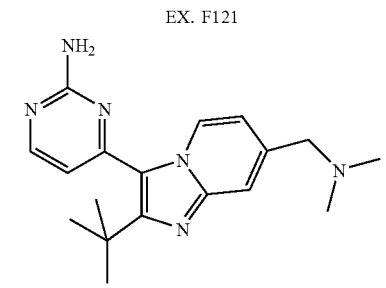
EX. F122
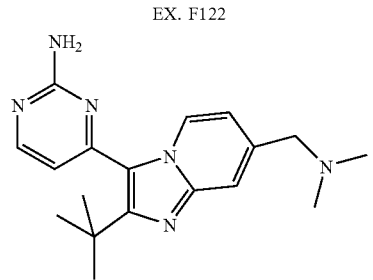
EX. F123
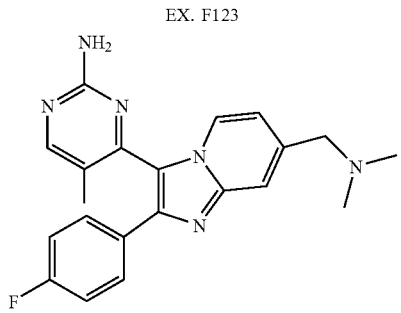
EX. F124
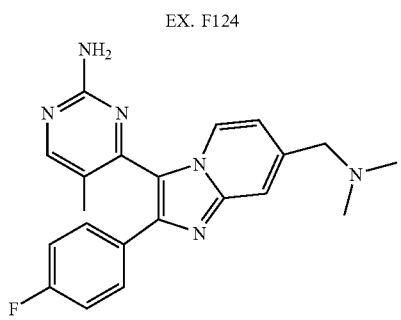
-continued
EX. F125
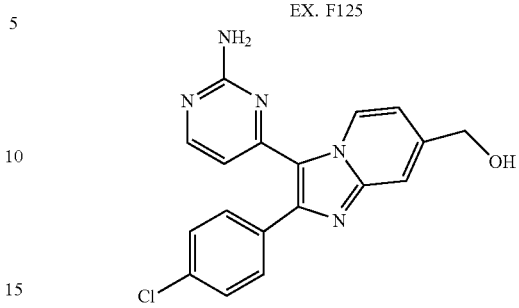
EX. F126
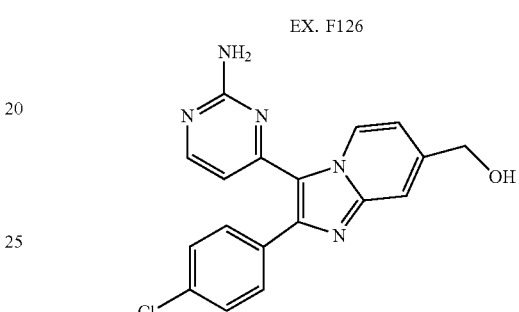
EX. F127
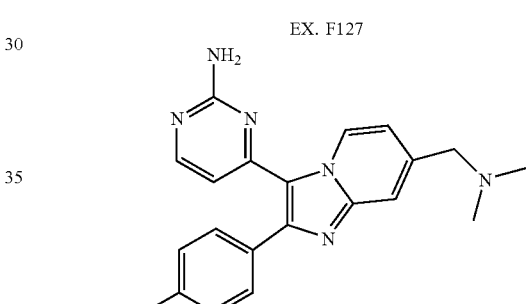
EX. F128
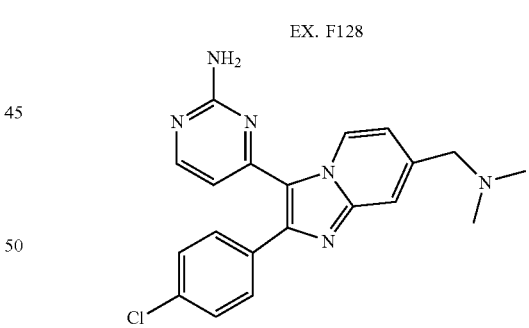
EX. F129
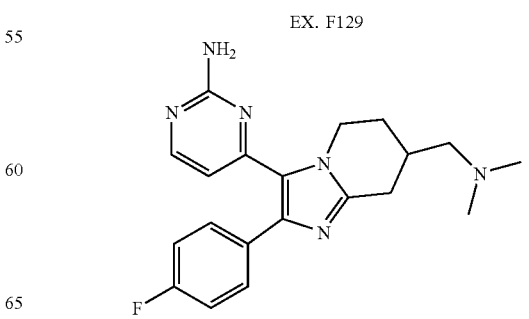

-continued
EX. F130
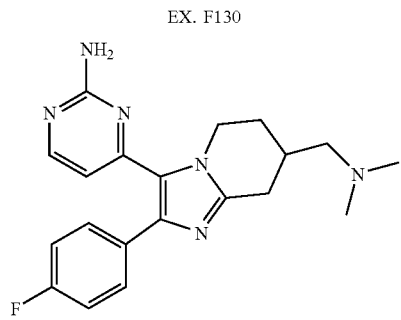
EX. F131
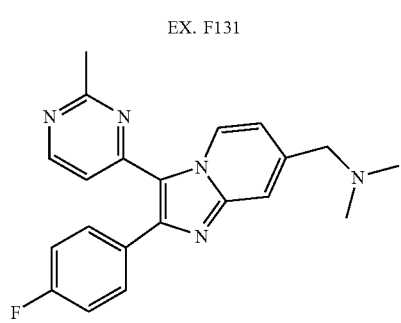
EX. F132
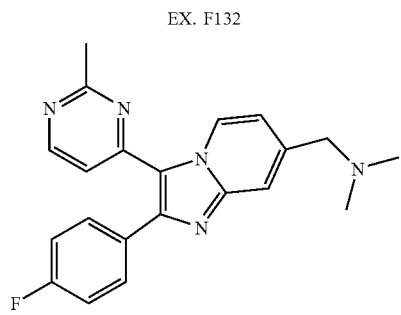
EX. F133
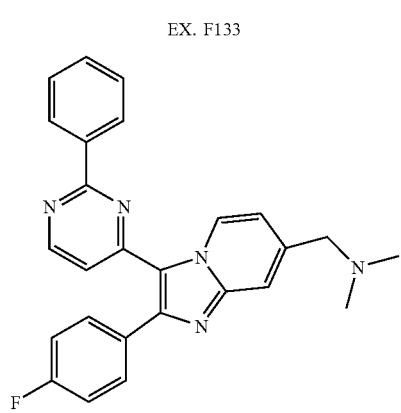
-continued
EX. F134
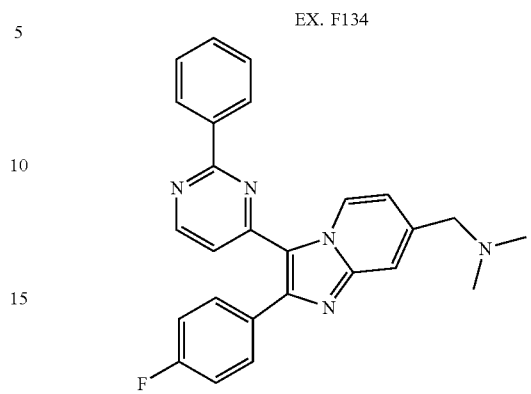
EX. F135
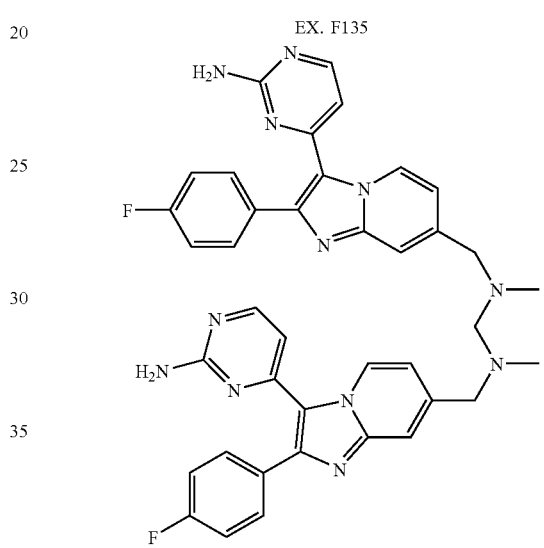
EX. F136
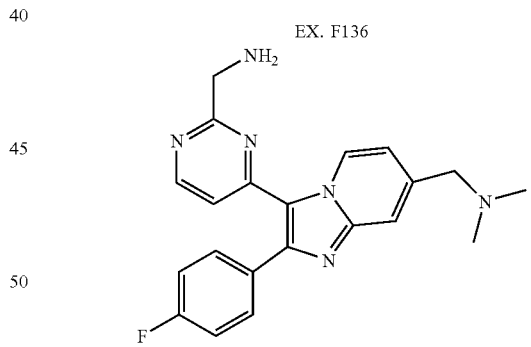
EX. F137
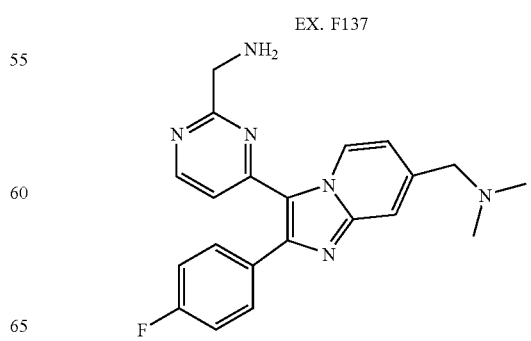

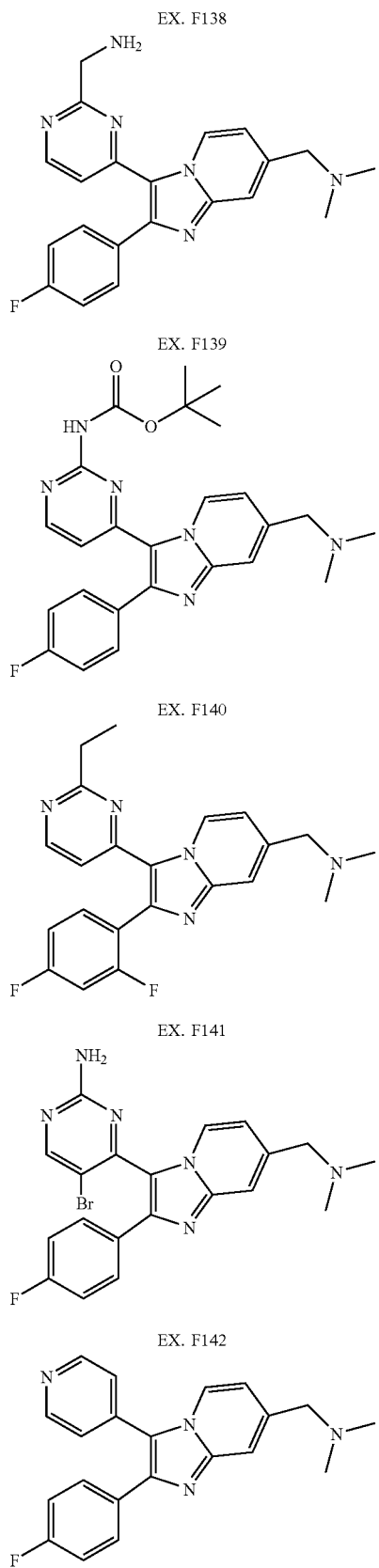
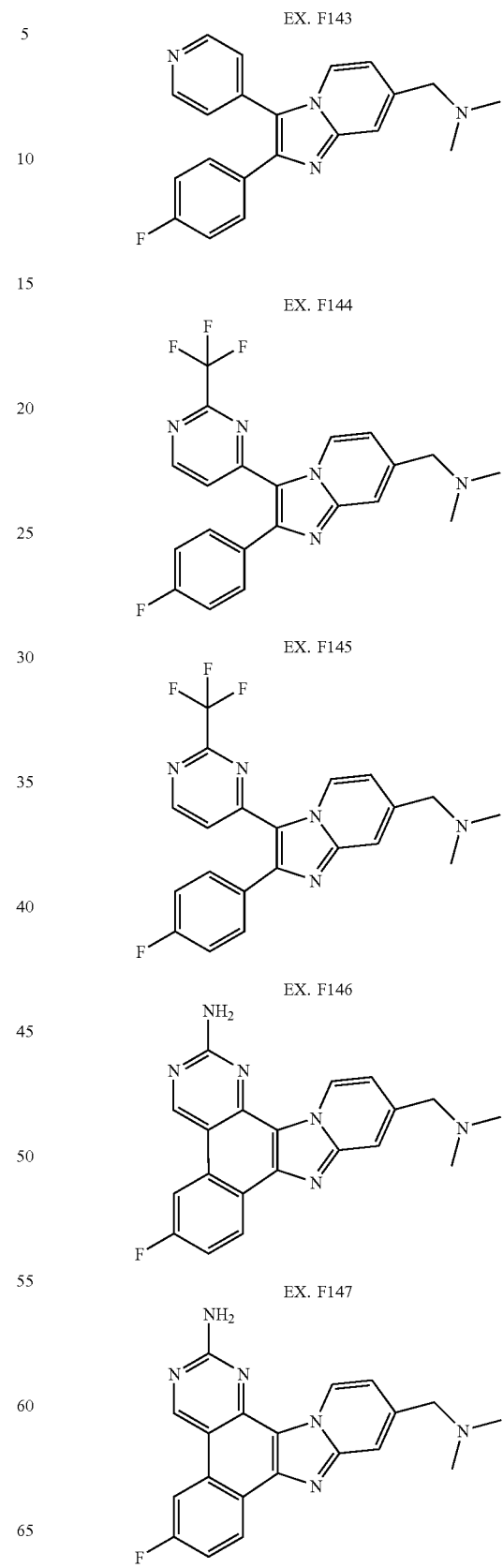

-continued
EX. F148
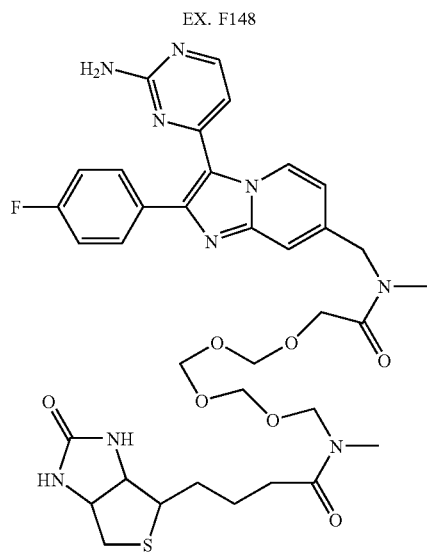
EX. F149
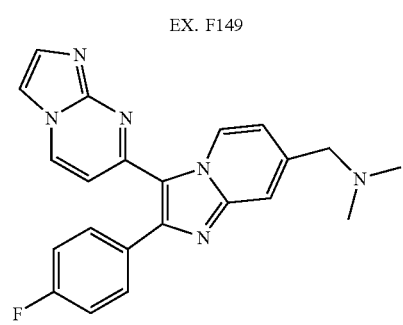
EX. F150
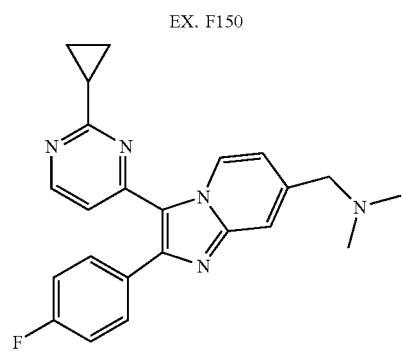
EX. F151
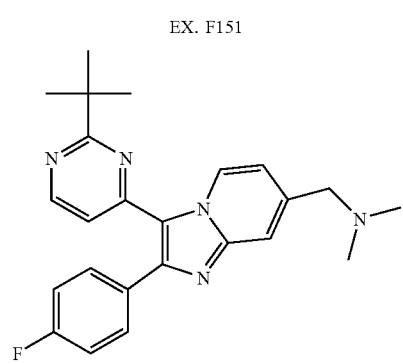
-continued
EX. F152
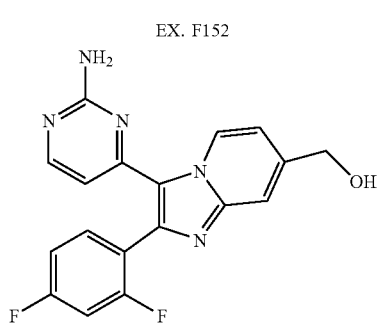
EX. F153
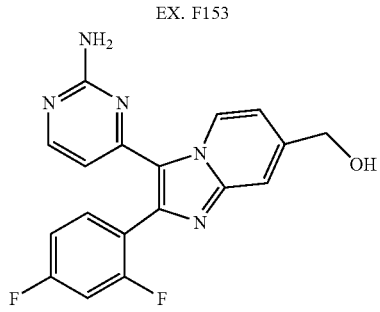
EX. F154
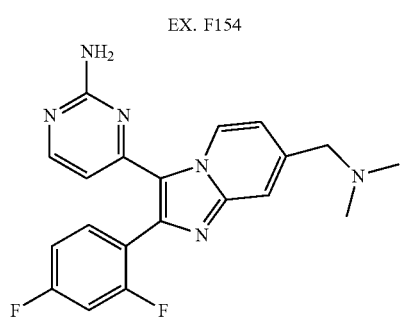
EX. F155
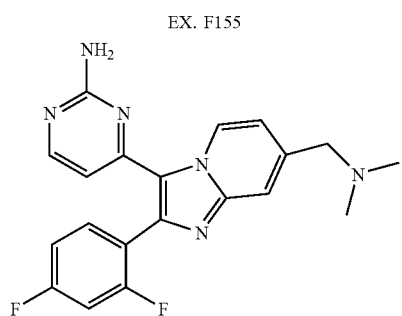
EX. F156
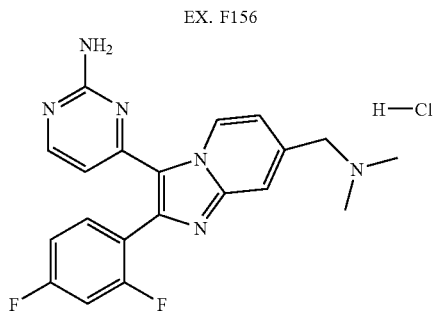

-continued
EX. F157
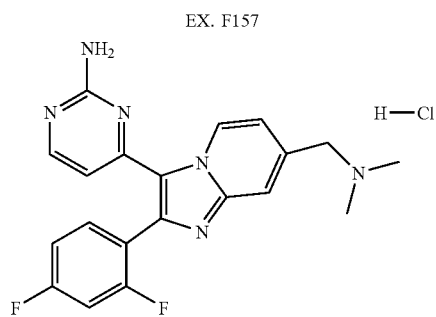
EX. F158
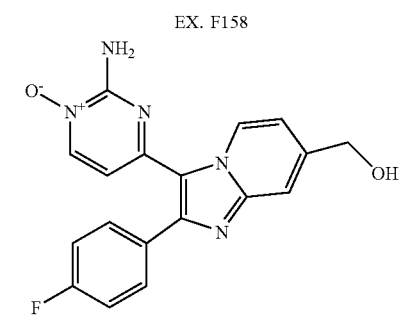
EX. F159
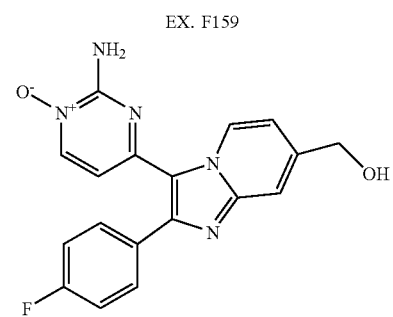
EX. F160
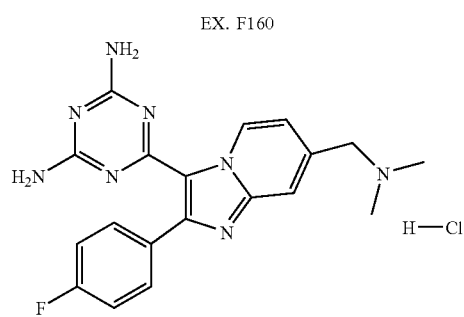
EX. F161
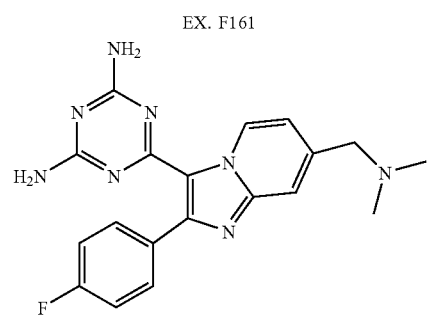
-continued
EX. F162
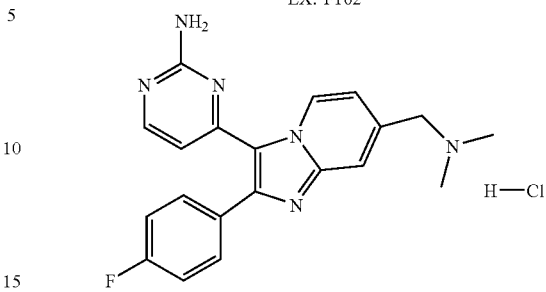
EX. F163
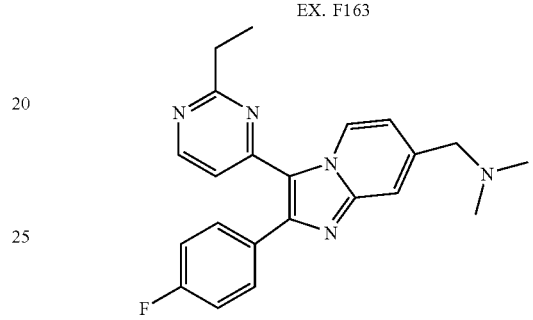
EX. F164
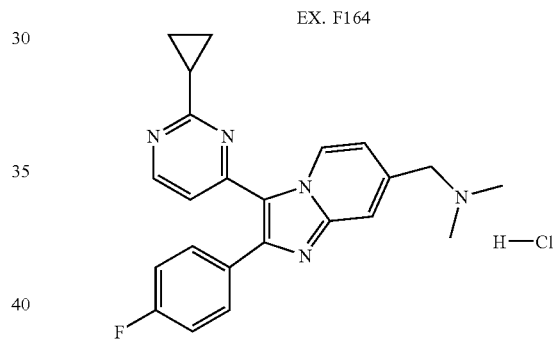
EX. F165
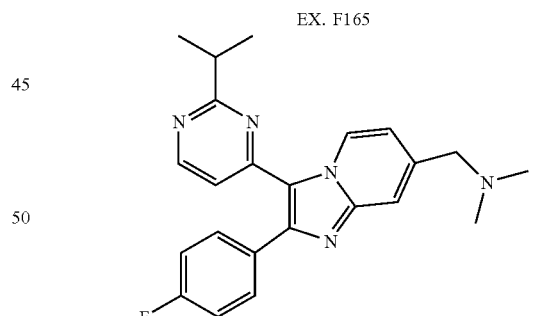
EX. F166
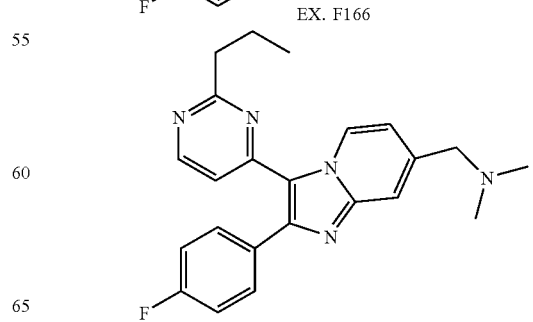

-continued
EX. F167
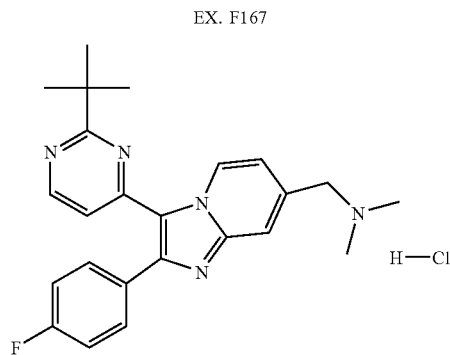
EX. F168
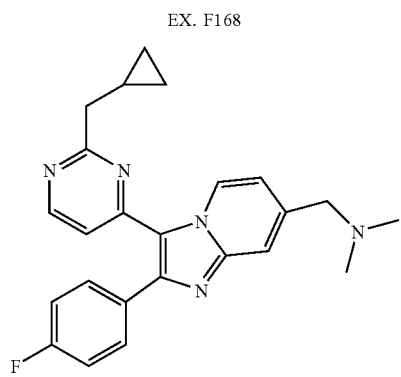
EX. F169
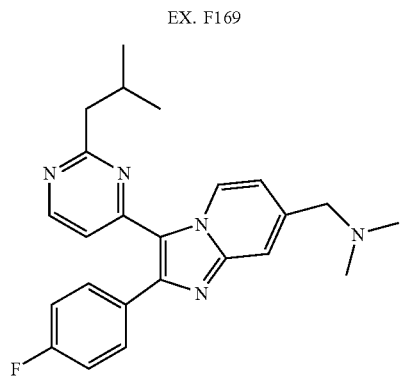
EX. F170
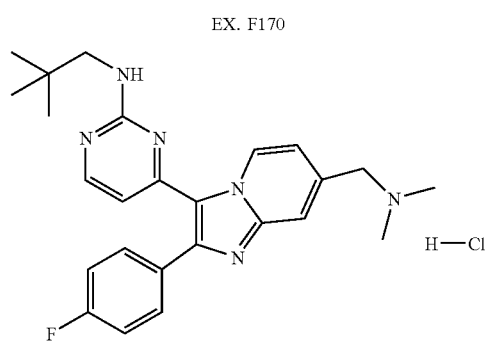
-continued
EX. F171
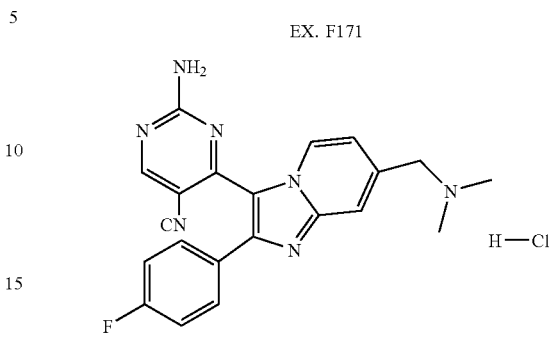
EX. F172
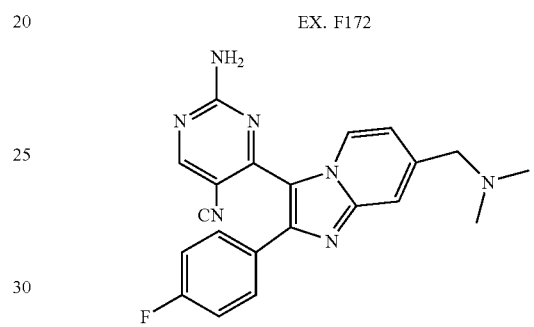
EX. F173
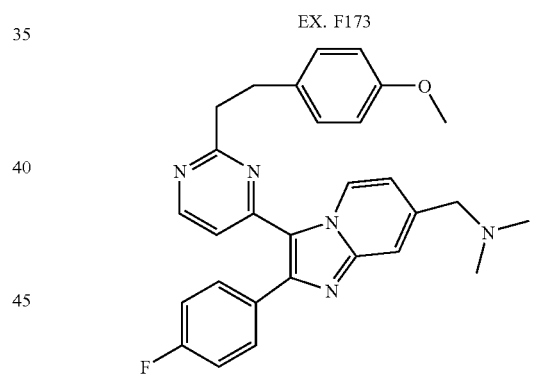
EX. F174
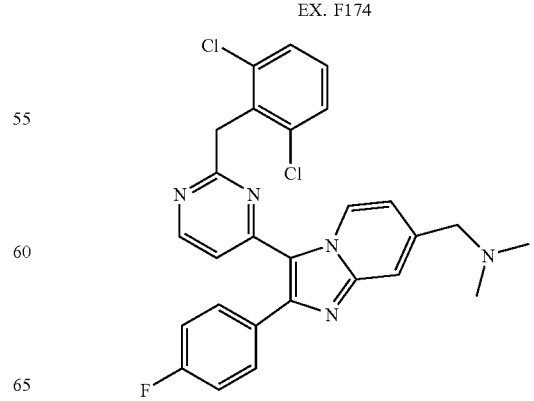

-continued
EX. F175
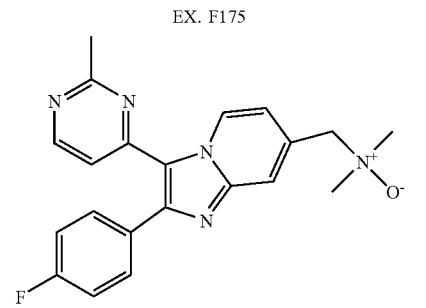
EX. F176
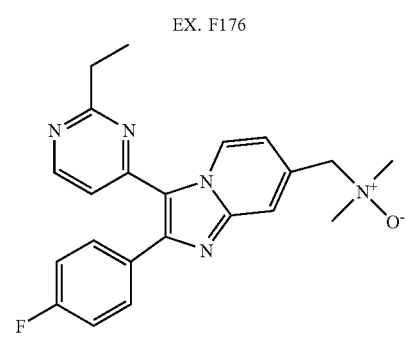
EX. F177
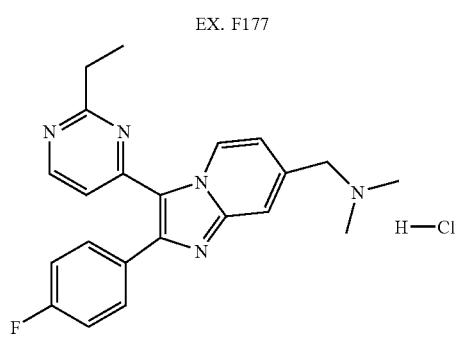
EX. F178
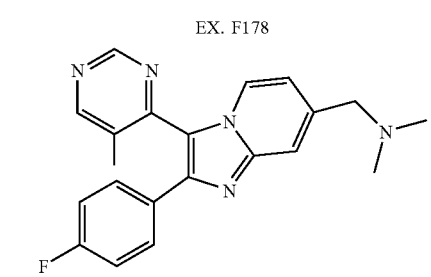
EX. F179
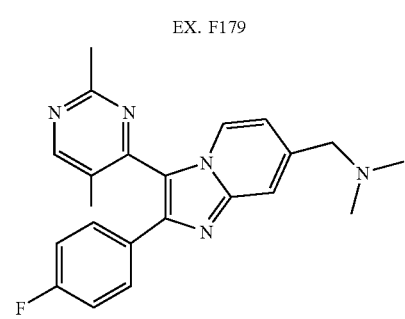
-continued
EX. F180
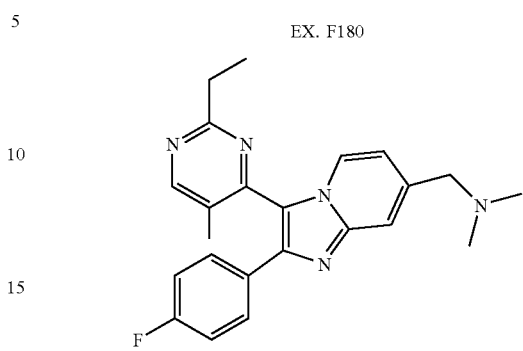
EX. F181
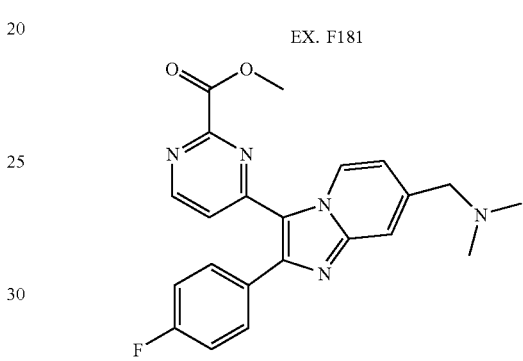
EX. F182
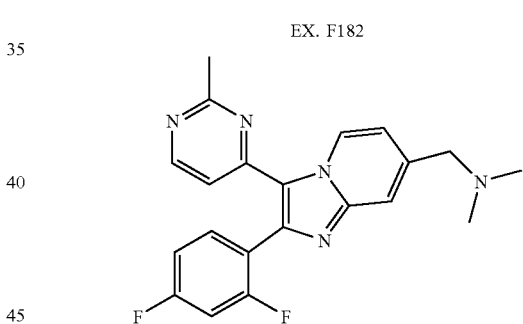
What is claimed is:
1. A compound of the formula (I):
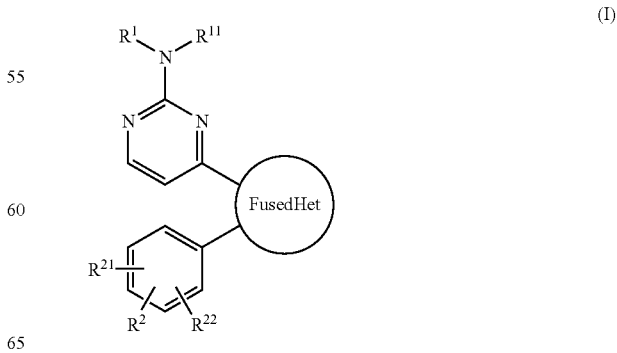
or a pharmaceutically acceptable salt thereof, wherein FusedHet is

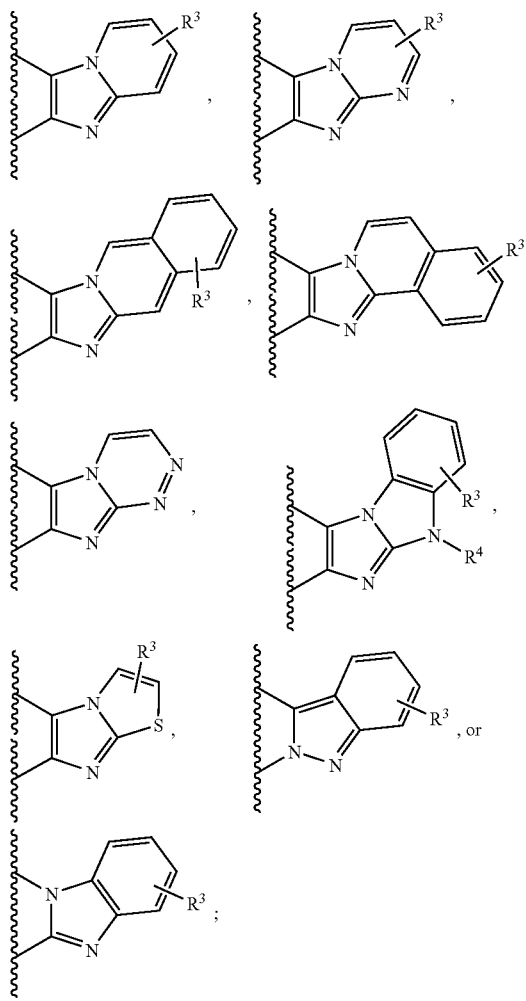

R¹ is H,
—$C_{1-6}$alkyl,
—$C(O)(C_{1-6}$alkyl),
—$C(O)$—$C_{1-6}$alkyl-aryl,
—$C_{0-4}$alkyl-aryl,
—$C_{0-4}$alkyl-indanyl,
$C_{0-4}$alkyl-imidazolyl,
—$C_{0-4}$alkyl-thiazolyl,
—$C_{0-4}$alkyl-pyrazolyl,
—$C_{0-4}$alkyl-oxadiazolyl,
—$C_{0-4}$alkyl-$C_{3-6}$cycloalkyl,
—$C_{0-4}$alkyl-$C_{1-4}$alkoxy,
—$C_{1-4}$alkyl-N($C_{0-4}$alkyl)(—$C_{0-4}$alkyl),
—$C_{1-4}$alkyl-N(—$C_{0-4}$alkyl)—CO—$C_{1-4}$alkoxy,
$C_{1-4}$alkyl-piperadinyl,
—$C_{0-4}$alkyl-triazolyl,
—$C_{1-4}$alkyl-imidazothiazolyl,
—$C_{1-4}$alkyl-benzimidazolyl,
—$C_{1-4}$alkyl-benzothiazolyl,
—$C_{1-4}$alkyl-benzotetrahydrofuranyl,
$C_{1-4}$alkyl-benzodioxolyl,
—$C_{1-4}$alkyl-(heterocyclo$C_4O_2$alkyl),
—$C_{1-4}$alkyl-(heterocyclo$C_5O_1$alkyl),
—$C_{1-4}$alkyl-tetrahydrofuran, or
—$C_{1-4}$alkyl-oxetanyl;

R¹¹ is H or $C_{1-6}$alkyl;
or R¹ and R¹¹, together with the N to which they are attached, form a morpholinyl;
R², R²¹, R²² each independently is H, halogen, or —$C_{1-4}$alkyl;
R³ is H,
—$C_{1-4}$alkyl,
—$C_{3-6}$cycloalkyl,
—$C_{1-4}$alkyl-aryl,
—$C_{1-4}$alkyl-azetidinyl,
—$C_{1-4}$alkyl-azetidinyl-CO—$C_{0-4}$alkyl-N($C_{0-4}$alkyl)($C_{0-4}$alkyl),
—$C_{1-4}$alkyl-pyrrolidinyl,
—$C_{1-4}$alkyl-piperidinyl,
—$C_{1-4}$alkyl-morpholinyl,
—$C_{1-4}$alkyl-N($C_{0-4}$alkyl)($C_{0-4}$alkyl),
—$C_{0-4}$alkyl-N($C_{0-4}$alkyl)($C_{0-4}$alkyl-$C_{1-4}$alkoxy),
—$C_{0-4}$alkyl-N($C_{0-4}$alkyl-$C_{1-4}$alkoxy)($C_{0-4}$alkyl-$C_{1-4}$alkoxy),
—$C_{1-4}$alkyl-N($C_{0-4}$alkyl)—($C_{1-4}$alkyl)-aryl,
—$C_{1-4}$alkyl-N($C_{0-4}$alkyl)—$C_{1-4}$alkyl-tetrahydrofuranyl,
—$C_{1-4}$alkyl-N($C_{0-4}$alkyl)—$C_{1-4}$alkyl-azetidinyl,
—$C_{1-4}$alkyl-N($C_{0-4}$alkyl)—$C_{1-4}$alkyl-N($C_{0-4}$alkyl)($C_{0-4}$alkyl),
—$C_{1-4}$alkyl-N($C_{0-4}$alkyl)—$C_{1-4}$alkyl-N($C_{0-4}$alkyl)—$C_{0-4}$alkyl-$SO_2C_{1-4}$alkyl),
—CO—N($C_{0-4}$alkyl)—$C_{1-4}$alkyl-aryl,
CO N($C_{0-4}$alkyl)—$C_{1-4}$alkyl-N($C_{0-4}$alkyl)($C_{0-4}$alkyl),
—$C_{0-4}$alkyl-CO—$C_{0-4}$alkyl,
—$C_{0-4}$alkyl-CO—$C_{0-4}$alkoxy,
—$C_{0-4}$alkyl-CO—N($C_{0-4}$alkyl)—$C_{1-4}$alkyl-$C_{1-4}$alkoxy,
—$C_{0-4}$alkyl-CO—N($C_{0-4}$alkyl)—$C_{1-4}$alkyl-aryl,
—$C_{0-4}$alkyl-CO-piperidinyl,
—$C_{1-4}$alkyl-N($C_{0-4}$alkyl)—$C_{0-4}$alkyl-CO—$C_{0-4}$alkyl-N($C_{0-4}$alkyl)($C_{0-4}$alkyl),
$C_{0-4}$alkyl-CO—$C_{0-4}$alkyl-N($C_{0-4}$alkyl)($C_{0-4}$alkyl),
O $C_{1-4}$alkyl-aryl,
$C_{1-4}$alkyl O $C_{1-4}$alkyl,
—$C_{0-4}$alkyl-N($C_{0-4}$alkyl)—$C_{0-4}$alkyl-CO—$C_{0-4}$alkyl,
—$C_{0-4}$alkyl-N($C_{0-4}$alkyl)—$C_{0-4}$alkyl-CO—$C_{0-4}$alkoxy,
—$C_{0-4}$alkyl-N($C_{0-4}$alkyl)—$C_{0-4}$alkyl-CO—$C_{0-4}$alkyl-aryl,
—$C_{0-4}$alkyl-N($C_{0-4}$alkyl)—$C_{0-4}$alkyl-CO—$C_{0-4}$alkyl(aryl)$_2$,
—$C_{0-4}$alkyl-N($C_{0-4}$alkyl)—$C_{0-4}$alkyl-CO—$C_{0-4}$alkyl-pyrrolyl,
—$C_{0-4}$alkyl-N($C_{0-4}$alkyl)—$C_{0-4}$alkyl-CO—$C_{0-4}$alkyl-pyrrolidinyl,
—$C_{0-4}$alkyl-N($C_{0-4}$alkyl)—$C_{0-4}$alkyl-CO—$C_{0-4}$alkyl-azetidinyl,
—$C_{0-4}$alkyl-N($C_{0-4}$alkyl) $C_{0-4}$alkyl-CO—$C_{2-4}$alkenyl-pyrrolidinyl,
—$C_{0-4}$alkyl-N($C_{0-4}$alkyl) $C_{0-4}$alkyl-CO $C_{0-4}$alkyl thiophenyl,
—$C_{0-4}$alkyl-N($C_{0-4}$alkyl)—$C_{0-4}$alkyl-CO—$C_{2-4}$alkenyl-thiophenyl,
—$C_{0-4}$alkyl-N($C_{0-4}$alkyl)—$C_{0-4}$alkyl-CO—S—$C_{1-4}$alkyl-aryl,
—$C_{0-4}$alkyl-N($C_{0-4}$alkyl)—$C_{0-4}$alkyl-CO—$C_{3-6}$cyclolkyl,
—$C_{0-4}$alkyl-N($C_{0-4}$alkyl)—$C_{0-4}$alkyl-CO—O—$C_{1-4}$alkyl-aryl,
—$C_{0-4}$alkyl-CO—N($C_{0-4}$alkyl)—$C_{0-4}$alkyl-$C_{1-4}$alkoxy, —$C_{1-4}$alkyl-N($C_{0-4}$alkyl)(—$SO_2C_{1-4}$alkyl),
$C_{0-4}$alkyl-N($C_{0-4}$alkyl)—$C_{1-4}$alkyl-$SO_2C_{1-4}$alkyl,
—$C_{0-4}$alkyl-S—$C_{1-4}$alkyl-aryl,
—$C_{1-4}$alkyl-PO($C_{1-4}$alkoxy)($C_{1-4}$alkoxy),
—$C_{1-4}$alkyl-azetidinyl-CO—N($C_{0-4}$alkyl)($C_{0-4}$alkyl),
—$C_{1-4}$alkyl-(heterocyclo$C_4N_1O_1$alkyl),
—$C_{0-4}$alkyl-CO—(heterocyclo$C_5N_1$alkyl),
—$C_{0-4}$alkyl-CO—N($C_{0-4}$alkyl)-(heterocyclo$C_5N_1$alkyl),
—$C_{1-4}$alkyl-(heterocyclo$C_4N_2$alkyl)—$C_{1-4}$alkyl,
$C_{1-4}$alkyl-(heterocyclo$C_4N_2$alkyl)—CO—$C_{0-4}$alkoxy,
—$C_{1-4}$alkyl-(heterocyclo$C_4N_2$alkyl)—$C_{1-4}$alkyl-N($C_{0-4}$ alkyl)($C_{0-4}$alkyl),
—$C_{1-4}$alkyl-(heterobicyclo$C_5N_2$alkyl)—$C_{1-4}$alkyl, or
—$C_{1-4}$alkyl-NH-(heterobicyclo$C_7N_1$alkyl); and
$R^4$ is —$C_{1-6}$alkyl;
wherein any of the above aryl, hetaryl, cycloalkyl, or heterocycloalkyl optionally is substituted with 1–4 substituents, each substituent independently is halogen, $NO_2$, —CN, —$C_{1-4}$alkyl, —$C_{0-4}$alkoxy, S $C_{1-4}$alkyl, or $C_{0-4}$alkyl-(CO)—$C_{0-4}$alkoxy: and any of the above alkyl optionally is substituted with 1–4 substituents, each substituent independently is halogen, —$N_3$, —CN, —COOH, or —$C_{0-4}$alkoxy.

2. The compound according to claim 1, wherein FusedHet is

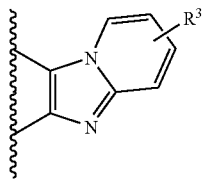, or a pharmaceutically acceptable addition salt thereof.

3. The compound according to claim 1, wherein FusedHet is

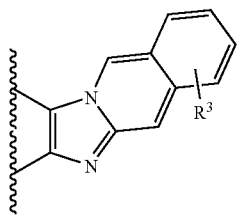, or a pharmaceutically acceptable addition salt thereof.

4. The compound according to claim 1, wherein FusedHet is

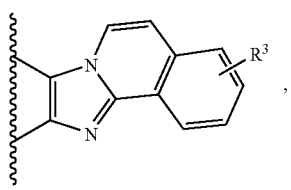, or a pharmaceutically acceptable addition salt thereof.

5. The compound according to claim 1, wherein FusedHet is

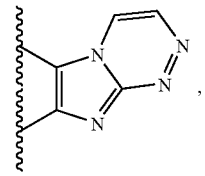, or a pharmaceutically acceptable addition salt thereof.

6. The compound according to claim 1, wherein FusedHet is

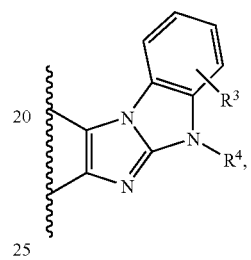, or a pharmaceutically acceptable addition salt thereof.

7. The compound according to claim 1, wherein FusedHet is

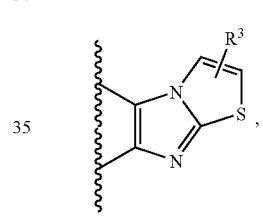, or a pharmaceutically acceptable addition salt thereof.

8. The compound according to claim 1, wherein FusedHet is

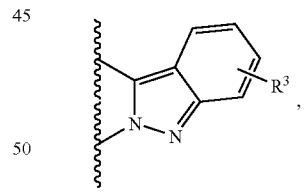, or a pharmaceutically acceptable addition salt thereof.

9. The compound according to claim 1, wherein FusedHet is

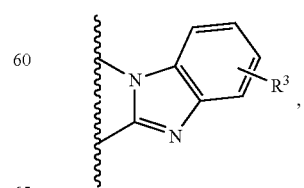, or a pharmaceutically acceptable addition salt thereof.

10. The compound according to claim 1 represented by
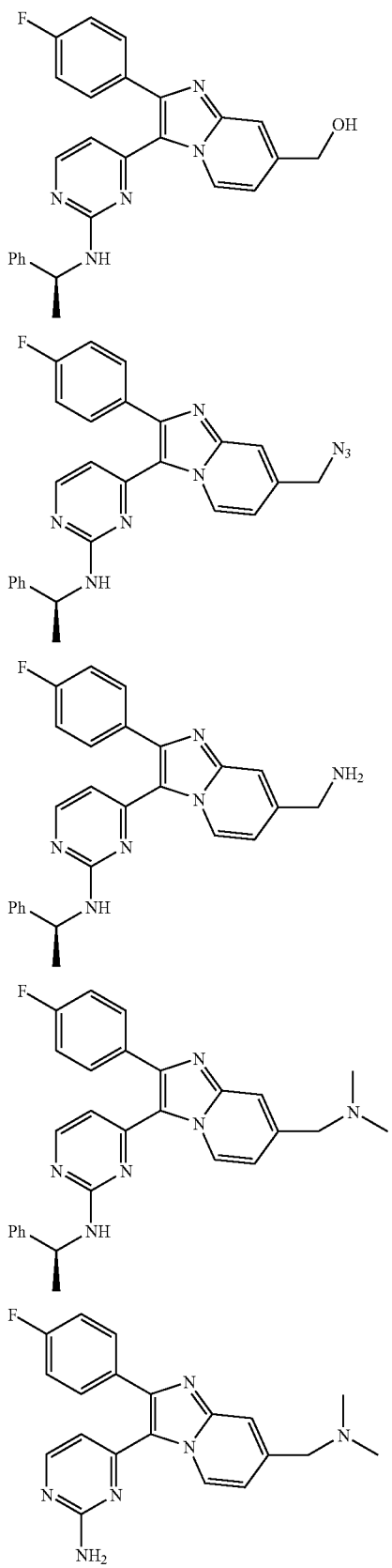
-continued
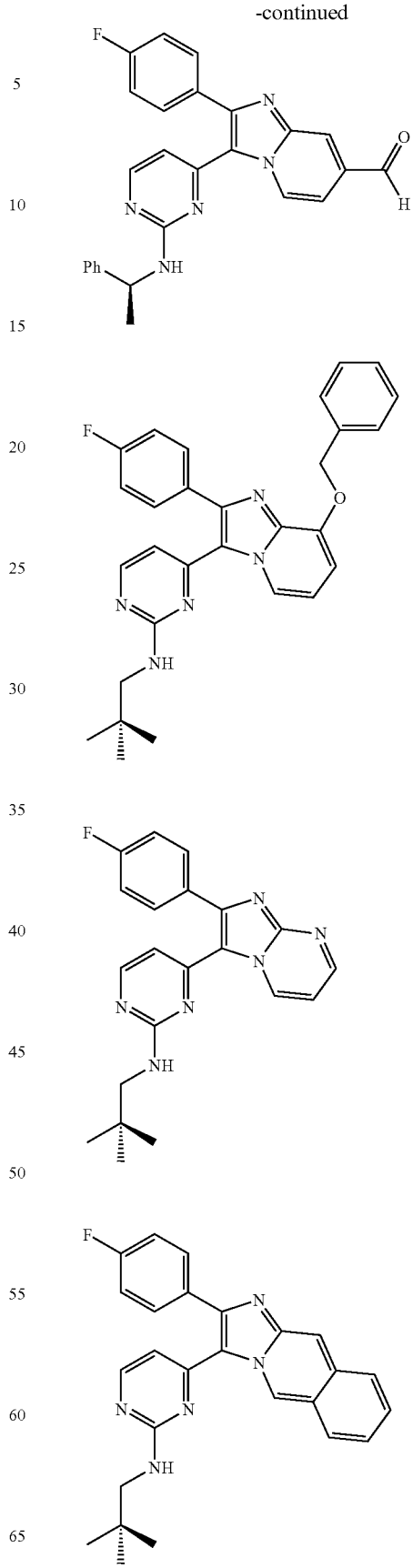

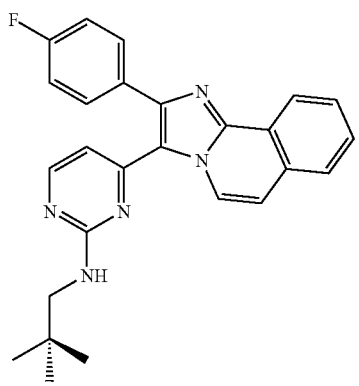
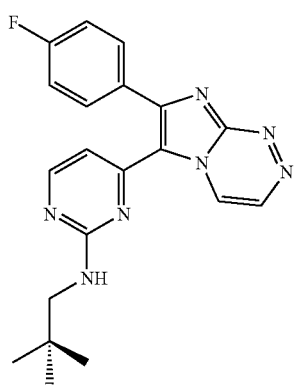
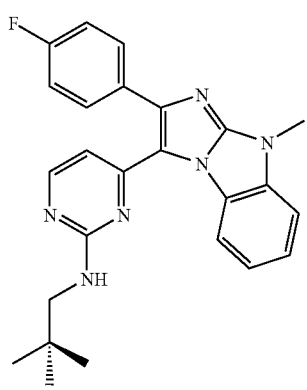
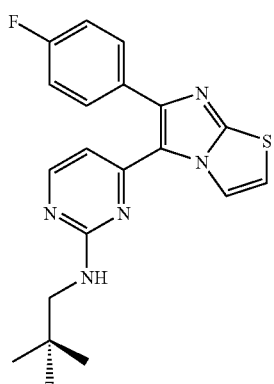
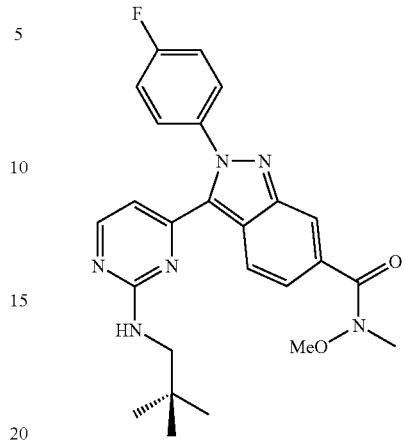
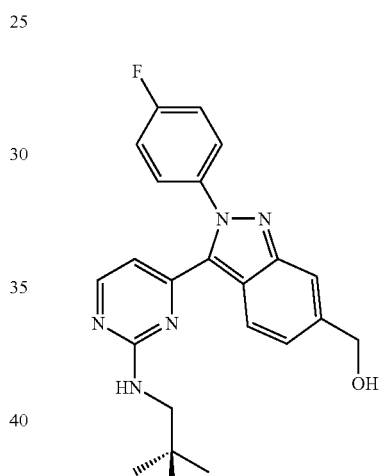
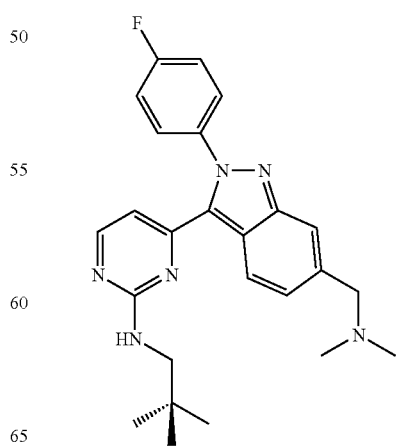

371
-continued
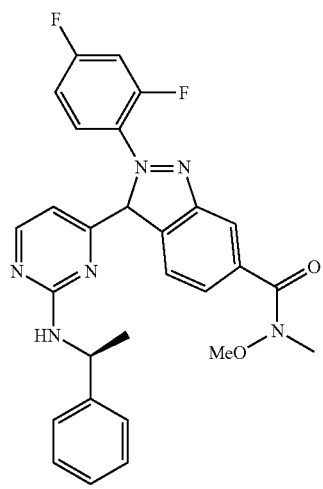
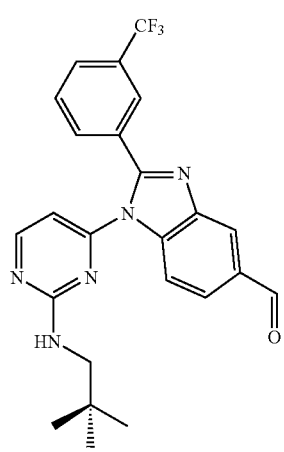
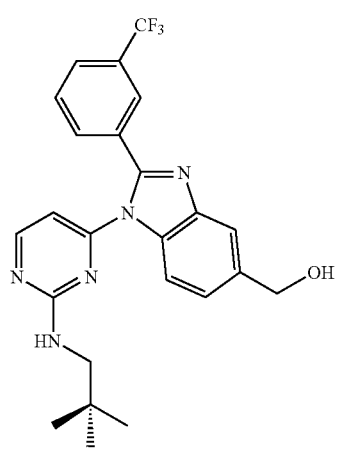
372
-continued
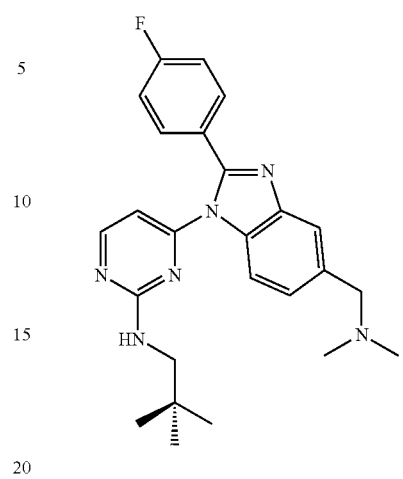
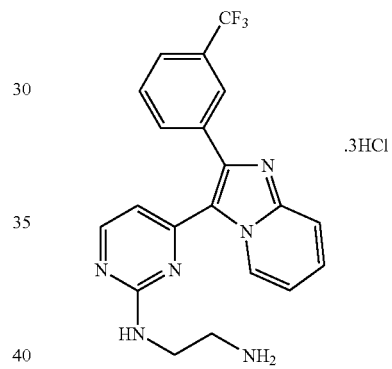
.3HCl
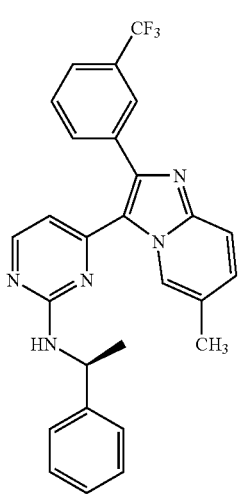

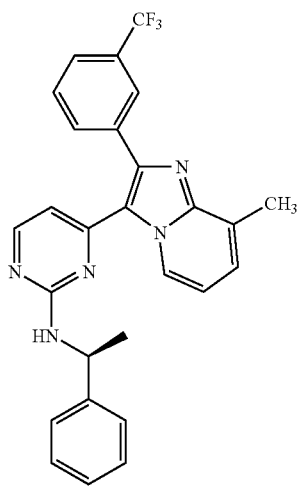
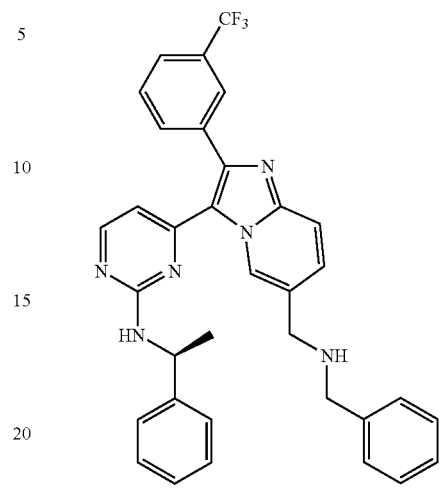
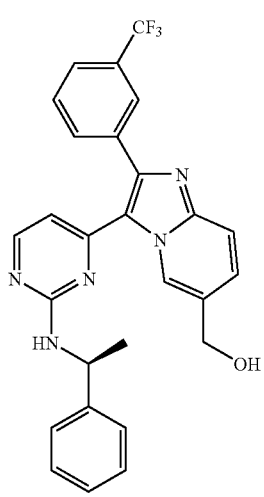
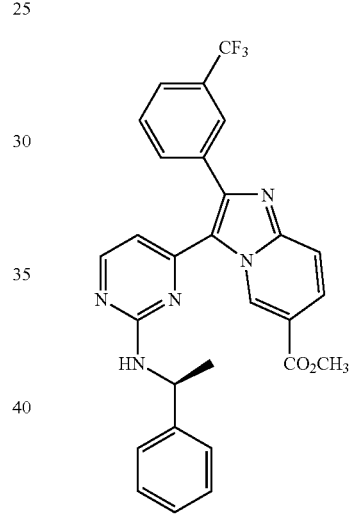
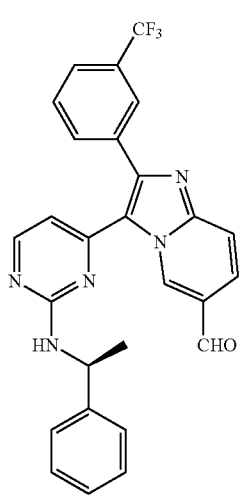
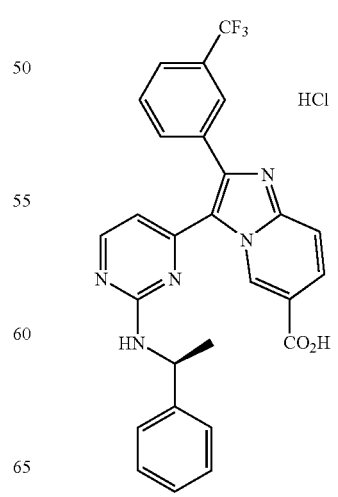

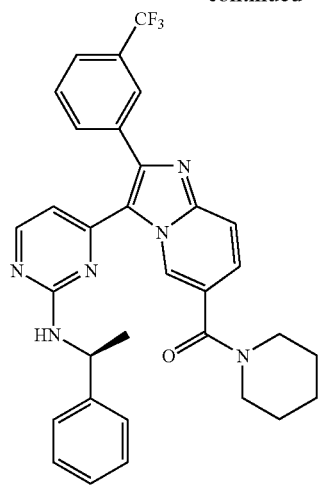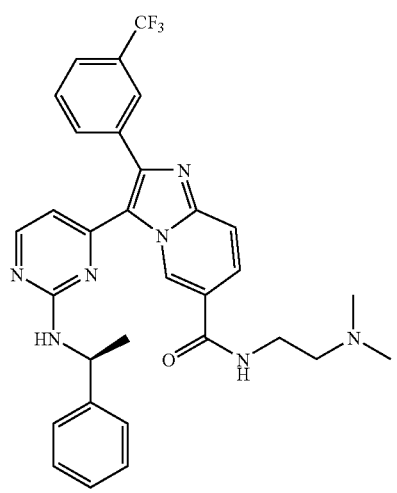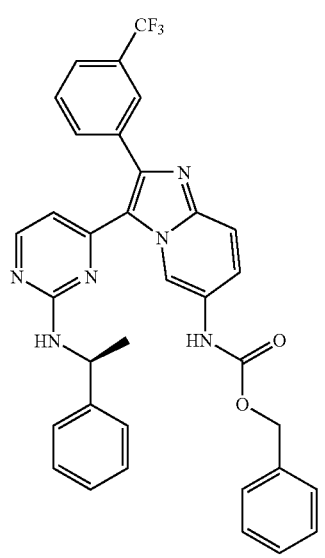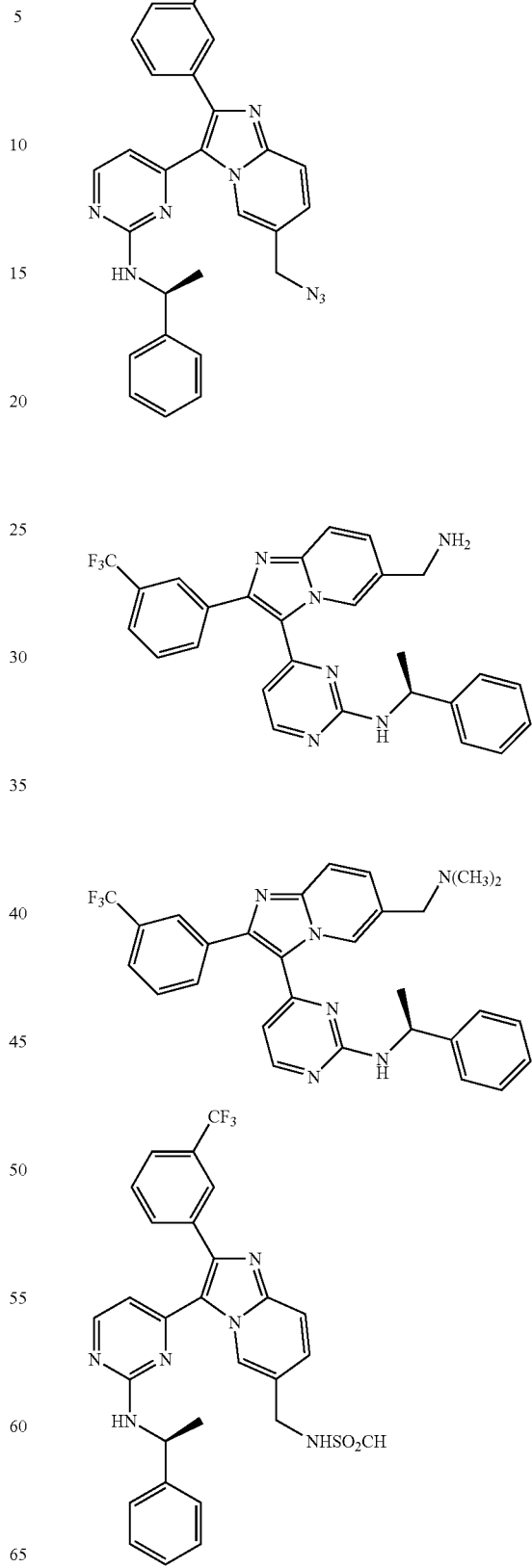

377
-continued
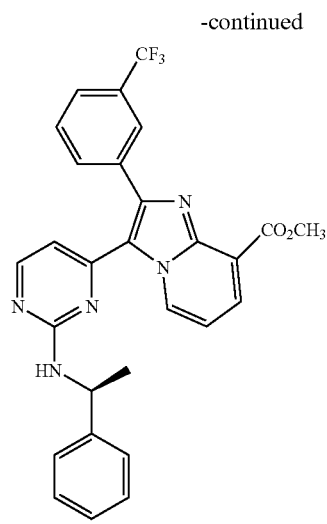
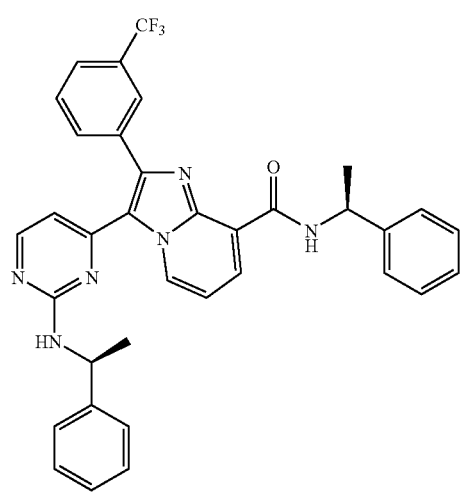
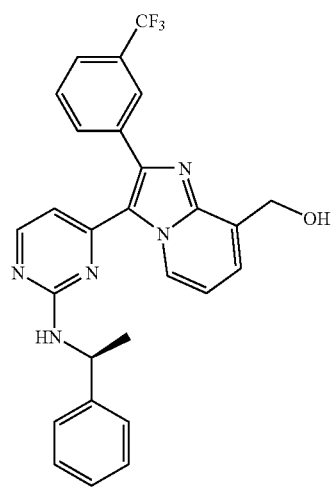
378
-continued
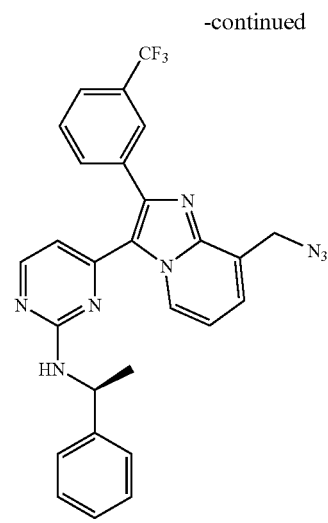
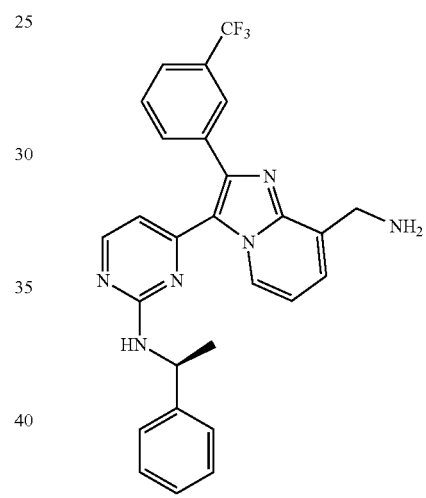
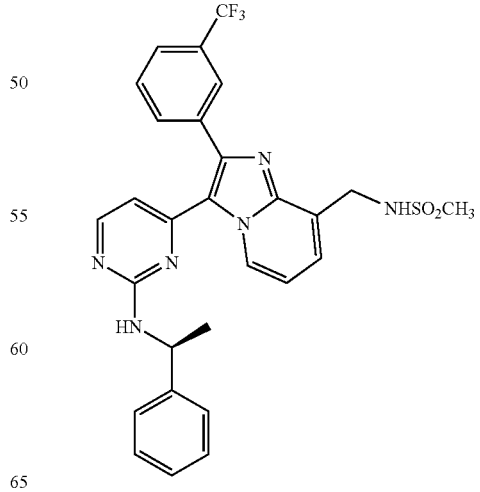

379
-continued
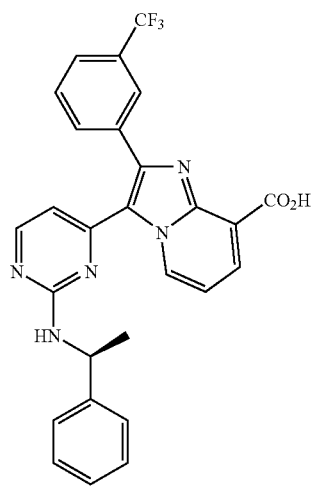
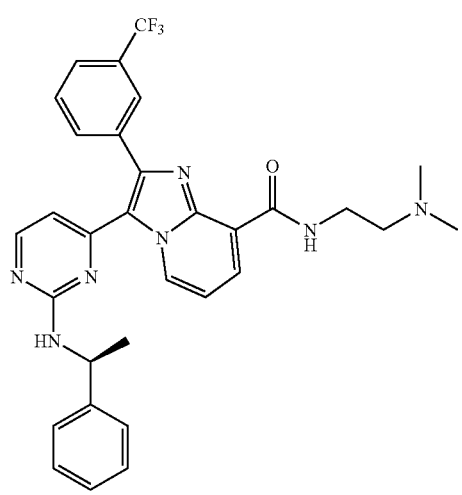
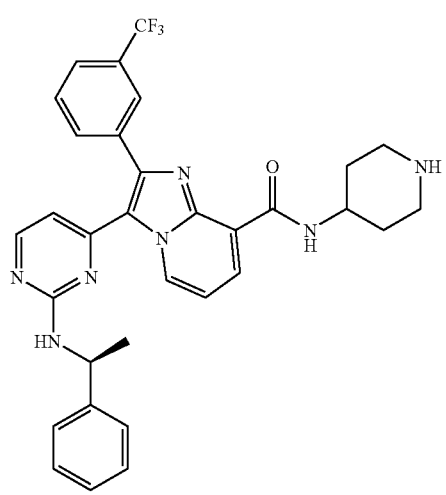
380
-continued
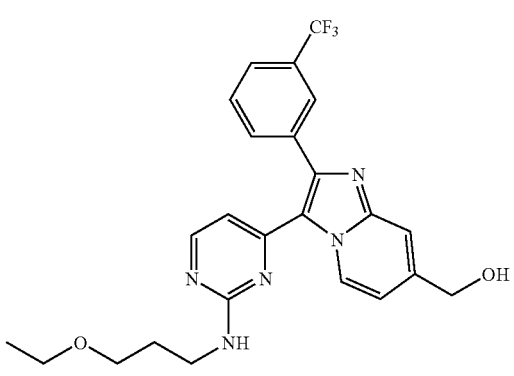
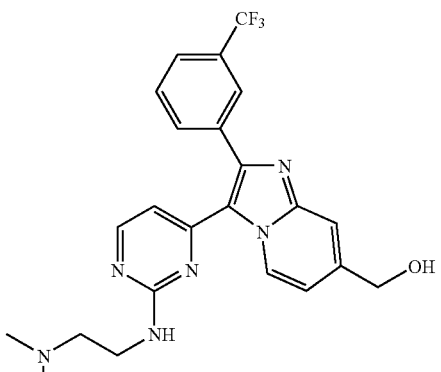
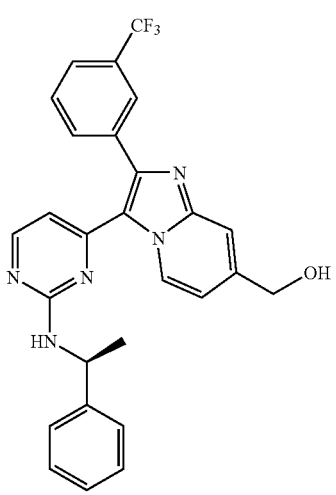

381
-continued
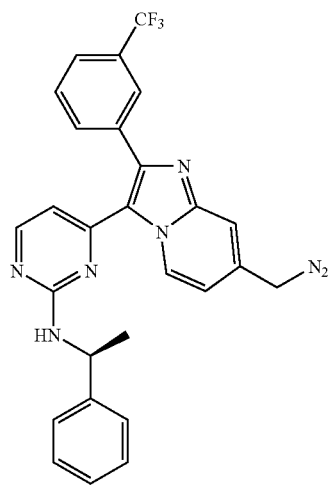
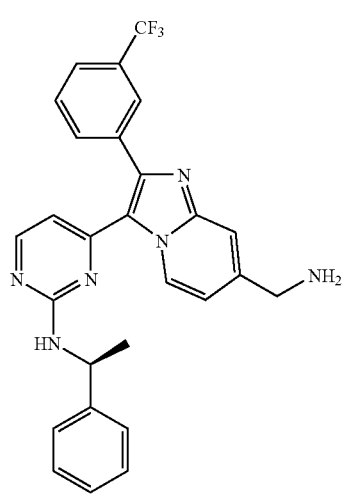
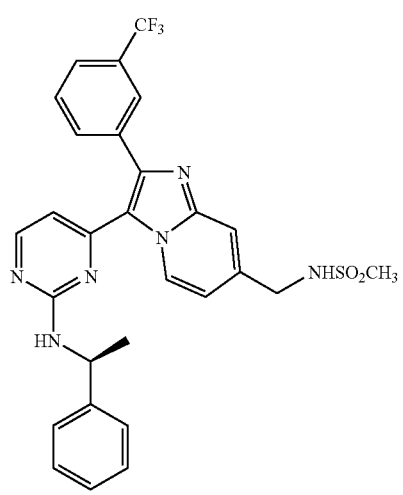
382
-continued
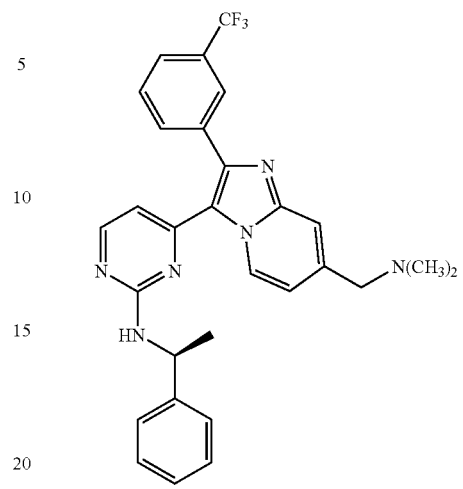
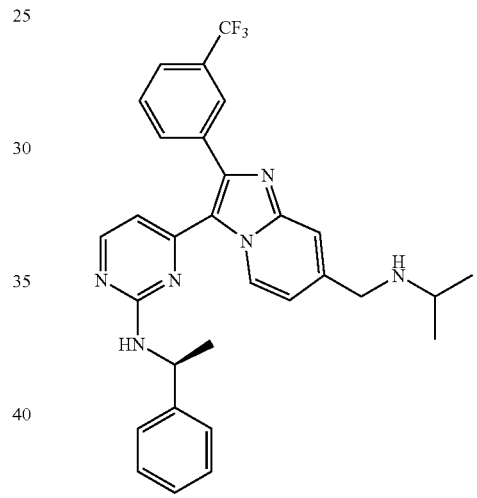
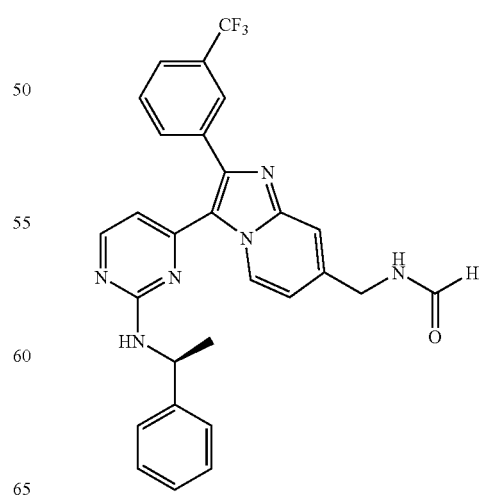

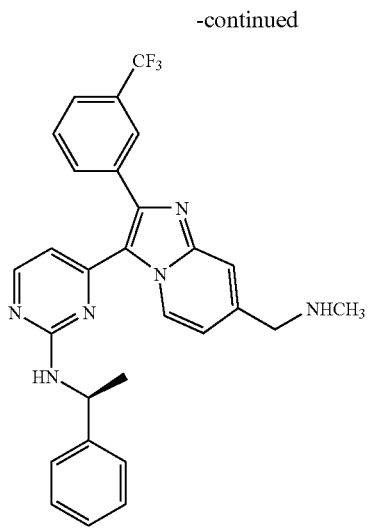

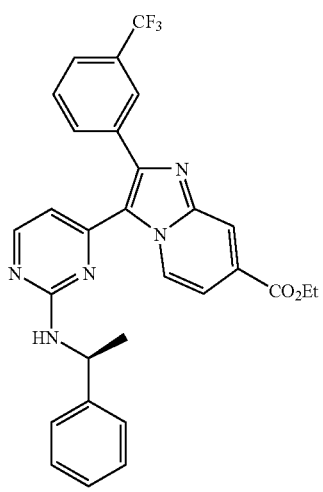

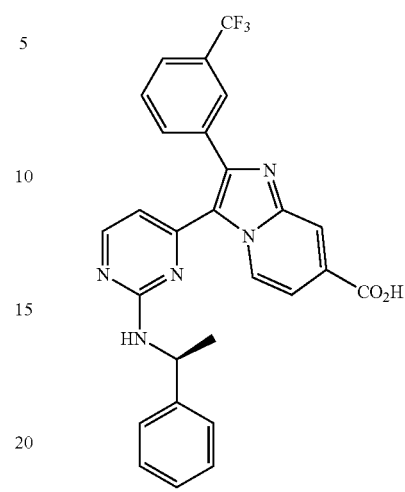

or a pharmaceutically acceptable salt thereof.

11. The compound according to claim 1 represented by:

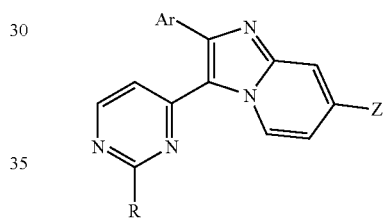

wherein Ar, R, and Z are

| Ar Group | R Group | Z Group |
|---|---|---|
| 2,4-Difluorophenyl | NHCH$_2$C(CH$_3$)$_3$ | CH$_2$OH |
| 2,4-Difluorophenyl | NHCH$_2$C(CH$_3$)$_3$ | CH$_2$N(CH$_3$)$_2$ |
| 2,4-Difluorophenyl | HN–cyclohexyl | CH$_2$OH |
| 2,4-Difluorophenyl | HN–cyclohexyl | CH$_2$N(CH$_3$)$_2$ |
| 2,4-Difluorophenyl | NHCH$_2$C(CH$_3$)$_3$ | CH$_2$OCH$_3$ |
| 3-Trifluoromethylphenyl | NHCH$_2$C(CH$_3$)$_3$ | CH$_2$–morpholino |

-continued

| Ar Group | R Group | Z Group |
| --- | --- | --- |
| 3-Trifluoromethylphenyl | NHCH$_2$C(CH$_3$)$_3$ | CH$_2$-N-piperazine-N-CH$_2$CH$_2$NMe$_2$ |
| 3-Trifluoromethylphenyl | NHCH$_2$C(CH$_3$)$_3$ | CH$_2$-N-piperazine-N-isopropyl |
| 3-Trifluoromethylphenyl | NHCH$_2$C(CH$_3$)$_3$ | CH$_2$OH |
| 3-Trifluoromethylphenyl | NHCH$_2$C(CH$_3$)$_3$ | CH$_2$N(CH$_3$)$_2$ |
| 2-Chloro-4-fluorophenyl | NHCH$_2$C(CH$_3$)$_3$ | CH$_2$OH |
| 2-Chloro-4-fluorophenyl | NHCH$_2$C(CH$_3$)$_3$ | CHO |
| 2-Chloro-4-fluorophenyl | NHCH$_2$C(CH$_3$)$_3$ | CH$_2$N(CH$_3$)$_2$ |
| 2-Chlorophenyl | NHCH$_2$C(CH$_3$)$_3$ | CH$_2$OH |
| 2-Chlorophenyl | NHCH$_2$C(CH$_3$)$_3$ | CH$_2$N(CH$_3$)$_2$ |
| 4-Chlorophenyl | NHCH$_2$C(CH$_3$)$_3$ | CH$_2$OH |
| 4-Chlorophenyl | NHCH$_2$C(CH$_3$)$_3$ | CH$_2$N(CH$_3$)$_2$ |
| 3,4-Dichlorophenyl | NHCH$_2$C(CH$_3$)$_3$ | CH$_2$OH |
| 3,4-Dichlorophenyl | NHCH$_2$C(CH$_3$)$_3$ | CH$_2$N(CH$_3$)$_2$ |
| 2,3-Dichlorophenyl | NHCH$_2$C(CH$_3$)$_3$ | CH$_2$OH |
| 2,3-Dichlorophenyl | NHCH$_2$C(CH$_3$)$_3$ | CH$_2$N(CH$_3$)$_2$ |
| 4-Fluorophenyl | NHCH$_2$C(CH$_3$)$_3$ | H |
| 4-Fluorophenyl | NHCH$_2$C(CH$_3$)$_2$CH$_2$OH | H |
| 4-Fluorophenyl | NHCH$_2$C(CH$_3$)$_2$CH$_2$OH | CH$_2$NHCH$_3$ |
| 4-Fluorophenyl | NHCH$_2$C(CH$_3$)$_2$CH$_2$OH | CH$_2$N(CH$_3$)SO$_2$CH$_3$ |
| 4-Fluorophenyl | HN-CH(Ph)(CH$_2$OH) (R) | CH$_3$ |
| 4-Fluorophenyl | NHCH$_2$C(CH$_3$)$_3$ | CH$_2$NHSO$_2$CH$_3$ |
| 4-Fluorophenyl | NHCH$_2$C(CH$_3$)$_3$ | CH$_2$N(CH$_3$)SO$_2$CH$_3$ |
| 4-Fluorophenyl | NHCH$_2$C(CH$_3$)$_3$ | CH$_2$PO(OMe)$_2$ |
| 4-Fluorophenyl | NHCH$_2$C(CH$_3$)$_3$ | CH$_2$SO$_2$CH$_3$ |
| 4-Fluorophenyl | NHCH$_2$C(CH$_3$)$_3$ | CHO | or a pharmaceutically acceptable salt thereof.

12. The compound according to claim 1 represented by:

[Structure: imidazo-thiazole fused with pyrimidine bearing Ar and R substituents]

wherein Ar and R are:

| Ar Group | R Group |
| --- | --- |
| 2,4-Difluorophenyl | NHCH$_2$C(CH$_3$)$_3$ |
| 3-Trifluoromethylphenyl | NHCH$_2$C(CH$_3$)$_3$ |
| 3-Trifluoromethylphenyl | (S)-NH-CH(Ph)- |
| 3-Trifluoromethylphenyl | NH(CH$_2$)$_3$OCH$_3$ |
| 4-Fluorophenyl | NH-CH$_2$-(2-chlorophenyl) |

-continued
| Ar Group | R Group |
|---|---|
| 4-Fluorophenyl | 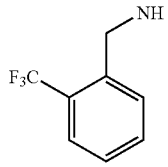 |
| 4-Fluorophenyl | 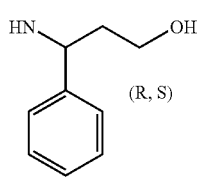 |
| 4-Fluorophenyl | NHCH₂C(CH₃)₂CH₂OH |
| 4-Fluorophenyl | 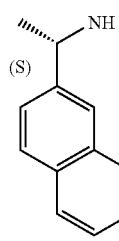 |
| 4-Fluorophenyl | 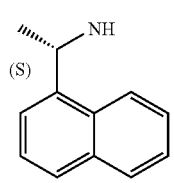 |
| 4-Fluorophenyl | 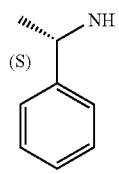 |
| 4-Fluorophenyl | NH(CH₂)₃OCH₃ |
| 4-Fluorophenyl |  |
| 4-Fluorophenyl |  |
| 4-Fluorophenyl | 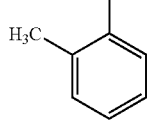 |
-continued
| Ar Group | R Group |
|---|---|
| 4-Fluorophenyl | 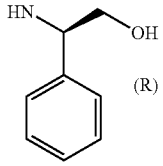 |
| 4-Fluorophenyl | 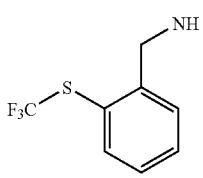 |
| 4-Fluorophenyl | 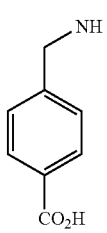 |
| 4-Fluorophenyl | 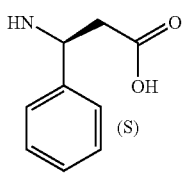 |
| 4-Fluorophenyl | 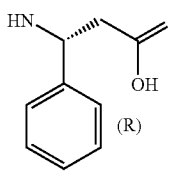 |
| 4-Fluorophenyl | 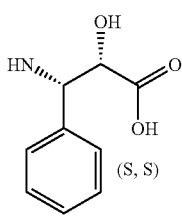 |
| 4-Fluorophenyl | 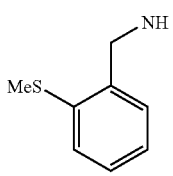 |
| 4-Fluorophenyl | 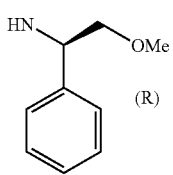 |

-continued

| Ar Group | R Group |
|---|---|
| 4-Fluorophenyl | 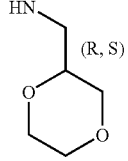 (R, S) |
| 4-Fluorophenyl | 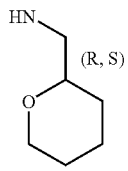 (R, S) |
| 4-Fluorophenyl | 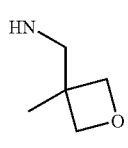 | or a pharmaceutically acceptable salt thereof.

13. The compound according to claim 1 represented by:

| R Group | Z Group |
|---|---|
| NHCH$_2$C(CH$_3$)$_3$ | CON(OMe)Me |
| NHCH$_2$C(CH$_3$)$_3$ | CHO |
| NHCH$_2$C(CH$_3$)$_3$ | CH$_2$OH |
| NHCH$_2$C(CH$_3$)$_3$ | CH$_2$N(CH$_3$)$_2$ |
| 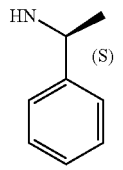 (S) | CON(OMe)Me |

-continued

| R Group | Z Group |
|---|---|
| 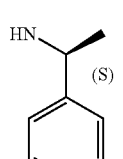 (S) | CHO |
| 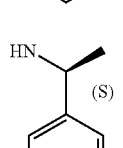 (S) | CH$_2$OH |
| 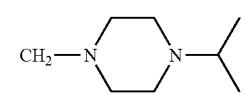 (S) | CH$_2$N(CH$_3$)$_2$ | or a pharmaceutically acceptable salt thereof.

14. The compound according to claim 1 represented by:

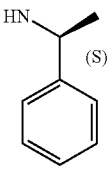

wherein Ar, R, and Z are

| Ar Group | R Group | Z Group |
|---|---|---|
| 4-Fluorophenyl | NHCH$_2$C(CH$_3$)$_3$ | CH$_2$OH |
| 4-Fluorophenyl | NHCH$_2$C(CH$_3$)$_3$ | CON(OMe)Me |
| 3-Trifluoromethylphenyl | NHCH$_2$C(CH$_3$)$_3$ | CON(OMe)Me |
| 3-Trifluoromethylphenyl | NHCH$_2$C(CH$_3$)$_3$ | CH$_2$N(CH$_3$)$_2$ |
| 2-Chlorophenyl | NHCH$_2$C(CH$_3$)$_3$ | CH$_2$N(CH$_3$)$_2$ |
| 2-Chloro-4-fluorophenyl | NHCH$_2$C(CH$_3$)$_3$ | CH$_2$N(CH$_3$)$_2$ |
| 2,4-Difluorophenyl | NHCH$_2$C(CH$_3$)$_3$ | CH$_2$N(CH$_3$)$_2$ |
| 2,4-Difluorophenyl | NHCH$_2$C(CH$_3$)$_3$ | CH$_2$OH |
| 2,4-Difluorophenyl | NHCH$_2$C(CH$_3$)$_3$ | CON(OMe)Me |
| 2,4-Difluorophenyl | NHCH$_2$C(CH$_3$)$_3$ | 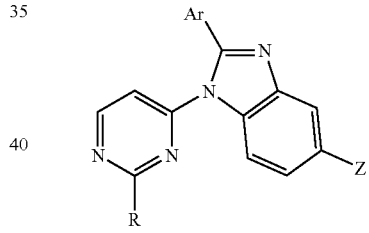 |
| 2,4-Difluorophenyl | NHCH$_2$C(CH$_3$)$_3$ | 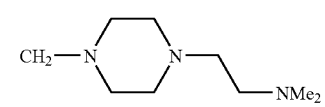 |

-continued

| Ar Group | R Group | Z Group |
|---|---|---|
| 2,4-Difluorophenyl | NHCH₂C(CH₃)₃ | CH₂—N(bicyclic diazabicycle)NH |
| 2,4-Difluorophenyl | NHCH₂C(CH₃)₃ | CH₂—N(morpholino) |
| 2,4-Difluorophenyl | NHCH₂C(CH₃)₃ | CH₂—NH (bicyclic azabicycle) |
| 2,4-Difluorophenyl | NHCH₂C(CH₃)₃ | CH₂NH(CH₂)₂OCH₃ |
| 2,4-Difluorophenyl | NHCH₂C(CH₃)₃ | CH₂NH(CH₂)₂N(CH₃)₂ |
| 2,4-Difluorophenyl | NH(CH₂)₃OCH₃ | CON(OMe)Me |
| 2,4-Difluorophenyl | NH-CH₂-(2-methylphenyl) | CON(OMe)Me |
| 2,4-Difluorophenyl | HN-CH(Ph)-CH₂OH (R) | CON(OMe)Me |
| 2,4-Difluorophenyl | NHCH₂C(CH₃)₂CH₂OH | CH₂OH |
| 2,4-Difluorophenyl | HN-CH₂-(3-methyloxetan-3-yl) | CON(OMe)Me |
| 2,4-Difluorophenyl | HN-CH(CH₃)-Ph (S) | CH₂N(CH₃)₂ |
| 2,4-Difluorophenyl | HN-CH(CH₃)-Ph (S) | CH₂—N(morpholino) |
| 2,4-Difluorophenyl | HN-CH(CH₃)-Ph (S) | CH₂—N(diazabicycle)NH |
| 2,4-Difluorophenyl | NHCH₂C(CH₃)₂CH₂OH | CH₂N(CH₃)₂ |

-continued

| Ar Group | R Group | Z Group |
|---|---|---|
| 2,4-Difluorophenyl | NH(CH$_2$)$_3$OCH$_3$ | 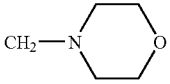 |
| 2,4-Difluorophenyl | NH(CH$_2$)$_3$OCH$_3$ | CH$_2$N(CH$_3$)$_2$ |
| 2,4-Difluorophenyl | NHCH$_2$C(CH$_3$)$_2$CH$_2$OH | CON(OMe)Me |
| 2,4-Difluorophenyl | NH(CH$_2$)$_4$OH | CH$_2$N(CH$_3$)$_2$ |
| 2,4-Difluorophenyl | 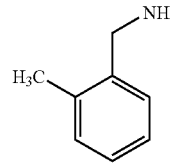 | CH$_2$N(CH$_3$)$_2$ |
| 2,4-Difluorophenyl | 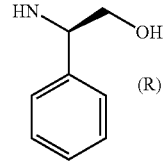 | CH$_2$N(CH$_3$)$_2$ |
| 2,4-Difluorophenyl | 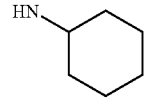 | CH$_2$N(CH$_3$)$_2$ |
| 2,4-Difluorophenyl | 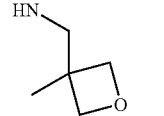 | CH$_2$N(CH$_3$)$_2$ |
| 2,4-Difluorophenyl | 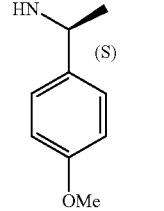 | CH$_2$N(CH$_3$)$_2$ |
| 2,4-Difluorophenyl | 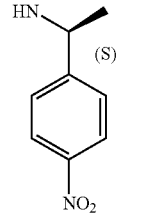 | CH$_2$N(CH$_3$)$_2$ |
| 2,4-Difluorophenyl | 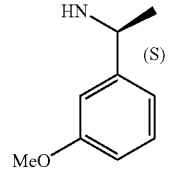 | CH$_2$N(CH$_3$)$_2$ |

-continued
| Ar Group | R Group | Z Group |
|---|---|---|
| 2,4-Difluorophenyl | 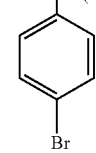 HN—(S)—C6H4—Br | CH₂N(CH₃)₂ |
| 2,4-Difluorophenyl | 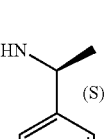 HN—(S)—C6H4—CN | CH₂N(CH₃)₂ |
| 2,4-Difluorophenyl | 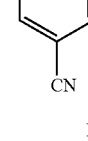 HN—(S)—C6H4(3-CO₂Me) | CH₂N(CH₃)₂ |
| 2,4-Difluorophenyl | 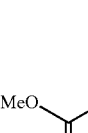 HN—(S)—C6H4(4-CO₂Me) | CH₂N(CH₃)₂ |
| 2,4-Difluorophenyl | NH(CH₂)₃CO₂H | CH₂N(CH₃)₂ |
or a pharmaceutically acceptable salt thereof.
15. The compound according to claim 1 represented by
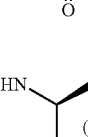
wherein R is
| R |
|---|
| 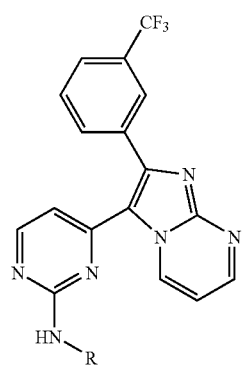 |

-continued
| R |
|---|
| 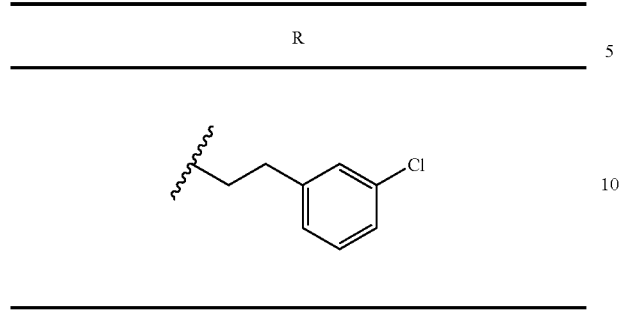 |
or a pharmaceutically acceptable salt thereof.
16. The compound according to claim 1 represented by
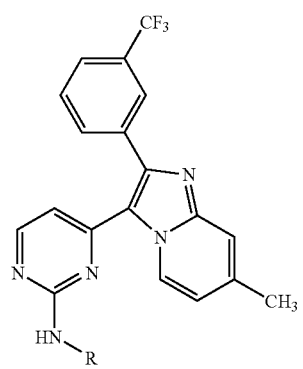
wherein R is
| R |
|---|
| 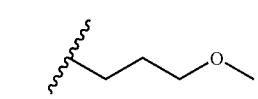 |
| 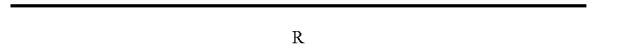 |
| 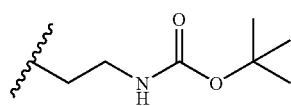 |
or a pharmaceutically acceptable salt thereof.
17. The compound according to claim 1 represented by
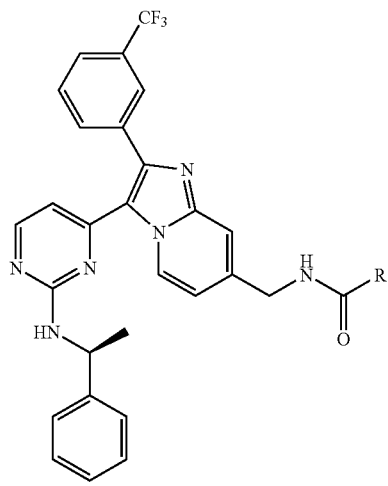
wherein R is
| R |
|---|
| 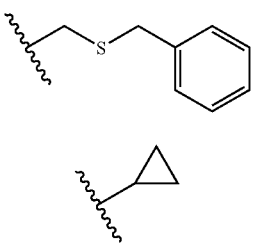 |
| 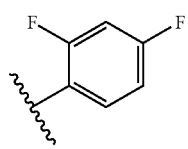 |
| 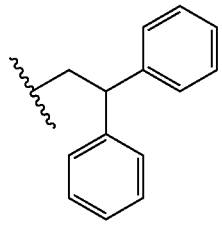 |
| 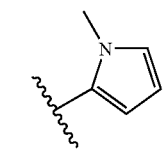 |
| 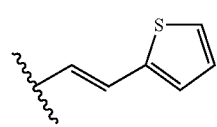 |
or a pharmaceutically acceptable salt thereof.

18. The compound according to claim 1 represented by
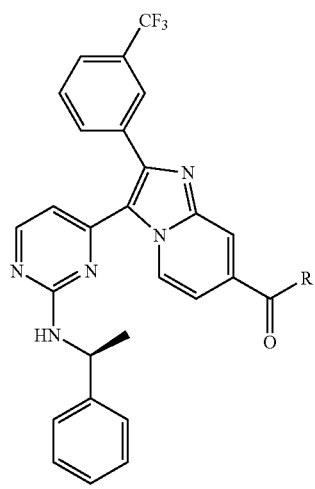
wherein R is
| R |
|---|
| 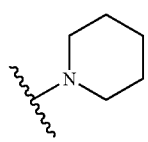 |
| 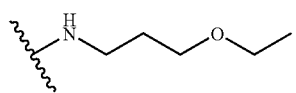 |
| 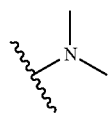 |
| 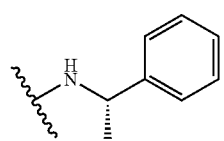 |
| 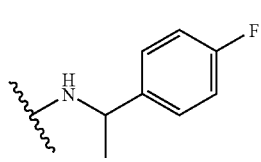 |
or a pharmaceutically acceptable salt thereof.
19. The compound according to claim 1 represented by
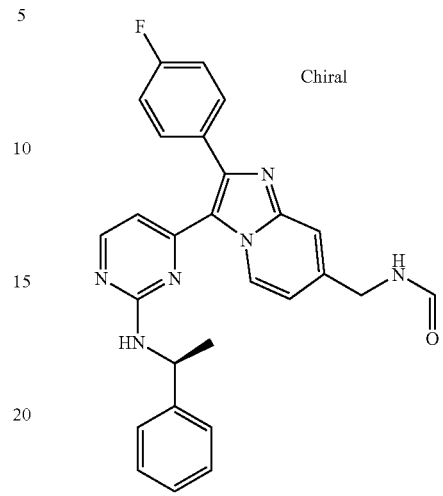
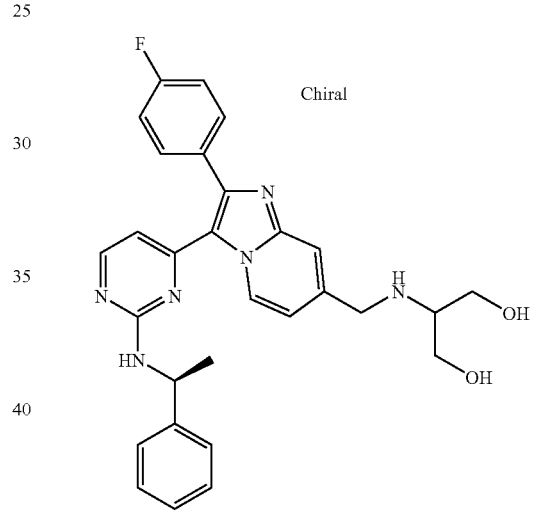
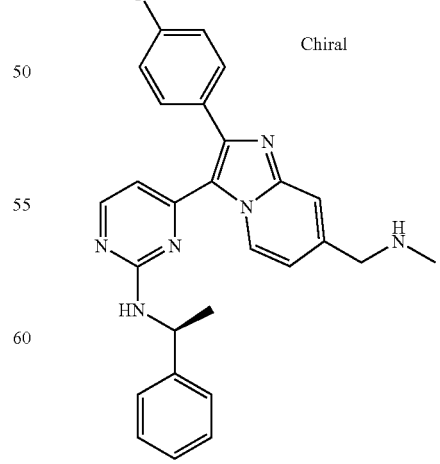

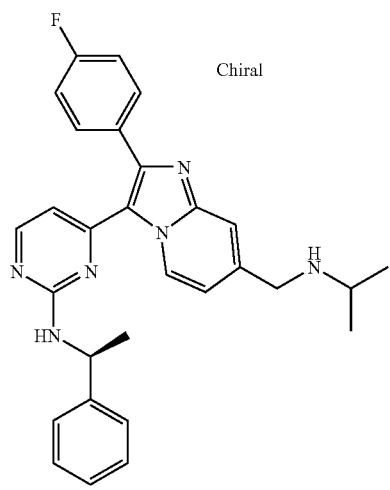
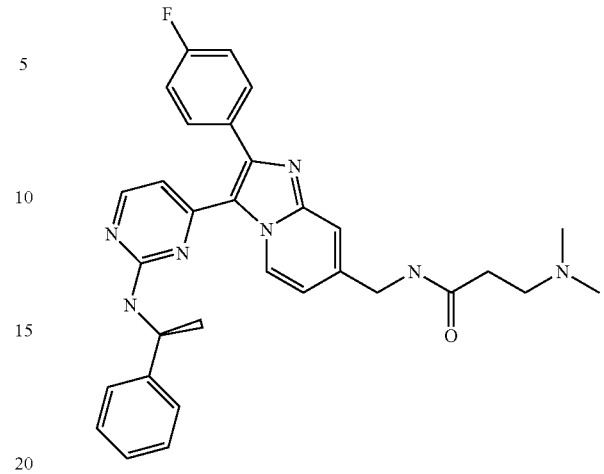
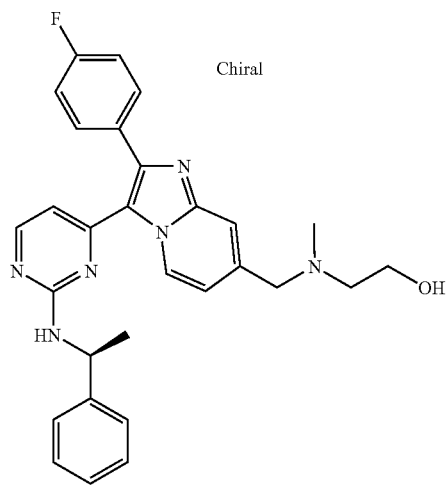
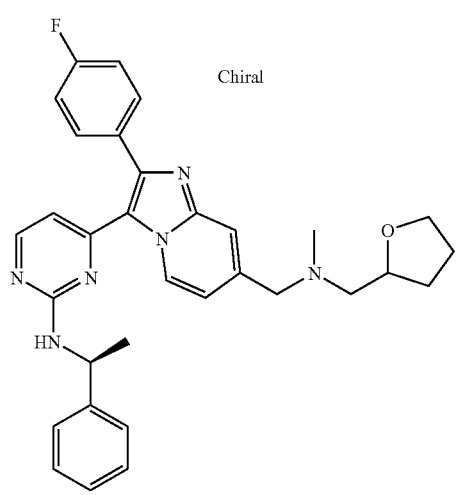
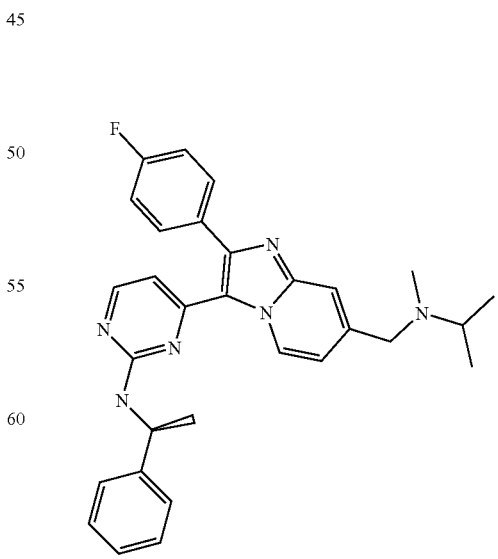

403
-continued
404
-continued
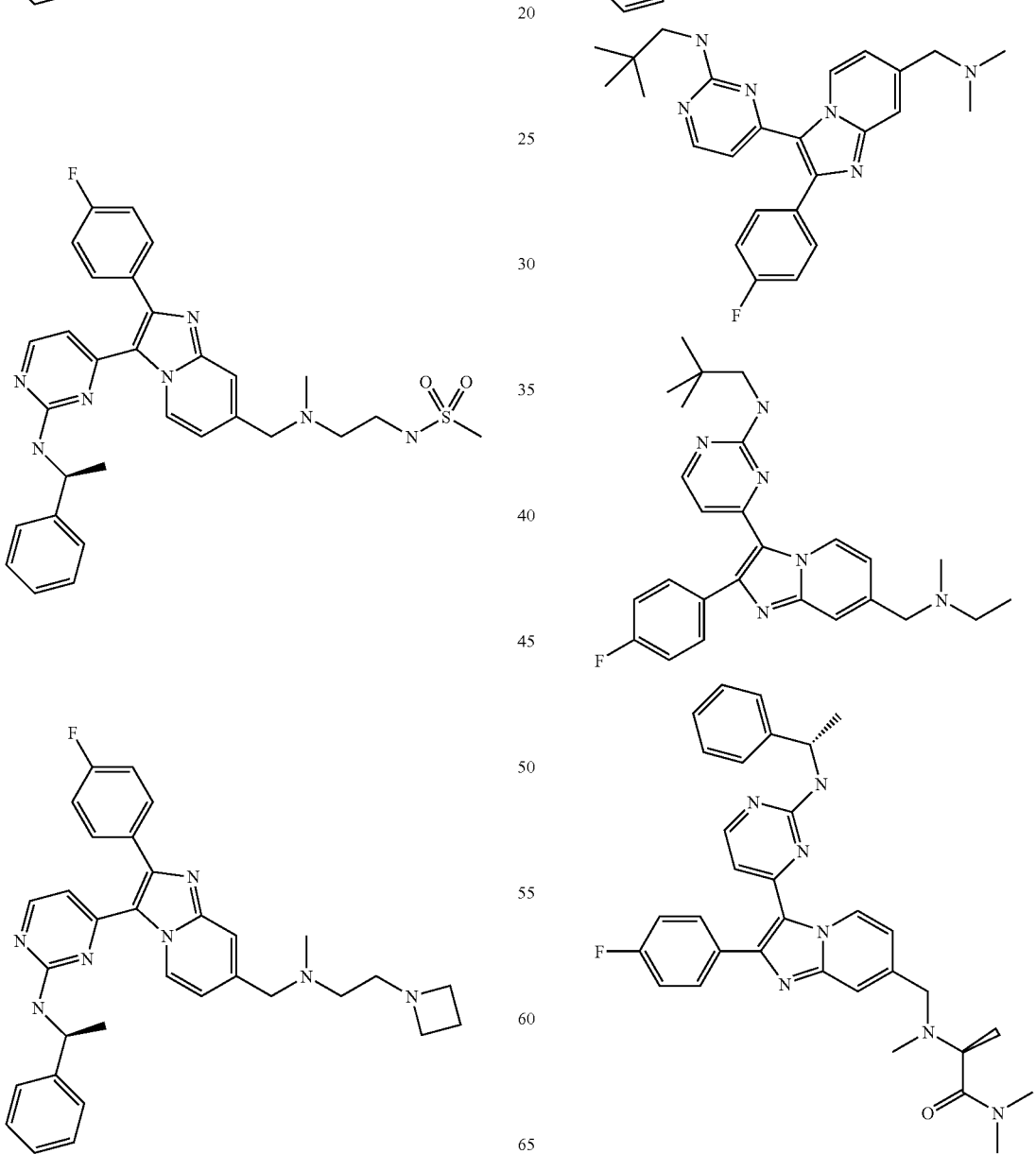

405
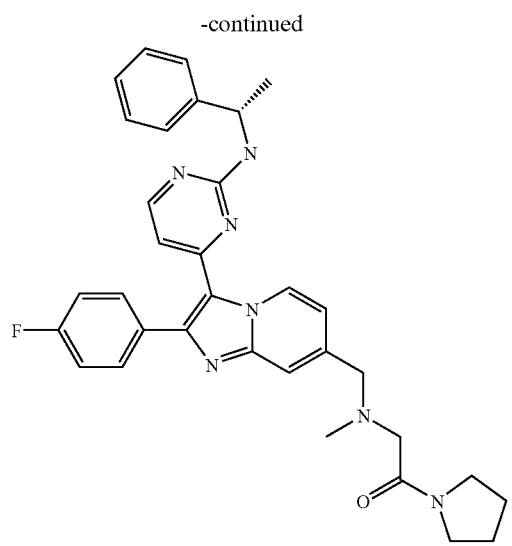
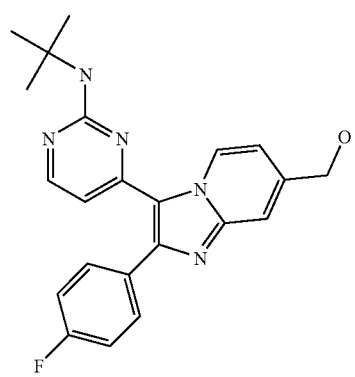
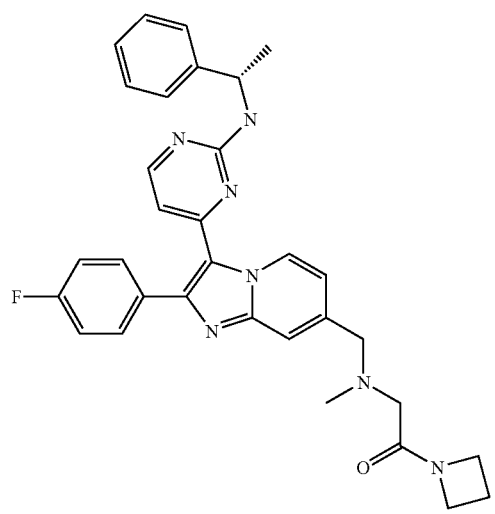
406
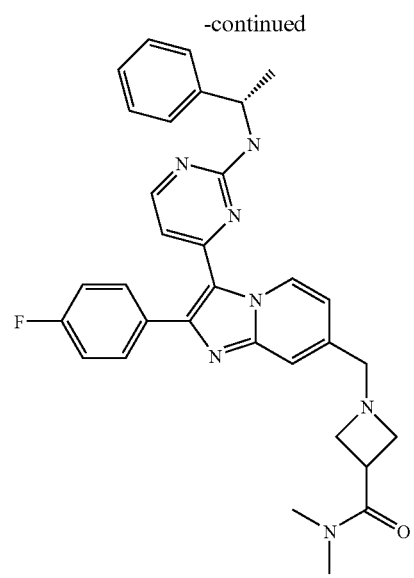
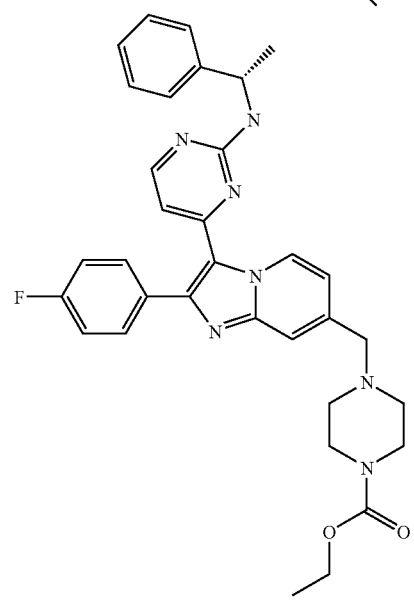

-continued
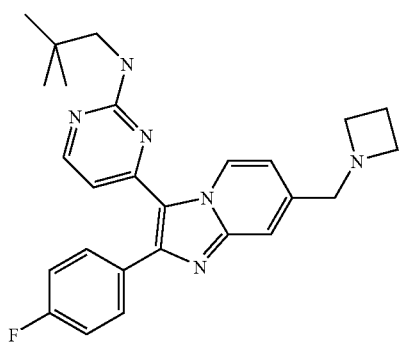
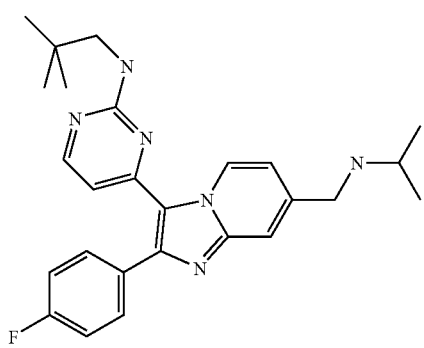
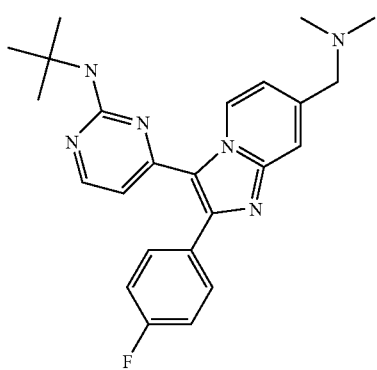
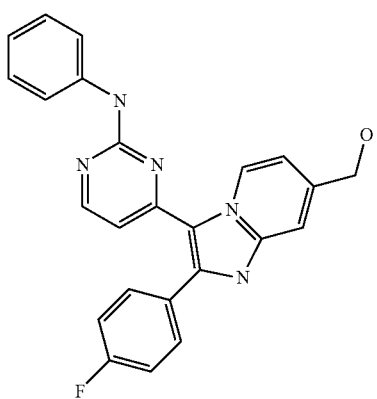
-continued
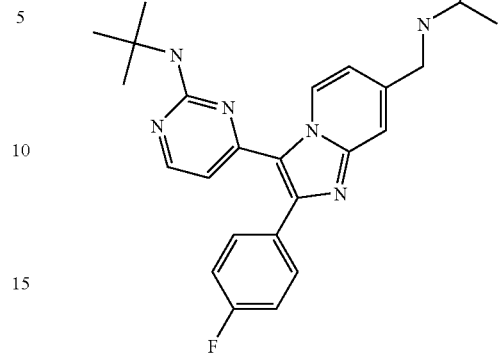
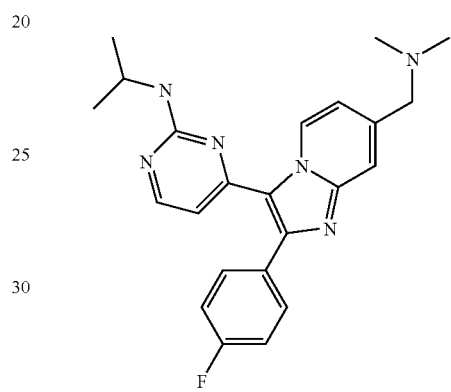
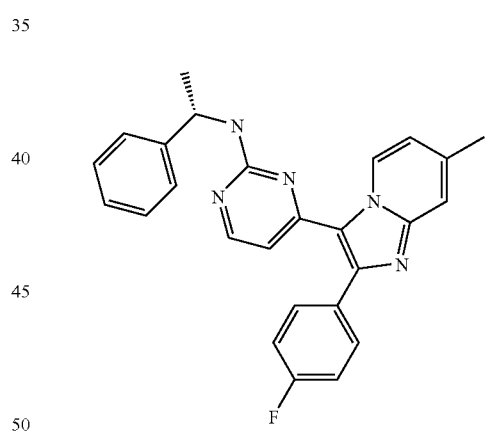
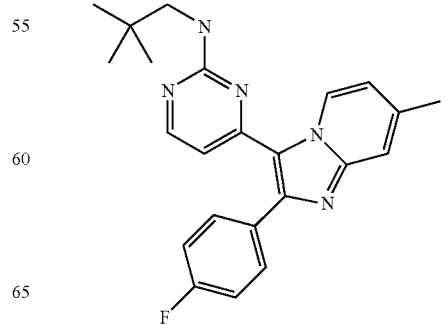

-continued
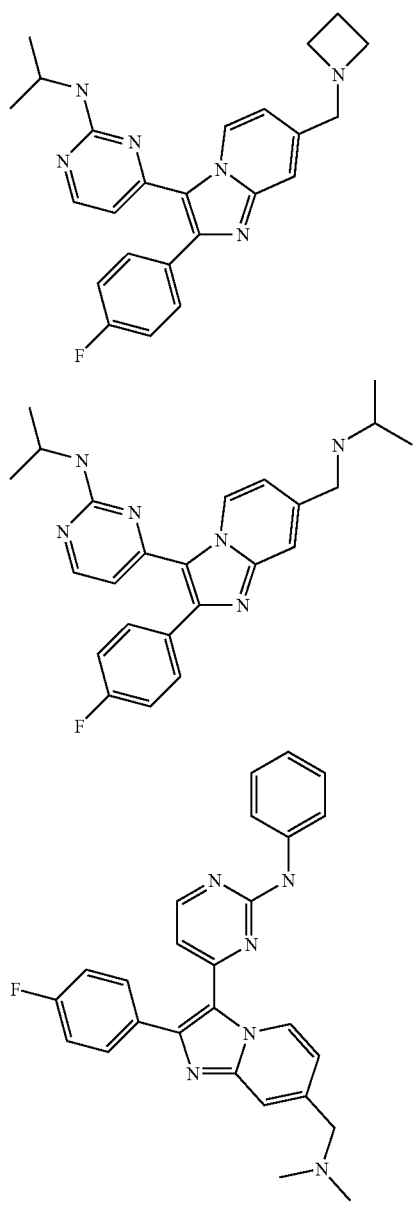
or a pharmaceutically acceptable salt thereof.
20. The compound according to claim 1 represented by
-continued
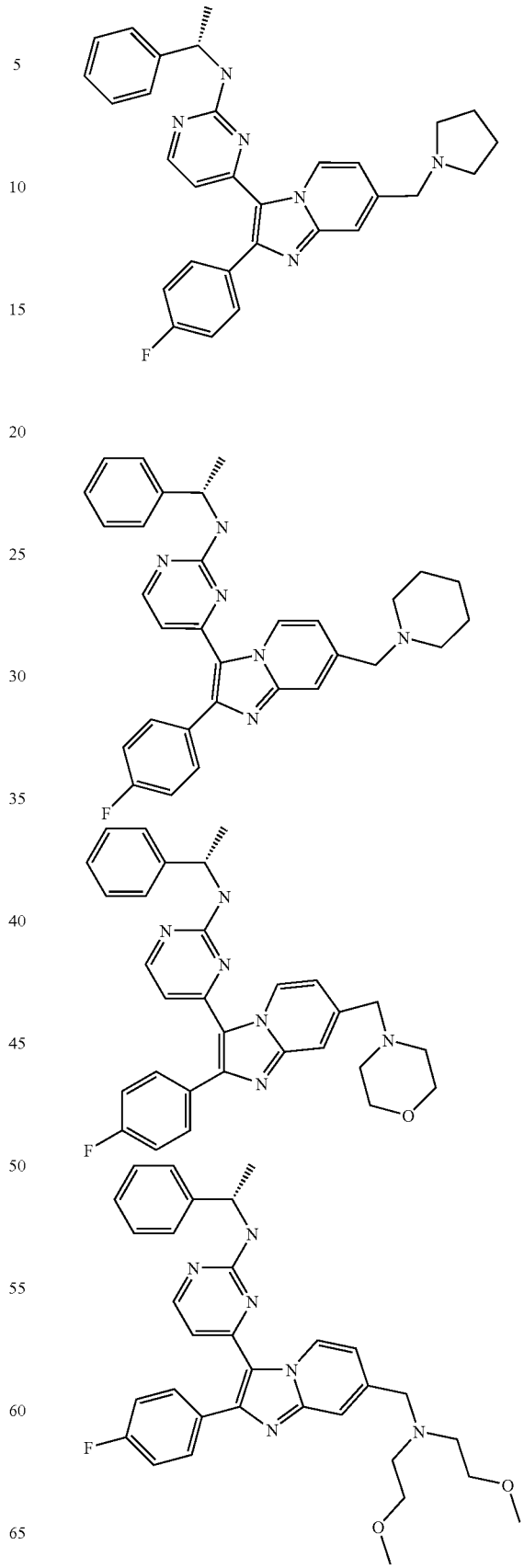

411
-continued
412
-continued
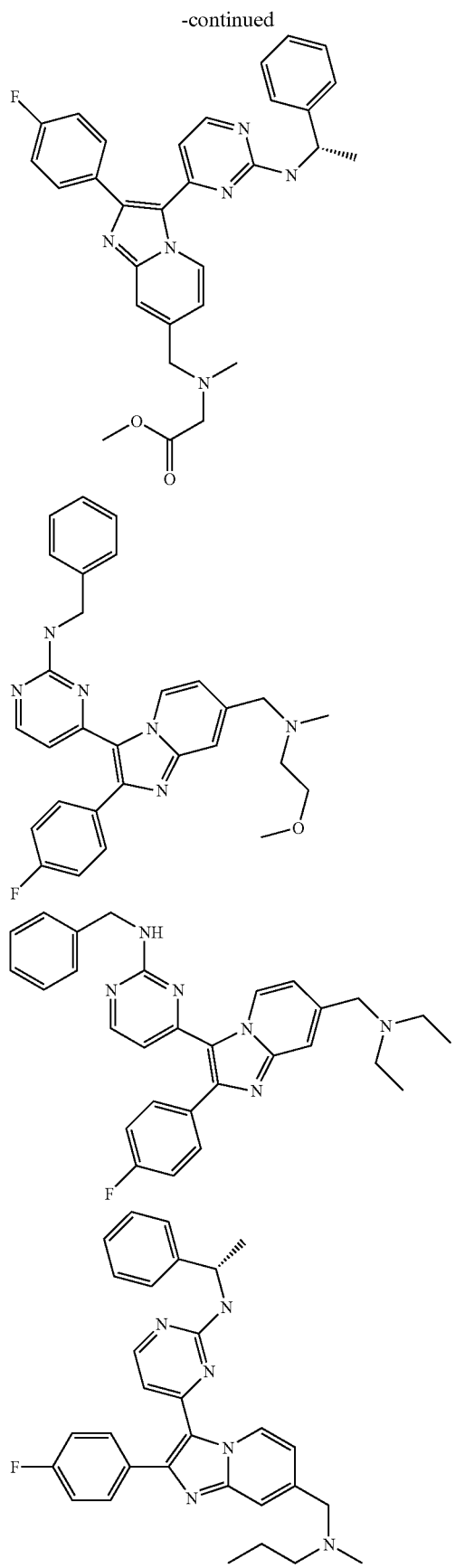
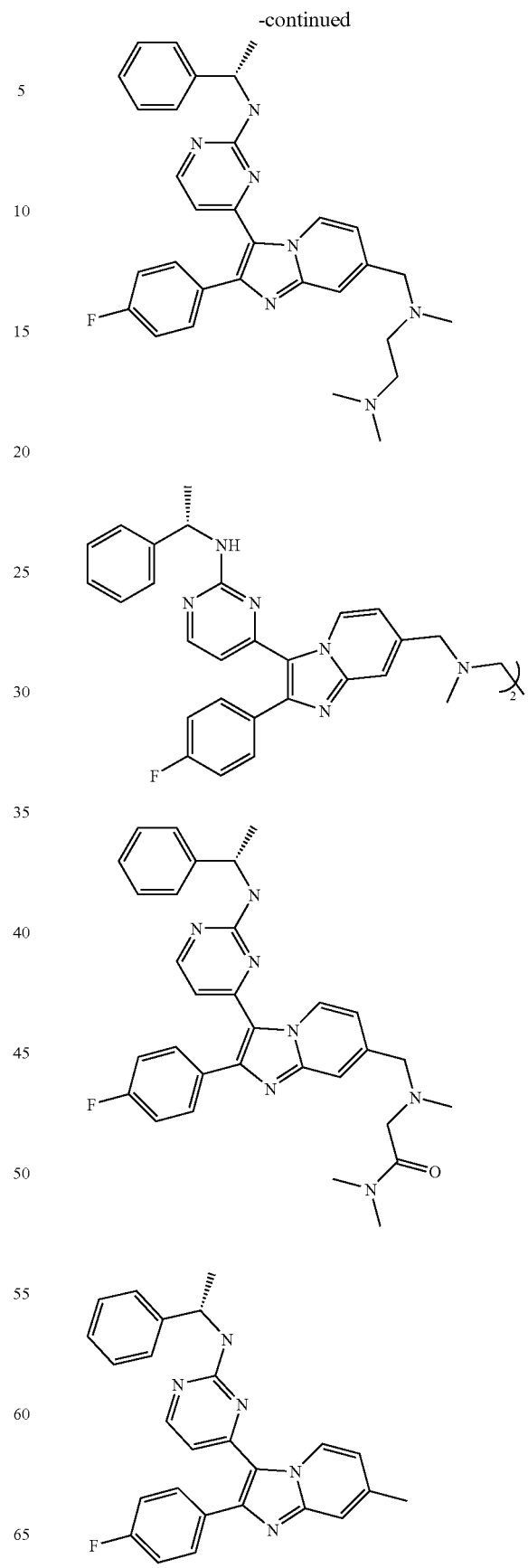

413
-continued
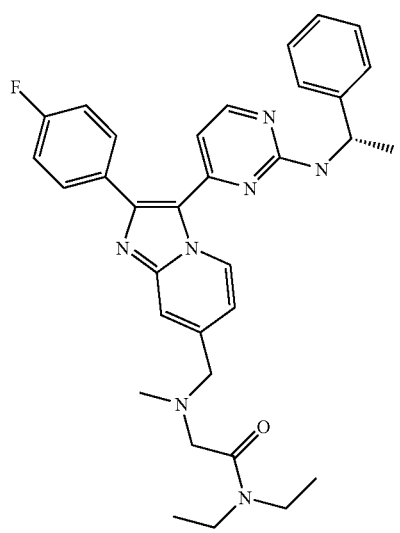
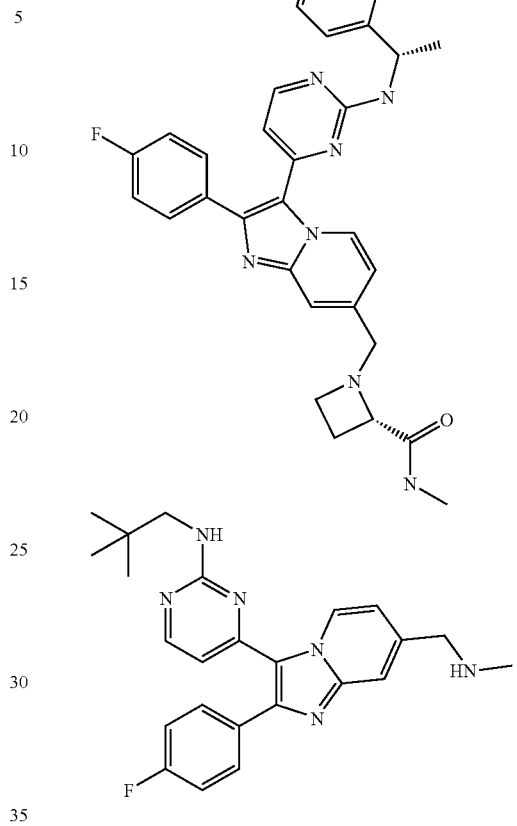
or a pharmaceutically acceptable salt thereof.
21. The compound according to claim 1 represented by
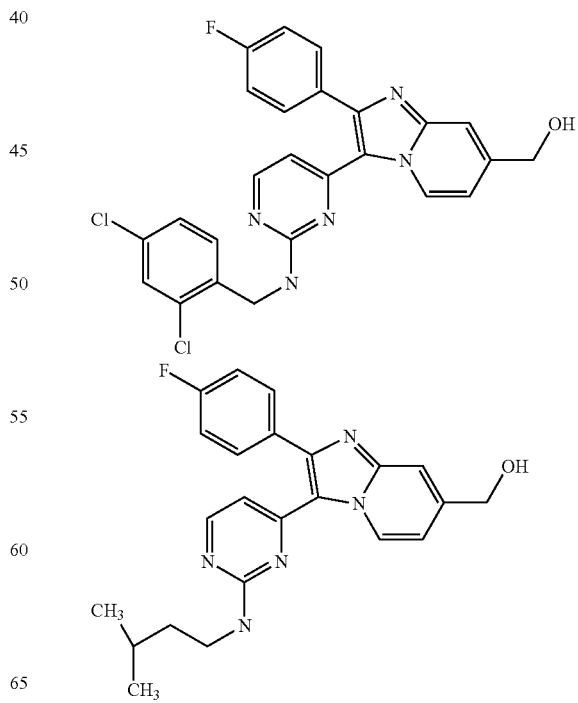

-continued
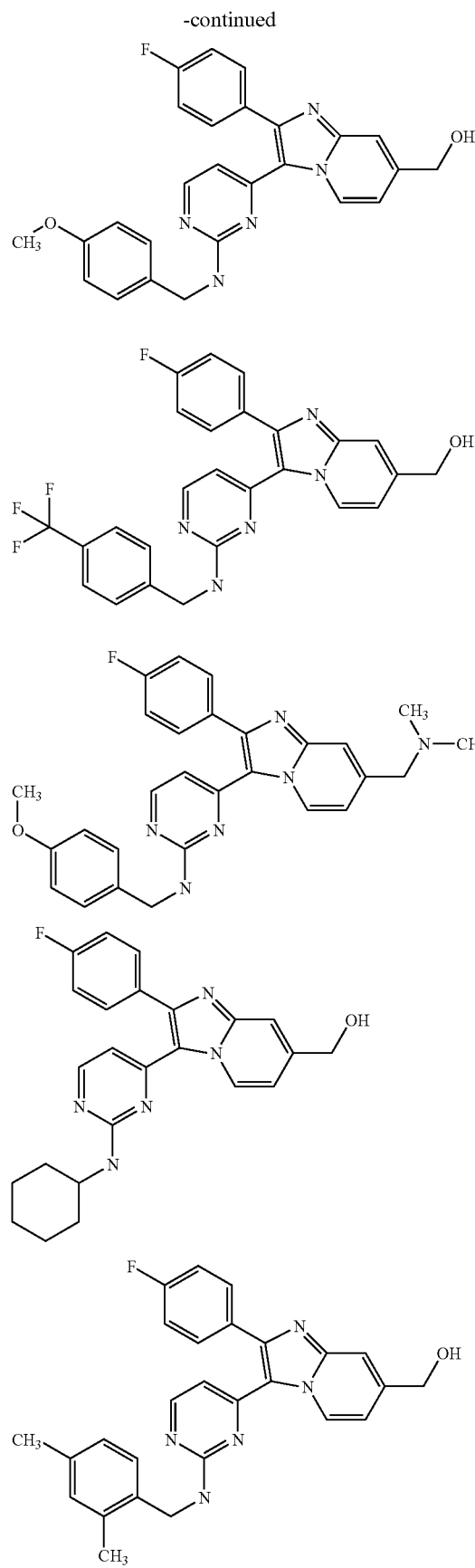
-continued
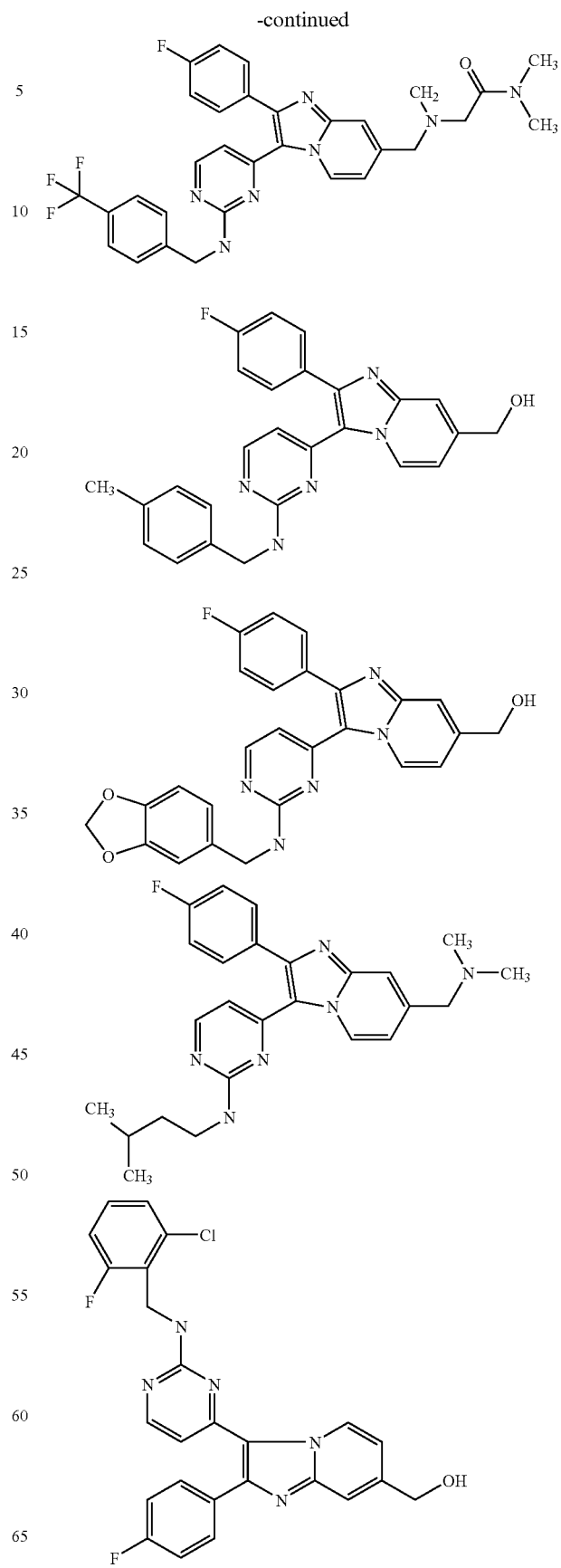

417
-continued
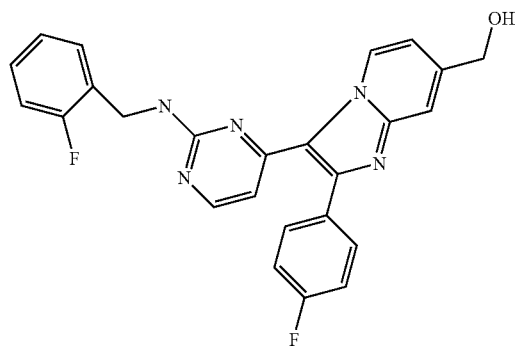
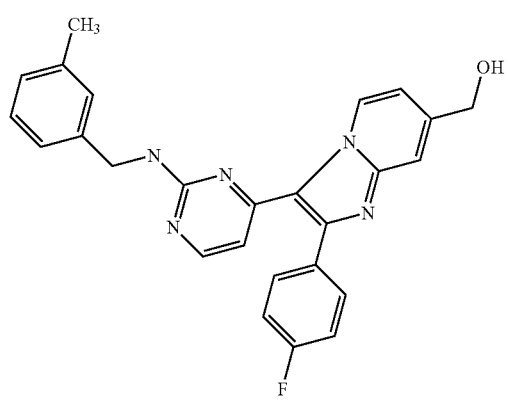
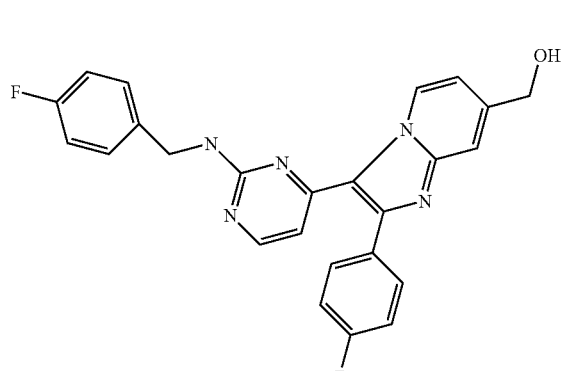
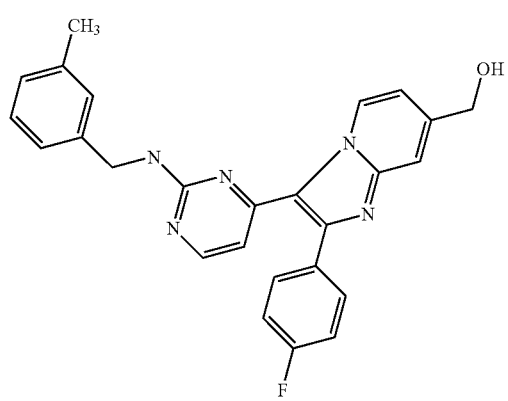
418
-continued
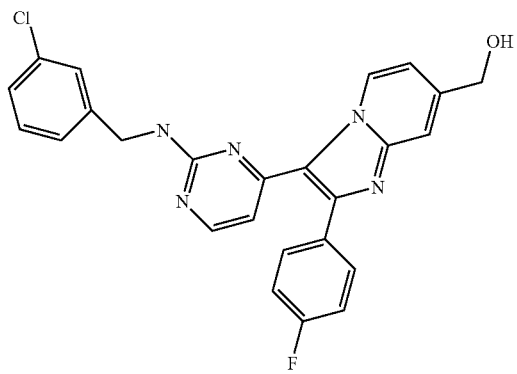
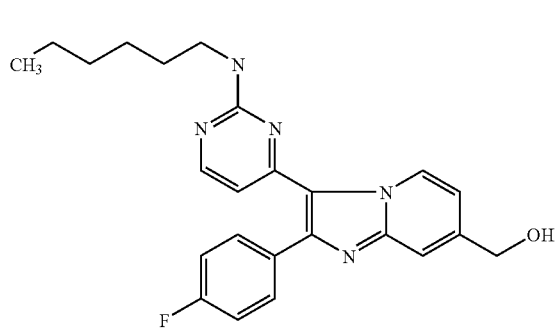
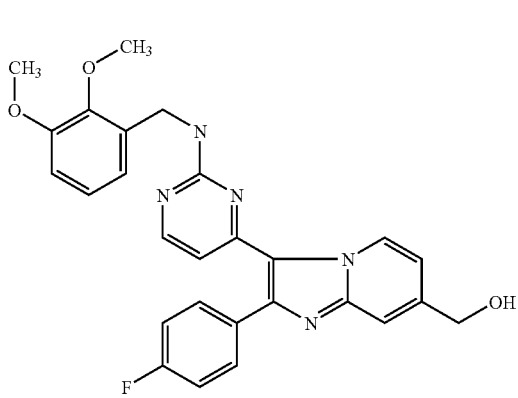
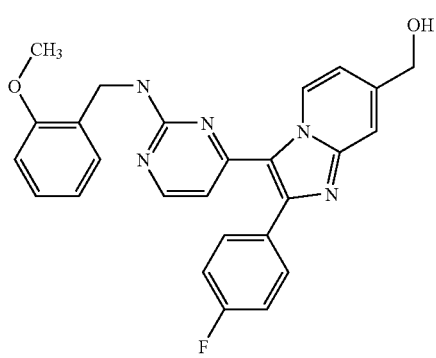

-continued
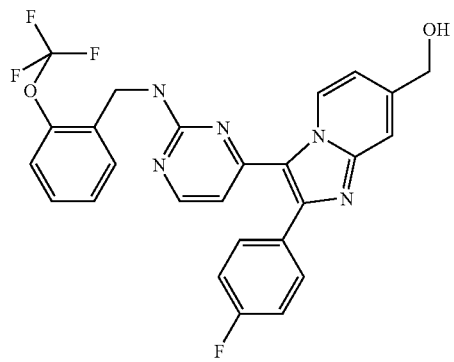
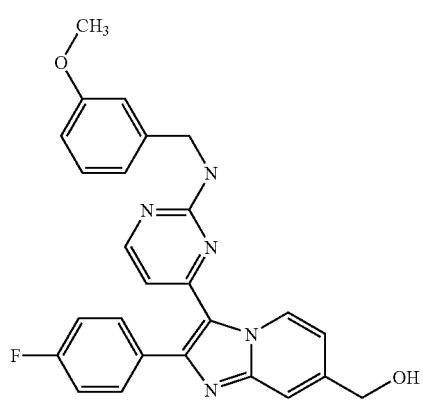
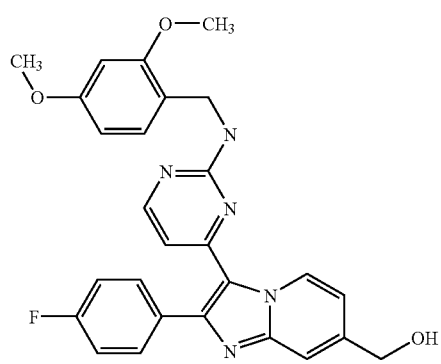
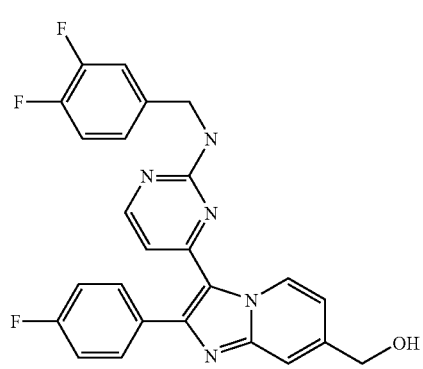
-continued
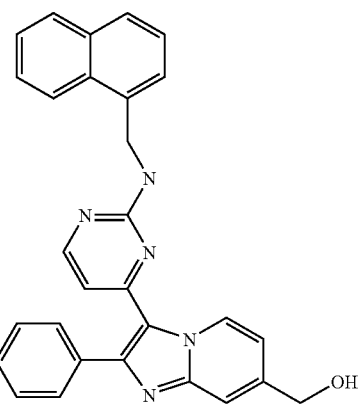
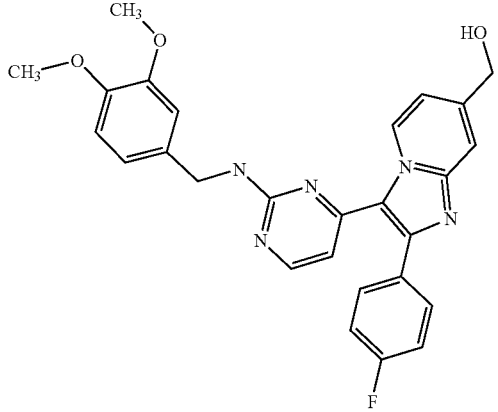
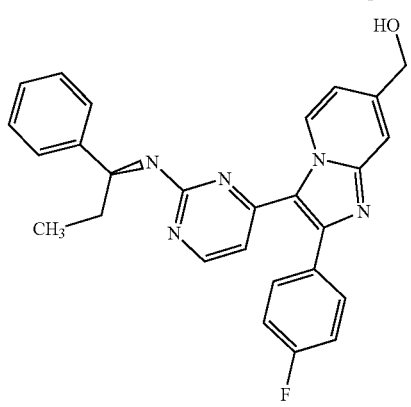
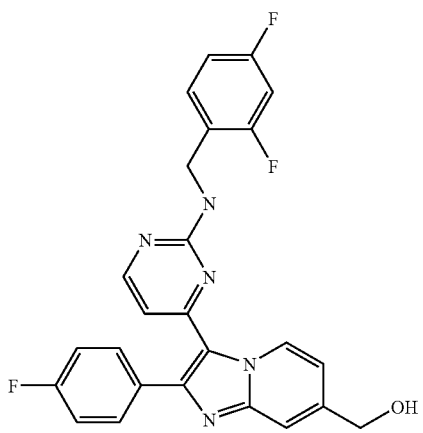

-continued
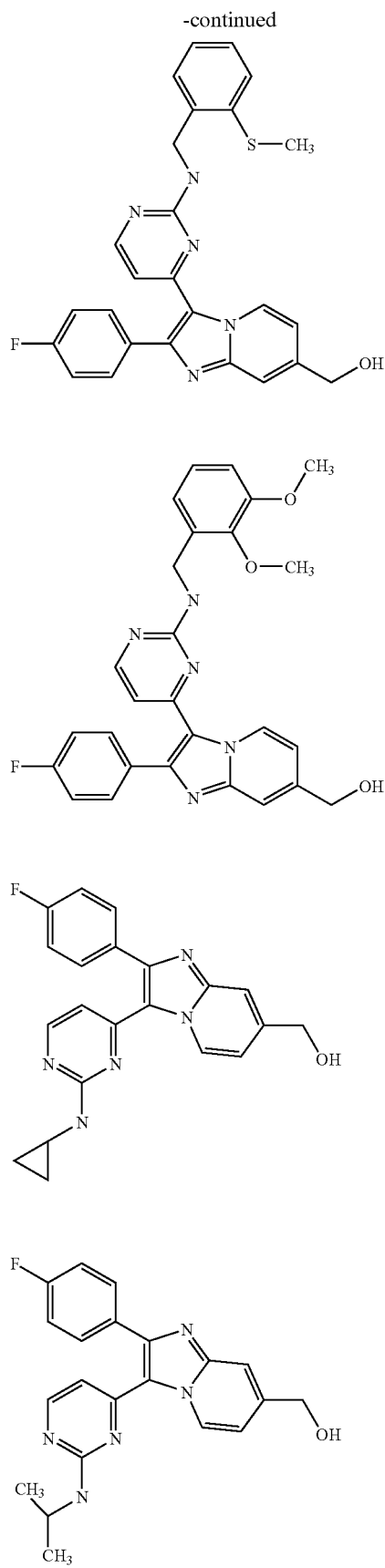
-continued
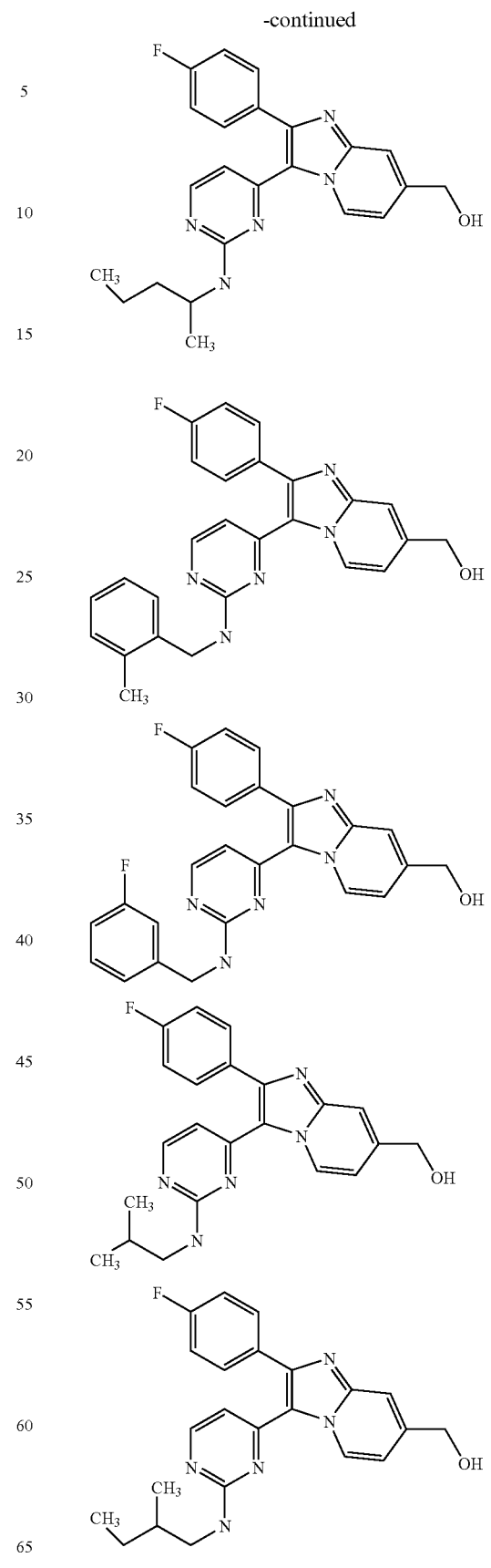

-continued
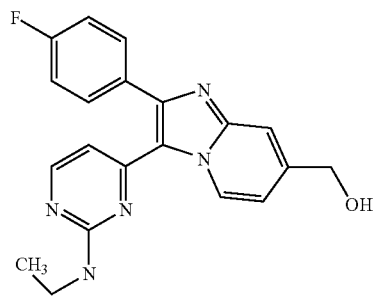
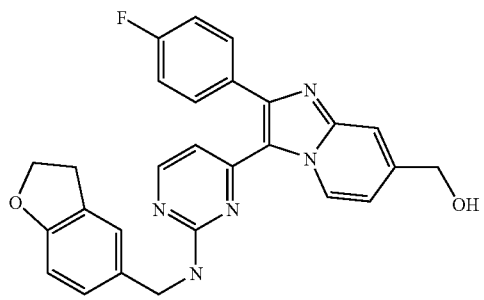
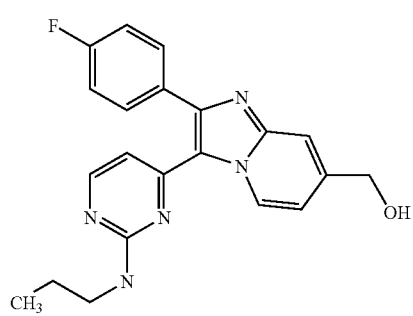
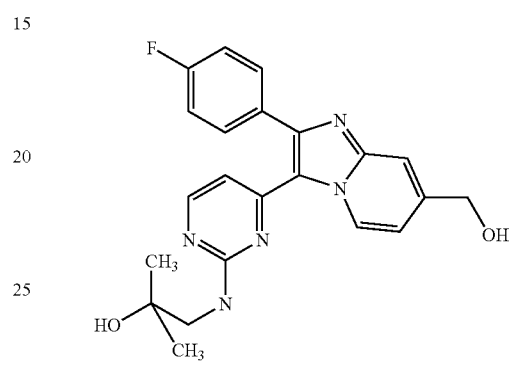
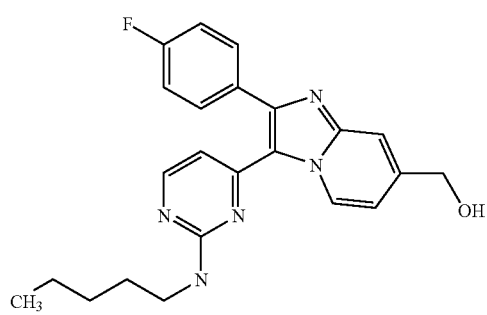
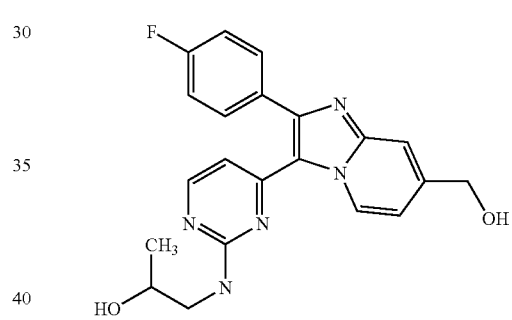
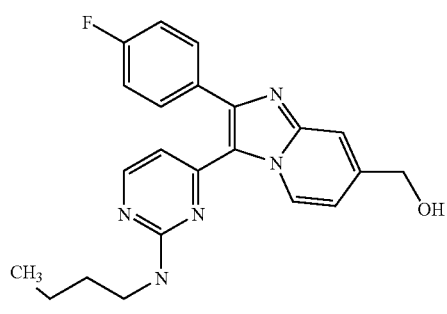
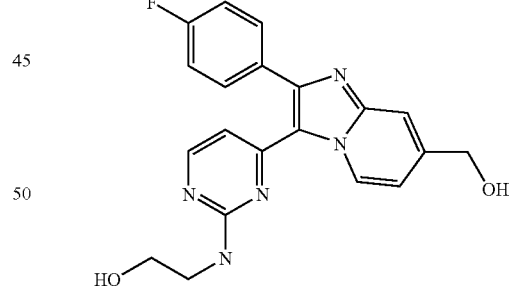
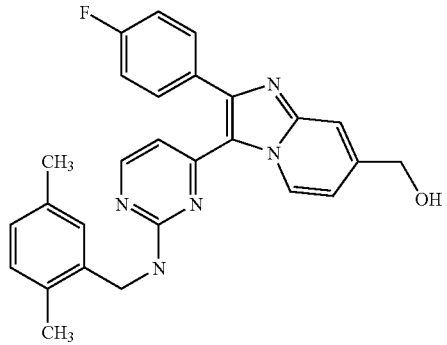
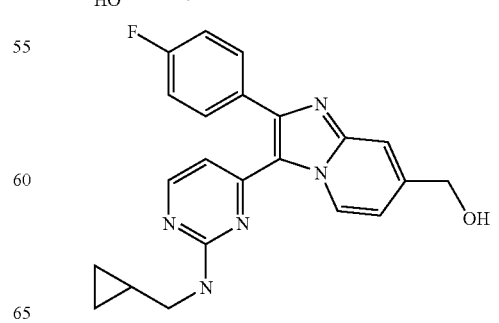

425 426
-continued
-continued
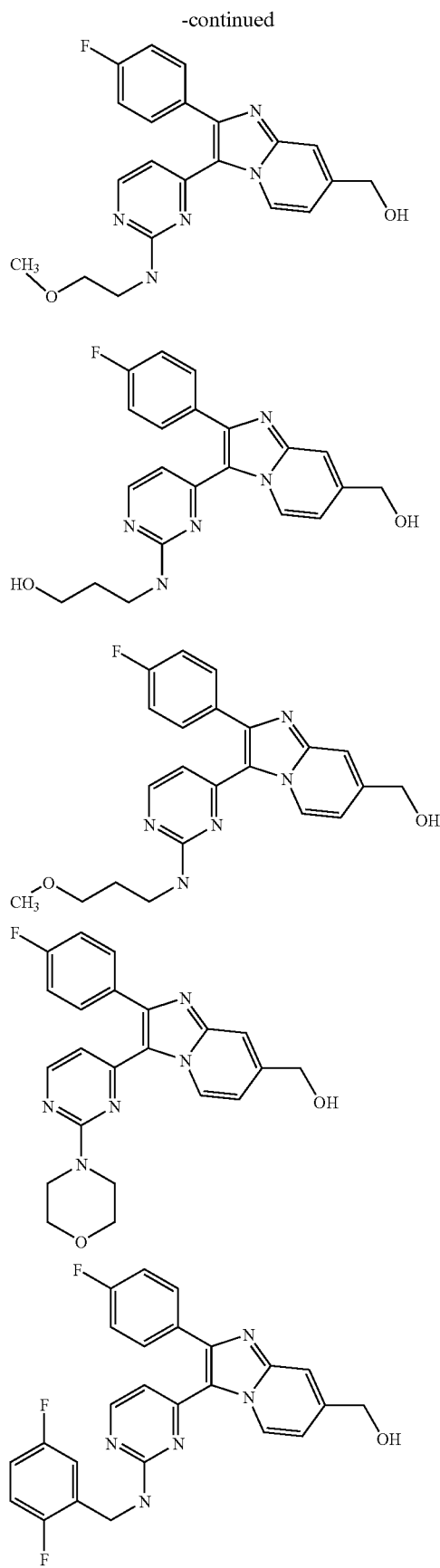
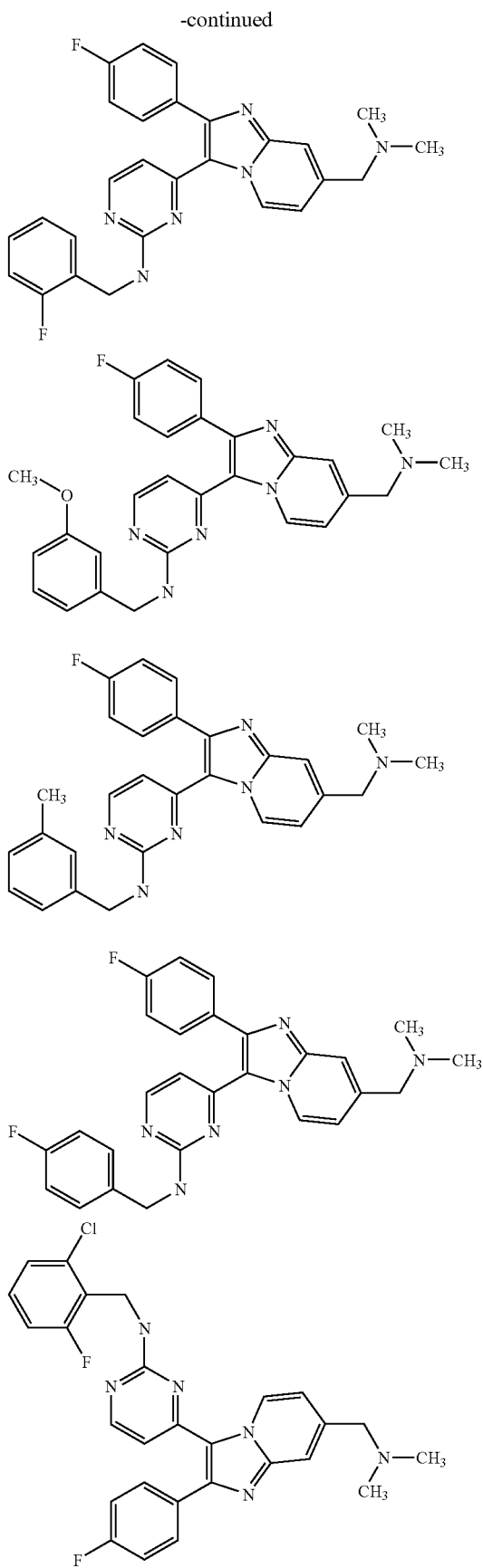

427
-continued
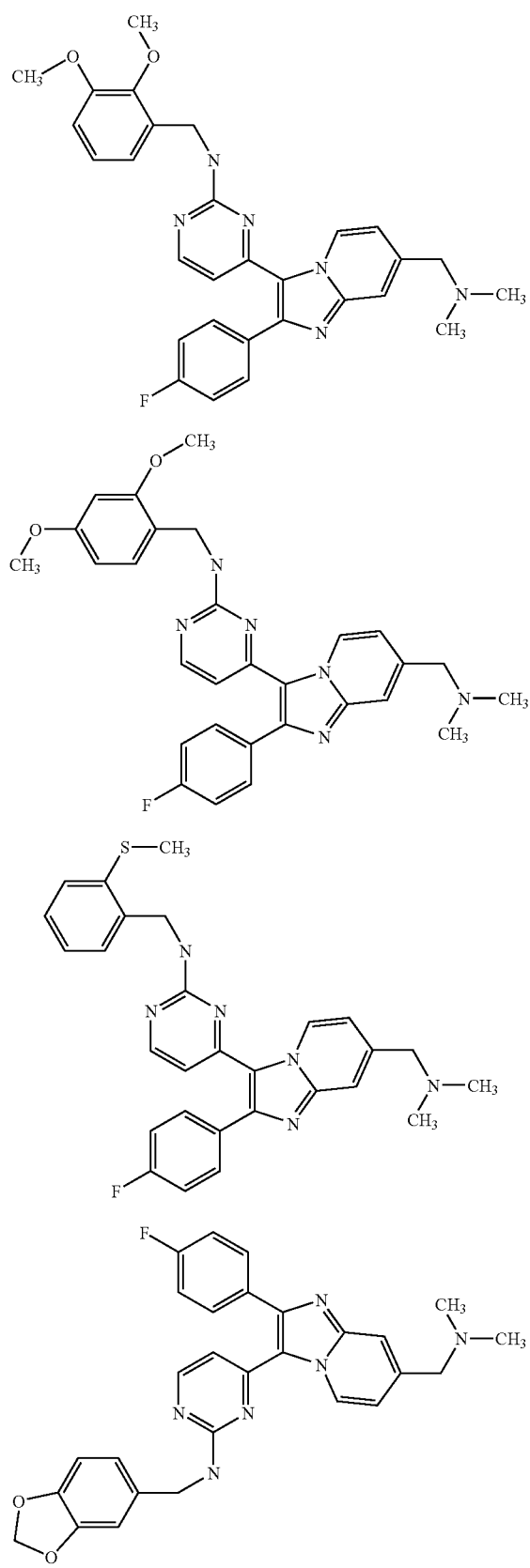
428
-continued
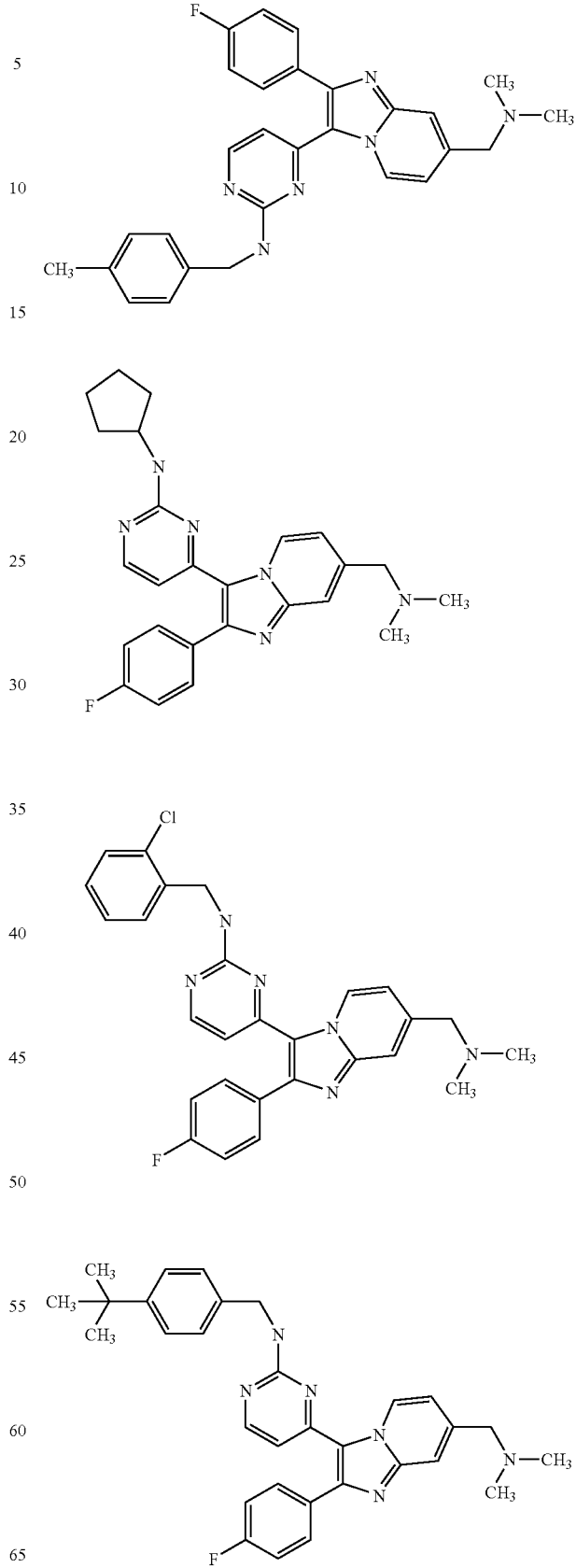

-continued
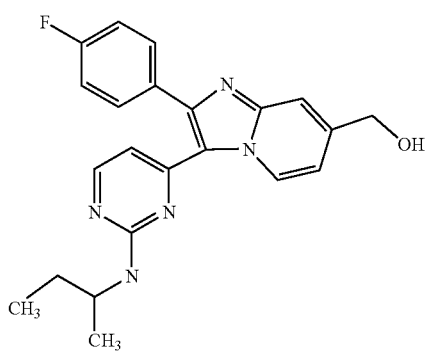
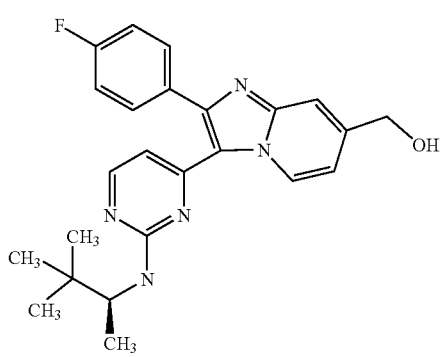
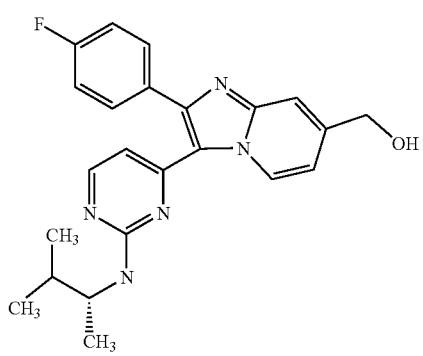
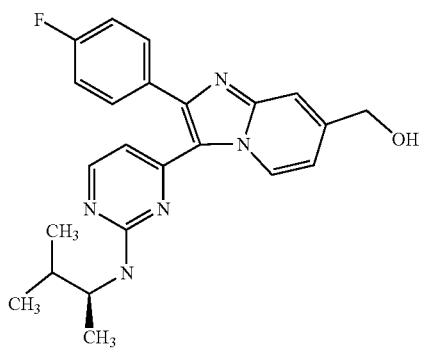
-continued
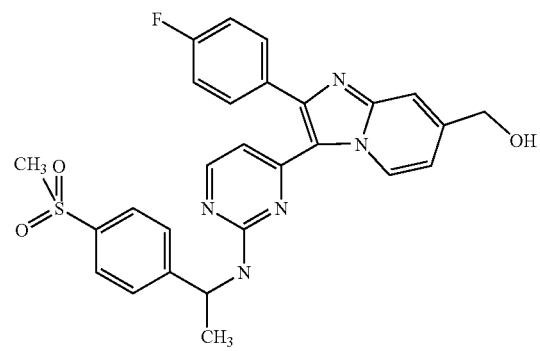
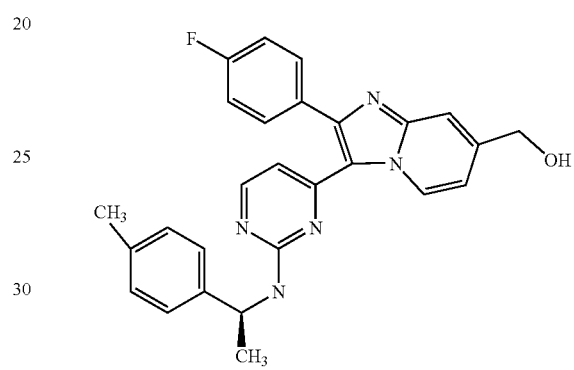
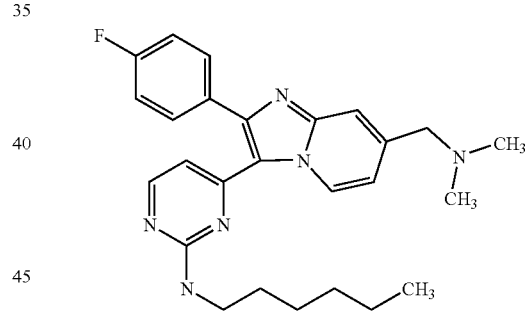
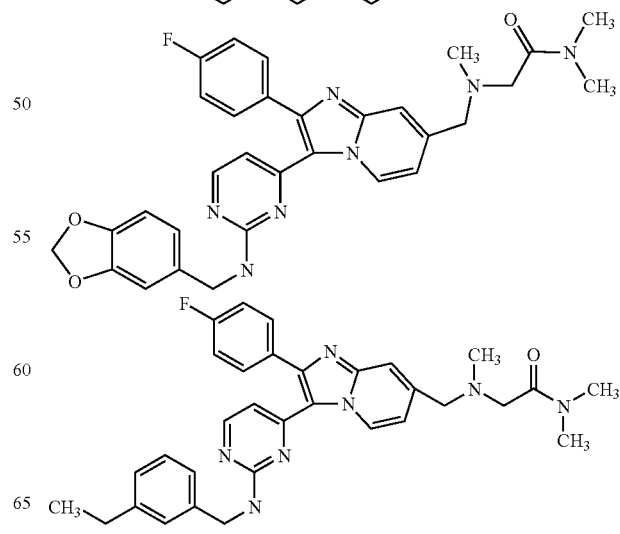

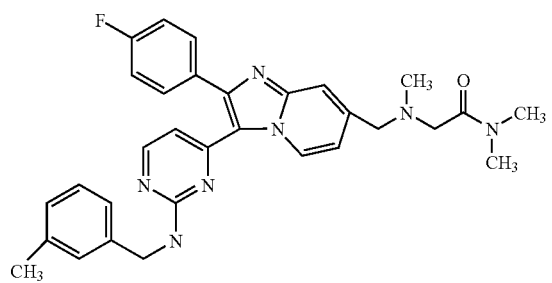
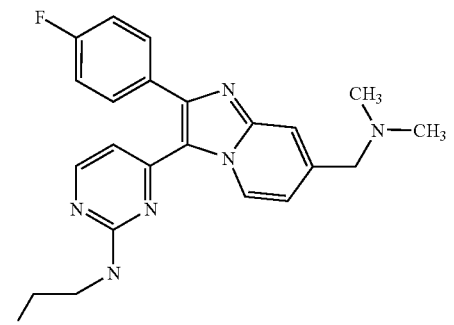

433
-continued
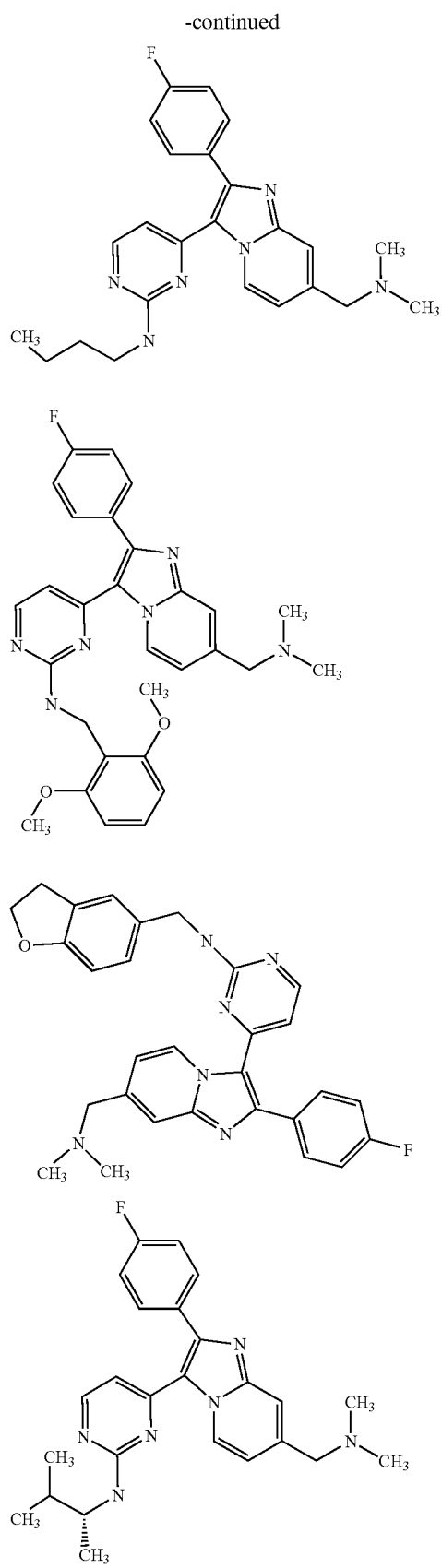
434
-continued
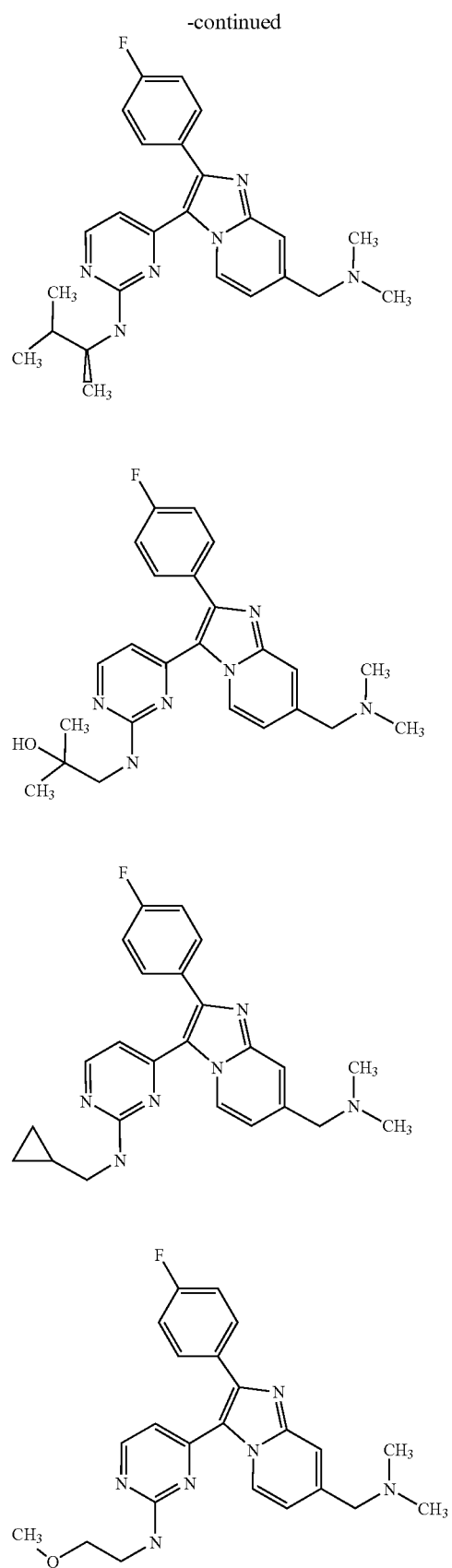

-continued
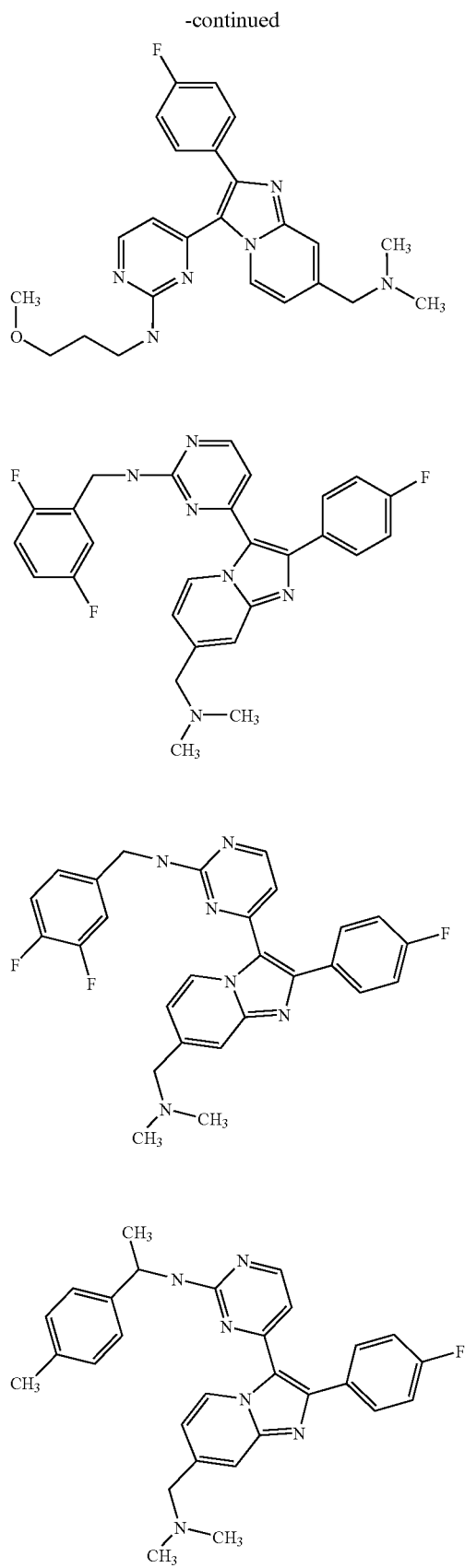
-continued
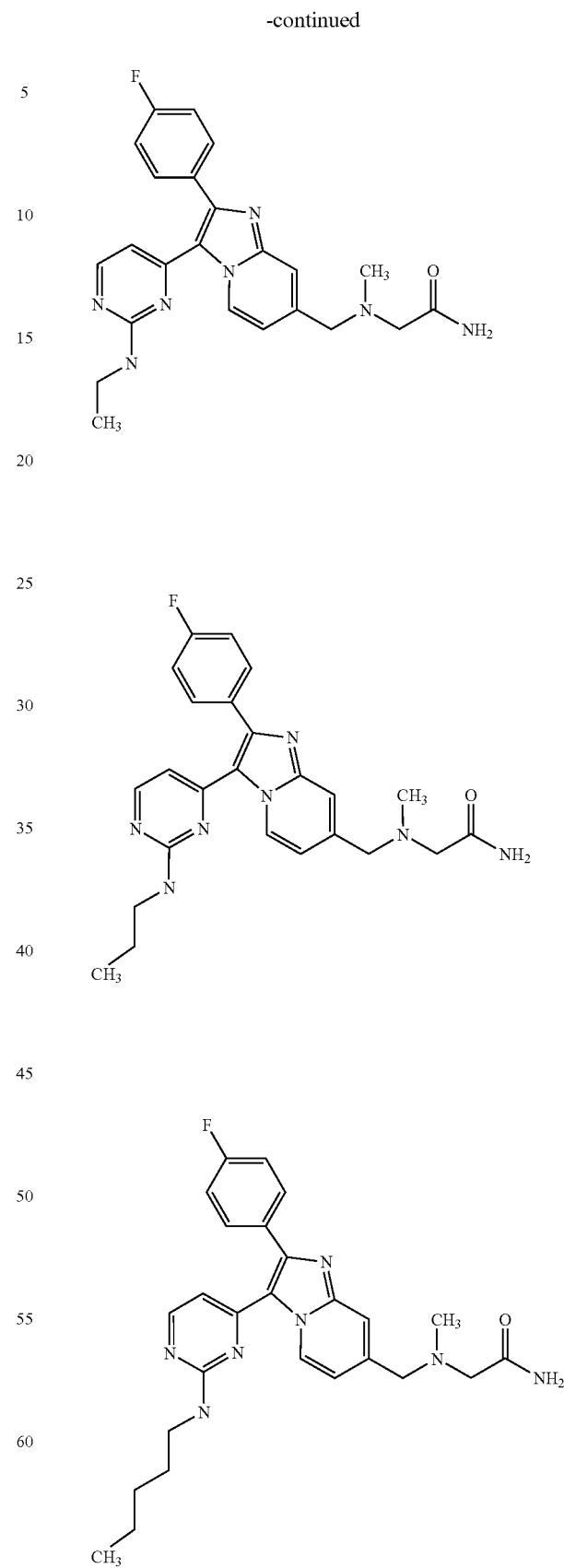

437 438
-continued                                    -continued
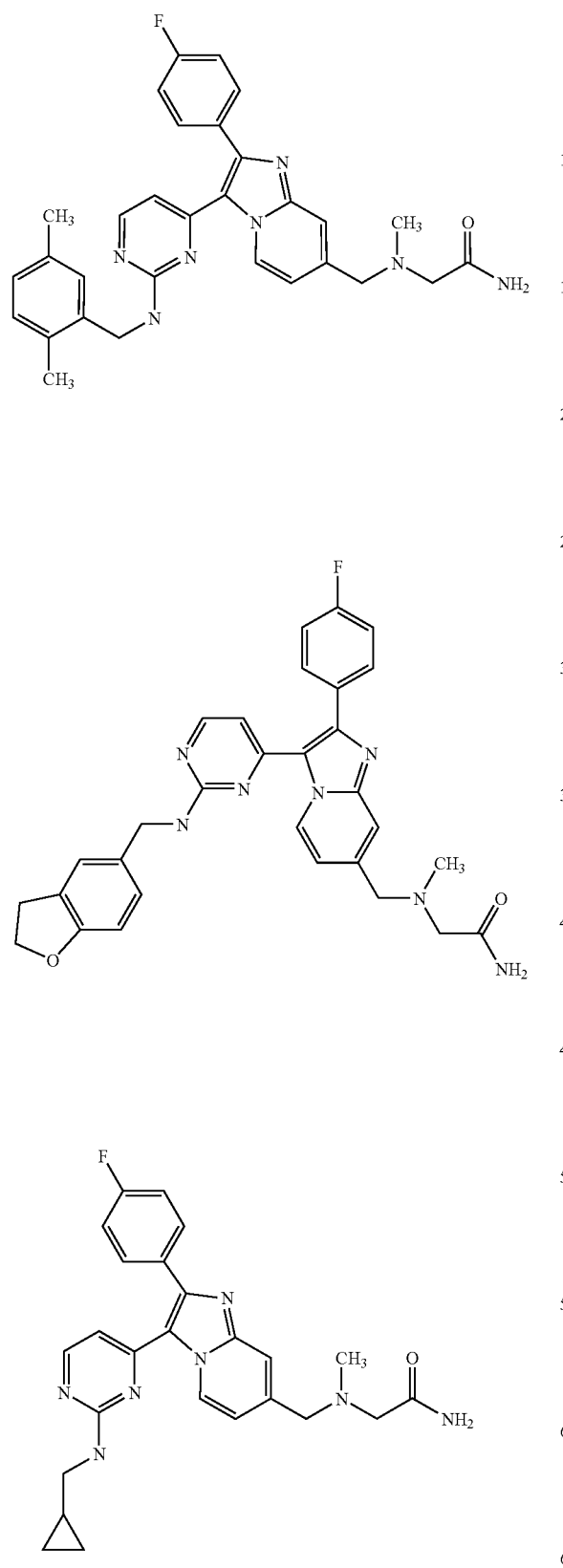
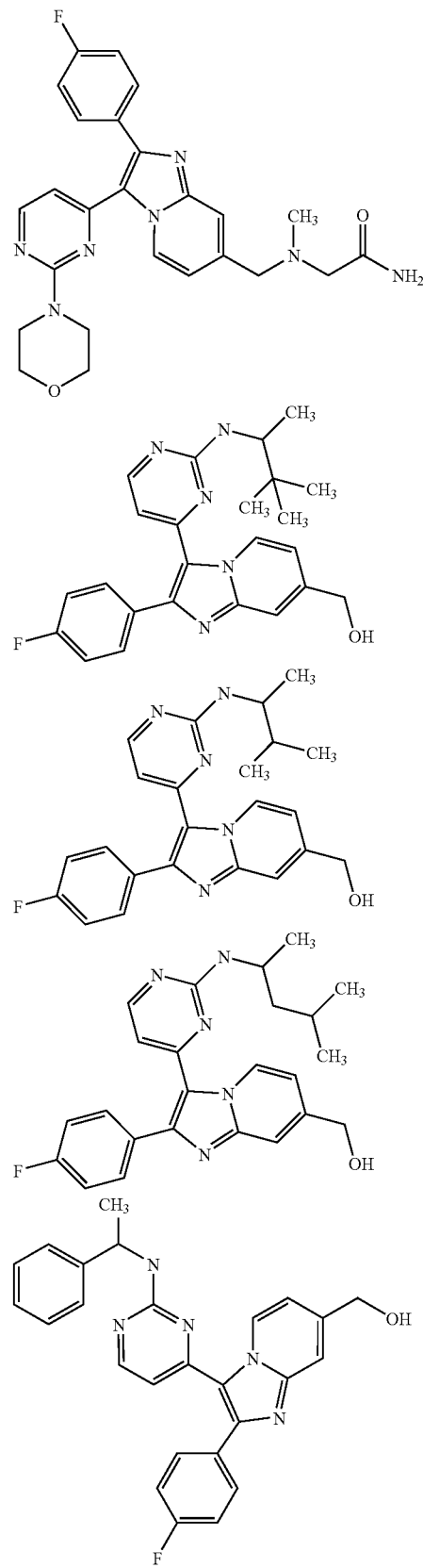

-continued
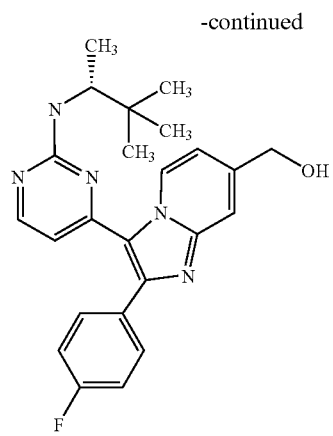
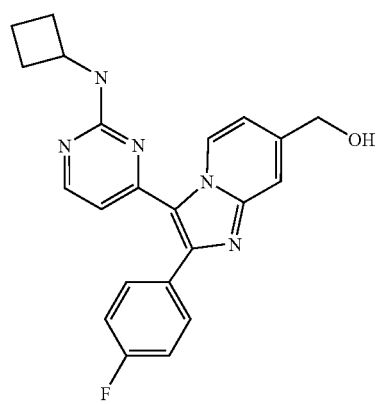
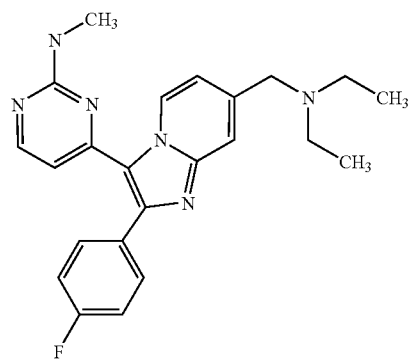
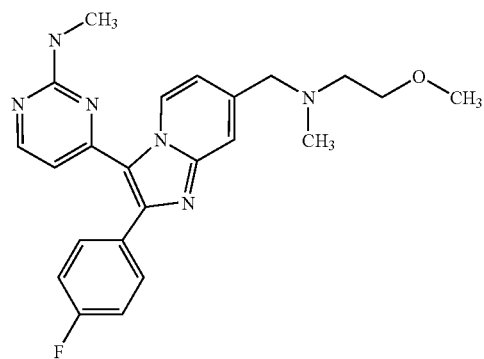
-continued
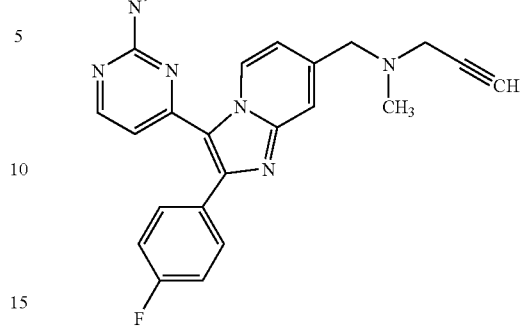
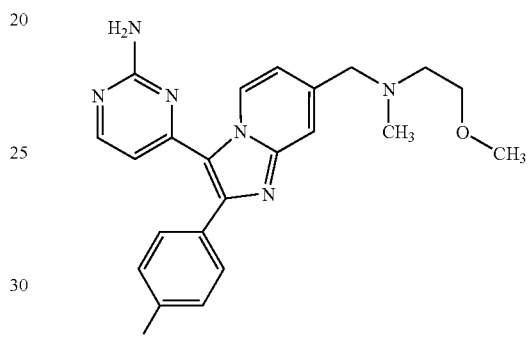
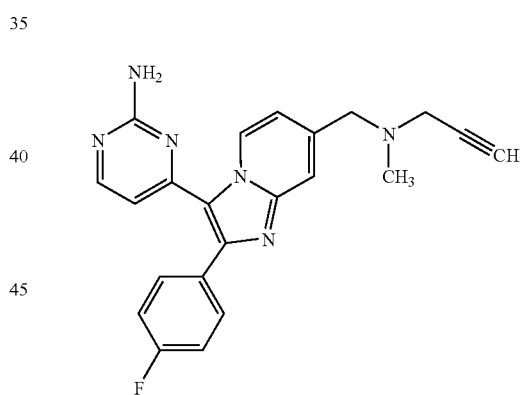
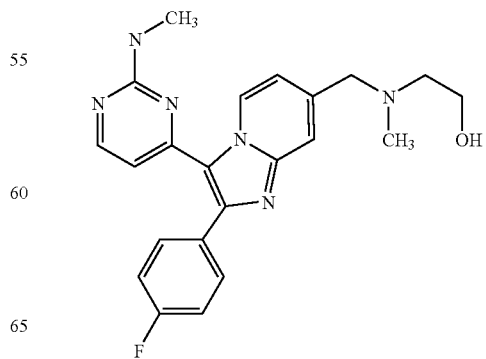

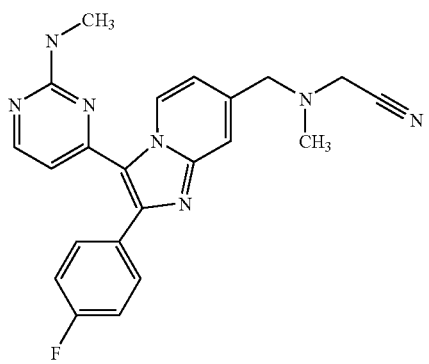
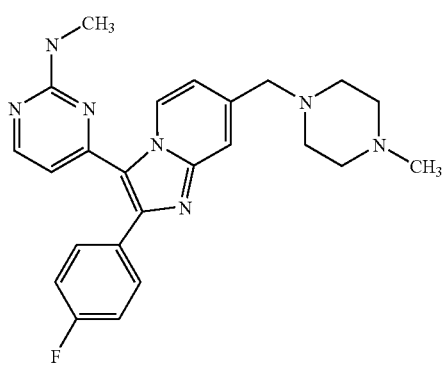
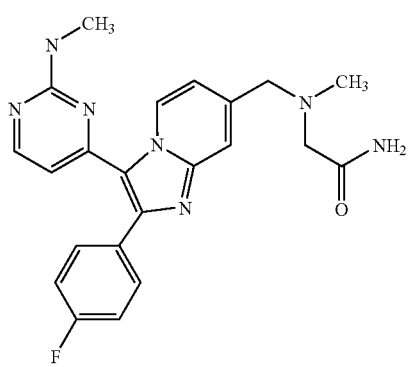
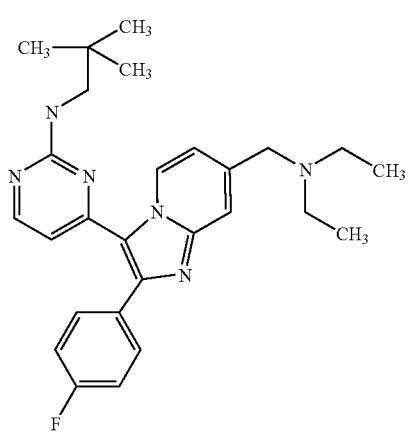
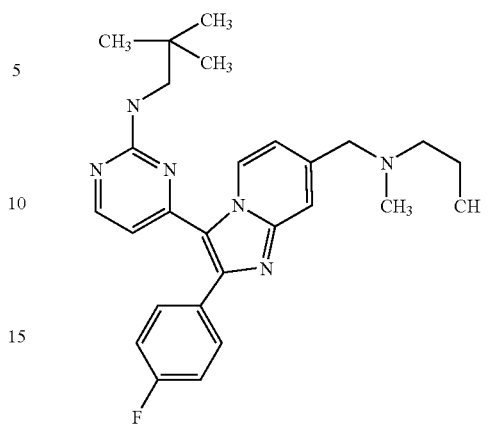
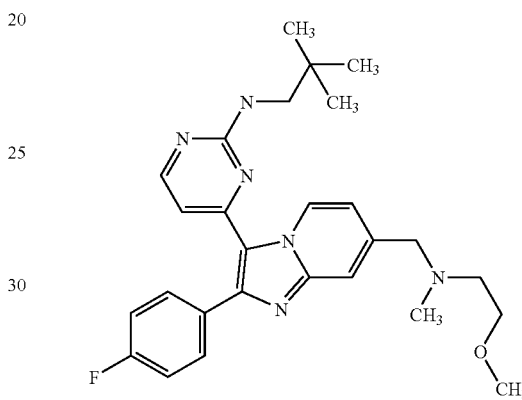
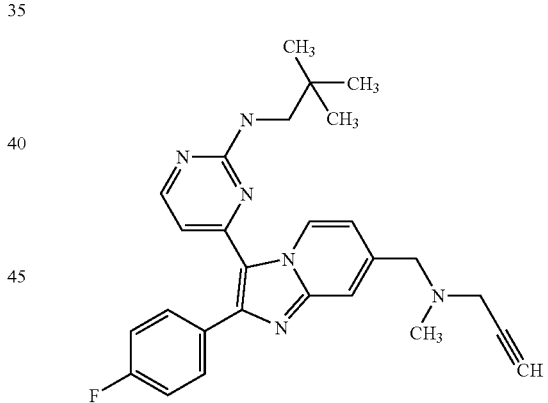
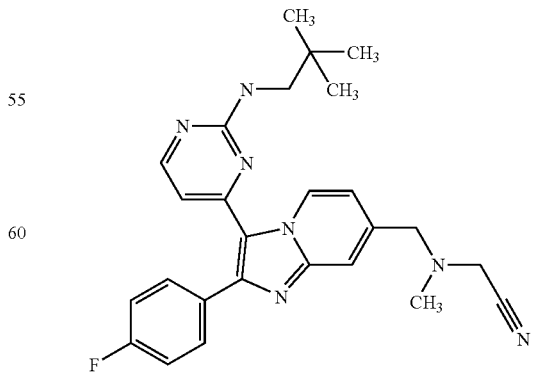

-continued
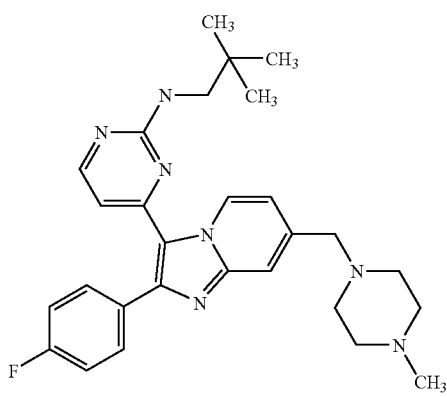
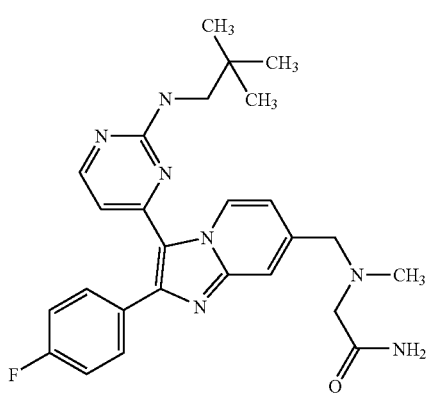
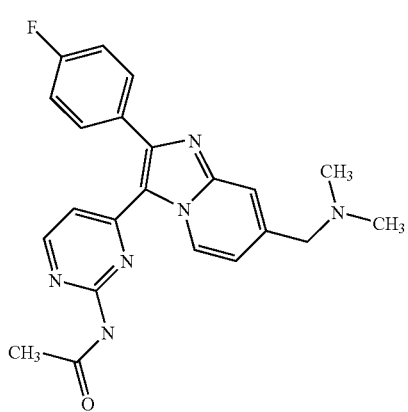
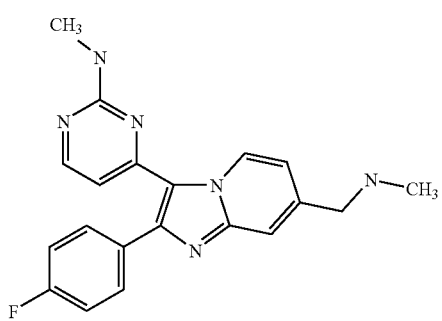
-continued
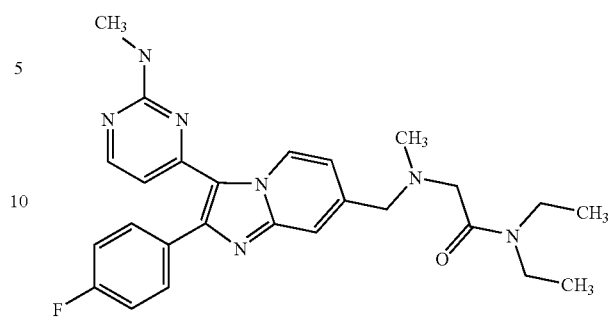
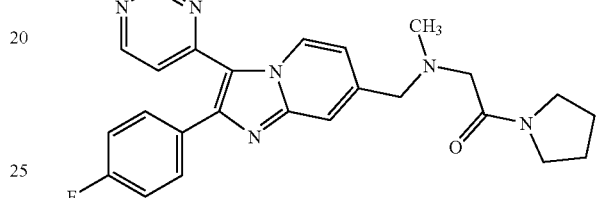
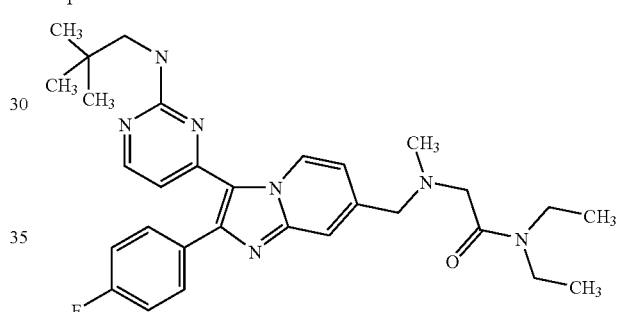
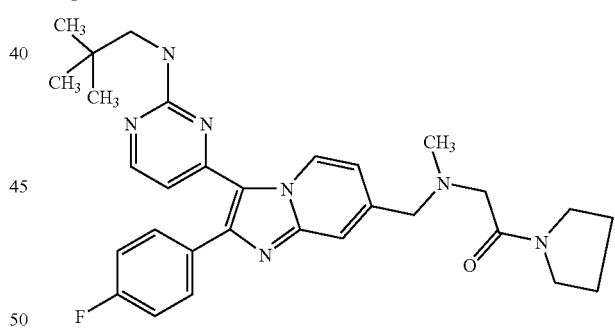
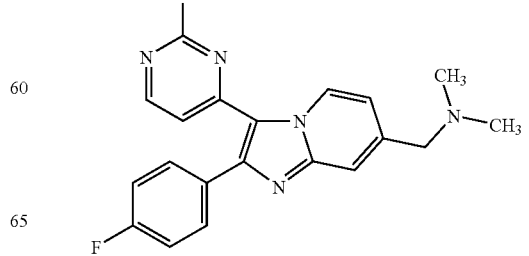

445
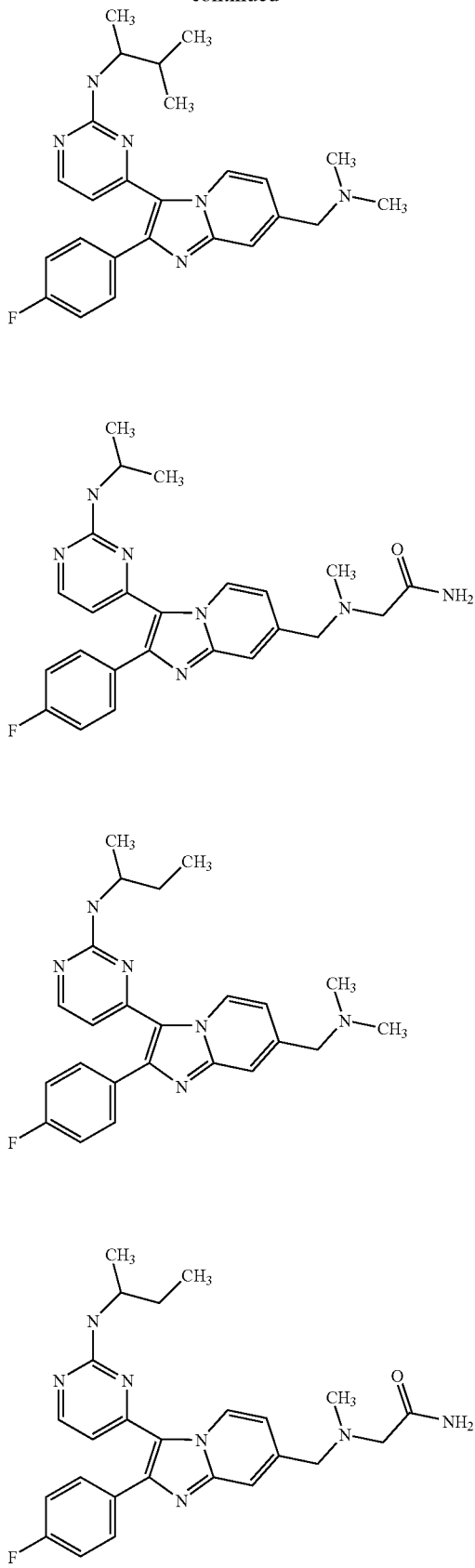
446
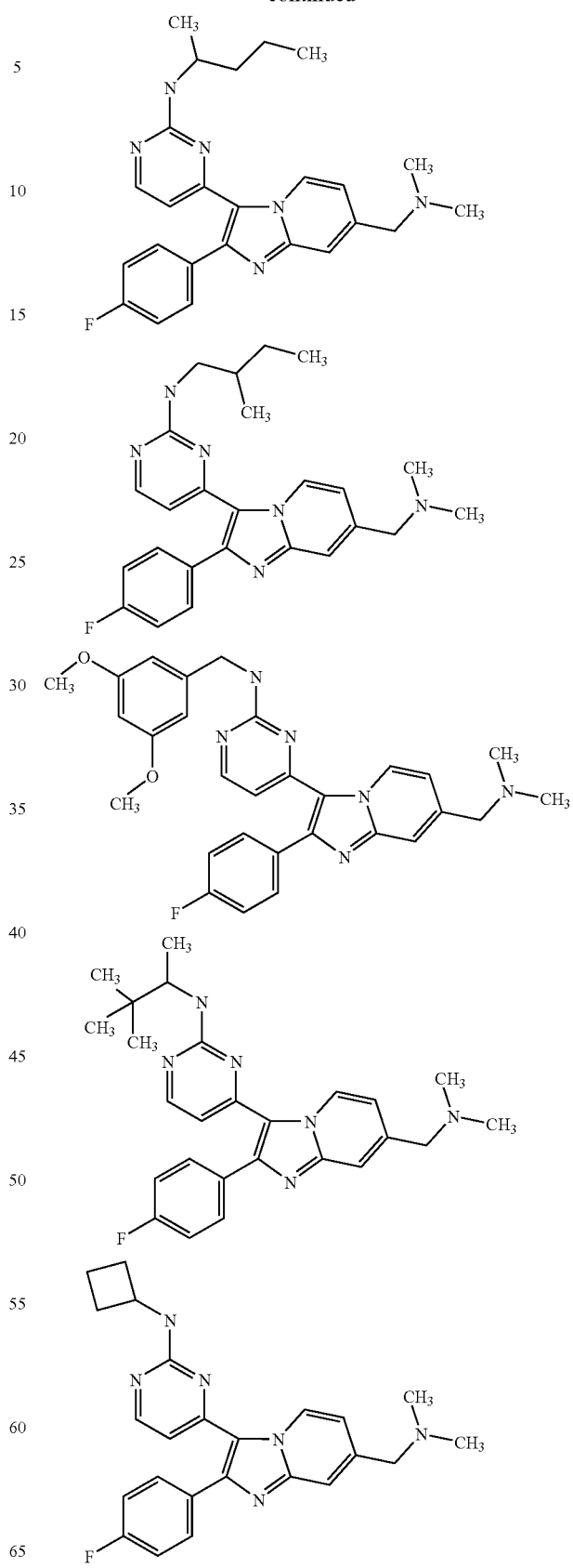

-continued
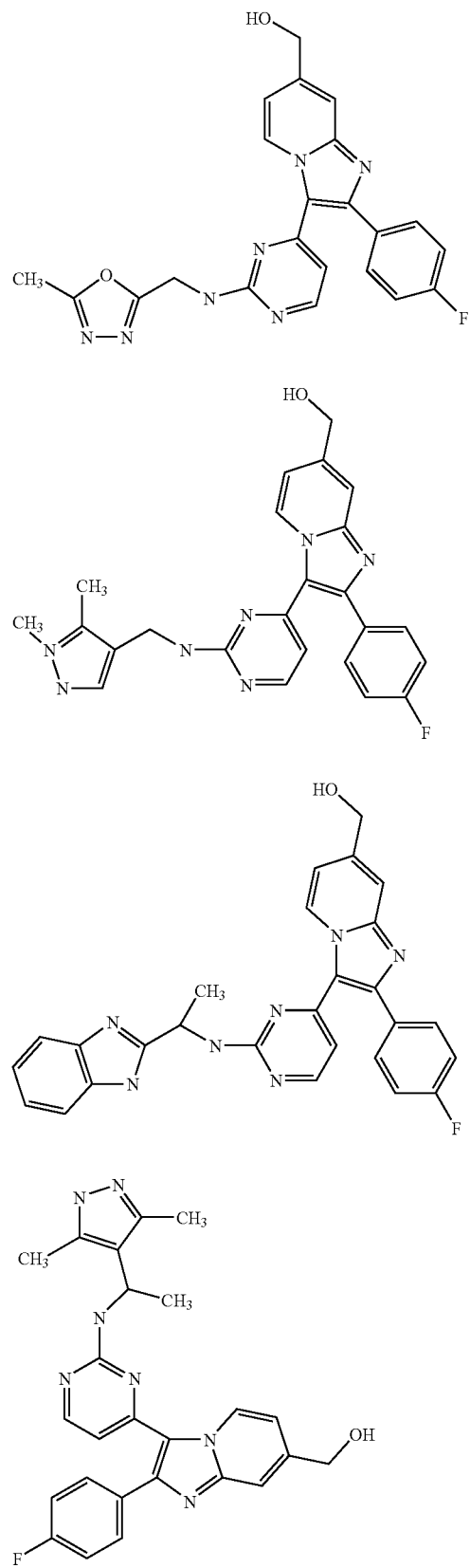
-continued
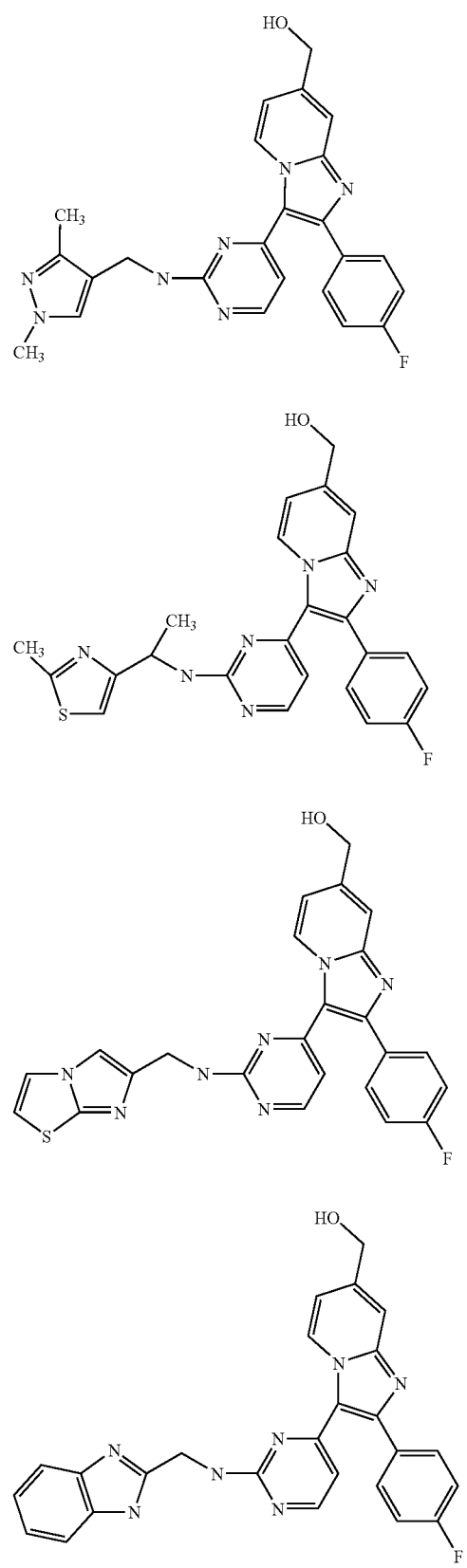

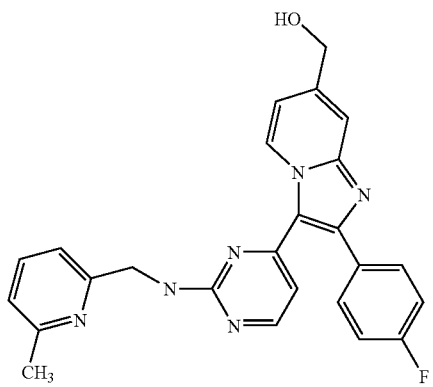
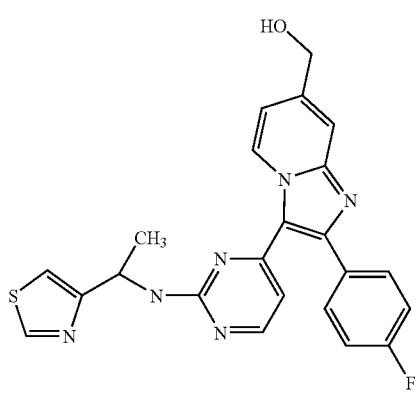
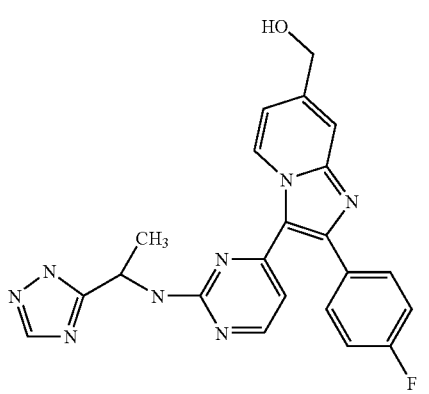
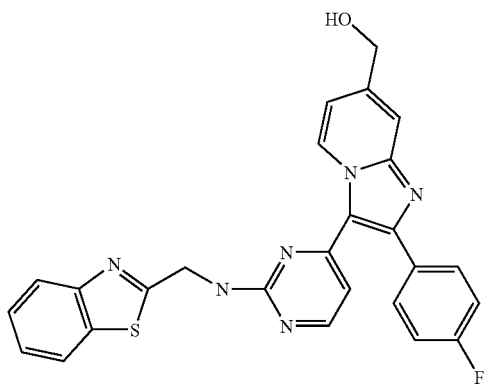
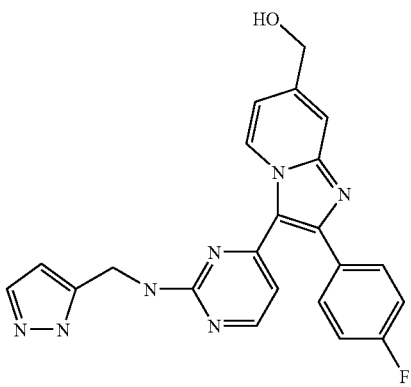
or a pharmaceutically acceptable salt thereof.
22. A compound represented by
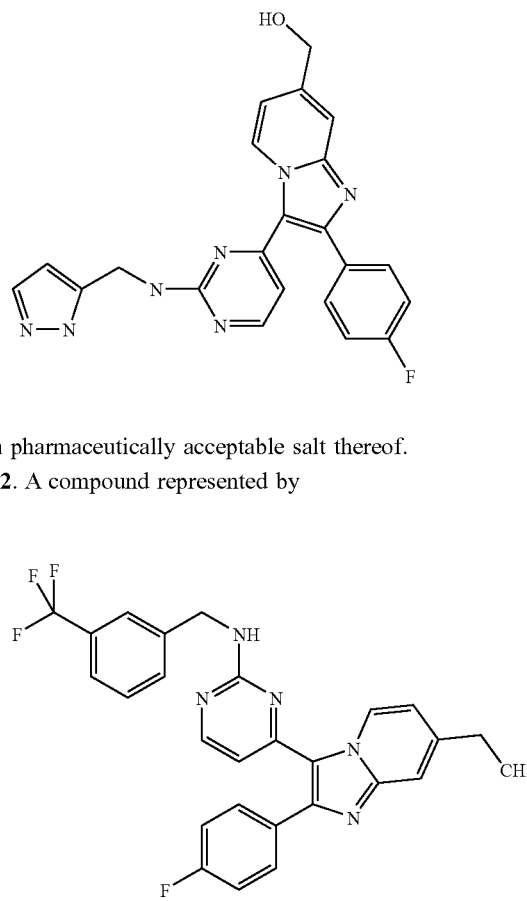
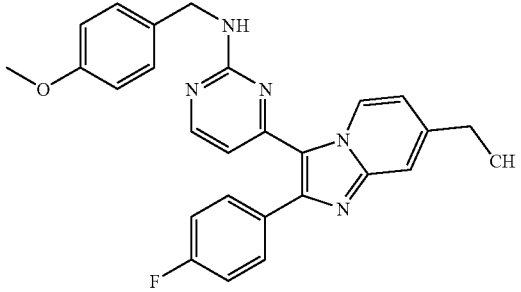
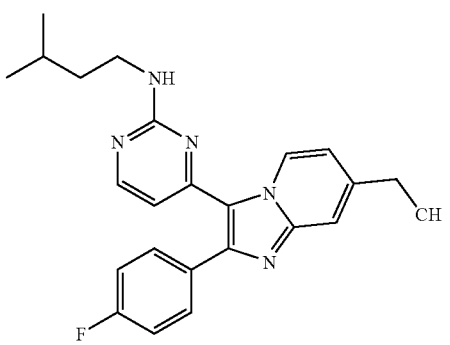

451
-continued
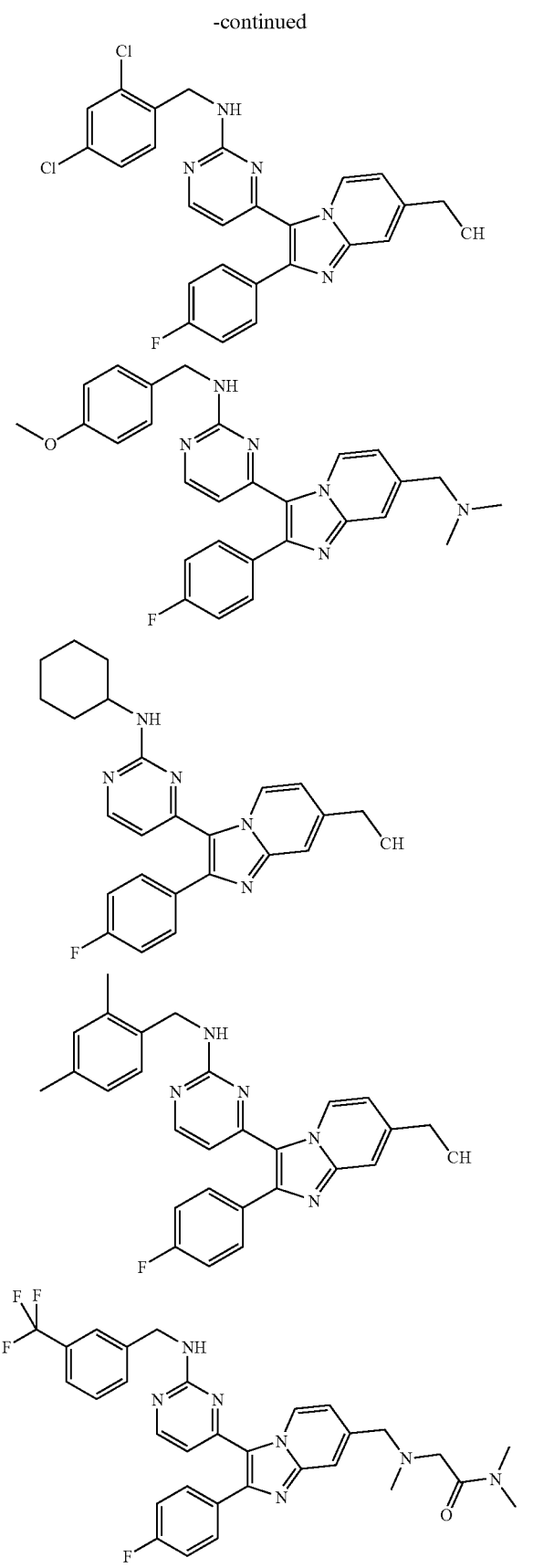
452
-continued
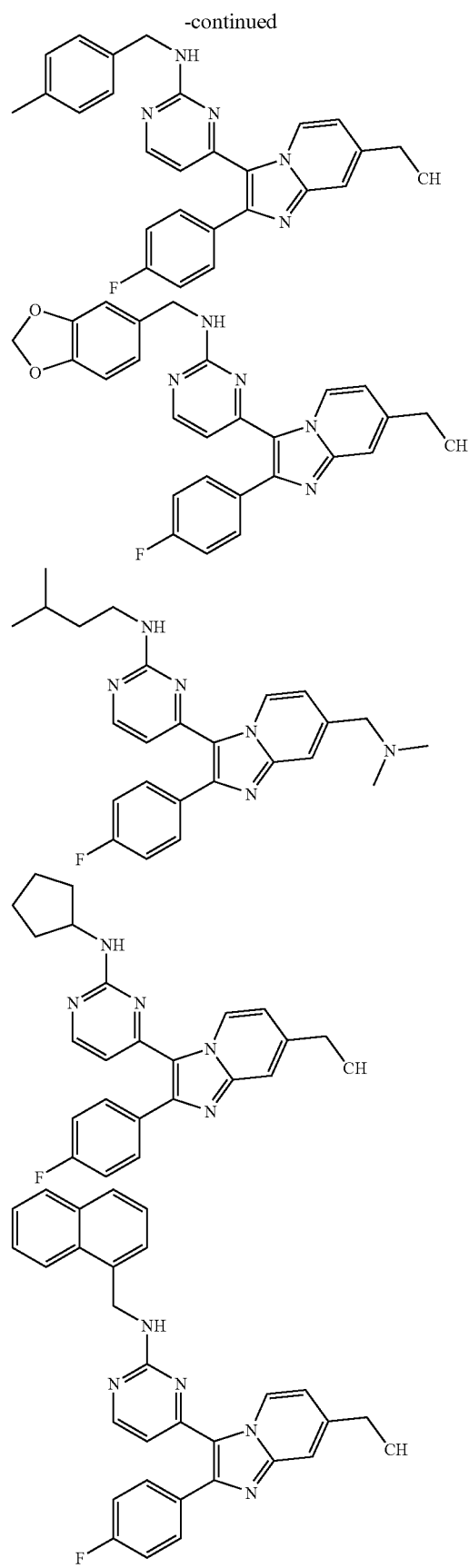

453
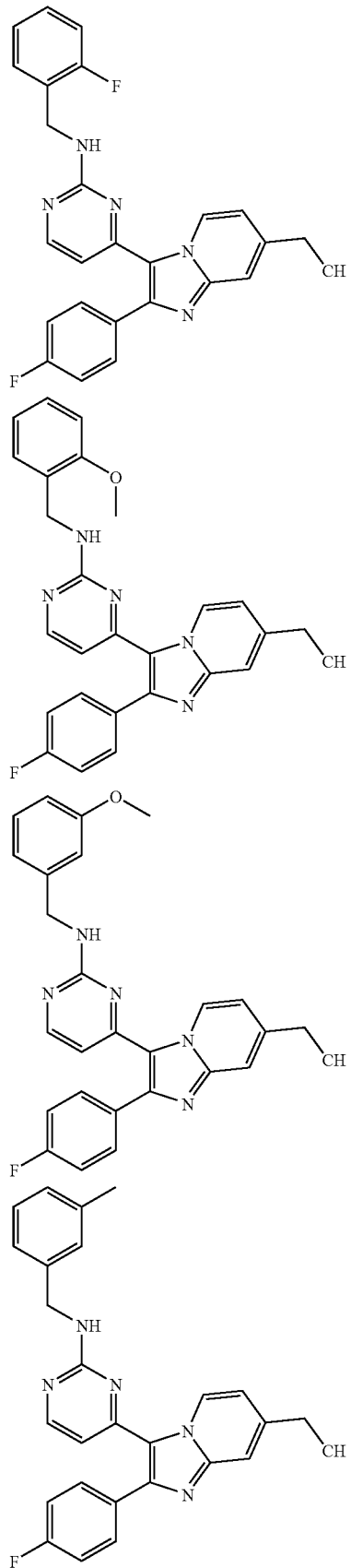
454
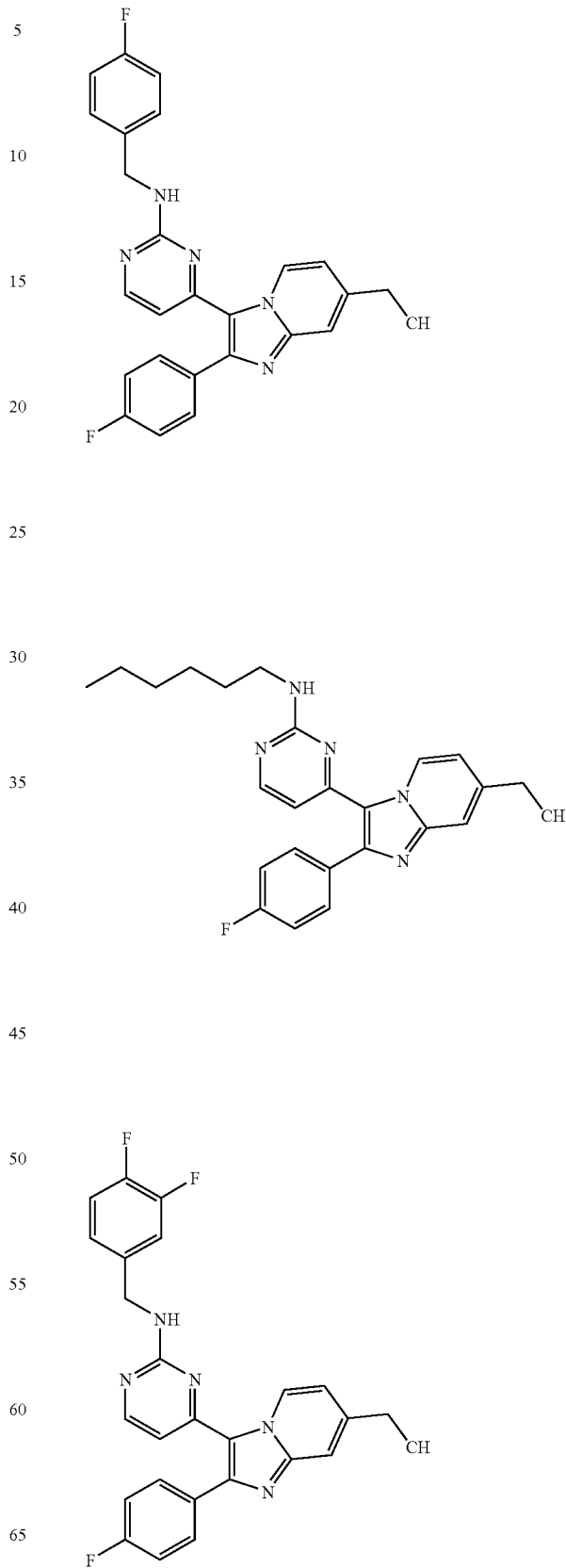

-continued
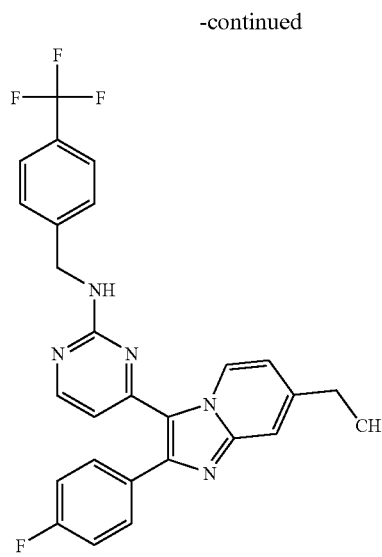
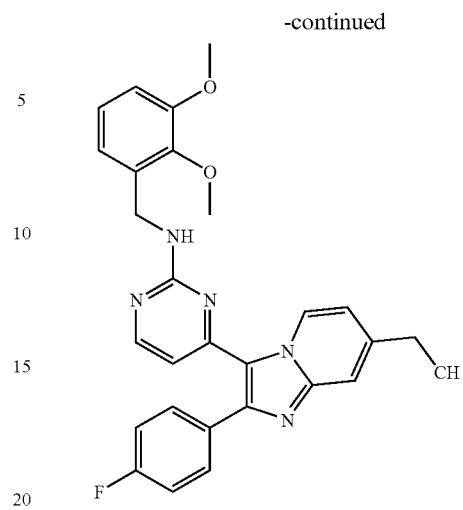
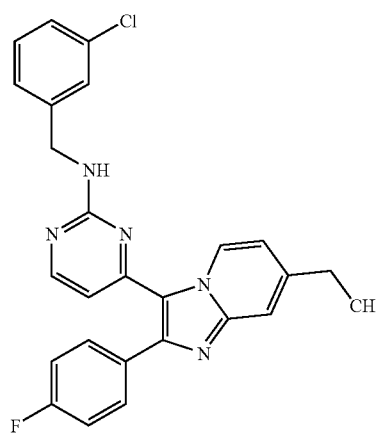
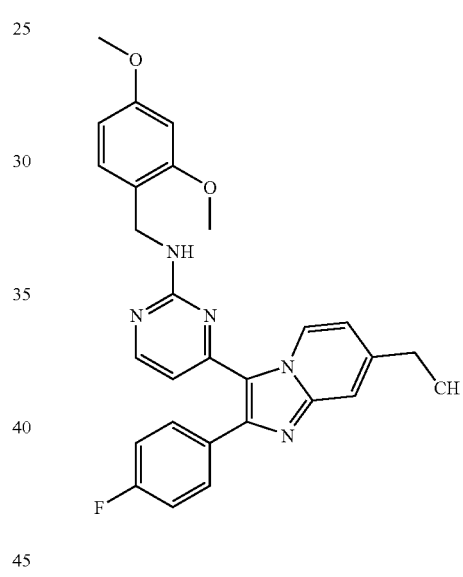
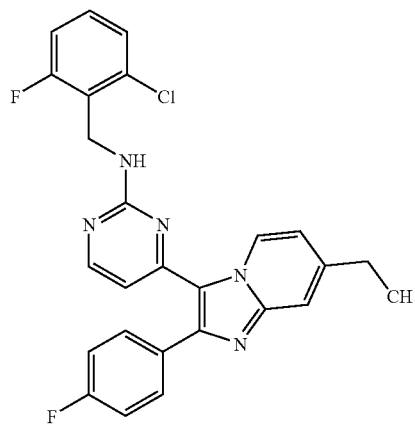
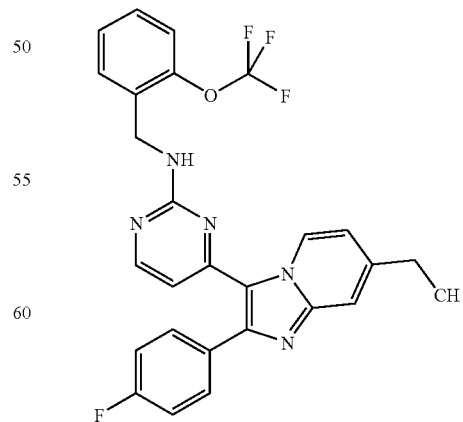

457 458
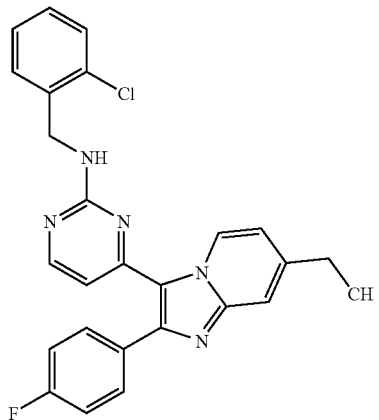
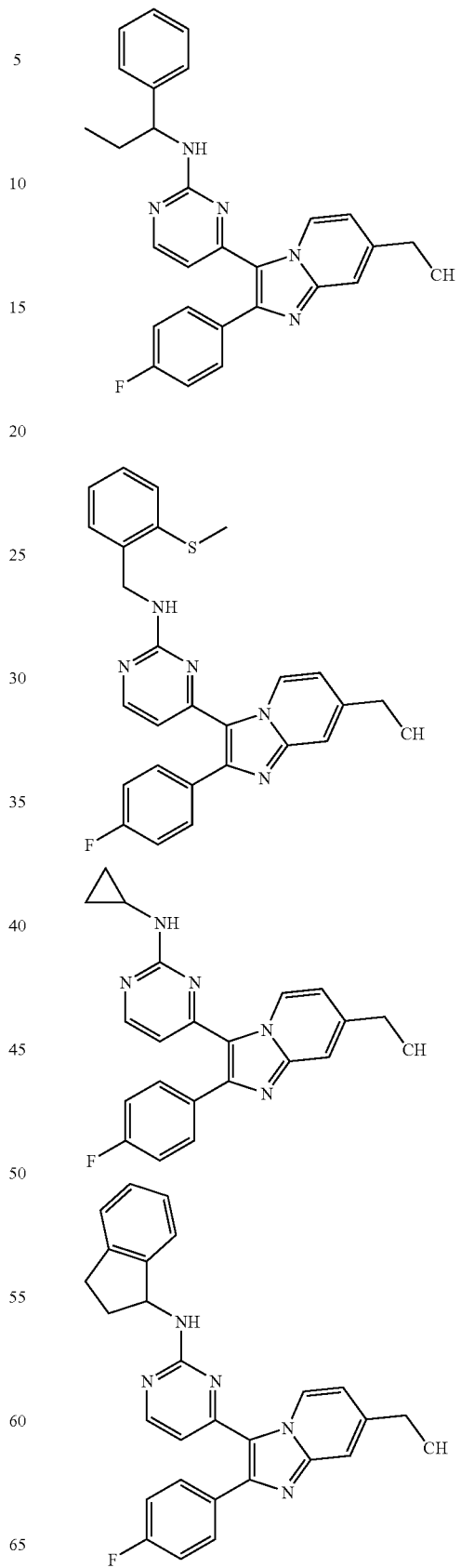

459
-continued
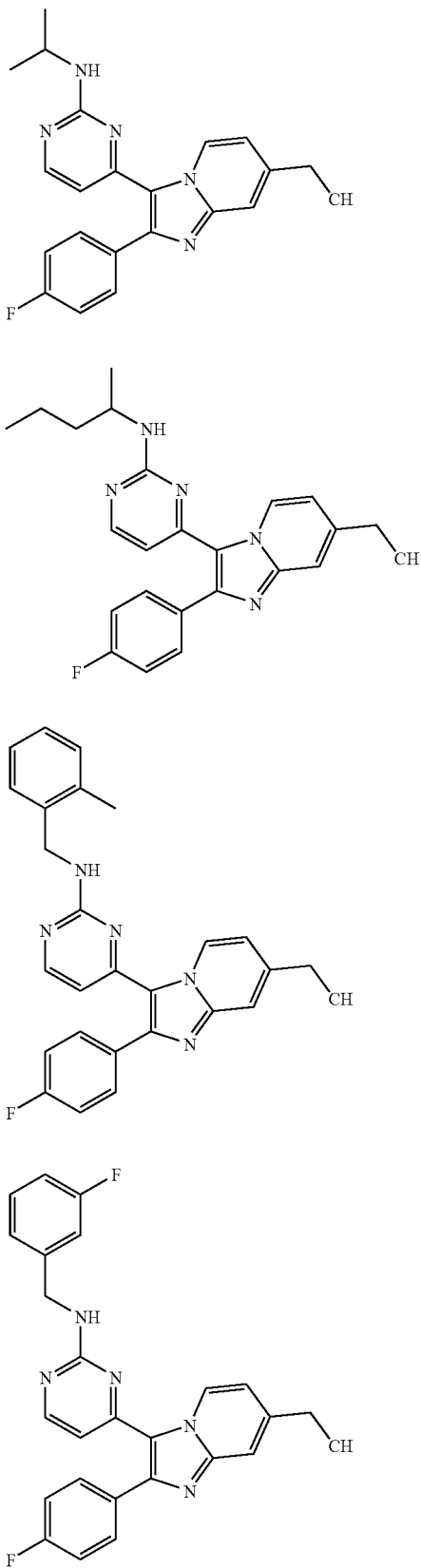
460
-continued
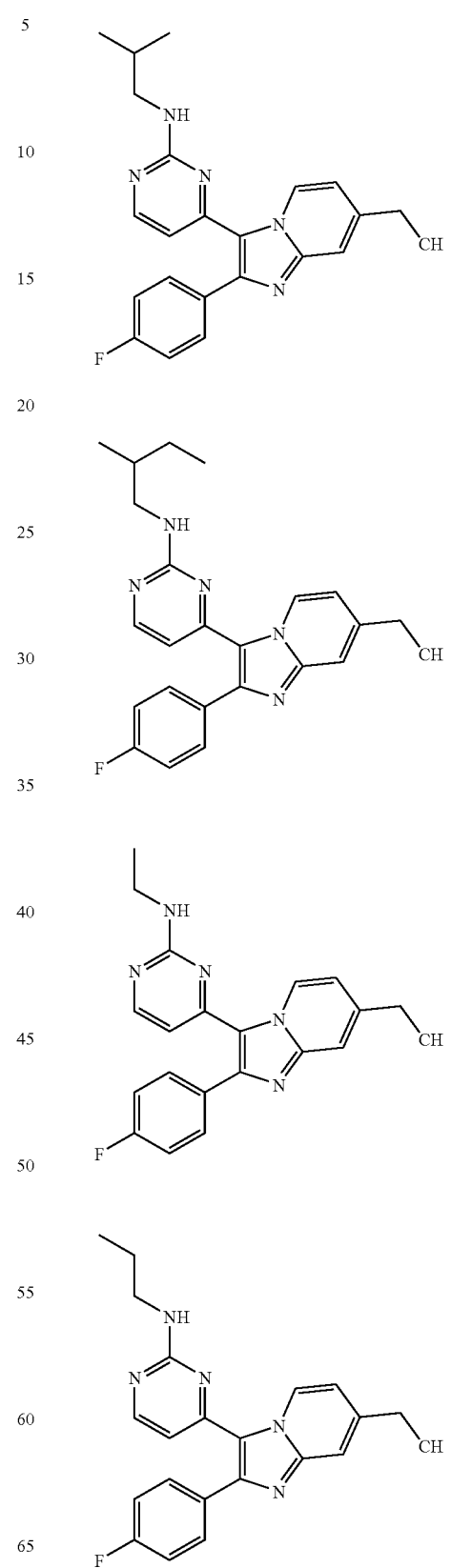

461
-continued
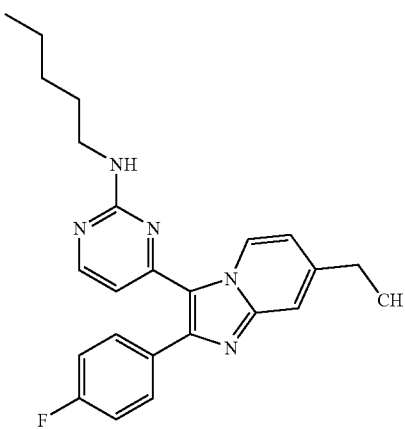
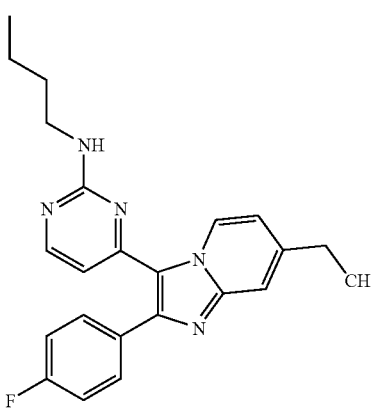
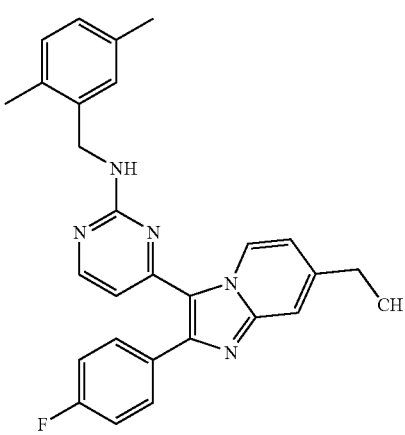
462
-continued
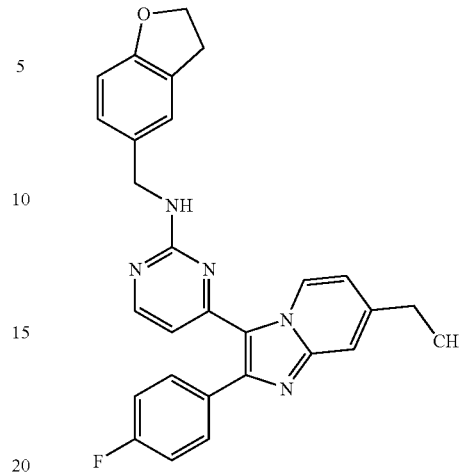
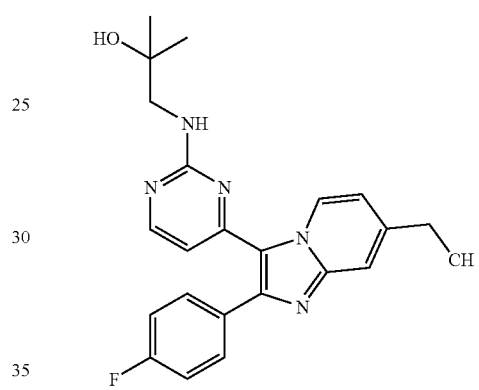
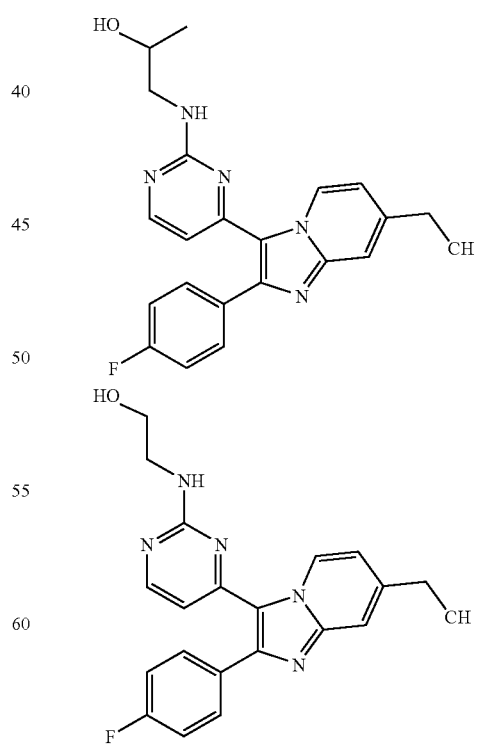

463
-continued
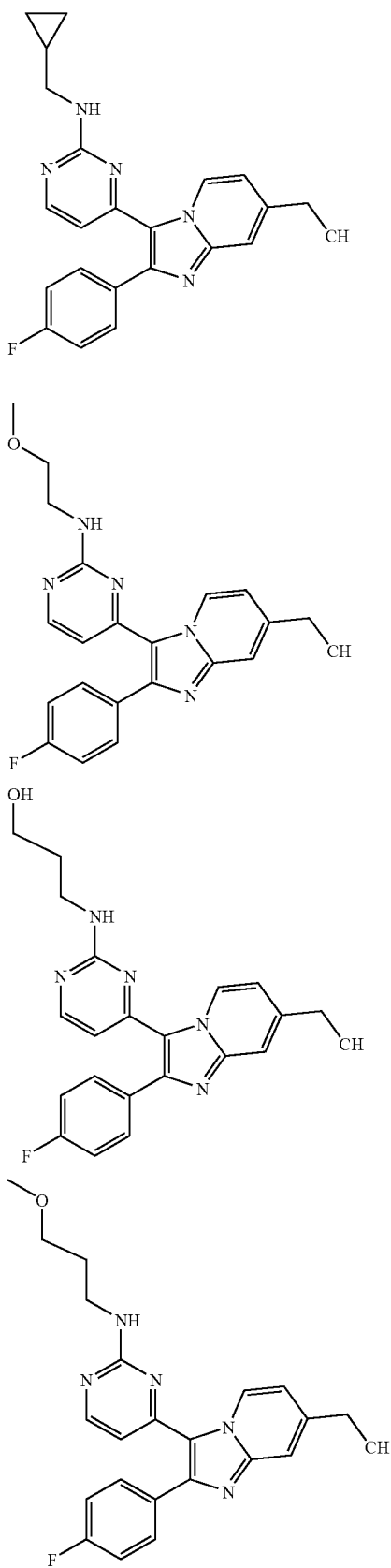
464
-continued
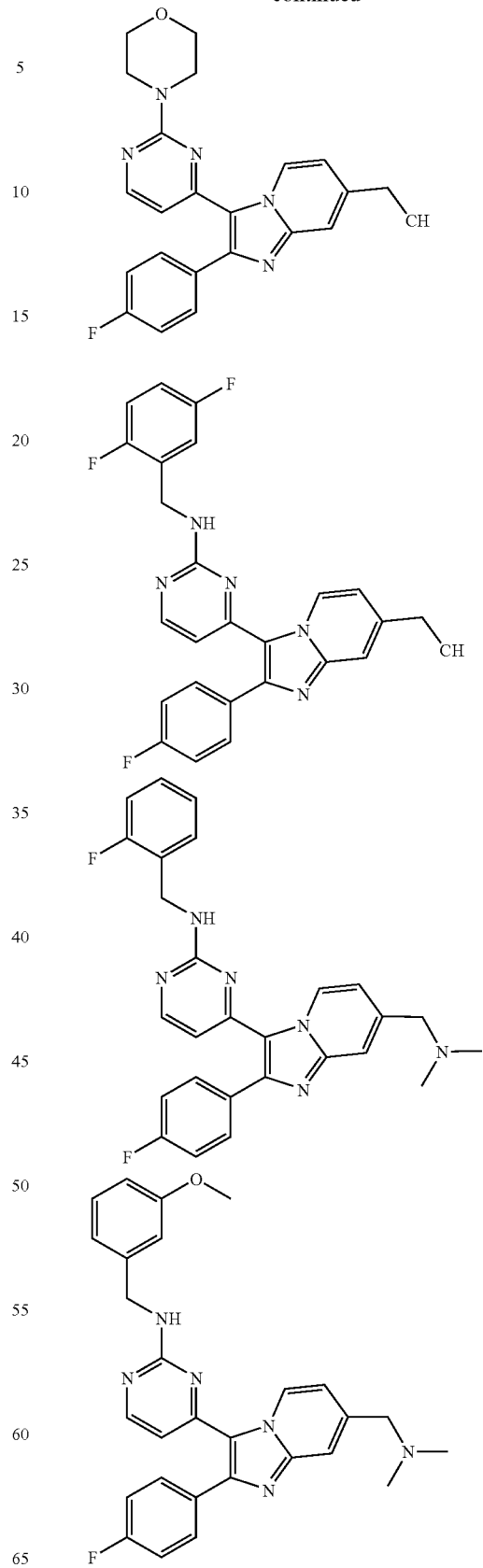

465
466
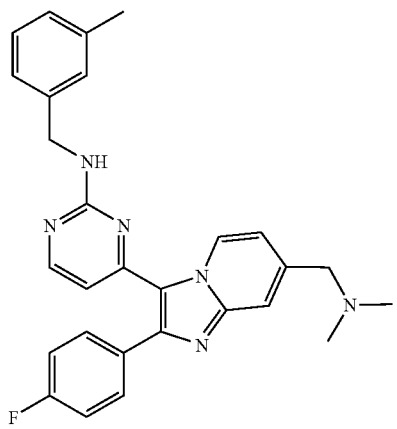
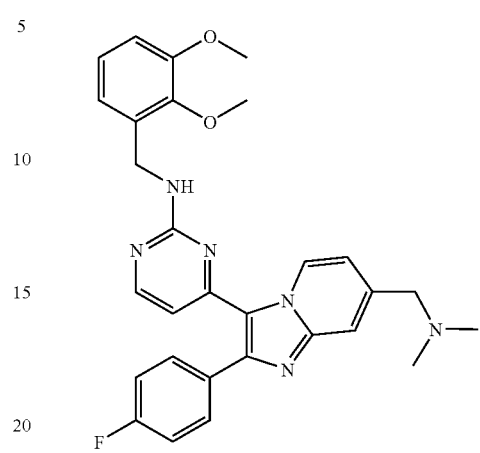
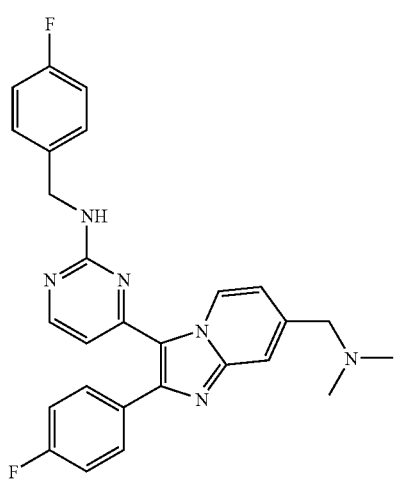
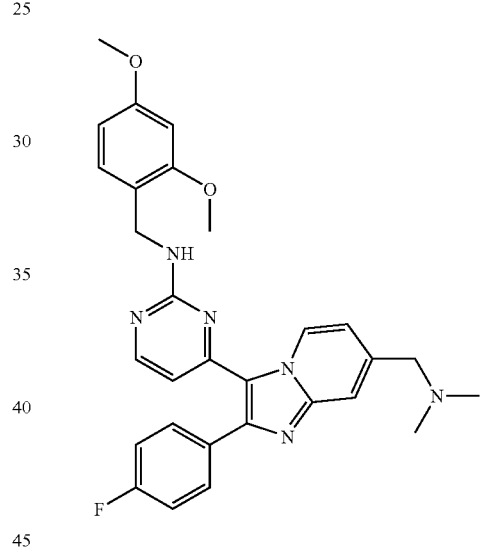
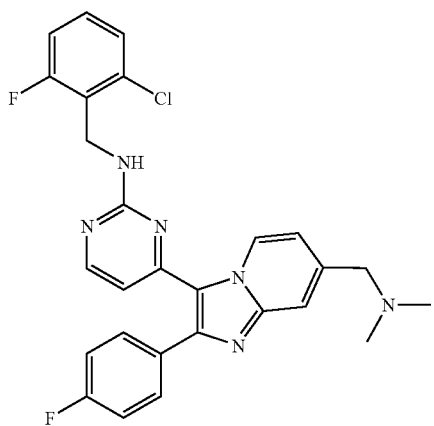
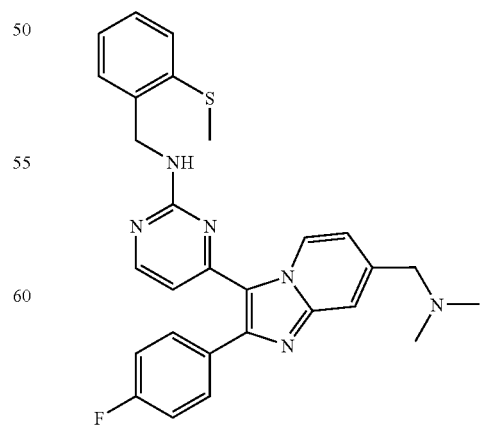

467
-continued
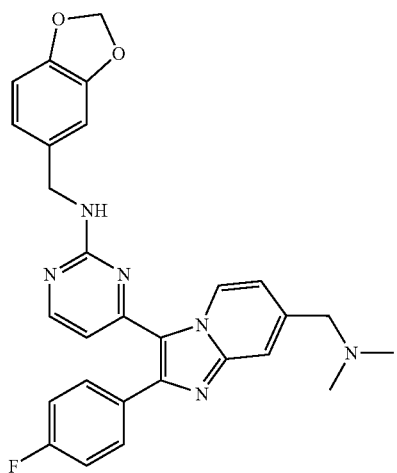
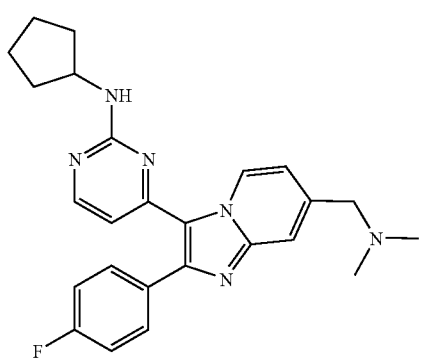
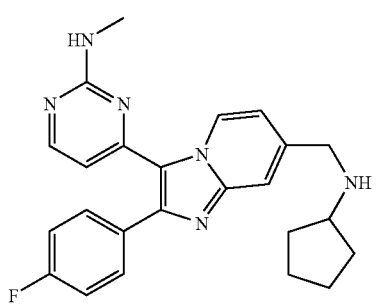
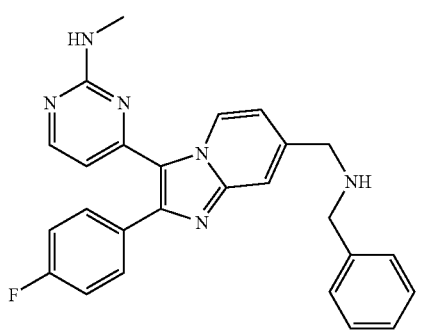
468
-continued
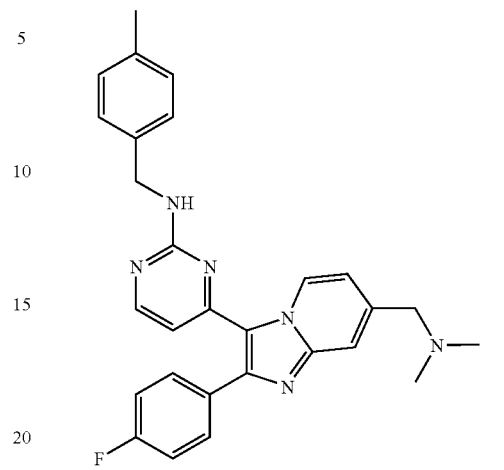
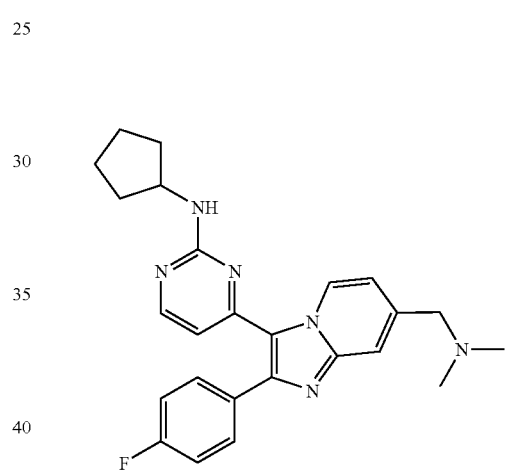
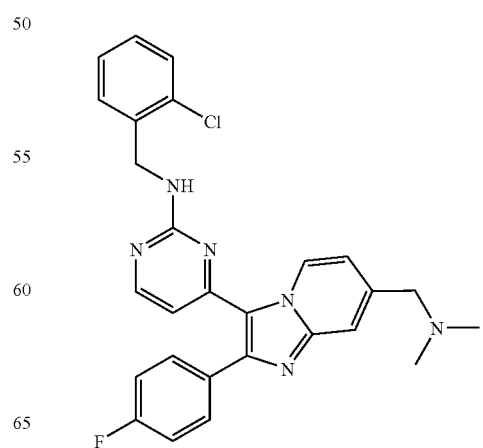

469
-continued
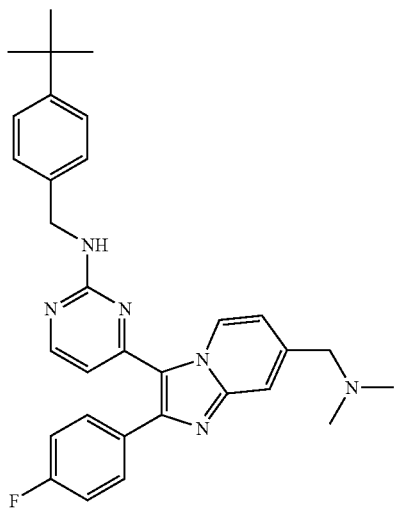
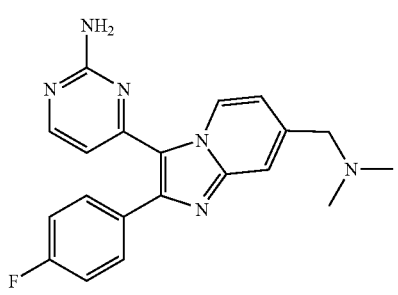
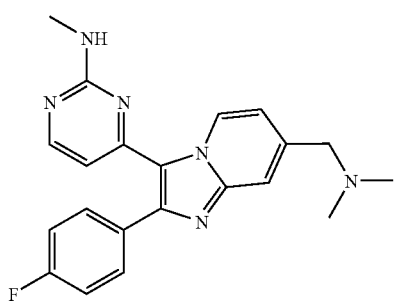
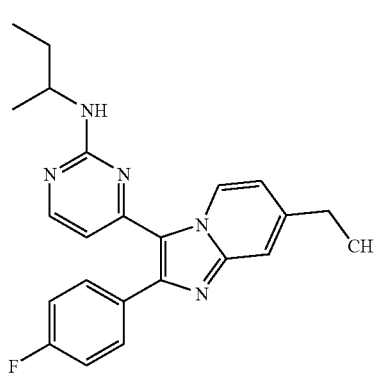
470
-continued
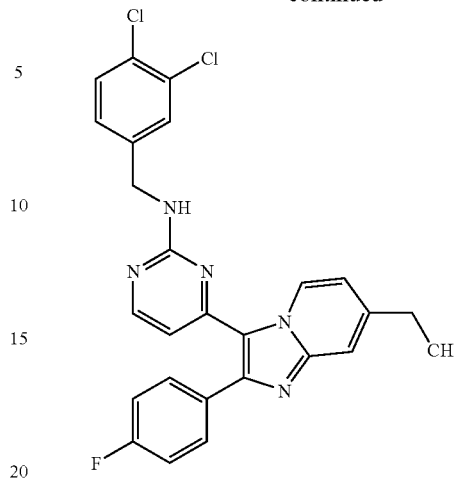
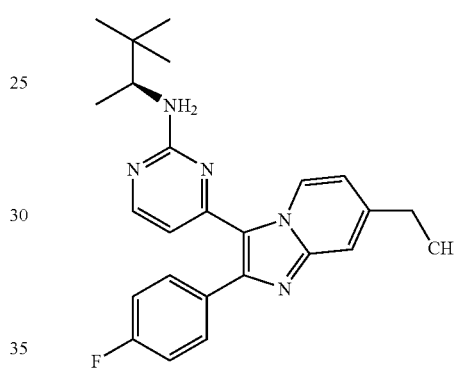
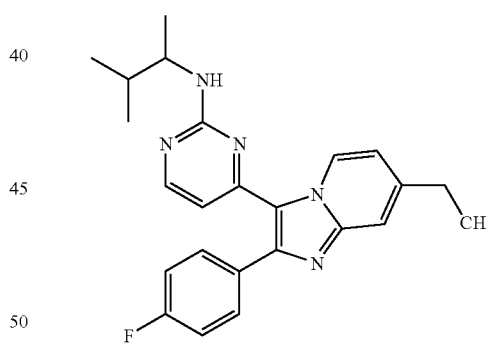
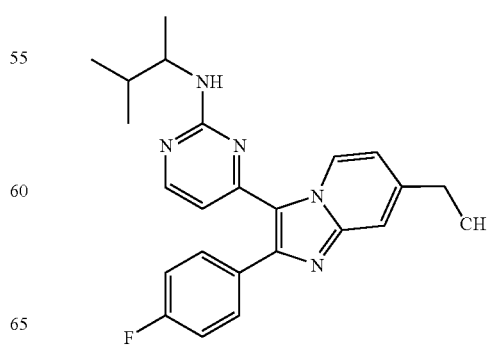

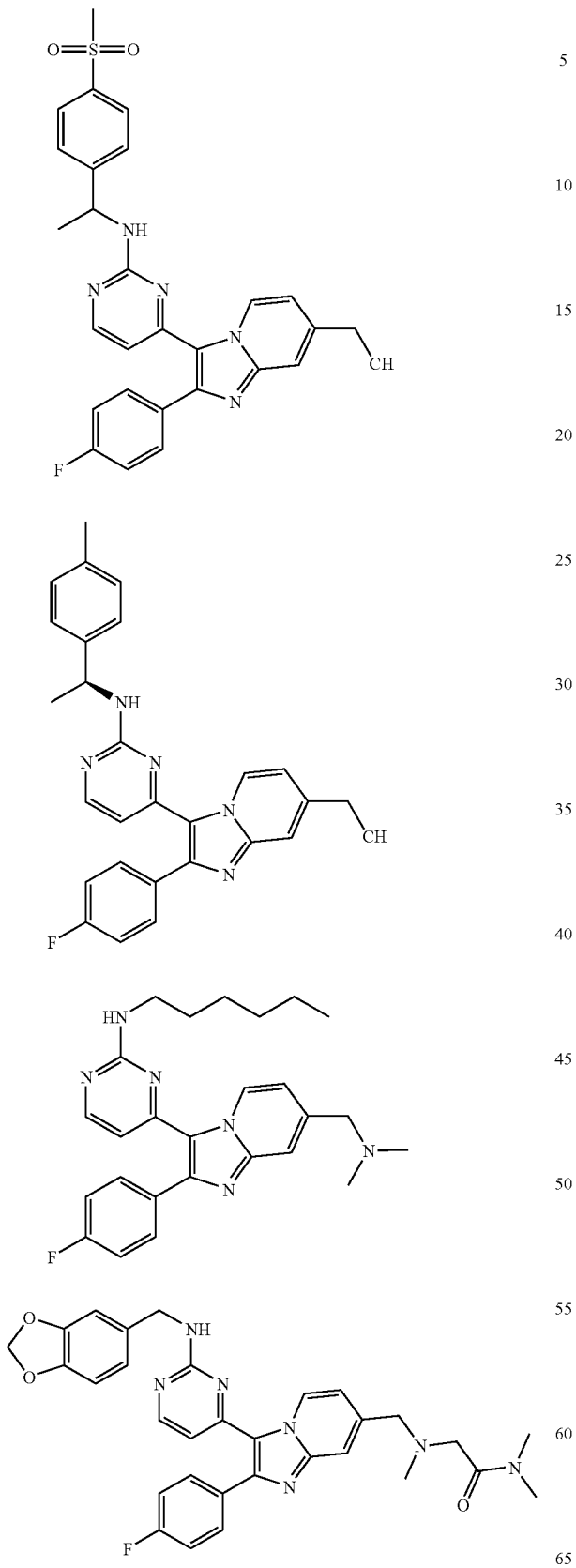

-continued
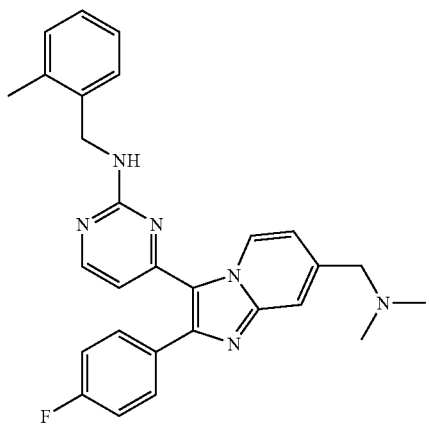
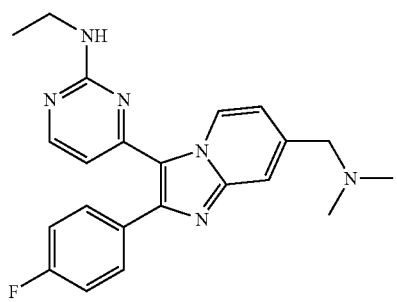
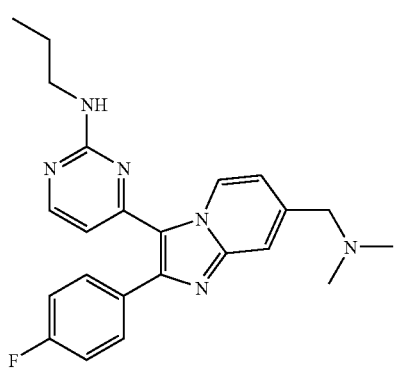
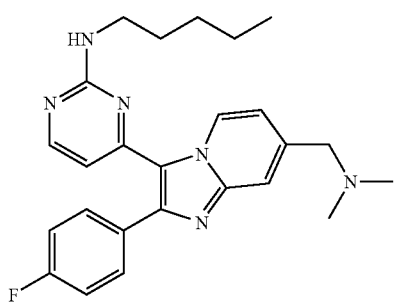
-continued
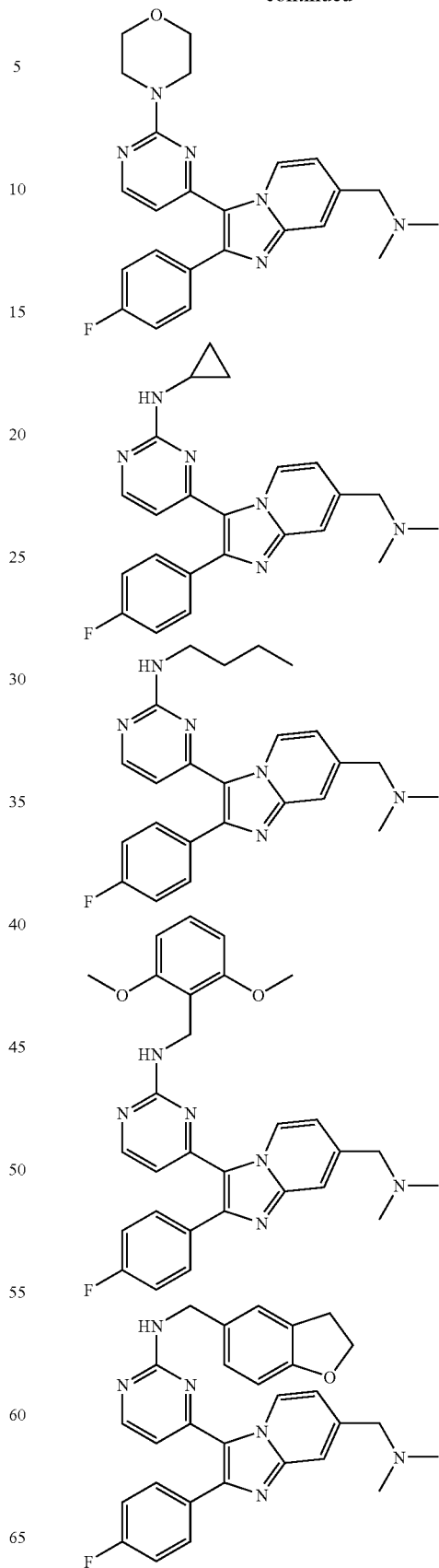

475
-continued
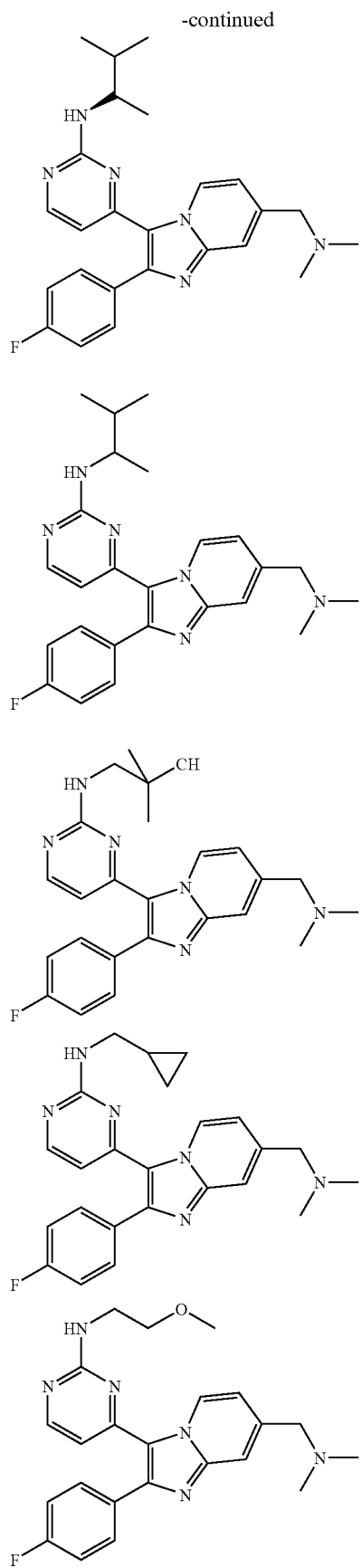
476
-continued
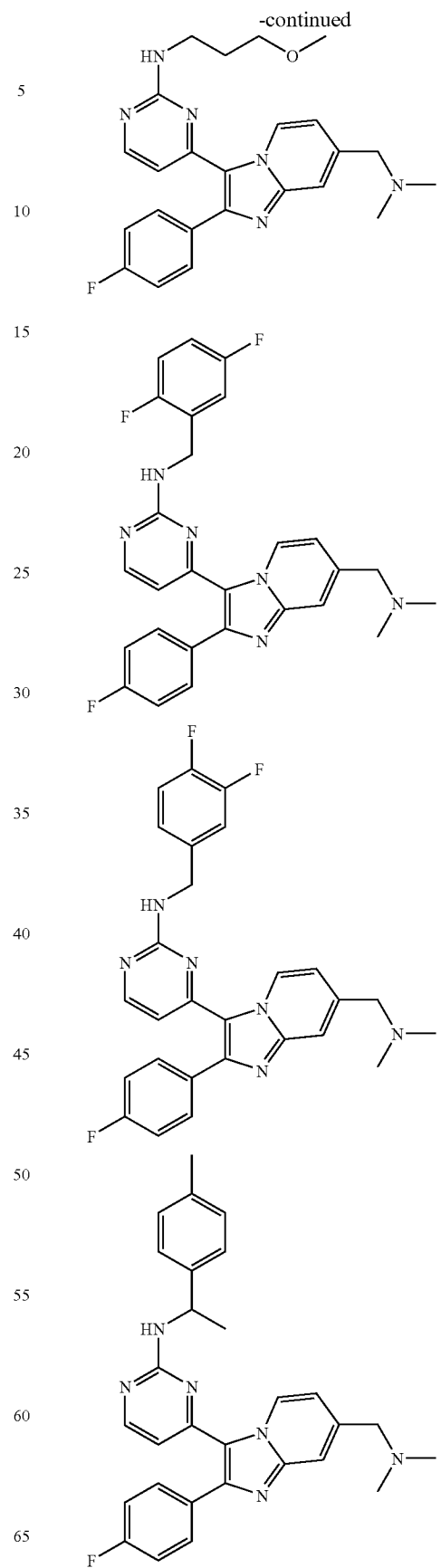

477
-continued
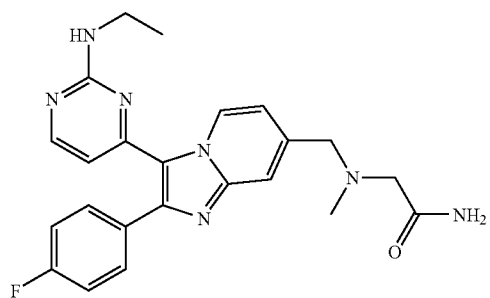
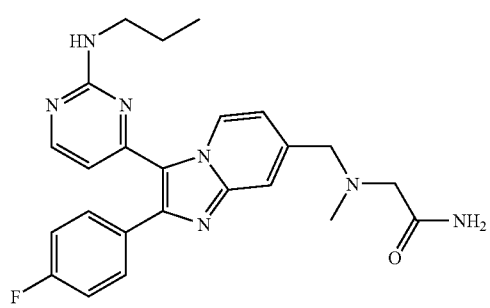
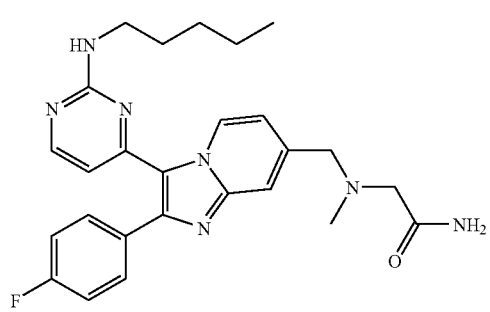
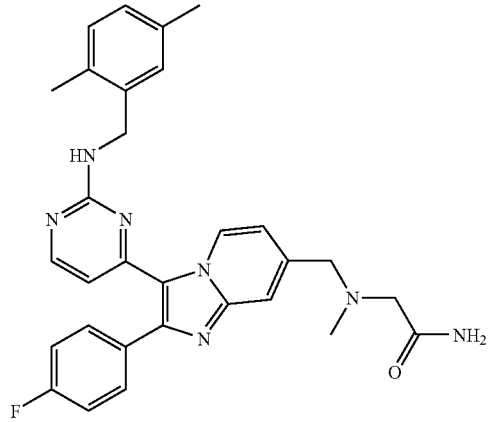
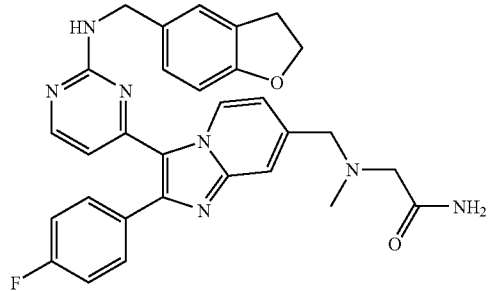
478
-continued
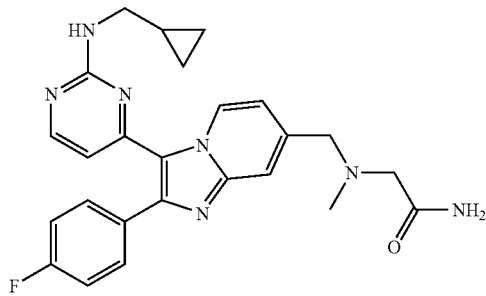
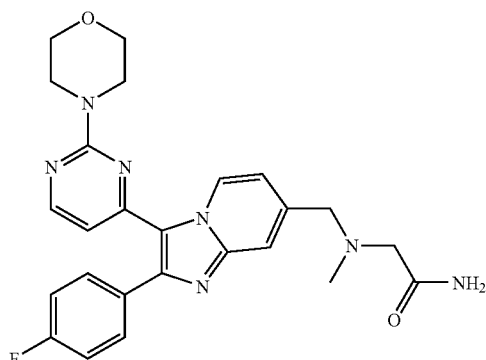
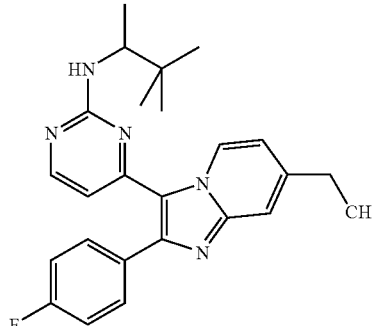
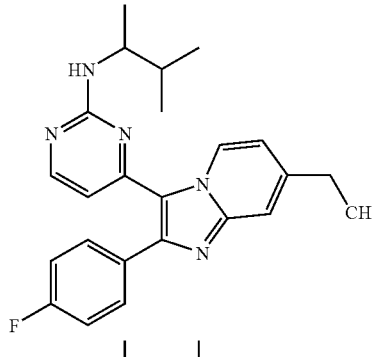
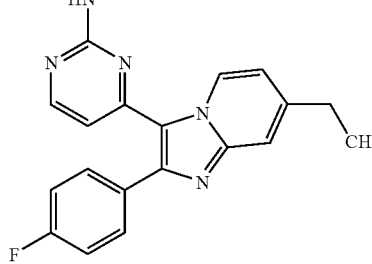

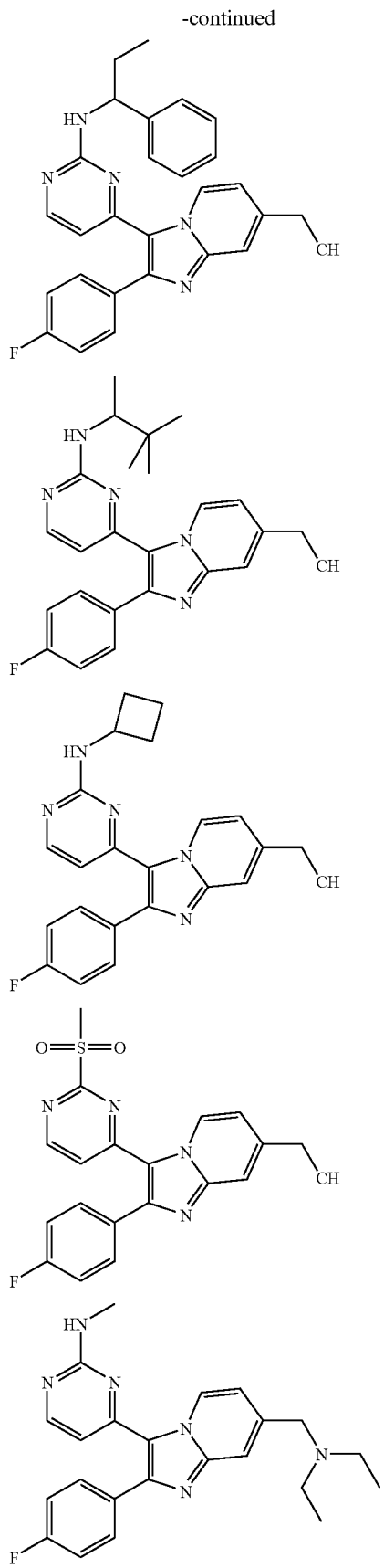
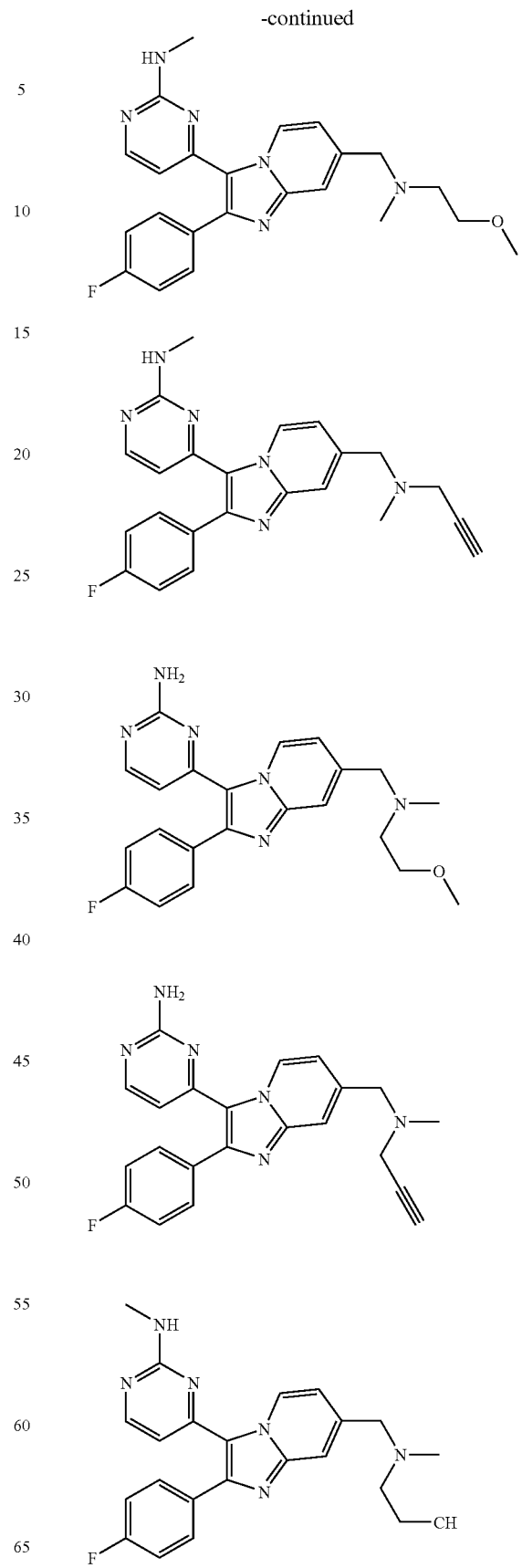

481
-continued
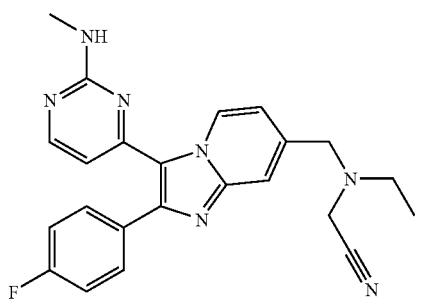
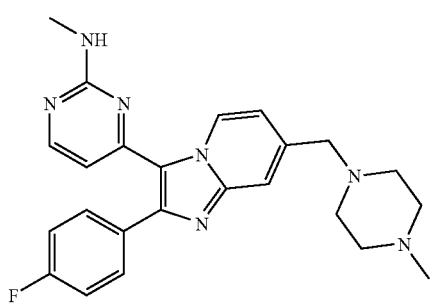
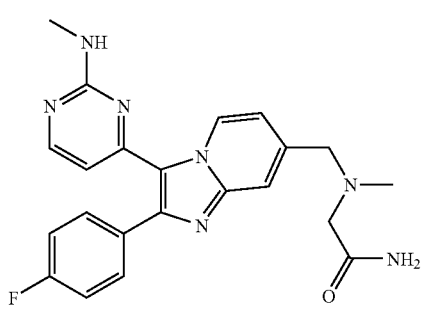
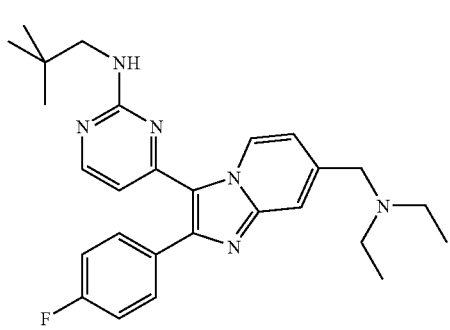
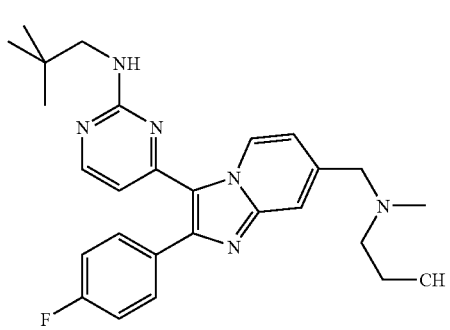
482
-continued
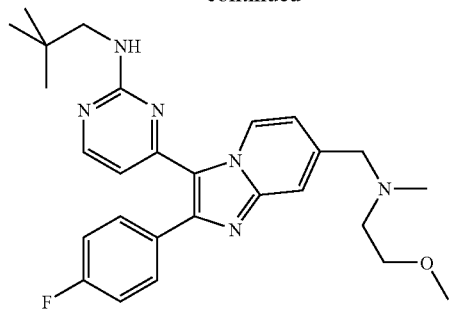
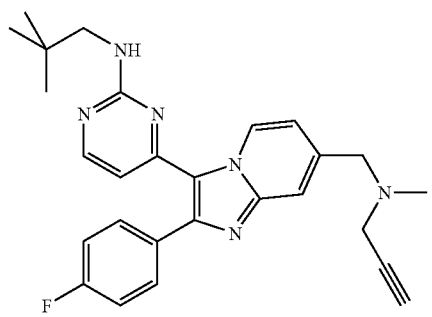
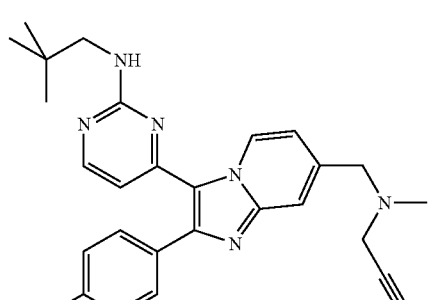
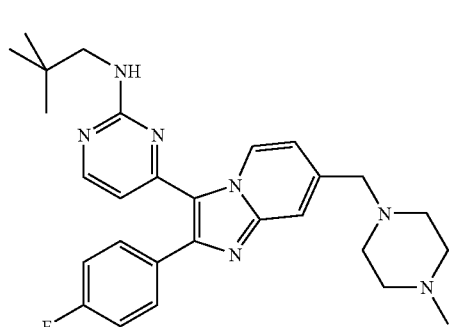
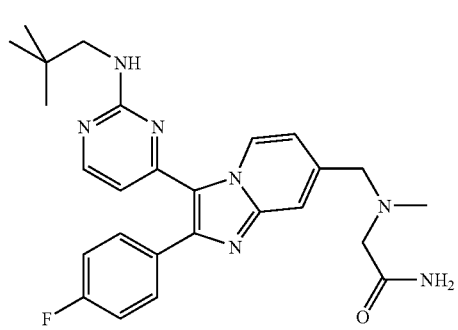

483
-continued
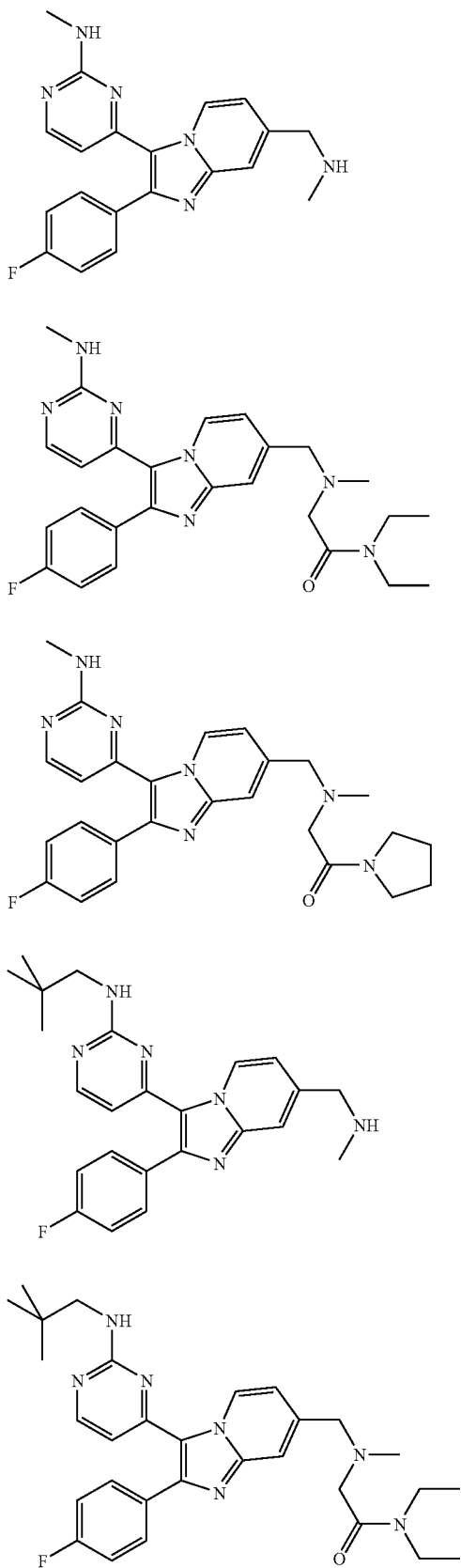
484
-continued
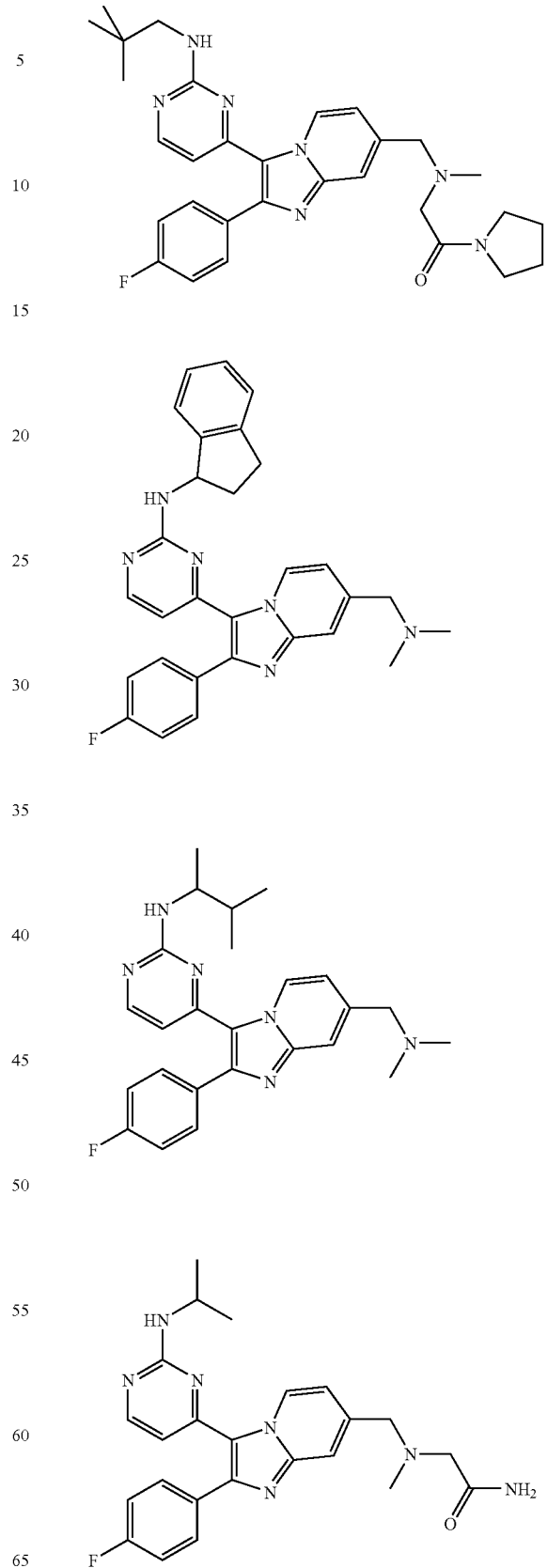

485
-continued
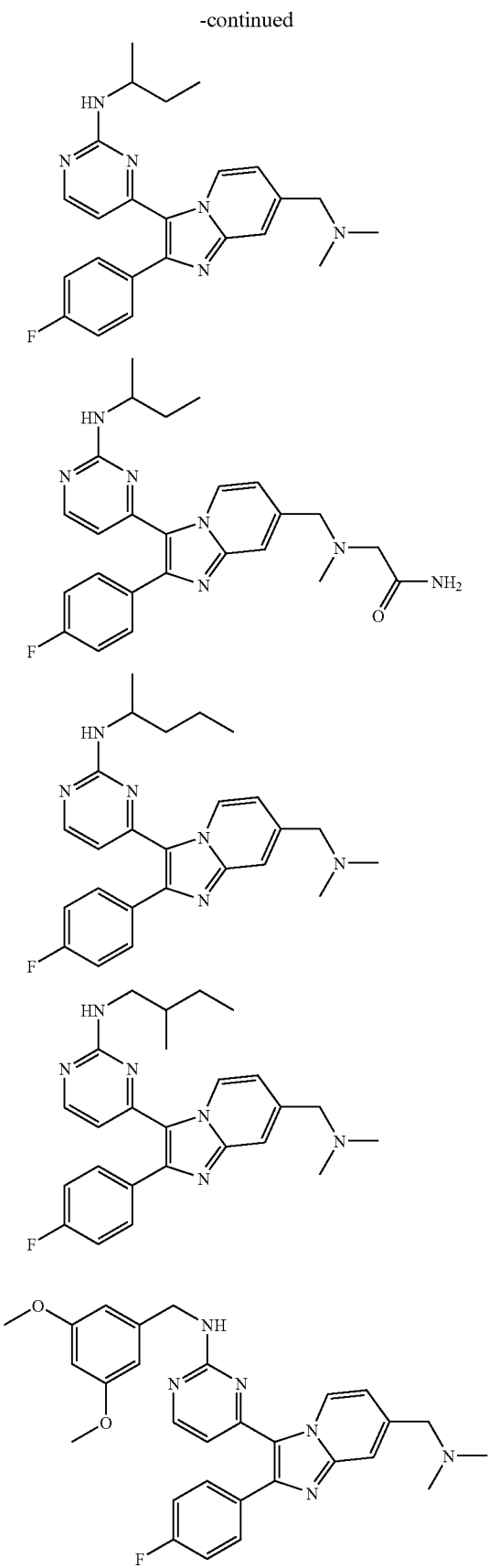
486
-continued
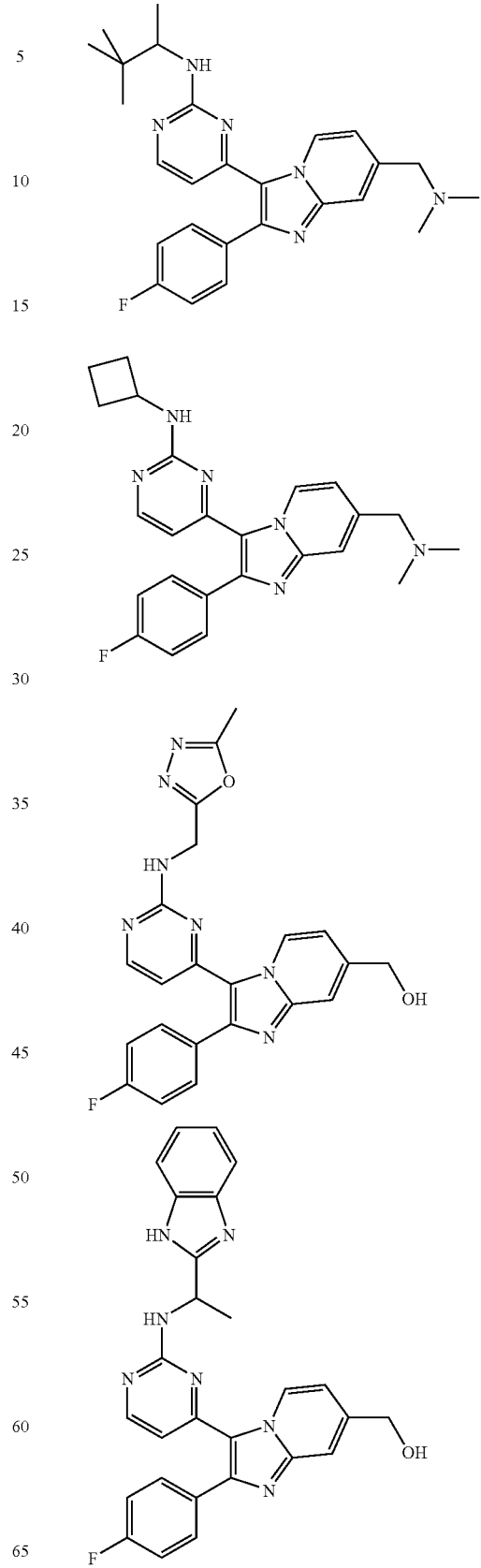

487
-continued
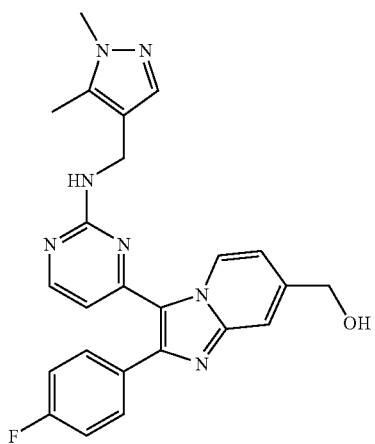
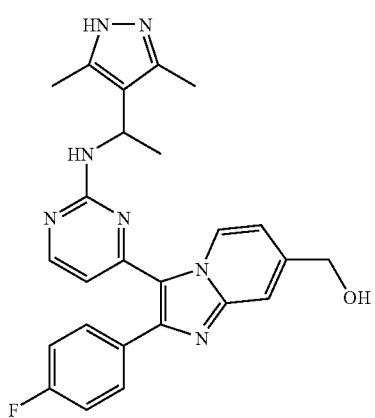
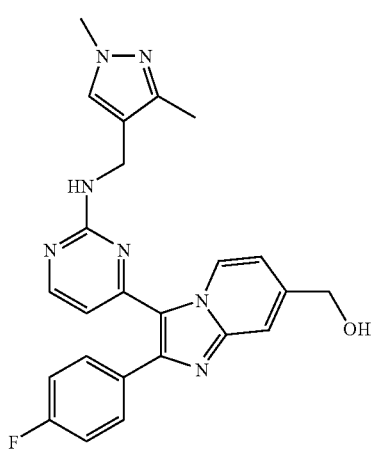
488
-continued
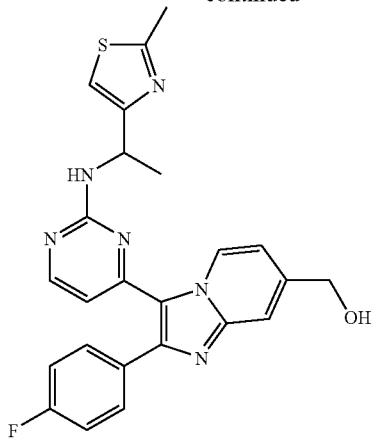
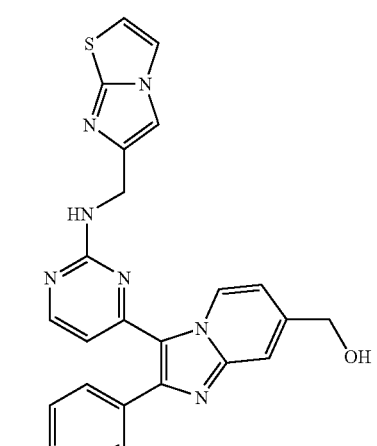
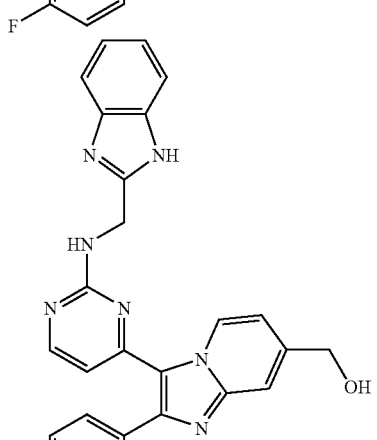
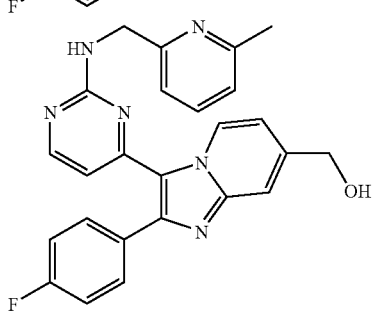

489
-continued
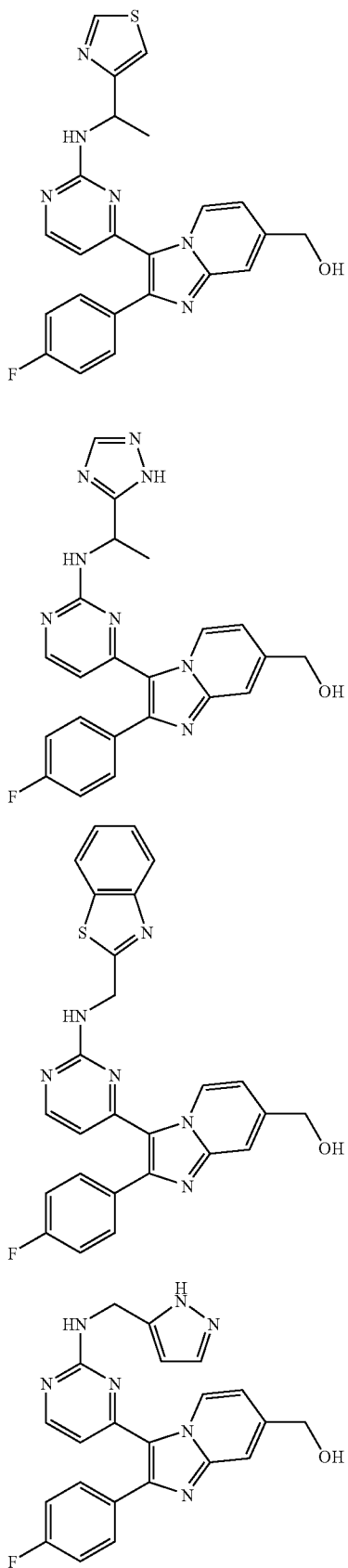
490
-continued
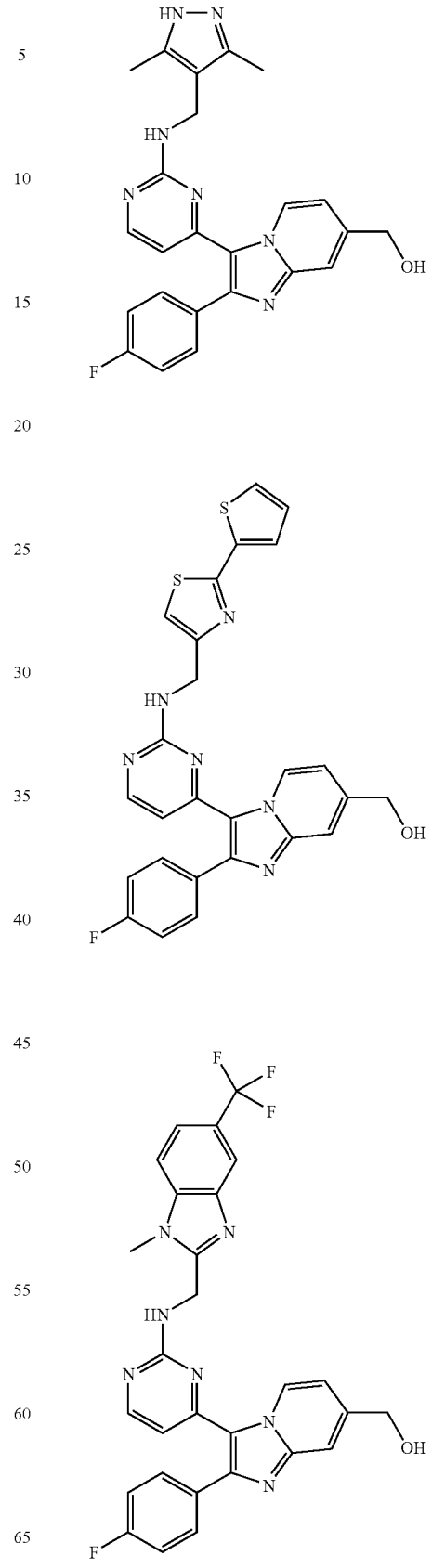

491
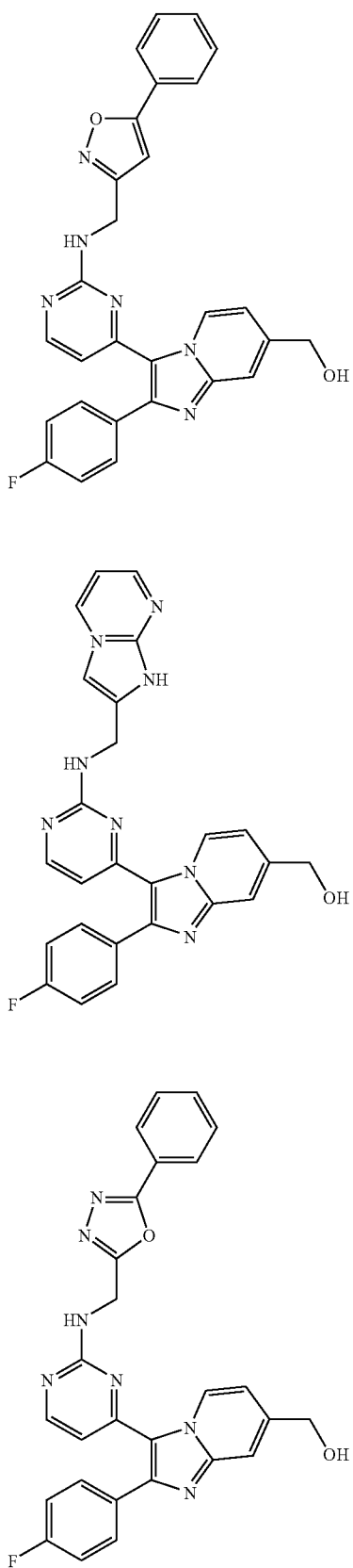
492
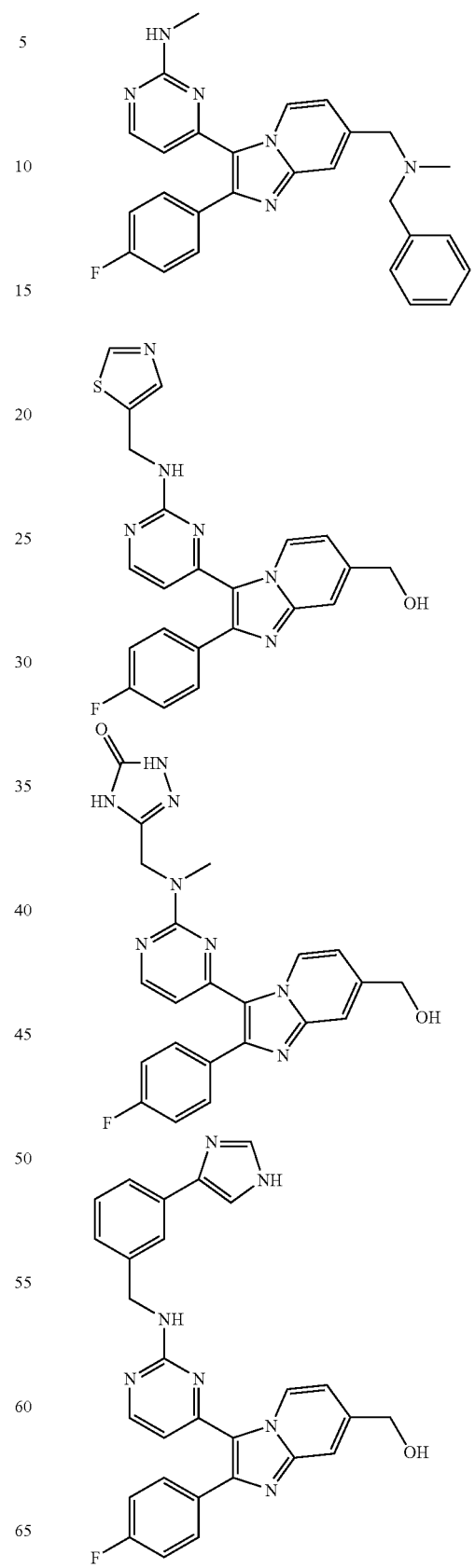

493
-continued
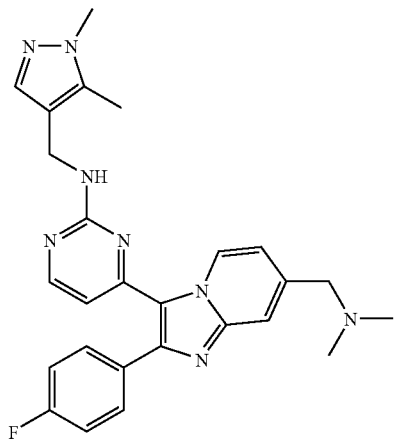
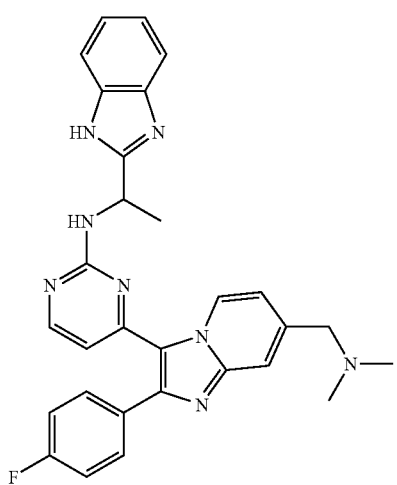
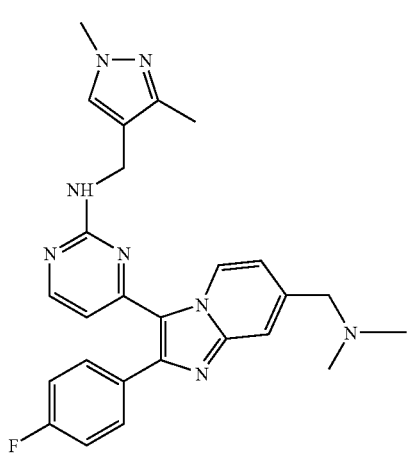
494
-continued
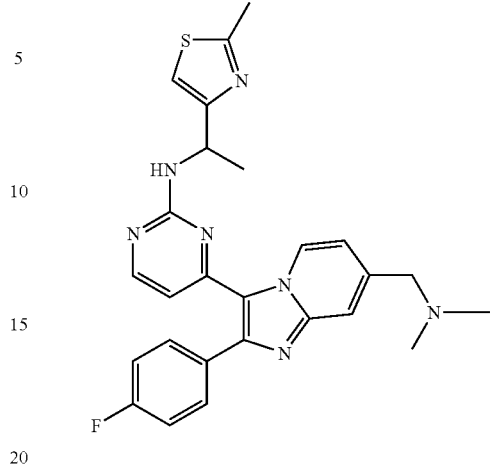
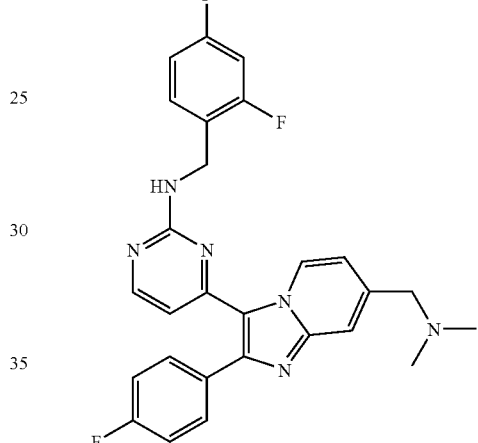
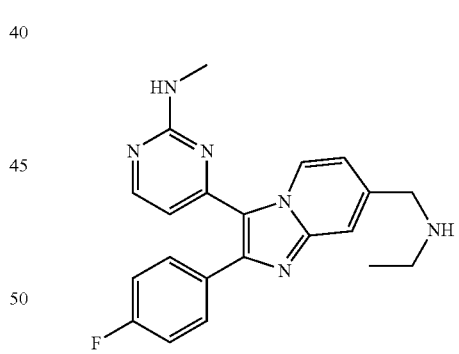
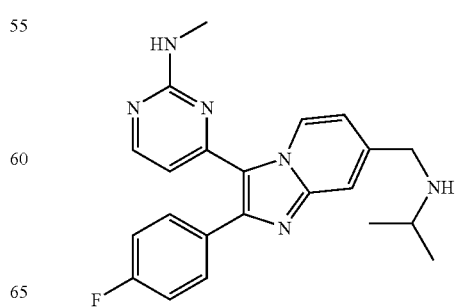

-continued
495
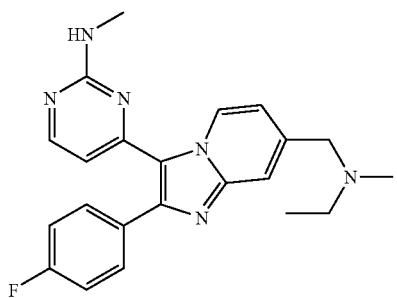
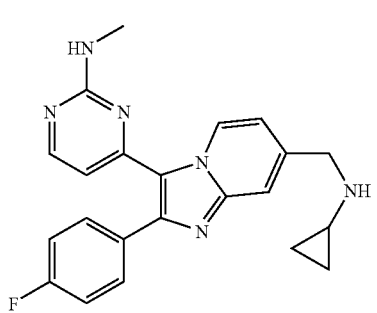
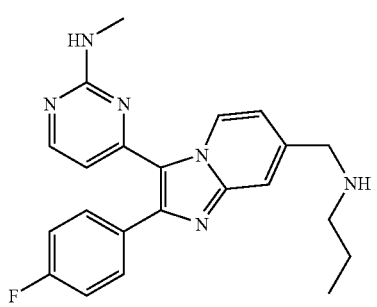
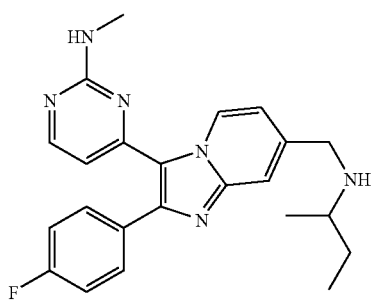
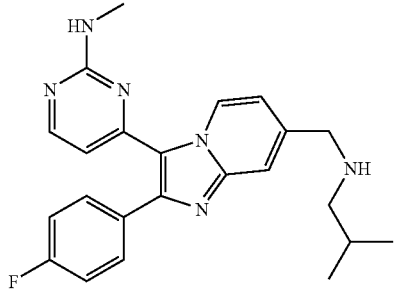
496
-continued
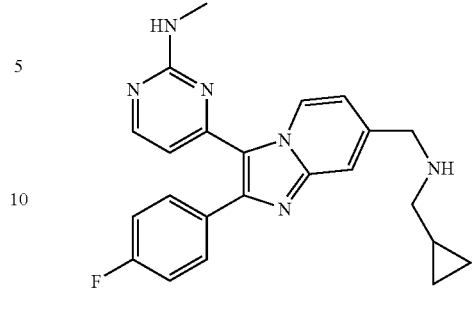
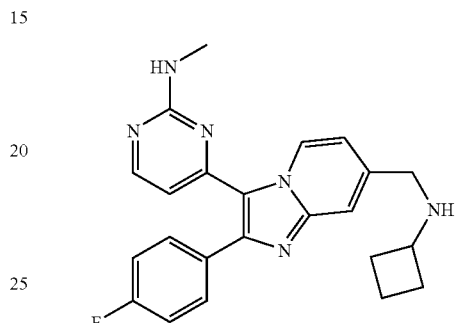
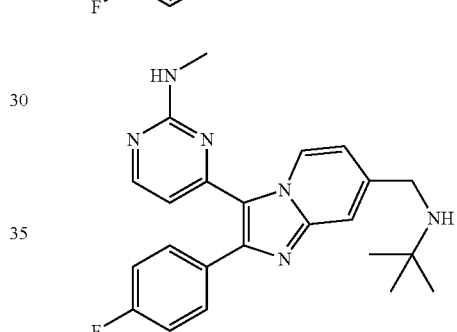
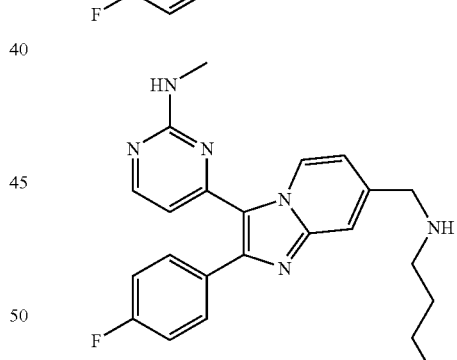
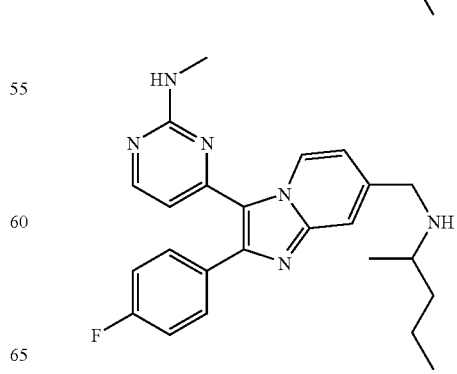

497
-continued
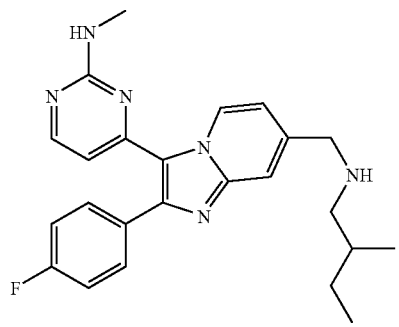
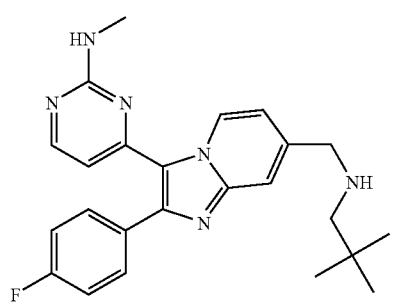
or a pharmaceutically acceptable salt thereof.
23. A compound represented by
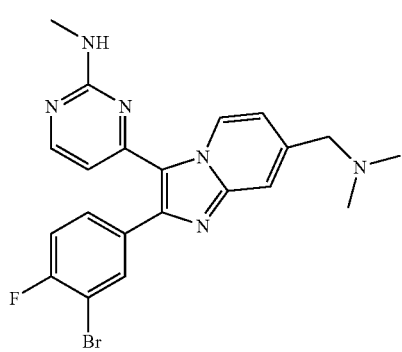
498
-continued
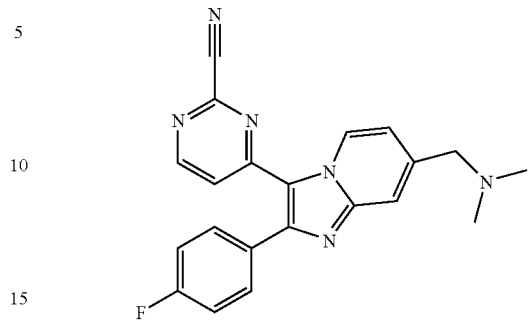
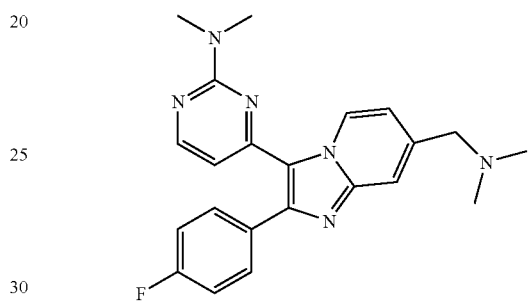
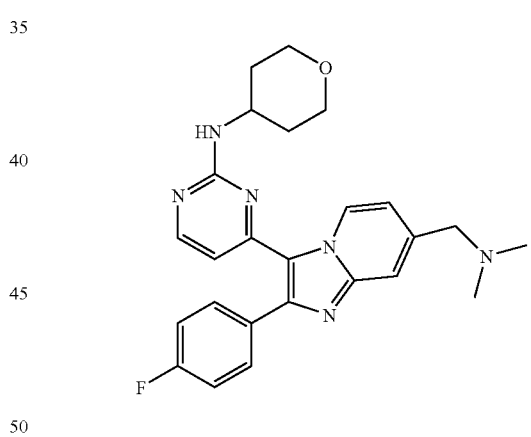
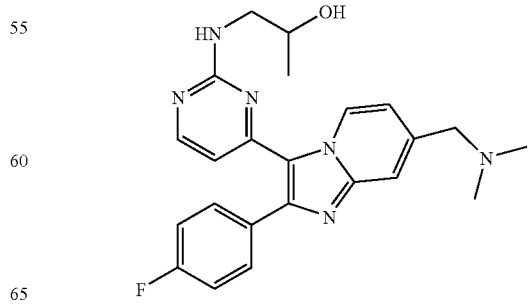

| 499 | 500 |
|---|---|
| -continued | -continued |
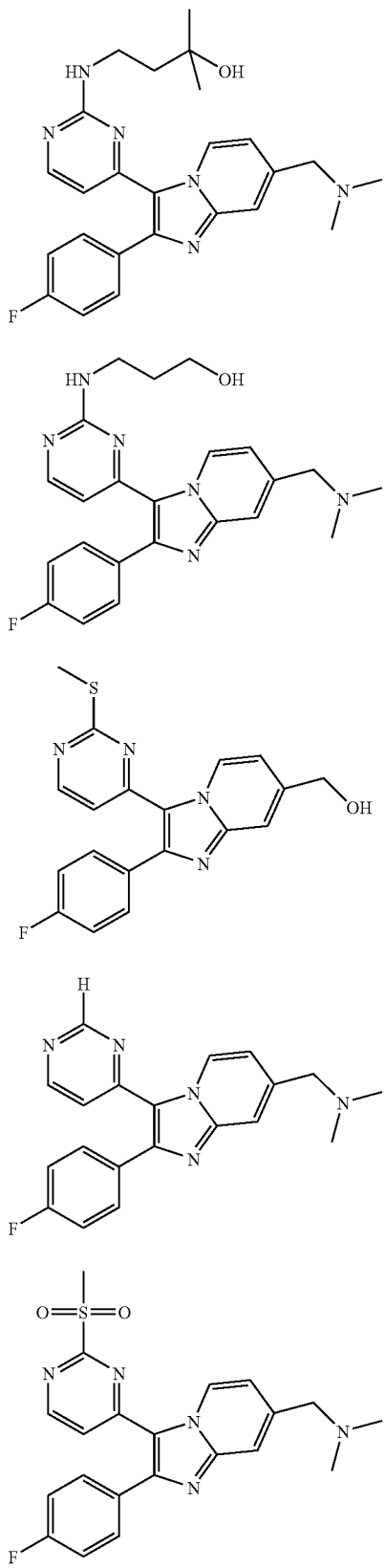
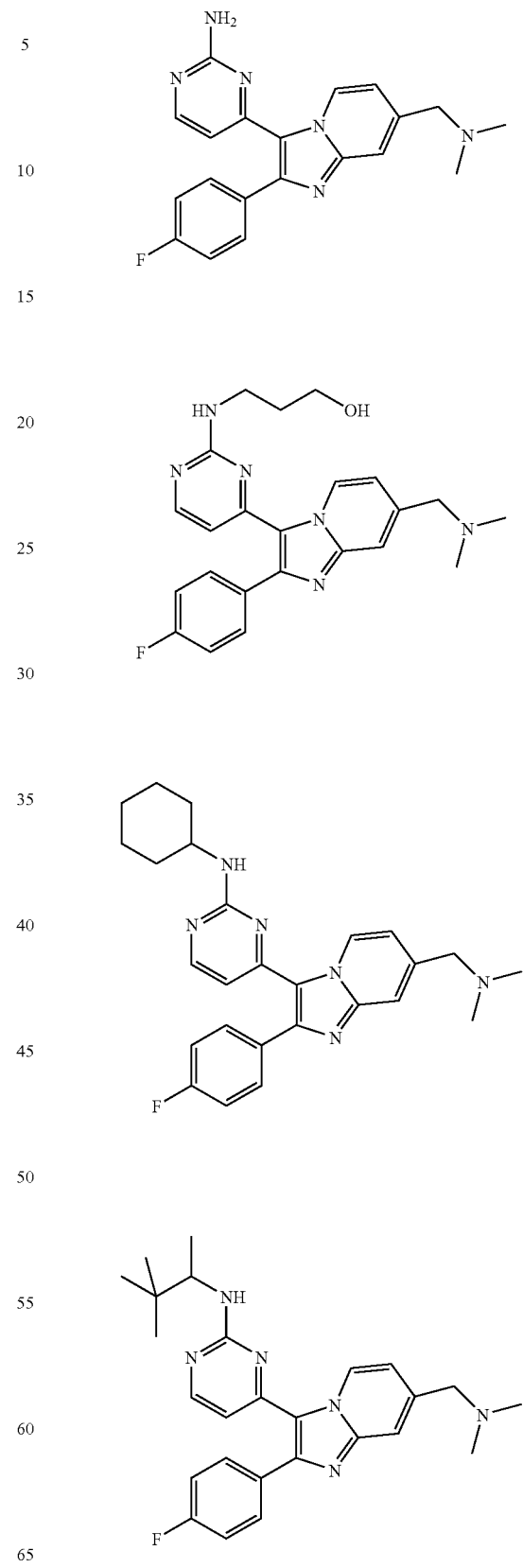

| 501 | 502 |
|---|---|
| -continued | -continued |
| 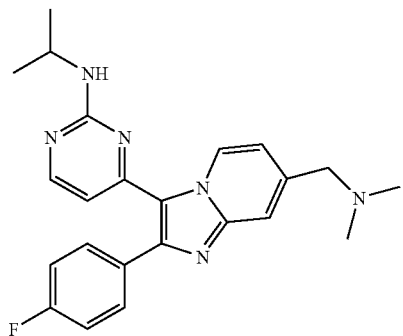 | 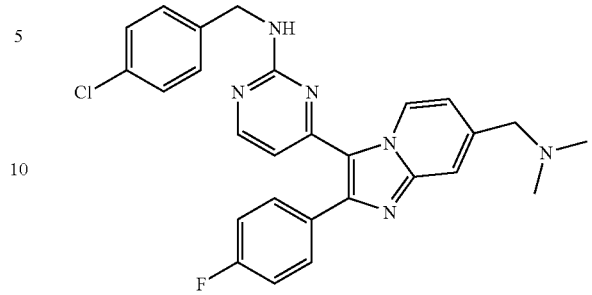 |
| 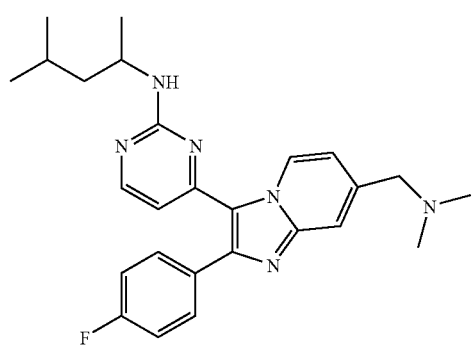 | 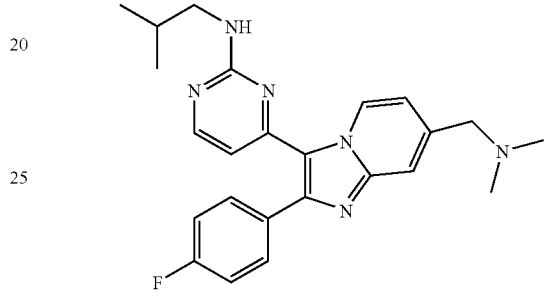 |
| 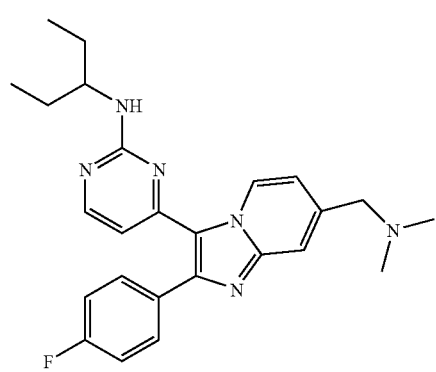 | 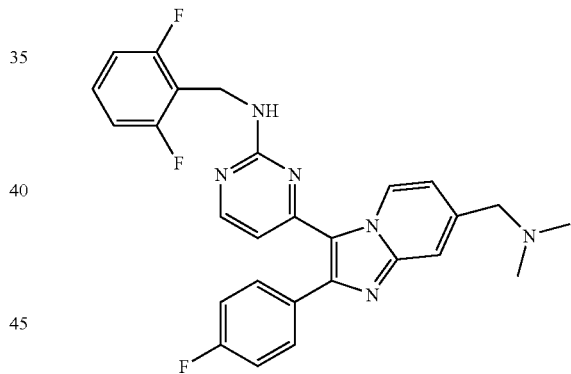 |
| 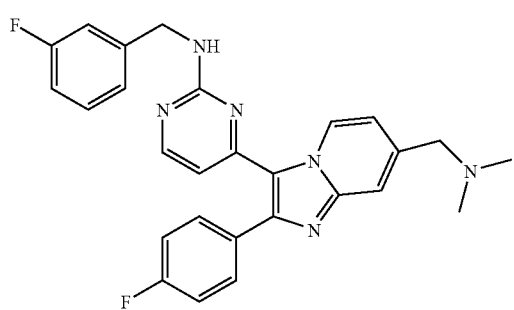 | 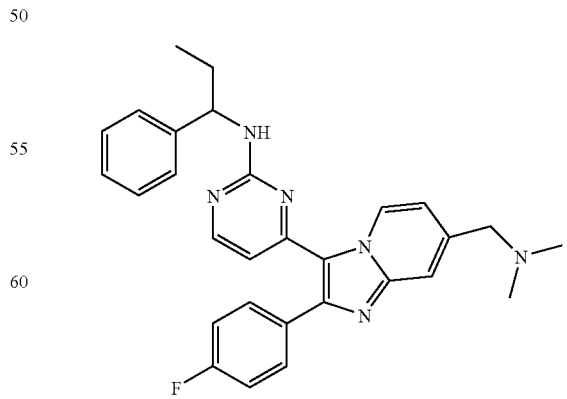 |

503
-continued
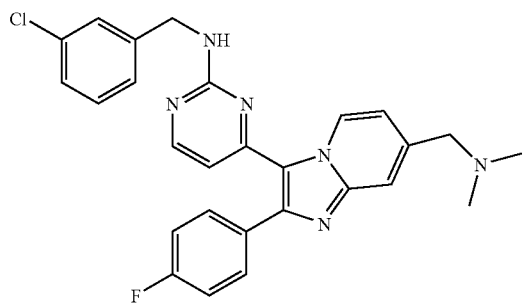
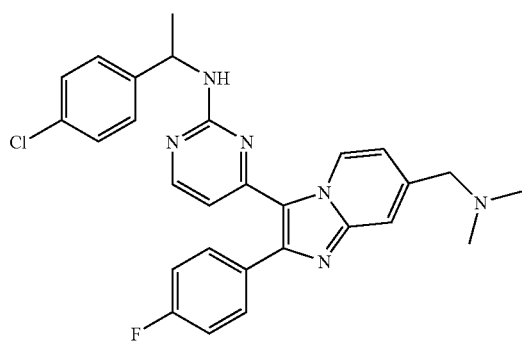
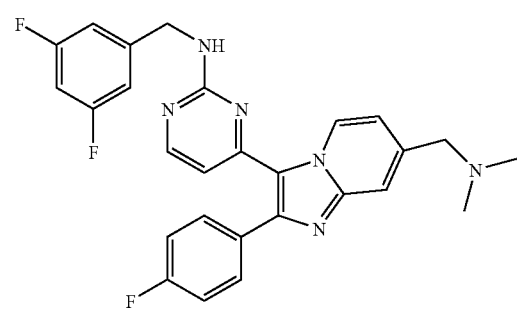
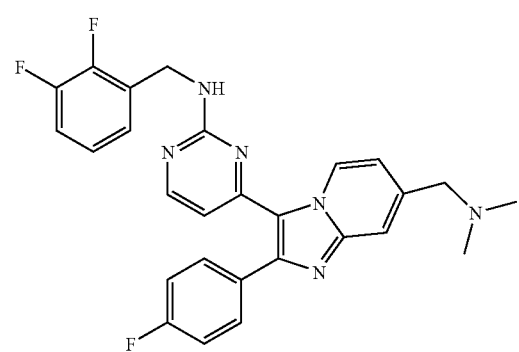
504
-continued
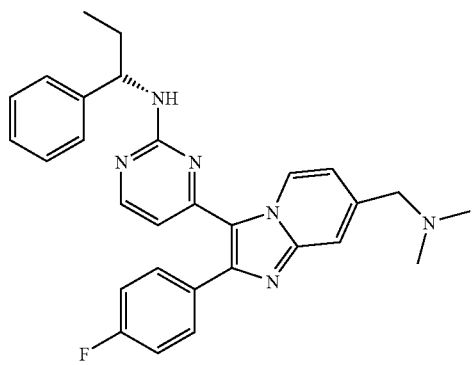
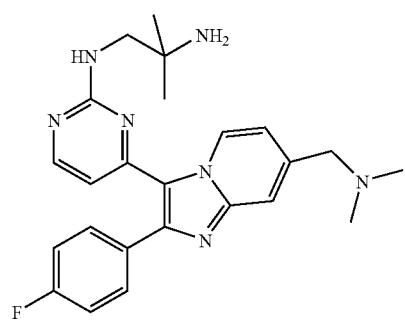

505
-continued
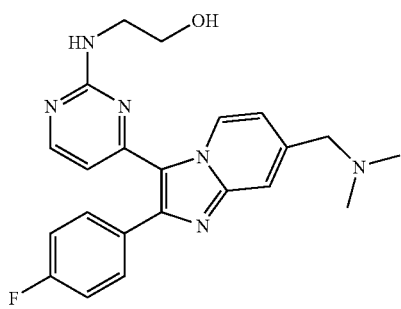
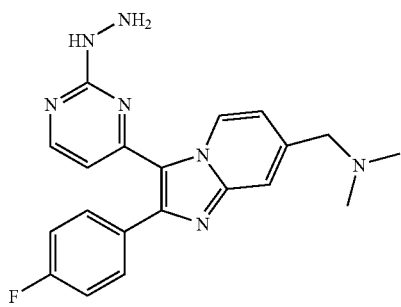
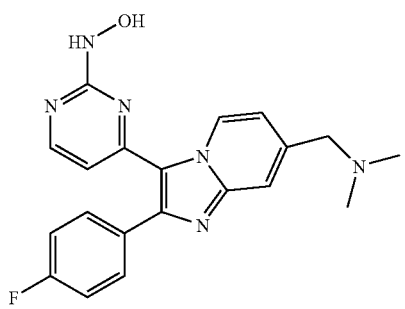
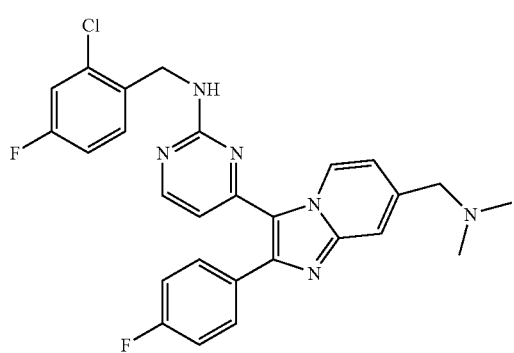
506
-continued
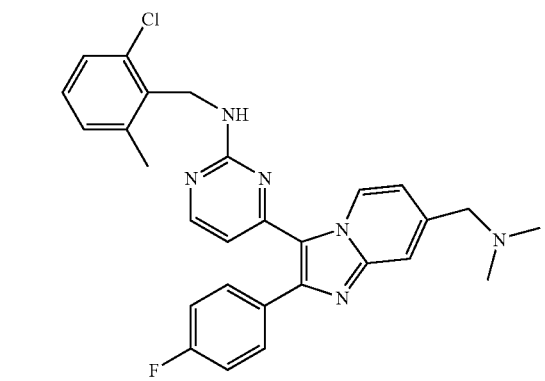
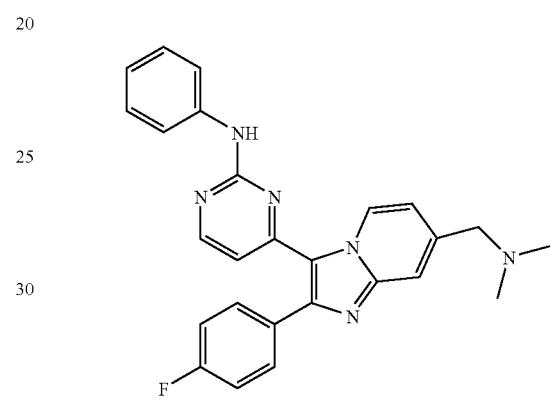
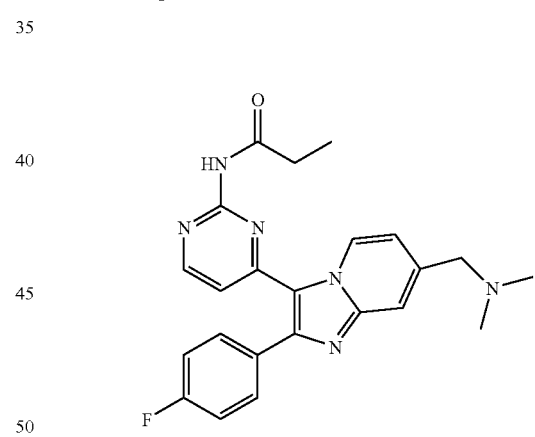
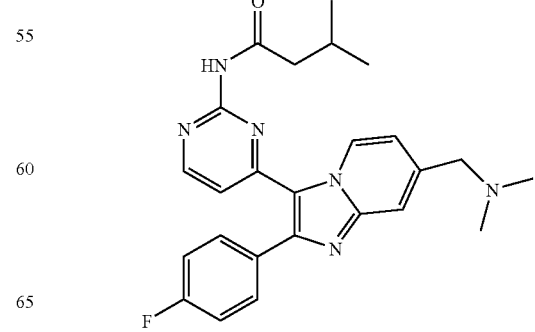

| 507 | 508 |
|---|---|
| -continued | -continued |
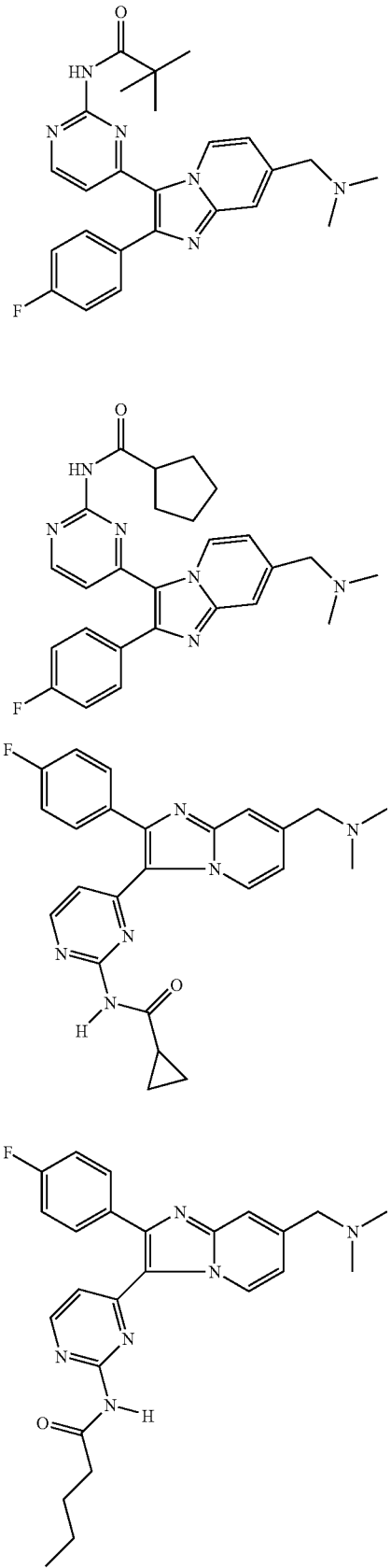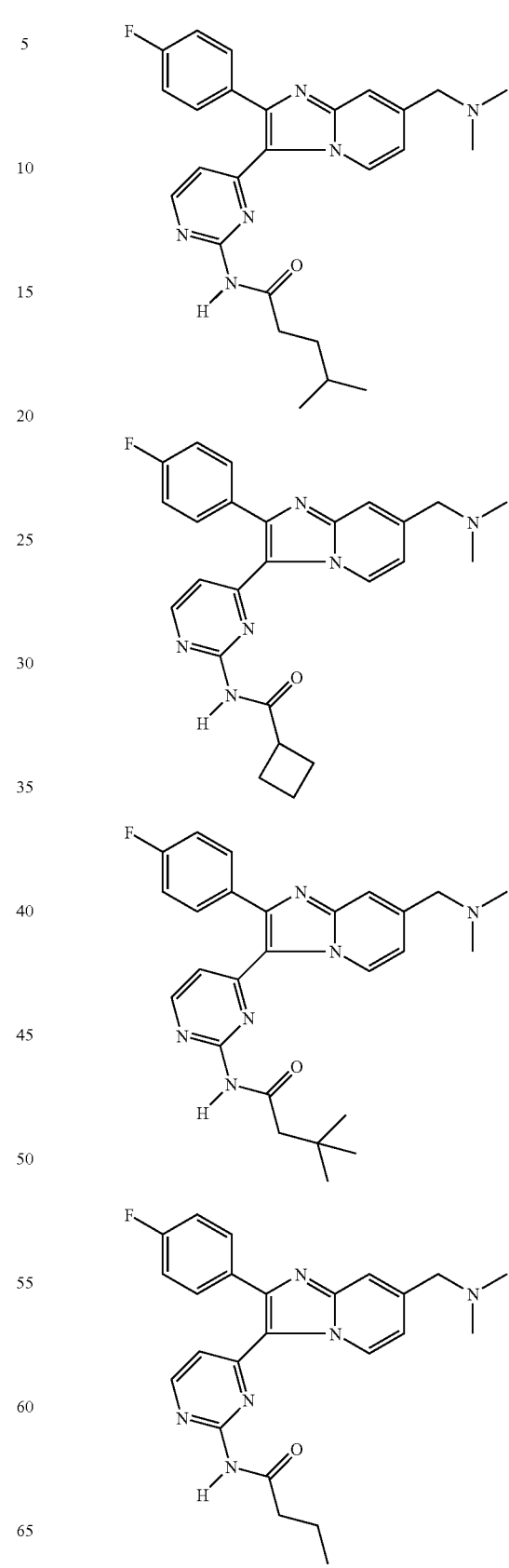

509 -continued
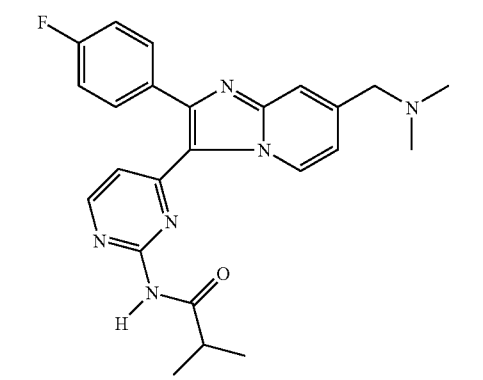
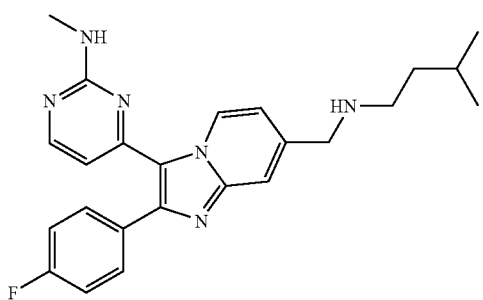
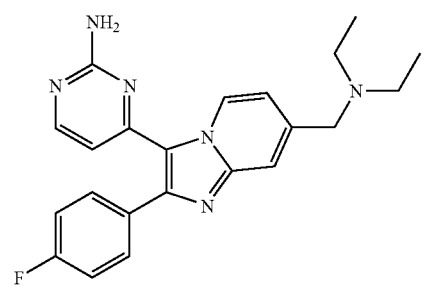
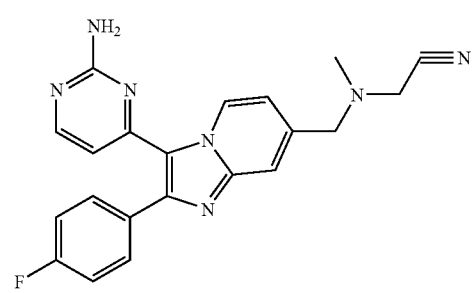
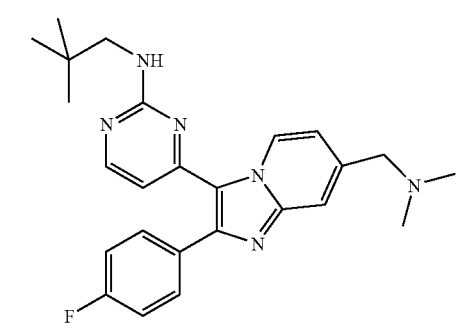
510 -continued
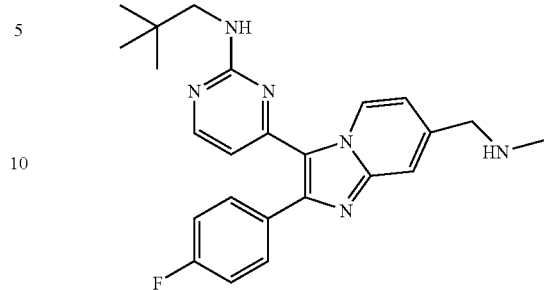
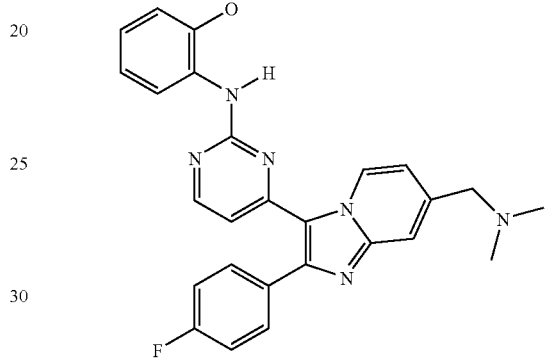
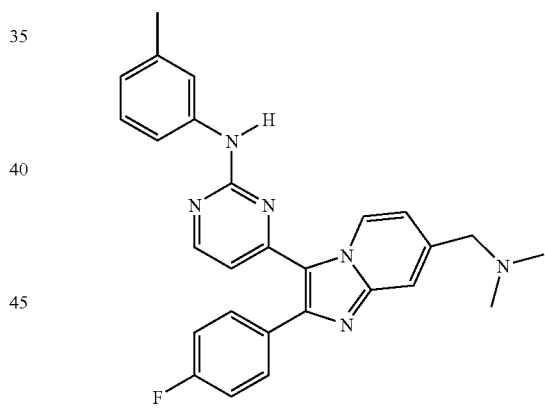

| 511 | 512 |
|---|---|
| -continued | -continued |
| 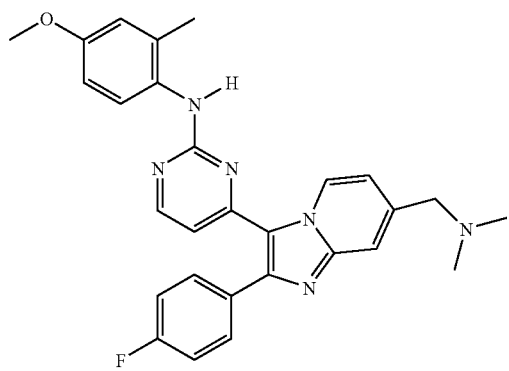 | 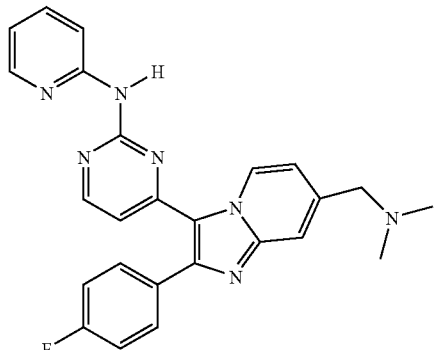 |
| 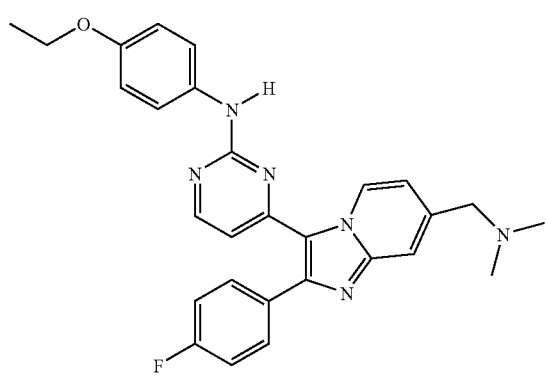 | 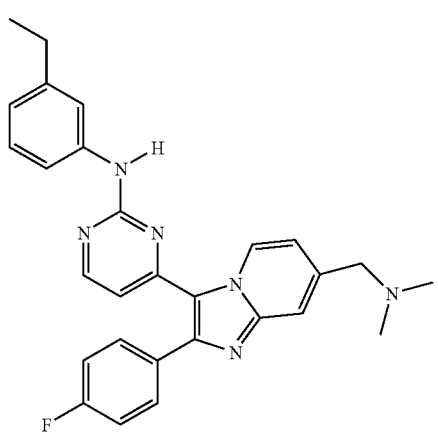 |
| 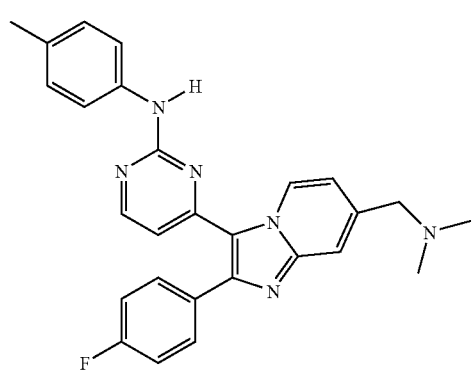 | 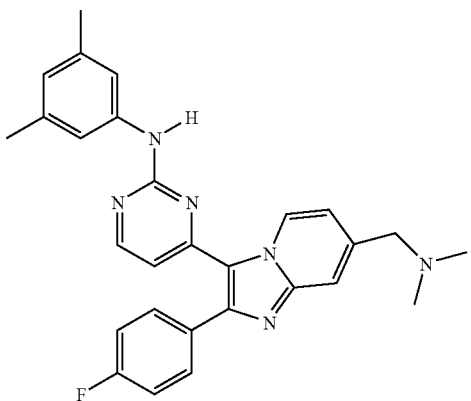 |
| 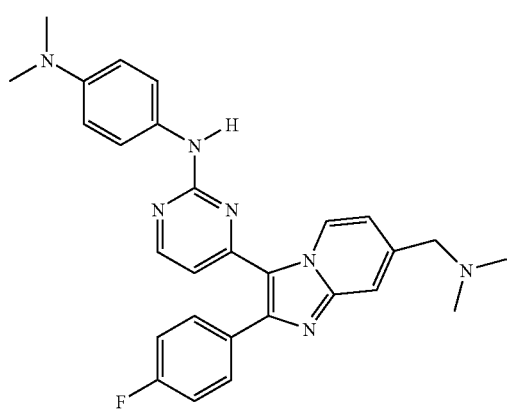 | 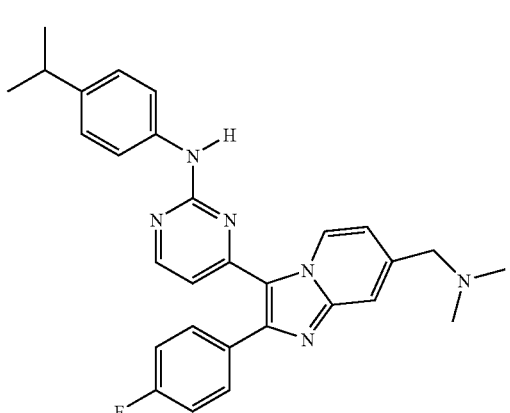 |

| 513 | 514 |
|---|---|
| -continued | -continued |
| 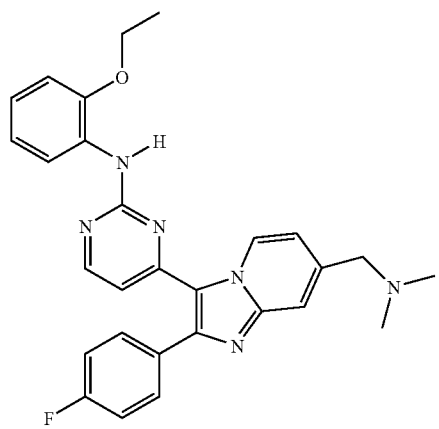 | 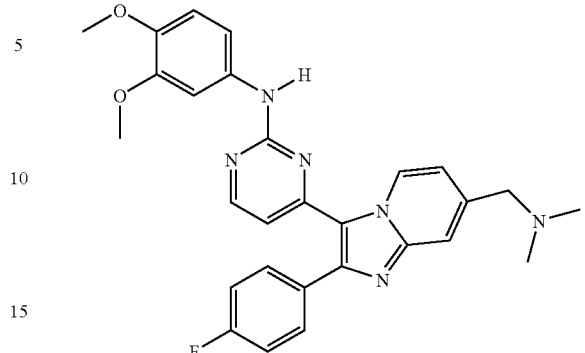 |
| 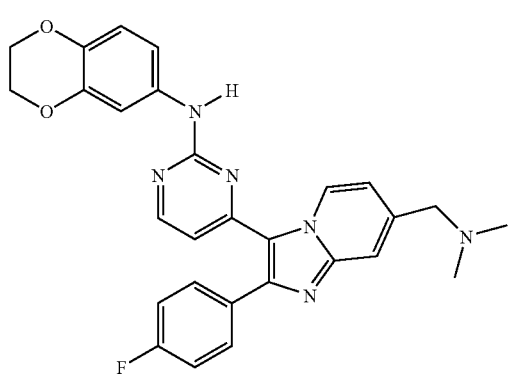 | 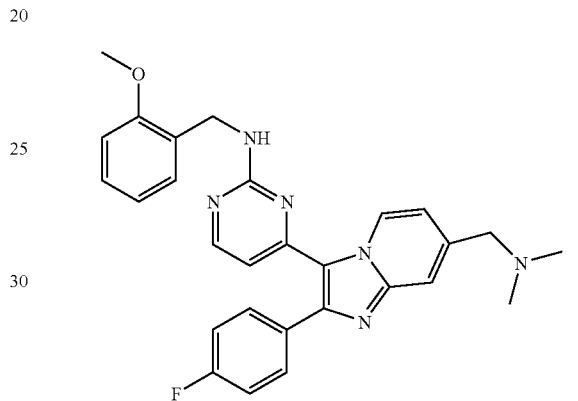 |
| 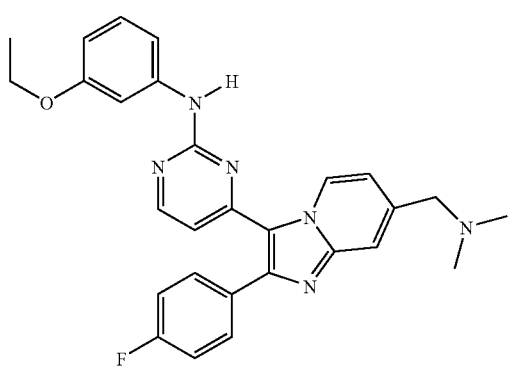 | 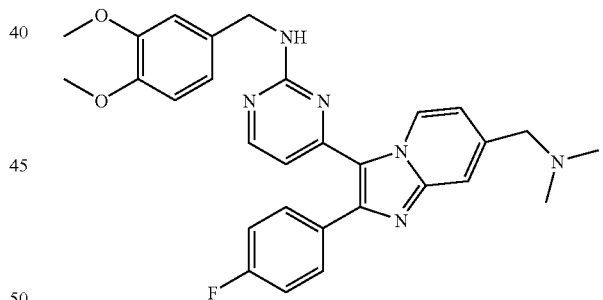 |
| 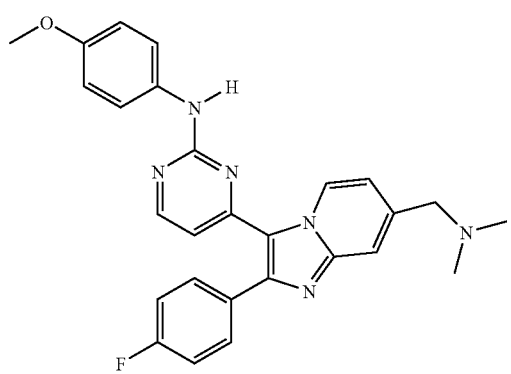 | 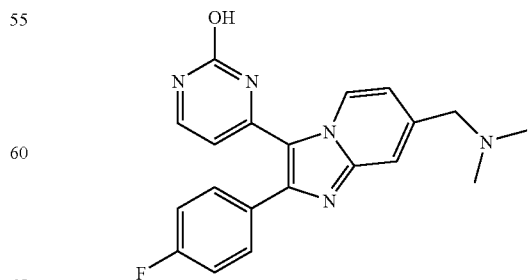 |

515
-continued
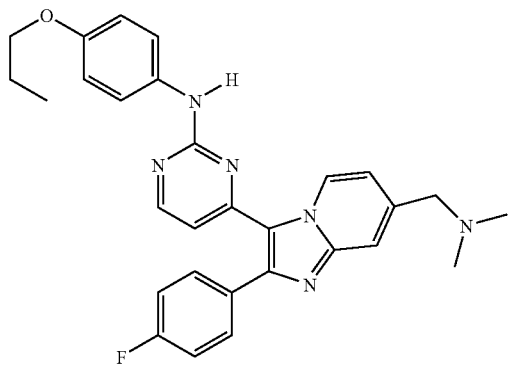
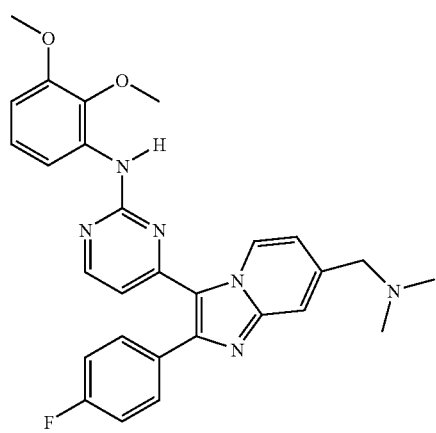
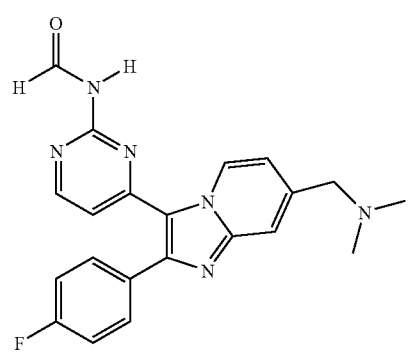
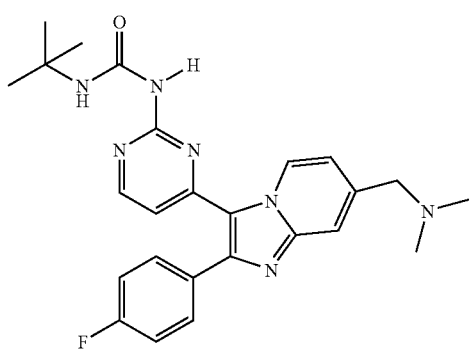
516
-continued
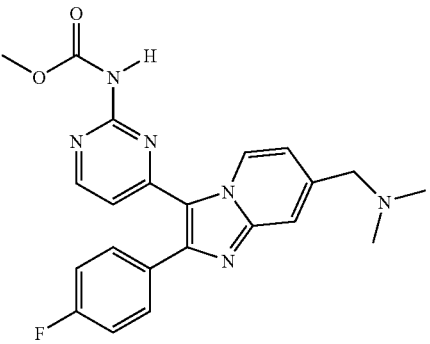
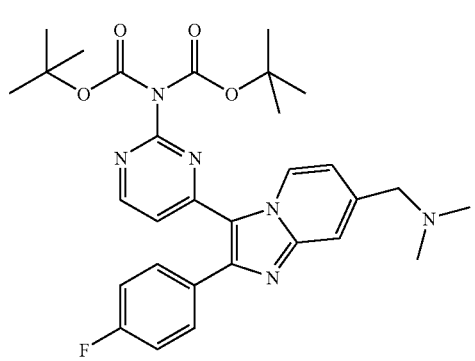
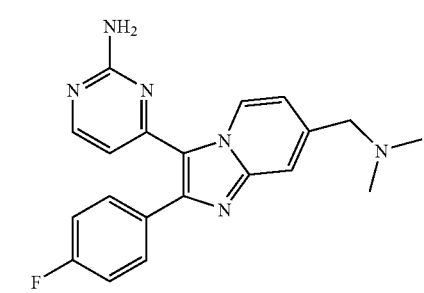
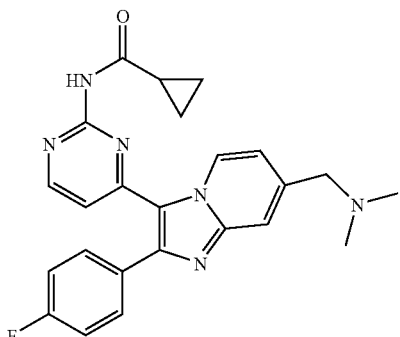

| 517 | 518 |
|---|---|
| -continued | -continued |
| 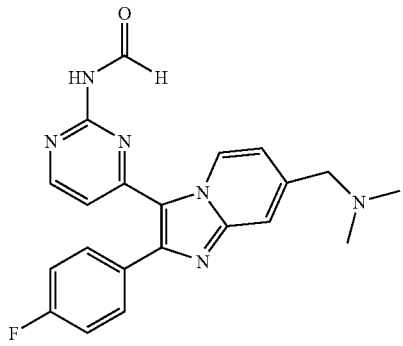 | 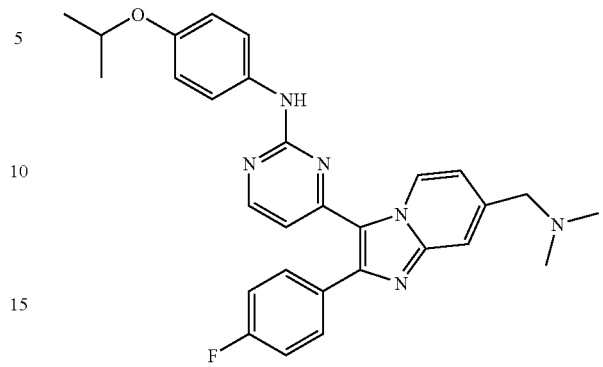 |
| 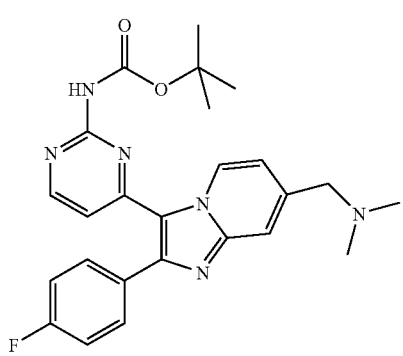 | 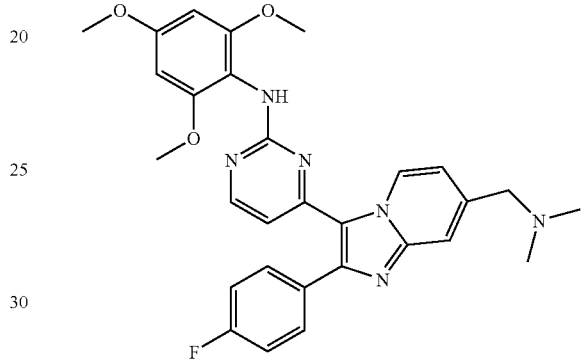 |
| 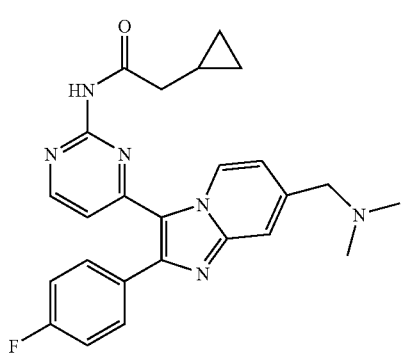 | 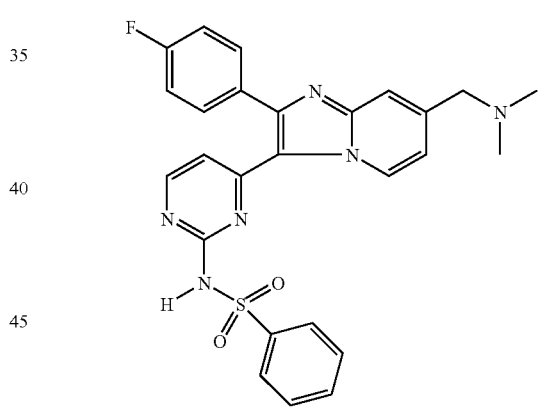 |
| 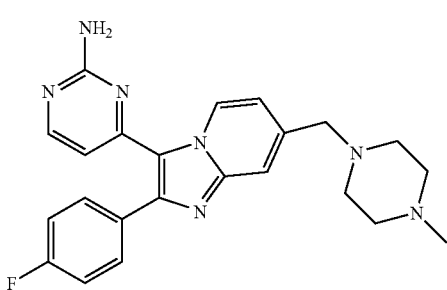 | 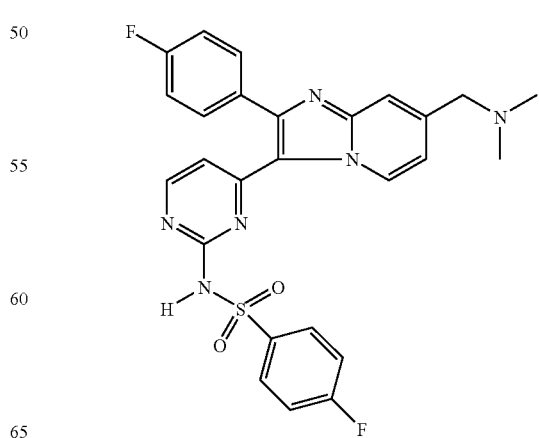 |

| 519 | 520 |
|---|---|
| -continued | -continued |
| 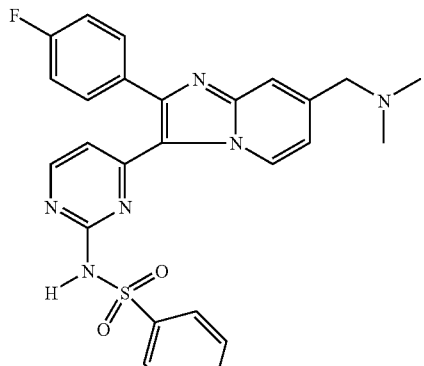 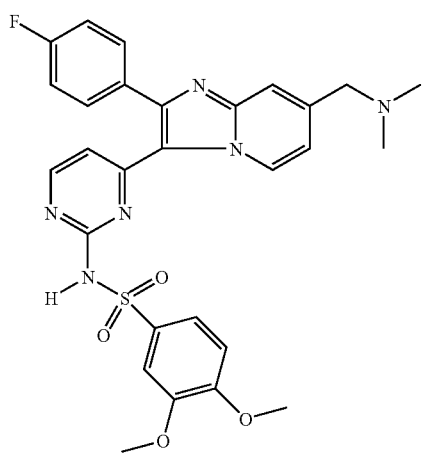 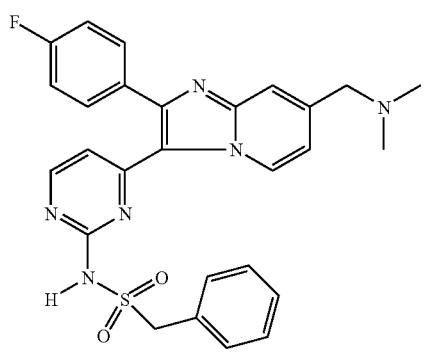 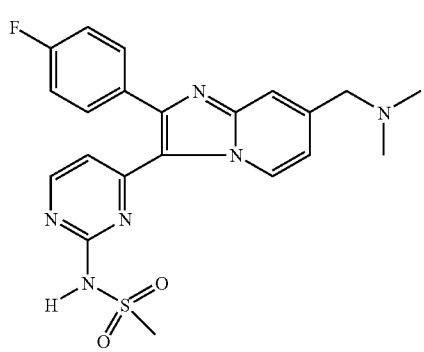 | 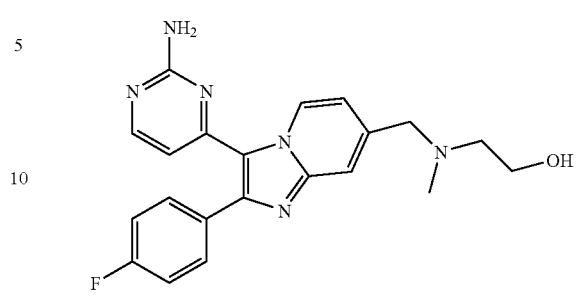 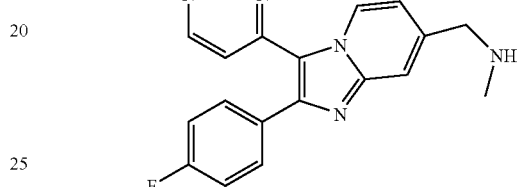 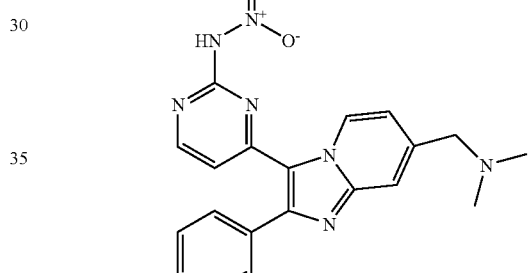 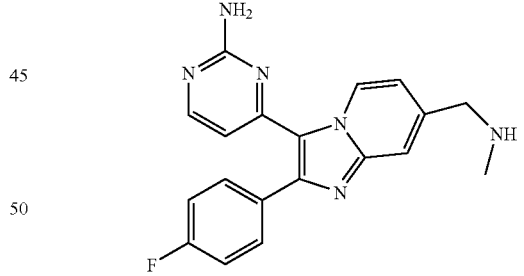 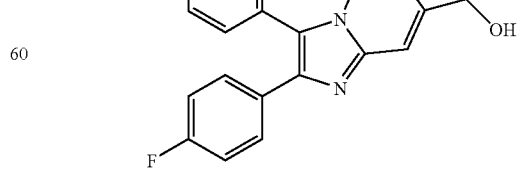 |

521
-continued
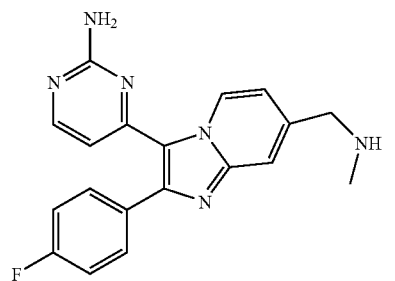
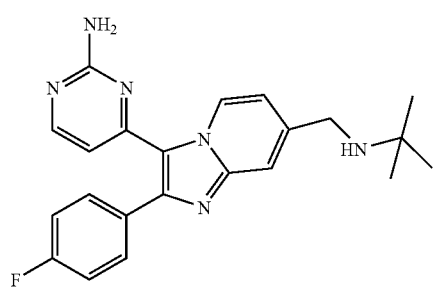
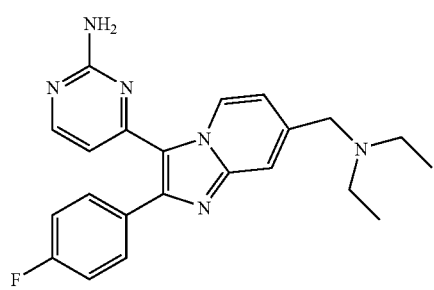
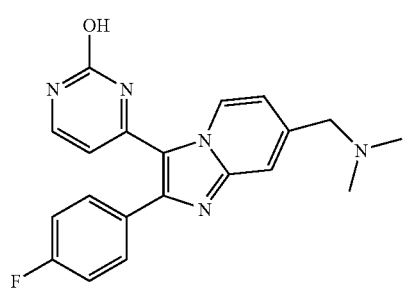
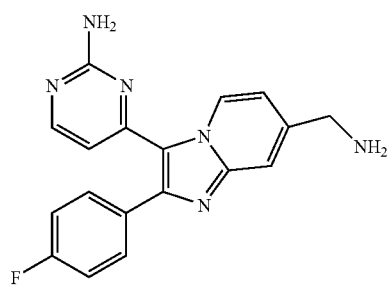
522
-continued
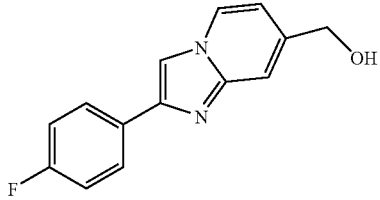
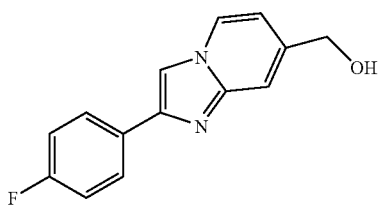
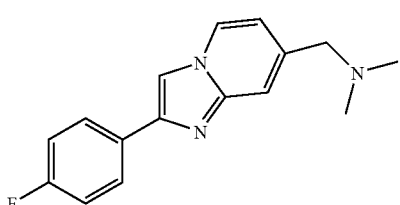
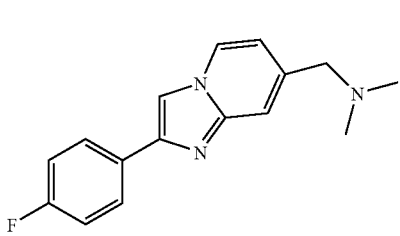

-continued
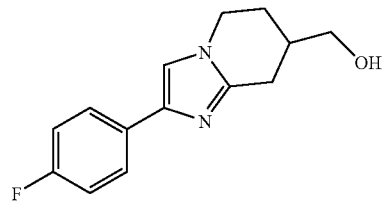
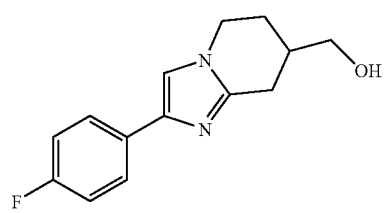
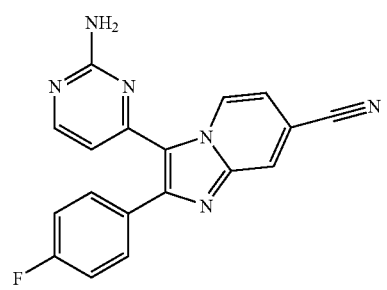
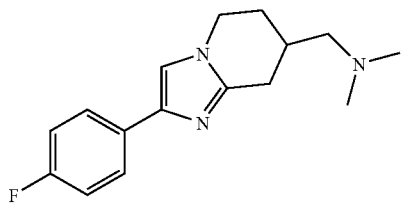
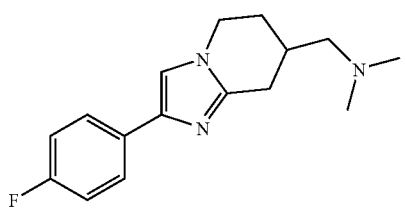
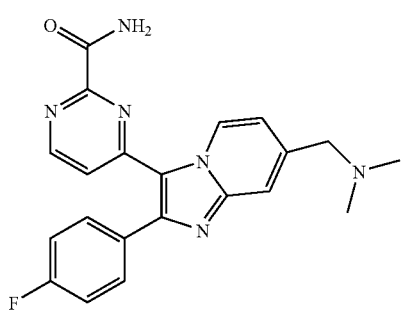
-continued
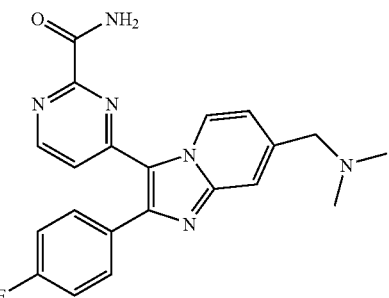
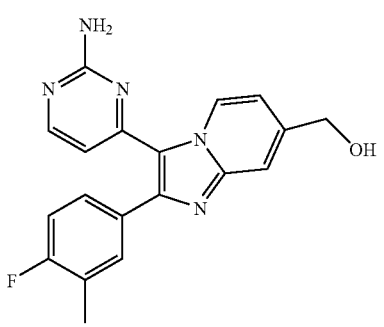
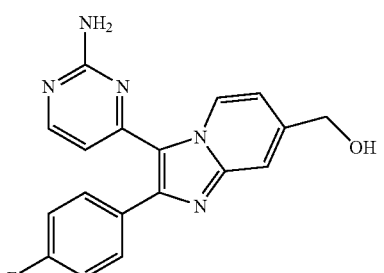
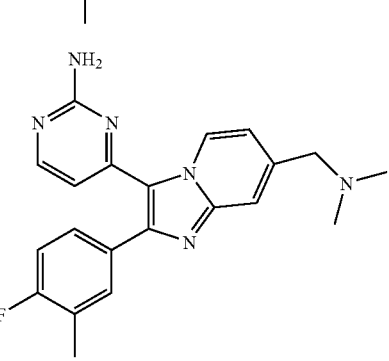
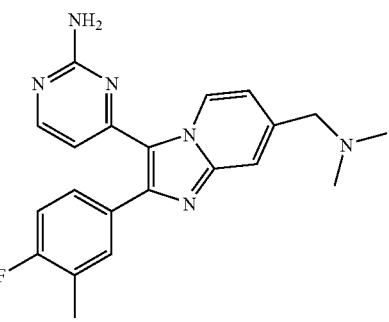

-continued
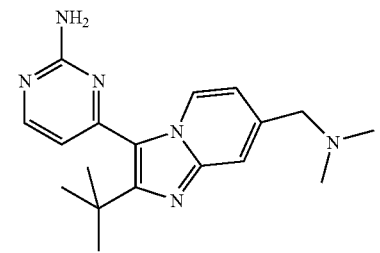
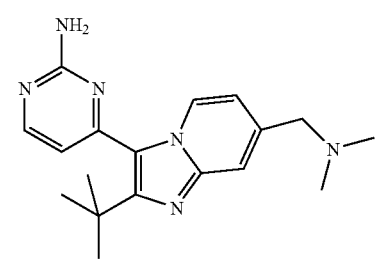
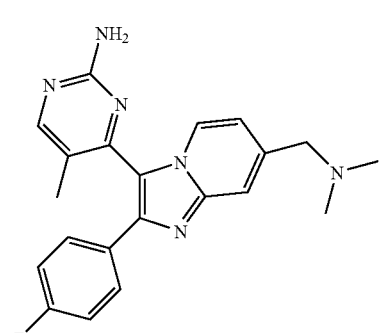
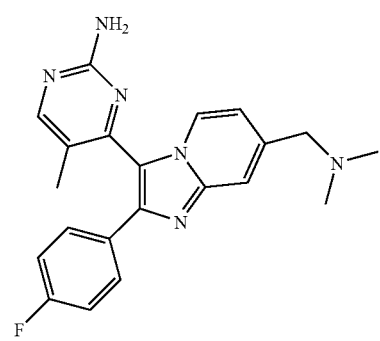
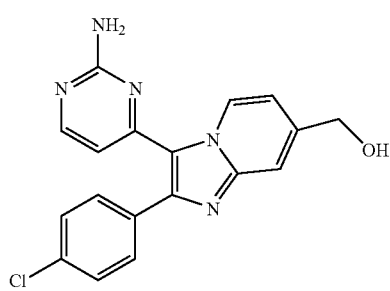
-continued
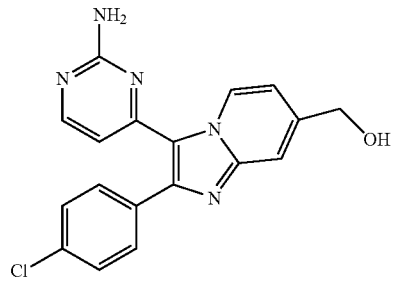
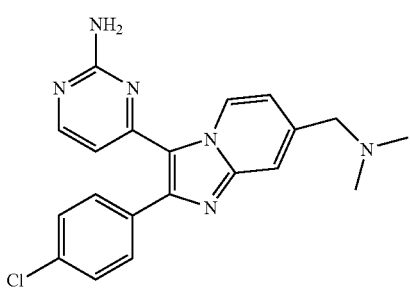
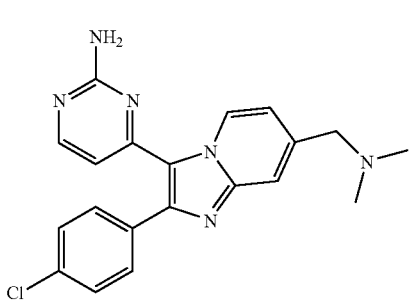
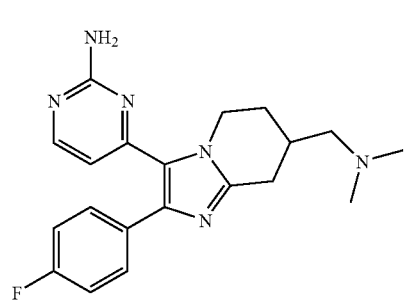
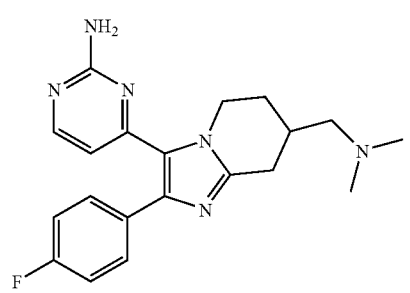

-continued
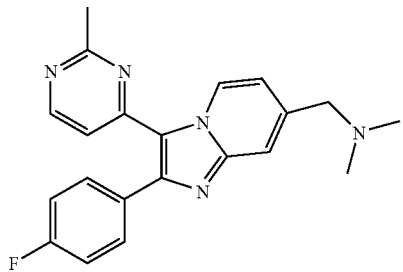
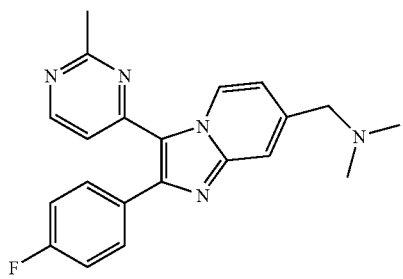
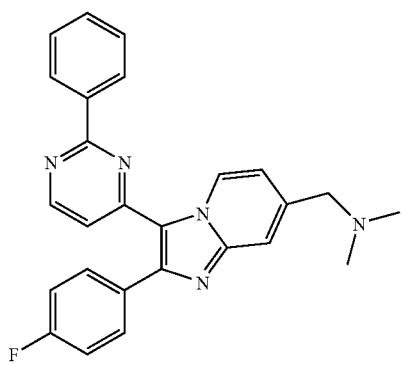
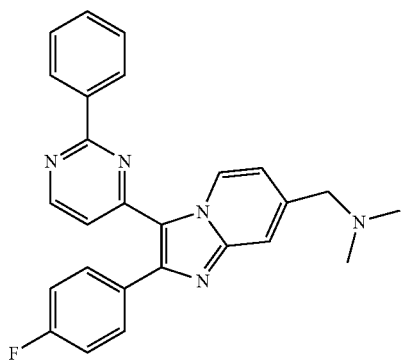
-continued
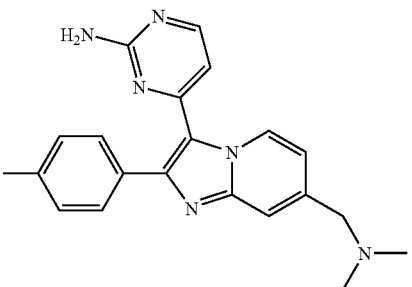
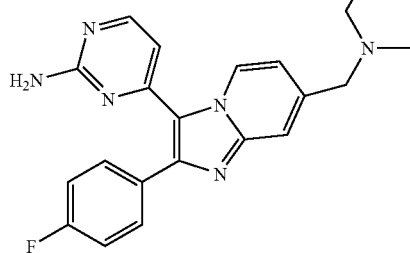
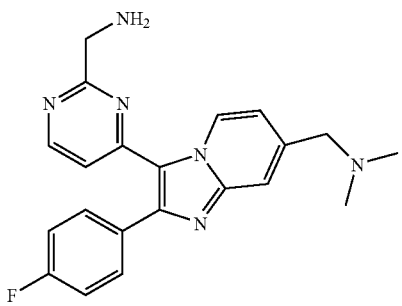
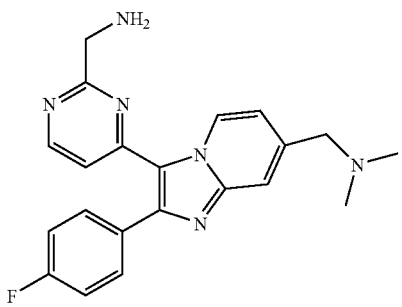
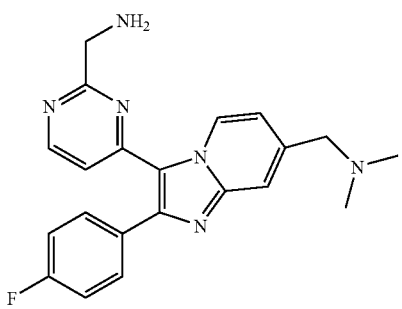

529
-continued
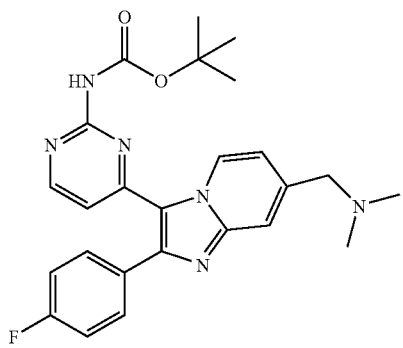
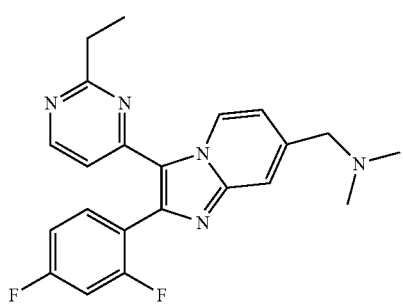
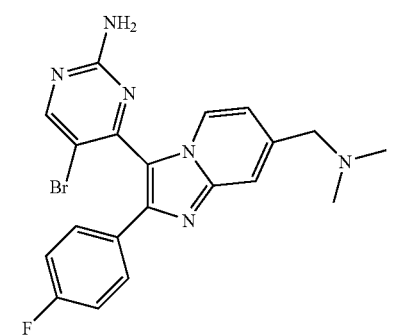
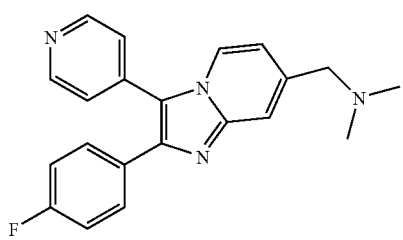
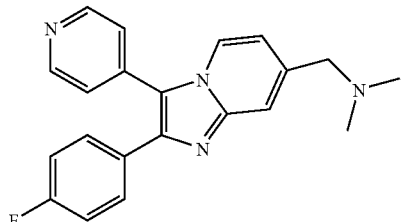
530
-continued
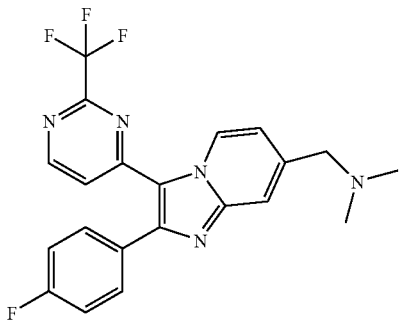
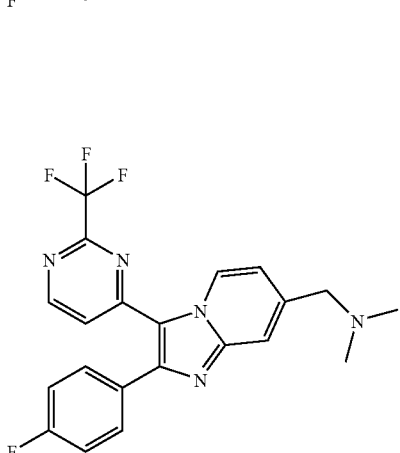

531 -continued 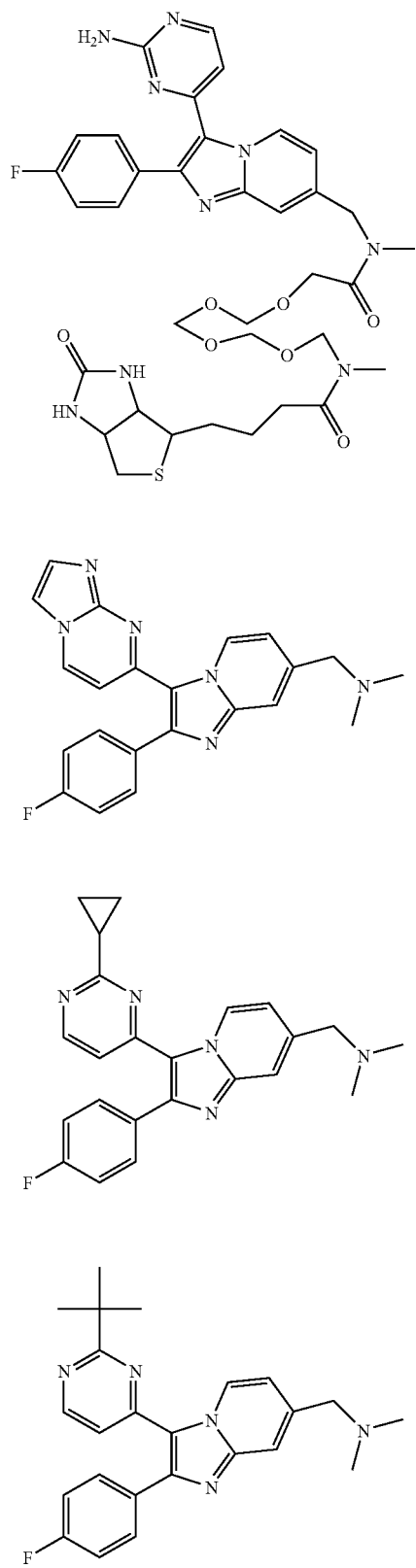
532 -continued 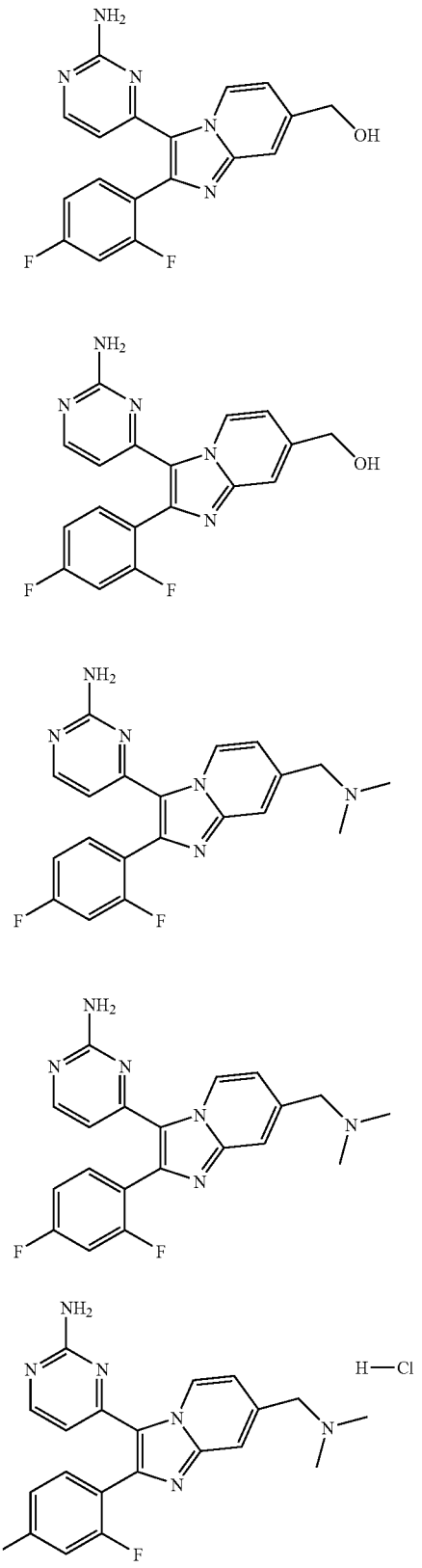

533
-continued
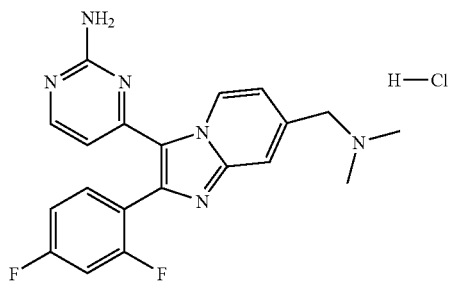
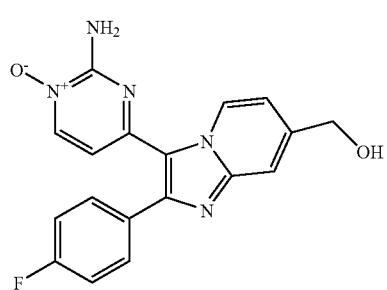
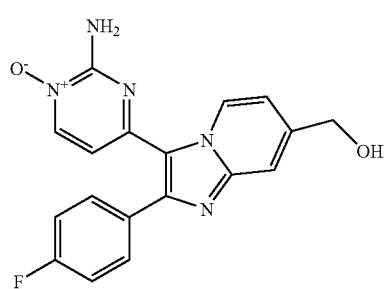
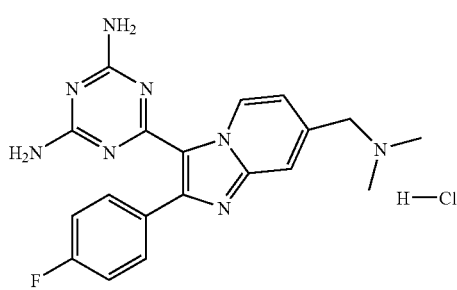
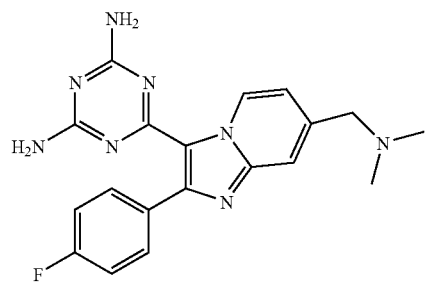
534
-continued
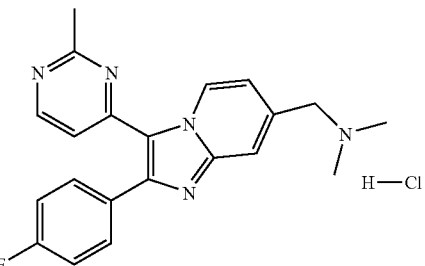
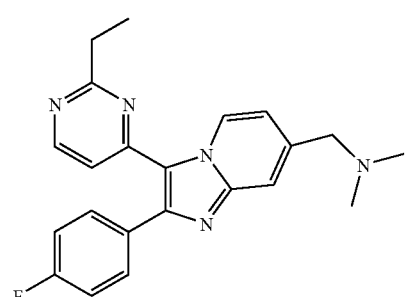
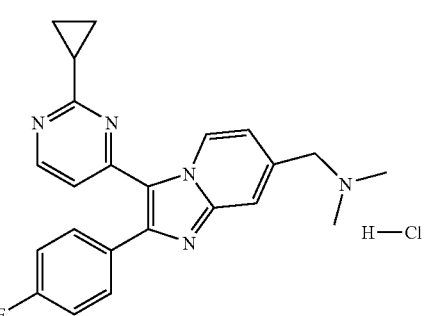
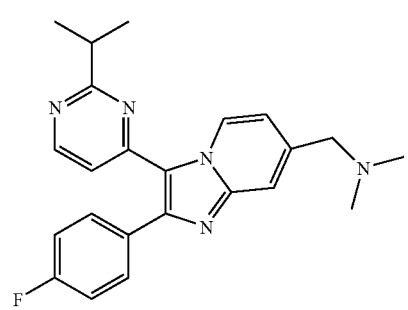
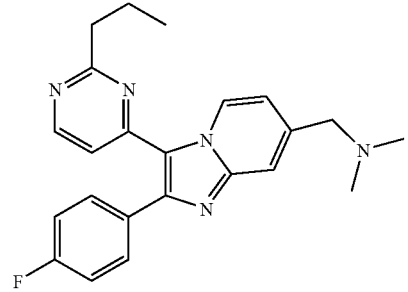

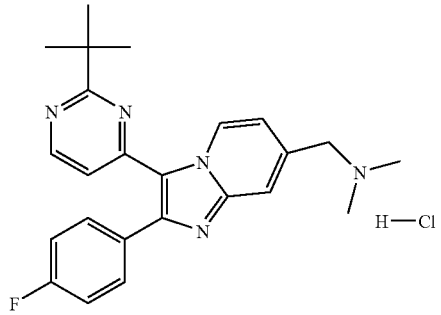
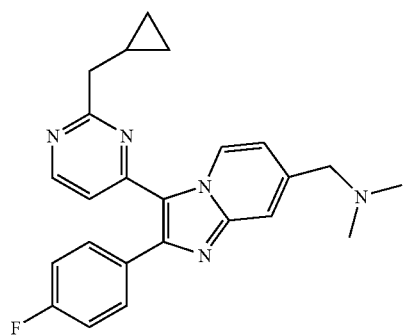
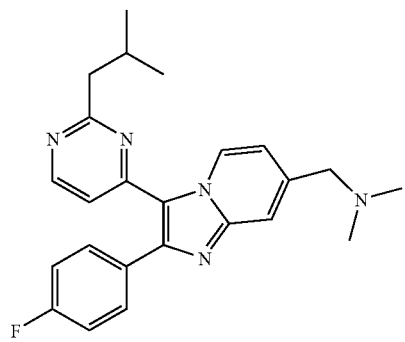
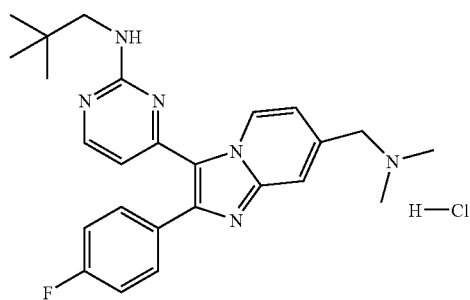
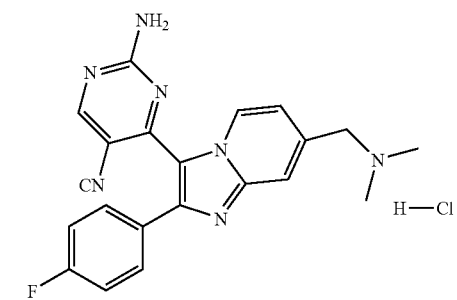
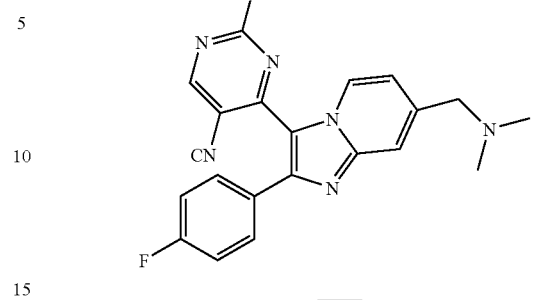
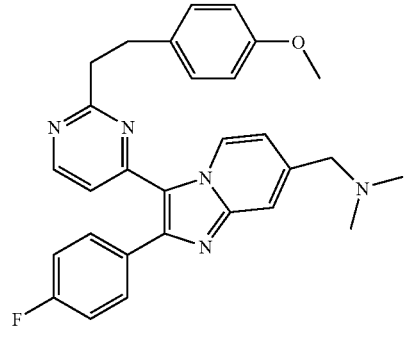
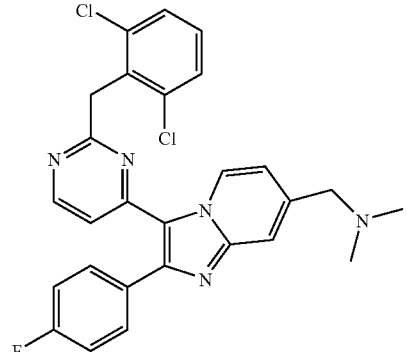
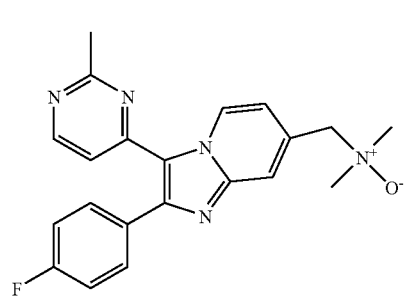
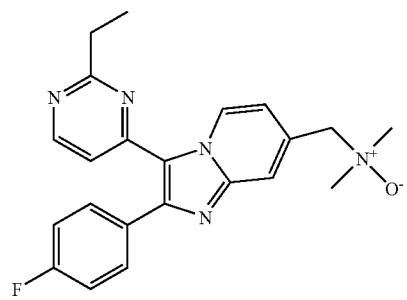

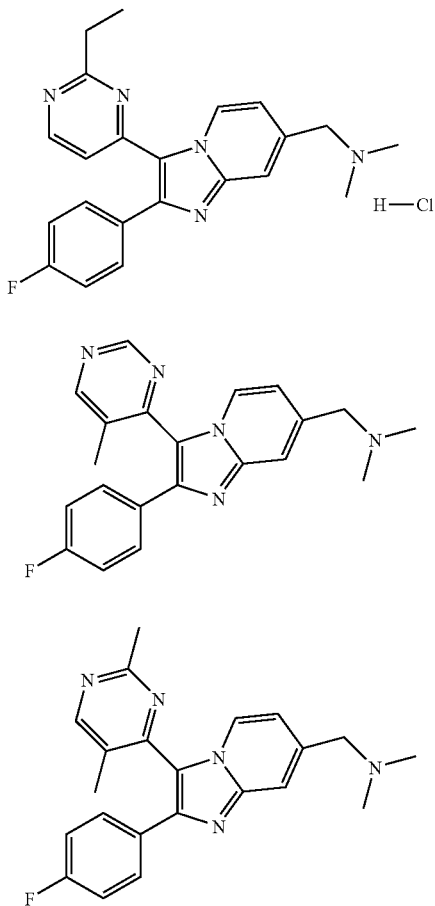

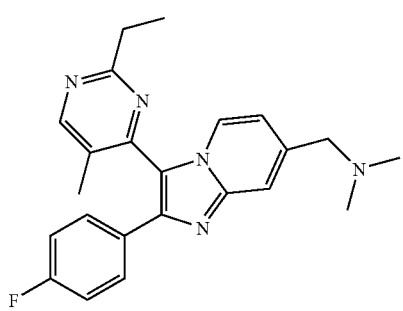

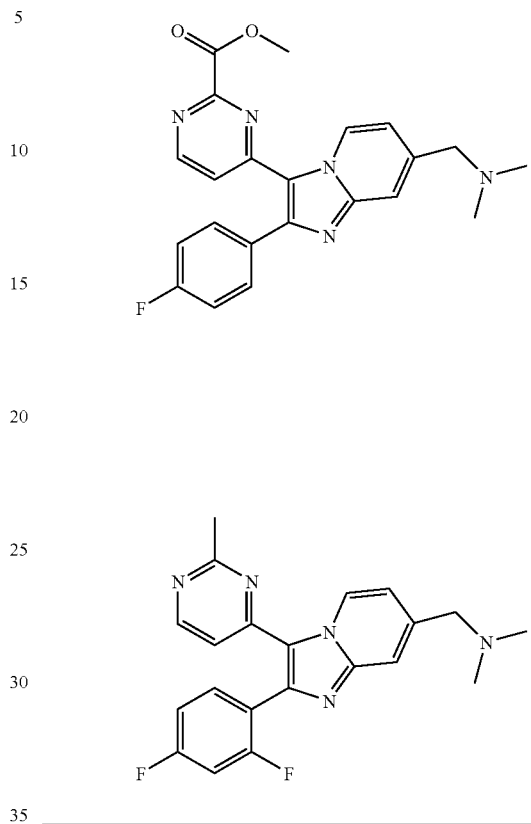

or a pharmaceutically acceptable salt thereof.

24. A pharmaceutical composition comprised of a compound in accordance with claim 1 in combination with a pharmaceutically acceptable carrier.

25. A method of treating a cytokine mediated disease in a mammal, comprising:
administering to a mammalian patient in need of such treatment a compound as described in claim 1 in an amount which is effective to treat said rheumatoid arthritis.

* * * * *